(12) United States Patent
Wellmar et al.

(10) Patent No.: US 9,771,372 B2
(45) Date of Patent: Sep. 26, 2017

(54) COMPOUNDS USEFUL AS S100-INHIBITORS

(71) Applicant: Active Biotech AB, Lund (SE)

(72) Inventors: Ulf Wellmar, Sodra Sandby (SE); David Liberg, Lomma (SE); Maria Ekblad, Sodra Sandby (SE); Marie Bainbridge, Didcot (GB); Stephen East, Wallingford (GB); Jonathan Hargrave, Bath (GB); Natacha Prevost, Montbazin (FR)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 15/312,762

(22) PCT Filed: May 22, 2015

(86) PCT No.: PCT/EP2015/061468
§ 371 (c)(1),
(2) Date: Nov. 21, 2016

(87) PCT Pub. No.: WO2015/177367
PCT Pub. Date: Nov. 26, 2015

(65) Prior Publication Data
US 2017/0204098 A1  Jul. 20, 2017

(30) Foreign Application Priority Data
May 23, 2014  (EP) .................................... 14169757

(51) Int. Cl.
C07D 487/04  (2006.01)
(52) U.S. Cl.
CPC .................................. *C07D 487/04* (2013.01)
(58) Field of Classification Search
CPC .................................................... C07D 487/04
See application file for complete search history.

(56) References Cited

U.S. PATENT DOCUMENTS

2006/0111416 A1  5/2006  Lane et al.
2009/0186879 A1  7/2009  Aso et al.

FOREIGN PATENT DOCUMENTS

| WO | 00/59502 A1 | 10/2000 |
|---|---|---|
| WO | 01/68612 A2 | 9/2001 |
| WO | 02/08224 A1 | 1/2002 |
| WO | 02/069965 A1 | 9/2002 |
| WO | 03/008413 A1 | 1/2003 |
| WO | 03/051277 A2 | 6/2003 |
| WO | 2008/042282 A2 | 4/2008 |
| WO | 2008/118454 A2 | 10/2008 |
| WO | 2008/157270 A1 | 12/2008 |
| WO | 2010/009290 A1 | 1/2010 |
| WO | 2010/101949 A1 | 9/2010 |
| WO | 2013/067260 A1 | 5/2013 |
| WO | WO-2015/086525 A1 * | 6/2015 |

OTHER PUBLICATIONS

International Search Report for corresponding International Application No. PCT/EP2015/061468 mailed Aug. 5, 2015.
Written Opinion of the International Search Authority for corresponding International Application No. PCT/EP2015/061468 mailed Aug. 5, 2015.
Acharyya et al., "A CXCL1 Paracrine Network Links Cancer Chemoresistance and Metastasis", Cell, vol. 150, Jul. 6, 2012, pp. 165-178.
Arai et al., "S100A8 and S100A9 Overexpression Is Associated with Poor Pathological Parameters in Invasive Ductal Carcinoma of the Breast", Current Caner Drug Targets, vol. 8, No. 4, 2008, pp. 243-252.
Attia et al., "Immunology of Spontaneous Mammary Carcinomas in Mice V. Acquired Tumor Resistance and Enhancement in Strain A Mice Infected with Mammary Tumor Virus", Cancer Research, vol. 26, Part 1, Aug. 1966, pp. 1787-1800.
Bhardwaj et al., "The calcium-binding proteins MRPS and MRP14 form a membrane-associated heterodimer in a subset of monocytedmacrophages present in acute but absent in chronic inflammatory lesions", Eur. J. Immunol., vol. 22, 1992, pp. 1891-1897.
Bjork et al., "Identification of Human S100A9 as a Novel Target for Treatment of Autoimmune Disease via Binding to Quinoline-3-Carboxamides", PLOS Biology, vol. 7, Issue 4, Apr. 2009, pp. 0800-0812.
Carta et al., "Design, synthesis, and preliminary in vitro and in silico antiviral activity of [4,7]phenantrolines and 1-oxo-1,4-dihydro-[4,7]phenantrolines against single-stranded positive-sense RNA genome viruses", Science Direct, Bioorganic & Medicinal Chemistry, vol. 15, 2007, pp. 1914-1927.
Chang et al., "The Role of S100a9 in the Pathogenesis of Alzheimer's Disease: The Therapeutic Effects of S100a9 Knockdown or Knockout", Neurodegenerative Diseases, DOI: 10.1159/000333781, published online on Feb. 1, 2012, pp. 1-5.
Chaudhari et al., "Novel and Facile Transofrmation of N,N-Disubstituted Glycylamides into Corresponding Cyanamides by Using Pentavalent Iodine Reagents in Combination with Tetraethylammonium Bromide", Letter, No. 18, 2007, pp. 2815-2818.

(Continued)

*Primary Examiner* — Laura L. Stockton
(74) *Attorney, Agent, or Firm* — Renner, Otto, Boisselle & Sklar, LLP

(57) ABSTRACT

A compound of formula (I) or a pharmaceutically acceptable salt thereof and a pharmaceutical composition comprising the compound. The compound is an inhibitor of interactions between S100A9 and interaction partners such as RAGE, TLR4 and EMMPRIN and as such is useful in the treatment of disorders such as cancer, autoimmune disorders, inflammatory disorders and neurodegenerative disorders.

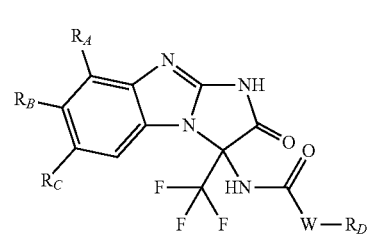

(I)

33 Claims, 3 Drawing Sheets

(56) References Cited

OTHER PUBLICATIONS

Cheng et al., "Inhibition of dendritic cell differentiation and accumulation of myeloid-derived suppressor cells in cancer is regulated by S100A9 protein", The Journal of Experimental Medicine, Sep. 22, 2008, pp. 1-15.
Deane et al., "A multimodal RAGE-specific inhibitor reduces amyloid β-mediated brain disorder in a mouse model of Alzheimer disease", The Journal of Clinical Investigation, vol. 122, No. 4, Apr. 2012, pp. 1377-1392.
Foell et al., "S100 proteins expressed in phagocytes: a novel group of damage-associated molecular pattern molecules", Journal of Leukocyte Biology, vol. 81, Jan. 2007, pp. 28-37.
Foell et al., "Proinflammatory S100 Proteins in Arthritis and Autoimmune Disease", Arthritis & Rheumatism, vol. 50, No. 12, Dec. 2004, pp. 3762-3771.
Ghavami et al., "S100A8/A9 at low concentration promotes tumor cell growth via RAGE ligation and MAP kinase-dependent pathway", Journal of Leukocyte Biology, vol. 83, Jun. 2008, pp. 1-9.
Ha et al., "S100a9 Knockdown Decreases the Memory Impairment and the Neuropathology in Tg2576 Mice, AD Animal Model", PLoS ONE, vol. 1, Issue 1, Jan. 2010, pp. 1-11.
Hibino et al., "S100A9 is a Novel Ligand of EMMPRIN That Promotes Melanoma Metastasis", Cancer Research, vol. 73, No. 1, Jan. 1, 2013, pp. 172-183.
Hiratsuka et al., "Tumour-mediated upregulation of chemoattractants and recruitment of myeloid cells predetermines lung metastasis", Letters, Nature Cell Biology, vol. 8, No. 12, Dec. 2006, 14 pages.
Marenholz et al., "S100 proteins in mouse and man: from evolution to function and pathology (including an update of the nomenclature)", Biochemical and Biophysical Research Communications, vol. 322, 2004, pp. 1111-1122.
Ryckman et al., "Proinflammator Activities of S100: Proteins S100A8, S100A9, and S100A8/A9 Induce Neutrophil Chemotaxis and Adhesion", The Journal of Immunology, 2003, pp. 3233-3242.
Shepherd et al., "Inflammatory S100A9 and S100A12 proteins in Alzheimer's disease", Neurobiology of Aging, vol. 27, 2006, pp. 1554-1563.
Sinha et al., "Proinflammatory S100 Proteins Regulate the Accumulation of Myeloid-Derived Suppressor Cells", The Journal of Immunology, 2008, pp. 4666-4675.
Srikrishna, "S100A8 and S100A9: New Insights into Their Roles in Malignancy", Journal of Innate Immunity, vol. 4, 2012, pp. 31-40.
Vogl et al., "Mrp8 and Mrp14 are endogenous activators of Toll-like receptor 4, promoting lethal, endotoxin-induced shock", Nature Medicine, vol. 13, No. 9, Sep. 2007, pp. 1042-1049.
Wang et al., "Increased Myeloid-Derived Suppressor Cells in Gastric Cancer Correlate with Cancer Stage and Plasma S100A8/A9 Proinflammatory Proteins", The Journal of Immunology, vol. 190, 2013, pp. 794-804.
You et al., "Silica gel accelerated aza-Michael addition of amines to a,b-unsaturated amides", Tetrahedron Letters, vol. 49, 2008, pp. 5147-5149.
Descours et al., "Reactions of N-(omega-Chloroalkynoyl)-carbonimidic Dichlorides: A New Synthesis of 2-Oxo-1,2,3,4-tetrahydropyrimido[1,2-alpha]brnzimidazoles, 2-Oxo-2,3-dihydro-1H-imidazo[1,2-alpha]benzimidazoles, and 2-Oxo-2,3,5,10-tetrahydro-1H-imidazo[1,2-b][2,4]benzodiazepines", Synthesis, No. 12, Dec. 1, 1983, pp. 1033-1036.
Messina et al., "Solid-Phase Synthesis of 5-Noranagrelide Derivatives", ACS Combinatorial Science, vol. 16, Dec. 4, 2013, pp. 33-38.
Troxler et al., "Synthese von Pyrimido[1,2-alpha]penzimidazolen durch Umsetzung von 2-Aminobenzimidazol mit Acetylendicarbonsaure-dimethylester und ihre Uberfuhrung in Imidazo[1,2-alpha]benzimidazle", Helvetica Chimica Acta, vol. 58, No. 8, Aug. 1, 1974, pp. 2356-2364.

\* cited by examiner

A

B

COMPOUNDS USEFUL AS S100-INHIBITORS

This application is a national phase of International Application No. PCT/EP2015/061468 filed May 22, 2015, and claims priority to Application No. EP 14169757.3 filed May 23, 2014.

FIELD OF THE INVENTION

The present invention relates to novel N-(2-oxo-3-(trifluoromethyl)-2,3-dihydro-1H-benzo[d]imidazo[1,2-a]imidazol-3-yl)amide derivatives, pharmaceutical compositions of these derivatives and their use as medicaments. More particularly the invention relates to such derivatives for use in the treatment of cancer, autoimmune disorders, inflammatory disorders and neurodegenerative disorders.

BACKGROUND OF THE INVENTION

S100A9 belongs to the S100-family of calcium-binding proteins and has been recognized as an attractive novel therapeutic target for the treatment of e.g. autoimmunity, inflammatory disease, neurodegenerative disease and cancer. Other S100 proteins have distinct roles in many different biological processes and are connected to a number of diseases including cancer, cardiomyopathies, atherosclerosis, Alzheimer's disease and inflammatory diseases. Twenty-one of the human genes, including S100A9, are located at chromosomal region 1q21, which is frequently altered in tumors (Marenholz et al., 2004). Interestingly, although the primary sequence diverges between family members, the 3D-structures of the different proteins are very similar.

S100A9 is often co-expressed with S100A8, another member of the S100 protein family, and they are highly expressed in myeloid cells, such as neutrophils and monocytes, but can also be induced in other cells or tissues (Srikrishna 2012). They form non-covalent homo- and heterocomplexes that can be specifically released in response to cellular activation (Foell et al., 2007, Ryckman et al., 2003). S100A9 can functionally be described as a damage-associated molecular pattern (DAMP) molecule which is released in tissues and induces signaling by interacting with receptors such as RAGE and TLR4 (Foell et al., 2007, below). As for many other DAMP molecules, S100A9 also has intracellular roles in addition to its extracellular functions, e.g. by binding to the cytoskeleton and influencing cytoskeletal rearrangements and thereby cellular migration (Srikrishna 2012)

A pro-inflammatory role for S100A9 is supported by elevated S100A9 serum levels in inflammatory diseases and by high concentrations of S100A9 at local sites of inflammation, for example in the synovial fluid of rheumatoid arthritis patients (Foell et al., 2004). High levels of S100A9 have also been found in several forms of cancer and a high expression level has been shown to correlate with poor tumor differentiation in some of these cancer forms (Arai et al., 2008). Elevated S100A9 levels in pathological conditions of chronic inflammation as well as in cancer argue for a possible role in inflammation-associated carcinogenesis.

A role for S100A9 in the coupling between the immune system and cancer is also supported by studies showing that S100A8 and S100A9 are highly expressed in and important for the function of myeloid-derived suppressor cells (MDSCs) (Cheng et al., 2008, Sinha et al., 2008, Wang et al., 2013), a mixture of immature myeloid cells that suppress T- and NK-cell activation and promote angiogenesis and tumor growth. By interfering with S100A9-regulated accumulation of tumor infiltrating MDSCs, the balance between these processes may change in favor of an anti-angiogenic and less immune suppressive milieu with inhibited tumor progression. Furthermore, there are data suggesting a role for S100A9 in recruiting both inflammatory cells and tumor cells to metastatic sites (Hiratsuka et al., 2006, Acharyya et al. 2012, Hibino et al., 2013). Thus, blocking the function of S100A9 may provide a new approach to prevention of metastasis.

Although a number of possible biological functions of S100A9 have been proposed, the exact role of S100A9 in inflammation, in cancer and in other diseases is still unknown. Members of the S100 protein family have been reported to interact with the pro-inflammatory molecule RAGE and studies showed that S100A9 is the strongest RAGE binder within the S100 family in the presence of physiological levels of $Ca^{2+}$ and $Zn^{2+}$ (Björk et al. 2009). These studies further demonstrated that S100A9 interacts with toll-like receptor 4 (TLR4). As for the S100A9-RAGE interaction, the S100A9-TLR4 interaction appears to be strictly dependent on the presence of physiological levels of both $Ca^{2+}$ and $Zn^{2+}$. Another receptor for S100A9 that may be important in cancer is EMMPRIN (CD147), this protein is expressed on different cell types and the S100A9-EMMPRIN interaction has been shown to be involved in melanoma metastasis (Hibino et al., 2013).

S100A8 and S100A9 proteins have predominantly been described as cytoplasmic proteins that are secreted from myeloid cells upon activation. It is generally believed that the major biological functions relevant to inflammation require the release of the S100 proteins to the extracellular space. In this model, extracellular S100A9 would bind to e.g. the pro-inflammatory receptors RAGE and TLR4 and result in an inflammatory response. This is supported by studies showing that S100A8/A9 induces TNFα, production in human peripheral blood monocytes via TLR4 (Vogl et al. 2007). Also, S100A9 in complex with S100A8 has shown growth promoting activity directly on tumors cells via RAGE signaling (Ghavami et al., 2008). S100A9 also exists in a membrane-associated form on monocytes (Bhardwaj et al., 1992). Membrane associated S100A9 opens up for the possibility of cell-cell or cell-ECM signaling involving S100A9.

The collected data suggest that S100A9 have important roles in inflammation, cancer growth, cancer metastasis and in their connections. Novel compounds that inhibit the activity of S100A9 in these processes, and thereby disturb the tumor microenvironment, would be attractive in treatment of cancer of different types.

Besides cancer, inflammation and autoimmunity, S100A9 has strong connections to neurodegenerative disease. S100A9 is upregulated in the brain in Alzheimer's disease (AD) patients and in mouse disease models (Shepherd et al., 2006, Ha et al., 2010). Furthermore, knock-down or deletion of S100A9 in mice models of AD inhibits cognition decline and plaque burden in the brain (Ha et al., 2010, Chang et al., 2012). A role for RAGE is also evident in AD where inhibition of RAGE reduces disease in a mouse AD model (Deane et al., 2013). Inhibition of S100A9 and its interactions represents a new promising approach for therapeutic intervention in AD and other neurodegenerative diseases.

SUMMARY OF THE INVENTION

In a first aspect, there is provided a compound of formula (I)

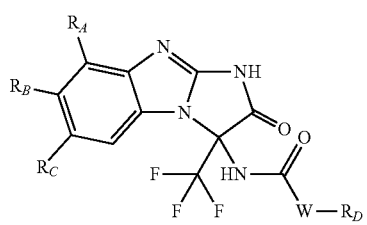

or a pharmaceutically acceptable salt thereof, wherein
$R_A$, $R_B$ and $R_C$ are independently selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$, or
one of $R_A$ and $R_C$ together with $R_B$ forms a biradical —$(CH_2)_m$— wherein m is an integer of from 3 to 5, and the other one of $R_A$ and $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$;
each $R_{16}$ is independently selected from halogen, cyano, nitro, $R_{17}O$, C1-C6 alkyl optionally substituted by $R_{17}O$, C3-C6 cycloalkyl optionally substituted by $R_{17}O$, $R_{18}C(O)$, $R_{19}S$, $R_{20}S(O)_2$, $R_{21}OC(O)$, $(R_{22}ON)C(R_{23})$, $R_{24}R_{25}NC(O)$, $R_{26}R_{27}N$, $R_{28}S(O)_2NR_{29}$, and $R_{30}S(O)_2NR_{31}C(O)$;
each one of $R_1$-$R_{31}$ is independently selected from H, C1-C6 alkyl, and C3-C6 cycloalkyl;
W is a direct bond or $X_1$—$X_2$—$X_3$;
$X_1$ is C1-C2 alkylene, optionally substituted by C1-C4 alkyl or $R_{32}O$;
$X_2$ is O or is absent;
$X_3$ is a direct bond or C1-C2 alkylene, optionally substituted by C1-C4 alkyl or $R_{32}O$;
$R_{32}$ is selected from H and C1-C4 alkyl;
$R_D$ is C1-C6 alkyl, or a cyclic moiety selected from phenyl, 4- to 6-membered heterocyclyl, C4-C6 cycloalkyl, or C5-C6 cycloalkenyl, wherein said cyclic moiety is optionally substituted by one or more $R_{33}$;
each $R_{33}$ is independently selected from halogen, cyano, C1-C6 alkyl optionally substituted by $R_{34}O$, C3-C6 cycloalkyl, phenyl, 5- or 6-membered heterocyclyl, $R_{34}O$, $R_{35}OC(O)$, $R_{36}S(O)_2$, $R_{37}C(O)$, $R_{38}R_{39}N$, $R_{40}R_{41}N(CO)$; and two $R_{33}$, attached to one and the same carbon atom may form, together with the carbon atom to which they are both attached, a 4- to 6-membered ring optionally containing one more heteroatoms in the ring;
$R_{34}$ is independently selected from H, C1-C6 alkyl, and C3-C6 cycloalkyl; wherein said alkyl or cycloalkyl is optionally substituted by $R_{42}O$;
each one of $R_{35}$-$R_{36}$ is independently selected from H, C1-C6 alkyl, and C3-C6 cycloalkyl;

$R_{37}$ is independently selected from C1-C6 alkyl, and C3-C6 cycloalkyl, wherein said alkyl or cycloalkyl is optionally substituted by $R_{43}O$;
$R_{38}$ and $R_{39}$ are independently selected from H, C1-C6 alkyl, and C3-C6 cycloalkyl, wherein said alkyl or cycloalkyl is optionally substituted by $R_{44}R_{45}N$ or $R_{46}O$, or
$R_{38}$ and $R_{39}$ together with the nitrogen atom to which they are both attached, form a 4- to 6-membered heterocyclic ring optionally containing one or more further heteroatoms and optionally substituted by C1-C6 alkyl;
$R_{40}$ and $R_{41}$ are independently selected from H, C1-C6 alkyl, and C3-C6 cycloalkyl, wherein said alkyl or cycloalkyl is optionally substituted by $R_{47}R_{48}N$ or $R_{49}O$, or
$R_{40}$ and $R_{41}$ together with the nitrogen atom to which they are both attached, form a 4- to 6-membered heterocyclic ring optionally containing one or more further heteroatoms and optionally substituted by C1-C6 alkyl;
$R_{44}$ and $R_{45}$ are independently selected from H, C1-C6 alkyl, and C3-C6 cycloalkyl, or $R_{44}$ and $R_{45}$ together with the nitrogen atom to which they are both attached, form a 4- to 6-membered saturated heterocyclic ring optionally containing one or more further heteroatoms and optionally substituted by C1-C6 alkyl;
$R_{47}$ and $R_{48}$ are independently selected from H, C1-C6 alkyl, and C3-C6 cycloalkyl, or $R_{47}$ and $R_{48}$ together with the nitrogen atom to which they are both attached, form a 4- to 6-membered saturated heterocyclic ring optionally containing one or more further heteroatoms and optionally substituted by C1-C6 alkyl;
$R_{42}$, $R_{43}$, $R_{46}$ and $R_{49}$ are independently selected from H, C1-C6 alkyl, and C3-C6 cycloalkyl;
any alkyl is optionally substituted by one or more F.

The compounds of formula (I) as defined herein above are useful as inhibitors of interactions between S100A9 and interaction partners such as RAGE, TLR4 and EMMPRIN. Thus, according to a further aspect, compounds of formula (I) as defined herein above are provided for use as inhibitors of interactions of S100A9 and its interaction partners and for use in the treatment of disorders associated with functions of S100A9, e.g. inflammatory diseases, neurodegenerative diseases, autoimmune diseases and cancer.

According to one aspect, compounds of formula (I) are provided for use in therapy, e.g. for the treatment of inflammatory diseases, neurodegenerative diseases, autoimmune diseases and cancer.

According to a further aspect, a pharmaceutical composition is provided, comprising a compound of formula (I), or a pharmaceutically acceptable salt thereof, and at least one pharmaceutically acceptable excipient. The pharmaceutical composition of the invention is useful for the treatment of diseases selected from inflammatory diseases, autoimmune diseases, neurodegenerative diseases and cancer.

DETAILED DESCRIPTION OF THE INVENTION

Figure 1:
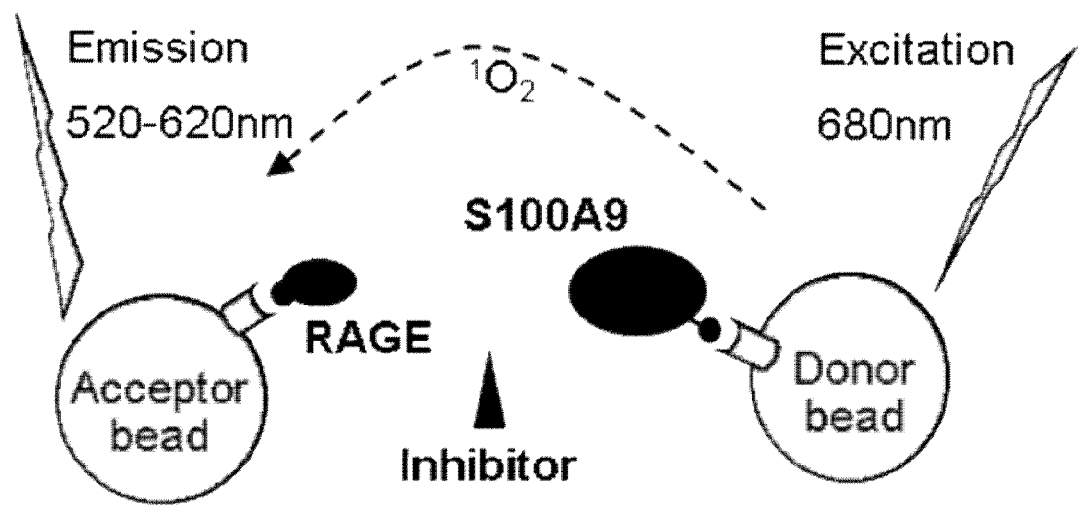
FIG. 1 is a schematic representation of an assay of the inhibition of the interaction between biotinylated human S100A9 and human RAGE-Fc using a small molecule S100A9 binder.

Some definitions of terms used herein are provided herein below. The listing is not exhaustive and it is noted that any term and expression used herein should be given its usual meaning, unless otherwise specified or clearly apparent from the context. Thus, for example, the term alkyl, either alone or as part of a radical, includes straight or branched chain alkyl of the general formula $C_nH_{2n+1}$.

The term alkenyl refers to a biradical of formula $-(C_nH_{2n})-$. For example, a C2 alkenyl is a radical of formula $-CH_2CH_2-$, i.e.:

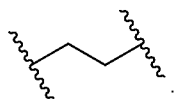

The term C1-C6 alkyl includes any alkyl group having 1, 2, 3, 4, 5 or 6 carbon atoms.

The term C1-C4 alkyl includes methyl, ethyl, n-propyl, isopropyl, n-butyl, isobutyl and tert-butyl.

The term C1-C3 alkyl includes methyl, ethyl, n-propyl and isopropyl.

The term cycloalkyl refers to a cyclic alkyl radical of the general formula $C_nH_{2n-1}$.

The term cycloalkenyl refers to a cyclic alkenylradical of the general formula $C_nH_{2n-3}$.

The term C3-C6 cycloalkyl refers to cyclopropyl, cyclobutyl, cyclopentyl and cyclohexyl.

The term phenyl refers to a $C_6H_5$ radical of the formula

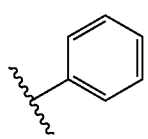

The term heterocyclyl refers to a saturated or unsaturated and aromatic or non-aromatic cyclic moiety containing at least one heteroatom in the ring.

The term heteroaryl refers to an aromatic heterocyclyl, e.g. a pyridyl (also referred to as pyridinyl), tetrazolyl, furyl or pyridiminyl.

The term pyridyl refers to a $C_5NH_5$ radical of formula

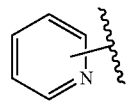

including 2-pyridyl, 3-pyridyl and 4-pyridyl.

The term pyrimidinyl refers to a $C_4N_2H_4$ radical of formula

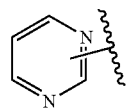

including 2-pyrimidinyl, 4-pyrimidinyl and 5-pyrimidinyl.

The term thiazolyl refers to 1,2-thiazolyl and 1,3-thiazolyl.

The term 1,2-thiazolyl refers to a radical of formula

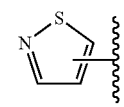

including 1,2-thiazol-3-yl, 1,2-thiazoly-4-yl, and 1,2-thiazoly-5-yl.

The term 1,3-thiazolyl refers to a radical of formula

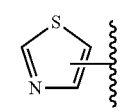

including 1,3-thiazol-2-yl, 1,3-thiazol-4-yl and 1,3-thiazol-5-yl.

The term halogen refers to F, Cl, Br and I, preferably F, Cl and Br.

The term hydroxy refers to a radical of the formula —OH.

The term alkoxy refers to a radical of the formula RO, wherein R is alkyl.

The term RO refers to a radical of formula

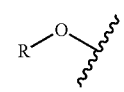

The term cyano refers to a radical of the formula —C≡N (i.e. —CN).

The term RC(O) refers to a moiety of formula

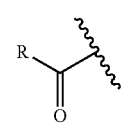

The radical RS is a radical of formula

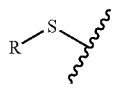

The term RS(O)₂ refers to a radical of formula

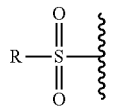

The term ROC(O) refers to a radical of formula

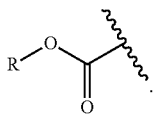

The term (RON)C(R') refers to a radical of formula

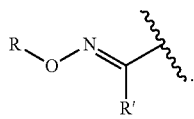

The term RR'N refers to a radical of formula

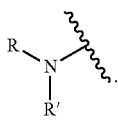

The term RR'NC(O)

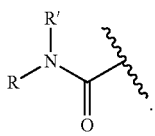

The term RS(O)₂NR' refers to a radical of formula

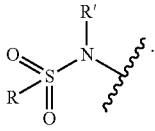

The term RS(O)₂NR'C(O) refers to a radical of formula

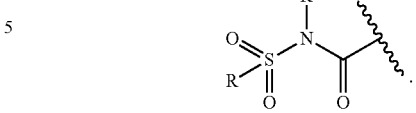

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use. The term pharmaceutically acceptable salt of a compound refers to a salt that is pharmaceutically acceptable, as defined herein, and that possesses the desired pharmacological activity of the parent compound. Pharmaceutically acceptable salts include acid addition salts formed with inorganic acids, e.g. hydrochloric acid, hydrobromic acid, sulfuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include e.g. diethanolamine, ethanolamine, N-methylglucamine, triethanolamine, and tromethamine. Acceptable inorganic bases include e.g. aluminum hydroxide, calcium hydroxide, potassium hydroxide, sodium carbonate and sodium hydroxide.

Whenever a chiral carbon is present in a chemical structure, it is intended that all stereoisomers associated with that chiral carbon are encompassed by the structure, unless otherwise specified. Using the Cahn-Ingold-Prelog RS notational system, any asymmetric carbon atom may be present in the (R)- or (S)-configuration, and the compound may be present as a mixture of its stereoisomers, e.g. a racemic mixture, or one stereoisomer only.

Some of the compounds of the invention may exist in tautomeric forms. Any such tautomer is contemplated to be within the scope of the invention.

Also, in a compound of formula (I) as defined herein, any hydrogen atom may be replaced by a deuterium ($^2$H), and any such deuterated compound of formula (I), comprising one or more deuteriums in place of the corresponding number of hydrogen atoms, is considered to be within the scope of the invention.

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgment of the attending medical or veterinary practitioner, etc.

As used herein the terms "treatment" or "treating" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undetectable. The term can also mean prolonging survival as compared to expected survival without the treatment.

The term mammal refers to a human or any mammalian animal, e.g. a primate, a farm animal, a pet animal, or a laboratory animal. Examples of such animals are monkeys, cows, sheep, horses, pigs, dogs, cats, rabbits, mice, rats etc. Preferably, the mammal is a human.

The term cancer refers to any malignant growth or tumor caused by abnormal and uncontrolled cell division; it may spread to other parts of the body through the lymphatic system or the blood stream and includes both solid tumors and blood-borne tumors. Exemplary cancers include adrenocortical carcinoma, AIDS-related cancers, AIDS-related lymphoma, anal cancer, anorectal cancer, appendix cancer, childhood cerebellar astrocytoma, childhood cerebral astrocytoma, basal cell carcinoma, biliary cancer, extrahepatic bile duct cancer, intrahepatic bile duct cancer, urinary bladder cancer, bone and joint cancer, osteosarcoma and malignant fibrous histiocytoma, brain tumor, brain stem glioma, cerebellar astrocytoma, cerebral astrocytoma/malignant glioma, ependymoma, medulloblastoma, visual pathway and hypothalamic glioma, breast cancer, bronchial adenomas/carcinoids, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary syndrome, endometrial cancer, esophageal cancer, extracranial germ cell tumor, extragonadal germ cell tumor, eye cancer, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypopharyngeal cancer, ocular cancer, Kaposi's sarcoma, renal cancer, laryngeal cancer, acute lymphoblastic leukemia, acute myeloid leukemia, hairy cell leukemia, lip and oral cavity cancer, lung cancer, non-small cell lung cancer, small cell lung cancer, non-Hodgkin's lymphoma, primary central nervous system lymphoma, Waldenstrom's macroglobulinemia, intraocular (eye) melanoma, Merkel cell carcinoma, malignant mesothelioma, metastatic squamous neck cancer, cancer of the tongue, multiple endocrine neoplasia syndrome, myelodysplastic syndromes, myelodysplastic/myeloproliferative diseases, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rhabdomyosarcoma, salivary gland cancer, Ewing's sarcoma family of tumors, soft tissue sarcoma, uterine cancer, uterine sarcoma, skin cancer (non-melanoma), skin cancer (melanoma), small intestine cancer, squamous cell carcinoma, testicular cancer, throat cancer, thymoma, thymoma and thymic carcinoma, thyroid cancer, transitional cell cancer of the renal pelvis and ureter and other urinary organs, gestational trophoblastic tumor, urethral cancer, vaginal cancer, vulvar cancer, and Wilm's tumor.

The term autoimmune disorder (or autoimmune disease) refers to any disorder arising from an inappropriate immune response of the body against substances and tissues normally present in the body (autoimmunity). Such response may be restricted to certain organs or involve a particular tissue in different places. Exemplary autoimmune disorders are acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, glomerulonephritis, Goodpasture's syndrome, Graves' disease, Guillain-Barre syndrome (GBS), Hashimoto's encephalopathy, Hashimoto's thyroiditis, Henoch-Schonlein purpura, herpes gestationis (aka gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, Majeed syndrome, Meniere's disease, microscopic polyangiitis, mixed connective tissue disease, morphea, Mucha-Habermann disease (aka pityriasis lichenoides et varioliformis acuta), multiple sclerosis, myasthenia gravis, myositis, narcolepsy, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome another form of APS, Schnitzler syndrome, Scleritis, Scleroderma, Serum Sickness, Sjögren's syndrome, spondyloarthropathy, stiff person syndrome, subacute bacterial endocarditis (SBE), Susac's syndrome, Sweet's syndrome, sympathetic ophthalmia, systemic lupus erythematosis, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis.

The term inflammatory disorder (or inflammatory disease) refers to a pathological state associated with inflammation, typically caused by leukocyte infiltration. The inflammatory disorder may be acute or chronic. Exemplary inflammatory disorders include inflammatory skin diseases, including, without limitation, psoriasis and atopic dermatitis, systemic scleroderma and sclerosis, responses associated with inflammatory bowel disease (IBD) (such as Crohn's disease and ulcerative colitis), ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms, cerebral edema secondary to stroke, cranial trauma, hypovolemic shock, asphyxia, adult respiratory distress syndrome, acute-lung injury, Behçet's Disease, dermatomyositis; polymyositis; multiple sclerosis (MS); dermatitis; meningitis; encephalitis; uveitis, osteoarthritis, lupus nephritis, autoimmune diseases such as rheumatoid arthritis (RA), Sjorgen's syndrome, vasculitis, diseases involving leukocyte diapedesis, central nervous system (CNS) inflammatory disorder, multiple organ injury syndrome secondary to septicemia or trauma, alcoholic hepatitis, bacterial pneumonia, antigen-antibody complex mediated diseases including glomerulonephritis, sepsis, sarcoidosis, immunopathologic responses to tissue or organ transplantation, inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis, etc.

The term neurogenerative disorder (or neurogenerative disease) refers to disorders associated with a progressive loss of structure or function of neurons affecting the structure or function of the brain, spinal cord or peripheral nervous system. Exemplary neurodegenerative disorders include mitochondrial encephalomyopathies and gut dysmotility syndromes, ataxia syndromes including Friedreich's ataxia and spinocerebellar ataxia (SCA), spinal cord injury, familial and sporadic amyotrophic lateral sclerosis (FALS and ALS, respectively), familial and sporadic Parkinson's disease, familial and sporadic Alzheimer's disease, Huntington's disease, olivopontocerebellar atrophy, multiple system atrophy, progressive supranuclear palsy, diffuse lewy body disease and synucleinopathies, Down Syndrome, corticodentatonigral degeneration, progressive familial myoclonic epilepsy, strionigral degeneration, torsion dystonia, familial tremor, Gilles de la Tourette syndrome, and Hallervorden-Spatz disease.

The term excipient refers to pharmaceutically acceptable chemicals, such as known to those of ordinary skill in the art of pharmacy to aid the administration of the medicinal agent. It a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

According to a first aspect there is provided a compound of formula (I)

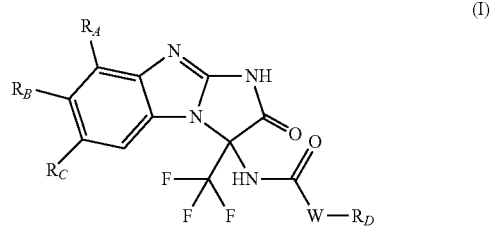

as defined herein above, or a pharmaceutically acceptable salt thereof.

In a compound of formula (I), the moieties $R_A$, $R_B$ and $R_C$ are independently selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$; or one of $R_A$ and $R_C$ together with $R_B$ forms a biradical —$(CH_2)_m$— wherein m is an integer of from 3 to 5, and the other one of $R_A$ and $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$.

In some embodiments, $R_A$, $R_B$ and $R_C$ are independently selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$.

In some other embodiments, one of $R_A$ and $R_C$ together with $R_B$ forms a biradical —$(CH_2)_m$— wherein m is an integer of from 3 to 5, and the other one of $R_A$ and $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$.

Thus, the moiety $R_A$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$; or forms together with $R_B$ a biradical —$(CH_2)_m$— wherein m is an integer of from 3 to 5.

In some embodiments, $R_A$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$.

In some embodiments, $R_A$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, and $R_{14}S(O)_2NR_{15}C(O)$.

In some embodiments, $R_A$ is selected from H, halogen, cyano, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $R_{12}S(O)_2NR_{13}$, and $R_{14}S(O)_2NR_{15}C(O)$.

In some embodiments, $R_A$ is selected from H, halogen, C1-C6 alkyl and $R_2C(O)$, e.g. H, halogen, and C1-C6 alkyl, or H and halogen.

In some embodiments, $R_A$ is H.

In some other embodiments, $R_A$ is selected from halogen, C1-C6 alkyl and $R_2C(O)$, e.g. C1-C6 alkyl and $R_2C(O)$, e.g. $R_A$ is $R_2C(O)$, or $R_A$ is C1-C6 alkyl.

In some embodiments, $R_A$ is selected from H, halogen, cyano, C1-C6 alkyl, C3-C6 cycloalkyl, $R_2C(O)$, $R_4S(O)_2$, $R_5OC(O)$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$; e.g. from H, halogen, phenyl optionally substituted by one or more moieties $R_{16}$, and 5- or 6-membered heterocyclyl optionally substituted by one or more moieties $R_{16}$, e.g. from H, phenyl optionally substituted by one or more moieties $R_{16}$, and 5- or 6-membered heterocyclyl optionally substituted by one or more moieties $R_{16}$, or from phenyl optionally substituted by one or more moieties $R_{16}$, and 5- or 6-membered heterocyclyl optionally substituted by one or more moieties $R_{16}$.

In some embodiments, when $R_A$ is phenyl optionally substituted by one or more moieties $R_{16}$, or 5- or 6-membered heterocyclyl optionally substituted by one or more moieties $R_{16}$, it more particularly is phenyl optionally substituted by one or more moieties $R_{16}$. In some embodiments, when $R_A$ is phenyl optionally substituted by one or more moieties $R_{16}$, or 5- or 6-membered heterocyclyl optionally substituted by one or more moieties $R_{16}$, it more particularly is 5- or 6-membered heterocyclyl optionally substituted by one or more moieties $R_{16}$.

The moiety $R_B$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$; or forms together with either $R_A$ or $R_C$ a biradical —$(CH_2)_m$— wherein m is an integer of from 3 to 5.

In some embodiments, $R_B$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$.

In some embodiments, $R_B$ is selected from H, halogen, $R_1O$, C1-C6 alkyl optionally substituted by $R_1O$, C3-C6 cycloalkyl optionally substituted by $R_1O$, phenyl optionally substituted by one or more moieties $R_{16}$, and 5- or 6-membered heterocyclyl optionally substituted by one or more moieties $R_{16}$.

In some embodiments, $R_B$ is phenyl optionally substituted by one or more moieties $R_{16}$, or 5- or 6-membered heterocyclyl optionally substituted by one or more moieties $R_{16}$.

In some embodiments, $R_B$ is selected from H, halogen, $R_1O$, C1-C6 alkyl optionally substituted by $R_1O$, and C3-C6 cycloalkyl optionally substituted by $R_1O$, e.g. from H, halogen, and C1-C6 alkyl optionally substituted by $R_1O$.

In some embodiments, $R_B$ is selected from H, halogen, C1-C6 alkyl optionally substituted by $R_1O$, and C3-C6 cycloalkyl optionally substituted by $R_1O$, e.g. from H and halogen.

In some embodiments, $R_B$ is selected from H, halogen, C1-C6 alkyl and C3-C6 cycloalkyl, e.g. from H, halogen, and C1-C6 alkyl, e.g. from H and C1-C6 alkyl.

In some embodiments, $R_B$ is selected from halogen, C1-C6 alkyl optionally substituted by $R_1O$, and C3-C6 cycloalkyl optionally substituted by $R_1O$, e.g. from halogen, and C1-C6 alkyl optionally substituted by $R_1O$; or from halogen, and C1-C6 alkyl, e.g. $R_B$ is halogen.

In some embodiments, $R_B$ is H.

The moiety $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$, or forms together with $R_B$ a biradical —$(CH_2)_m$— wherein m is an integer of from 3 to 5.

In some embodiments, $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$.

In some embodiments, $R_C$ is selected from H, halogen, $R_1O$, C1-C6 alkyl optionally substituted by $R_1O$, C3-C6 cycloalkyl optionally substituted by $R_1O$, $R_2C(O)$, phenyl optionally substituted by one or more moieties $R_{16}$, and 5- or 6-membered heterocyclyl optionally substituted by one or more moieties $R_{16}$.

In some embodiments, $R_C$ is phenyl optionally substituted by one or more moieties $R_{16}$, or 5- or 6-membered heterocyclyl optionally substituted by one or more moieties $R_{16}$.

In some embodiments, $R_C$ is selected from H, halogen, $R_1O$, C1-C6 alkyl optionally substituted by $R_1O$, C3-C6 cycloalkyl optionally substituted by $R_1O$, and $R_2C(O)$.

In some embodiments, $R_C$ is selected from H, halogen, $R_1O$, C1-C6 alkyl optionally substituted by $R_1O$, and C3-C6 cycloalkyl optionally substituted by $R_1O$, e.g. from H, halogen, C1-C6 alkyl optionally substituted by $R_1O$, and C3-C6 cycloalkyl optionally substituted by $R_1O$, or from H, halogen, C1-C6 alkyl, and C3-C6 cycloalkyl, in particular from H, halogen and C1-C6 alkyl, or from H and C1-C6 alkyl.

In some embodiments, $R_C$ is H.

In some embodiments, one of $R_A$ and $R_C$ forms together with $R_B$ a biradical —$(CH_2)_m$— wherein m is an integer of from 3 to 5, e.g. m is 3 or 4, or m is 3. In such embodiments, the other one of $R_A$ and $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$. In these embodiments, the other one of $R_A$ and $R_C$ preferably is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, and $R_{14}S(O)_2NR_{15}C(O)$; e.g. from H, halogen, cyano, $R_1O$, C1-C6 alkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, and $R_{14}S(O)_2NR_{15}C(O)$; e.g. from H, halogen and C1-C3 alkyl; such as H, F and methyl; or H and F, in particular H.

In some embodiments, at least one of $R_A$, $R_B$ and $R_C$ is phenyl optionally substituted by one or more moieties $R_{16}$, or 5- or 6-membered heterocyclyl optionally substituted by one or more moieties $R_{16}$.

In some embodiments, one of $R_A$, $R_B$ and $R_C$ is phenyl optionally substituted by one or more moieties $R_{16}$, or 5- or 6-membered heterocyclyl optionally substituted by one or more moieties $R_{16}$.

In some embodiments, when one of $R_A$, $R_B$ and $R_C$ is phenyl optionally substituted by one or more moieties $R_{16}$, or 5- or 6-membered heterocyclyl optionally substituted by one or more moieties $R_{16}$, the two others of $R_A$, $R_B$ and $R_C$ are as defined herein above, but are not phenyl optionally substituted by one or more moieties $R_{16}$, or 5- or 6-membered heterocyclyl optionally substituted by one or more moieties $R_{16}$.

For example, in some embodiments, when one of $R_A$, $R_B$ and $R_C$ is phenyl optionally substituted by one or more moieties $R_{16}$, or 5- or 6-membered heterocyclyl optionally substituted by one or more moieties $R_{16}$, the two others of $R_A$, $R_B$ and $R_C$ are selected from H, halogen, C1-C6 alkyl, C3-C6 cycloalkyl and $R_2C(O)$, or from H, halogen C1-C6 alkyl and $R_2C(O)$, e.g. from H, F, Cl, and C1-C3 alkyl; or from H, F and methyl; e.g. both are H or F, or both are H.

In some embodiments, $R_A$, $R_B$ and $R_C$ are independently selected from H, halogen, cyano, C1-C4 alkyl, $R_1O$, $R_2C(O)$, $R_3S$, and $R_4S(O)_2$; or one of $R_A$ and $R_C$, together with $R_B$, forms a biradical —$(CH_2)_m$— wherein m is an integer of from 3 to 5, and the other one of $R_A$ and $R_C$ is selected from H, halogen, cyano, C1-C4 alkyl, $R_1O$, $R_2C(O)$, $R_3S$, and $R_4S(O)_2$.

When anyone of $R_A$, $R_B$ and $R_C$ is selected from halogen, it more particularly may be selected from F, Cl or Br, or from F and Cl, in particular Cl.

When anyone of $R_A$, $R_B$ and $R_C$ is selected from C1-C6 alkyl optionally substituted by $R_1O$ and C3-C6 cycloalkyl optionally substituted by $R_1O$, it more particularly may be selected from C1-C6 alkyl optionally substituted by $R_1O$, e.g. from C1-C4 alkyl optionally substituted by $R_1O$, or C1-C3 alkyl optionally substituted by $R_1O$, in particular methyl optionally substituted by $R_1O$.

In some embodiments, when anyone of $R_A$, $R_B$ and $R_C$ is selected from C1-C6 alkyl optionally substituted by $R_1O$ and C3-C6 cycloalkyl optionally substituted by $R_1O$, it more particularly is selected from C1-C6 alkyl, or from C1-C4 alkyl, or C1-C3 alkyl, in particular methyl.

In some embodiments, when anyone of $R_A$, $R_B$ and $R_C$ is selected from C3-C6 cycloalkyl optionally substituted by $R_1O$, it more particularly is selected from C3-C6 cycloalkyl, or from C3-C5 cycloalkyl, or from C3-C4 cycloalkyl, e.g. cyclopropyl.

In some embodiments, $R_A$, $R_B$ and $R_C$ are all H, i.e. the compound of formula (I) is a compound of formula (Ia)

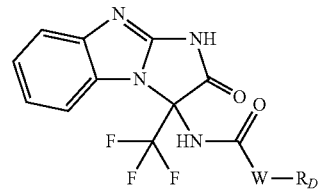

(Ia)

wherein W and $R_D$ are as defined herein.

In some other embodiments, at least one of $R_A$, $R_B$ and $R_C$ is different from H.

In some embodiments, $R_A$ is as defined herein above, but is different from H; or $R_B$ is as defined herein above, but is different from H.

In some embodiments, two of $R_A$, $R_B$ and $R_C$ are different from H, i.e. $R_A$ and $R_B$ are different from H, or $R_A$ and $R_C$ are different from H, or $R_B$ and $R_C$ are different from H.

In some embodiments, $R_A$ is H and the compound may then be represented by formula (Ib)

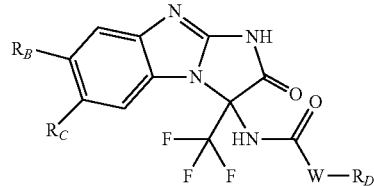

(Ib)

wherein $R_B$, $R_C$, W and $R_D$ are as defined herein, e.g. $R_B$ and $R_C$ are as defined herein above, but neither $R_B$ nor $R_C$ is H.

In some other embodiments, $R_A$ is different from H. In some embodiments, $R_A$ and $R_B$ are different from H and $R_C$ is H. In some other embodiments, $R_A$ and $R_C$ are different from H and $R_B$ is H.

In some embodiments, $R_A$ is different from H and $R_B$ and $R_C$ are both H, i.e. the compound may be represented by formula (Ic)

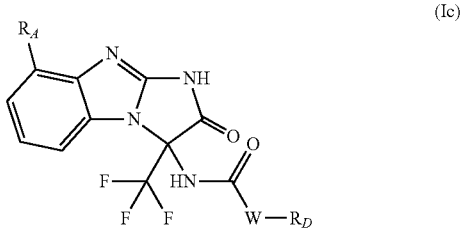

(Ic)

wherein $R_A$, W and $R_D$ are as defined herein.

When anyone of $R_A$, $R_B$, and $R_C$ is $R_1O$, C1-C6 alkyl optionally substituted by $R_1O$, or C3-C6 cycloalkyl optionally substituted by $R_1O$, the moiety $R_1$ is selected from H, C1-C6 alkyl, and C3-C6 cycloalkyl, e.g. from H, C1-C4 alkyl, and C3-C4 cycloalkyl, or from H, C1-C3 alkyl and cyclopropyl. In some embodiments, the moiety $R_1$ is selected from H and C1-C6 alkyl, e.g. from H and C1-C4 alkyl, or from H and C1-C3 alkyl, such as from H and $CH_3$, in particular H. In some embodiments, the moiety $R_1$ is as defined herein above, but is not H; e.g. $R_1$ is $CH_3$.

In some embodiments, when anyone of $R_A$, $R_B$, and $R_C$ is selected from $R_1O$, C1-C6 alkyl optionally substituted by $R_1O$ and C3-C6 cycloalkyl optionally substituted by $R_1O$, it more particularly may be selected from $R_1O$ and C1-C6 alkyl optionally substituted by $R_1O$, e.g. from $R_1O$ and C1-C3 alkyl optionally substituted by $R_1O$, or from $R_1O$ and C1-C2 alkyl optionally substituted by $R_1O$, e.g. it may be selected from $R_1O$, $R_1OCH_2$, and $R_1OCH(CH_3)$, in particular $R_1O$.

When anyone of $R_A$, $R_B$, and $R_C$ is $R_2C(O)$, $R_2$ is H, C1-C6 alkyl, or C3-C6 cycloalkyl. In some embodiments, $R_2$ is selected from H, C1-C4 alkyl, and C3-C4 cycloalkyl, or from H, C1-C3 alkyl and cyclopropyl. In some embodiments, $R_2$ is selected from H and C1-C6 alkyl, e.g. from H and C1-C4 alkyl, or from H and C1-C3 alkyl, such as from H, $CH_3$ and $(CH_3)_2CH$, in particular $CH_3$. In some embodiments, the moiety $R_2$ is as defined herein above, but is not H.

When anyone of $R_A$, $R_B$, and $R_C$ is $R_3S$, $R_3$ is H, C1-C6 alkyl, or C3-C6 cycloalkyl. In some embodiments, $R_3$ is selected from H, C1-C4 alkyl, and C3-C4 cycloalkyl, or from H, C1-C3 alkyl and cyclopropyl. In some embodiments, $R_3$ is selected from H and C1-C6 alkyl, e.g. from H and C1-C4 alkyl, or from H and C1-C3 alkyl, such as from H and $CH_3$, in particular $CH_3$. In some embodiments, the moiety $R_3$ is as defined herein above, but is not H.

When anyone of $R_A$, $R_B$, and $R_C$ is $R_4SO_2$, $R_4$ is H, C1-C6 alkyl, or C3-C6 cycloalkyl. In some embodiments, $R_4$ is selected from H, C1-C4 alkyl, and C3-C4 cycloalkyl, or from H, C1-C3 alkyl and cyclopropyl. In some embodiments, $R_4$ is selected from H and C1-C6 alkyl, e.g. from H and C1-C4 alkyl, or from H and C1-C3 alkyl, such as from H and $CH_3$, in particular $CH_3$. In some embodiments, the moiety $R_4$ is as defined herein above, but is not H.

When anyone of $R_A$, $R_B$, and $R_C$ is $R_5OC(O)$, $R_5$ is H, C1-C6 alkyl, or C3-C6 cycloalkyl. In some embodiments, $R_5$ is selected from H, C1-C4 alkyl, and C3-C4 cycloalkyl, or from H, C1-C3 alkyl and cyclopropyl. In some embodiments, $R_5$ is selected from H and C1-C6 alkyl, e.g. from H and C1-C4 alkyl, or from H and C1-C3 alkyl, such as from H and $CH_3$, in particular H.

When anyone of $R_A$, $R_B$, and $R_C$ is $(R_6ON)C(R_7)$, $R_6$ is H, C1-C6 alkyl, or C3-C6 cycloalkyl. In some embodiments, $R_6$ is selected from H, C1-C4 alkyl, and C3-C4 cycloalkyl, or from H, C1-C3 alkyl and cyclopropyl. In some embodiments, $R_6$ is selected from H and C1-C6 alkyl, e.g. from H and C1-C4 alkyl, or from H and C1-C3 alkyl, such as from H and $CH_3$, in particular H. $R_7$ is H, C1-C6 alkyl, and C3-C6 cycloalkyl. In some embodiments, $R_7$ is selected from H, C1-C4 alkyl, and C3-C4 cycloalkyl, or from H, C1-C3 alkyl and cyclopropyl. In some embodiments, $R_7$ is selected from H and C1-C6 alkyl, e.g. from H and C1-C4 alkyl, or from H and C1-C3 alkyl, such as from H and $CH_3$, in particular $CH_3$. In some embodiments, the moiety $R_7$ is as defined herein above, but is not H. In some embodiments, $R_6$ is H and $R_7$ is as defined herein above, but different from H, e.g. $R_7$ is $CH_3$.

When anyone of $R_A$, $R_B$, and $R_C$ is $R_8R_9NC(O)$ or $R_{10}R_{11}N$, each one of $R_8$, $R_9$, $R_{10}$ and $R_{11}$ is independently selected from H, C1-C6 alkyl, and C3-C6 cycloalkyl, e.g. from H, C1-C4 alkyl, and C3-C4 cycloalkyl, or from H, C1-C3 alkyl and cyclopropyl. In some embodiments, when anyone of $R_A$, $R_B$, and $R_C$ is $R_8R_9NC(O)$ or $R_{10}R_{11}N$, each one of $R_8$, $R_9$, $R_{10}$ and $R_{11}$ is independently selected from H and C1-C6 alkyl, e.g. from H and C1-C4 alkyl, or from H and C1-C3 alkyl, such as from H and $CH_3$.

When anyone of $R_A$, $R_B$, and $R_C$ is $R_{12}S(O)_2NR_{13}$, or $R_{14}S(O)_2NR_{15}C(O)$, each one of $R_{12}$, $R_{13}$, $R_{14}$ and $R_{15}$ is independently selected from H, C1-C6 alkyl, and C3-C6 cycloalkyl, e.g. from H, C1-C4 alkyl, and C3-C4 cycloalkyl, or from H, C1-C3 alkyl and cyclopropyl. In some embodiments, when anyone of $R_A$, $R_B$, and $R_C$ is $R_{12}S(O)_2NR_{13}$, or $R_{14}S(O)_2NR_{15}C(O)$, each one of $R_{12}$, $R_{13}$, $R_{14}$ and $R_{15}$ is independently selected from H and C1-C6 alkyl, e.g. from H and C1-C4 alkyl, or from H and C1-C3 alkyl, such as from H and $CH_3$. In some embodiments, $R_{12}$ is as defined herein above, but is not H, and $R_{13}$ is H. In some embodiments, $R_{14}$ is as defined herein above, but is not H, and $R_{15}$ is H. In some embodiments, $R_{12}$ and $R_{14}$ are as defined herein above, but are not H, and $R_{13}$ and $R_{15}$ are both H.

In some embodiments, when anyone of $R_A$, $R_B$ and $R_C$ is phenyl optionally substituted by one or more moieties $R_{16}$, or 5- or 6-membered heterocyclyl optionally substituted by one or more moieties $R_{16}$, said phenyl or heterocyclyl is substituted by 0, 1, 2 or 3 moieties $R_{16}$, e.g. 0, 1 or 2 moieties $R_{16}$, or 0 or 1 moiety $R_{16}$, e.g. 1 moiety $R_{16}$.

In some embodiments, when anyone of $R_A$, $R_B$ and $R_C$ is phenyl optionally substituted by one or more moieties $R_{16}$, or 5- or 6-membered heterocyclyl optionally substituted by one or more moieties $R_{16}$, it more particularly is phenyl substituted by 0, 1, 2 or 3 moieties $R_{16}$, or 0, 1 or 2 moieties $R_{16}$.

In some embodiments, when anyone of $R_A$, $R_B$ and $R_C$ is phenyl optionally substituted by one or more moieties $R_{16}$, or 5- or 6-membered heterocyclyl optionally substituted by one or more moieties $R_{16}$, it more particularly is 5- or 6-membered heterocyclyl substituted by 0, 1, 2 or 3 moieties $R_{16}$, or e.g. 0, 1 or 2 moieties $R_{16}$.

In some embodiments, when anyone of $R_A$, $R_B$ and $R_C$ is phenyl substituted by one moiety $R_{16}$, said moiety is in para position on said phenyl ring.

In some embodiments, $R_A$ is phenyl optionally substituted by one or more moieties $R_{16}$, or 5- or 6-membered heterocyclyl optionally substituted by one or more moieties $R_{16}$. In some of these embodiments, the compound of formula (I) may be represented by formula (Id)

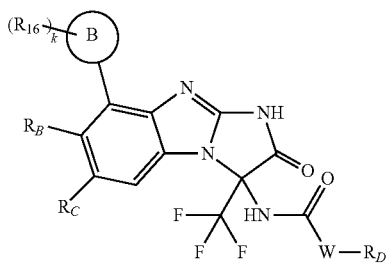

(Id)

wherein ring B is phenyl or 5- or 6-membered heterocyclyl, k is an integer of from 0 to 3, and $R_{16}$, $R_B$, $R_C$, W and $R_D$ are as defined herein.

In some embodiments, ring B is phenyl, and the compound of formula (Ic) may be represented by formula (Ie)

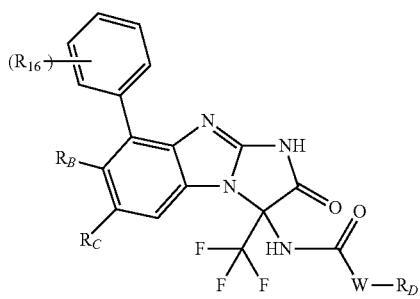

(Ie)

wherein k, $R_{16}$, $R_B$, $R_C$, W and $R_D$ are as defined herein.

In some embodiments of a compound of formula (Ie), k is 1 and $R_{16}$ is in para-position, i.e. the compound may be represented by formula (If)

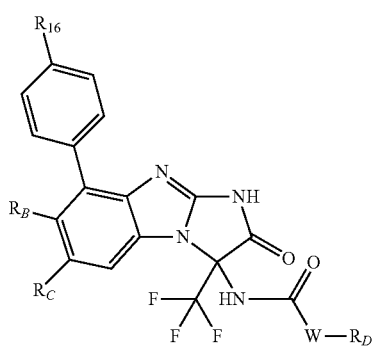

(If)

wherein $R_{16}$, $R_B$, $R_C$, W and $R_D$ are as defined herein.

In some embodiments of a compound of formula (Ic), (Id), (Ie) and (If), $R_B$ and $R_C$ are both H.

In some embodiments, when anyone of $R_A$, $R_B$ and $R_C$ is 5- or 6-membered heterocyclyl optionally substituted by one or more moieties $R_{16}$, said heterocyclyl is 5-membered. In some embodiments, when anyone of $R_A$, $R_B$ and $R_C$ is 5- or 6-membered heterocyclyl optionally substituted by one or more moieties $R_{16}$, said heterocyclyl is 6-membered. Any 5- or 6-membered heterocyclyl comprises 1 or more heteroatoms in the ring, e.g. 1, 2, 3 or 4 heteroatoms. In some embodiments, the heterocyclyl is aromatic. In some other embodiments, the heterocyclyl is non-aromatic, and saturated or unsaturated, e.g. the heterocyclyl is non-aromatic and mono-unsaturated. For example, the heterocyclyl may be selected from

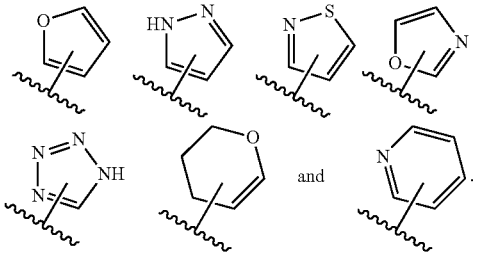

When anyone of $R_A$, $R_B$ and $R_C$ is phenyl optionally substituted by one or more moieties $R_{16}$, or 5- or 6-membered heterocyclyl optionally substituted by one or more moieties $R_{16}$, each moiety $R_{16}$ is independently selected from halogen, cyano, nitro, $R_{17}O$, C1-C6 alkyl optionally substituted by $R_{17}O$, C3-C6 cycloalkyl optionally substituted by $R_{17}O$, $R_{18}C(O)$, $R_{19}S$, $R_{20}S(O)_2$, $R_{21}OC(O)$, $(R_{22}ON)C(R_{23})$, $R_{24}R_{25}NC(O)$, $R_{26}R_{27}N$, $R_{28}S(O)_2NR_{29}$, and $R_{30}S(O)_2NR_{31}C(O)$.

In some embodiments, each $R_{16}$ is independently selected from halogen, cyano, nitro, $R_{17}O$, C1-C6 alkyl optionally substituted by $R_{17}O$, C3-C6 cycloalkyl optionally substituted by $R_{17}O$, $R_{19}S$, $R_{20}S(O)_2$, $R_{21}OC(O)$, and $R_{26}R_{27}N$.

In some embodiments, each $R_{16}$ is independently selected from halogen, cyano, nitro, $R_{17}O$, C1-C6 alkyl optionally substituted by $R_{17}O$, $R_{19}S$, $R_{20}S(O)_2$, $R_{21}OC(O)$, and $R_{26}R_{27}N$.

In some embodiments, each $R_{16}$ is independently selected from halogen, cyano, nitro, $R_{17}O$, C1-C6 alkyl optionally substituted by $R_{17}O$, $R_{19}S$, $R_{20}S(O)_2$, $R_{21}OC(O)$, and $R_{26}R_{27}N$.

In some embodiments, each $R_{16}$ is independently selected from $R_{17}O$, C1-C6 alkyl optionally substituted by $R_{17}O$, and C3-C6 cycloalkyl optionally substituted by $R_{17}O$, e.g. from $R_{17}O$, C1-C6 alkyl optionally substituted by $R_{17}O$, in particular from $R_{17}O$.

When $R_{16}$ is C1-C6 alkyl optionally substituted by $R_{17}O$, it e.g. may be C1-C4 alkyl optionally substituted by $R_{17}O$, e.g. C1-C3 alkyl optionally substituted by $R_{17}O$.

In some embodiments, each $R_{16}$ is independently selected from F, Cl, cyano, nitro, $CH_3$, $CF_3$, $(CH_3)_3C$, $CH_3O$, $CH_3S$, $CH_3S(O)_2$, COOH, $NH_2$, and $(CH_3)_2N$.

When any $R_{16}$ is $R_{17}O$, C1-C6 alkyl optionally substituted by $R_{17}O$, or C3-C6 cycloalkyl optionally substituted by $R_{17}O$, the moiety $R_{17}$ is H, C1-C6 alkyl, or C3-C6 cycloalkyl. In some embodiments, $R_{17}$ is selected from H, C1-C4 alkyl, and C3-C4 cycloalkyl, or from H, C1-C3 alkyl and cyclopropyl. In some embodiments, $R_{17}$ is selected from H and C1-C6 alkyl, e.g. from H and C1-C4 alkyl, or from H and C1-C3 alkyl, such as from H and $CH_3$, in particular H.

In some other embodiments, the moiety $R_{17}$ is as defined herein above, but is not H; e.g. $R_{17}$ is $CH_3$.

When any $R_{16}$ is $R_{18}C(O)$, the moiety $R_{18}$ is H, C1-C6 alkyl, or C3-C6 cycloalkyl. In some embodiments, $R_{18}$ is selected from H, C1-C4 alkyl, and C3-C4 cycloalkyl, or from H, C1-C3 alkyl and cyclopropyl. In some embodiments, $R_{18}$ is selected from H and C1-C6 alkyl, e.g. from H and C1-C4 alkyl, or from H and C1-C3 alkyl, such as from H and $CH_3$, in particular H. In some other embodiments, the moiety $R_{18}$ is as defined herein above, but is not H; e.g. $R_{18}$ is $CH_3$.

When any $R_{16}$ is $R_{19}S$, the moiety $R_{19}$ is H, C1-C6 alkyl, or C3-C6 cycloalkyl. In some embodiments, $R_{19}$ is selected from H, C1-C4 alkyl, and C3-C4 cycloalkyl, or from H, C1-C3 alkyl and cyclopropyl. In some embodiments, $R_{19}$ is selected from H and C1-C6 alkyl, e.g. from H and C1-C4 alkyl, or from H and C1-C3 alkyl, such as from H and $CH_3$, in particular H. In some other embodiments, the moiety $R_{19}$ is as defined herein above, but is not H; e.g. $R_{19}$ is $CH_3$.

When any $R_{16}$ is $R_{20}S(O)_2$, the moiety $R_{20}$ is H, C1-C6 alkyl, or C3-C6 cycloalkyl. In some embodiments, $R_{20}$ is selected from H, C1-C4 alkyl, and C3-C4 cycloalkyl, or from H, C1-C3 alkyl and cyclopropyl. In some embodiments, $R_{20}$ is selected from H and C1-C6 alkyl, e.g. from H and C1-C4 alkyl, or from H and C1-C3 alkyl, such as from H and $CH_3$, in particular H. In some other embodiments, the moiety $R_{20}$ is as defined herein above, but is not H; e.g. $R_{20}$ is $CH_3$.

When any $R_{16}$ is $R_{21}OC(O)$, the moiety $R_{21}$ is H, C1-C6 alkyl, or C3-C6 cycloalkyl. In some embodiments, $R_{21}$ is selected from H, C1-C4 alkyl, and C3-C4 cycloalkyl, or from H, C1-C3 alkyl and cyclopropyl. In some embodiments, $R_{21}$ is selected from H and C1-C6 alkyl, e.g. from H and C1-C4 alkyl, or from H and C1-C3 alkyl, such as from H and $CH_3$, in particular H. In some other embodiments, the moiety $R_{21}$ is as defined herein above, but is not H; e.g. $R_{21}$ is $CH_3$.

When any $R_{16}$ is $(R_{22}ON)C(R_{23})$, $R_{22}$ is H, C1-C6 alkyl, or C3-C6 cycloalkyl. In some embodiments, $R_{22}$ is selected from H, C1-C4 alkyl, and C3-C4 cycloalkyl, or from H, C1-C3 alkyl and cyclopropyl. In some embodiments, $R_{22}$ is selected from H and C1-C6 alkyl, e.g. from H and C1-C4 alkyl, or from H and C1-C3 alkyl, such as from H and $CH_3$, in particular H. $R_{23}$ is H, C1-C6 alkyl, or C3-C6 cycloalkyl. In some embodiments, $R_{23}$ is selected from H, C1-C4 alkyl, and C3-C4 cycloalkyl, or from H, C1-C3 alkyl and cyclopropyl. In some embodiments, $R_{23}$ is selected from H and C1-C6 alkyl, e.g. from H and C1-C4 alkyl, or from H and C1-C3 alkyl, such as from H and $CH_3$, in particular $CH_3$. In some embodiments, the moiety $R_{23}$ is as defined herein above, but is not H. In some embodiments, $R_{22}$ is H and $R_{23}$ is as defined herein above, but different from H, e.g. $R_{23}$ is $CH_3$.

When any $R_{16}$ is $R_{24}R_{25}NC(O)$ or $R_{26}R_{27}N$, each one of $R_{24}$, $R_{25}$, $R_{26}$ and $R_{27}$ is independently selected from H, C1-C6 alkyl, and C3-C6 cycloalkyl, e.g. from H, C1-C4 alkyl, and C3-C4 cycloalkyl, or from H, C1-C3 alkyl and cyclopropyl. In some embodiments, when any $R_{16}$ is $R_{24}R_{25}NC(O)$ or $R_{26}R_{27}N$, each one of $R_{24}$, $R_{25}$, $R_{26}$ and $R_{27}$ is independently selected from H and C1-C6 alkyl, e.g. from H and C1-C4 alkyl, or from H and C1-C3 alkyl, such as from H and $CH_3$.

When any $R_{16}$ is $R_{28}S(O)_2NR_{29}$ or $R_{30}S(O)_2NR_{31}C(O)$, each one of $R_{28}$, $R_{29}$, $R_{30}$ and $R_{31}$ is independently selected from H, C1-C6 alkyl, and C3-C6 cycloalkyl, e.g. from H, C1-C4 alkyl, and C3-C4 cycloalkyl, or from H, C1-C3 alkyl and cyclopropyl. In some embodiments, when any $R_{16}$ is $R_{28}S(O)_2NR_{29}$, or $R_{30}S(O)_2NR_{31}C(O)$, each one of $R_{28}$, $R_{29}$, $R_{30}$ and $R_{31}$ is independently selected from H and C1-C6 alkyl, e.g. from H and C1-C4 alkyl, or from H and C1-C3 alkyl, such as from H and $CH_3$. In some embodiments, $R_{28}$ and $R_{30}$ are as defined herein above, but are not H, and $R_{29}$ and $R_{31}$ are both H.

When one of $R_A$ and $R_C$, together with $R_B$, forms a biradical $—(CH_2)_m—$ wherein m is an integer of from 3 to 5, m e.g. is 3 or 4, in particular 3, e.g. $R_B$ and $R_C$ form together a biradical $—(CH_2)_3—$.

For example, in some embodiments of a compound of formula (I), one of $R_A$, $R_B$ and $R_C$ is H and the other two are independently selected from halogen, cyano, C1-C4 alkyl, $R_1O$, $R_2C(O)$, $R_3S$, and $R_4S(O)_2$; or, if adjacent, in some embodiments the two other form a biradical $—(CH_2)_m—$ wherein m is an integer of from 3 to 5.

In some embodiments, one of $R_A$, $R_B$ and $R_C$ is H, and the other two are selected from halogen, cyano, C1-C4 alkyl, and $R_1O$, e.g. from halogen, C1-C3 alkyl, and C1-C3 alkoxy, e.g. from F, Cl, methyl and methoxy; or from halogen and C1-C3 alkyl, such as F, Cl, and methyl.

In some embodiments, one of $R_A$, $R_B$ and $R_C$ is H and the other two are both selected from halogen, e.g. both are F or Cl, or both are Cl.

In other embodiments, the two of $R_A$, $R_B$ and $R_C$ that are different from H are both selected from C1-C3 alkyl and $R_1O$, e.g. both are selected from methyl and methoxy. In some embodiments, the two of $R_A$, $R_B$ and $R_C$ that are different from H are identical with each others, e.g. both are Cl, or both are methyl, or both are $R_1O$, e.g. methoxy.

For example, in some embodiments of a compound of formula (I), e.g. a compound of formula (Ib), $R_B$ and $R_C$ are both selected from halogen, cyano, C1-C4 alkyl, and $R_1O$. For example, $R_B$ and $R_C$ may be both selected from halogen, e.g. both $R_B$ and $R_C$ are F or Cl, or both $R_B$ and $R_C$ are Cl. In other embodiments, $R_B$ and $R_C$ are both selected from C1-C4 alkyl and $R_1O$, e.g. both $R_B$ and $R_C$ are selected from methyl and methoxy, e.g. both are methyl. In a compound of formula (I), e.g. of formula (Ib), $R_B$ and $R_C$ may be different from each other, or may be identical.

In a compound of formula (I), the linking moiety W is a direct bond or $X_1—X_2—X_3$. In some embodiments, W is a direct bond, i.e. the compound may be represented by formula (Ig)

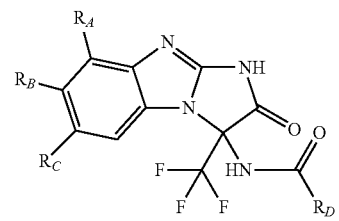

(Ig)

wherein $R_A$, $R_B$, $R_C$, and $R_D$ are as defined herein.

In some other embodiments, W is $X_1—X_2—X_3$, and the compound may be represented by formula (Ih)

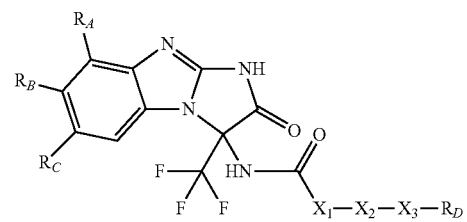

(Ih)

wherein $R_A$, $R_B$, $R_C$, $R_D$, $X_1$, $X_2$ and $X_3$ are as defined herein.

In a compound of formula (Ih)
$X_1$ is C1-C2 alkylene, optionally substituted by C1-C4 alkyl or $R_{32}O$;
$X_2$ is O or is absent; and
$X_3$ is a direct bond or C1-C2 alkylene, optionally substituted by C1-C4 alkyl or $R_{32}O$.

In some embodiments, $X_1$ is C1-C2 alkylene, optionally substituted by C1-C4 alkyl, e.g. $X_1$ is C1 alkylene optionally substituted by C1-C4 alkyl.

In some embodiments, $X_1$ is C1 alkylene, optionally substituted by C1-C4 alkyl or $R_{32}O$. In some embodiments, $X_1$ is C1-C2 alkylene, e.g. $X_1$ is C1 alkylene (i.e. $CH_2$).

The moiety $X_2$ is absent or O. In some embodiments, $X_2$ is absent, i.e. the compound may be represented by formula (Ij)

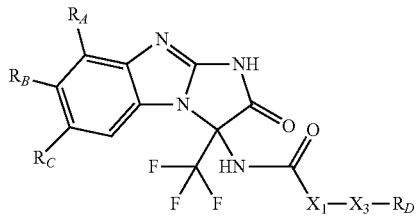

(Ij)

wherein $R_A$, $R_B$, $R_C$, $R_D$, $X_1$, and $X_3$ are as defined herein.

In a compound of formula (Ij), $X_1$ is C1-C2 alkylene, optionally substituted by C1-C4 alkyl or $R_{32}O$, and $X_3$ is a direct bond or C1-C2 alkylene, optionally substituted by C1-C4 alkyl or $R_{32}O$; e.g. $X_1$ is C1-C2 alkylene, optionally substituted by C1-C4 alkyl or $R_{32}O$, and $X_3$ is a direct bond or C1-C2 alkylene, e.g. $X_3$ is C1-C2 alkylene, or $X_3$ is C1 alkylene.

In some other embodiments of a compound of formula (Ij), $X_1$ is C1-C2 alkylene, optionally substituted by C1-C4 alkyl or $R_{32}O$, and $X_3$ is a direct bond or C1 alkylene.

In some other embodiments of a compound of formula (Ij), $X_1$ is C1-C2 alkylene, optionally substituted by C1-C4 alkyl or $R_{32}O$, and $X_3$ is a direct bond.

In some other embodiments of a compound of formula (Ij), $X_1$ is C1 alkylene, optionally substituted by C1-C4 alkyl or $R_{32}O$, and $X_3$ is a direct bond or C1-C2 alkylene, optionally substituted by C1-C4 alkyl or $R_{32}O$; e.g. $X_1$ is C1 alkylene, optionally substituted by C1-C4 alkyl or $R_{32}O$, and $X_3$ is a direct bond or C1-C2 alkylene.

In some other embodiments, $X_2$ is O, i.e. the compound may be represented by formula (Ik)

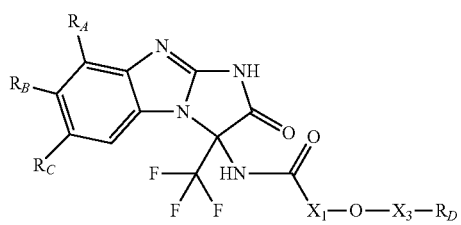

(Ik)

wherein $R_A$, $R_B$, $R_C$, $R_D$, $X_1$, and $X_3$ are as defined herein.

The moiety $X_3$ is a direct bond or C1-C2 alkylene, optionally substituted by C1-C4 alkyl or $R_{32}O$. In some embodiments, $X_3$ is a direct bond or C1 alkylene, optionally substituted by C1-C4 alkyl or $R_{32}O$. In some embodiments, $X_3$ is a direct bond or C1 alkylene. In some embodiments, $X_3$ is a direct bond, i.e. the compound of formula (Ih) may be represented by formula (Im)

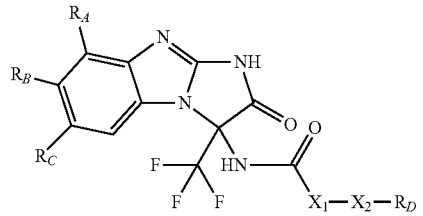

(Im)

wherein $R_A$, $R_B$, $R_C$, $R_D$, $X_1$, and $X_2$ are as defined herein.

In some embodiments of a compound of formula (Im), $X_2$ is O. In some other embodiments of a compound of formula (Im), $X_2$ is absent, and the compound may then be represented by formula (In)

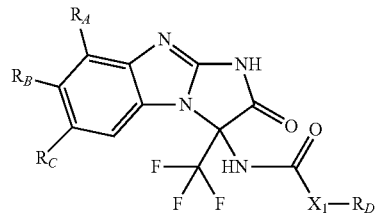

(In)

wherein $R_A$, $R_B$, $R_C$, $R_D$, and $X_1$ are as defined herein.

When either $X_1$ or $X_3$, or both $X_1$ and $X_3$ are substituted by a moiety selected from C1-C4 alkyl or $R_{32}O$, said moiety more particularly may be selected from C1-C3 alkyl and $R_{32}O$, or from C1-C2 alkyl and $R_{32}O$, in particular from $CH_3$ and $R_{32}O$. In some embodiments, said moiety is selected from C1-C4 alkyl, or C1-C3 alkyl, or from C1-C2 alkyl, or $CH_3$. In some embodiments, neither $X_1$ nor $X_3$ is substituted. In some embodiments, said moiety is $R_{32}O$.

The moiety $R_{32}$ is selected from H and C1-C4 alkyl. In some embodiments, $R_{32}$ is selected from H and C1-C3 alkyl, or from H and C1-C2 alkyl, in particular from H and $CH_3$, e.g. H. In some other embodiments, $R_{32}$ is selected from C1-C4 alkyl, e.g. C1-C3 alkyl, or C1-C2 alkyl, in particular $CH_3$.

In some embodiments, W is a direct bond, $CH_2$, $CH_2CH_2$, $CH_2CH_2CH_2$, $CH(CH_3)$, $CH(CH_3)CH_2$, $CH(OH)$, $CH(OCH_3)$, $CH(CH_3)O$, or $CH(CH_3)OCH_2$; e.g. W is a direct bond, $CH_2$, $CH_2CH_2$, $CH_2CH_2CH_2$, $CH(CH_3)$, $CH(CH_3)CH_2$, $CH(OH)$, or $CH(OCH_3)$.

In some embodiments, W is a direct bond, $CH_2$, $CH_2CH_2$, or $CH_2CH_2CH_2$, e.g. W is $CH_2CH_2$, or $CH_2CH_2CH_2$, e.g. W is $CH_2CH_2$.

In some embodiments, W is a direct bond, $CH_2$ or $CH_2CH_2$, e.g. W is a direct bond or $CH_2$, e.g. W is $CH_2$.

In some other embodiments, W is a $CH_2CH_2$, $CH_2CH_2CH_2$, $CH(CH_3)$, $CH(CH_3)CH_2$, $CH(OH)$, $CH(OCH_3)$, $CH(CH_3)O$, or $CH(CH_3)OCH_2$.

In a compound of formula (I), the moiety $R_D$ is C1-C6 alkyl, or a cyclic moiety selected from phenyl, 4- to 6-membered heterocyclyl, C4-C6 cycloalkyl, and C5-C6 cycloalkenyl, wherein said cyclic moiety is optionally substituted by one or more $R_{33}$; e.g. the moiety $R_D$ is C1-C6 alkyl, or a cyclic moiety selected from phenyl, 4- to 6-membered heterocyclyl, and C4-C6 cycloalkyl, wherein said cyclic moiety is optionally substituted by one or more $R_{33}$.

When $R_D$ is C1-C6 alkyl, it e.g. may be selected from C3-C6 alkyl, or from C3-C5 alkyl. In some embodiments, when $R_D$ is C1-C6 alkyl, W is a direct bond.

In some embodiments, the moiety $R_D$ is a cyclic moiety selected from phenyl, 4- to 6-membered heterocyclyl, C4-C6 cycloalkyl, and C5-C6 cycloalkenyl, e.g. from phenyl, 4- to 6-membered heterocyclyl, and C4-C6 cycloalkyl, wherein said cyclic moiety is optionally substituted by one or more $R_{33}$. In some embodiments, the compound of formula (I) may be represented by formula (Io)

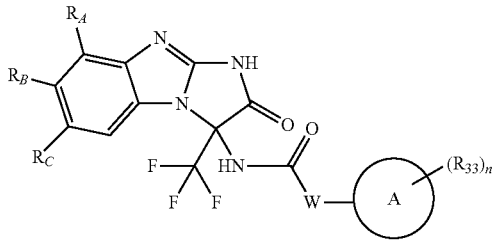

(Io)

wherein $R_A$, $R_B$, $R_C$, W and $R_{33}$ are as defined herein, ring A is phenyl, 4- to 6-membered heterocyclyl, C4-C6 cycloalkyl, or C5-C6 cycloalkenyl, and n is an integer of from 0 to 3.

In a compound of formula (Io), ring A is substituted by n moieties $R_{33}$, whereby n is an integer of from 0 to 3. In some embodiments, n is an integer of from 0 to 2, e.g. n is 0, 1 or 2, or n is 1 or 2. In some embodiments, n is 0. In other embodiments, n is 1. In still other embodiments, n is 2 or 3, e.g. n is 2.

In a compound of formula (Io), each moiety $R_{33}$ is independently selected from halogen, cyano, C1-C6 alkyl optionally substituted by $R_{34}O$, C3-C6 cycloalkyl, phenyl, 5- or 6-membered heterocyclyl, $R_{34}O$, $R_{35}OC(O)$, $R_{36}S(O)_2$, $R_{37}C(O)$, $R_{38}R_{39}N$, $R_{40}R_{41}N(CO)$; and when n is at least 2, two $R_{33}$ attached to one and the same carbon atom may form, together with the carbon atom to which they are both attached, a 4- to 6-membered ring optionally containing one more heteroatoms in the ring, e.g. two $R_{33}$ attached to one and the same carbon atom form a biradical —$CH_2$-L-$CH_2$— wherein L is $CH_2$, NH or O, e.g. L is NH.

In some embodiments, each moiety $R_{33}$ is independently selected from halogen, cyano, C1-C6 alkyl optionally substituted by $R_{34}O$, C3-C6 cycloalkyl, phenyl, 5- or 6-membered heterocyclyl, $R_{34}O$, $R_{35}OC(O)$, $R_{36}S(O)_2$, $R_{37}C(O)$, $R_{38}R_{39}N$, $R_{40}R_{41}N(CO)$; e.g. each moiety $R_{33}$ is independently selected from halogen, cyano C1-C6 alkyl optionally substituted by $R_{34}O$, C3-C6 cycloalkyl, phenyl, 5- or 6-membered heterocyclyl, $R_{34}O$, $R_{36}S(O)_2$, $R_{37}C(O)$, $R_{38}R_{39}N$, and $R_{40}R_{41}N(CO)$.

In some other embodiments, when n is 2 or 3, e.g. when n is 2, two $R_{33}$ attached to one and the same carbon atom may form, together with the carbon atom to which they are both attached, a 4- to 6-membered ring optionally containing one more heteroatoms in the ring, e.g. two $R_{33}$ attached to one and the same carbon atom form a biradical —$CH_2$-L-$CH_2$— wherein L is $CH_2$, NH or O, e.g. L is NH.

When a moiety $R_{33}$ is halogen, said halogen may be F, Cl or Br, in particular F or Cl.

When a moiety $R_{33}$ is C1-C6 alkyl optionally substituted by $R_{34}O$, said C1-C6 alkyl in particular may be C1-C4 alkyl, more particularly C1-C3 alkyl, e.g. methyl or ethyl.

In some embodiments, when a moiety $R_{33}$ is C1-C6 alkyl optionally substituted by $R_{34}O$, it more particularly is not substituted by any $R_{34}O$, i.e. said $R_{33}$ is C1-C6 alkyl, or C1-C4 alkyl, or C1-C3 alkyl, e.g. methyl or ethyl.

In some embodiments of a compound of formula (Io), when a moiety $R_{33}$ is C1-C6 alkyl optionally substituted by $R_{34}O$, it e.g. may be a moiety of formula $R_{34}O(CH_2)_p$, wherein p is an integer of from 1 to 3, e.g. p is 1 or 2, or p is 1.

In a moiety $R_{34}O$, $R_{34}$ is H, C1-C6 alkyl, or C3-C6 cycloalkyl; wherein said alkyl or cycloalkyl is optionally substituted by $R_{42}O$. In some embodiments, $R_{34}$ is H C1-C3 alkyl, or C3-C4 cycloalkyl, wherein said alkyl or cycloalkyl is optionally substituted by $R_{42}O$. In some embodiments, $R_{34}$ is H, or C1-C6 alkyl, wherein said alkyl is optionally substituted by $R_{42}O$, e.g. $R_{34}$ is H, or C1-C3 alkyl, wherein said alkyl is optionally substituted by $R_{42}O$. In some embodiments, $R_{34}$ is H, $CH_3$, $CH_3CH_2$, $CF_3CH_2$, or $CH_3OCH_2CH_2$.

In a moiety $R_{35}OC(O)$, $R_{35}$ is H, C1-C6 alkyl, or C3-C6 cycloalkyl. In some embodiments, $R_{35}$ is selected from H, C1-C4 alkyl, and C3-C4 cycloalkyl, or from H, C1-C3 alkyl and cyclopropyl. In some embodiments, $R_{35}$ is selected from H and C1-C6 alkyl, e.g. from H and C1-C4 alkyl, or from H and C1-C3 alkyl, such as from H and $CH_3$, in particular $CH_3$. In some embodiments, the moiety $R_{35}$ is as defined herein above, but is not H.

In a moiety $R_{36}S(O)_2$, $R_{36}$ is H, C1-C6 alkyl, or C3-C6 cycloalkyl. In some embodiments, $R_{36}$ is selected from H, C1-C4 alkyl, and C4-C6 cycloalkyl, or from H, C1-C3 alkyl and cyclopentyl. In some embodiments, $R_{36}$ is selected from H and C1-C6 alkyl, e.g. from H and C1-C4 alkyl, or from H and C1-C3 alkyl, such as from H, $CH_3$ and $CH_3CH_2$. In some embodiments, the moiety $R_{36}$ is as defined herein above, but is not H, e.g. $R_{36}$ is methyl, ethyl or cyclopentyl.

In a moiety $R_{37}C(O)$, $R_{37}$ is selected from C1-C6 alkyl, or C3-C6 cycloalkyl, wherein said alkyl or cycloalkyl is optionally substituted by $R_{43}O$. In some embodiments, $R_{37}$ is selected from C1-C5 alkyl, and C4-C6 cycloalkyl, or from C1-C4 alkyl and C4-C5 cycloalkyl, e.g. from $CH_3$, $CF_3CH_2$, $(CH_3)_2CHCH_3$ or cyclopentyl. In some embodiments, $R_{37}$ is selected from C1-C6 alkyl optionally substituted by $R_{43}O$, and C3-C6 cycloalkyl. When the C1-C6 alkyl is substituted by $R_{43}O$, said alkyl e.g. may be C1-C4 alkyl, or C1-C3 alkyl, such as methyl.

In a moiety $R_{38}R_{39}N$, $R_{38}$ and $R_{39}$ are independently selected from H, C1-C6 alkyl, and C3-C6 cycloalkyl, wherein said alkyl or cycloalkyl is optionally substituted by $R_{44}R_{45}N$ or $R_{46}O$, or $R_{38}$ and $R_{39}$, together with the nitrogen atom to which they are both attached, form a 4- to 6-membered heterocyclic ring optionally containing one or more further heteroatoms and optionally substituted by C1-C6 alkyl, e.g. C1-C3 alkyl, or C1-C2 alkyl, e.g. $CH_3$.

In some embodiments, $R_{38}$ and $R_{39}$ are independently selected from H, C1-C6 alkyl, and C3-C6 cycloalkyl, wherein said alkyl or cycloalkyl is optionally substituted by $R_{44}R_{45}N$ or $R_{46}O$; e.g. $R_{38}$ is selected from H, C1-C4 alkyl and C3-C4 cycloalkyl; e.g. H and C1-C3 alkyl, such as H and $CH_3$, and $R_{39}$ is selected from H, C1-C6 alkyl, and C3-C6 cycloalkyl, wherein said alkyl or cycloalkyl is optionally substituted by $R_{44}R_{45}N$ or $R_{46}O$.

In some embodiments, $R_{38}$ is selected from H, C1-C4 alkyl and C3-C4 cycloalkyl; e.g. H and C1-C3 alkyl, such as H and $CH_3$, e.g. H; and $R_{39}$ is selected from H, C1-C6 alkyl, and C3-C6 cycloalkyl, wherein said alkyl or cycloalkyl is optionally substituted by $R_{44}R_{45}N$ or $R_{46}O$; or $R_{38}$ and $R_{39}$ together with the nitrogen atom to which they are both attached, form a 4- to 6-membered heterocyclic ring optionally containing one or more further heteroatoms and optionally substituted by C1-C6 alkyl, e.g. C1-C3 alkyl, or C1-C2 alkyl, e.g. methyl; e.g. $R_{38}$ and $R_{39}$ together with the nitrogen atom to which they are both attached, form a 4- to 6-membered heterocyclic ring optionally containing one or more further heteroatoms, or $R_{38}$ and $R_{39}$ together with the nitrogen atom to which they are both attached, form a 4- to 6-membered heterocyclic ring containing no further heteroatoms, such as azetidinyl.

In some embodiments, $R_{38}$ is selected from H, C1-C4 alkyl and C3-C4 cycloalkyl; e.g. H and C1-C3 alkyl, such as H and $CH_3$, e.g. H; and $R_{39}$ is selected from H, C1-C6 alkyl, and C3-C6 cycloalkyl, or $R_{38}$ and $R_{39}$ together with the nitrogen atom to which they are both attached, form a 4- to 6-membered heterocyclic ring optionally containing one or more further heteroatoms and optionally substituted by C1-C6 alkyl, e.g. C1-C3 alkyl, or C1-C2 alkyl, or $CH_3$; e.g. $R_{38}$ and $R_{39}$ together with the nitrogen atom to which they are both attached, form a 4- to 6-membered heterocyclic ring optionally containing one or more further heteroatoms, or $R_{38}$ and $R_{39}$ together with the nitrogen atom to which they are both attached, form a 4- to 6-membered heterocyclic ring containing no further heteroatoms. For example, $R_{38}R_{39}N$ may be selected from

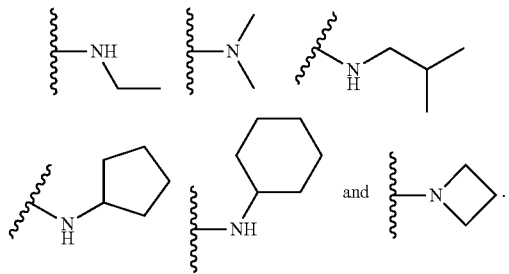

In some embodiments, $R_{38}$ is selected from H, C1-C4 alkyl and C3-C4 cycloalkyl; e.g. H and C1-C3 alkyl, such as H and $CH_3$, e.g. H; and $R_{39}$ is selected from H, C1-C6 alkyl, and C3-C6 cycloalkyl, wherein said alkyl or cycloalkyl is substituted by $R_{44}R_{45}N$ or $R_{46}O$; e.g. $NR_{38}R_{39}$ is selected from

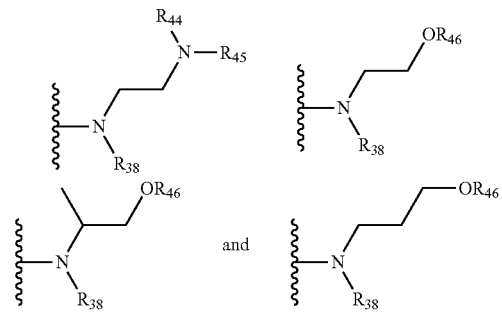

wherein $R_{38}$ is as defined herein above, e.g. $R_{38}$ is H or C1-C3 alkyl, in particular $R_{38}$ is H or $CH_3$.

In some of embodiments, when $R_{39}$ is C1-C6 alkyl or C3-C6 cycloalkyl, optionally substituted by $R_{44}R_{45}N$ or $R_{46}O$, $R_{39}$ more particularly is C1-C6 alkyl optionally substituted by $R_{44}R_{45}N$ or $R_{46}O$, e.g. C1-C6 alkyl optionally substituted by $R_{44}R_{45}N$, e.g. C1-C4 optionally substituted by $R_{44}R_{45}N$, or C1-C3 optionally substituted by $R_{44}R_{45}N$.

In some other embodiments, when $R_{39}$ is C1-C6 alkyl or C3-C6 cycloalkyl, optionally substituted by $R_{44}R_{45}N$ or $R_{46}O$, $R_{39}$ more particularly is C1-C6 alkyl optionally sub-stituted by $R_{46}O$, e.g. C1-C4 optionally substituted by $R_{46}O$, or C1-C3 optionally substituted by $R_{46}O$.

In some embodiments, $R_{38}$ is selected from H, C1-C4 alkyl and C3-C4 cycloalkyl; e.g. H and C1-C3 alkyl, such as H and $CH_3$, e.g. H; and $R_{39}$ is selected from H, C1-C6 alkyl, and C3-C6 cycloalkyl, e.g from H and C1-C6 alkyl, wherein said alkyl or cycloalkyl is substituted by $R_{44}R_{45}N$.

In some embodiments, $R_{38}$ is selected from H, C1-C4 alkyl and C3-C4 cycloalkyl; e.g. H and C1-C3 alkyl, such as H and $CH_3$, e.g. H; and $R_{39}$ is selected from H, C1-C6 alkyl, and C3-C6 cycloalkyl, wherein said alkyl or cycloalkyl is substituted by $R_{46}O$.

In the moiety $R_{40}R_{41}NC(O)$, $R_{40}$ and $R_{41}$ are independently selected from H, C1-C6 alkyl, and C3-C6 cycloalkyl, wherein said alkyl or cycloalkyl is optionally substituted by $R_{47}R_{48}N$ or $R_{49}O$, or $R_{40}$ and $R_{41}$ together with the nitrogen atom to which they are both attached, form a 4- to 6-membered heterocyclic ring optionally containing one or more further heteroatoms and optionally substituted by C1-C6 alkyl.

In some embodiments, $R_{40}$ and $R_{41}$ are independently selected from H, C1-C6 alkyl, and C3-C6 cycloalkyl, wherein said alkyl or cycloalkyl is optionally substituted by $R_{47}R_{48}N$ or $R_{49}O$; e.g. $R_{40}$ is selected from H, C1-C4 alkyl and C3-C4 cycloalkyl; e.g. H and C1-C3 alkyl, such as H and $CH_3$, and $R_{41}$ is selected from H, C1-C6 alkyl, and C3-C6 cycloalkyl, wherein said alkyl or cycloalkyl is optionally substituted by $R_{47}R_{48}N$ or $R_{49}O$.

In some embodiments, $R_{40}$ is selected from H, C1-C4 alkyl and C3-C4 cycloalkyl; e.g. H and C1-C3 alkyl, such as H and $CH_3$, e.g. H; and $R_{41}$ is selected from H, C1-C6 alkyl, and C3-C6 cycloalkyl, wherein said alkyl or cycloalkyl is optionally substituted by $R_{47}R_{48}N$ or $R_{49}O$; or $R_{40}$ and $R_{41}$ together with the nitrogen atom to which they are both attached, form a 4- to 6-membered heterocyclic ring optionally containing one or more further heteroatoms and optionally substituted by C1-C6 alkyl, e.g. C1-C3 alkyl, or C1-C2 alkyl, or $CH_3$; e.g. $R_{40}$ and $R_{41}$ together with the nitrogen atom to which they are both attached, form a 4- to 6-membered heterocyclic ring optionally containing one or more further heteroatoms, or $R_{40}$ and $R_{41}$ together with the nitrogen atom to which they are both attached, form a 4- to 6-membered heterocyclic ring containing no further heteroatoms, such as azetidinyl.

In some embodiments, $R_{40}$ is selected from H, C1-C4 alkyl and C3-C4 cycloalkyl; e.g. H and C1-C3 alkyl, such as H and $CH_3$, e.g H; and $R_{41}$ is selected from H, C1-C6 alkyl, and C3-C6 cycloalkyl, or $R_{40}$ and $R_{41}$ together with the nitrogen atom to which they are both attached, form a 4- to 6-membered heterocyclic ring optionally containing one or more further heteroatoms and optionally substituted by C1-C6 alkyl, e.g. C1-C3 alkyl, or C1-C2 alkyl, or $CH_3$; e.g. $R_{40}$ and $R_{41}$ together with the nitrogen atom to which they are both attached, form a 4- to 6-membered heterocyclic ring optionally containing one or more further heteroatoms, or $R_{40}$ and $R_{41}$ together with the nitrogen atom to which they are both attached, form a 4- to 6-membered heterocyclic ring containing no further heteroatoms.

In some embodiments, $R_{40}$ is selected from H, C1-C4 alkyl and C3-C4 cycloalkyl; e.g. H and C1-C3 alkyl, such as H and $CH_3$, e.g H; and $R_{41}$ is selected from H, C1-C6 alkyl, and C3-C6 cycloalkyl, wherein said alkyl or cycloalkyl is substituted by $R_{47}R_{48}N$ or $R_{49}O$; e.g. $R_{40}R_{41}NC(O)$ is selected from

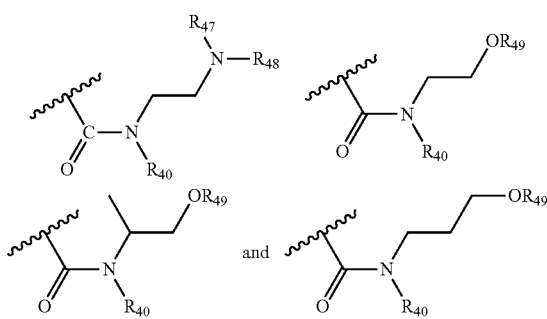

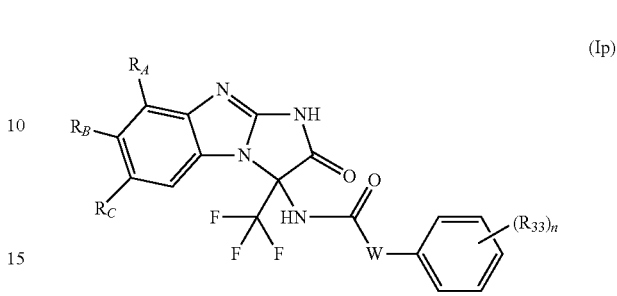

wherein $R_{40}$ is as defined herein above, e.g. $R_{40}$ is H or C1-C3 alkyl, in particular $R_{40}$ is H or $CH_3$.

In some of embodiments, when $R_{41}$ is C1-C6 alkyl or C3-C6 cycloalkyl, optionally substituted by $R_{47}R_{48}N$ or $R_{49}O$, $R_{41}$ more particularly is C1-C6 alkyl optionally substituted by $R_{47}R_{48}N$ or $R_{49}O$, e.g. C1-C6 alkyl optionally substituted by $R_{47}R_{48}N$, e.g. C1-C4 optionally substituted by $R_{47}R_{48}N$, or C1-C3 optionally substituted by $R_{47}R_{48}N$.

In some other embodiments, when $R_{41}$ is C1-C6 alkyl or C3-C6 cycloalkyl, optionally substituted by $R_{47}R_{48}N$ or $R_{49}O$, $R_{41}$ more particularly is C1-C6 alkyl optionally substituted by $R_{49}O$, e.g. C1-C4 optionally substituted by $R_{49}O$, or C1-C3 optionally substituted by $R_{49}O$.

In some embodiments, $R_{40}$ is selected from H, C1-C4 alkyl and C3-C4 cycloalkyl; e.g. H and C1-C3 alkyl, such as H and $CH_3$, e.g H; and $R_{41}$ is selected from H, C1-C6 alkyl, and C3-C6 cycloalkyl, e.g. from H and C1-C6 alkyl, wherein said alkyl or cycloalkyl is substituted by $R_{47}R_{48}N$.

In some embodiments, $R_{40}$ is selected from H, C1-C4 alkyl and C3-C4 cycloalkyl; e.g. H and C1-C3 alkyl, such as H and $CH_3$, e.g H; and $R_{41}$ is selected from H, C1-C6 alkyl, and C3-C6 cycloalkyl, wherein said alkyl or cycloalkyl is substituted by $R_{49}O$.

In the moieties $R_{42}O$, $R_{43}O$, $R_{46}O$ and $R_{49}O$, $R_{42}$, $R_{43}$, $R_{46}$ and $R_{49}$ are independently selected from H, C1-C6 alkyl, and C3-C6 cycloalkyl. In some embodiments, each one of $R_{42}$, $R_{43}$, $R_{46}$ and $R_{49}$ is selected from H and C1-C6 alkyl, e.g. from H and C1-C3 alkyl, or from H and C1-C2 alkyl, such as from H and $CH_3$.

In the moiety $R_{42}O$, $R_{42}$ is H, C1-C6 alkyl, or C3-C6 cycloalkyl. In some embodiments, $R_{42}$ is H, C1-C3 alkyl, or C3-C4 cycloalkyl, e.g. H, C1-C3 alkyl or cyclopropyl. In some embodiments, $R_{42}$ is H, or C1-C6 alkyl, e.g. $R_{42}$ is H, or C1-C3 alkyl. In some embodiments, $R_{42}$ is H or $CH_3$.

In the moiety $R_{43}O$, $R_{43}$ is H, C1-C6 alkyl, or C3-C6 cycloalkyl. In some embodiments, $R_{43}$ is H, C1-C3 alkyl, or C3-C4 cycloalkyl, e.g. H, C1-C3 alkyl or cyclopropyl. In some embodiments, $R_{43}$ is H, or C1-C6 alkyl, e.g. $R_{43}$ is H, or C1-C3 alkyl. In some embodiments, $R_{43}$ is H or $CH_3$.

In the moiety $R_{46}O$, $R_{46}$ is H, C1-C6 alkyl, or C3-C6 cycloalkyl. In some embodiments, $R_{46}$ is H, C1-C3 alkyl, or C3-C4 cycloalkyl, e.g. H, C1-C3 alkyl or cyclopropyl. In some embodiments, $R_{46}$ is H, or C1-C6 alkyl, e.g. $R_{46}$ is H, or C1-C3 alkyl. In some embodiments, $R_{46}$ is H or $CH_3$.

In the moiety $R_{49}O$, $R_{49}$ is H, C1-C6 alkyl, or C3-C6 cycloalkyl. In some embodiments, $R_{49}$ is H, C1-C3 alkyl, or C3-C4 cycloalkyl, e.g. H, C1-C3 alkyl or cyclopropyl. In some embodiments, $R_{49}$ is H, or C1-C6 alkyl, e.g. $R_{49}$ is H, or C1-C3 alkyl. In some embodiments, $R_{49}$ is H or $CH_3$.

In a compound of formula (Io), ring A is C4-C6 cycloalkyl, C5-C6 cycloalkenyl, phenyl or 4- to 6-membered heterocyclyl. In some embodiments, ring A is C4-C6 cycloalkyl, e.g. ring A is C5-C6 cycloalkyl.

In embodiments wherein ring A is phenyl, the compound of formula (Io) may be represented by formula (Ip)

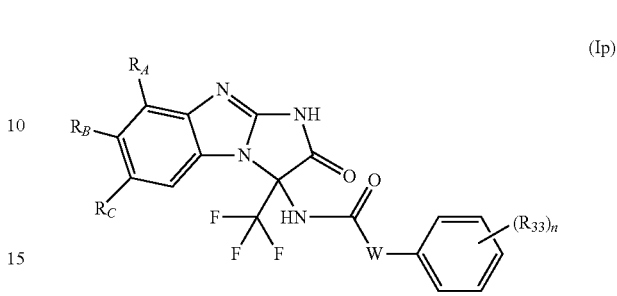

wherein $R_A$, $R_B$, $R_C$, $R_{33}$, n and W are as defined herein.

In a compound of formula (Ip), n is an integer of from 0 to 3. In some embodiments of a compound of formula (Ip), n is an integer of from 0 to 2, e.g. n is 0, 1 or 2.

In a compound of formula (Ip), each $R_{33}$ is independently selected from halogen, cyano, C1-C6 alkyl optionally substituted by $R_{34}O$, C3-C6 cycloalkyl, phenyl, 5- or 6-membered heterocyclyl, $R_{34}O$, $R_{35}OC(O)$, $R_{36}S(O)_2$, $R_{37}C(O)$, $R_{38}R_{39}N$, and $R_{40}R_{41}N(CO)$.

In some embodiments of a compound of formula (Ip), each $R_{33}$ is independently selected from halogen, cyano, C1-C6 alkyl optionally substituted by $R_{34}O$, phenyl, 5- or 6-membered heterocyclyl, $R_{34}O$, $R_{35}OC(O)$, $R_{36}S(O)_2$, $R_{37}C(O)$, $R_{38}R_{39}N$, and $R_{40}R_{41}N(CO)$.

In some embodiments of a compound of formula (Ip), each $R_{33}$ is independently selected from halogen, cyano, phenyl, C1-C6 alkyl optionally substituted by $R_{34}O$, $R_{36}S(O)_2$, and $R_{38}R_{39}N$. In some embodiments, each $R_{33}$ is independently selected from halogen, cyano, C1-C6 alkyl optionally substituted by $R_{34}O$, $R_{34}O$, $R_{36}S(O)_2$, and $R_{38}R_{39}N$. In some embodiments, each $R_{33}$ is independently selected from halogen, cyano, and C1-C6 alkyl optionally substituted by $R_{34}O$. In some embodiments, each $R_{33}$ is halogen, e.g. $R_{33}$ is independently selected from F, Cl and Br, in particular, F and Cl.

In some embodiments of in a compound of formula (Ip), when $R_{33}$ is C1-C6 alkyl substituted by $R_{34}O$ or $R_{34}O$, $R_{33}$ may be represented as $R_{34}O(CH_2)_p$ wherein p is an integer of from 0 to 3 and $R_{34}$ is H or C1-C4 alkyl, more particularly C1-C3 alkyl, in particular methyl. In such embodiments, the integer p more particularly may be selected from 0 to 2, e.g. p is 0. In some particular embodiments of a compound of formula (Ip), any $R_{34}O(CH_2)_p$ is C1-C4 alkoxy, e.g. C1-C3 alkoxy, in particular methoxy.

In some embodiments of a compound of formula (Ip), when an $R_{33}$ is $R_{36}S(O)_2$, $R_{36}$ is H or C1-C4 alkyl, and more particularly may be selected from C1-C4 alkyl, e.g. $R_{36}$ is C1-C3 alkyl, in particular $R_{36}$ is methyl. Thus, in some particular embodiments of a compound of formula (Ip), any $R_{36}S(O)_2$ is $CH_3(SO)_2$.

In some embodiments of a compound of formula (Ip), at least one $R_{33}$ is $R_{38}R_{39}N$ wherein $R_{38}$ and $R_{39}$ are as defined herein above. In some of the these embodiments, $R_{38}$ is H or C1-C4 alkyl; and $R_{39}$ is H, C3-C6 cycloalkyl, or C1-C4 alkyl optionally substituted with a moiety selected from $R_{46}O$ and $R_{44}R_{45}N$; and $R_{44}$, $R_{45}$ and $R_{46}$ are independently selected from H and C1-C4 alkyl; or $R_{38}$ and $R_{39}$ form together a biradical $-(CH_2)_s-$ wherein s is an integer of from 3 to 5. In some of these embodiments, $R_{38}$ is H and $R_{39}$ is C1-C4 alkyl optionally substituted with a moiety selected from $R_{44}R_{45}N$ and $R_{46}O$; in particular $R_{38}$ is H and $R_{39}$ is C1-C4 alkyl optionally substituted with $R_{46}O$. In some embodiments of a compound of formula (Ip), any $R_{38}R_{39}N$ is selected from $NHR_{39}$, wherein $R_{39}$ is as defined herein, and in particular is C1-C4 alkyl substituted with $R_{46}O$, e.g. $R_{38}R_{39}N$ is $NH(CH_2CH_2OCH_3)$.

In a compound of formula (Ip), W is as defined herein above. In some embodiments, W is a direct bond, and the compound of formula (Ip) may then be represented by formula (Iq)

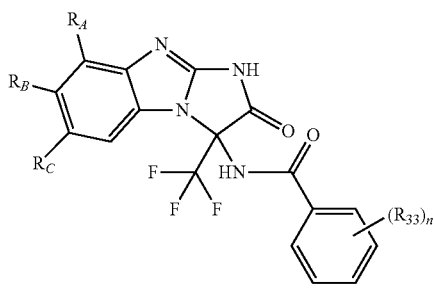

wherein $R_A$, $R_B$, $R_C$, n and $R_{33}$ are as defined herein.

In some embodiments of a compound of formula (Ip), W is C1-C3 alkylene, optionally substituted by C1-C4 alkyl, e.g. C1-C3 alkyl, in particular methyl, or $R_{32}O$, wherein $R_{32}$ is H or C1-C4 alkyl, H or C1-C3 alkyl, in particular H or methyl.

In some embodiments of a compound of formula (Ip), W is a direct bond, $CH_2$, $CH_2CH_2$, $CH(CH_3)$, $CH(OH)$, or $CH(OCH_3)$.

In some embodiments of a compound of formula (Ip) $R_A$, $R_B$ and $R_C$ are independently selected from H, halogen, C1-C4 alkyl, and $R_1O$;
$R_1$ is C1-C4 alkyl;
W is a direct bond or C1-C3 alkylene optionally substituted by C1-C4 alkyl or $R_{32}O$;
$R_{32}$ is H or C1-C4 alkyl;
n is an integer of from 0 to 3;
each $R_{33}$ is independently selected from halogen, cyano, phenyl, $R_{34}O(CH_2)_p$, $R_{36}S(O)_2$, and $R_{38}R_{39}N$;
$R_{34}$ is C1-C4 alkyl;
p is 0;
$R_{36}$ C1-C4 alkyl;
$R_{38}$ is H;
$R_{39}$ is C1-C4 alkyl substituted with $R_{46}O$; and
$R_{46}$ is C1-C4 alkyl.

In some embodiments of a compound of formula (Io), ring A is 5- or 6-membered heterocyclyl, whereby the heterocyclyl may be saturated or unsaturated, and aromatic or non-aromatic. In some embodiments, ring A is 5- or 6-membered heteroaryl. In some of these embodiments, the number n of moieties $R_{33}$ on ring A is from 0 to 2, in particular 0 or 1, more particularly n is 1.

In some embodiments, when ring A is 5- to 6-membered heteroaryl, any $R_{33}$ is independently selected from halogen, C1-C4 alkyl optionally substituted by $R_{34}O$, C3-C6 cycloalkyl, $R_{37}C(O)$, $R_{38}R_{39}N$, and $R_{40}R_{41}N(CO)$.

In still other embodiments, when ring A is 5- to 6-membered heteroaryl, any $R_{33}$ is independently selected from halogen, C1-C4 alkyl, C3-C6 cycloalkyl, C1-C4 alkyl optionally substituted by $R_{34}O$, $R_{37}C(O)$, $R_{38}R_{39}N$, and $R_{40}R_{41}N(CO)$.

In some embodiments, when ring A is 5- to 6-membered heteroaryl, any $R_{33}$ is independently selected from halogen, C1-C4 alkyl optionally substituted by $R_{34}O$, and $R_{38}R_{39}N$.

In some particular embodiments, when ring A is 5- to 6-membered heteroaryl, any $R_{33}$ is $R_{38}R_{39}N$.

For example, in some embodiments, ring A is 5- to 6-membered heteroaryl, n is 1 and $R_{33}$ is halogen, C1-C4 alkyl optionally substituted by $R_{34}O$, or $R_{38}R_{39}N$; in particular $R_{38}R_{39}N$.

In some embodiments, ring A is 5- or 6-membered heteroaryl, n is 1, $R_{33}$ is $R_{38}R_{39}N$, $R_{38}$ is H, $R_{39}$ is C1-C4 alkyl substituted with $R_{46}O$; and $R_{46}$ is C1-C4 alkyl.

In some embodiments, when ring A is 5- or 6-membered heteroaryl,
$R_A$, $R_B$ and $R_C$ are independently selected from H, halogen, cyano, C1-C4 alkyl, and $R_2C(O)$; e.g. from H, halogen, C1-C4 alkyl, and $R_2C(O)$;
W is a direct bond or C1-C3 alkylene;
n is 0 or 1;
each $R_{33}$ is independently selected from halogen, C1-C4 alkyl; C3-C6 cycloalkyl, C1-C4 alkyl optionally substituted by $R_{34}O$, $R_{37}C(O)$, $R_{38}R_{39}N$, and $R_{40}R_{41}N(CO)$;
$R_{34}$ is H or C1-C4 alkyl;
$R_{38}$ is H or C1-C4 alkyl; and $R_{39}$ is C3-C6 cycloalkyl or C1-C4 alkyl optionally substituted with a moiety selected from $R_{44}R_{45}N$ and $R_{46}O$; or $R_{38}$ and $R_{39}$ form together a biradical $—(CH_2)_s—$
wherein s is an integer of from 3 to 5;
$R_{40}$ is H or C1-C4 alkyl;
$R_{41}$ is C1-C4 alkyl substituted with $R_{49}O$;
$R_{44}$, $R_{45}$ and $R_{46}$ are independently selected from H and C1-C4 alkyl; and
$R_{49}$, is C1-C4 alkyl.

In some particular embodiments, when ring A is 5- to 6-membered heteroaryl, it more specifically is 5-membered heteroaryl. In some embodiments, when ring A is 5-membered heteroaryl, it more specifically is thiazolyl, in particular 1,3-thiazolyl.

In some embodiments, the compound may be represented by formula (Ir)

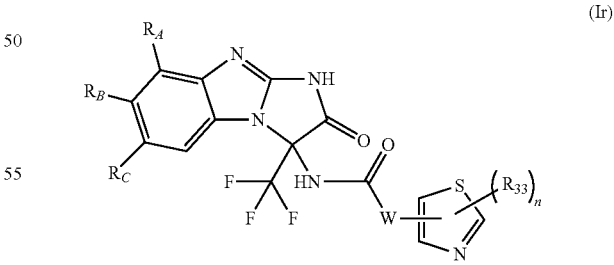

wherein $R_A$, $R_B$, $R_C$, $R_{33}$, W and n are as defined herein.

In some embodiments of a compound of formula (Ir), W is a direct bond. In some embodiments of a compound of formula (Ir), n is 1. In some embodiments of a compound of formula (Ir), ring A is 1,3-thiazol-4-yl In some embodiments of a compound of formula (Ir), ring A is 1,3-thiazol-4-yl and n is 1. In some embodiments, when ring A is 1,3-thiazol-4-yl and n is 1, $R_{33}$ is in 2-position, i.e. the compound of formula (I) may be represented by formula (Id-1)

(Is)

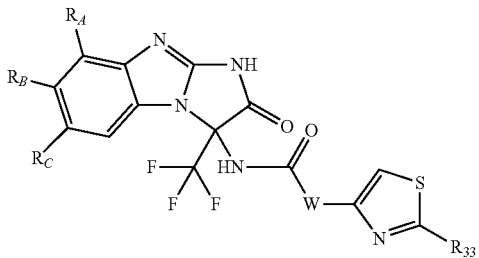

wherein $R_A$, $R_B$, $R_C$, $R_{33}$ and W are as defined herein.

In some particular embodiments of a compound of formula (Is), $R_{33}$ is selected from halogen, such as Br, $R_{34}O$, and $R_{38}R_{39}N$, e.g. from halogen and $R_{38}R_{39}N$, in particular $R_{38}R_{39}N$. More particularly, $R_{33}$ is $R_{38}R_{39}N$, wherein $R_{38}$ is H or C1-C3 alkyl, e.g. H or methyl, in particular H, $R_{39}$ is C3-C6 cycloalkyl or C1-C4 alkyl optionally substituted with $R_{46}O$, and $R_{46}$ is C1-C4 alkyl. In some embodiments, the compound is as represented by formula (It)

(It)

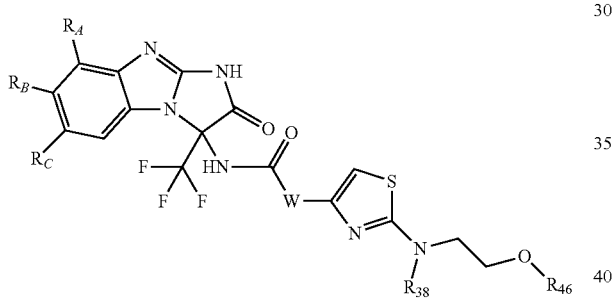

wherein $R_A$, $R_B$, $R_C$, W, R38 and $R_{46}$ are as defined herein.

In some embodiments of a compound of formula (Io), when ring A is 5-membered heteroaryl, e.g. thiazolyl, $R_A$, $R_B$ and $R_C$ are independently selected from H, halogen, cyano, C1-C6 alkyl, $R_2C(O)$, or phenyl optionally substituted by one or more moieties $R_{16}$; e.g. from H, halogen, cyano, C1-C6 alkyl and $R_2C(O)$; or from H, halogen, C1-C4 alkyl, and $R_2C(O)$;

W is a direct bond;

n is or 1;

$R_{33}$ is halogen, $R_{34}O$, or $R_{38}R_{39}N$, e.g. halogen or $R_{38}R_{39}N$;

$R_{38}$ is H;

$R_{39}$ is C1-C4 alkyl, optionally substituted by $R_{46}O$, or C3-C6 cycloalkyl, e.g. C1-C4 alkyl, substituted by $R_{46}O$; and $R_{46}$ is C1-C4 alkyl.

In some other particular embodiments, when ring A is 5- or 6-membered heteroaryl, it more specifically is 6-membered heteroaryl, e.g. 6-membered heteroaryl containing one or 2 heteroatoms in the ring, e.g. 1 or 2 N, e.g. ring A is pyrimidinyl or pyridinyl, in particular pyridinyl. In embodiments where ring A is pyridinyl, the compound of formula (I) may be represented by formula (Iu)

(Iu)

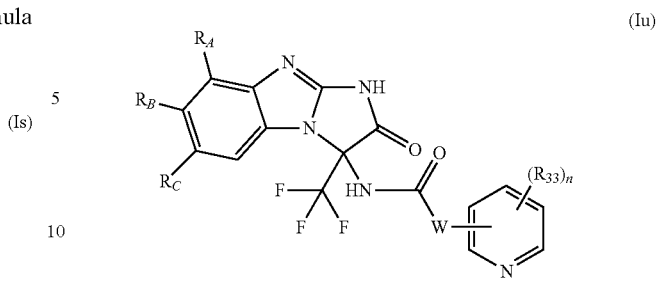

wherein $R_A$, $R_B$, $R_C$, W, n and $R_{33}$ are as defined herein.

In some of these embodiments, W is a direct bond or C1-C3 alkylene, e.g. W is —CH$_2$CH$_2$—, in particular W is a direct bond.

When ring A is pyridinyl, it e.g. may be 2-pyridinyl or 3-pyridinyl. In some embodiments, ring A is 2-pyridinyl, i.e. the compound of formula (Iu) may be represented by formula (Iv)

(Iv)

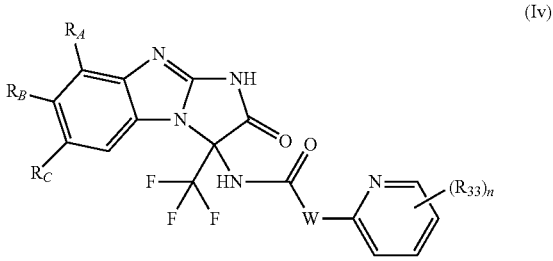

wherein $R_A$, $R_B$, $R_C$, W, n and $R_{33}$ are as defined herein.

In some of these embodiments, the 2-pyridinyl is substituted with one moiety $R_{33}$ only. For example, in some embodiments the 2-pyridinyl is substituted with one moiety $R_{33}$ only, attached in 6-position on the pyrididinyl ring, and the compound may then be represented by formula (Iw)

(Iw)

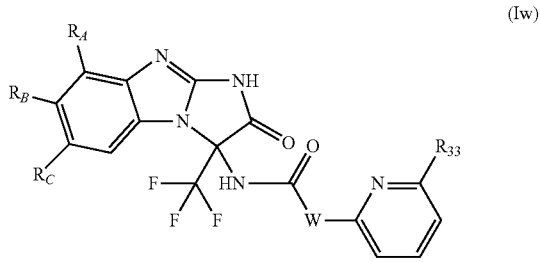

wherein $R_A$, $R_B$, $R_C$, W and $R_{33}$ are as defined herein.

In embodiments wherein ring A is 3-pyridinyl, the compound of formula (Iu) may be represented by formula (Ix)

(Ix)

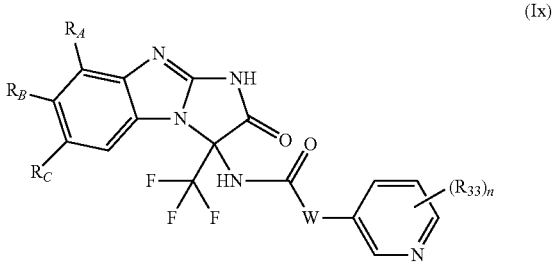

wherein $R_A$, $R_B$, $R_C$, W, n and $R_{33}$ are as defined herein.

In some of the embodiments wherein ring A is 3-pyridinyl, the 3-pyridinyl is substituted with one moiety $R_{33}$ only. For example, in some embodiments when the 3-pyridinyl is substituted with one moiety $R_{33}$ only, the compound of formula (Ix) is represented by formula (Iy)

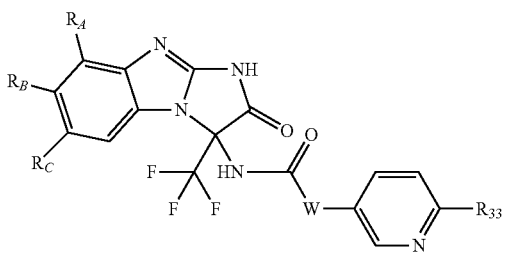

(Iy)

wherein $R_A$, $R_B$, $R_C$, W and $R_{33}$ are as defined herein.

In a compound of formula (Iu), (Iv), (Iw), (Ix) or (Iy), $R_{33}$ is as defined herein. In some embodiments, $R_{33}$ is selected from halogen, C1-C4 alkyl, C3-C6 cycloalkyl, $R_{34}O(CH_2)_p$, $R_{43}O(CH_2)_qC(O)$, $R_{38}R_{39}N$, and $R_{40}R_{41}N(CO)$.

In some embodiments, of a compound of formula (Iu), $R_A$, $R_B$ and $R_C$ are independently selected from H, halogen, cyano, and C1-C4 alkyl; W is a direct bond or C1-C3 alkylene; n is 0 or 1; and $R_{33}$ is halogen, C1-C4 alkyl optionally substituted by $R_{34}O$; C3-C6 cycloalkyl, $R_{34}O$, $R_{37}C(O)$, $R_{38}R_{39}N$, or $R_{40}R_{41}N(CO)$.

In some embodiments of a compound of formula (Io), when ring A is 4- to 6-membered heterocyclyl, ring A more specifically is a 4- to 6-membered non-aromatic, e.g. saturated heterocyclyl. In some embodiments, the heterocyclyl is 4- or 5-membered, e.g. 4-membered. In some other embodiments, the heterocyclyl is 5- or 6-membered, e.g. 5-membered. In still other embodiments, the heterocyclyl is 6-membered.

When ring A is 4- to 6-membered saturated heterocyclyl, said ring preferably contains 1 or 2 heteroatoms in the ring, whereby each ring heteroatom preferably is selected from N and O.

In some embodiments, ring A is 4- to 6-membered saturated heterocyclyl containing one N and optionally also one O in the ring.

In some embodiments, ring A is 4- to 6-membered saturated heterocyclyl containing one ring heteroatom only, selected from N and O.

In some embodiments, ring A is 4- to 6-membered saturated heterocyclyl containing one ring heteroatom only, which is N.

When ring A is 4- to 6-membered saturated heterocyclyl containing an N in the ring, said N may be the point of attachment of the linking moiety W or, when it is not the point of attachment of the linking moiety W, said N may be substituted by one moiety $R_{33}$, or unsubstituted (i.e. carrying a hydrogen atom).

In some embodiments, when A is 4- to 6-membered heterocyclyl, containing one N in the ring, the compound of formula (I) may be represented by formula (Iz)

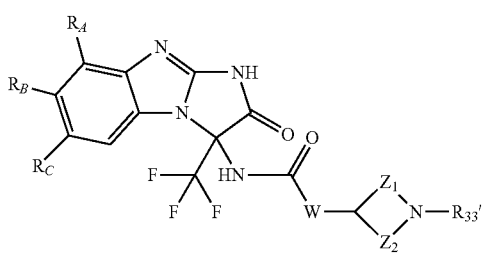

(Iz)

wherein $R_A$, $R_B$, $R_C$ and W are as defined herein, $Z_1$ is $(CH_2)_u$, and $Z_2$ is $(CH_2)_v$, wherein u and v are both integers of from 0 to 4, and u+v is an integer of from 2 to 4; and $R_{33}'$ is H or $R_{33}$ as defined herein above.

In some embodiments of a compound of formula (Iz), both u and v are 1. In some embodiments of a compound of formula (Iz), u+v is 3 or 4. In some of these embodiments, u is 0 and v is 3 or 4. In some other of these embodiments, u is 1 and v is 2 or 3. In still other of these embodiments both u and v are 2.

In a compound of formula (Iz), $R_{33}'$ is H or $R_{33}$ as defined herein above. In some embodiments of a compound of formula (Iz), $R_{33}'$ is C1-C4 alkyl, pyridyl, $R_{36}S(O)_2$, or $R_{37}C(O)$. In some particular embodiments, $R_{33}'$ is $R_{37}C(O)$, or $R_{36}S(O)_2$; e.g. $R_{33}'$ is $R_{37}C(O)$.

In some embodiments of a compound of formula (Io), ring A is 4- to 6-membered heterocyclyl attached to the linking moiety W through at ring heteroatom which is N. For example, in such embodiments, ring A may be morpholin-4-yl, pyrrolidin-1-yl or azetidin-1-yl.

In some embodiments, ring A is morpholin-4-yl. In some embodiments, ring A is pyrrolidin-1-yl.

In some embodiments, when ring A is morpholin-4-yl or pyrrolidin-1-yl, n is 0. In some embodiments, when ring A is morpholin-4-yl or pyrrolidin-1-yl, W is C1-C3 alkylene.

In some embodiments, ring A is azetidin-1-yl. In some embodiments, when ring A azetidin-1-yl, n is 2 and both $R_{33}$ are attached to the same carbon atom and are F.

In some embodiments, when ring A is azetidin-1-yl, W is C1-C3 alkylene.

In some particular embodiments, when ring A is 4- to 6-membered heterocyclyl,
$R_A$, $R_B$ and $R_C$ are independently selected from H, halogen, and C1-C4 alkyl,
W is a direct bond or C1-C3 alkylene;
n is an integer of from 0 to 2; and
each $R_{33}$ is independently selected from halogen, C1-C4 alkyl, pyridyl, and $R_{37}C(O)$.

When ring A is C4-C6 cycloalkyl or C5-C6 cycloalkenyl, it more preferably is C4-C6 cycloalkyl. In some embodiments of a compound of formula (Io) ring A is a C4 to C6 cycloalkyl, i.e. cyclobutyl, cyclopentyl or cyclohexyl. In these embodiments, the compound may be represented by formula (Iaa)

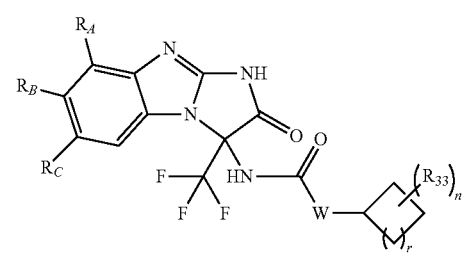

(Iaa)

wherein $R_A$, $R_B$, $R_C$, W, $R_{33}$ and n are as defined herein and r is an integer of from 1 to 3.

In a compound of formula (Iaa) the moiety W is as defined herein above. In some embodiments, the moiety W is a direct bond, C1-C3 alkylene, or C1-C3 alkylene substituted by C1-C4 alkyl, e.g. W is a direct bond or C1-C3 alkylene, in particular W is a direct bond, $CH_2$, $CH_2CH_2$ or $CH_2CH_2CH_2$.

In some embodiments of a compound of formula (Iaa), W is a direct bond. In some other embodiments, W is C1-C3 alkylene optionally substituted by C1-C4 alkyl or $R_{32}O$; in particular W is C1-C3 alkylene, optionally substituted by C1-C4 alkyl, e.g., W is $CH_2$, $CH_2CH_2$ or $CH_2CH_2CH_2$, optionally substituted by C1-C4 alkyl, in particular W is $CH_2CH_2$ optionally substituted by C1-C4 alkyl. In some embodiments W is $CH_2$, $CH_2CH_2$ or $CH_2CH_2CH_2$.

In a compound of formula (Iaa), r is an integer of from 1 to 3. In some embodiments, r is 2 or 3, i.e. ring A is cyclopentyl or cyclohexyl, e.g. cyclohexyl. In some other embodiments, r is 1 or 2, i.e. ring A is cyclobutyl or cyclopentyl. In some particular embodiments, r is 2, i.e. ring A is cyclopentyl.

In some particular embodiments of the compound of formula (Iaa), W is $CH_2CH_2$, r is 2, and n is an integer as defined herein above, preferably n is 0, 1 or 2, e.g. n is 0 or 1. In some embodiments of a compound of formula (Iaa), n is 0. In some other embodiments of a compound of formula (Iaa), n is 1, e.g. n is 1 and $R_{33}$ is $R_{34}O$, in particular OH.

In some embodiments of a compound of formula (Iaa), when n is 2, the two $R_{33}$ are attached to one and the same carbon atom of ring A and form a biradical —$CH_2$-L-$CH_2$— wherein L is $CH_2$, NH or O, e.g. L is NH.

For example, in some embodiments of a compound of formula (Iaa), r is 1, n is 2 and the two $R_{33}$ present in the compound are attached to one and the same carbon atom and form a biradical $CH_2$-L-$CH_2$. In some of these embodiments, the compound of formula (Iaa) may be represented by formula (Iab)

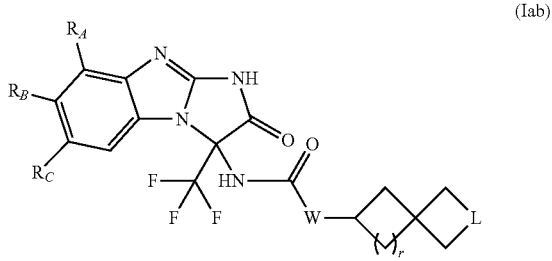

(Iab)

wherein $R_A$, $R_A$, $R_B$, $R_C$, $R_{33}$, W, r and L are as defined herein.

In some embodiments of a compound of formula (Iab), r is 1. In some embodiments of a compound of formula (Iab), L is NH. In some particular embodiments of a compound of formula (Iab), r is 1 and L is NH.

In some embodiments of a compound of formula (Iaa), $R_A$, $R_B$ and $R_C$ are independently selected from H, halogen, cyano, C1-C4 alkyl, $R_1O$, $R_2C(O)$, $R_3S$, and $R_4S(O)_2$; or one of $R_A$ and $R_C$ together with $R_B$ forms a biradical —$(CH_2)_m$— wherein m is an integer of from 3 to 5, and the other one of $R_A$ and $R_C$ is selected from H, halogen, cyano, C1-C4 alkyl, $R_1O$, $R_2C(O)$, $R_3S$, and $R_4S(O)_2$;

$R_1$, $R_2$, $R_3$ and $R_4$ are independently selected from C1-C4 alkyl;

W is a direct bond or C1-C3 alkylene optionally substituted by C1-C4 alkyl;

n is an integer of from 0 to 2, $R_{33}$ is OH or, when n is 2, two $R_{33}$ are attached to one and the same carbon atom and form a biradical —$CH_2$—NH—$CH_2$—.

In the compounds of the invention, any alkyl, whether part of a functional group or not, may optionally be substituted with one or more F.

Studies have shown efficacy of the compounds of the invention in vitro and in vivo in mice and, although the compounds have been developed toward S100A9 inhibition, they can also show activity to other S100 proteins. The present invention therefore relates to compounds as defined herein, as S100 protein inhibitors, mainly as S100A9 inhibitors and to their use in treatment or prevention of S100-protein related diseases, in particular diseases related to the activity of S100A9 protein.

In particular, the present invention relates to the compounds of formula (I) as defined herein, to pharmaceutical compositions comprising said compounds, to the use of such compositions in the therapeutic treatment of conditions selected from in particular cancer, but also autoimmune diseases, inflammatory diseases and neurodegenerative diseases, to a method of treatment of such conditions, and to said compounds for use in the treatment of conditions selected from in particular cancer, but also autoimmune diseases, inflammatory diseases and neurodegenerative diseases, as well as the use of said compounds in the manufacture of pharmaceutical compositions for the treatment of such conditions.

The present invention includes pharmaceutical compositions comprising at least one compound according to formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

For inhalation or nasal administration, suitable pharmaceutical formulations are as particles, aerosols, powders, mists or droplets, e.g. with an average size of about 10 µm in diameter or less. For example, compositions for inhalation may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery. The composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

According to one aspect, the present invention relates to a method of treatment of a disease that responds to inhibition of a member of the S100 protein family, e.g. S100A9, e.g. a cancer, an autoimmune disease, an inflammatory disease, or a neurodegenerative disease, which method comprises administering a therapeutically effective amount of a compound of formula (I), or pharmaceutically acceptable salt thereof, to a warm-blooded animal, e.g., a human, in need of such treatment.

In some embodiments, the disorder treated according to the present invention is a cancer, e.g. a cancer such as defined herein above.

In some other embodiments, the disorder treated according to the present invention is an autoimmune disorder, e.g. and autoimmune disorder such as defined herein above.

In some other embodiments, the disorder treated according to the present invention is an inflammatory disorder, e.g. an inflammatory disorder such as defined herein above.

In some other embodiments, the disorder treated according to the present invention is an neurodegenerative disorder, e.g. a neurodegenerative disorder such as defined herein above.

The preparation of compounds according to the present invention is well within the capacity of the person of ordinary skill in the art. For example, a compound of formula (I) may be prepared in a reaction sequence as generally illustrated in Reaction Scheme 1. Thus, in a general method for preparing a compound of formula (I) as defined herein a primary amide 1 is first reacted with an alkyl 3,3,3-trifluoro-2-oxopropanoate 2, wherein R' is an alkyl group, e.g. a C1-C3 alkyl group, such as methyl, in the presence of an organic base, e.g. pyridine or triethyl amine, in a suitable solvent medium, e.g. DMF, DMSO or N-methyl pyrrolidine, followed by the addition of a reagent such as thionyl chloride or oxalyl chloride, to provide an "acyl imine intermediate" of the general formula 3.

The acyl imine 3 is then reacted with an aminobenzimidazole 4 in a suitable solvent medium, e.g. DMF, DMSO or N-methyl pyrrolidine, to provide the compound formula (I) wherein $R_A$, $R_{A'}$, $R_B$, $R_C$, $R_{33}$, n, W and ring A are as defined herein.

Reaction Scheme 1

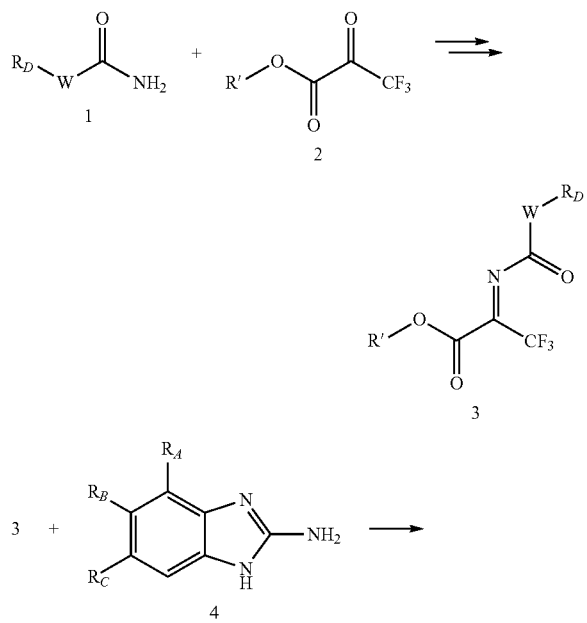

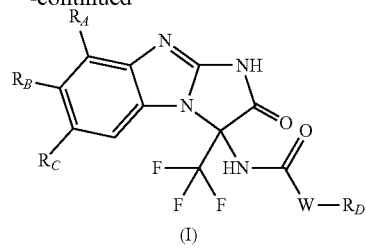

(I)

The following examples will enable a person skilled in the art to more clearly understand and practice the present invention. These examples, however, should not be considered as limiting the scope of the invention, but merely as being illustrative and representative thereof.

EXAMPLES

All pyridine used was anhydrous (stored under nitrogen over activated 4 Å mol sieves).

All DMF used was anhydrous (stored under nitrogen over activated 4 Å mol sieves).

All naming of molecules was performed using Marvin-Sketch 14.10.27.0

HPLC methods are as follows:

"Low pH Method A" refers to HPLC purification using a mobile phase consisting of 0.2% formic acid in a gradient of 0-100% MeCN in water. The stationary phase consisted of a Waters Sunfire C18 column, 10 μm particle size, 30×100 mm.

"Low pH Method B" refers to HPLC purification using a mobile phase consisting of 0.1% formic acid in a gradient of 0-100% MeCN in water. The stationary phase consisted of a Waters Sunfire C18 column, 5 μm particle size, 19×100 mm.

"High pH" refers to HPLC purification using a mobile phase consisting of 0.2% aqueous ammonia in a gradient of 5-100% MeCN in water. The stationary phase consisted of a Waters X-bridge C18 column, 10 μm particle size, 30×100 mm.

"Neutral" refers to HPLC purification using a mobile phase (without modifier) consisting of a gradient of 10-100% MeCN in water. The stationary phase consisted of a Waters Sunfire C18 column, 10 μm particle size, 30×100 mm.

SFC chromatography was carried out using a Chiralpak AD-H column with a mobile phase of supercritical $CO_2$ and MeOH containing 0.1% formic acid.

Microwave reactions were carried out using a CEM Discover, Biotage Initiator+ or Activent microwave apparatus.

The term "acyl imine intermediate" refers to the product of the reaction between a primary amide ($RCONH_2$) and alkyl 3,3,3-trifluoro-2-oxopropanoate. General formula:

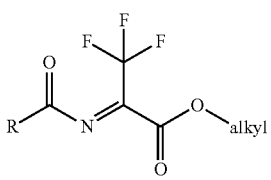

For example the product of the reaction between benzamide and methyl 3,3,3-trifluoro-2-oxopropanoate, i.e. (methyl (2Z)-2-{[(Z)-benzoyl]imino}-3,3,3-trifluoropropanoate) is considered an "acyl imine intermediate".

Intermediate 1

(Z)-methyl 2-(benzoylimino)-3,3,3-trifluoropropanoate

To a stirred solution of benzamide (3.00 g, 24.8 mmol) in DMF (60 mL) was added pyridine (2.00 mL, 24.8 mmol) followed by methyl 3,3,3-trifluoro-2-oxopropanoate (3.86 g, 24.8 mmol) dropwise under nitrogen and the solution stirred for 1 h. Additional methyl 3,3,3-trifluoro-2-oxopropanoate (1.53 g) was added and the reaction stirred for a further 2 h. The resulting solution was cooled to 0° C. under nitrogen, then thionyl chloride (1.80 mL, 24.8 mmol) was added and the solution stirred for a further 2 h at 0° C. The reaction mixture was concentrated. The residue was filtered through a short pad of silica, using EtOAc as eluent, to afford the title compound (5.47 g, 85%); MeOH adduct observed in MS: m/z=291.8 (MH)$^+$.

MeOH adduct observed in MS:

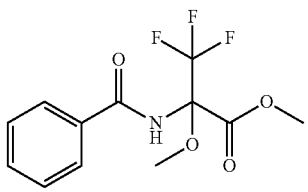 [SMILES: COC(=O)C(NC(=O)c1ccccc1)(OC)C(F)(F)F]

Intermediate 2

N-[4-oxo-3-(trifluoromethyl)-2,5,7-triazatricyclo [6.4.0.0$^{2,6}$]dodeca-1(8),6,9,11-tetraen-3-yl]prop-2-enamide To a stirred solution of acrylamide (1.00 g, 14.1 mmol) in anhydrous DMF (25 mL), under nitrogen, was added pyridine (1.13 mL, 14.1 mmol) followed by methyl 3,3,3-trifluoro-2-oxopropanoate (1.45 mL, 14.1 mmol). The reaction mixture was stirred at room temperature for 1 h and then thionyl chloride (1.02 mL, 14.1 mmol) was added dropwise. The solution was stirred for 3 h at room temperature and then concentrated. The residue was filtered through a short pad of silica, eluting with EtOAc (100 mL), and the filtrate was concentrated. The acyl imine intermediate that remained was dissolved in anhydrous DMF (20 mL) and 2-aminobenzimidazole (1.87 g, 14.1 mmol) and triethylamine (1.87 mL, 14.1 mmol) were added under nitrogen. The solution was stirred for 16 h at room temperature and then concentrated. The residue was dissolved in EtOAc (25 mL) and washed with water (25 mL) and brine (25 mL). The organic phase was dried (MgSO$_4$), filtered and concentrated. The crude product was purified by silica chromatography, using 0-5% MeOH in DCM as eluent, to afford the title compound as a white solid (1.05 g, 24%); m/z=311.0 (MH)$^+$.

Intermediate 3

3-cyclopentylpropanamide

A solution of 3-cyclopentylpropanoyl chloride (5.00 g, 31.1 mmol) in anhydrous THF (40 mL) was added dropwise, over 30 min, to aqueous ammonia (9.35 mL, 93.4 mmol) and THF (10 mL) at 0° C. under nitrogen. The solution was allowed to warm to room temperature and stirred for 1 h. The reaction mixture was concentrated and partitioned between water (50 mL) and EtOAc (3×25 mL). The combined organic phases were dried (MgSO$_4$), filtered and concentrated to afford 3-cyclopentylpropanamide as a white solid (3.95 g, 90%); $^1$H NMR (500 MHz, Chloroform-d) δ 0.97-1.11 (m, 2H). 1.39-1.50 (m, 2H), 1.50-1.62 (m, 4H), 1.63-1.76 (m, 3H), 2.11-2.20 (m, 2H), 5.47 (s, 1H), 5.76 (s, 1H).

Intermediate 4

(Z)-methyl 2-((3-cyclopentylpropanoyl)imino)-3,3,3-trifluoropropanoate

The procedure for the preparation of (Z)-methyl 2-(benzoylimino)-3,3,3-trifluoropropanoate was used except that 3-cyclopentylpropanamide was used instead of benzamide. No additional charge of methyl 3,3,3-trifluoro-2-oxopropanoate was necessary. Eluent was 50-100% EtOAc in heptane (66%); H$_2$O adduct observed in MS: m/z=296.1 (M−1)$^−$.

Intermediate 5

(Z)-methyl 3,3,3-trifluoro-2-((3-phenylpropanoyl) imino)propanoate

The procedure for the preparation of (Z)-methyl 2-(benzoylimino)-3,3,3-trifluoropropanoate was used except that 3-phenylpropanamide was used instead of benzamide. No additional charge of methyl 3,3,3-trifluoro-2-oxopropanoate was necessary; (99%); H$_2$O adduct observed in MS: m/z=306.1 (MH)$^+$.

H$_2$O adduct observed in MS:

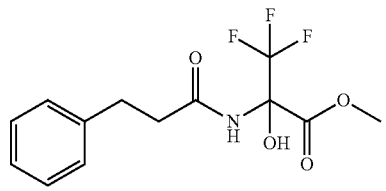 [SMILES: COC(=O)C(O)(NC(=O)CCc1ccccc1)C(F)(F)F]

Intermediate 6

3-(2-chlorophenyl)propanamide

To a solution of 3-(2-chlorophenyl)propanoic acid (1.0 g, 5.42 mmol) in DCM (100 mL) was added thionyl chloride (0.39 mL, 5.42 mmol) dropwise under nitrogen. The solution was stirred at room temperature for 3 h and then concentrated. The residue was dissolved in anhydrous THF (10 mL) and cooled to 0° C. 7M Ammonia in methanol (1.55 mL) was added dropwise under nitrogen. The reaction was stirred at room temperature for 4 h and then concentrated. The residue was dissolved in EtOAc (50 mL) and washed with saturated NaHCO$_3$ (aq) (2×25 mL) and brine (25 mL). The organic phase was dried (MgSO$_4$), filtered and concentrated, to afford the title compound as a yellow solid (530 mg, 53%); m/z=183.9, 185.9 (MH)$^+$.

Intermediate 7

N-[10,11-dimethyl-4-oxo-3-(trifluoromethyl)-2,5,7-triazatricyclo[6.4.0.0$^{2,6}$]dodeca-1(8),6,9,11-tetraen-3-yl]prop-2-enamide To a stirred solution of acrylamide (1.00 g, 14.1 mmol) in DMF (25 mL), under nitrogen, was added methyl 3,3,3-trifluoro-2-oxopropanoate (1.45 mL, 14.1 mmol) followed by pyridine (1.13 mL, 14.1 mmol). The reaction mixture was stirred at room temperature for 1 h and then cooled to 0° C. Thionyl chloride (1.02 mL, 14.1 mmol) was added dropwise to the solution. The reaction mixture was allowed to warm to room temperature, stirred for a further 24 h and then concentrated. The acyl imine intermediate was dissolved in DMF (25 mL) and triethylamine (1.87 mL, 14.1 mmol) and 5,6-dimethyl-1H-1,3-benzodiazol-2-amine (2.27 g, 14.1 mol) were added under nitrogen. The reaction mixture was stirred for 5 h at room temperature then concentrated. The residue was dissolved in DCM (100 mL) and washed with water (2×100 mL). The organic phase was dried (MgSO$_4$), filtered and concentrated. The crude product was purified by silica chromatography, using 0-5% MeOH in DCM as eluent, to afford the title compound as a white solid (1.30 g, 27%); m/z=339.0 (MH)$^+$.

Intermediate 8

6-(2,2,2-trifluoroethoxy)pyridine-3-carboxamide

To a stirred solution of 6-(2,2,2-trifluoroethoxy)pyridine-3-carboxylic acid (1.00 g, 4.52 mmol) in DCM (50 mL) and DMF (0.1 mL) was added thionyl chloride (328 µL, 4.52 mmol) dropwise under nitrogen. The reaction mixture was stirred at room temperature for 3 h and then concentrated. The residue was dissolved in anhydrous THF (25 mL), cooled to 5° C. and excess aqueous ammonia was added. The reaction mixture was allowed to warm to room temperature and stirred for a further 3 h. The mixture was extracted with EtOAc (3×50 mL) and the combined organic phases were washed with saturated NaHCO$_3$ (aq) (50 mL) and brine (50 mL). The organic phase was dried (MgSO$_4$), filtered and concentrated to afford the title compound as a white solid (798 mg, 80%); m/z=221.0 (MH)$^+$.

Intermediate 9

5,6-dichloro-1H-1,3-benzodiazol-2-amine

The title compound was prepared according to Int. Appl. No. PCT/US2007/020982 (Publ. No. WO2008042282) (quantitative yield); m/z=201.8, 203.9 (MH)$^+$.

Intermediate 10 tert-butyl 6-carbamoyl-2-azaspiro[3.3]heptane-2-carboxylate

To a stirred solution of 2-[(tert-butoxy)carbonyl]-2-azaspiro[3.3]heptane-6-carboxylic acid (700 mg, 2.90 mmol) in DCM (100 mL), under nitrogen, was added triethylamine (386 µL, 2.90 mmol). The reaction was cooled to 0° C. and chloro(ethoxy)methanone (304 µL, 3.19 mmol) was added dropwise. The reaction was allowed to warm to room temperature and stirred for 2 h. The reaction was then cooled to 0° C. and aqueous ammonia (290 µL, 2.90 mmol) was added. The reaction was allowed to warm to room temperature and stirred for 3 h. The reaction was diluted with DCM (100 mL) and washed with water (3×50 mL) and 10% NaHCO$_3$ (aq) (50 mL). The organic phase was dried (MgSO$_4$), filtered and concentrated to afford the title compound as a white solid (601 mg, 86%); m/z=184.9 (MH-$^t$Bu)$^+$.

Intermediate 11 tert-butyl 6-{[[10,11-dichloro-4-oxo-3-(trifluoromethyl)-2,5,7-triazatricyclo[6.4.0.0$^{2,6}$]-dodeca-1(12),6,8,10-tetraen-3-yl]carbamoyl}-2-azaspiro[3.3]heptane-2-carboxylate To a stirred solution of tert-butyl 6-carbamoyl-2-azaspiro[3.3]heptane-2-carboxylate (515 mg, 2.14 mmol) in DMF (20 mL), under nitrogen, was added pyridine (173 µL, 2.14 mmol) and methyl 3,3,3-trifluoro-2-oxopropanoate (669 mg, 4.29 mmol). The reaction mixture was stirred for 16 h at room temperature and then cooled to 0° C. Thionyl chloride (156 mL, 2.14 mmol) added dropwise and the solution was stirred at 0° C. for 1 h before being concentrated. The residue was filtered through a short pad of silica, eluting with DCM/DMF (10:1), and the filtrate was concentrated. The acyl imine intermediate that remained was dissolved in DMF (20 mL) under nitrogen. 5,6-Dichloro-1H-1,3-benzodiazol-2-amine (325 mg, 1.61 mmol) and triethylamine (285 µL, 2.14 mmol) were added to the solution and the reaction was stirred for 3 h at room temperature before being concentrated. The residue was dissolved in EtOAc (50 mL) and washed with water (3×50 mL) and brine (2×50 mL). The organic phase was dried (MgSO$_4$), filtered and concentrated. The crude product was purified by silica chromatography, eluting with 0-7% MeOH in DCM, to afford the title compound as an off-white solid (411 mg, 35%); m/z 491.8, 493.8 (MH-tBu)$^+$.

Intermediate 12

3-(2,6-dichlorophenyl)propanamide

To a stirred solution of 3-(2,6-dichlorophenyl)propanoic acid (1.00 g, 4.59 mmol) in DCM (20 mL) was added thionyl chloride (1.67 mL, 23.0 mmol) dropwise, under argon. The reaction mixture was refluxed for 3 h and then concentrated. The residue was dissolved in DCM (10 mL) and cooled to 0° C. Ammonia gas was bubbled through the reaction for 10 min. The reaction was concentrated and diluted with water (10 mL). The resulting white solid was collected by filtration and dried to afford the title compound as a white solid (700 mg, 70%); m/z=218.3, 220.3 (MH)$^+$.

Intermediate 13

6-(cyclohexylamino)pyridine-3-carboxamide

To a solution of 6-chloropyridine-3-carboxamide (1.00 g, 6.40 mmol) in NMP (5 mL), in a microwave tube, were added N,N-diisopropylethylamine (2.19 mL, 12.8 mmol) and cyclohexylamine (2.93 mL, 25.6 mmol). The reaction mixture was heated in the microwave at 200° C. for 1 h and concentrated. The residue was purified by silica chromatography, using 2% MeOH in DCM as eluent, to afford the title compound as an off-white solid (350 mg, 25%); m/z=220.2 (MH)$^+$.

Intermediate 14

3-(pyridin-3-yl)propanamide

To a solution of 3-(pyridine-3-yl)propionic acid (500 mg, 3.27 mmol) in DCM (10 mL), at 0° C. was added oxalyl chloride (0.84 ml, 9.81 mmol) dropwise. The reaction was allowed to warm to room temperature, stirred for 3 h and then concentrated. The residue was dissolved in DCM (15 mL), cooled to 0° C. and ammonia gas bubbled through the solution for 15 min. The reaction was then concentrated and the resulting white solid was triturated in water (8 mL). The solid was filtered and dried under vacuum to afford the title compound as white solid (200 mg, 40%); m/z=151.2 (MH)$^+$.

Intermediate 15

4-(pyrrolidin-1-yl)butanamide

Aqueous ammonia (303 µL, 16.2 mmol) was added to ethyl 4-(pyrrolidin-1-yl)butanoate, prepared according to Int. Appl. No. PCT/US2009/050797 (Publ. No. WO2010009290), (1.00 g, 5.40 mmol), in a sealed tube. The reaction was stirred at room temperature for 16 h and then concentrated. The residue was purified by silica chromatography, using 5% MeOH in DCM as eluent, to afford the title compound as a colourless oil (750 mg, 89%); $^1$H NMR (400 MHz, DMSO-d$_6$) δ 1.57-1.72 (m, 8H), 2.01-2.09 (m, 2H), 2.28-2.36 (m, 2H), 2.50-2.58 (m, 2H), 6.68 (s, 1H), 7.20 (s, 1H).

Intermediate 16 ethyl 4-(morpholin-4-yl)butanoate

To a stirred solution of ethyl 4-bromobutanoate (2.93 mL, 20.0 mmol) in toluene (30 mL) was added morpholine (7.14 mL, 80.0 mmol). The solution was refluxed for 10 h. The resulting white solid was removed by filtration and washed with diethyl ether (100 mL). The filtrate was concentrated to afford the title compound as a yellow oil (3.20 g, 78%); $^1$H NMR (400 MHz, DMSO-d$_6$) δ 1.17 (t, 3H), 1.62-1.70 (m, 2H), 2.21-2.32 (m, 8H), 3.51-3.57 (m, 4H), 4.03 (q, 2H).

Intermediate 17

4-(morpholin-4-yl)butanamide

Aqueous ammonia (4 mL) was added to ethyl 4-(morpholin-4-yl)butanoate (700 mg, 3.30 mol) and the reaction mixture was stirred at room temperature for 3 h. The mixture was concentrated and azeotroped with toluene to afford the title compound as a yellow semi-solid (410 mg, 65%); $^1$H NMR (400 MHz, DMSO-d$_6$) δ 1.62-1.70 (m, 2H), 2.21-2.32 (m, 8H), 3.51-3.57 (m, 4H), 7.22 (s, 2H).

Intermediate 18 ethyl 2-[(5,6-dichloro-1H-1,3-benzodiazol-2-yl)amino]-3,3,3-trifluoro-2-[3-(morpholin-4-yl)propanamido]propanoate To a solution of 3-(morpholin-4-yl)propanamide, prepared according to literature (You et. al., 2008); (500 mg, 3.16 mmol), in DMF (5 mL) were added ethyl 3,3,3-trifluoro-2-oxopropanoate (419 µL, 3.16 mmol) and pyridine (269 µL, 3.16 mmol) were added. The reaction mixture was stirred for 2 h at room temperature under argon and then thionyl chloride (230 µL, 3.16 mmol) was added dropwise to the solution. Stirring was continued for a further 24 h and then the reaction was concentrated. The resulting acyl imine was dissolved in DMF (5 ml) and then added to a solution of 5,6-dichloro-1H-1,3-benzodiazol-2-amine (615 mg, 3.05 mmol) in DMF (5 mL). Triethylamine (422 µL, 3.05 mmol) was added and the reaction mixture stirred at room temperature for 16 h. The reaction was diluted with brine (25 mL) and extracted with EtOAc (2×35 mL). The combined organic phases were washed with water, dried (Na$_2$SO$_4$), filtered and concentrated. The crude product was purified by silica chromatography, using 2% MeOH in DCM as eluent, to afford the title compound as a brown oil (427 mg, 1%); m/z=512.5 (MH)$^+$.

Intermediate 19 tert-butyl 2-(2-carbamoylethyl)piperidine-1-carboxylate

To a stirred solution of 3-{1-[(tert-butoxy)carbonyl]piperidin-2-yl}propanoic acid (200 mg, 0.78 mmol) in chloroform (20 mL) were added triethylamine (108 µL, 0.78 mmol) and isobutyl chloroformate (93 µL, 0.78 mmol) at 0° C. under argon. The reaction mixture was stirred at room temperature for 2 h, and then ammonia gas was bubbled through the reaction mixture for 15 min. The reaction mixture was diluted with DCM and washed with 5% NaHCO$_{3(aq)}$ and 1M HCl$_{(aq)}$. The organic phase was dried (Na$_2$SO$_4$), filtered and concentrated. The crude product was purified by silica chromatography, using 2% MeOH in DCM as eluent, to afford the title compound as a colourless oil (110 mg, 55%); $^1$H NMR (400 MHz, DMSO-d$_6$) δ 1.16-1.26 (m, 1H), 1.37 (s, 9H), 1.43-1.64 (m, 6H), 1.80-2.04 (m, 3H), 2.73 (d, 1H), 3.80 (d, 1H), 4.07 (s, 1H), 6.70 (s, 1H), 7.24 (s, 1H).

Intermediate 20 tert-butyl 4-(carbamoylmethyl)piperidine-1-carboxylate

The procedure for the preparation of tert-butyl 2-(2-carbamoylethyl)piperidine-1-carboxylate was used except that 2-{1-[(tert-butoxy)carbonyl]piperidin-4-yl}acetic acid was used instead of 3-{1-[(tert-butoxy)carbonyl]piperidin-2-yl}propanoic acid (72%); $^1$H NMR (400 MHz, DMSO-d$_6$) δ 0.90-1.04 (m, 2H), 1.37 (s, 9H), 1.52-1.64 (m, 2H), 1.72-1.84 (m, 1H), 1.90-2.00 (m, 2H), 2.66 (s, 2H), 3.87 (d, 2H), 6.75 (s, 1H), 7.24 (s, 1H)

Intermediate 21

1H,5H,6H,7H-indeno[5,6-d]imidazol-2-amine

The procedure for the preparation of 5,6-dichloro-1H-1,3-benzodiazol-2-amine was used, except that 2,3-dihydro-1H-indene-5,6-diamine was used instead of 4,5-dichlorobenzene-1,2-diamine (quantitative yield); m/z=173.9 (MH)$^+$.

Intermediate 22

4,5-dimethyl-1H-1,3-benzodiazol-2-amine

The procedure for the preparation of 5,6-dichloro-1H-1,3-benzodiazol-2-amine was used, except that 3,4-dimethylbenzene-1,2-diamine was used instead of 4,5-dichlorobenzene-1,2-diamine (83%); m/z=162.0 (MH)+.

Intermediate 23

4-methyl-1H-1,3-benzodiazol-2-amine

The procedure for the preparation of 5,6-dichloro-1H-1,3-benzodiazol-2-amine was used, except that 3-methylbenzene-1,2-diamine was used instead of 4,5-dichlorobenzene-1,2-diamine (quantitative yield); m/z=148.0 (MH)+.

Intermediate 24

4,5-difluoro-1H-1,3-benzodiazol-2-amine

The procedure for the preparation of 5,6-dichloro-1H-1,3-benzodiazol-2-amine was used, except that 3,4-difluorobenzene-1,2-diamine was used instead of 4,5-dichlorobenzene-1,2-diamine (60%); m/z=170.0 (MH)+.

Intermediate 25

3,4-dichlorobenzene-1,2-diamine

To a solution of 2,3-dichloro-6-nitroaniline, available via a literature method (Carta et al., 2007) (1.08 g, 5.21 mmol) in MeOH (4.40 mL) was added a solution of tin(II)chloride dihydrate (4.71 g, 20.87 mmol) in concentrated HCl (6.60 mL). The reaction was heated at 70° C. for 4 h. The reaction mixture was concentrated to half the volume, basified with 5M NaOH(aq), diluted with EtOAc (20 mL) and stirred for 30 min. The resulting precipitate was removed by filtration. The filtrate was washed with brine (20 mL), dried ($Na_2SO_4$), filtered and concentrated to give the desired product as a pale brown solid (0.87 g, 94%); m/z=176.9, 178.9 (MH)+.

Intermediate 26

4,5-dichloro-1H-1,3-benzodiazol-2-amine

The procedure for the preparation of 5,6-dichloro-1H-1,3-benzodiazol-2-amine was used, except that 3,4-dichlorobenzene-1,2-diamine was used instead of 4,5-dichlorobenzene-1,2-diamine (48%); m/z=201.9, 203.9 (MH)+.

Intermediate 27

4-chloro-1H-1,3-benzodiazol-2-amine

The procedure for the preparation of 5,6-dichloro-1H-1,3-benzodiazol-2-amine was used, except that 3-chlorobenzene-1,2-diamine (available according to a method described in Int. Appl. No. PCT/US2008/003935 (Pub. No. WO2008118454)) was used instead of 4,5-dichlorobenzene-1,2-diamine (57%); m/z=167.9, 169.9 (MH)+.

Intermediate 28

4-chloro-1H-imidazo[4,5-c]pyridin-2-amine

To a solution of 2-chloropyridine-3,4-diamine (0.92 g, 6.42 mmol) in DCE (36 mL) was added ethyl N-carbothioylcarbamate (0.83 mL, 7.1 mmol) dropwise under nitrogen. After 10 min, EDC.HCl (1.35 g, 7.1 mmol) and N,N-diisopropylethylamine (5.60 mL, 32.1 mmol) were added. After refluxing for 2 h the reaction was concentrated. The residue was dissolved in 1M NaOH(aq) (50 mL), washed with DCM (2×40 mL) and neutralised with 1M HCl. The resulting precipitate was collected by filtration and triturated in DCM. The carbamate was taken up in EtOH (10 vol) and 2M NaOH(aq) (3 eq) was added. The reaction was heated at reflux for 8 h. Reaction was concentrated, taken up in water, neutralised with 3M HCl(aq), extracted with propan-2-ol/chloroform (3×50 mL), dried (Na2SO4), filtered and concentrated to give the title compound as a white solid (0.43 g, 40%). m/z=168.9, 170.9 (MH)+.

Intermediate 29

4,6-difluoro-1H-1,3-benzodiazol-2-amine

The procedure for the preparation of 5,6-dichloro-1H-1,3-benzodiazol-2-amine was used, except that 3,5-difluorobenzene-1,2-diamine was used instead of 4,5-dichlorobenzene-1,2-diamine (48%); m/z=169.9 (MH)+.

Intermediate 30 oxane-4-carboxamide

To a stirred solution of oxane-4-carboxylic acid (800 mg, 6.15 mmol) in chloroform (5 mL) were added triethylamine (1.28 mL, 9.22 mmol) and isobutyl chloroformate (884 µl, 7.37 mmol) dropwise at 0° C. under argon. The reaction mixture was stirred at 0° C. for 2 h and then ammonia gas was passed through the solution for 15 min. The reaction mixture was concentrated. The residue was dissolved in propan-2-ol/chloroform (1:4, 25 mL) and washed with water, 5% $NaHCO_{3(aq)}$ and then 1M $HCl_{(aq)}$. The organic phase was dried ($Na_2SO_4$), filtered and concentrated. The crude product was purified by trituration in DCM to afford the title compound as a white solid (1.20 g, 91%); $^1$H NMR (400 MHz, DMSO-$d_6$) δ 1.44-1.63 (m, 4H), 2.23-2.34 (m, 1H), 3.27 (td, 2H), 3.82 (ddd, 2H), 6.75 (s, 1H), 7.22 (s, 1H).

Intermediate 31

N-[10,11-dichloro-4-oxo-3-(trifluoromethyl)-2,5,7-triazatricyclo[6.4.0.0$^{2,6}$]dodeca-1(8),6,9,11-tetraen-3-yl]prop-2-enamide To a stirred solution of prop-2-enamide (170 mg, 2.38 mmol) in DMF (8 mL) were added methyl 3,3,3-trifluoro-2-oxopropanoate (400 µL, 3.96 mmol) and pyridine (190 µL, 2.38 mmol) at room temperature under nitrogen. The reaction mixture was stirred for 2 h. Thionyl chloride (180 µL, 2.38 mmol) was added dropwise at 0° C. and the reaction mixture was stirred for 1 h. The reaction mixture was concentrated and the residue filtered through a short pad of silica, eluting with DCM, under nitrogen. The filtrate was concentrated, and the acyl intermediate that remained was dissolved in DMF (6 mL) under nitrogen. The solution of acyl intermediate was added to a solution of 5,6-dichloro-1H-1,3-benzodiazol-2-amine (400 mg, 1.98 mmol) in DMF (8 mL) followed by triethylamine (320 µL, 2.38 mmol). The reaction mixture was stirred for 17 h and then concentrated. The residue was dissolved in EtOAc (25 mL) and washed with water (30 mL). The aqueous phase was extracted with EtOAc (20 mL) and the combined organic extracts were washed with 10% citric acid$_{(aq)}$ (2×15 mL), brine (25 mL), and then dried (MgSO$_4$), filtered and concentrated. The crude product was triturated in DCM and purified by silica chromatography, using 0-10% MeOH in DCM as eluent, to afford the title compound as a light brown solid (41 mg, 5%); m/z=378.8, 380.8 (MH)$^+$.

Intermediate 32

6-[(2-methoxyethyl)(methyl)amino]pyridine-2-carboxamide

To a solution of 6-fluoropyridine-2-carboxamide (500 mg, 3.57 mmol) in DMF (10 mL) were added (2-methoxyethyl)(methyl)amine (636 mg, 7.14 mmol) and K$_2$CO$_3$ (1.23 g, 8.92 mmol). The reaction mixture was stirred at 100° C. for 12 h. Additional (2-methoxyethyl)(methyl)amine (636 mg, 7.14 mmol) was added and the reaction was heated at 100° C. for a further 7 h. The reaction mixture was then concentrated. The residue was dissolved in EtOAc (100 mL) and washed with water (3×50 mL) and brine (3×50 mL). The organic phase was dried (MgSO$_4$), filtered and concentrated to afford the title compound as a white solid (580 mg, 78%); m/z 210.0 (MH)$^+$.

Intermediate 33 tert-butyl 3-carbamoyl-3-fluoroazetidine-1-carboxylate

To a stirred solution of 1-[(tert-butoxy)carbonyl]-3-fluoroazetidine-3-carboxylic acid, available via literature method: Faming Zhuanli Shenqing, 102731362, 17 Oct. 2012; (1.00 g, 4.56 mmol) in DCM (70 mL) were added DMF (200 μl, 2.60 mmol) and oxalyl chloride (490 μl, 5.70 mmol) at 0° C. under nitrogen. The resulting solution was stirred at 0° C. for 2 h and then aqueous ammonia (2.28 ml, 22.81 mmol) was added dropwise to the solution. After stiffing for a further 30 min at 0° C. the reaction was allowed to warm to room temperature. After stiffing for 1 h the reaction mixture was diluted with water (30 mL). The organic phase was washed with water (3×30 mL), dried (Na$_2$SO$_4$), filtered and concentrated to afford the title compound as a yellow solid (990 mg, 99%); m/z=162.9 (MH-$^t$Bu)$^+$.

Intermediate 34

3-cyclobutylpropanamide

To a stirred solution of 3-cyclobutylpropanoic acid (984 mg, 7.67 mmol) in DCM (50 mL) were added triethylamine (1.00 mL, 7.67 mmol) and ethyl chloroformate (731 μL, 7.67 mmol) dropwise at 0° C. under nitrogen. The reaction mixture was stirred at room temperature for 2 h. Aqueous ammonia (769 μL, 7.67 mmol) was added at 0° C. and the reaction was allowed to warm to room temperature over 1 h. The reaction mixture was diluted with DCM (50 mL), extracted with water (3×100 mL) and 10% NaHCO$_{3(aq)}$ (100 mL). The combined aqueous phases were acidified with 10% citric acid$_{(aq)}$ (10 mL) and then extracted with DCM (3×75 mL). The combined organic extracts were dried (MgSO$_4$), filtered and concentrated to afford the title compound as a white solid (548 mg, 56%); m/z=128.0 (MH)$^+$.

Intermediate 35

3-(3,4,5-trimethoxyphenyl)propanamide

To a stirred solution of 3-(3,4,5-trimethoxyphenyl)propanoic acid (1.00 g, 4.16 mmol) in DCM (20 mL) were added DMF (80 μl, 1.04 mmol) and oxalyl chloride (719 μl, 8.32 mmol) dropwise at 0° C. under argon. The reaction was allowed to warm to room temperature over 3 h and was then concentrated. The residue was dissolved in DCM, cooled to 0° C. and the resulting solution was saturated with ammonia gas. The reaction mixture was stirred for 2 h and then concentrated. The residue was diluted with water and the resulting precipitate was collected by filtration affording the title compound as a white solid (690 mg, 66%); 1H NMR (400 MHz, DMSO-d$_6$) δ 2.35 (t, 2H), 2.74 (t, 2H), 3.62 (s, 3H), 3.75 (s, 6H), 6.53 (s, 2H), 6.78 (s, 1H), 7.30 (s, 1H).

Intermediate 36

3-methanesulfonylbenzamide

To a stirred solution of 3-methanesulfonylbenzoic acid (1.50 g, 7.49 mmol) in DCM (7 mL) were added DMF (144 μl, 1.87 mmol) and oxalyl chloride (1.29 ml, 14.98 mmol) dropwise at 0° C. under argon. The reaction was allowed to warm to room temperature over 3 h and was then concentrated. The residue was dissolved in THF, cooled to 0° C. and the resulting solution was saturated with ammonia gas. The reaction mixture was stirred for 2 h and then concentrated. The residue was diluted with MeOH/DCM and the resulting precipitate was removed by filtration. The filtrate was concentrated to afford the title compound as a white solid (750 mg, 42%); m/z=200.3 (MH)$^+$.

Intermediate 37

4-bromo-1H-1,3-benzodiazol-2-amine

The procedure for the preparation of 5,6-dichloro-1H-1,3-benzodiazol-2-amine was used, except that 3-bromobenzene-1,2-diamine was used instead of 4,5-dichlorobenzene-1,2-diamine (62%); m/z=211.8, 213.8 (MH)$^+$.

Intermediate 38

2-amino-5-chloro-1H-1,3-benzodiazole-4-carbonitrile

The procedure for the preparation of 5,6-dichloro-1H-1,3-benzodiazol-2-amine was used, except that 2,3-diamino-6-chlorobenzonitrile (available via a literature method: PCT Int. Appl., 2003051277, 26 Jun. 2003) was used instead of 4,5-dichlorobenzene-1,2-diamine (60%); m/z=192.9, 194.9 (MH)$^+$.

Intermediate 39

4-fluoro-1H-1,3-benzodiazol-2-amine

The procedure for the preparation of 5,6-dichloro-1H-1,3-benzodiazol-2-amine was used, except that 3-fluorobenzene-1,2-diamine (available via a literature method: PCT Int. Appl., 2002008224, 31 Jan. 2002) was used instead of 4,5-dichlorobenzene-1,2-diamine (43%); m/z=151.9 (MH)$^+$.

Intermediate 40

4,6-dimethyl-1H-1,3-benzodiazol-2-amine

The procedure for the preparation of 5,6-dichloro-1H-1,3-benzodiazol-2-amine was used, except that 3,5-dimethylbenzene-1,2-diamine (available via a literature method: PCT Int. Appl., 2003008413, 30 Jan. 2003) was used instead of 4,5-dichlorobenzene-1,2-diamine (quantitative yield); m/z=162.0 (MH)$^+$.

Intermediate 41

4-chloro-5-fluoro-3H-1,3-benzodiazol-2-amine

A solution of BrCN (198 mg, 1.87 mmol) in MeCN (2 mL) was added dropwise to a stirred solution of 3-chloro-4-fluorobenzene-1,2-diamine, available via a literature method: Oriental Journal of Chemistry, 2007, 23, 571-576; (300 mg, 1.87 mmol) in MeCN/H2O (11:1, 8 mL) at 0° C. After stiffing for 18 h the reaction mixture was diluted with saturated NaHCO$_{3(aq)}$ (30 mL). The precipitate was removed by filtration and the filtrate was concentrated. The residue was diluted with water (30 mL), sonicated, filtered and washed with water to give the title compound as an orange-brown solid (110 mg, 32%); m/z=185.9, 187.9 (MH)$^+$.

Intermediate 42

5-chloro-4-methyl-1H-1,3-benzodiazol-2-amine

The procedure for the preparation of 5,6-dichloro-1H-1,3-benzodiazol-2-amine was used, except that 4-chloro-3-methylbenzene-1,2-diamine (available via a literature method: U.S. Pat. Appl. Publ., 20060111416, 25 May 2006) was used instead of 4,5-dichlorobenzene-1,2-diamine (99%); m/z=181.9, 183.9 (MH)$^+$.

Intermediate 43

4-chloro-3-fluorobenzene-1,2-diamine

A microwave tube was charged with 1,3-dichloro-2-fluoro-4-nitrobenzene (2.00 g, 9.52 mmol), phenylmethanamine (4.17 mL, 38.1 mmol) and THF (20 mL). The reaction mixture was heated in the microwave at 80° C. for 3 h before being concentrated. The residue was dissolved in EtOAc (40 mL) and washed with 0.5M HCl$_{(aq)}$ (20 mL) and then brine (20 mL). The organic phase was dried (Na$_2$SO$_4$), filtered and concentrated.

The residue was dissolved in MeOH (15 mL) and the flask was evacuated and flushed with nitrogen (×3). 10% Pd/C (60 mg, 0.06 mmol) was added to the stirred solution. The flask was evacuated and flushed with nitrogen (×3) and then evacuated and flushed with hydrogen (×3). After stirring for 18 h the reaction was filtered through celite, rinsed with EtOH and concentrated to give the crude product as a brown solid. The crude product was purified by silica chromatography, using 20-60% EtOAc in heptane as eluent, to give the title compound as a reddish-brown solid (655 mg, 72%); m/z=160.9, 162.9 (MH)$^+$.

Intermediate 44

5-chloro-4-fluoro-1H-1,3-benzodiazol-2-amine

The procedure for the preparation of 5,6-dichloro-1H-1,3-benzodiazol-2-amine was used, except that 4-chloro-3-fluorobenzene-1,2-diamine was used instead of 4,5-dichlorobenzene-1,2-diamine (99%); m/z=185.9, 187.9 (MH)$^+$.

Intermediate 45

2-fluoro-3-methoxy-6-nitroaniline

A microwave tube was charged with 2,3-difluoro-1-methoxy-4-nitrobenzene (1.00 g, 5.29 mmol) and 7M ammonia in MeOH (15 mL). The reaction mixture was heated in the microwave 80° C. for 40 min before being concentrated. The residue was diluted with EtOAc (30 mL) and washed with water (30 mL) and brine (30 mL). The organic phase was dried (Na$_2$SO$_4$), filtered and concentrated to give the title product as a yellow solid (0.97 g, 99%); m/z=186.9 (MH)$^+$.

Intermediate 46

3-fluoro-4-methoxybenzene-1,2-diamine

A flask charged with 2-fluoro-3-methoxy-6-nitroaniline (0.97 g, 5.26 mmol) and MeOH (25 mL) was evacuated and flushed with nitrogen (×3). 10% Pd/C (112 mg, 0.11 mmol) was then added to the stirred solution. The flask was evacuated and flushed with nitrogen (×3) and then evacuated and flushed with hydrogen (×3). After stiffing for 18 h the reaction was filtered through celite, rinsed with MeOH and concentrated to give the title as a brown solid. (822 mg, 97%). m/z=157.0 (MH)$^+$.

Intermediate 47

4-fluoro-5-methoxy-1H-1,3-benzodiazol-2-amine

A solution of BrCN (640 mg, 6.04 mmol) in MeCN (2 mL) was added dropwise to a stirred solution of 3-fluoro-4-methoxybenzene-1,2-diamine (820 mg, 5.25 mmol) at 0° C. After stiffing for 18 h the reaction mixture was concentrated. The residue was diluted with saturated NaHCO$_{3(aq)}$ (20 mL) and sonicated. The precipitate was collected by filtration and washed with water to afford the title compound as a red solid (970 mg, quantitative yield); m/z=182.0 (MH)$^+$.

Intermediate 48

7-(trifluoromethyl)-1H-1,3-benzodiazol-2-amine

A 5M solution of BrCN in MeCN (0.87 mL, 4.35 mmol) was added dropwise to a stirred solution of 3-(trifluoromethyl)benzene-1,2-diamine (700 mg, 3.97 mmol) in MeCN/water (5:1, 14 mL) at 0° C. After stiffing for 14 h the reaction mixture was diluted with saturated NaHCO$_{3(aq)}$ (10 mL). The precipitate was collected by filtration and washed with water (20 mL) and diethyl ether (40 mL) to afford the title compound as a yellow solid (540 mg, 66%); m/z=202.1 (MH)$^+$.

Intermediate 49

4-(methylsulfanyl)-1H-1,3-benzodiazol-2-amine

The procedure for the preparation of 5,6-dichloro-1H-1,3-benzodiazol-2-amine was used, except that 3-(methylsulfanyl)benzene-1,2-diamine (available via a literature method: *J. Med. Chem.* 2005, 48, 8253-8260) was used instead of 4,5-dichlorobenzene-1,2-diamine (99%); m/z=178.0 (MH)+.

Intermediate 50

(4S)-4-benzyl-3-(3-cyclopentylpropanoyl)-1,3-oxazolidin-2-one

To a stirred solution of (4S)-4-benzyl-1,3-oxazolidin-2-one (1.00 g, 5.64 mmol) in anhydrous THF (50 mL) was added 2.5M n-butyllithium in hexanes (2.26 mL, 5.65 mmol) dropwise at −78° C. under nitrogen. The reaction was stirred at −78° C. for 1 h and then 3-cyclopentylpropanoyl chloride (864 µl, 5.64 mmol) was added dropwise. The reaction was allowed to warm to room temperature and stirred for a further 1 h. The reaction was quenched with saturated $NH_4Cl_{(aq)}$ (25 mL) at 0° C., diluted with water (30 mL) and extracted with EtOAc (3×30 mL). The combined organic extracts were washed with brine, dried ($MgSO_4$), filtered and concentrated. The crude product was purified by silica chromatography, using 33% EtOAc in heptane as eluent, to afford the title compound as a white solid (1.55 g, 90%); m/z=302.0 (MH)+.

Intermediate 51

(4S)-4-benzyl-3-[(2S)-2-(cyclopentylmethyl)propanoyl]-1,3-oxazolidin-2-one

To a stirred solution of (4S)-4-benzyl-3-(3-cyclopentylpropanoyl)-1,3-oxazolidin-2-one (1.50 g, 4.98 mmol) in anhydrous THF (60 mL) was added a 1M NaHMDS in THF (7.47 mL, 7.47 mmol) dropwise at −78° C. under nitrogen. The reaction was stirred at −78° C. for 30 min and then iodomethane (930 µl, 14.93 mmol) was added dropwise. After 3 h at −78° C. the reaction was allowed to warm to room temperature. After stirring for a further 2 h the reaction was quenched with saturated $NH_4Cl_{(aq)}$ at 0° C. On warming to room temperature, the reaction mixture was extracted with EtOAc (3×50 mL). The combined organic extracts were washed with brine (50 mL), dried ($MgSO_4$), filtered and concentrated. The crude product was purified by silica chromatography, using 0-40% EtOAc in heptane as eluent, to afford the title compound as a white solid (1.03 g, 65%); m/z=316.2 (MH)+.

Intermediate 52

(2S)-3-cyclopentyl-2-methylpropanoic acid

To a stirred solution of (4S)-4-benzyl-3-[(2S)-2-(cyclopentylmethyl)propanoyl]-1,3-oxazolidin-2-one (1.00 g, 3.17 mmol) in THF (20 mL) was added lithium hydroxide monohydrate (532 mg, 12.68 mmol) followed by hydrogen peroxide (570 µl, 19.02 mmol). The reaction mixture was stirred at room temperature for 5 h and then concentrated to half the volume. EtOAc (25 mL) and 1M $HCl_{(aq)}$ (25 mL) were added and the organic phase was washed with brine and then concentrated. The residue was dissolved in EtOAc (25 ml) and extracted with 1M $NaOH_{(aq)}$. The aqueous phase was acidified with 1M $HCl_{(aq)}$ to pH 3 and extracted with EtOAc (3×50 mL). The combined organic extracts were dried ($MgSO_4$), filtered and concentrated to afford the title compound as a colourless oil (395 mg); m/z=178.0 (M+Na)+.

Intermediate 53

(2S)-3-cyclopentyl-2-methylpropanamide

To a stirred solution of (2S)-3-cyclopentyl-2-methylpropanoic acid (395 mg, 2.53 mmol) in DCM (40 mL) were added DMF (100 µl, 1.30 mmol) and oxalyl chloride (271 µl, 3.16 mmol) at 0° C. under nitrogen. The reaction mixture was stirred at 0° C. for 3 h and then aqueous ammonia (1.27 ml, 12.64 mmol) was added. The reaction was allowed to warm to room temperature and stirred for a further 2 h. The reaction mixture was diluted with DCM (50 mL) and washed with water (2×50 mL) and 10% citric $acid_{(aq)}$ (2×50 mL). The combined aqueous was back extracted with DCM (50 mL) and then the organic extracts were combined and dried ($MgSO_4$), filtered and concentrated to afford the title compound as an off-white solid (294 mg, 75%); m/z=156.0 (MH)+.

Intermediate 54

(2S)-1-methanesulfonylpyrrolidine-2-carboxamide

To a solution of (2S)-1-methanesulfonylpyrrolidine-2-carboxylic acid (1.00 g, 5.18 mmol) in DCM (75 mL) were added ethyl chloroformate (510 µL, 5.18 mmol) and triethylamine (690 µL, 5.18 mmol) at 0° C. under nitrogen. The reaction mixture was stirred for 3 h at room temperature. Aqueous ammonia (1.55 mL, 15.53 mmol) was added at 0° C. The reaction mixture was stirred for 1 h and was then diluted with DCM (25 mL) and extracted with water (3×50 mL). The combined organic extracts were concentrated. The residue was diluted with DCM (50 mL), sonicated and filtered. The filtrate was dried ($MgSO_4$), filtered and concentrated to afford the title compound as a beige solid (415 mg, 38%); m/z=192.9 (MH)+.

Intermediate 55

Diastereomeric mixture. (S)-{[10,11-dimethyl-4-oxo-3-(trifluoromethyl)-2,5,7-triazatricyclo-[6.4.0.0$^{2,6}$]dodeca-1(8),6,9,11-tetraen-3-yl]carbamoyl}(phenyl)methyl acetate To a solution of (S)-carbamoyl(phenyl)methyl acetate, available via a literature method: *Org. Biomol. Chem.* 2011, 9, 3011-3019; (0.63 g, 3.26 mmol) in DMF (20 mL) were added methyl 3,3,3-trifluoro-2-oxopropanoate (1.22 g, 7.82 mmol) followed by pyridine (315 µl, 3.91 mmol) under nitrogen. The solution was stirred for 2 h at room temperature. Thionyl chloride (284 µl, 3.91 mmol) was added dropwise at 0° C. and the reaction mixture was stirred at 0° C. for a further 1 h. The reaction mixture was concentrated and the residue filtered through a short pad of silica, eluting with DCM, under nitrogen. The filtrate was concentrated, and the acyl intermediate that remained was dissolved in DMF (5 mL) under nitrogen. The solution of acyl intermediate was added to a stirred solution of 5,6-dimethyl-1H-1,3-benzodiazol-2-amine (525 mg, 3.26 mmol) in DMF (20 mL) followed by triethylamine (546 µl, 3.91 mmol). The reaction mixture was stirred for 16 h and then concentrated. The residue was dissolved in EtOAc (50 mL) and washed with water (4×50 mL), brine (3×50 mL) and then dried ($MgSO_4$), filtered and concentrated. The crude product was purified by reverse phase C18 chromatography, using acidic eluent, to afford the title compound as an off-white solid as a mixture of diastereomers (536 mg, 36%); m/z=461.0 (MH)+

Intermediate 56

3-cyclopentyl-N-[4-oxo-3-(trifluoromethyl)-9-{2-[tris(propan-2-yl)silyl]ethynyl}-2,5,7-triazatricyclo[6.4.0.0$^{2,6}$]dodeca-1(12),6,8,10-tetraen-3-yl]propanamide (239986)

A microwave tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), copper(I) iodide (2.5 mg, 0.01 mmol), Pd(PPh$_3$)$_2$Cl$_2$ (9.2 mg, 0.01 mmol), PPh$_3$ (11 mg, 0.04 mmol), de-gassed DMF (1 mL), ethynyltris(propan-2-yl)silane (121 µL, 0.54 mmol) and diethylamine (346 µL, 3.27 mmol). The reaction was stirred in the microwave at 120° C. for 35 min. The reaction was concentrated. The residue was dissolved in DCM (15 mL), washed with water (10 mL) and brine (10 mL) and then dried (Na$_2$SO$_4$), filtered and concentrated. The crude product was purified by silica chromatography, using 0-2% MeOH in DCM as eluent, to afford the title compound as a brown oil (100 mg, 49%); m/z=561.2 (MH)+.

Intermediate 57

4-(trifluoromethoxy)-1H-1,3-benzodiazol-2-amine (239991)

The procedure for the preparation of 5,6-dichloro-1H-1,3-benzodiazol-2-amine was used, except that 3-(trifluoromethoxy)benzene-1,2-diamine was used instead of 4,5-dichlorobenzene-1,2-diamine (91%); m/z=218.0 (MH)+.

Intermediate 58

4-iodo-1H-1,3-benzodiazol-2-amine (239995)

To a stirred solution of 4-bromo-1H-1,3-benzodiazol-2-amine (1.00 g, 4.72 mmol) in dioxane (25 mL), under nitrogen, was added potassium iodide (1.57 g, 9.43 mmol), copper(I) iodide (90 mg, 0.47 mmol) and N,N'-dimethylethane-1,2-diamine (102 µL, 0.94 mmol). Initially, the reaction was heated for 2 h at 100° C. Then the reaction was heated for a further 38 h at 125° C. During this period, additional potassium iodide (2.35 g, 14.15 mmol), copper(I) iodide (180 mg, 0.94 mmol) and N,N'-dimethylethane-1,2-amine (204 µL, 1.88 mmol) was added portionwise. The reaction was then concentrated and the residue was diluted with EtOAc (40 mL) and water (40 mL). The resulting precipitate was removed by filtration and the aqueous phase was extracted with IPA/CHCl$_3$ (1:1, 2×40 mL). The combined organic extracts were washed with brine (25 mL), dried (MgSO$_4$), filtered and concentrated. The crude product was purified by trituration in DCM to afford the title compound as a purple solid (775 mg, 64%); m/z=259.9 (MH)+.

Intermediate 59 phenyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (239996)

A sealed tube was charged with 3-cyclopentyl-N-[9-iodo-4-oxo-3-(trifluoromethyl)-2,5,7-triazatricyclo[6.4.0.0$^{2,6}$]dodeca-1(12),6,8,10-tetraen-3-yl]propanamide (200 mg, 0.40 mmol), anhydrous MeCN (2 mL), palladium(II) acetate (9 mg, 0.04 mmol) and tri-tert-butylphosphonium tetrafluoroborate (46 mg, 0.16 mmol). The reaction was de-gassed and phenyl formate (108 µL, 0.99 mmol) was added followed by triethylamine (137 µL, 0.99 mmol). The reaction was flushed with nitrogen, sealed and stirred at 80° C. for 16 h. The reaction was allowed to cool to room temperature and concentrated. The residue was dissolved in EtOAc (8 mL) and washed with saturated citric acid$_{(aq)}$ (2×7 mL), water (7 mL) and brine (7 mL). The organic phase was dried (MgSO$_4$), filtered and concentrated. The crude product was purified by silica chromatography, using 0-2% MeOH in DCM as eluent, to afford the title compound as a yellow solid (65 mg, 64%); m/z=501.2 (MH)+.

Intermediate 60

4-bromo-6-chloro-1H-1,3-benzodiazol-2-amine (239916)

The procedure for the preparation of 5,6-dichloro-1H-1,3-benzodiazol-2-amine was used, except that 3-bromo-5-chlorobenzene-1,2-diamine (available via a literature method: PCT Int. Appl., 2013067260) was used instead of 4,5-dichlorobenzene-1,2-diamine (84%); m/z=245.8, 247.8 (MH)+

Intermediate 61

6-bromo-4-fluoro-1H-1,3-benzodiazol-2-amine (239926)

The procedure for the preparation of 5,6-dichloro-1H-1,3-benzodiazol-2-amine was used, except that 5-bromo-3-fluorobenzene-1,2-diamine was used instead of 4,5-dichlorobenzene-1,2-diamine (quantitative yield); m/z=229.8, 231.8 (MH)+.

Intermediate 62

6-chloro-5-methoxy-1H-1,3-benzodiazol-2-amine (239941)

The procedure for the preparation of 5,6-dichloro-1H-1,3-benzodiazol-2-amine was used, except that 4-chloro-5-methoxybenzene-1,2-diamine was used instead of 4,5-dichlorobenzene-1,2-diamine (61%); m/z=198.0, 199.9 (MH)+.

Intermediate 63

2-bromo-3-methoxy-6-nitroaniline (239933)

To a stirred solution of 2-bromo-3-fluoro-6-nitroaniline (1.00 g, 4.26 mmol) in MeOH (43 mL), under nitrogen, was added 5.4M NaOMe in MeOH (1.7 mL, 9.4 mmol). The reaction was heated at 90° C. for 1 h and then concentrated. The residue was diluted with water. The resulting precipitate was collected by filtration, washed with water to afford the title compound as a yellow solid (1.05 g, quantitative yield); m/z=246.9, 248.8 (MH)+.

Intermediate 64

3-bromo-4-methoxybenzene-1,2-diamine (239933)

A stirred suspension of 2-bromo-3-methoxy-6-nitroaniline (1.15 g, 4.66 mmol) and tin(II) chloride dihydrate (5.25 g, 23.28 mmol) in EtOAc (47 mL) was heated at 80° C. for 1 h. The reaction was allowed to cool to room temperature and the pH was adjusted to pH14 using 5M NaOH$_{(aq)}$. The resulting suspension was stirred for 15 min and then filtered through Celite™ rinsing with EtOAc. The organic phase from the filtrate was washed with brine, dried (MgSO$_4$), filtered and concentrated to afford the title compound as a yellow solid (970 mg, 96%); m/z=216.9, 218.9 (MH)$^+$.

Intermediate 65

4-bromo-5-methoxy-1H-1,3-benzodiazol-2-amine (239933)

The procedure for the preparation of 5,6-dichloro-1H-1,3-benzodiazol-2-amine was used, except that 3-bromo-4-methoxybenzene-1,2-diamine was used instead of 4,5-dichlorobenzene-1,2-diamine (58%); m/z=241.9, 243.9 (MH)$^+$.

Intermediate 66

5-bromo-4-fluoro-1H-1,3-benzodiazol-2-amine (239937)

The procedure for the preparation of 5,6-dichloro-1H-1,3-benzodiazol-2-amine was used, except that 4-bromo-3-fluorobenzene-1,2-diamine was used instead of 4,5-dichlorobenzene-1,2-diamine (73%); m/z=229.8, 231.8 (MH)$^+$.

Intermediate 67 ethyl (2S)-2-[(3-methylbut-2-en-1-yl)oxy]propanoate (239949/239952)

To a stirred suspension of sodium hydride (60%, 0.61 g, 15.24 mmol) in THF (20 mL), at 0° C. under nitrogen, was added a solution of ethyl (2S)-2-hydroxypropanoate (1.50 g, 12.7 mmol) in THF (5 mL). The reaction was stirred for 30 min at 0° C. Then a solution of 4-bromo-2-methyl-2-butene (2.27 g, 15.2 mmol) in THF (5 mL) was added dropwise and the reaction mixture was allowed to warm to room temperature. After 18 h, the reaction was diluted with water (20 mL) and EtOAc (20 mL). The aqueous layer was extracted with EtOAc (2×20 mL). The combined organic extracts were washed with brine (20 mL) and then dried (MgSO$_4$), filtered and concentrated to afford the title compound as a brown oil (2.00 g, 81%); $^1$H NMR (500 MHz, Chloroform-d) δ 1.24 (t, 3H), 1.35 (d, 3H), 1.63 (s, 3H), 1.70 (s, 3H), 3.88 (dd, 1H), 3.93 (q, 1H), 4.06 (dd, 1H), 4.12-4.20 (m, 2H), 5.28-5.35 (m, 1H).

Intermediate 68

(2S)-2-[(3-methylbut-2-en-1-yl)oxy]propanoic acid (239949/239952)

To a solution of ethyl (2S)-2-[(3-methylbut-2-en-1-yl)oxy]propanoate (600 mg, 2.90 mmol) in MeOH (10 mL) at 0° C. was added a solution of LiOH.H$_2$O (609 mg, 14.50 mmol) in water (5 mL). The reaction was stirred at room temperature for 18 h. The reaction was diluted with EtOAc (20 mL) and extracted with water (20 mL). The aqueous layer was acidified to pH1 with 3M HCl$_{(aq)}$ and then extracted with EtOAc (4×20 mL). The combined organic extracts were washed with brine (30 mL), dried (MgSO$_4$), filtered and concentrated to afford the title compound as a yellow liquid (440 mg, 86%); $^1$H NMR (250 MHz, Chloroform-d) δ 1.43 (d, 3H), 1.66 (s, 3H), 1.74 (s, 3H), 3.95-4.17 (m, 3H), 5.34 (ddt, 1H), 11.09 (s, 1H).

Intermediate 69

(2S)-2-[(3-methylbut-2-en-1-yl)oxy]propanamide (239949/239952)

To a stirred solution of (2S)-2-[(3-methylbut-2-en-1-yl)oxy]propanoic acid (400 mg, 2.28 mmol) in DCM (5 mL) was added oxalyl chloride (391 μL, 4.51 mmol) dropwise. DMF (2 drops) was added and the reaction stirred at room temperature for 2 h. The reaction mixture was concentrated and the residue was dissolved in DCM (5 mL). The resulting solution was added dropwise to a solution of aqueous ammonia (1.30 mL, 11.4 mmol) in DCM (2 mL). The reaction was stirred at room temperature for 18 h and then concentrated. The residue was dissolved in EtOAc (20 mL) and washed with water (20 mL). The aqueous layer was extracted with EtOAc (3×20 mL). The combined organic extracts were washed with brine (30 mL), dried (MgSO$_4$), filtered and concentrated to afford the title compound as a yellow solid (200 mg, 54%); $^1$H NMR (250 MHz, Chloroform-d) δ 1.40 (d, 3H), 1.68 (s, 3H), 1.76 (s, 3H), 3.86 (q, 1H), 4.04 (d, 2H), 5.27-5.40 (m, 1H), 5.60 (s, 1H), 6.54 (s, 1H).

Intermediate 70

(2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(3-methylbut-2-en-1-yl)oxy]propanamide (239949/239952)

To a solution of amide (2S)-2-[(3-methylbut-2-en-1-yl)oxy]propanamide (180 mg, 1.145 mmol) in anhydrous DCM (5 mL) was added pyridine (93 μL, 1.15 mmol) followed by methyl 3,3,3-trifluoro-2-oxopropanoate (358 mg, 2.29 mmol) under nitrogen. The reaction was stirred at room temperature for 1.5 h. Thionyl chloride (84 μL, 1.2 mmol) was added at 0° C. The reaction was stirred for 1 h at 0° C. The reaction mixture was filtered through a short pad of silica, eluting with DCM, under nitrogen. The filtrate was concentrated, and the acyl intermediate that remained was dissolved in DMF (3 mL) under nitrogen. A solution of 5,6-dimethyl-1H-1,3-benzodiazol-2-amine (154 mg, 3.57 mmol) in DMF (2 mL) was added followed by triethylamine (160 μL, 1.15 mmol). The reaction was stirred for 2 days before being concentrated. The residue was dissolved in EtOAc and washed with brine. The aqueous layer was extracted with EtOAc (3×25 mL). The combined organic extracts were dried (MgSO$_4$), filtered and concentrated. The crude product was dissolved in DCM. The resulting precipitate was removed by filtration. The filtrate was concentrated to afford the title compound as an orange solid (270 mg, 67%); m/z=425.1 (MH)$^+$.

Intermediate 71 ethyl (2R)-2-[(3-methylbut-2-en-1-yl)oxy]propanoate (239958/239959)

The procedure for the preparation of ethyl (2S)-2-[(3-methylbut-2-en-1-yl)oxy]propanoate was used, except that ethyl (2R)-2-hydroxypropanoate was used instead of ethyl (2S)-2-hydroxypropanoate (84%); $^1$H NMR (500 MHz, Chloroform-d) δ 1.25 (t, 3H), 1.36 (d, 3H), 1.63 (s, 3H), 1.69-1.72 (m, 3H), 3.90 (dd, 1H), 3.95 (q, 1H), 4.04-4.09 (m, 1H), 4.12-4.23 (m, 2H), 5.30-5.35 (m, 1H).

Intermediate 72

(2R)-2-[(3-methylbut-2-en-1-yl)oxy]propanoic acid (239958/239959)

The procedure for the preparation of (2S)-2-[(3-methylbut-2-en-1-yl)oxy]propanoic acid was used, except that ethyl (2R)-2-[(3-methylbut-2-en-1-yl)oxy]propanoate was used instead of ethyl (2S)-2-[(3-methylbut-2-en-1-yl)oxy]propanoate (91%); $^1$H NMR (250 MHz, Chloroform-d) δ 1.45 (d, 3H), 1.68 (s, 3H), 1.76 (s, 3H), 3.97-4.18 (m, 3H), 5.30-5.40 (m, 1H), 8.36 (s, 1H).

Intermediate 73

(2R)-2-[(3-methylbut-2-en-1-yl)oxy]propanamide (239958/239959)

The procedure for the preparation of (2S)-2-[(3-methylbut-2-en-1-yl)oxy]propanamide was used, except that (2R)-2-[(3-methylbut-2-en-1-yl)oxy]propanoic acid was used instead of ethyl (2S)-2-[(3-methylbut-2-en-1-yl)oxy]propanoic acid (29%); $^1$H NMR (250 MHz, Chloroform-d) δ 1.34 (d, 3H), 1.62 (s, 3H), 1.70 (s, 3H), 3.80 (q, 1H), 3.98 (d, 2H), 5.16-5.38 (m, 1H), 6.44 (s, 1H), 6.56 (s, 1H).

Intermediate 74

(2R)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(3-methylbut-2-en-1-yl)oxy]propanamide (239958/239959)

The procedure for the preparation of (2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(3-methylbut-2-en-1-yl)oxy]propanamide was used, except that (2R)-2-[(3-methylbut-2-en-1-yl)oxy]propanamide was used instead of (2S)-2-[(3-methylbut-2-en-1-yl)oxy]propanamide (68%); m/z=425.0 (MH)$^+$.

Intermediate 75

(2R)-2-(3-chlorophenoxy)propanamide (239968/29969)

To a stirred solution of (2S)-2-hydroxypropanamide (500 mg, 5.61 mmol) in anhydrous DCM (50 mL) at 0° C. under nitrogen was added methane sulfonylchloride (434 μL, 5.61 mmol) followed by triethylamine (783 μL, 5.61 mmol). The reaction was allowed to warm to room temperature and was stirred for 1 h. The reaction was diluted with water and the organic phase was dried (MgSO$_4$), filtered and concentrated. The residue was dissolved in anhydrous acetonitrile (50 mL) and 3-chlorophenol (721 mg, 5.61 mmol) and K$_2$CO$_3$ (776 mg, 5.61 mmol) were added. The resulting suspension was heated at 70° C. for 16 h and then concentrated. The residue was dissolved in EtOAc (100 mL) and washed with water (100 mL) and brine (100 mL) and then dried (MgSO$_4$), filtered and concentrated. The crude product was purified by silica chromatography, using 0-100% EtOAc in heptane as eluent, to afford the title compound as a white solid (220 mg, 20%); m/z=200.2, 202.3 (MH)$^+$.

Intermediate 76

(2S)-2-cyclohexylpropanamide (239985)

To a stirred solution of [(tert-butoxycarbonyl)amino](cyclohexyl)acetic acid (500 mg, 3.2 mmol) in DCM (50 mL), at 0° C. under nitrogen, was added DMF (2 drops) followed by thionyl chloride (0.25 mL, 3.4 mmol). The resulting solution was stirred for 1.5 h at room temperature and then concentrated. The residue was dissolved in anhydrous THF (20 mL). The reaction was cooled to 0° C. and 0.5M ammonia in THF (32 mL) was added. The reaction was allowed to warm to room temperature and was stirred for 2.5 days. The reaction was concentrated. The residue was dissolved in DCM (30 mL) and washed with water (30 mL). The aqueous layer was extracted with DCM (30 mL) and IPA/CHCl$_3$ (1:1, 30 mL). The combined organic extracts were washed with brine (30 mL), dried (Na$_2$SO$_4$), filtered and concentrated. The crude product was triturated in EtOAc to give the title compound as a white solid (150 mg, 31%); m/z=156.0 (MH)$^+$.

Intermediate 77 ethyl (2S)-2-(cyclopent-1-en-1-ylmethoxy)propanoate (239997/239998)

To a stirred suspension of sodium hydride (60%, 0.81 g, 20.3 mmol) in THF (35 mL) at 0° C. under nitrogen was added a solution of ethyl (2S)-2-hydroxypropanoate (2.00 g, 16.9 mmol) in THF (5 mL). The mixture was stirred for 30 min at 0° C. A solution of 1-(bromomethyl)cyclopent-1-ene available via a literature method: J. Am. Chem. Soc., 2013, 135, 10769-10775; (3.27 g, 20.3 mmol) in THF (5 mL) was added dropwise to the reaction mixture at 0° C. The reaction was then allowed to warm to room temperature and stirred for 18 h. Water (20 mL) and EtOAc (150 mL) were added to the reaction mixture. The aqueous layer was extracted with EtOAc (2×20 mL). The combined organic extracts were washed with brine (20 mL) and then dried (Na$_2$SO$_4$), filtered and concentrated. The crude product was purified by silica chromatography, using 5-30% EtOAc in heptane as eluent, to afford the title compound as a yellow (1.75 g, 50%); $^1$H NMR (500 MHz, Chloroform-d) δ 1.31 (t, 3H), 1.42 (d, 3H), 1.86-1.98 (m, 2H), 2.29-2.39 (m, 4H), 3.97-4.04 (m, 2H), 4.16-4.20 (m, 1H), 4.20-4.26 (m, 2H), 5.64-5.70 (m, 1H).

Intermediate 78

(2S)-2-(cyclopent-1-en-1-ylmethoxy)propanoic acid (239997/239998)

To a solution of the ethyl (2S)-2-(cyclopent-1-en-1-ylmethoxy)propanoate (1.75 g, 8.39 mmol) in MeOH (12 mL) and water (4 mL) was added 7.5M NaOH$_{(aq)}$ (1.34 mL, 10.1 mmol) dropwise. The reaction was stirred at room temperature for 3 h. The MeOH was evaporated and the pH of the residue was adjusted to pH1 with 1M HCl$_{(aq)}$. The acidic aqueous solution was extracted with EtOAc (4×20 mL). The combined organic extracts were washed with brine (10 mL), dried (Na$_2$SO$_4$), filtered and concentrated to afford the title compound as a yellow oil (1.09 g, 76%); $^1$H NMR (500

MHz, Chloroform-d) δ 1.48 (d, 3H), 1.89-2.00 (m, 2H), 2.28-2.42 (m, 4H), 4.07 (q, 1H), 4.11 (d, 1H), 4.21 (d, 1H), 5.66-5.74 (m, 1H).

Intermediate 79

(2S)-2-(cyclopent-1-en-1-ylmethoxy)propanamide (239997/239998)

To a stirred solution of (2S)-2-(cyclopent-1-en-1-ylmethoxy)propanoic acid (1.10 g, 6.46 mmol) in DCM (15 mL) was added oxalyl chloride (832 μL, 9.69 mmol) dropwise. DMF (2 drops) was added and the reaction stirred at room temperature for 2 h. The reaction mixture was concentrated. The residue was dissolved in DCM (15 mL) and aqueous ammonia (3 mL) was added. The reaction was stirred at room temperature for 30 min and was then concentrated. The residue was dissolved in DCM (50 mL) and washed with water. The organic phase was dried ($Na_2SO_4$), filtered and concentrated to afford the title compound as a brown solid (1.15 g, quantitative yield); $^1$H NMR (500 MHz, Chloroform-d) δ 1.43 (d, 3H), 1.94 (m, 2H), 2.24-2.43 (m, 4H), 3.91 (q, 1H), 4.04-4.19 (m, 2H), 5.41 (s, 1H), 5.69 (s, 1H), 6.57 (s, 1H).

Intermediate 80 phenyl 11-chloro-3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (240015)

The procedure for the preparation of phenyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate was used, except that N-[11-chloro-9-iodo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide was used instead of 3-cyclopentyl-N-[9-iodo-4-oxo-3-(trifluoromethyl)-2,5,7-triazatricyclo[6.4.0.0$^{2,6}$]dodeca-1(12),6,8,10-tetraen-3-yl]propanamide. The crude product was purified by automated reverse phase HPLC (low pH Method A) to afford the title compound as a white solid (39%); m/z=535.2, 537.2 (MH)$^+$.

Intermediate 81

2-(2-methoxyethoxy)pyridine-4-carbonitrile (240032)

To a stirred suspension of sodium hydride (60%, 347 mg, 8.66 mmol) in anhydrous dioxane (10 mL) at 0° C. was added dropwise a solution of 2-methoxyethan-1-ol (549 mg, 7.22 mmol) in anhydrous dioxane (5 mL). The reaction was allowed to warm to room temperature and stirred for 2 h. A solution of 2-chloropyridine-4-carbonitrile (1.00 g, 7.22 mmol) in anhydrous dioxane (5 mL) was added dropwise to the reaction mixture at 0° C. and then allowed to stir at room temperature for 20 h. The reaction was diluted with water (40 mL) and EtOAc (40 mL). The aqueous phase was extracted with EtOAc (3×50 mL). The combined organic extracts were washed with brine (30 mL), dried (MgSO$_4$), filtered and concentrated. EtOAc (10 mL) was added to the crude product. The resulting precipitate was removed by filtration and the filtrate concentrated. The resulting residue was purified by silica chromatography, using 0-100% EtOAc in heptane as eluent, to afford the title compound as a green oil (255 mg, 20%); m/z=179.0 (MH)$^+$.

Intermediate 82

2-(2-methoxyethoxy)pyridine-4-carboxamide (240032)

To a stirred solution of 2-(2-methoxyethoxy)pyridine-4-carbonitrile in water/EtOH (1:1, 4 mL) was added 2M NaOH$_{(aq)}$ (0.65 mL, 1.3 mmol) and 28% $H_2O_{2(aq)}$ (0.14 mL, 1.3 mmol). The reaction was stirred at room temperature for 18 h and was then diluted with saturated NaHCO$_{3(aq)}$ (20 mL) and EtOAc (20 mL). The aqueous phase was extracted with EtOAc (3×20 mL). The combined organic extracts were washed with brine (30 mL), dried (MgSO$_4$), filtered and concentrated to afford the title compound as a yellow solid (180 mg, 73%); m/z=197.0 (MH)$^+$.

Intermediate 83 phenyl 3-(3-cyclopentylpropanamido)-10-methoxy-4-oxo-3-(trifluoromethyl)-2,5,7-triazatricyclo[6.4.0.0$^{2,6}$]dodeca-1(12),6,8,10-tetraene-9-carboxylate (240026)

A sealed tube was charged with 3-cyclopentyl-N-[9-iodo-10-methoxy-4-oxo-3-(trifluoromethyl)-2,5,7-triazatricyclo[6.4.0.0$^{2,6}$]dodeca-1(12),6,8,10-tetraen-3-yl]propanamide (65%, 300 mg, 0.36 mmol), anhydrous MeCN (2 mL), palladium(II) acetate (8 mg, 0.04 mmol) and tri-tert-butylphosphonium tetrafluoroborate (42 mg, 0.15 mmol). The reaction was de-gassed and phenyl formate (0.1 mL, 0.9 mmol) was added followed by triethylamine (157 μL, 0.91 mmol). The reaction was flushed with nitrogen, sealed and stirred at 80° C. for 16 h. Additional palladium(II) acetate (8 mg, 0.04 mmol) and tri-tert-butylphosphonium tetrafluoroborate (42 mg, 0.15 mmol), phenyl formate (0.1 mL, 0.9 mmol) and triethylamine (157 μL, 0.91 mmol) were added. The reaction was flushed with nitrogen, sealed and stirred at 80° C. for a further 6 h. The reaction was allowed to cool to room temperature and concentrated. The residue was dissolved in EtOAc (15 mL) and washed with saturated citric acid$_{(aq)}$ (15 mL). The aqueous layer was extracted with EtOAc (15 mL). The combined organic extracts were washed with water (15 mL) and brine (25 mL) and then dried (MgSO$_4$), filtered and concentrated. The crude product was purified by reverse phase C18 chromatography, using acidic eluent, to afford the title compound as a white solid (115 mg, 58%); m/z=531.2 (MH)$^+$.

Example 1

6-chloro-N-[10,11-dimethyl-4-oxo-3-(trifluoromethyl)-2,5,7-triazatricyclo[6.4.0.0$^{2,6}$]-dodeca-1(8),6,9,11-tetraen-3-yl]pyridine-2-carboxamide (ABR 239471)

To a stirred solution of 6-chloropyridine-2-carboxamide (1.00 g, 13.0 mmol) in DMF (8 mL) were added pyridine (1.05 mL, 13.0 mmol) and ethyl 3,3,3-trifluoro-2-oxo-propanoate (1.73 mL, 13.0 mmol) dropwise, under argon. The reaction mixture stirred at room temperature for 1 h and then thionyl chloride (0.95 mL, 13.0 mmol) was added dropwise. The reaction mixture stirred at room temperature for further 16 h and then concentrated to provide the acyl imine intermediate. The acyl imine intermediate was dissolved DMF (5 mL) and added to a solution of 5,6-dimethyl-1H-1,3-benzodiazol-2-amine (2.03 g, 13.0 mmol) in DMF (7 mL), followed by triethylamine (1.80 mL, 13.0 mmol). The reaction mixture stirred at room temperature for 4 h. The reaction was diluted with brine (25 mL) and extracted with EtOAc (2×50 mL). The combined organic phases were washed with the water, dried ($Na_2SO_4$), filtered and concentrated. The crude product was purified by silica chromatography, using 3% MeOH in DCM as eluent, to afford the title compound as an off-white solid (0.6 g, 22%); m/z=423.4, 425.4 $(MH)^+$ Example 2

N-[10,11-dichloro-4-oxo-3-(trifluoromethyl)-2,5,7-triazatricyclo[6.4.0.0$^{2,6}$]dodeca-1(12),6,8,10-tetraen-3-yl]-6-fluoropyridine-2-carboxamide (ABR 239472)

To a solution of 6-fluoropyridine-2-carboxamide (700 mg, 4.75 mmol) in DMF (7 mL), under argon, were added ethyl 3,3,3-trifluoro-2-oxopropanoate (629 µL, 4.75 mmol) and pyridine (383 µL, 4.75 mmol). The reaction mixture was stirred at room temperature for 1 h and then thionyl chloride (344 µL, 4.75 mmol) was added dropwise. Stifling was continued for a further 2.5 h and then the reaction was concentrated to provide the acyl imine intermediate. The resulting acyl imine intermediate was dissolved in DMF (5 mL) and then added to a solution of 5,6-dichloro-1H-1,3-benzodiazol-2-amine (519 mg, 2.57 mmol) in DMF (5 mL). Triethylamine (0.35 ml, 2.56 mmol) was added and the reaction mixture stirred at room temperature for 2 h. The reaction was diluted with brine (30 mL) and extracted with EtOAc (2×50 mL). The combined organic phases were washed with the water, dried ($Na_2SO_4$), filtered and concentrated. The crude product was purified by silica chromatography, using 3% MeOH in DCM as eluent, to afford the title compound as an off-white solid (300 mg, 25%); m/z=448.4, 450.4 $(MH)^+$.

Example 3

N-[4-oxo-3-(trifluoromethyl)-2,5,7-triazatricyclo[6.4.0.0$^{2,6}$]dodeca-1(12),6,8,10-tetraen-3-yl]benzamide (ABR 238128)

To a stirred solution of benzamide (1.00 g, 8.26 mmol) in DMF (40 mL) was added pyridine (666 µL, 8.26 mmol) followed by methyl 3,3,3-trifluoro-2-oxopropanoate (1.29 g, 8.26 mmol) dropwise under nitrogen. The resulting solution was stirred for 30 min under nitrogen and then thionyl chloride (0.60 mL, 8.26 mmol) was added and the solution stirred for a further 1 h at room temperature. 1H-1,3-Benzodiazol-2-amine (1.10 g, 8.26 mmol) and triethylamine (0.10 mL, 0.72 mmol) were added to the reaction mixture, and the solution stirred at room temperature for 6 h and then at 50° C. for 3 h. The reaction mixture was concentrated, dissolved in EtOAc (100 mL) and washed with water (3×50 mL). The organic phase was dried ($MgSO_4$), filtered and concentrated. The crude product was purified by silica chromatography, eluting with 20-50% EtOAc in heptane, followed by automated reverse phase HPLC (low pH Method A) to afford the title compound as a white solid (12 mg, 0.4%)

Example 4

2-cyclohexyl-N-[4-oxo-3-(trifluoromethyl)-2,5,7-triazatricyclo[6.4.0.0$^{2,6}$]dodeca-1(12),6,8,10-tetraen-3-yl]acetamide (ABR 238883)

To a stirred solution of 2-cyclohexylacetamide (425 mg, 3.01 mmol) in DMF (15 mL) was added pyridine (243 µL, 3.01 mmol) and methyl 3,3,3-trifluoro-2-oxopropanoate (470 mg, 3.01 mmol) under nitrogen. The resulting solution was stirred for 1 h at room temperature and then thionyl chloride (218 µL, 3.01 mmol) was added dropwise to the solution at 0° C. under nitrogen. The reaction mixture was allowed to warm to room temperature and then stirred for a further 16 h. The reaction mixture was concentrated to afford the acyl imine intermediate which was used without further purification.

To a portion of the acyl imine intermediate (200 mg, 0.72 mmol) in DMF (5 mL) was added 1H-1,3-benzodiazol-2-amine (95 mg, 0.72 mmol) followed by triethylamine (95 µL, 0.72 mmol). The reaction mixture was stirred at room temperature under nitrogen for 3 h and then concentrated. The resulting brown oil was purified by automated reverse phase HPLC (low pH Method A) to afford the title compound as an off-white solid (58 mg, 22%).

Example 5

3-(morpholin-4-yl)-N-[4-oxo-3-(trifluoromethyl)-2,5,7-triazatricyclo[6.4.0.0$^{2,6}$]-dodeca-1(12),6,8,10-tetraen-3-yl]propanamide (ABR 238798)

To a stirred solution of 3-(morpholin-4-yl)propanamide (1.00 g, 6.32 mmol) in DMF (10 mL) was added pyridine (510 µL, 6.32 mmol) followed by methyl 3,3,3-trifluoro-2-oxopropanoate (649 µL, 6.32 mmol), under nitrogen. The reaction mixture was stirred for 1 h at room temperature and then thionyl chloride (459 µL, 6.32 mmol) was added. The reaction mixture was stirred for 48 h and then concentrated. The residue was dissolved in DCM (10 mL) and filtered through a short pad of celite. The filtrate was concentrated to afford the acyl imine intermediate (1.2 g) which was used without further purification. To a portion of the acyl imine intermediate (250 mg, 0.84 mmol) in DMF (3 mL) was added 2-aminobenzimidazole (112 mg, 0.84 mmol) and triethylamine (109 µL, 0.84 mmol). The reaction mixture was stirred at room temperature under nitrogen for 16 h. The reaction mixture was purified by silica chromatography, using 0-5% MeOH in DCM as eluent, to afford the title compound as an off-white solid (98 mg, 30%).

Example 6

N-[4-oxo-3-(trifluoromethyl)-2,5,7-triazatricyclo[6.4.0.0$^{2,6}$]dodeca-1(12),6,8,10-tetraen-3-yl]-3-(pyrrolidin-1-yl)propanamide (ABR 238799)

To a stirred solution of 3-(pyrrolidin-1-yl)propanamide, prepared according to literature (You et al., 2008) (1.00 g, 7.03 mmol) in DMF (10 mL) was added pyridine (567 µL, 7.03 mmol) followed by methyl 3,3,3-trifluoro-2-oxopropanoate (722 µL, 7.03 mmol) under nitrogen. The resulting reaction mixture was stirred at room temperature for 1 h and then thionyl chloride (510 µL, 7.03 mmol) was added. The reaction mixture was stirred for a further 6 h at room temperature and then concentrated to afford the acyl imine intermediate (1.78 g) which was used without further purification. To a portion of the acyl imine intermediate (200 mg, 0.71 mmol) in DMF (3 mL) was added 2-aminobenzimidazole (95 mg, 0.71 mmol) followed by triethylamine (92 µL, 0.71 mmol) under nitrogen. The reaction mixture was stirred at room temperature for 2 h and then concentrated. The residue was dissolved in EtOAc (25 mL) and washed with water (2×20 mL). The organic phase was dried (MgSO$_4$), filtered and concentrated. The crude product was purified by silica chromatography, using 0-5% MeOH in DCM as eluent, to afford the title compound as an off-white solid (49 mg, 18%).

Example 7

3-(oxan-4-yl)-N-[4-oxo-3-(trifluoromethyl)-2,5,7-triazatricyclo[6.4.0.0$^{2,6}$]dodeca-1(12),6,8,10-tetraen-3-yl]propanamide (ABR 238816)

To a stirred solution of N-[4-oxo-3-(trifluoromethyl)-2,5,7-triazatricyclo[6.4.0.0$^{2,6}$]-dodeca-1(8),6,9,11-tetraen-3-yl]prop-2-enamide (25 mg, 0.08 mmol) and 4-iodooxane (80 mg, 0.26 mmol) in an EtOH (5 mL) and water (1.5 mL) mix was added zinc dust (101.0 mg, 1.54 mmol) and copper iodide (98.2 mg, 0.51 mmol) under nitrogen. The reaction mixture was sonicated at room temperature for 5 h. The reaction mixture was filtered through celite and washed with EtOAc (3×25 mL). The filtrate was washed with brine (50 mL), dried (MgSO$_4$), filtered and concentrated. The crude product was purified by automated reverse phase HPLC (low pH Method A) to afford the title compound as a white solid (17 mg, 16%).

Example 8

2-bromo-N-[4-oxo-3-(trifluoromethyl)-2,5,7-triazatricyclo[6.4.0.0$^{2,6}$]dodeca-1(8),6,9,11-tetraen-3-yl]benzamide (ABR 238803)

To a stirred solution of 2-bromobenzamide (177 mg, 0.88 mmol) in DMF (6 mL) were added pyridine (71 µL, 0.88 mmol) and ethyl 3,3,3-trifluoro-2-oxopropanoate (90 µL, 0.88 mol) dropwise. The reaction mixture stirred at room temperature for 1 h and then thionyl chloride (64 µµL, 0.88 mmol) was added dropwise. The reaction mixture stirred for 16 h and then concentrated to provide the acyl imine intermediate. The acyl imine intermediate was dissolved in DMF (4 mL) and added to a solution of 1H-1,3-benzodiazol-2-amine (118 mg, 0.88 mmol) in DMF (2 mL), followed by triethylamine (118 µL, 0.88 mmol). The reaction mixture was stirred at room temperature for 4 h. The reaction was diluted with brine (25 mL) and extracted with EtOAc (2×50 mL). The combined organic phases were washed with the water, dried (Na$_2$SO$_4$), filtered and concentrated. The crude product was purified by preparative TLC in 10% MeOH in DCM to afford the title compound as a brown solid (10 mg, 3%).

Example 9

3-cyclopentyl-N-[4-oxo-3-(trifluoromethyl)-2,5,7-triazatricyclo[6.4.0.0$^{2,6}$]dodeca-1(8),6,9,11-tetraen-3-yl]propanamide (ABR 238789)

The procedure for the preparation of 2-bromo-N-[3-oxo-4-(trifluoromethyl)-2,5,7-triazatricyclo[6.4.0.0$^{2,6}$]dodeca-1 (12),6,8,10-tetraen-4-yl]benzamide was used except that 3-cyclopentylpropanamide was used instead of 2-bromobenzamide. The crude product was purified by silica chromatography, using 2.5% MeOH in DCM as eluent (12%).

Example 10

3,5-dimethoxy-N-[3-oxo-4-(trifluoromethyl)-2,5,7-triazatricyclo[6.4.0.0$^{2,6}$]dodeca-1(12),6,8,10-tetraen-4-yl]benzamide (ABR 238802)

The procedure for the preparation of 2-bromo-N-[3-oxo-4-(trifluoromethyl)-2,5,7-triazatricyclo[6.4.0.0$^{2,6}$]dodeca-1 (12),6,8,10-tetraen-4-yl]benzamide was used except that 3,5-dimethoxybenzamide was used instead of 2-bromobenzamide. The crude product was purified by preparative TLC, using 5% MeOH in DCM as eluent (2%).

Example 11

6-methyl-N-[3-oxo-4-(trifluoromethyl)-2,5,7-triazatricyclo[6.4.0.0$^{2,6}$]dodeca-1(12),6,8,10-tetraen-4-yl]pyridine-3-carboxamide (ABR 238843)

The procedure for the preparation of 2-bromo-N-[3-oxo-4-(trifluoromethyl)-2,5,7-triazatricyclo[6.4.0.0$^{2,6}$]dodeca-1 (12),6,8,10-tetraen-4-yl]benzamide was used except that 6-methylpyridine-3-carboxamide was used instead of 2-bromobenzamide. The crude product was purified by preparative TLC, using 10% MeOH in DCM as eluent (2%).

Example 12

3,5-dichloro-N-[4-oxo-3-(trifluoromethyl)-2,5,7-triazatricyclo[6.4.0.0$^{2,6}$]dodeca-1(12),6,8,10-tetraen-3-yl]benzamide (ABR 238895)

The procedure for the preparation of 2-bromo-N-[3-oxo-4-(trifluoromethyl)-2,5,7-triazatricyclo[6.4.0.0$^{2,6}$]dodeca-1 (12),6,8,10-tetraen-4-yl]benzamide was used except that 3,5-dichlorobenzamide was used instead of 2-bromobenzamide. The crude product was purified by preparative TLC, using 5% MeOH in DCM as eluent (8%).

Example 13

3-cyclohexyl-N-[3-oxo-4-(trifluoromethyl)-2,5,7-triazatricyclo[6.4.0.0$^{2,6}$]dodeca-1(12),6,8,10-tetraen-4-yl]propanamide (ABR 238219)

The general procedure for the preparation of 2-bromo-N-[3-oxo-4-(trifluoromethyl)-2,5,7-triazatricyclo[6.4.0.0$^{2,6}$] dodeca-1(12),6,8,10-tetraen-4-yl]benzamide was used but with the following changes. In the first stage of the reaction, to form the acyl imine intermediate, 3-cyclohexylpropanamide was used instead of 2-bromobenzamide and after the addition of thionyl chloride the reaction mixture was stirred for 2 h instead of 16 h. In the second stage of the reaction, 1H-1,3-benzodiazol-2-amine was used instead of 1H-1,3-benzodiazol-2-amine and the reaction was stirred for 16 h instead of 4 h. The crude product was purified by preparative TLC, using 10% MeOH in DCM as eluent (10%).

Example 14

N-[10,11-dimethyl-4-oxo-3-(trifluoromethyl)-2,5,7-triazatricyclo[6.4.0.0$^{2,6}$]dodeca-1(8),6,9,11-tetraen-3-yl]benzamide (ABR 238786)

To a stirred solution of methyl (Z)-benzoylimino-3,3,3-trifluoropropanoate (150 mg, 0.58 mmol) and 5,6-dimethyl- 1H-1,3-benzodiazol-2-amine (93 mg, 0.58 mmol) in DMF (2 mL) was added triethylamine (60 µL, 0.58 mmol), under nitrogen. The reaction mixture was stirred for 1 h at room temperature and then concentrated. The residue was dissolved in EtOAc (25 mL), washed with water (2×20 mL) and brine (20 mL). The organic phase was dried ($MgSO_4$), filtered and concentrated. The crude product was purified by automated reverse phase HPLC (low pH Method A) to afford the title compound as a white solid (47 mg, 21%).

Example 15

N-[10,11-dimethyl-4-oxo-3-(trifluoromethyl)-2,5,7-triazatricyclo[6.4.0.0$^{2,6}$]dodeca-1(8),6,9,11-tetraen-3-yl]-3-phenylpropanamide (ABR 238787)

3-Phenylpropanamide (500 mg, 3.35 mmol) was dissolved in DMF (15 mL) and methyl 3,3,3-trifluoro-2-oxopropanoate (523.03 mg, 3.35 mmol) and pyridine (270 µL, 3.35 mmol) were added under nitrogen at room temperature. The reaction mixture was stirred for 1 h and then thionyl chloride (243 µL, 3.35 mmol) was added. The reaction mixture was stirred at room temperature for a further 16 h and then concentrated. The residue was filtered through a short plug of silica, eluting with EtOAc, and the filtrate concentrated to afford the acyl imine intermediate (502 mg) which was used without further purification. To a solution of 5,6-dimethyl-1H-1,3-benzodiazol-2-amine (84.18 mg, 0.52 mmol) in DMF (5 mL) was added triethylamine (67.17 µL, 0.52 mmol) followed by the acyl imine intermediate (150 mg, 0.52 mmol). The reaction mixture was stirred at room temperature for 3 h and then concentrated. The residue was dissolved in EtOAc (20 mL) and washed with 10% citric acid(aq) (20 mL), water (20 mL) and brine (20 mL). The organic phase was dried ($MgSO_4$), concentrated and purified by automated reverse phase HPLC (low pH Method A) to afford the title compound as an off-white solid (76 mg, 35%).

Example 16

3-(2-chlorophenyl)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]propanamide (ABR 238908)

To a stirred solution of 3-(2-chlorophenyl)propanamide (500 mg, 2.72 mmol) in DMF (10 mL), under nitrogen, was added methyl 3,3,3-trifluoro-2-oxopropanoate (425 mg, 2.72 mmol) followed by pyridine (220 µL, 2.72 mmol). The reaction mixture was stirred at room temperature for 2 h and then thionyl chloride (198 µL, 2.72 mmol) was added. The reaction mixture was stirred for a further 16 h and then concentrated. The residue was filtered through a short pad of celite and then silica, eluting with EtOAc, and the filtrate concentrated to afford the acyl imine intermediate as a yellow oil (850 mg) which was used without further purification. To a solution of 5,6-dimethyl-1H-1,3-benzodiazol-2-amine (50 mg, 0.31 mmol) in DMF (5 mL) was added a portion of the acyl imine intermediate (100 mg, 0.31 mmol), followed by triethylamine (41 µL, 0.31 mmol) under nitrogen. The reaction mixture was stirred at room temperature for a further 8 h. The reaction mixture was concentrated and purified by automated reverse phase HPLC (low pH Method A) to afford the title compound as a beige solid (30 mg, 21%).

Example 17

3,5-dichloro-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]benzamide (ABR 239340)

To a stirred solution of 3,5-dichlorobenzamide (300 mg, 1.58 mmol) in DMF (20 mL) was added pyridine (127 µL, 1.58 mmol) followed by methyl 3,3,3-trifluoro-2-oxopropanoate (370 mg, 2.37 mmol) under nitrogen. The reaction mixture was stirred at room temperature for 2 h and then cooled to 0° C. Thionyl chloride (115 µL, 1.58 mmol) was added dropwise and the solution was stirred for a further 1 h at this temperature. The reaction mixture was concentrated, passed through a short pad of silica eluting with EtOAc, under nitrogen. The filtrate was evaporated immediately and the acyl imine intermediate that remained was redissolved in DMF (10 mL). To this solution was added 5,6-dimethyl-1H-1,3-benzodiazol-2-amine (191 mg, 1.18 mmol) and triethylamine (210 µL, 1.58 mmol). The resulting reaction mixture was stirred for 3 h and then concentrated. The residue was dissolved in EtOAc (40 mL) and washed with water (2×30 mL) and brine (2×30 mL). The organic phase was dried ($MgSO_4$), filtered and concentrated. The crude product was purified by automated reverse phase HPLC (high pH method) to afford the desired product as a white solid (45 mg, 6%).

Example 18

N-[10,11-dimethyl-4-oxo-3-(trifluoromethyl)-2,5,7-triazatricyclo[6.4.0.0$^{2,6}$]dodeca-1(8),6,9,11-tetraen-3-yl]-4-phenylbenzamide (ABR 239078)

To a stirred solution of 4-phenylbenzamide (250 mg, 1.27 mmol) in DMF (15 mL) was added methyl 3,3,3-trifluoro-2-oxopropanoate (198 mg, 1.27 mmol) followed by pyridine (102 µL, 1.27 mmol) under nitrogen. The reaction mixture was stirred at room temperature for 16 h and then cooled to 0° C. Thionyl chloride (92 µL, 1.27 mmol) was added dropwise and the reaction was allowed to warm to room temperature. The reaction was stirred for a further 2 h and was then concentrated. The residue was filtered through a short pad of silica, eluting with EtOAc, and the filtrate was concentrated to provide the acyl imine intermediate. The acyl imine intermediate was dissolved in DMF (10 mL) and 5,6-dimethyl-1H-1,3-benzodiazol-2-amine (204 mg, 1.27 mmol) was added followed by triethylamine (177 µL, 1.27 mmol). The reaction mixture was stirred at room temperature and then at 80° C. for 18 h. The reaction mixture was then concentrated. The crude product was purified by silica chromatography, eluting with 0-5% MeOH in DCM, followed by automated reverse phase HPLC (low pH Method A) to afford the title compound as a white solid (38 mg, 6%).

Example 19

4-cyclopentyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]butanamide (ABR 238854)

An oven-dry flask was charged with N-[10,11-dimethyl-3-oxo-4-(trifluoromethyl)-2,5,7-triazatricyclo[6.4.0.0$^{2,6}$]dodeca-1(12),6,8,10-tetraen-4-yl]prop-2-enamide (80 mg, 0.24 mmol) followed by EtOH (5 mL) and (iodomethyl)cyclopentane (99 mg, 0.47 mmol). Zinc dust (93 mg, 1.42 mmol) and copper iodide (90 mg, 0.47 mmol) were then added to the reaction mixture, followed by water (1.5 mL). The reaction mixture was de-gassed with nitrogen for 2 min and then the suspension was placed in a sonic bath for 6 h at room temperature. The reaction mixture was charged with further copper iodide (90 mg, 0.47 mmol), zinc dust (93 mg, 1.42 mmol) and (iodomethyl)cyclopentane (99 mg, 0.47 mmol) and the reaction sonicated for a further 3 h. The reaction mixture was filtered through a pad of celite and washed further with EtOAc (100 mL). The organic filtrate was concentrated and purified by silica chromatography, using 5-10% MeOH in DCM as eluent, followed by automated reverse phase HPLC (low pH Method A) to afford the title compound as a beige solid (11 mg, 11%).

Example 20

2-cyclohexyl-N-[10,11-dimethyl-4-oxo-3-(trifluoromethyl)-2,5,7-triazatricyclo-[6.4.0.0$^{2,6}$]dodeca-1 (8),6,9,11-tetraen-3-yl]acetamide (ABR 238884)

To an oven dried flask was added 2-cyclohexylacetamide (425 mg, 3.01 mmol), followed by DMF (15 mL) and pyridine (243 µL, 3.01 mmol) under nitrogen. Methyl 3,3, 3-trifluoro-2-oxopropanoate (470 mg, 3.01 mmol) was added to the solution and stirred for 1 h. Thionyl chloride (218.4 µL, 3.01 mmol) was added dropwise to the solution at 0° C. under nitrogen. The reaction mixture was allowed to warm to room temperature and then stirred for a further 16 h. The reaction mixture was concentrated to afford the acyl imine intermediate which was used without further purification. The acyl imine intermediate (200 mg, 0.72 mmol) was dissolved in DMF (5 mL) and 5,6-dimethyl-1H-1,3-benzodiazol-2-amine (115 mg, 0.72 mmol) and triethylamine (95 µL, 0.72 mmol) were added under nitrogen. The reaction mixture was stirred at room temperature 3 h. The reaction was concentrated under high vacuum and then purified by automated reverse phase HPLC (low pH Method A) to afford the title compound as an off-white solid (150 mg, 51%).

Example 21

N-[10,11-dimethyl-4-oxo-3-(trifluoromethyl)-2,5,7-triazatricyclo[6.4.0.0$^{2,6}$]dodeca-1(8),6,9,11-tetraen-3-yl]-6-(2,2,2-trifluoroethoxy)pyridine-3-carboxamide (ABR 238950)

To a solution of 6-(2,2,2-trifluoroethoxy)pyridine-3-carboxamide (500 mg, 2.27 mmol) in DMF (15 mL) was added pyridine (183 µL, 2.27 mmol) followed by methyl 3,3,3-trifluoro-2-oxopropanoate (354 mg, 2.27 mmol) under nitrogen. The solution was stirred at room temperature for 1 h and then cooled to 0° C. Thionyl chloride (165 µL, 2.27 mmol) was added dropwise and the reaction mixture was stirred at room temperature for a further 16 h and was then concentrated. The resulting acyl imine intermediate (643 mg, 1.8 mmol) and 5,6-dimethyl-1H-1,3-benzodiazol-2-amine (289.38 mg, 1.8 mmol) were immediately dissolved in DMF (10 mL) and triethylamine (0.24 mL, 1.8 mmol) was added under nitrogen. The reaction mixture was stirred at room temperature for 16 h and then concentrated. The resulting residue was triturated in DCM/MeOH (20:1). The resulting off-white solid was collected by filtration. A 50 mg sample of the crude solid was purified by automated reverse phase HPLC (low pH Method A) to afford the title compound as a white solid (25 mg, 3%).

Example 22

1-cyclopentanecarbonyl-N-[10,11-dimethyl-4-oxo-3-(trifluoromethyl)-2,5,7-triazatricyclo-[6.4.0.0$^{2,6}$] dodeca-1(12),6,8,10-tetraen-3-yl]pyrrolidine-3-carboxamide (ABR 239208)

To a stirred solution of N-[10,11-dimethyl-4-oxo-3-(trifluoromethyl)-2,5,7-triazatricyclo-[6.4.0.0$^{2,6}$]dodeca-1(12), 6,8,10-tetraen-3-yl]pyrrolidine-3-carboxamide hydrochloride (95 mg, 0.23 mmol) in anhydrous DCM (3 mL) at 0° C., under nitrogen, was added cyclopentanecarbonyl chloride (29 µL, 0.24 mmol) followed by triethylamine (63 µL, 0.45 mmol). The reaction mixture was allowed to warm to room temperature and was stirred for 16 h. Water (10 mL) and DCM (10 mL) were added to the reaction mixture was stirred vigorously for 5 min. The layers were separated and the aqueous layer back extracted further with DCM (2×20 mL). The combined organic phases were dried (MgSO$_4$), filtered and concentrated to afford the crude product (containing a mixture of 4 stereoisomers) as a brown oil. This was purified by SFC using a Chiralpak AD-H column, with a mobile phase of CO$_2$ and MeOH containing 0.1% formic acid, to afford one isomer of the title compound with unknown stereochemistry (6 mg, 6%).

Example 23

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(morpholin-4-yl)propanamide (ABR 238814)

To a stirred solution of 3-(morpholin-4-yl)propanamide (1.00 g, 6.32 mmol) in DMF (10 mL) was added pyridine (510 µL, 6.32 mmol) followed by methyl 3,3,3-trifluoro-2-oxo-propanoate (649 µL, 6.32 mmol) under nitrogen. The reaction mixture was stirred for 1 h at room temperature and then thionyl chloride (459 µL, 6.32 mmol) was added. The reaction mixture was stirred for a further 48 h and was then concentrated. The residue was dissolved in DCM (10 mL) and filtered through a short pad of celite. The filtrate was concentrated to afford the acyl imine intermediate (1.2 g) which was used without further purification. To a portion of the acyl imine intermediate (250 mg, 0.84 mmol), under nitrogen, was added 5,6-dimethyl-1H-1,3-benzodiazol-2-amine (136 mg, 0.84 mmol) in DMF (3 mL) followed by triethylamine (109 µL, 0.84 mmol). The reaction mixture was stirred at room temperature for 3 h and was then concentrated. The residue was dissolved in DCM (25 mL) and washed with water (2×25 mL). The organic phase was dried (MgSO$_4$), filtered and concentrated. The crude product was purified by automated reverse phase HPLC (low pH Method A) to afford the title compound as a light yellow solid (36 mg, 10%).

Example 24

N-[10,11-dimethyl-4-oxo-3-(trifluoromethyl)-2,5,7-triazatricyclo[6.4.0.0$^{2,6}$]dodeca-1(12),6,8,10-tetraen-3-yl]pyrrolidine-3-carboxamide hydrochloride (ABR 239077)

To a stirred solution of tert-butyl 3-{[10,11-dimethyl-4-oxo-3-(trifluoromethyl)-2,5,7-triaza-tricyclo[6.4.0.0$^{2,6}$]dodeca-1(12),6,8,10-tetraen-3-yl]carbamoyl}pyrrolidine-1-carboxylate (110 mg, 0.23 mmol) in diethyl ether (10 mL)

was added 2M HCl in ether (114 µL, 0.23 mmol) dropwise under nitrogen. The reaction mixture was stirred at room temperature for 16 h and then concentrated to afford the title compound as a white solid as a mixture of stereoisomers (94 mg, 98%).

Example 25

N-[10,11-dimethyl-4-oxo-3-(trifluoromethyl)-2,5,7-triazatricyclo[6.4.0.0$^{2,6}$]dodeca-1(12),6,8,10-tetraen-3-yl]piperidine-4-carboxamide hydrochloride (ABR 239205)

To a stirred solution of tert-butyl 4-{[10,11-dimethyl-4-oxo-3-(trifluoromethyl)-2,5,7-triazatricyclo[6.4.0.0$^{2,6}$]dodeca-1(12),6,8,10-tetraen-3-yl]carbamoyl}piperidine-1-carboxylate (715 mg, 1.44 mmol) in DCM (20 mL) and diethyl ether (20 mL) was added 2M HCl in ether (1.44 mL, 2.88 mmol) dropwise under nitrogen. The reaction mixture was stirred at room temperature for 16 h. The reaction was concentrated, azeotroped with diethyl ether (2×20 mL) and dried under vacuum to afford the title compound as the hydrochloride salt as a beige solid (609 mg, 98%).

Example 26

N-[10,11-dimethyl-4-oxo-3-(trifluoromethyl)-2,5,7-triazatricyclo[6.4.0.0$^{2,6}$]dodeca-1(12),6,8,10-tetraen-3-yl]-1-(2-methoxyacetyl)piperidine-4-carboxamide (ABR 239227)

To a stirred solution of N-[10,11-dimethyl-4-oxo-3-(trifluoromethyl)-2,5,7-triazatricyclo-[6.4.0.0$^{2,6}$]dodeca-1(12),6,8,10-tetraen-3-yl]piperidine-4-carboxamide hydrochloride (75 mg, 0.17 mmol) in DCM (10 mL) was added 2-methoxyacetyl chloride (23 mg, 0.21 mmol), followed by triethylamine (46 µL, 0.35 mmol) at 0° C. under nitrogen. The reaction mixture was allowed to warm to room temperature and then stirred for 4 h. The mixture was diluted with DCM (30 mL) and washed with water (2×20 mL). The organic phase was concentrated and purified by automated reverse phase HPLC (low pH Method A) to afford the title compound as a white solid (17 mg, 21%).

Example 27

3-cyclopentyl-N-[10,11-dimethyl-4-oxo-3-(trifluoromethyl)-2,5,7-triazatricyclo[6.4.0.0$^{2,6}$]-dodeca-1(12),6,8,10-tetraen-3-yl]propanamide (ABR 238788)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dimethyl-1H-1,3-benzodiazol-2-amine was used instead of 1H-1,3-benzodiazol-2-amine and 3-cyclopentylpropanamide was used instead of 2-bromobenzamide (10%).

Example 28

6-chloro-N-[10,11-dimethyl-4-oxo-3-(trifluoromethyl)-2,5,7-triazatricyclo[6.4.0.0$^{2,6}$]-dodeca-1(12),6,8,10-tetraen-3-yl]pyridine-3-carboxamide (ABR 238911)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dimethyl-1H-1,3-benzodiazol-2-amine was used instead of 1H-1,3-benzodiazol-2-amine and 6-chloropyridine-3-carboxamide was used instead of 2-bromobenzamide. The crude product was purified by silica chromatography, using 3% MeOH in DCM as eluent (13%).

Example 29

3-(2,6-dichlorophenyl)-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]propanamide (ABR 238998)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dimethyl-1H-1,3-benzodiazol-2-amine was used instead of 1H-1,3-benzodiazol-2-amine and 3-(2,6-dichlorophenyl)propanamide was used instead of 2-bromobenzamide. The crude product was purified by silica chromatography, using 3% MeOH in DCM as eluent (3%).

Example 30

2-bromo-N-[10,11-dimethyl-4-oxo-3-(trifluoromethyl)-2,5,7-triazatricyclo-[6.4.0.0$^{2,6}$]dodeca-1(8),6,9,11-tetraen-3-yl]benzamide (ABR 239004)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dimethyl-1H-1,3-benzodiazol-2-amine was used instead of 1H-1,3-benzodiazol-2-amine. The cruded product was purified by silica chromatography, using 3% MeOH in DCM as eluent (3%).

Example 31

6-(cyclohexylamino)-N-[10,11-dimethyl-4-oxo-3-(trifluoromethyl)-2,5,7-triazatricyclo-[6.4.0.0$^{2,6}$]dodeca-1(12),6,8,10-tetraen-3-yl]pyridine-3-carboxamide (ABR 239024)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dimethyl-1H-1,3-benzodiazol-2-amine was used instead of 1H-1,3-benzodiazol-2-amine and 6-(cyclohexylamino)pyridine-3-carboxamide was used instead of 2-bromobenzamide. The crude product was purified by silica chromatography, using 3% MeOH in DCM as eluent (6%).

Example 32

N-[10,11-dimethyl-4-oxo-3-(trifluoromethyl)-2,5,7-triazatricyclo[6.4.0.0$^{2,6}$]dodeca-1(12),6,8,10-tetraen-3-yl]-6-methylpyridine-3-carboxamide (ABR 239031)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dimethyl-1H-1,3-benzodiazol-2-amine was used instead of 1H-1,3-benzodiazol-2-amine and 6-methylpyridine-3-carboxamide was used instead of 2-bromobenzamide. The crude product was purified by silica chromatography, using 3% MeOH in DCM as eluent (6%).

Example 33

3-cyclohexyl-N-[10,11-dimethyl-3-oxo-4-(trifluoromethyl)-2,5,7-triazatricyclo-[6.4.0.0$^{2,6}$]dodeca-1(12),6,8,10-tetraen-4-yl]propanamide (ABR 238804)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 3-cyclohexylpropanamide was used instead of 2-bromobenzamide and after the addition of thionyl chloride the reaction mixture was stirred for 2 h instead of 16 h. In the second stage of the reaction, 5,6-dimethyl-1H-1,3-benzodiazol-2-amine was used instead of 1H-1,3-benzodiazol-2-amine and the reaction was stirred for 16 h instead of 4 h. The crude product was purified by preparative TLC, using 10% MeOH in DCM as eluent (3%).

Example 34

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(pyridin-3-yl)propanamide (ABR 239084)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 3-(pyridin-3-yl)propanamide was used instead of 2-bromobenzamide and after the addition of thionyl chloride the reaction mixture was stirred for 2 h instead of 16 h. In the second stage of the reaction, 5,6-dimethyl-1H-1,3-benzodiazol-2-amine was used instead of 1H-1,3-benzodiazol-2-amine and the reaction was stirred for 16 h instead of 4 h. The crude product was purified by silica chromatography, using 4% MeOH in DCM as eluent (1%).

Example 35

6-(cyclohexylamino)-N-[10,11-dimethyl-4-oxo-3-(trifluoromethyl)-2,5,7-triazatricyclo-[6.4.0.0$^{2,6}$]dodeca-1(12),6,8,10-tetraen-3-yl]pyridine-2-carboxamide (ABR 238974)

To a solution of 6-chloro-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]pyridine-2-carboxamide (200 mg, 0.47 mmol) in NMP (2 mL) was added N,N-diisopropylethylamine (0.16 mL, 1.89 mmol), followed by cyclohexylamine (0.22 mL, 1.89 mmol). The reaction mixture was heated in the microwave at 200° C. for 1 h and then concentrated. The residue was purified by silica chromatography, using 5% MeOH in DCM as eluent, to afford the title compound as yellow solid (15 mg, 7%).

Example 36

6-cyclohexyl-N-[10,11-dimethyl-4-oxo-3-(trifluoromethyl)-2,5,7-triazatricyclo[6.4.0.0$^{2,6}$]-dodeca-1(12),6,8,10-tetraen-3-yl]pyridine-2-carboxamide (ABR 239059)

A microwave tube was charged with 6-chloro-N-[10,11-dimethyl-4-oxo-3-(trifluoro-methyl)-2,5,7-triazatricyclo[6.4.0.0$^{2,6}$]dodeca-1(8),6,9,11-tetraen-3-yl]pyridine-2-carbox-amide (100 mg, 0.24 mmol), cyclohexene boronic acid (29 mg, 0.24 mmol), SPhos (9 mg, 0.02 mmol), Na$_2$CO$_3$ (50 mg, 0.47 mmol) and DMF/water (9:1, 10 mL). The reaction mixture was degassed with argon for 15 min. Palladium(II) acetate (5 mg, 0.02 mmol) was added and the reaction mixture was heated in the microwave at 100° C. for 30 min. The reaction was allowed to cool to room temperature and filtered through a pad of celite. The filtrate was diluted with water (10 mL) and extracted with ethyl acetate (2×15 mL). The combined organic phases were dried (Na$_2$SO$_4$), filtered and concentrated. The crude compound was purified by automated reverse phase HPLC (low pH Method B) to afford the title compound as an off-white solid (10 mg, 9%).

Example 37

N-[10,11-dichloro-4-oxo-3-(trifluoromethyl)-2,5,7-triazatricyclo[6.4.0.0$^{2,6}$]dodeca-1(8),6,9,11-tetraen-3-yl]-3-phenylpropanamide (ABR 239019)

To a stirred solution of methyl (2E)-3,3,3-trifluoro-2-[(3-phenylpropanoyl)imino]-propanoate (100 mg, 0.35 mmol) and 5,6-dichloro-1H-1,3-benzodiazol-2-amine (70 mg, 0.35 mmol) in DMF (5 mL), under nitrogen, was added triethylamine (46 µL, 0.35 mmol). The reaction mixture was stirred at room temperature for 16 h and then concentrated. The residue was purified by silica chromatography, using 0-10% MeOH in DCM as eluent, to afford the title compound as an off white solid (57 mg, 36%).

Example 38

N-[10,11-dichloro-4-oxo-3-(trifluoromethyl)-2,5,7-triazatricyclo[6.4.0.0$^{2,6}$]dodeca-1(8),6,9,11-tetraen-3-yl]benzamide (ABR 238949)

To a stirred solution of 5,6-dichloro-1H-1,3-benzodiazol-2-amine (100 mg, 0.49 mmol) and methyl (Z)-benzoylimino-3,3,3-trifluoropropanoate (128 mg, 0.49 mmol) in DMF (2 mL), was added triethylamine (66 µL, 0.49 mmol) under nitrogen. The reaction mixture was stirred for 16 h at room temperature, concentrated and purified by automated reverse phase HPLC (low pH Method A) to afford the title compound as a white solid (24 mg, 11%).

Example 39

3-cyclopentyl-N-[10,11-dichloro-4-oxo-3-(trifluoromethyl)-2,5,7-triazatricyclo[6.4.0.0$^{2,6}$]-dodeca-1(12),6,8,10-tetraen-3-yl]propanamide (ABR 238926)

To a stirred solution of 3-cyclopentylpropanamide (3.50 g, 24.8 mmol) in DMF (50 mL) was added methyl 3,3,3-trifluoro-2-oxopropanoate (3.87 g, 24.8 mmol) followed by pyridine (2.00 mL, 24.8 mmol) at room temperature under nitrogen. The reaction mixture was stirred at room temperature for 4 h and then cooled to 0° C. Thionyl chloride (1.80 mL, 24.8 mmol) was added dropwise to this solution and the reaction mixture was stirred at room temperature for 16 h. The reaction mixture was concentrated and filtered through a short pad of silica, eluting with DCM (100 mL). The filtrate was concentrated, and the acyl imine intermediate that remained was immediately dissolved in DMF (30 mL) under nitrogen. 5,6-Dichloro-1H-1,3-benzodiazol-2-amine (4.01 g, 19.8 mmol) was added to the solution followed by triethylamine (3.96 mL, 29.7 mmol). The resulting mixture was stirred at room temperature for 2 h and then concentrated. The residue was dissolved in EtOAc (200 mL), washed with water (4×100 mL) and brine (2×100 mL), dried (MgSO$_4$), filtered and concentrated. The crude product was purified by silica chromatography, using 3% MeOH in DCM as eluent, to afford a dark brown foam. This was dissolved in MeOH (100 mL) and decolourised with charcoal. The resulting suspension was filtered through celite and washed with MeOH. The filtrate was concentrated to afford the title compound as a light yellow solid (3.2 g, 29%).

Example 40

N-[10,11-dichloro-4-oxo-3-(trifluoromethyl)-2,5,7-triazatricyclo[6.4.0.0$^{2,6}$]dodeca-1(12),6,8,10-tetraen-3-yl]-2-azaspiro[3.3]heptane-6-carboxamide (ABR 239424)

To a stirred solution of tert-butyl 6-{[10,11-dichloro-4-oxo-3-(trifluoromethyl)-2,5,7 triazatricyclo[6.4.0.0$^{2,6}$]dodeca-1(12),6,8,10-tetraen-3-yl]carbamoyl}-2-azaspiro[3.3]-heptane-2-carboxylate (100 mg, 0.18 mmol) in DCM (25 mL) was added TFA (1.0 mL, 13.1 mmol) dropwise. The solution was stirred at room temperature under nitrogen for 16 h and then concentrated. The resulting solid was azeotroped with diethyl ether and dried under vacuum to afford the title compound as the TFA salt as a light pink solid was (78 mg, 76%).

Example 41

Diastereomeric mixture. (2S)—N-[10,11-dichloro-4-oxo-3-(trifluoromethyl)-2,5,7-triaza-tricyclo [6.4.0.0$^{2,6}$]dodeca-1(12),6,8,10-tetraen-3-yl]pyrrolidine-2-carboxamide (ABR 239426)

tert-Butyl-(2S)-2-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate (50 mg, 0.1 mmol) was dissolved in DCM (10 mL) and TFA (0.5 mL, 3.3 mmol) was added. The reaction mixture was stirred at room temperature for 16 h and then concentrated. The resulting solid was azeotroped with toluene (2×20 mL) and dried under vacuum to afford the title compound as the TFA salt as a mixture of diastereomers (49 mg, 95%).

Example 42

Diastereomeric mixture N-[10,11-dichloro-4-oxo-3-(trifluoromethyl)-2,5,7-triazatricyclo-[6.4.0.0$^{2,6}$]dodeca-1(12),6,8,10-tetraen-3-yl]pyrrolidine-3-carboxamide (ABR 239136)

To a stirred solution of tert-butyl 3-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}pyrrolidine-1-carboxylate (466 mg, 0.89 mmol) in diethyl ether (10 mL) was added 2M HCl in ether (0.67 mL, 1.34 mmol) dropwise under nitrogen. The reaction mixture was stirred for 24 h and then concentrated. A 100 mg sample was then purified by automated reverse phase HPLC (high pH method) to afford the title compound as the hydrochloride salt as a white solid as a mixture of diastereomers (34 mg).

Example 43

N-[10,11-dichloro-4-oxo-3-(trifluoromethyl)-2,5,7-triazatricyclo[6.4.0.0$^{2,6}$]dodeca-1(12),6,8,10-tetraen-3-yl]piperidine-4-carboxamide (ABR 239206)

tert-Butyl-4-{[10,11-dichloro-4-oxo-3-(trifluoromethyl)-2,5,7-triazatricyclo[6.4.0.0$^{2,6}$]-dodeca-1(12),6,8,10-tetraen-3-yl]carbamoyl}piperidine-1-carboxylate (810 mg, 1.51 mmol) was dissolved in diethyl ether (20 mL) and DCM (20 mL). 2M HCl in ether (6.04 mL, 12.08 mmol) was added portionwise over 74 h. The reaction mixture was concentrated and the resulting solid triturated with ether. A sample of this material was purified by automated reverse phase HPLC (high pH method) to afford the title compound as a white solid (7 mg).

Example 44

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(2-methoxyacetyl)piperidine-4-carboxamide (ABR 239228)

To a stirred solution of N-[10,11-dichloro-4-oxo-3-(trifluoromethyl)-2,5,7-triaza-tricyclo[6.4.0.0$^{2,6}$]dodeca-1(12), 6,8,10-tetraen-3-yl]piperidine-4-carboxamide hydrochloride (75 mg, 0.16 mmol) in DCM (10 mL), under nitrogen, was added triethylamine (42 µL, 0.32 mmol) followed by 2-methoxyacetyl chloride (21 mg, 0.19 mmol). The reaction mixture was stirred at room temperature for 2 h and then diluted with DCM (20 mL) and washed with water (2×20 mL). The organic phase was dried (MgSO$_4$), filtered and concentrated. The crude product was purified by silica chromatography, using 5-10% MeOH in DCM as eluent, to afford the title compound as a yellow solid at approximately 75% purity (16 mg, 20%). The title compound was tested in biological assays without further purification.

Example 45

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(3-methylbutanoyl)piperidine-4-carboxamide (ABR 239229)

To a stirred solution of N-[10,11-dichloro-4-oxo-3-(trifluoromethyl)-2,5,7-triazatricyclo-[6.4.0.0$^{2,6}$]dodeca-1(12), 6,8,10-tetraen-3-yl]piperidine-4-carboxamide hydrochloride (75 mg, 0.16 mmol) in DCM (10 mL), under nitrogen, was added 3-methylbutanoyl chloride (23 mg, 0.19 mmol) followed by triethylamine (42 µL, 0.32 mmol). The reaction mixture was stirred at room temperature for 6 h. The reaction mixture was diluted with DCM (25 mL) and washed with water (3×25 mL). The organic phase was dried (MgSO$_4$), filtered and concentrated. The crude product was purified by automated reverse phase HPLC (high pH method) to afford the title compound as a light yellow solid at approximately 73% purity (29 mg, 35%). The title compound was tested in biological assays without further purification.

Example 46

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(3,3,3-trifluoropropanoyl)piperidine-4-carboxamide (ABR 239232)

To a stirred solution of N-[10,11-dichloro-4-oxo-3-(trifluoromethyl)-2,5,7-triazatricyclo-[6.4.0.0$^{2,6}$]dodeca-1(12), 6,8,10-tetraen-3-yl]piperidine-4-carboxamide hydrochloride (75 mg, 0.16 mmol) in DCM (10 mL), under nitrogen, was added 3,3,3-trifluoropropanoyl chloride (28 mg, 0.19 mmol) followed by triethylamine (42 µL, 0.32 mmol). The solution was stirred at room temperature for 4 h and then additional 3,3,3-trifluoropropanoyl chloride (28 mg, 0.19 mmol) was added. After stiffing for a further 8 h the reaction mixture was diluted with DCM (20 mL) and washed with water (3×25 mL). The organic phase was dried (MgSO$_4$), filtered and concentrated. The crude reaction product was purified by automated reverse phase HPLC (low pH Method A) to afford the desired product as a white solid (5 mg, 6%).

Example 47

N-[10,11-dichloro-4-oxo-3-(trifluoromethyl)-2,5,7-triazatricyclo[6.4.0.0$^{2,6}$]dodeca-1(12),6,8,10-tetraen-3-yl]azetidine-3-carboxamide (ABR 239257)

To a stirred solution of tert-butyl 3-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}azetidine-1-carboxylate (800 mg, 1.57 mmol) in DCM (100 mL) at 0° C. was added TFA (3.53 mL, 4.72 mmol) dropwise. The solution was stirred at 0° C. for 1 h and then allowed to warm to room temperature. After 3 h the reaction mixture was evaporated to approximately 15 mL and then diethyl ether (50 mL) added. The suspension was concentrated and the resulting solid azeotroped with diethyl ether a further 3 times. The solid was free based through an SCX column washing with MeOH/DCM (1:1) and then eluting with 2M ammonia in MeOH. The basic filtrate was collected and concentrated to afford the title compound as a white solid (507 mg, 79%).

Example 48

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(ethanesulfonyl)azetidine-3-carboxamide (ABR 239402)

To a stirred solution of N-[10,11-dichloro-4-oxo-3-(trifluoromethyl)-2,5,7-triazatricyclo-[6.4.0.0$^{2,6}$]dodeca-1(12),6,8,10-tetraen-3-yl]azetidine-3-carboxamide (50 mg, 0.12 mmol) in anhydrous THF (5 mL) was added ethanesulfonyl chloride (13 µL, 0.13 mmol) followed by 2M NaOH(aq) (92 µL, 0.18 mmol). The reaction mixture was stirred at room temperature for 2 h. A further portion of ethanesulfonyl chloride (13 µL, 0.13 mmol) followed by 2M NaOH(aq) (92 µL, 0.18 mmol) was added. The reaction mixture was stirred for 2 h and then concentrated. The residue was dissolved in EtOAc (100 mL) and washed with water (2×25 mL) and brine (50 mL). The organic phase was dried (MgSO$_4$), filtered and concentrated. The crude product purified by automated reverse phase HPLC (low pH Method A) to afford the title compound as a white solid (31 mg, 51%).

Example 49

1-acetyl-N-[10,11-dichloro-4-oxo-3-(trifluoromethyl)-2,5,7-triazatricyclo-[6.4.0.0$^{2,6}$]-dodeca-1(12),6,8,10-tetraen-3-yl]azetidine-3-carboxamide (ABR 239403)

To a stirred solution of N-[10,11-dichloro-4-oxo-3-(trifluoromethyl)-2,5,7-triazatricyclo-[6.4.0.0$^{2,6}$]dodeca-1(12), 6,8,10-tetraen-3-yl]azetidine-3-carboxamide (100 mg, 0.25 mmol) in DCM (10 mL) was added acetyl chloride (19 µL, 0.27 mmol) followed by triethylamine (49 µL, 0.37 mmol). The reaction mixture was stirred at room temperature for 2 h. The reaction mixture was washed with water (2×25 mL) and the organic layer concentrated. The crude product was purified by automated reverse phase HPLC (low pH Method A) and azeotroped in water to afford the title compound as a white solid (19 mg, 17%).

Example 50

(rac).1-cyclopentanecarbonyl-N-[10,11-dichloro-4-oxo-3-(trifluoromethyl)-2,5,7-triaza-tricyclo [6.4.0.0$^{2,6}$]dodeca-1(12),6,8,10-tetraen-3-yl]pyrrolidine-3-carboxamide (ABR 239137)

To a stirred solution of N-[10,11-dichloro-4-oxo-3-(trifluoromethyl)-2,5,7-triazatricyclo-[6.4.0.0$^{2,6}$]-dodeca-1(12), 6,8,10-tetraen-3-yl]pyrrolidine-3-carboxamide hydrochloride (95 mg, 0.21 mmol) in DCM (3 mL) at 0° C. was added cyclopentanecarbonyl chloride (26 µL, 0.22 mmol) dropwise followed by triethylamine (58 µL, 0.41 mmol) under nitrogen. The reaction mixture was allowed to warm to room temperature and then stirred for a further 16 h. The reaction mixture was diluted with water (20 mL) and DCM (20 mL) and the layers separated. The organic phase was washed with water (20 mL), dried (MgSO$_4$), filtered and concentrated. The crude product was purified by automated reverse phase HPLC (low pH Method A) to afford the title compound as a mixture of diastereomers (5 mg, 5%). Tested without further purification.

Example 51

(3R)-1-(cyclopentanesulfonyl)-N-[10,11-dichloro-4-oxo-3-(trifluoromethyl)-2,5,7-triaza-tricyclo [6.4.0.0$^{2,6}$]dodeca-1(12),6,8,10-tetraen-3-yl]pyrrolidine-3-carboxamide (ABR 239139)

To a stirred solution of (3R)—N-[10,11-dichloro-4-oxo-3-(trifluoromethyl)-2,5,7-triaza-tricyclo[6.4.0.0$^{2,6}$]dodeca-1 (8),6,9,11-tetraen-3-yl]pyrrolidine-3-carboxamide hydrochloride (817 mg, 1.78 mmol) in THF (20 mL) was added cyclopentanesulfonyl chloride (258 µL, 1.96 mmol) followed by 2M NaOH$_{(aq)}$ (1.83 mL, 3.66 mmol). The reaction mixture was stirred at room temperature for 3 h. Additional cyclopentane-sulfonyl chloride (70 µL, 0.53 mmol) was added and stiffing was continued for a further 16 h. The reaction mixture was then concentrated and partitioned between EtOAc (50 mL) and water (50 mL). The organic phase was dried (MgSO$_4$), filtered and concentrated. The crude product was purified by silica chromatography, using 0-10% MeOH in DCM as eluent, to afford the title compound as an off-white solid (304 mg, 31%).

Example 52

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(pyridin-2-yl)azetidine-3-carboxamide (ABR 239404)

A suspension of N-[10,11-dichloro-4-oxo-3-(trifluoromethyl)-2,5,7-triazatricyclo-[6.4.0.0$^{2,6}$]dodeca-1(12),6,8,10-tetraen-3-yl]azetidine-3-carboxamide (100 mg, 0.25 mmol) and potassium carbonate (51 mg, 0.37 mmol) in DMF (2 mL) was stirred at room temperature. To the suspension was added 2-chloropyridine (28 μL, 0.29 mmol) and the reaction mixture was stirred for 16 h at 120° C. The reaction mixture was concentrated and partitioned between EtOAc (25 mL) and water (25 mL). The organic phase was washed with water (3×25 mL) and brine (2×25 mL), dried (MgSO$_4$), filtered and concentrated. The crude product was purified by automated reverse phase HPLC (low pH Method A) to afford the desired product as a white solid as the formic acid salt (18 mg, 15%).

Example 53

3-cyclohexyl-N-[10,11-dichloro-4-oxo-3-(trifluoromethyl)-2,5,7-triazatricyclo[6.4.0.0$^{2,6}$]-dodeca-1(12),6,8,10-tetraen-3-yl]propanamide (ABR 239034)

The procedure for the preparation of 2-bromo-N-[3-oxo-4-(trifluoromethyl)-2,5,7-triaza-tricyclo[6.4.0.0$^{2,6}$]dodeca-1(12),6,8,10-tetraen-4-yl]benzamide was used except that 5,6-dichloro-1H-1,3-benzodiazol-2-amine was used instead of 1H-1,3-benzodiazol-2-amine and 3-cyclohexylpropanamide was used instead of 2-bromobenzamide. The crude product was purified by silica chromatography, using 2.5% MeOH in DCM as eluent (6%).

Example 54

N-[10,11-dichloro-4-oxo-3-(trifluoromethyl)-2,5,7-triazatricyclo[6.4.0.0$^{2,6}$]dodeca-1(12),6,8,10-tetraen-3-yl]cyclopentanecarboxamide (ABR 239114)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, cyclopentanecarboxamide was used instead of 2-bromobenzamide and after the addition of thionyl chloride the reaction mixture was stirred for 2.5 h instead of 16 h. In the second stage of the reaction, 5,6-dichloro-1H-1,3-benzodiazol-2-amine was used instead of 1H-1,3-benzodiazol-2-amine and the reaction was stirred for 2 h instead of 4 h. The crude product was purified by silica chromatography, using 2% MeOH in DCM as eluent (9%).

Example 55

N-[10,11-dichloro-4-oxo-3-(trifluoromethyl)-2,5,7-triazatricyclo[6.4.0.0$^{2,6}$]dodeca-1(12),6,8,10-tetraen-3-yl]cyclohexanecarboxamide (ABR 239115)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, cyclohexanecarboxamide was used instead of 2-bromobenzamide and after the addition of thionyl chloride the reaction mixture was stirred for 2.5 h instead of 16 h. In the second stage of the reaction, 5,6-dichloro-1H-1,3-benzodiazol-2-amine was used instead of 1H-1,3-benzodiazol-2-amine and the reaction was stirred for 16 h instead of 4 h. The crude product was purified by silica chromatography, using 3% MeOH in DCM as eluent, followed by trituration in DCM/pentane (2%).

Example 56

3-chloro-N-[10,11-dichloro-4-oxo-3-(trifluoromethyl)-2,5,7-triazatricyclo[6.4.0.0$^{2,6}$]-dodeca-1(12),6,8,10-tetraen-3-yl]benzamide (ABR 239414)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 3-chlorobenzamide was used instead of 2-bromobenzamide and after the addition of thionyl chloride the reaction mixture was stirred for 18 h instead of 16 h. In the second stage of the reaction, 5,6-dichloro-1H-1,3-benzodiazol-2-amine was used instead of 1H-1,3-benzodiazol-2-amine and the reaction was stirred for 18 h instead of 4 h. The crude product was purified by silica chromatography, using 2-4% MeOH in DCM as eluent (3%).

Example 57

3,5-dichloro-N-[10,11-dichloro-4-oxo-3-(trifluoromethyl)-2,5,7-triazatricyclo-[6.4.0.0$^{2,6}$]dodeca-1(12),6,8,10-tetraen-3-yl]benzamide (ABR 239427)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 3,5-dichlorobenzamide was used instead of 2-bromobenzamide and after the addition of thionyl chloride the reaction mixture was stirred for 18 h instead of 16 h. In the second stage of the reaction, 5,6-dichloro-1H-1,3-benzodiazol-2-amine was used instead of 5,6-dimethyl-1H-1,3-benzodiazol-2-amine and the reaction was stirred for 18 h instead of 4 h. The crude product was purified by silica chromatography, using 4% MeOH in DCM as eluent (5%).

Example 58

N-[10,11-dichloro-4-oxo-3-(trifluoromethyl)-2,5,7-triazatricyclo[6.4.0.0$^{2,6}$]dodeca-1(12),6,8,10-tetraen-3-yl]-4-(pyrrolidin-1-yl)butanamide (ABR 239155)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 4-(pyrrolidin-1-yl)butanamide was used instead of 2-bromobenzamide and after the addition of thionyl chloride the reaction mixture was stirred for 72 h instead of 16 h. In the second stage of the reaction, 5,6-dichloro-1H-1,3-benzodiazol-2-amine was used instead of 1H-1,3-benzodiazol-2-amine and the reaction was stirred for 16 h instead of 4 h. The crude product was purified by automated reverse phase HPLC (low pH Method B) (1%).

Example 59

N-[10,11-dichloro-4-oxo-3-(trifluoromethyl)-2,5,7-triazatricyclo[6.4.0.0$^{2,6}$]dodeca-1(12),6,8,10-tetraen-3-yl]-4-(morpholin-4-yl)butanamide (ABR 239161)

The general procedure for the preparation of 2-bromo-N-[3-oxo-4-(trifluoromethyl)-2,5,7-triazatricyclo[6.4.0.0$^{2,6}$]

dodeca-1(12),6,8,10-tetraen-4-yl]benzamide was used but with the following changes. In the first stage of the reaction, to form the acyl imine intermediate, 4-(morpholin-4-yl)butanamide was used instead of 2-bromobenzamide and after the addition of thionyl chloride the reaction mixture was stirred for 2.5 h instead of 16 h. In the second stage of the reaction, 5,6-dichloro-1H-1,3-benzodiazol-2-amine was used instead of 1H-1,3-benzodiazol-2-amine and the reaction was stirred for 16 h instead of 4 h. The crude product was purified by silica chromatography, using 20% MeOH in DCM as eluent (11%).

Example 60

N-[10,11-dichloro-4-oxo-3-(trifluoromethyl)-2,5,7-triazatricyclo[6.4.0.0$^{2,6}$]dodeca-1(12),6,8,10-tetraen-3-yl]-2-(morpholin-4-yl)acetamide (ABR 239358)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 2-(morpholin-4-yl)acetamide: prepared according to literature (Chaudhari et al. 2007); was used instead of 2-bromobenzamide and after the addition of thionyl chloride the reaction mixture was stirred for 18 h instead of 16 h. In the second stage of the reaction, 5,6-dichloro-1H-1,3-benzodiazol-2-amine was used instead of 1H-1,3-benzodiazol-2-amine and the reaction was stirred for 16 h instead of 4 h. The crude product was purified by automated reverse phase HPLC (low pH Method B) (4%).

Example 61

N-[10,11-dichloro-4-oxo-3-(trifluoromethyl)-2,5,7-triazatricyclo[6.4.0.0$^{2,6}$]dodeca-1(12),6,8,10-tetraen-3-yl]-3-(morpholin-4-yl)propanamide (ABR 239259)

To a solution of 2-[(5,6-dichloro-1H-1,3-benzodiazol-2-yl)amino]-3,3,3-trifluoro-2-[3-(morpholin-4-yl)propanamido]propanoate (0.20 g, 0.39 mmol) in toluene (3 mL) was added trimethylaluminium (75 µL, 0.39 mmol) dropwise, under argon, at 0° C. The reaction was allowed to warm to room temperature, stirred for 1 h at room temperature and then heated at 100° C. for 16 h. The reaction was allowed to cool to room temperature and ice/water was added. The resulting precipitate was removed by filtration and the filtrate was extracted with EtOAc (2×20 mL). The combined organic phases were separated, dried (Na$_2$SO$_4$), filtered and concentrated. The crude product was purified by silica chromatography, using 4% MeOH in DCM as eluent, to afford the title compound as a grey solid (15 mg, 8%).

Example 62

6-chloro-N-[10,11-dichloro-4-oxo-3-(trifluoromethyl)-2,5,7-triazatricyclo[6.4.0.0$^{2,6}$]-dodeca-1(12),6,8,10-tetraen-3-yl]pyridine-2-carboxamide (ABR 239356)

The general procedure for the preparation of 2-bromo-N-[3-oxo-4-(trifluoromethyl)-2,5,7-triazatricyclo[6.4.0.0$^{2,6}$]dodeca-1(12),6,8,10-tetraen-4-yl]benzamide was used but with the following changes. In the first stage of the reaction, to form the acyl imine intermediate, 6-chloropyridine-2-carboxamide was used instead of 2-bromobenzamide. In the second stage of the reaction, 5,6-dichloro-1H-1,3-benzodiazol-2-amine was used instead of 1H-1,3-benzodiazol-2-amine and the reaction was stirred for 16 h instead of 4 h. The crude product was purified by silica chromatography, using 2% MeOH in DCM as eluent (14%).

Example 63

6-(azetidin-1-yl)-N-[10,11-dichloro-4-oxo-3-(trifluoromethyl)-2,5,7-triazatricyclo[6.4.0.0$^{2,6}$]-dodeca-1(12),6,8,10-tetraen-3-yl]pyridine-2-carboxamide (ABR 239354)

To a solution of 6-chloro-N-[10,11-dichloro-4-oxo-3-(trifluoromethyl)-2,5,7-triaza-tricyclo[6.4.0.0$^{2,6}$]dodeca-1(12),6,8,10-tetraen-3-yl]pyridine-2-carboxamide (200 mg, 0.43 mmol) in DMF (3 mL), in a sealed tube, were added K$_2$CO$_3$ (59 mg, 0.43 mmol) and azetidine (25 mg, 0.43 mmol). The reaction mixture was heated at 100° C. for 16 h. The reaction mixture was diluted with water (15 mL) and extracted with EtOAc (2×25 mL). The combined organic phases were washed with brine (15 mL), dried (Na$_2$SO$_4$), filtered and concentrated. The crude product was purified by automated reverse phase HPLC (low pH Method B) to afford the title compound as a white solid (70 mg, 33%).

Example 64

N-[10,11-dichloro-4-oxo-3-(trifluoromethyl)-2,5,7-triazatricyclo[6.4.0.0$^{2,6}$]dodeca-1(12),6,8,10-tetraen-3-yl]-6-(2,2,2-trifluoroethoxy)pyridine-2-carboxamide (ABR 239390)

The procedure for the preparation 6-(azetidin-1-yl)-N-[10,11-dichloro-4-oxo-3-(trifluoro-methyl)-2,5,7-triazatricyclo[6.4.0.0$^{2,6}$]dodeca-1(12),6,8,10-tetraen-3-yl]pyridine-2-carboxamide was used except that 2,2,2-trifluoroethan-1-ol was used instead of azetidine (15%).

Example 65

N-[10,11-dichloro-4-oxo-3-(trifluoromethyl)-2,5,7-triazatricyclo[6.4.0.0$^{2,6}$]dodeca-1(12),6,8,10-tetraen-3-yl]-6-(dimethylamino)pyridine-2-carboxamide (ABR 239391)

The procedure for the preparation of N-[10,11-dichloro-4-oxo-3-(trifluoromethyl)-2,5,7-triazatricyclo[6.4.0.0$^{2,6}$]dodeca-1(12),6,8,10-tetraen-3-yl]-6-(dimethylamino)pyridine-2-carboxamide was used except that dimethylamine (70 wt. % in water) was used instead of azetidine (52%).

Example 66

6-(cyclohexylamino)-N-[10,11-dichloro-4-oxo-3-(trifluoromethyl)-2,5,7-triazatricyclo-[6.4.0.0$^{2,6}$]dodeca-1(12),6,8,10-tetraen-3-yl]pyridine-2-carboxamide (ABR 239409)

The procedure for the preparation of N-[10,11-dichloro-4-oxo-3-(trifluoromethyl)-2,5,7-triazatricyclo[6.4.0.0$^{2,6}$]dodeca-1(12),6,8,10-tetraen-3-yl]-6-(dimethylamino)pyridine-2-carboxamide was used except that cyclohexylamine was used instead of azetidine and the reaction was heated for 2 h instead of 16 h. The crude product was purified by silica chromatography, using 3% MeOH in DCM as eluent, followed by re-cyrstallisation in DCM/MeOH to afford the title compound (31%).

Example 67

N-[10,11-dimethyl-4-oxo-3-(trifluoromethyl)-2,5,7-triazatricyclo[6.4.0.0$^{2,6}$]dodeca-1(12),6,8,10-tetraen-3-yl]-6-(ethylamino)pyridine-2-carboxamide (ABR 239101)

A sealed tube was charged with 6-chloro-N-[10,11-dimethyl-4-oxo-3-(trifluoromethyl)-2,5,7-triazatricyclo[6.4.0.0$^{2,6}$]dodeca-1(12),6,8,10-tetraen-3-yl]pyridine-2-carboxamide (150 mg, 0.35 mmol) and ethylamine (70 wt. % in water, 56 µL, 1.06 mmol). The reaction was heated at 100° C. for 16 h. The reaction mixture was diluted with water (10 mL) and extracted with EtOAc (2×25 mL). The combined organic phases were dried (Na$_2$SO$_4$), filtered and concentrated. The crude product was purified by automated reverse phase HPLC (low pH Method B) to afford the title compound as a white solid (31 mg, 20%).

Example 68

N-[10,11-dichloro-4-oxo-3-(trifluoromethyl)-2,5,7-triazatricyclo[6.4.0.0$^{2,6}$]dodeca-1(12),6,8,10-tetraen-3-yl]-2-(piperidin-4-yl)acetamide (ABR 239386)

A solution of 4M HCl in dioxane (3 mL, 12.0 mmol) was added to tert-butyl 4-({[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}methyl)piperidine-1-carboxylate (60 mg, 0.11 mmol) at 0° C. The reaction mixture stirred at room temperature for 3 h and concentrated. The residue was triturated in diethyl ether/EtOH to afford the title compound as the hydrochloride salt as a white solid (41 mg, 77%).

Example 69

N-[10,11-dichloro-4-oxo-3-(trifluoromethyl)-2,5,7-triazatricyclo[6.4.0.0$^{2,6}$]dodeca-1(12),6,8,10-tetraen-3-yl]-3-(piperidin-2-yl)propanamide (ABR 239393)

A solution of 4M HCl in dioxane (5 mL, 20.0 mmol) was added to tert-butyl 2-(2-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}ethyl)piperidine-1-carboxylate (200 mg, 0.35 mmol) at 0° C. The reaction mixture stirred at room temperature for 3 h and concentrated. The residue was triturated in diethyl ether/EtOH to afford the title compound as the hydrochloride salt as an off-white solid (140 mg, 60%).

Example 70

N-[10,11-dichloro-4-oxo-3-(trifluoromethyl)-2,5,7-triazatricyclo[6.4.0.0$^{2,6}$]dodeca-1(12),6,8,10-tetraen-3-yl]-6-(ethylamino)pyridine-2-carboxamide (ABR 239355)

To a solution of 6-chloro-N-[10,11-dichloro-4-oxo-3-(trifluoromethyl)-2,5,7-triaza-tricyclo[6.4.0.0$^{2,6}$]dodeca-1(12),6,8,10-tetraen-3-yl]pyridine-2-carboxamide (2.00 g, 4.31 mmol) in EtOH (20 mL), in a sealed tube, were added cesium hydroxide monohydrate (722 mg, 4.31 mmol) and 2M ethylamine in THF (194 mg, 4.31 mmol). The reaction was heated at 100° C. for 16 h. The reaction mixture was diluted with water (15 mL) and extracted with EtOAc (2×25 mL). The combined organic phases were washed with brine (15 mL), dried (Na$_2$SO$_4$), filtered and concentrated. The crude product was purified by automated reverse phase HPLC (low pH Method B) to afford the title compound as an orange solid (172 mg, 8%).

Example 71

N-[10,11-dichloro-4-oxo-3-(trifluoromethyl)-2,5,7-triazatricyclo[6.4.0.0$^{2,6}$]dodeca-1(12),6,8,10-tetraen-3-yl]-6-[(2-methoxyethyl)amino]pyridine-2-carboxamide (ABR 239432)

To a solution of N-[10,11-dichloro-4-oxo-3-(trifluoromethyl)-2,5,7-triazatricyclo-[6.4.0.0$^{2,6}$]dodeca-1(12),6,8,10-tetraen-3-yl]-6-fluoropyridine-2-carboxamide (150 mg, 0.33 mmol) in DMF (2 mL), in a sealed tube, were added K$_2$CO$_3$ (93 mg, 0.67 mmol) and 2-methoxyethan-1-amine (25 mg, 0.34 mmol). The reaction mixture was heated at 100° C. for 2 h. The reaction mixture was diluted with water (15 mL) and extracted with EtOAc (2×25 mL). The combined organic phases were washed with brine (15 mL), dried (Na$_2$SO$_4$), filtered and concentrated. The crude product was purified by automated reverse phase HPLC (low pH Method B) to afford the title compound as an off-white solid (35 mg, 21%).

Example 72

N-[10,11-difluoro-4-oxo-3-(trifluoromethyl)-2,5,7-triazatricyclo[6.4.0.0$^{2,6}$]dodeca-1(12),6,8,10-tetraen-3-yl]benzamide (ABR 238928)

To a stirred solution of 5,6-difluoro-1H-1,3-benzodiazol-2-amine (60 mg, 0.35 mmol) in DMF (2 mL) was added methyl (Z)-benzoylimino-3,3,3-trifluoropropanoate (92 mg, 0.35 mmol) and triethylamine (47 µL, 0.35 mmol) under nitrogen. The solution was at room temperature for 3 h and then concentrated. The residue was purified by automated reverse phase HPLC (low pH Method A) to afford the title compound as a yellow solid (39 mg, 28%).

Example 73

3-cyclopentyl-N-[10,11-difluoro-4-oxo-3-(trifluoromethyl)-2,5,7-triazatricyclo-[6.4.0.0$^{2,6}$]dodeca-1(12),6,8,10-tetraen-3-yl]propanamide (ABR 238925)

To a stirred solution of 5,6-difluoro-1H-1,3-benzodiazol-2-amine (100 mg, 0.59 mmol) and methyl (2Z)-2-[(3-cyclopentylpropanoyl)imino]-3,3,3-trifluoropropanoate (165 mg, 0.59 mmol) in DMF (2 mL) was added triethylamine (79 µL, 0.59 mmol) under nitrogen. The reaction mixture was stirred at room temperature for a further 4 h, concentrated and purified by automated reverse phase HPLC (low pH Method A) to afford the title compound as an off-white solid (44 mg, 18%).

Example 74

2-cyclohexyl-N-[10,11-difluoro-4-oxo-3-(trifluoromethyl)-2,5,7-triazatricyclo[6.4.0.0$^{2,6}$]-dodeca-1(8),6,9,11-tetraen-3-yl]acetamide (ABR 238929)

To a stirred solution of 5,6-difluoro-1H-1,3-benzodiazol-2-amine (75 mg, 0.44 mmol) and methyl (2Z)-2-[(2-cyclohexylacetyl)imino]-3,3,3-trifluoropropanoate (124 mg, 0.44 mmol) in DMF (2 mL) was added triethylamine (59 μL, 0.44 mmol) under nitrogen. The reaction mixture was stirred at room temperature for 2 h and then concentrated. The crude product was purified by automated reverse phase HPLC (low pH Method A) to afford the desired product as a beige solid (85 mg, 46%).

Example 75

N-[10,11-dimethoxy-4-oxo-3-(trifluoromethyl)-2,5,7-triazatricyclo[6.4.0.0$^{2,6}$]dodeca-1(12),6,8,10-tetraen-3-yl]benzamide (ABR 238995)

To a stirred solution of 5,6-dimethoxy-1H-1,3-benzodiazol-2-amine (100 mg, 0.52 mmol) and methyl (Z)-benzoylimino-3,3,3-trifluoropropanoate (134.15 mg, 0.52 mmol) in DMF (2 mL) was added triethylamine (68.91 μL, 0.52 mmol) under nitrogen. The reaction mixture was stirred at room temperature for 16 h and then concentrated. The residue was purified by automated reverse phase HPLC (low pH Method A) followed by trituration in MeOH to afford the title compound as an off-white solid (15 mg, 7%).

Example 76

3-cyclopentyl-N-[10,11-dimethoxy-4-oxo-3-(trifluoromethyl)-2,5,7-triazatricyclo-[6.4.0.0$^{2,6}$]dodeca-1(12),6,8,10-tetraen-3-yl]propanamide (ABR 238927)

To a stirred solution of 5,6-dimethoxy-1H-1,3-benzodiazol-2-amine (100 mg, 0.52 mmol) and methyl (2Z)-2-[(3-cyclopentylpropanoyl)imino]-3,3,3-trifluoropropanoate (145 mg, 0.52 mmol) in DMF (2 mL), was added triethylamine (69 μL, 0.52 mmol) under nitrogen. The reaction mixture was stirred for 4 h and then concentrated. The residue was purified by automated reverse phase HPLC (low pH Method A) followed by trituration with ether to afford the title compound as a yellow solid (31 mg, 14%).

Example 77

N-[9-bromo-10,11-dimethyl-4-oxo-3-(trifluoromethyl)-2,5,7-triazatricyclo[6.4.0.0$^{2,6}$]dodeca-1(8),6,9,11-tetraen-3-yl]benzamide (ABR 239170)

To a stirred solution of N-[10,11-dimethyl-4-oxo-3-(trifluoromethyl)-2,5,7-triazatricyclo-[6.4.0.0$^{2,6}$]dodeca-1(8),6,9,11-tetraen-3-yl]benzamide (84 mg, 0.22 mmol) in DCM (5 mL) was added N-bromosuccinimide (39 mg, 0.22 mmol) at 0° C. The reaction mixture was stirred at room temperature for 2 h. The reaction mixture was diluted with DCM (20 mL) and washed with water (2×20 mL). The organic phase was concentrated and purified by automated reverse phase HPLC (low pH Method A) to afford the title compound as a white solid (41 mg, 41%).

Example 78

3-cyclopentyl-N-[12-oxo-11-(trifluoromethyl)-10,13,15-triazatetracyclo[7.6.0.0$^{3,7}$.0$^{10,14}$]-pentadeca-1(9),2,7,14-tetraen-11-yl]propanamide (ABR 239320)

To a stirred solution of 3-cyclopentylpropanamide (93 mg, 0.57 mmol) in DMF (1.5 mL) was added methyl 3,3,3-trifluoro-2-oxopropanoate (72 μL, 0.71 mmol) followed by pyridine (57 μL, 0.71 mmol) at room temperature under nitrogen. The reaction mixture was stirred at room temperature for 1 h. Thionyl chloride (51 μL, 0.71 mmol) was added at 0° C. and the reaction mixture was then stirred at room temperature for 1 h. The reaction mixture was concentrated and the residue filtered through a short pad of silica, eluting with DCM (50 mL), under nitrogen. The filtrate was concentrated, and the acyl intermediate that remained was dissolved in DMF (2 mL) under nitrogen. 1H,5H,6H,7H-Indeno[5,6-d]imidazol-2-amine (98 mg, 0.57 mmol) and triethylamine (113 μL, 0.85 mmol) were added and the reaction mixture was stirred at room temperature for 18 h. The reaction mixture was diluted with EtOAc (20 mL), washed with water (4×10 mL) and brine (10 mL). The organic phase was dried (Na$_2$SO$_4$), filtered and concentrated. The crude product was purified by silica chromatography, using 50% EtOAc in heptane as eluent, to afford the title compound as a white solid (66 mg, 28%).

Example 79

N-[10-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide and N-[11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239329)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 5-chloro-1H-1,3-benzodiazol-2-amine was used instead of 1H,5H,6H,7H-indeno[5,6-d]imidazol-2-amine. The crude product was purified by trituration in the minimum volume of DCM to afford the title compounds, as a 1:1 mixture of regioisomers, (34%).

Example 80

3-cyclopentyl-N-[9,10-dimethyl-4-oxo-3-(trifluoromethyl)-2,5,7-triazatricyclo[6.4.0.0$^{2,6}$]-dodeca-1(12),6,8,10-tetraen-3-yl]propanamide (ABR 239330)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4,5-dimethyl-1H-1,3-benzodiazol-2-amine was used instead of 1H,5H,6H,7H-indeno[5,6-d]imidazol-2-amine. An additional equivalent of thionyl chloride was added at 0° C. 1 h after the initial charge and the reaction was then stirred at for 1 h at room temperature before being concentrated. The crude product was purified by trituration in the minimum volume of DCM to afford the title compound (38%).

Example 81

3-cyclopentyl-N-[9-methyl-4-oxo-3-(trifluoromethyl)-2,5,7-triazatricyclo[6.4.0.0$^{2,6}$]dodeca-1(12),6,8,10-tetraen-3-yl]propanamide (ABR 239343)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propan-amide was used except that 4-methyl-1H-1,3-benzodiazol-2-amine was used instead of 1H,5H,6H,7H-indeno[5,6-d]imidazol-2-amine. The crude product was purified by trituration in the minimum volume of DCM to afford the title compound (17%).

Example 82

3-cyclopentyl-N-[9,10-difluoro-4-oxo-3-(trifluoromethyl)-2,5,7-triazatricyclo[6.4.0.0$^{2,6}$]-dodeca-1(12),6,8,10-tetraen-3-yl]propanamide (ABR 239371)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propan-amide was used except that 4,5-difluoro-1H-1,3-benzodiazol-2-amine was used instead of 1H,5H,6H,7H-indeno[5,6-d]imidazol-2-amine. The crude product was purified by trituration in the minimum volume of DCM to afford the title compound (33%).

Example 83

3-cyclopentyl-N-[9,10-dichloro-4-oxo-3-(trifluoromethyl)-2,5,7-triazatricyclo[6.4.0.0$^{2,6}$]-dodeca-1(12),6,8,10-tetraen-3-yl]propanamide (ABR 239375)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propan-amide was used except that 4,5-dichloro-1H-1,3-benzodiazol-2-amine was used instead of 1H,5H,6H,7H-indeno[5,6-d]imidazol-2-amine. The crude product was purified by trituration in the minimum volume of DCM to afford the title compound (28%).

Example 84

3-cyclopentyl-N-[9,11-dichloro-4-oxo-3-(trifluoromethyl)-2,5,7-triazatricyclo[6.4.0.0$^{2,6}$]-dodeca-1(12),6,8,10-tetraen-3-yl]propanamide (ABR 239394)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propan-amide was used except that 4,6-dichloro-1H-1,3-benzodiazol-2-amine was used instead of 1H,5H,6H,7H-indeno[5,6-d]imidazol-2-amine. An additional equivalent of thionyl chloride was added at 0° C. 1 h after the initial charge and the reaction was then stirred at for 1 h at room temperature before being concentrated. The crude product was purified by automated reverse phase HPLC (low pH Method A) to afford the title compound (27%).

Example 85

N-[9-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239399)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propan-amide was used except that 4-chloro-1H-1,3-benzodiazol-2-amine was used instead of 1H,5H,6H,7H-indeno[5,6-d]imidazol-2-amine. An additional equivalent of thionyl chloride was added at 0° C. 1 h after the initial charge and the reaction was then stirred at for 1 h at room temperature before being concentrated. The crude product was purified by trituration in the minimum volume of DCM to afford the title compound (19%).

Example 86

3-cyclopentyl-N-[9,11-difluoro-4-oxo-3-(trifluoromethyl)-2,5,7-triazatricyclo-[6.4.0.0$^{2,6}$]dodeca-1(12),6,8,10-tetraen-3-yl]propanamide (ABR 239422)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propan-amide was used except that 4,6-difluoro-1H-1,3-benzodiazol-2-amine was used instead of 1H,5H,6H,7H-indeno[5,6-d]imidazol-2-amine. The crude product was purified by silica chromatography, using 44% EtOAc in heptane as eluent, followed by trituration in the minimum volume of DCM to afford the title compound (11%).

Example 87

N-[10,11-dichloro-4-oxo-3-(trifluoromethyl)-2,5,7-triazatricyclo[6.4.0.0$^{2,6}$]dodeca-1(12),6,8,10-tetraen-3-yl]oxane-4-carboxamide (ABR 239441)

To a stirred solution of oxane-4-carboxamide (500 mg, 3.87 mmol) in DMF (15 mL) was added pyridine (312 µl, 3.87 mmol) followed by ethyl 3,3,3-trifluoro-2-oxopropanoate (658 mg, 3.87 mmol) at room temperature under argon. The reaction mixture was stirred at room temperature for 1 h and then thionyl chloride (422 µl, 5.81 mmol) was added. The reaction was stirred for a further 16 h and was then concentrated. The acyl intermediate that remained was dissolved in DMF (5 mL) under argon. A solution of 5,6-dichloro-1H-1,3-benzodiazol-2-amine (587 mg, 2.90 mmol) in DMF (7 mL) and triethylamine (861 µl, 6.19 mmol) were added and the reaction mixture was stirred at room temperature for 4 h. The reaction mixture was diluted with water (10 mL) and extracted with EtOAc (2×15 mL). The combined organic extracts were washed with brine, dried (MgSO$_4$), filtered and concentrated. The crude product was purified by silica chromatography. Further purification was carried out by trituration in DCM/MeOH and then pentane to afford the title compound (20 mg, 1%).

Example 88

N-[10,11-dichloro-4-oxo-3-(trifluoromethyl)-2,5,7-triazatricyclo[6.4.0.0$^{2,6}$]dodeca-1(8),6,9,11-tetraen-3-yl]-3-(1-hydroxycyclopentyl)propanamide (ABR 239702)

A solution of cyclopentanone (234 µl, 2.63 mmol) and DMPU (127 µl, 1.05 mmol) in anhydrous de-gassed THF (30 mL) and MeOH (3 mL) was stirred at 0° C. under nitrogen. A solution of 0.1M samarium iodide in THF (10.55 mL, 1.06 mmol) and a solution of N-[10,11-dichloro-4-oxo-3-(trifluoromethyl)-2,5,7-triazatricyclo[6.4.0.0$^{2,6}$]dodeca-1(8),6,9,11-tetraen-3-yl]prop-2-enamide (100 mg, 0.26 mmol) in anhydrous THF (5 mL) were added dropwise simultaneously, over 10 min. The reaction mixture was stirred at 0° C. for 20 min. The reaction was poured into cold water (100 mL) and extracted with EtOAc (3×50 mL). The combined organic phases were washed with 1M HCl$_{(aq)}$ and brine (2×50 mL), dried (MgSO$_4$), filtered and concentrated.

The crude compound was purified by automated reverse phase HPLC (low pH Method A) to afford the title compound as a white solid (22 mg, 18%)

Example 89

Diastereomer 1: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-1-methanesulfonylpyrrolidine-2-carboxamide (ABR 239679

To a stirred solution of (2S)-1-methanesulfonylpyrrolidine-2-carboxamide (400 mg, 2.08 mmol) in DMF (6 mL) was added methyl 3,3,3-trifluoro-2-oxopropanoate (320 μL, 3.13 mmol) followed by pyridine (170 μL, 2.08 mmol) at room temperature, under nitrogen. The reaction mixture was stirred at room temperature for 19 h. Thionyl chloride (150 μL, 2.08 mmol) was added at 0° C. and the reaction was stirred for 1 h. The reaction mixture was concentrated and the residue filtered through a short pad of silica, eluting with DCM, under nitrogen. The filtrate was concentrated, and the acyl intermediate that remained was dissolved in DMF (5 mL) under nitrogen. A solution of 5,6-dimethyl-1H-1,3-benzodiazol-2-amine (280 mg, 1.74 mmol) in DMF (5 mL) and triethylamine (280 μL, 2.08 mmol) were added. The reaction mixture was stirred at room temperature for 17 h and was then concentrated. The residue was diluted with EtOAc (40 mL) and washed with water (2×30 mL), 10% citric acid$_{(aq)}$ (2×20 mL) and brine (20 mL). The organic phase was dried (MgSO$_4$), filtered and concentrated. The crude product was purified by trituration in DCM to give a clean mixture of diastereomers. The mixture of diastereomers was separated by automated reverse phase HPLC (low pH Method A) to afford Diastereomer 1 as a single diastereomer of undefined stereochemistry at the quaternary centre as a white solid (82 mg, 10%).

Example 90

N-[10,11-dichloro-4-oxo-3-(trifluoromethyl)-2,5,7-triazatricyclo[6.4.0.0$^{2,6}$]dodeca-1(8),6,9,11-tetraen-3-yl]-6-[(3-methoxypropyl)amino]pyridine-2-carboxamide (ABR 239523)

To a solution of N-[10,11-dichloro-4-oxo-3-(trifluoromethyl)-2,5,7-triazatricyclo[6.4.0.0^ {2,6}]dodeca-1(12),6,8,10-tetraen-3-yl]-6-fluoropyridine-2-carboxamide (250 mg, 0.56 mmol) in DMF (3 mL), in a sealed tube, were added K$_2$CO$_3$ (185 mg, 1.34 mmol) and 3-methoxypropan-1-amine (62 mg, 0.70 mmol). The reaction mixture was heated at 100° C. for 4 h. Additional 3-methoxypropan-1-amine (62 mg, 0.70 mmol) was added. The reaction was heated at 100° C. for a further 8 h and was then concentrated. The residue was dissolved in EtOAc (50 mL) and washed with water (3×25 mL) and then brine (3×25 mL). The organic phase was dried (MgSO$_4$), filtered and concentrated. The crude compound was purified by automated reverse phase HPLC (low pH Method A) to afford the title compound as a yellow oil (35 mg, 12%)

Example 91

N-[10,11-dichloro-4-oxo-3-(trifluoromethyl)-2,5,7-triazatricyclo[6.4.0.0$^{2,6}$]dodeca-1(8),6,9,11-tetraen-3-yl]-6-[(2-hydroxyethyl)amino]pyridine-2-carboxamide (ABR 239539)

To a solution of N-[10,11-dichloro-4-oxo-3-(trifluoromethyl)-2,5,7-triazatricyclo[6.4.0.0$^{2,6}$]dodeca-1(12),6,8,10-tetraen-3-yl]-6-fluoropyridine-2-carboxamide (100 mg, 0.22 mmol) in DMF (3 mL), in a sealed tube, were added K$_2$CO$_3$ (74 mg, 0.54 mmol) and 2-aminoethan-1-ol (27 mg, 0.45 mmol). The reaction mixture was heated at 100° C. for 18 h and was then concentrated. The residue was dissolved in EtOAc (50 mL) and washed with water (3×25 mL) and brine (3×25 mL). The organic phase was dried (MgSO$_4$), filtered and concentrated. The crude compound was purified by automated reverse phase HPLC (low pH Method A) to afford the title compound as a yellow oil (51 mg, 47%).

Example 92

Diastereomeric mixture. N-[10,11-dichloro-4-oxo-3-(trifluoromethyl)-2,5,7-triazatricyclo-[6.4.0.0$^{2,6}$]dodeca-1(8),6,9,11-tetraen-3-yl]-6-{[(2S)-1-methoxypropan-2-yl]amino}pyridine-2-carboxamide (ABR 239540)

To a solution of N-[10,11-dichloro-4-oxo-3-(trifluoromethyl)-2,5,7-triazatricyclo[6.4.0.0$^{2,6}$]dodeca-1(12),6,8,10-tetraen-3-yl]-6-fluoropyridine-2-carboxamide (100 mg, 0.22 mmol) in DMF (3 mL), in a sealed tube, were added K$_2$CO$_3$ (74 mg, 0.54 mmol) and (2S)-1-methoxypropan-2-amine (40 mg, 0.45 mmol). Initially, the reaction mixture was heated for 16 h at 100° C. Then the reaction was heated for a further 20 h. During this period, additional (2S)-1-methoxypropan-2-amine (80 mg, 0.90 mmol) and K$_2$CO$_3$ (74 mg, 0.54 mmol) were added portionwise with the reaction at room temperature during retreatment. The reaction was then concentrated. The residue was dissolved in EtOAc (50 mL) and washed with water (3×25 mL) and brine (2×25 mL). The organic phase was dried (MgSO$_4$), filtered and concentrated. The crude compound was purified by automated reverse phase HPLC (low pH Method A) to afford the title compound as a yellow solid as mixture of diastereomers (15 mg, 13%).

Example 93

N-[10,11-dichloro-4-oxo-3-(trifluoromethyl)-2,5,7-triazatricyclo[6.4.0.0$^{2,6}$]dodeca-1(8),6,9,11-tetraen-3-yl]-6-{[2-(dimethylamino)ethyl]amino}pyridine-2-carboxamide (ABR 239587)

To a solution of N-[10,11-dichloro-4-oxo-3-(trifluoromethyl)-2,5,7-triazatricyclo[6.4.0.0$^{2,6}$]dodeca-1(12),6,8,10-tetraen-3-yl]-6-fluoropyridine-2-carboxamide (100 mg, 0.22 mmol) in DMF (3 mL), in a sealed tube, were added K$_2$CO$_3$ (93 mg, 0.67 mmol) and (2-aminoethyl)dimethylamine (59 mg, 0.67 mmol). The reaction mixture was heated at 100° C. for 16 h and was then concentrated. The residue was dissolved in EtOAc (50 mL) and washed with water (2×25 mL) and brine (2×25 mL). The organic phase was dried (MgSO$_4$), filtered and concentrated. The crude compound was purified by automated reverse phase HPLC (low pH Method A) to afford the title compound as the formic acid salt as a pink solid (38 mg, 33%).

Example 94

N-[10,11-dichloro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)(methyl)amino]pyridine-2-carboxamide (ABR 239537)

To a stirred solution of 6-[(2-methoxyethyl)(methyl)amino]pyridine-2-carboxamide (571 mg, 2.73 mmol) in DMF (10 mL) was added methyl 3,3,3-trifluoro-2-oxopropanoate (852 mg, 5.46 mmol) followed by pyridine (220 µl, 2.73 mmol) at room temperature under nitrogen. The reaction mixture was stirred at room temperature for 16 h. Thionyl chloride (198 µl, 2.73 mmol) was added at 0° C. and the reaction mixture was then stirred at room temperature for 1 h. The reaction mixture was concentrated and the residue filtered through a short pad of silica, eluting with DCM, under nitrogen. The filtrate was concentrated, and the acyl intermediate that remained was dissolved in DMF (10 mL) under nitrogen. 5,6-Dichloro-1H-1,3-benzodiazol-2-amine (441 mg, 2.18 mmol) and triethylamine (381 µl, 2.72 mmol) were added and the reaction mixture was stirred at room temperature for 2 h. The reaction mixture was concentrated. The residue was dissolved in EtOAc (100 mL), washed with water (3×50 mL) and then brine (3×50 mL). The organic phase was dried ($MgSO_4$), filtered and concentrated. The crude product was purified by silica chromatography, using 0-10% MeOH in DCM as eluent. Further purification was carried out using automated reverse phase HPLC (high pH) to afford the title compound as a yellow solid (24 mg, 2%).

Example 95 methyl 6-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}pyridine-2-carboxylate (ABR 239572)

To a stirred solution of methyl 6-carbamoylpyridine-2-carboxylate (1.00 g, 5.55 mmol) in DMF (15 mL) was added methyl 3,3,3-trifluoro-2-oxopropanoate (1.14 mL, 11.11 mmol) followed by pyridine (450 µL, 5.55 mmol) at room temperature under nitrogen. The reaction mixture was stirred at room temperature for 1.5 h. Thionyl chloride (405 µL, 5.55 mmol) was added at 0° C. and the reaction mixture was then stirred for 1 h. The reaction mixture was concentrated and the residue filtered through a short pad of silica, eluting with DCM, under nitrogen. The filtrate was concentrated, and the acyl intermediate that remained was dissolved in DMF (15 mL) under nitrogen. 5,6-Dichloro-1H-1,3-benzodiazol-2-amine (935 mg, 4.63 mmol) and triethylamine (739 µL, 5.55 mmol) were added and the reaction mixture was stirred at room temperature for 20 h. The reaction mixture was concentrated. The residue was diluted with EtOAc (50 mL), washed with water (3×50 mL) and brine (2×50 mL). The organic phase was dried ($MgSO_4$), filtered and concentrated. The crude product was purified by silica chromatography, using 0-3% MeOH in DCM as eluent, to give the title compound as a brown oil (35 mg, 2%).

Example 96

2-N-[10,11-dichloro-4-oxo-3-(trifluoromethyl)-2,5,7-triazatricyclo[6.4.0.0$^{2,6}$]dodeca-1(8),6,9,11-tetraen-3-yl]-6-N-(2-methoxyethyl)pyridine-2,6-dicarboxamide (ABR 239588)

2-Methoxyethan-1-amine (13 µL, 0.15 mmol) was added to a stirred suspension of 1,4-diazabicyclo[2.2.2]octane-trimethylaluminum (1:2, 39 mg, 0.15 mmol) in THF (2 mL), under nitrogen. The reaction was heated at 40° C. for 30 min. A solution of methyl 6-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}pyridine-2-carboxylate (50 mg, 0.1 mmol) in THF (0.5 mL) was added and the reaction was then heated at 70° C. for 16 h. Additional 1,4-diazabicyclo[2.2.2]octane-trimethylaluminum (1:2, 39 mg, 0.15 mmol) and 2-methoxyethan-1-amine (13 µL, 0.15 mmol) were added and the reaction was heated at 70° C. for a further 4 h. The reaction was quenched by the dropwise addition of cold water and washed with EtOAc (3×10 mL). The aqueous layer was acidified using 10% citric acid$_{(aq)}$ (5 mL) and extracted with EtOAc (3×10 mL). The combined organic phases were washed with brine (2×25 mL), dried ($MgSO_4$), filtered and concentrated. The crude product was purified by automated reverse phase HPLC (high pH) to afford the title compound as a brown solid (13 mg, 15%).

Example 97

N-[10,11-dichloro-4-oxo-3-(trifluoromethyl)-2,5,7-triazatricyclo[6.4.0.0$^{2,6}$]dodeca-1(8),6,9,11-tetraen-3-yl]-6-(hydroxymethyl)pyridine-2-carboxamide (ABR 239602)

Sodium tetrahydroborate (110 mg, 2.87 mmol) was added to a stirred solution of methyl 6-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}pyridine-2-carboxylate (200 mg, 0.41 mmol) in THF/MeOH (4:1, 10 mL) at 0° C. The reaction was stirred for 24 h. Additional sodium tetrahydroborate (220 mg, 5.74 mmol) was then added portionwise at 0° C. over a 40 h period. The reaction was quenched by the dropwise addition of saturated $NH_4Cl_{(aq)}$, diluted with water and acidified using 10% citric acid$_{(aq)}$. The aqueous phase was extracted with EtOAc (3×25 mL). The combined organic extracts were dried ($MgSO_4$), filtered and concentrated. The crude product was purified by automated reverse phase HPLC (neutral pH) to afford the title compound as a white solid (35 mg, 19%).

Example 98

N-[10,11-dichloro-4-oxo-3-(trifluoromethyl)-2,5,7-triazatricyclo[6.4.0.0$^{2,6}$]dodeca-1(12),6,8,10-tetraen-3-yl]-3-fluorobenzamide (ABR 239440)

To a stirred solution of 3-fluorobenzamide (500 mg, 3.59 mmol) in DMF (5 mL) was added pyridine (306 µl, 3.59 mmol) followed by ethyl 3,3,3-trifluoro-2-oxopropanoate (476 µl, 3.59 mmol) at room temperature under argon. The reaction mixture was stirred at room temperature for 1 h. Thionyl chloride (231 µl, 3.18 mmol) was added at 0° C. and the reaction mixture was then stirred at room temperature for 2.5 h. The reaction mixture was concentrated. The acyl intermediate that remained was dissolved in DMF (2 mL) under argon. 5,6-Dichloro-1H-1,3-benzodiazol-2-amine (545 mg, 2.70 mmol) and triethylamine (503 µl, 3.59 mmol) were added and the reaction mixture was stirred at room temperature for 16 h. The reaction mixture was diluted with water and extracted with EtOAc. The organic phase was washed with brine, dried ($Na_2SO_4$), filtered and concentrated. The crude product was purified by silica chromatography, using 3% MeOH in DCM as eluent. Further purification was carried out by trituration in DCM/MeOH and then pentane to afford the title compound as an off-white solid (22 mg, 1%).

Example 99

N-[10,11-dichloro-4-oxo-3-(trifluoromethyl)-2,5,7-triazatricyclo[6.4.0.0$^{2,6}$]dodeca-1(12),6,8,10-tetraen-3-yl]-3,5-difluorobenzamide (ABR 239446)

To a stirred solution of 3,5-difluorobenzamide (500 mg, 3.18 mmol) in DMF (5 mL) was added pyridine (271 µl, 3.18 mmol) followed by ethyl 3,3,3-trifluoro-2-oxopropanoate (422 µl, 3.18 mmol) at room temperature under argon. The reaction mixture was stirred at room temperature for 1 h. Thionyl chloride (231 µl, 3.18 mmol) was added at 0° C. The reaction mixture was stirred at room temperature for 16 h and then the reaction mixture was concentrated. The acyl intermediate that remained was dissolved in DMF (2 mL) under argon. 5,6-Dichloro-1H-1,3-benzodiazol-2-amine (482 mg, 2.39 mmol) and triethylamine (668 µl, 4.77 mmol) were added and the reaction mixture was stirred at room temperature for 4 h. The reaction mixture was diluted with water and extracted with EtOAc. The organic phase was washed with brine, dried ($Na_2SO_4$), filtered and concentrated. The crude product was purified by silica chromatography, using 3% MeOH in DCM as eluent. Further purification was carried out by trituration from DCM/MeOH and then pentane to afford the title compound as an off-white solid (20 mg, 1%).

Example 100

3-cyano-N-[10,11-dichloro-4-oxo-3-(trifluoromethyl)-2,5,7-triazatricyclo[6.4.0.0$^{2,6}$]dodeca-1(8),6,9,11-tetraen-3-yl]benzamide (ABR 239453)

To a stirred solution of 3-cyanobenzamide (650 mg, 4.45 mmol) in DMF (7 mL) was added pyridine (378 µl, 4.45 mmol) followed by ethyl 3,3,3-trifluoro-2-oxopropanoate (590 µl, 4.45 mmol) at room temperature under argon. The reaction mixture was stirred at room temperature for 1 h. Thionyl chloride (323 µl, 4.45 mmol) was added at 0° C. The reaction mixture was then stirred at room temperature for a further 16 h and before the reaction mixture was concentrated.

The acyl intermediate that remained was dissolved in DMF (5 mL) under argon. 5,6-Dichloro-1H-1,3-benzodiazol-2-amine (674 mg, 3.34 mmol) and triethylamine (934 µl, 6.67 mmol) were added and the reaction mixture was stirred at room temperature for 16 h. The reaction mixture was diluted with water and extracted with EtOAc. The organic phase was washed with brine, dried ($Na_2SO_4$), filtered and concentrated. The crude product was purified by silica chromatography, using 3% MeOH in DCM as eluent. Further purification was carried out by trituration in DCM/MeOH and then pentane to afford the title compound as a white solid (25 mg, 1%).

Example 101

N-[10,11-dichloro-4-oxo-3-(trifluoromethyl)-2,5,7-triazatricyclo[6.4.0.0$^{2,6}$]dodeca-1(8),6,9,11-tetraen-3-yl]-2-[(2-methoxyethyl)amino]-1,3-thiazole-4-carboxamide (ABR 239601)

To a stirred solution of 2-bromo-1,3-thiazole-4-carboxamide (360 mg, 1.74 mmol) in DMF (15 mL) was added methyl 3,3,3-trifluoro-2-oxopropanoate (543 mg, 3.48 mmol) followed by pyridine (140 µl, 1.74 mmol) at room temperature under nitrogen. The reaction mixture was stirred at room temperature for 16 h. Thionyl chloride (126 µl, 1.74 mmol) was added at 0° C. and the reaction mixture was then stirred for 1 h. The reaction mixture was concentrated and the residue was filtered through a short pad of silica, eluting with DCM, under nitrogen. The filtrate was concentrated, and the acyl intermediate that remained was dissolved in DMF (10 mL) under nitrogen. A solution of 5,6-dichloro-1H-1,3-benzodiazol-2-amine (293 mg, 1.45 mmol) in DMF (10 mL) and triethylamine (231 µl, 1.74 mmol) were added and the reaction mixture was stirred at room temperature for 2 h. The reaction mixture was concentrated. The residue was diluted with EtOAc (50 mL), washed with washed with 10% citric acid$_{(aq)}$ (2×25 mL), water (2×25 mL) and brine (2×25 mL). The organic phase was dried (MgSO$_4$), filtered and concentrated. The crude product was triturated in DCM to afford a mixture of 2-bromo-N-[10,11-dichloro-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide and 2-chloro-N-[10,11-dichloro-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide (746 mg).

A microwave tube was charged with a portion of the mixture of 2-bromo-N-[10,11-dichloro-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide and 2-chloro-N-[10, 11-dichloro-4-oxo-3-(trifluoromethyl)-2,5,7-triazatricyclo [6.4.0.0$^{2,6}$]dodeca-1(8),6,9,11-tetraen-3-yl]-1,3-thiazole-4-carboxamide (80 mg), K$_2$CO$_3$ (64 mg, 0.47 mmol), 2-methoxyethan-1-amine (40 µl, 0.47 mmol) and dioxane (2 mL). Initially, the reaction was heated in the microwave at 130° C. for 1 h. Then the reaction was then heated for a further 4 h. During this period, additional 2-methoxyethan-1-amine (160 µl, 1.88 mmol) and K$_2$CO$_3$ (256 mg, 1.88 mmol) were added portionwise with the reaction at room temperature during retreatment. Then the reaction mixture was concentrated. The residue was dissolved in EtOAc (25 mL) and washed with water (25 mL), 10% citric acid$_{(aq)}$ (25 mL) and brine (25 mL). The organic phase was dried (MgSO$_4$), filtered and concentrated. The crude product was purified by automated reverse phase HPLC (low pH Method A) to afford the title compound as a white solid (27 mg).

Example 102

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(2,2-difluoroethyl)azetidine-3-carboxamide (ABR 239437)

To a stirred solution of N-[10,11-dichloro-4-oxo-3-(trifluoromethyl)-2,5,7-triazatricyclo[6.4.0.0$^{2,6}$]dodeca-1(12),6, 8,10-tetraen-3-yl]azetidine-3-carboxamide (75 mg, 0.18 mmol) in DMF (2 mL) was added 1,1-difluoro-2-iodoethane (39 mg, 0.20 mmol) followed by K$_2$CO$_3$ (51 mg, 0.37 mmol). The reaction was heated at 80° C. for 16 h and then concentrated. The residue was dissolved in EtOAc (25 mL) and washed with water (2×25 mL) and brine (3×25 mL). The organic phase was dried (MgSO$_4$), filtered and concentrated. The crude product was purified by automated reverse phase HPLC (low pH Method A) to afford the title compound as a white solid as the formic acid salt (11 mg, 13%).

Example 103

N-[10,11-dichloro-4-oxo-3-(trifluoromethyl)-2,5,7-triazatricyclo[6.4.0.0$^{2,6}$]dodeca-1(8),6,9,11-tetraen-3-yl]-3-fluoroazetidine-3-carboxamide (ABR 239689)

To a stirred solution of tert-butyl 3-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}-3-fluoroazetidine-1-carboxylate (58 mg, 0.11 mmol) in DCM (20 mL) was added TFA (1 mL) at 0° C. under nitrogen. The reaction was allowed to warm to room temperature and stirred for 16 h. Then the reaction mixture was concentrated and azeotroped with toluene (3×20 mL). The crude product was purified by automated reverse phase HPLC (high pH) to afford the title compound as a white solid (11 mg, 23%).

Example 104

N-[10,11-dichloro-4-oxo-3-(trifluoromethyl)-2,5,7-triazatricyclo[6.4.0.0$^{2,6}$]dodeca-1(8),6,9,11-tetraen-3-yl]-3-(3,3-difluoroazetidin-1-yl)propanamide (ABR 239705)

To a solution of N-[10,11-dichloro-4-oxo-3-(trifluoromethyl)-2,5,7-triazatricyclo[6.4.0.0$^{2,6}$]-dodeca-1(8),6,9,11-tetraen-3-yl]prop-2-enamide (125 mg, 0.33 mmol) in MeCN (10 mL), in a sealed tube, were added 3,3-difluoroazetidine hydrochloride (56 mg, 0.43 mmol), silica (16 mg) and triethylamine (88 µl, 0.66 mmol). The reaction was heated at 80° C. for 3 h. The silica was removed by filtration and the filtrate was concentrated. The crude product was purified by automated reverse phase HPLC (low pH Method A) to afford the title compound as a white solid (22 mg, 14%).

Example 105

3-(3,3-difluoroazetidin-1-yl)-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]propanamide (ABR 239647)

To a solution of N-[10,11-dimethyl-4-oxo-3-(trifluoromethyl)-2,5,7-triazatricyclo[6.4.0.0$^{2,6}$]dodeca-1(8),6,9,11-tetraen-3-yl]prop-2-enamide (125 mg, 0.37 mmol) in MeCN (10 mL), in a sealed tube, were added 3,3-difluoroazetidine hydrochloride (62 mg, 0.48 mmol), silica (18 mg) and triethylamine (98 µl, 0.74 mmol). The reaction was heated at 70° C. for 3 h. The silica was removed by filtration and the filtrate was concentrated. The crude product was purified by automated reverse phase HPLC (low pH Method A) to afford the title compound as a white solid (45 mg, 28%).

Example 106

3-cyclobutyl-N-[10,11-dimethyl-4-oxo-3-(trifluoromethyl)-2,5,7-triazatricyclo[6.4.0.0$^{2,6}$]-dodeca-1(8),6,9,11-tetraen-3-yl]propanamide (ABR 239536)

To a stirred solution of 3-cyclobutylpropanamide (250 mg, 1.97 mmol) in DMF (20 mL) was added pyridine (159 µL, 1.97 mmol) followed by methyl 3,3,3-trifluoro-2-oxopropanoate (614 mg, 3.93 mmol) at room temperature under nitrogen. The reaction mixture was stirred at room temperature for 16 h. Thionyl chloride (147 µL, 1.97 mmol) was added at 0° C. and the reaction was stirred at 0° C. for 1 h. The reaction mixture was concentrated and the residue was filtered through a short pad of silica, eluting with DCM, under nitrogen. The filtrate was concentrated, and the acyl intermediate that remained was dissolved in DMF (10 mL) under nitrogen. 5,6-Dimethyl-1H-1,3-benzodiazol-2-amine (254 mg, 1.57 mmol) and triethylamine (261 µl, 1.97 mmol) were added. The reaction mixture was stirred at room temperature for 2 h and was then concentrated. The residue was diluted with EtOAc (50 mL) and washed with water (3×50 mL) and brine (2×50 mL). The organic phase was dried (Na$_2$SO$_4$), filtered and concentrated. The crude product was purified by silica chromatography, using 0-10% MeOH in DCM as eluent, to afford the title compound as a white solid (60 mg, 8%).

Example 107

N-[10,11-dimethyl-4-oxo-3-(trifluoromethyl)-2,5,7-triazatricyclo[6.4.0.0$^{2,6}$]dodeca-1(8),6,9,11-tetraen-3-yl]-3-(1-hydroxycyclopentyl)propanamide (ABR 239578)

A solution of cyclopentanone (210 µl, 2.36 mmol) and DMPU (285 µl, 2.36 mmol) in anhydrous de-gassed THF (20 mL) and MeOH (5 mL) was stirred at 0° C. under nitrogen. A solution of 0.1M samarium iodide in THF (23.6 mL, 2.36 mmol) and a solution of N-[10,11-dimethyl-4-oxo-3-(trifluoromethyl)-2,5,7-triazatricyclo[6.4.0.0$^{2,6}$]dodeca-1(8),6,9,11-tetraen-3-yl]prop-2-enamide (200 mg, 0.59 mmol) in anhydrous THF (5 mL) were added dropwise simultaneously, over 10 min. The reaction mixture was stirred at 0° C. for 20 min and then poured into cold water (100 mL) and extracted with EtOAc (3×50 mL). The combined organic phases were washed with brine (2×50 mL), dried (MgSO$_4$), filtered and concentrated. The crude compound was purified by automated reverse phase HPLC (low pH Method A) to afford the title compound as a white solid (70 mg, 31%)

Example 108

2-cyclopentyl-N-[10,11-dimethyl-4-oxo-3-(trifluoromethyl)-2,5,7-triazatricyclo[6.4.0.0$^{2,6}$]-dodeca-1(8),6,9,11-tetraen-3-yl]acetamide (ABR 239558)

To a stirred solution of 2-cyclopentylacetamide (350 mg, 2.75 mmol) in DMF (20 mL) was added pyridine (102 µL, 1.27 mmol) followed by methyl 3,3,3-trifluoro-2-oxopropanoate (395 mg, 2.53 mmol) at room temperature under nitrogen. The reaction mixture was stirred at room temperature for 16 h. Additional pyridine (204 µL, 2.54 mmol) and methyl 3,3,3-trifluoro-2-oxopropanoate (395 mg, 2.53 mmol) were added portionwise over a 3 day period. Thionyl chloride (92 µl, 1.27 mmol) was added at 0° C. and the reaction was stirred for 1 h at 0° C. Additional thionyl chloride (92 µl, 1.27 mmol) was added at 0° C. and the reaction was stirred for 18 h at room temperature. The reaction mixture was concentrated and the residue filtered through a short pad of silica, eluting with DCM, under nitrogen. The filtrate was concentrated, and the acyl intermediate that remained was dissolved in DMF (10 mL) under nitrogen. 5,6-Dimethyl-1H-1,3-benzodiazol-2-amine (355 mg, 2.20 mmol) and triethylamine (366 µl, 2.75 mmol) were added and the reaction mixture was stirred at room temperature for 18 h. Then the reaction mixture was diluted with EtOAc (30 mL) and washed with water (4×50 mL) and brine (2×50 mL). The organic phase was dried (MgSO$_4$), filtered and concentrated. The crude product was purified by silica chromatography, using 0-8% MeOH in DCM as eluent. Further purification was carried out by trituration in DCM to afford the title compound as a white solid (36 mg, 3%).

Example 109

N-[10,11-dimethyl-4-oxo-3-(trifluoromethyl)-2,5,7-triazatricyclo[6.4.0.0$^{2,6}$]dodeca-1(8),6,9,11-tetraen-3-yl]-3,5-difluorobenzamide (ABR 239456)

The general procedure for the preparation of N-[10,11-dichloro-4-oxo-3-(trifluoromethyl)-2,5,7-triazatricyclo

[6.4.0.0²,⁶]dodeca-1(12),6,8,10-tetraen-3-yl]oxane-4-carboxamide was used but with the following changes. In the first stage of the reaction, to form the acyl imine intermediate, 2-(3,5-difluorophenyl)acetamide was used instead of oxane-4-carboxamide. In the second stage of the reaction, 5,6-dimethyl-1H-1,3-benzodiazol-2-amine was used instead of 5,6-dichloro-1H-1,3-benzodiazol-2-amine. The crude product was purified by silica chromatography, using 3% MeOH in DCM as eluent. Further purification was carried out by trituration in DCM/MeOH and then pentane to afford the title compound (4%).

Example 110

N-[10,11-dimethyl-4-oxo-3-(trifluoromethyl)-2,5,7-triazatricyclo[6.4.0.0²,⁶]dodeca-1(8),6,9,11-tetraen-3-yl]-6-fluoropyridine-2-carboxamide (ABR 239784)

To stirred a solution of 6-fluoropyridine-2-carboxamide (1.51 g, 10.79 mmol) in DMF (5 mL) were added pyridine (870 μL, 10.79 mmol) and methyl 3,3,3-trifluoro-2-oxopropanoate (1.65 mL, 16.19 mmol) under nitrogen. The reaction was stirred at room temperature for 16 h. Thionyl chloride (790 μL, 10.79 mmol) was added dropwise at 0° C. The reaction mixture was stirred for a further 2 h and then concentrated. The residue was filtered through a short pad of silica, eluting with DCM, under nitrogen. The filtrate was concentrated, and the acyl intermediate that remained was dissolved in DMF (5 mL) under nitrogen. The solution of acyl intermediate was added to a solution of 5,6-dimethyl-1H-1,3-benzodiazol-2-amine (1.45 g, 8.99 mmol) in DMF (10 mL) followed by triethylamine (1.45 mL, 10.79 mmol). The reaction mixture was stirred for a further 16 h and then concentrated. The residue was dissolved in EtOAc (150 mL), washed with water (2×100 mL), 10% citric acid$_{(aq)}$ (50 mL) and brine (100 mL) and then dried (MgSO₄), filtered and concentrated. The crude product was purified by trituration in DCM to afford the title compound as a white solid (2.35 g, 61%).

Example 111

N-[10,11-dimethyl-4-oxo-3-(trifluoromethyl)-2,5,7-triazatricyclo[6.4.0.0²,⁶]dodeca-1(8),6,9,11-tetraen-3-yl]-6-[(2-methoxyethyl)amino]pyridine-2-carboxamide (ABR 239496)

To a solution of N-[10,11-dimethyl-4-oxo-3-(trifluoromethyl)-2,5,7-triazatricyclo[6.4.0.0²,⁶]-dodeca-1(8),6,9,11-tetraen-3-yl]-6-fluoropyridine-2-carboxamide (300 mg, 0.85 mmol) in DMF (7 mL), in a sealed tube, were added K₂CO₃ (235 mg, 1.70 mmol) and 2-methoxyethan-1-amine (128 mg, 1.70 mmol). The reaction mixture was heated at 90° C. for 4 h. The reaction mixture was diluted with water and extracted with EtOAc. The combined organic extracts were washed with brine, dried (Na₂SO₄), filtered and concentrated. The crude product was purified by automated reverse phase HPLC (low pH Method B) to afford the title compound as a white solid (60 mg, 15%).

Example 112

N-[10,11-dimethyl-4-oxo-3-(trifluoromethyl)-2,5,7-triazatricyclo[6.4.0.0²,⁶]dodeca-1(8),6,9,11-tetraen-3-yl]-2-phenylacetamide (ABR 239500)

To a stirred solution of 2-phenylacetamide (1.20 g, 8.88 mmol) in DMF (15 mL) was added pyridine (755 μL, 8.88 mmol) followed by ethyl 3,3,3-trifluoro-2-oxopropanoate (1.51 g, 8.88 mmol) at room temperature under argon. The reaction mixture was stirred at room temperature for 1 h. Thionyl chloride (644 μl, 8.88 mmol) was added. The reaction was stirred for a further 16 h at room temperature and was then concentrated. The acyl intermediate that remained was dissolved in DMF (5 mL) under argon. 5,6-Dimethyl-1H-1,3-benzodiazol-2-amine (1.07 g, 6.66 mmol) and triethylamine (1.62 mL, 11.54 mmol) were added and the reaction mixture was stirred at room temperature for 4 h. The reaction mixture was diluted water and extracted with EtOAc. The combined organic extracts were washed with brine, dried (Na₂SO₄), filtered and concentrated. The crude product was purified by silica chromatography, using 3% MeOH in DCM as eluent, to afford the title compound as a white solid (225 mg, 3%).

Example 113

2-(3,5-dichlorophenyl)-N-[10,11-dimethyl-4-oxo-3-(trifluoromethyl)-2,5,7-triazatricyclo-[6.4.0.0²,⁶]dodeca-1(8),6,9,11-tetraen-3-yl]acetamide (ABR 239503)

The general procedure for the preparation of N-[10,11-dichloro-4-oxo-3-(trifluoromethyl)-2,5,7-triazatricyclo[6.4.0.0²,⁶]dodeca-1(12),6,8,10-tetraen-3-yl]oxane-4-carboxamide was used but with the following changes. In the first stage of the reaction, to form the acyl imine intermediate, 2-(3,5-dichlorophenyl)acetamide was used instead of oxane-4-carboxamide. In the second stage of the reaction, 5,6-dimethyl-1H-1,3-benzodiazol-2-amine was used instead of 5,6-dichloro-1H-1,3-benzodiazol-2-amine. The crude product was purified by silica chromatography, using 3% MeOH in DCM as eluent, to afford the title compound as a white solid (4%).

Example 114

N-[10,11-dimethyl-4-oxo-3-(trifluoromethyl)-2,5,7-triazatricyclo[6.4.0.0²,⁶]dodeca-1(12),6,8,10-tetraen-3-yl]-3-(3,4,5-trimethoxyphenyl)propanamide (ABR 239529)

The general procedure for the preparation of N-[10,11-dichloro-4-oxo-3-(trifluoromethyl)-2,5,7-triazatricyclo[6.4.0.0²,⁶]dodeca-1(12),6,8,10-tetraen-3-yl]oxane-4-carboxamide was used but with the following changes. In the first stage of the reaction, to form the acyl imine intermediate, 3-(3,4,5-trimethoxyphenyl)propanamide was used instead of oxane-4-carboxamide. In the second stage of the reaction, 5,6-dimethyl-1H-1,3-benzodiazol-2-amine was used instead of 5,6-dichloro-1H-1,3-benzodiazol-2-amine. The crude product was purified by silica chromatography, using 3% MeOH in DCM as eluent, to afford the title compound as a white solid (10%).

Example 115

N-[10,11-dimethyl-4-oxo-3-(trifluoromethyl)-2,5,7-triazatricyclo[6.4.0.0²,⁶]dodeca-1(8),6,9,11-tetraen-3-yl]-3-methanesulfonylbenzamide (ABR 239489)

To a stirred solution of 3-methanesulfonylbenzamide (800 mg, 4.02 mmol) in DMF (10 mL) was added pyridine (342 μl, 4.02 mmol) followed by ethyl 3,3,3-trifluoro-2-oxopropanoate (532 μl, 4.02 mmol) at room temperature under argon. The reaction mixture was stirred at room temperature for 1 h and then thionyl chloride (292 µl, 4.02 mmol) was added at 0° C. The reaction was stirred for a further 18 h at room temperature and was then concentrated. The acyl intermediate that remained was dissolved in DMF (10 mL) under argon. 5,6-Dimethyl-1H-1,3-benzodiazol-2-amine (485 mg, 3.01 mmol) and triethylamine (562 µl, 4.02 mmol) were added and the reaction mixture was stirred at room temperature for 16 h. The reaction mixture was diluted with water and extracted with EtOAc. The combined organic extracts were washed with brine, dried ($Na_2SO_4$), filtered and concentrated. The crude product was purified by silica chromatography, using 3% MeOH in DCM as eluent. Further purification was carried out by automated reverse phase HPLC (low pH Method B) to afford the title compound as a white solid (20 mg, 0.5%)

Example 116

3-bromo-N-[10,11-dimethyl-4-oxo-3-(trifluoromethyl)-2,5,7-triazatricyclo[6.4.0.0$^{2,6}$]dodeca-1(8),6,9,11-tetraen-3-yl]benzamide (ABR 239785)

To a stirred solution of 3-bromobenzamide (777 mg, 3.88 mmol) in DMF (7 mL) were added methyl 3,3,3-trifluoro-2-oxopropanoate (395 µl, 3.88 mmol) followed by pyridine (313 µl, 3.88 mmol) at room temperature under nitrogen. The reaction mixture was stirred at room temperature for 1 h. Thionyl chloride (282 µl, 3.88 mmol) was added at 0° C. and the reaction mixture was then stirred at 0° C. for 1 h. The reaction mixture was concentrated and the residue filtered through a short pad of silica, eluting with DCM, under nitrogen. The filtrate was concentrated, and the acyl intermediate that remained was dissolved in DMF (7 mL) under nitrogen. A solution of 5,6-dimethyl-1H-1,3-benzodiazol-2-amine (98 mg, 0.57 mmol) in DMF (7 mL) and triethylamine (619 µl, 4.65 mmol) were added and the reaction mixture was stirred at room temperature for 18 h. The reaction mixture was diluted with EtOAc (80 mL) and water (40 mL). A precipitate was removed by filtration and kept. The organic phase was washed with water (3×40 mL) and brine (40 mL). The organic phase was then dried ($Na_2SO_4$), filtered, concentrated and triturated with EtOAc. The resulting solid was combined with the previous precipitate, dissolved in EtOAc (10 mL) and washed with 10% citric acid$_{(aq)}$ (10 mL), water (10 mL) and brine (10 mL). The organic phase was dried ($Na_2SO_4$), filtered and concentrated to afford the title compound as a white solid (120 mg, 8%).

Example 117

N-[10,11-dimethyl-4-oxo-3-(trifluoromethyl)-2,5,7-triazatricyclo[6.4.0.0$^{2,6}$]dodeca-1(8),6,9,11-tetraen-3-yl]-3-[(2-methoxyethyl)amino]benzamide (ABR 239638)

A microwave tube was charged with 3-bromo-N-[10,11-dimethyl-4-oxo-3-(trifluoro-methyl)-2,5,7-triazatricyclo[6.4.0.0$^{2,6}$]dodeca-1(8),6,9,11-tetraen-3-yl]benzamide (300 mg, 0.64 mmol), CuI (24 mg, 0.13 mmol), L-proline (30 mg, 0.26 mmol) and $K_3PO_4$ (273 mg, 1.28 mmol). De-gassed DMSO (9 mL) and 2-methoxyethan-1-amine (193 mg, 2.57 mmol) were added. The reaction mixture was heated in the microwave at 80° C. for 2 h and was then diluted with EtOAc (100 mL) and water (80 mL). The organic layer was washed with 2M aqueous ammonia (80 mL), water (80 mL) and brine (80 mL). The organic layer was then dried ($Na_2SO_4$), filtered and concentrated. The crude product was purified by automated reverse phase HPLC (low pH Method A) to afford the title compound as a grey solid (60 mg, 20%).

Example 118

2-bromo-N-[10,11-dimethyl-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide (ABR 239786)

To a stirred solution of 2-bromo-1,3-thiazole-4-carboxamide (456 mg, 2.20 mmol) in DMF (5 mL) were added methyl 3,3,3-trifluoro-2-oxopropanoate (431 µl, 4.23 mmol) and pyridine (178 µl, 2.20 mmol) at room temperature under nitrogen. The reaction mixture was stirred at room temperature for 1 h. Thionyl bromide (171 µl, 2.20 mmol) was added at 0° C. and the reaction mixture was then stirred at room temperature for 1 h. The reaction mixture was concentrated and the residue filtered through a short pad of silica, eluting with DCM, under nitrogen. The filtrate was concentrated, and the acyl intermediate that remained was dissolved in DMF (10 mL) under nitrogen. A solution of 5,6-dimethyl-1H-1,3-benzodiazol-2-amine (284 mg, 1.76 mmol) in DMF (10 mL) and triethylamine (352 µl, 2.64 mmol) were added and the reaction mixture was stirred at room temperature for 18 h. The reaction mixture was concentrated. The residue was diluted with EtOAc (50 mL) and washed with 10% citric acid$_{(aq)}$ (15 ml), water (2×20 mL) and brine (20 mL). The organic phase was dried ($Na_2SO_4$), filtered and concentrated. The crude product was purified by silica chromatography, using 5-20% MeOH in DCM as eluent, to afford the title compound as a white solid (200 mg, 24%).

Example 119

N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-[(2-methoxyethyl)amino]-1,3-thiazole-4-carboxamide (ABR 239655)

To a solution of 2-bromo-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-1,3-thiazole-4-carboxamide (263 mg, 0.55 mmol) in DMF (4 mL), in a sealed tube, were added $K_2CO_3$ (153 mg, 1.11 mmol) and 2-methoxyethan-1-amine (96 µl, 1.11 mmol). The reaction mixture was heated at 90° C. for 24 h and was then concentrated. The residue was diluted with water and the pH adjusted to pH 6 with 10% citric acid$_{(aq)}$. The aqueous was extracted with EtOAc (2×20 mL). The combined organic extracts were washed with water (2×15 mL) and brine (15 mL). The organic phase was dried ($Na_2SO_4$), filtered and concentrated. The crude product was purified by automated reverse phase HPLC (low pH Method A) to afford the title compound as a white solid (45 mg, 17%).

Example 120

N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239508)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4-bromo-1H-1,3- benzodiazol-2-amine was used instead of 1H,5H,6H,7H-indeno[5,6-d]imidazol-2-amine. The crude product was purified by trituration in DCM to afford the title compound (17%).

Example 121

N-[9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239436)

A microwave tube was charged with N-[9-bromo-4-oxo-3-(trifluoromethyl)-2,5,7-triazatricyclo-[6.4.0.0$^{2,6}$]dodeca-1(12),6,8,10-tetraen-3-yl]-3-cyclopentylpropanamide (150 mg, 0.33 mmol), Zn(CN)$_2$ (58 mg, 0.49 mmol), Pd(dppf)Cl$_2$ (40 mg, 0.05 mmol) and de-gassed DMF (3 mL). The reaction mixture was heated in the microwave at 180° C. for 10 min. The reaction mixture was re-treated with Zn(CN)$_2$ (58 mg, 0.49 mmol) and Pd(dppf)Cl$_2$ (40 mg, 0.05 mmol) and was heated in the microwave at 180° C. for a further 10 min. The reaction was filtered. The filtrate was diluted with EtOAc (15 mL) and washed with water (5×10 mL). The organic phase was dried (Na$_2$SO$_4$), filtered and concentrated. The crude compound was purified by silica chromatography, using 40% EtOAc in heptane as eluent, to afford the title compound as a white solid (18 mg, 14%).

Example 122

N-[9-acetyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239448)

A microwave tube was charged with N-[9-bromo-4-oxo-3-(trifluoromethyl)-2,5,7-triazatricyclo-[6.4.0.0$^{2,6}$]dodeca-1(12),6,8,10-tetraen-3-yl]-3-cyclopentylpropanamide (100 mg, 0.22 mmol), palladium(II) acetate (1.4 mg, 0.006 mmol), propane-1,3-diylbis(diphenylphosphane) (5.7 mg, 0.014 mmol), K$_2$CO$_3$ (36 mg, 0.26 mmol), 1-(ethenyloxy)butane (142 µl, 1.09 mmol) and de-gassed DMF/water (4:1, 1 mL), under nitrogen. The reaction was heated in the microwave at 100° C. for 1 h. The reaction was diluted with EtOAc (17 ml) and washed with water (4×5 mL), brine (6 mL). The organic phase was dried (Na$_2$SO$_4$), filtered and concentrated. The crude product was purified by automated reverse phase HPLC (low pH Method A) to afford the title compound as a white solid (56 mg, 61%).

Example 123

N-[10-chloro-9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239521)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 2-amino-5-chloro-1H-1,3-benzodiazole-4-carbonitrile was used instead of 1H,5H,6H,7H-indeno[5,6-d]imidazol-2-amine. After the addition of thionyl chloride the reaction was stirred at 0° C. for 1 h before being concentrated. A solid precipitated from the aqueous work-up and was collected by filtration to afford the title compound (36%).

Example 124

3-cyclopentyl-N-[9-fluoro-4-oxo-3-(trifluoromethyl)-2,5,7-triazatricyclo[6.4.0.0$^{2,6}$]dodeca-1(12),6,8,10-tetraen-3-yl]propanamide (ABR 239535)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4-fluoro-1H-1,3-benzodiazol-2-amine was used instead of 1H,5H,6H,7H-indeno[5,6-d]imidazol-2-amine. After the addition of thionyl chloride the reaction was stirred at 0° C. for 1 h before being concentrated. The crude product was purified by trituration DCM to afford the title compound (19%).

Example 125

3-cyclopentyl-N-[9,11-dimethyl-4-oxo-3-(trifluoromethyl)-2,5,7-triazatricyclo[6.4.0.0$^{2,6}$]-dodeca-1(12),6,8,10-tetraen-3-yl]propanamide (ABR 239545)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4,6-dimethyl-1H-1,3-benzodiazol-2-amine was used instead of 1H,5H,6H,7H-indeno[5,6-d]imidazol-2-amine. An additional equivalent of thionyl chloride was added at 0° C. 1 h after the initial charge and the reaction was then stirred at for a further 1 h at 0° C. before being concentrated. The crude product was purified by trituration in the minimum volume of DCM to afford the title compound (26%).

Example 126

N-[9-chloro-10-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239559)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4-chloro-5-fluoro-1H-1,3-benzodiazol-2-amine was used instead of 1H,5H,6H,7H-indeno[5,6-d]imidazol-2-amine. After the addition of thionyl chloride the reaction was stirred at 0° C. for 1 h before being concentrated. The crude product was purified by trituration in DCM to afford the title compound as a white solid (16%).

Example 127

N-[10-chloro-9-methyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239569)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 5-chloro-4-methyl-1H-1,3-benzodiazol-2-amine was used instead of 1H,5H,6H,7H-indeno[5,6-d]imidazol-2-amine. An additional equivalent of thionyl chloride was added at 0° C. 1 h after the initial charge and the reaction was then stirred at 0° C. for a further 1 h before being concentrated. The crude product was purified by trituration in DCM to afford the title compound (35%).

Example 128

3-cyclopentyl-N-[4-oxo-3,9-bis(trifluoromethyl)-2,5,7-triazatricyclo[6.4.0.0$^{2,6}$]dodeca-1(8),6,9,11-tetraen-3-yl]propanamide (ABR 239544)

To a stirred solution of 3-cyclopentylpropanamide (200 mg, 1.42 mmol) in DMF (20 mL) was added methyl 3,3,3-trifluoro-2-oxopropanoate (442 mg, 2.83 mmol) followed by pyridine (114 µl, 1.42 mmol) at room temperature under nitrogen. The reaction mixture was stirred at room temperature for 2 h. Thionyl chloride (103 µl, 1.42 mmol) was added at 0° C. and the reaction mixture was then stirred at 0° C. for 1 h. The reaction mixture was concentrated and the residue filtered through a short pad of silica, eluting with DCM, under nitrogen. The filtrate was concentrated, and the acyl intermediate that remained was dissolved in DMF (15 mL) under nitrogen. 4-(Trifluoromethyl)-1H-1,3-benzodiazol-2-amine (228 mg, 1.13 mmol) and triethylamine (188 µl, 1.42 mmol) were added and the reaction mixture was stirred at room temperature for 2 h. The reaction mixture was concentrated. The residue was diluted with EtOAc (100 mL) and washed with water (3×100 mL) and brine (3×100 mL). The organic phase was dried (MgSO$_4$), filtered, and concentrated. The crude product was triturated in DCM to afford the title compound as a white solid (194 mg, 31).

Example 129

N-[11-bromo-4-oxo-3,9-bis(trifluoromethyl)-2,5,7-triazatricyclo[6.4.0.0$^{2,6}$]dodeca-1(8),6,9,11-tetraen-3-yl]-3-cyclopentylpropanamide (ABR 239577)

To a stirred solution of 3-cyclopentyl-N-[4-oxo-3,9-bis(trifluoromethyl)-2,5,7-triazatricyclo-[6.4.0.0$^{2,6}$]dodeca-1(8),6,9,11-tetraen-3-yl]propanamide (50 mg, 0.11 mmol) in DCM (5 mL) was added NBS (30 mg, 0.17 mmol). The resulting suspension was stirred for 48 h at room temperature. Additional NBS (60 mg, 0.34 mmol) and DCM (25 mL) were added over the following 8 day period. Then the reaction mixture was diluted with DCM (50 mL) and washed with water (3×25 mL) and saturated NaHCO$_{3(aq)}$ (25 mL). The organic phase was dried (MgSO$_4$), filtered, and concentrated. The crude product was purified by automated reverse phase HPLC (low pH Method A) to afford the title compound as a white solid (14 mg, 24%).

Example 130

N-[10-chloro-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239603)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 5-chloro-4-fluoro-1H-1,3-benzodiazol-2-amine was used instead of 1H,5H,6H,7H-indeno[5,6-d]imidazol-2-amine. After the addition of thionyl chloride the reaction was stirred at 0° C. for 1 h before being concentrated. The crude product was purified by trituration in DCM to afford the title compound (3%).

Example 131

3-cyclopentyl-N-[9-fluoro-10-methoxy-4-oxo-3-(trifluoromethyl)-2,5,7-triazatricyclo-[6.4.0.0$^{2,6}$]dodeca-1(12),6,8,10-tetraen-3-yl]propanamide (ABR 239551)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4-fluoro-5-methoxy-1H-1,3-benzodiazol-2-amine was used instead of 1H,5H,6H,7H-indeno[5,6-d]imidazol-2-amine. After the addition of thionyl chloride the reaction was stirred at 0° C. for 1 h before being concentrated. The final step was worked up 2 h after the addition of 4-fluoro-5-methoxy-1H-1,3-benzodiazol-2-amine. The crude product was purified by trituration in DCM to afford the title compound (10%).

Example 132

3-cyclopentyl-N-[9-(methylsulfanyl)-4-oxo-3-(trifluoromethyl)-2,5,7-triazatricyclo-[6.4.0.0$^{2,6}$]dodeca-1(12),6,8,10-tetraen-3-yl]propanamide (ABR 239636)

The procedure for the preparation of 3-cyclopentyl-N-[12-oxo-11-(trifluoromethyl)-10,13,15-triazatetracyclo[7.6.0.0$^{3,7}$.0$^{10,14}$]pentadeca-1(9),2,7,14-tetraen-11-yl]propanamide was used except that 4-(methylsulfanyl)-1H-1,3-benzodiazol-2-amine was used instead of 1H,5H,6H,7H-indeno[5,6-d]imidazol-2-amine. After the addition of thionyl chloride the reaction was stirred at 0° C. for 1 h before being concentrated. The crude product was purified by silica chromatography, using 1-8% MeOH in DCM as eluent, to afford the title compound as a pale brown solid (quantitative yield).

Example 133

3-cyclopentyl-N-[9-methanesulfonyl-4-oxo-3-(trifluoromethyl)-2,5,7-triazatricyclo-[6.4.0.0$^{2,6}$]dodeca-1(12),6,8,10-tetraen-3-yl]propanamide (ABR 239639)

To a stirred solution of 3-cyclopentyl-N-[9-(methylsulfanyl)-4-oxo-3-(trifluoromethyl)-2,5,7-triazatricyclo[6.4.0.0$^{2,6}$]dodeca-1(12),6,8,10-tetraen-3-yl]propanamide (100 mg, 0.23 mmol) in MeOH (2 mL) was added a solution of oxone (359 mg, 0.59 mmol) in water (2 mL) dropwise at 0° C. After stirring for 4 h, the reaction was diluted with EtOAc (30 ml), washed with water (2×10 mL) and then brine (10 mL). The organic phase was dried (Na$_2$SO$_4$), filtered and concentrated to give the title product as a pale brown solid (100 mg, 93%).

Example 134

N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239730)

To a stirred solution of 3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (300 mg, 0.71 mmol) in DCM (30 mL) was added NBS (165 mg, 0.93 mmol). The resulting suspension was stirred for 18 h at room temperature. Additional NBS (165 mg, 0.93 mmol) was added. The reaction was stirred for a further 4 h and was then concentrated. The residue was dissolved in EtOAc (100 mL) and washed with water (2×50 mL), saturated citric acid$_{(aq)}$ (50 mL) and brine (50 mL). The organic phase was dried (MgSO$_4$), filtered, and concentrated. The crude product was purified by trituration in DCM to afford the title compound as a white solid (160 mg, 46%).

Example 135

N-[9,10-dichloro-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide (ABR 239538)

To a stirred solution of 6-fluoropyridine-2-carboxamide (140 mg, 1.00 mmol) in DMF (10 mL) was added methyl 3,3,3-trifluoro-2-oxopropanoate (312 mg, 2.00 mmol) followed by pyridine (81 µl, 1.00 mmol) at room temperature under nitrogen. The reaction mixture was stirred at room temperature for 16 h. Thionyl chloride (87 µl, 1.20 mmol) was added at 0° C. and the reaction mixture was then stirred at 0° C. for 1 h. The reaction mixture was concentrated and the residue filtered through a short pad of silica, eluting with DCM, under nitrogen. The filtrate was concentrated, and the acyl intermediate that remained was dissolved in DMF (10 mL) under nitrogen. 4,5-Dichloro-1H-1,3-benzodiazol-2-amine (151 mg, 0.75 mmol) and triethylamine (133 µl, 1.00 mmol) were added. The reaction mixture was stirred at room temperature for a further 2 h and was then concentrated. The residue was dissolved with EtOAc (100 mL) and washed with water (3×50 mL) and brine (3×50 mL). The organic phase was dried (MgSO$_4$), filtered, and concentrated. The crude product was purified by automated reverse phase HPLC (low pH Method A) to afford the title compound as a white solid (122 mg, 27%).

Example 136

N-[9,10-dichloro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]pyridine-2-carboxamide (ABR 239542)

To a solution of N-[9,10-dichloro-4-oxo-3-(trifluoromethyl)-2,5,7-triazatricyclo[6.4.0.0$^{2,6}$]-dodeca-1(8),6,9,11-tetraen-3-yl]-6-fluoropyridine-2-carboxamide (80 mg, 0.18 mmol) in DMF (3 mL), in a sealed tube, were added K$_2$CO$_3$ (62 mg, 0.45 mmol) and 2-methoxyethan-1-amine (27 mg, 0.36 mmol). The reaction mixture was heated at 100° C. for 12 h. Additional 2-methoxyethan-1-amine (27 mg, 0.36 mmol) and K$_2$CO$_3$ (62 mg, 0.45 mmol) were added. The reaction was heated at 100° C. for a further 6 h and was then concentrated. The residue was dissolved in EtOAc (50 mL) and washed with water (3×25 mL) and then brine (2×25 mL). The organic phase was dried (MgSO$_4$), filtered and concentrated. The crude compound was purified by automated reverse phase HPLC (high pH) to afford the title compound as a white solid (20 mg, 22%).

Example 137

N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide (ABR 239579)

To a stirred solution of 6-fluoropyridine-2-carboxamide (175 mg, 1.25 mmol) in DMF (10 mL) was added methyl 3,3,3-trifluoro-2-oxopropanoate (390 mg, 2.49 mmol) followed by pyridine (100 µl, 1.52 mmol) at room temperature under nitrogen. The reaction mixture was stirred at room temperature for 2 h. Thionyl chloride (91 µl, 1.25 mmol) was added at 0° C. and the reaction mixture was then stirred at 0° C. for 1 h. The reaction mixture was concentrated and the residue filtered through a short pad of silica, eluting with DCM, under an inert atmosphere. The filtrate was concentrated, and the acyl intermediate that remained was dissolved in DMF (10 mL) under an inert atmosphere. A solution of 2-amino-5-chloro-1H-1,3-benzodiazole-4-carbonitrile (200 mg, 1.04 mmol) in DMF (2 ml) and triethylamine (133 µl, 1.00 mmol) were added and the reaction mixture was stirred at room temperature for 4 h. The reaction mixture was concentrated. The residue was dissolved with EtOAc (50 mL) and washed with water (3×50 mL) and brine (3×50 mL). The organic phase was dried (MgSO$_4$), filtered, and concentrated. The crude product was purified by silica chromatography, using 0-10% MeOH in DCM as eluent. Further purification was carried out using automated reverse phase HPLC (low pH Method A) to afford the title compound as a brown solid (115 mg, 25%).

Example 138

N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]pyridine-2-carboxamide (ABR 239585)

To a solution of N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide (75 mg, 0.17 mmol) in DMF (2 mL), in a sealed tube, were added K$_2$CO$_3$ (71 mg, 0.51 mmol) and 2-methoxyethan-1-amine (39 mg, 0.51 mmol). Initially, the reaction mixture was heated for 2 h at 100° C. The reaction was then heated for a further 20 h. During this period, additional 2-methoxyethan-1-amine (80 mg, 1.02 mmol) was added portionwise with the reaction at room temperature during retreatment. Then the reaction mixture was concentrated. The residue was dissolved in EtOAc (100 mL) and washed with water (3×50 mL) and then brine (3×50 mL). The organic phase was dried (MgSO$_4$), filtered and concentrated. The crude compound was purified by automated reverse phase HPLC (low pH Method A) to afford the title compound as a white solid (22 mg, 26%).

Example 139

N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-2-[(2-methoxyethyl)amino]-1,3-thiazole-4-carboxamide (ABR 239624)

To a stirred solution of 2-bromo-1,3-thiazole-4-carboxamide (194 mg, 0.93 mmol) in DMF (10 mL) was added methyl 3,3,3-trifluoro-2-oxopropanoate (291 mg, 1.86 mmol) followed by pyridine (75 µL, 0.93 mmol) under nitrogen. The reaction mixture was stirred at room temperature for 16 h. Thionyl chloride (68 µL, 0.93 mmol) was added dropwise at 0° C. The solution was stirred for a further 1 h at 0° C. and then concentrated. The residue filtered through a short pad of silica, eluting with DCM, under nitrogen. The filtrate was concentrated, and the acyl intermediate that remained was dissolved in DMF (10 mL) under nitrogen. A solution of 2-amino-5-chloro-1H-1,3-benzodiazole-4-carbonitrile (150 mg, 0.78 mmol) in DMF (5 mL) and triethylamine (124 µl, 0.935 mmol) were added and the reaction mixture was stirred at room temperature for 2 h. The reaction was concentrated and the residue was dissolved in EtOAc (50 mL) and washed with 10% citric acid$_{(aq)}$ (25 mL), water (2×25 mL) and then brine (2×25 mL).

The organic phase was dried (MgSO$_4$), filtered and concentrated. The crude product was purified by silica chromatography, using 2-6% MeOH in DCM as eluent, to afford a mixture of 2-bromo-N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide and 2-chloro-N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide (84 mg).

A microwave tube was charged with a portion of the mixture of 2-bromo-N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide and 2-chloro-N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide (70 mg), K$_2$CO$_3$ (57 mg, 0.42 mmol), 2-methoxyethan-1-amine (36 µl, 0.42 mmol) and dioxane (2 mL). The reaction was heated in the microwave at 130° C. for 1 h. Additional 2-methoxyethan-1-amine (36 µl, 0.42 mmol) and K$_2$CO$_3$ (57 mg, 0.42 mmol) were added. The reaction was heated for a further 1 h and was then concentrated. The residue was dissolved in EtOAc (25 mL) and washed with water (25 mL), 10% citric acid$_{(aq)}$ (25 mL) and brine (25 mL). The organic phase was dried (MgSO$_4$), filtered and concentrated. The crude product was purified by automated reverse phase HPLC (low pH Method A) to afford the title compound as a white solid (3 mg).

Example 140

Diastereomeric mixture. N-[10-chloro-9-cyano-4-oxo-3-(trifluoromethyl)-2,5,7-triaza-tricyclo[6.4.0.0$^{2,6}$]dodeca-1(8),6,9,11-tetraen-3-yl]-6-{[(2S)-1-methoxypropan-2-yl]amino}-pyridine-2-carboxamide (ABR 239586)

To a solution of N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide (75 mg, 0.55 mmol) in DMF (2 mL), in a sealed tube, were added K$_2$CO$_3$ (185 mg, 1.34 mmol) and (2S)-1-methoxypropan-2-amine (49 mg, 0.55 mmol). Initially, the reaction mixture was heated for 6 h at 100° C. Then the reaction was heated for a further 22 h. During this period, additional K$_2$CO$_3$ (150 mg, 1.10 mmol) and (2S)-1-methoxypropan-2-amine (98 mg, 1.10 mmol) were added portionwise with the reaction at room temperature during retreatment. The reaction mixture was then concentrated. The residue was dissolved in EtOAc (50 mL) and washed with water (3×25 mL) and then brine (3×25 mL). The organic phase was dried (MgSO$_4$), filtered and concentrated. The crude compound was purified by automated reverse phase HPLC (low pH Method A) to afford the title compound as a yellow solid as mixture of diastereomers (14 mg, 15%).

Example 141

N-[9,10-difluoro-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide (ABR 239787)

To a stirred solution of 6-fluoropyridine-2-carboxamide (190 mg, 1.36 mmol) in DMF (2 mL) were added methyl 3,3,3-trifluoro-2-oxopropanoate (138 µl, 1.36 mmol) followed by pyridine (109 µl, 1.36 mmol) at room temperature under nitrogen. The reaction mixture was stirred at room temperature for 1 h. Thionyl chloride (99 µl, 1.36 mmol) was added at 0° C. and the reaction mixture was then stirred at room temperature for 1.5 h. The reaction mixture was concentrated and the residue filtered through a short pad of silica, eluting with DCM, under an inert atmosphere. The filtrate was concentrated, and the acyl intermediate that remained was dissolved in DMF (5 mL) under nitrogen. A solution of 4,5-difluoro-1H-1,3-benzodiazol-2-amine (153 mg, 0.90 mmol) in DMF (4 mL) and triethylamine (181 µl, 1.36 mmol) were added and the reaction mixture was stirred at room temperature for 18 h. The reaction mixture was diluted with EtOAc (30 mL), washed with water (4×20 mL) and brine (20 mL). The organic phase was dried (Na$_2$SO$_4$), filtered and concentrated. The crude product was purified by trituration in DCM to afford the title compound as a white solid (123 mg, 33%).

Example 142

N-[9,10-difluoro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]pyridine-2-carboxamide (ABR 239632)

To a solution of N-[9,10-difluoro-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide (123 mg, 0.30 mmol) in DMF (3 mL), in a sealed tube, were added K$_2$CO$_3$ (102 mg, 0.74 mmol) and 2-methoxyethan-1-amine (45 mg, 0.59 mmol). The reaction mixture was heated at 100° C. for 18 h. The reaction was diluted with EtOAc (50 mL) and was washed with water (3×25 mL) and then brine (3×25 mL). The organic phase was dried (Na$_2$SO$_4$), filtered and concentrated. The crude compound was purified by automated reverse phase HPLC (low pH Method A) to afford the title compound as a white solid (36 mg, 26%).

Example 143

Diastereomer 1: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-phenylpropanamide (ABR 239609)

Example 144

Diastereomer 2: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-phenylpropanamide (ABR 239621)

To a stirred solution of (2S)-2-phenylpropanamide (222 mg, 1.49 mmol) in DMF (10 mL) was added pyridine (120

µl, 1.49 mmol) followed by methyl 3,3,3-trifluoro-2-oxopropanoate (465 mg, 2.98 mmol), at room temperature under nitrogen. The reaction mixture was stirred at room temperature for 2 h. Thionyl chloride (108 µl, 1.49 mmol) was added at 0° C. and the reaction mixture was then stirred for 1 h at 0° C. Then the reaction mixture was concentrated and the residue was filtered through a short pad of silica, eluting with DCM, under nitrogen. The filtrate was concentrated, and the acyl intermediate that remained was dissolved in DMF (5 mL) under nitrogen. A solution of 5,6-dimethyl-1H-1,3-benzodiazol-2-amine (200 mg, 1.24 mmol) in DMF (5 mL) and triethylamine (198 µl, 1.49 mmol) were added and the reaction mixture was stirred at room temperature for 3 h. Then the reaction mixture was concentrated. The residue was diluted with EtOAc (50 mL), washed with washed with water (2×25 mL), 10% citric acid$_{(aq)}$ (2×25 ml) and brine (2×25 mL). The organic phase was dried (MgSO$_4$), filtered and concentrated. The crude product was purified by trituration in DCM to afford a clean mixture of diastereomers. Recrystallization in EtOAc/heptane afforded Diastereomer 1 as a single diastereomer of undefined stereochemistry at the quaternary centre as a white solid (95 mg, 18%). The mother liquor was concentrated and purified by automated reverse phase HPLC (low pH Method A) to afford Diastereomer 2 as a single diastereomer of undefined stereochemistry at the quaternary centre as a white solid (33 mg, 6%).

Example 145

Diastereomeric mixture. (2S)-3-cyclopentyl-N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-methylpropanamide (ABR 239666)

(a) Diastereomer 1: (2S)-3-cyclopentyl-N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-methylpropanamide (ABR 239667)

(b) Diastereomer 2: (2S)-3-cyclopentyl-N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-methylpropanamide (ABR 239668)

To a stirred solution of (2S)-3-cyclopentyl-2-methylpropanamide (254 mg, 1.64 mmol) in DMF (15 mL) was added pyridine (132 µL, 1.64 mmol) followed by methyl 3,3,3-trifluoro-2-oxopropanoate (511 mg, 3.28 mmol) at room temperature, under nitrogen. The reaction mixture was stirred at room temperature for 2 h. Thionyl chloride (118 µl, 1.64 mmol) was added at 0° C. and the reaction was stirred for 1 h at 0° C. Then the reaction mixture was concentrated and the residue filtered through a short pad of silica, eluting with DCM, under nitrogen. The filtrate was concentrated, and the acyl intermediate that remained was dissolved in DMF (10 mL) under nitrogen. A solution of 5,6-dimethyl-1H-1,3-benzodiazol-2-amine (220 mg, 1.36 mmol) in DMF (10 mL) and triethylamine (229 µl, 1.64 mmol) were added. The reaction mixture was stirred at room temperature for 2 h and was then concentrated. The residue was diluted with EtOAc (50 mL) and washed with water (3×50 mL) and then brine (3×50 mL). The organic phase was dried (MgSO$_4$), filtered and concentrated. The crude product was purified by trituration in DCM to afford the title compound as a yellow solid as a clean mixture of diastereomers. A portion was retained as the diastereomeric mixture (61 mg, 11%) and the remaining material was purified by SFC using a Chiralpak AD-H column, with a mobile phase of CO$_2$ and MeOH containing 0.1% formic acid, to afford Diastereomer 1 as a single diastereomer of undefined stereochemistry at the quaternary centre as a white solid (26 mg, 5%) and Diastereomer 2 as a single diastereomer of undefined stereochemistry at the quaternary centre as a white solid (40 mg, 7%).

Example 146

(a) Diastereomer 1: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-hydroxy-2-phenylacetamide (ABR 239664)

(b) Diastereomer 2: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-hydroxy-2-phenylacetamide (ABR 239665)

To a stirred solution of (S)-{[10,11-dimethyl-4-oxo-3-(trifluoromethyl)-2,5,7-triazatricyclo[6.4.0.0$^{2,6}$]dodeca-1(8),6,9,11-tetraen-3-yl]carbamoyl}(phenyl)methyl acetate (500 mg, 1.09 mmol) in MeOH (20 mL) was added 2M NaOH$_{(aq)}$ (597 µl, 1.20 mmol). The reaction mixture was heated at 40° C. for 3 h and then concentrated. The residue was dissolved in EtOAc (50 mL) and washed with 10% citric acid$_{(aq)}$ (2×30 mL) and then brine (2×30 mL). The organic phase was dried (MgSO$_4$), filtered and concentrated. The crude product was purified by reverse phase C18 chromatography, using acidic eluent, to give a clean mixture of diastereomers. The mixture of diastereomers was separated by automated reverse phase HPLC (low pH Method A) to afford Diastereomer 1 as a single diastereomer of undefined stereochemistry at the quaternary centre as a white solid (38 mg, 8%) and Diastereomer 2 as a single diastereomer of undefined stereochemistry at the quaternary centre as a white solid (80 mg, 18%).

Example 147

(a) Diastereomer 1: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methoxy-2-phenylacetamide (ABR 239622)

(b) Diastereomer 2: (2S)—N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methoxy-2-phenylacetamide (ABR 239623)

To a stirred solution of (2S)-2-methoxy-2-phenylacetamide (184 mg, 1.12 mmol) in DMF (10 mL) was added pyridine (90 µl, 1.12 mmol) followed by methyl 3,3,3-trifluoro-2-oxopropanoate (349 mg, 2.23 mmol) at room temperature under nitrogen. The reaction mixture was stirred at room temperature for 2 h. Thionyl chloride (81 µl, 1.12 mmol) was added at 0° C. and the reaction was stirred for 1 h at 0° C. The reaction mixture was concentrated and the residue was filtered through a short pad of silica, eluting with DCM, under nitrogen. The filtrate was concentrated, and the acyl intermediate that remained was dissolved in DMF (10 mL) under nitrogen. A solution of 5,6-dimethyl-1H-1,3-benzodiazol-2-amine (150 mg, 0.93 mmol) in DMF (5 mL) and triethylamine (149 µl, 1.12 mmol) were added. The reaction mixture was stirred at room temperature for 2 h and was then concentrated. The residue was diluted with EtOAc (50 mL) and washed with water (2×25 mL), 10% citric acid$_{(aq)}$ (2×25 mL) and brine (2×25 mL). The organic phase was dried (MgSO$_4$), filtered and concentrated. The crude product was purified by trituration in DCM to give a clean mixture of diastereomers. The mixture of diastereomers was separated by automated reverse phase HPLC (low pH Method A) to afford Diastereomer 1 as a single diastereomer of undefined stereochemistry at the quaternary centre as a white solid (50 mg, 12%) and Diastereomer 2 as a single diastereomer of undefined stereochemistry at the quaternary centre as a white solid (27 mg, 7%).

Example 148 methyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (ABR 239934)

To a stirred solution of 3-cyclopentylpropanamide (2.22 g, 15.7 mmol) in anhydrous DCM (50 mL) was added methyl 3,3,3-trifluoro-2-oxopropanoate (2.40 mL, 23.5 mmol) followed by pyridine (1.27 mL, 15.7 mmol) under nitrogen. The reaction was stirred at room temperature for 2 h. Thionyl chloride (1.14 mL, 15.69 mmol) was added at 0° C. The reaction was stirred for 1 h at 0° C. and then filtered through a short pad of silica, eluting with DCM, under nitrogen. The filtrate was concentrated, and the acyl intermediate that remained was dissolved in DMF (25 mL) under nitrogen. The solution of acyl intermediate was added to a solution of methyl 2-amino-1H-1,3-benzodiazole-4-carboxylate, available via a literature method: PCT Int. Appl., 2008157270; (2.50 g, 13.1 mmol) in DMF (25 mL) followed by triethylamine (5.22 mL, 39.2 mmol). The reaction mixture was stirred for a further 18 h and then concentrated. The residue was dissolved in EtOAc (100 mL) and washed with saturated citric acid$_{(aq)}$ (30 mL). The aqueous phase was extracted with EtOAc (100 mL). The combined organic extracts were washed with brine (2×15 mL) and then dried (MgSO$_4$), filtered and concentrated. The crude product was purified by silica chromatography, using 0-10% MeOH in DCM as eluent, to afford the title compound as a green solid (990 mg, 17%).

Example 149

3-cyclopentyl-N-[9-iodo-4-oxo-3-(trifluoromethyl)-2,5,7-triazatricyclo[6.4.0.0$^{2,6}$]dodeca-1(12),6,8,10-tetraen-3-yl]propanamide (ABR 240060)

To a stirred solution of 3-cyclopentylpropanamide (748 mg, 5.29 mmol) in anhydrous DCM (30 mL) was added methyl 3,3,3-trifluoro-2-oxopropanoate (0.65 mL, 6.35 mmol) followed by pyridine (0.43 mL, 5.29 mmol) under nitrogen. The reaction mixture was stirred at room temperature for 16 h. Thionyl chloride (0.38 mL, 5.29 mmol) was added at 0° C. The reaction was stirred for 2 h at 0° C. and was then filtered through a short pad of silica, eluting with DCM, under nitrogen. The filtrate was concentrated, and the acyl intermediate that remained was dissolved in DMF (10 mL) under nitrogen. The solution of acyl intermediate was added to a solution of 4-iodo-1H-1,3-benzodiazol-2-amine (1.10 g, 4.23 mmol) in DMF (10 mL) followed by triethylamine (0.70 mL, 5.29 mmol). The reaction mixture was stirred for a further 4 h and then concentrated. The residue was dissolved in EtOAc (50 mL) and washed with 10% citric acid$_{(aq)}$ (50 mL). The resulting precipitate was removed by filtration. The aqueous layer was extracted with EtOAc (25 mL). The combined organic extracts were washed with brine (2×50 mL), dried (MgSO$_4$), filtered and concentrated. The crude product was purified by trituration in DCM to afford the title compound as a white solid (798 mg, 27%).

Example 150

N-[9-bromo-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide (ABR 240061)

To a stirred solution of 2-methoxypyridine-3-carboxamide, available via a literature method: PCT Int. Appl., 2010101949; (300 mg, 1.97 mmol) in DMF (5 mL) was added methyl 3,3,3-trifluoro-2-oxopropanoate (0.24 mL, 2.37 mmol) followed by pyridine (0.16 mL, 1.97 mmol) under nitrogen. The reaction was stirred at room temperature for 16 h. Thionyl chloride (0.14 mL, 1.97 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (6 mL) under nitrogen. The solution of acyl intermediate was added to a solution of 4-bromo-1H-1,3-benzodiazol-2-amine (334 mg, 1.58 mmol) in DMF (5 mL) followed by triethylamine (0.26 mL, 1.97 mmol). The reaction mixture was stirred for a further 2 h and then concentrated. The residue was dissolved in EtOAc (30 mL) and washed with saturated citric acid$_{(aq)}$ (15 mL). The aqueous layer was extracted with EtOAc (2×15 mL). The combined organic extracts were washed with water (2×20 mL) and brine (2×20 mL) and then dried (MgSO$_4$), filtered and concentrated. The crude product was purified by trituration in DCM to afford the title compound as a white solid (334 mg, 44%).

Example 151

N-[9-bromo-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide (ABR 240062)

To a stirred suspension of N-[9-bromo-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide (334 mg, 0.7 mmol) in DCM (5 mL), at 0° C., under nitrogen, was added 1M tribromoborane in DCM (2.09 mL, 2.09 mmol). The reaction was allowed to warm to room temperature and stirred for 4 h. The reaction was cooled to 0° C. and additional 1M tribromoborane in DCM (2.09 mL, 2.09 mmol) was added. The reaction was allowed to warm to room temperature and stirred for 4 h. The reaction was quenched with water (15 mL) at 0° C. The resulting precipitate was collected by filtration and rinsed with water, DCM, EtOAc and water to afford the title compound as a white solid (208 mg, 65%).

Example 152

(2S)—N-[9-bromo-4-oxo-3-(trifluoromethyl)-2,5,7-triazatricyclo[6.4.0.0$^{2,6}$]dodeca-1(12),6,8,10-tetraen-3-yl]-2-cyclohexylpropanamide (ABR 240063)

To a stirred solution of (2S)-2-cyclohexylpropanamide (280 mg, 1.64 mmol) in DMF (5 mL) under nitrogen was added methyl 3,3,3-trifluoro-2-oxopropanoate (251 µL, 2.46 mmol) followed by pyridine (132 µL, 1.64 mmol). The reaction was stirred at room temperature for 1 h. Thionyl chloride (119 μL, 1.64 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (4 mL) under nitrogen. The solution of acyl intermediate was added to a solution of 4-bromo-1H-1,3-benzodiazol-2-amine (290 mg, 1.37 mmol) in DMF (2 mL) followed by triethylamine (204 μL, 1.53 mmol). The reaction was stirred for 16 h before being concentrated. The residue was dissolved in EtOAc (15 mL) and washed with saturated citric acid$_{(aq)}$ (15 mL). The aqueous layer was extracted with EtOAc (15 mL). The combined organic extracts were washed with brine (2×15 mL), dried (MgSO$_4$), filtered and concentrated. The crude product was purified by trituration in DCM to afford the title compound as a white solid (236 mg, 35%).

Example 153

(2S)-2-(cyclopent-1-en-1-ylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 240068)

To a solution of amide (2S)-2-(cyclopent-1-en-1-ylmethoxy)propanamide (346 mg, 2.05 mmol) in anhydrous DCM (5 mL) under nitrogen was added pyridine (165 μL, 2.05 mmol) followed by methyl 3,3,3-trifluoro-2-oxopropanoate (639 mg, 4.09 mmol). The reaction was stirred at room temperature for 18 h. Thionyl chloride (149 μL, 2.05 mmol) was added at 0° C. The reaction was stirred for 1 h at 0° C. The reaction was filtered through a short pad of silica, eluting with DCM, under nitrogen. The filtrate was concentrated, and the acyl intermediate that remained was dissolved in DMF (3 mL) under nitrogen. A solution of 5,6-dimethyl-1H-1,3-benzodiazol-2-amine (275 mg, 1.71 mmol) in DMF (2 mL) was added followed by triethylamine (286 μL, 2.05 mmol) were added. The reaction was stirred for 18 h before being concentrated. The residue was dissolved in EtOAc (30 mL) and washed with water (4×20 mL) and brine (20 mL). The organic phase was dried (Na$_2$SO$_4$), filtered and concentrated to afford the title compound as an orange solid (750 mg, quantitative yield).

Example 154

N-[11-chloro-9-iodo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 240064)

To a stirred solution of N-[9-bromo-11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (250 mg, 0.50 mmol) in dioxane (4 mL), under nitrogen, was added potassium iodide (250 mg, 1.5 mmol), copper(I) iodide (38 mg, 0.20 mmol) and N,N'-dimethylethane-1,2-diamine (43 μL, 0.4 mmol). Initially, the reaction was heated for at 150° C. 2 h. Then the temperature was reduced to 120° C. for 2 h and reduced further to 100° C. for a final 2 h. The reaction was then concentrated and the residue diluted with EtOAc (15 mL) and saturated citric acid$_{(aq)}$ (25 mL). The aqueous layer was extracted with EtOAc (15 mL). The combined organic extracts were washed with water (15 mL) and brine (30 mL) and then dried (MgSO$_4$), filtered and concentrated to afford the title compound as an orange solid (239 mg, 70%).

Example 155

N-[9-bromo-4-oxo-3-(trifluoromethyl)-2,5,7-triazatricyclo[6.4.0.0$^{2,6}$]dodeca-1(12),6,8,10-tetraen-3-yl] butanamide (ABR 240065)

To a stirred solution of butanamide (205 mg, 2.36 mmol) in anhydrous DCM (6 mL) was added methyl 3,3,3-trifluoro-2-oxopropanoate (0.24 mL, 2.4 mmol) followed by pyridine (0.18 mL, 2.3 mmol) under nitrogen. The reaction was stirred at room temperature for 1 h. Thionyl chloride (0.16 mL, 2.3 mmol) was added at 0° C. The reaction was stirred at 0° C. for 1 h and then filtered through a short pad of silica, eluting with DCM, under nitrogen. The filtrate was concentrated, and the acyl intermediate that remained was dissolved in DMF (3 mL) under nitrogen. The solution of acyl intermediate was added to a solution of 4-bromo-1H-1,3-benzodiazol-2-amine (400 mg, 1.89 mmol) in DMF (5 mL) followed by triethylamine (0.30 mL, 2.3 mmol). The reaction mixture was stirred for a further 1 h and then concentrated. The residue was diluted with EtOAc (60 mL) and 1M HCl$_{(aq)}$ (40 mL). The organic phase was washed with water (2×20 mL) and brine (20 mL) and then dried (Na$_2$SO$_4$), filtered and concentrated. The crude product was purified by silica chromatography, using 0-15% MeOH in DCM as eluent, to afford the title compound as a yellow oil (650 mg, 76%).

Example 156

N-[9-bromo-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide (ABR 240066)

To a stirred solution of 2-bromo-1,3-thiazole-4-carboxamide (2.93 g, 14.2 mmol) in DMF (80 mL) was added methyl 3,3,3-trifluoro-2-oxopropanoate (4.42 g, 28.3 mmol) followed by pyridine (1.14 mL, 14.2 mmol) under nitrogen. The reaction was stirred at room temperature for 16 h. Additional methyl 3,3,3-trifluoro-2-oxopropanoate (4.42 g, 28.3 mmol) was added and the reaction was stirred at a further 4 h. Thionyl chloride (1.03 mL, 14.2 mmol) was added at 0° C. The reaction was stirred for 2 h at 0° C. and then concentrated. The residue was filtered through a short pad of silica, eluting with DCM, under nitrogen. The filtrate was concentrated, and the acyl intermediate that remained was dissolved in DMF (10 mL) under nitrogen. The solution of acyl intermediate was added to a solution of 4-bromo-1H-1,3-benzodiazol-2-amine (2.50 g, 11.8 mmol) in DMF (40 mL) followed by triethylamine (1.88 mL, 14.2 mmol). The reaction mixture was stirred for a further 2 h and then concentrated. The residue was dissolved in EtOAc (200 mL), washed with 10% citric acid$_{(aq)}$ (2×100 mL), water (2×100 mL) and brine (2×100 mL) and then dried (MgSO$_4$), filtered and concentrated. The crude product was purified by trituration in DCM to afford a mixture of 2-bromo-N-[9-bromo-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide and N-[9-bromo-4-oxo-3-(trifluoromethyl)-2,5,7-triazatricyclo[6.4.0.0$^{2,6}$]dodeca-1(12),6,8,10-tetraen-3-yl]-2-chloro-1,3-thiazole-4-carboxamide (3.70 g).

A sealed tube was charged with a portion of the mixture of 2-bromo-N-[9-bromo-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide and N-[9-bromo-4-oxo-3-(trifluoromethyl)-2,5,7-triazatricyclo[6.4.0.0$^{2,6}$]dodeca-1(12),6,8,10-tetraen-3-yl]-2-chloro-1,3-thiazole-4-carboxamide (500 mg), cyclopentanamine (0.39 mL, 4.0 mmol), K$_2$CO$_3$ (546 mg, 3.95 mmol) and dioxane (5 mL). The tube was flushed with nitrogen, sealed and stirred at 130° C. for 20 h. Additional cyclopentanamine (0.16 mL, 1.6 mmol) and K$_2$CO$_3$ (219 mg, 1.58 mmol) were added and the reaction was then stirred at 130° C. for 4 h and 120° C. for 16 h. Then reaction mixture was concentrated and the resulting residue was diluted with EtOAc (30 mL) and water (30 mL). The aqueous phase was extracted with EtOAc (30 mL). The combined organic extracts were washed with water (2×25 mL) and brine (50 mL) and then dried (Na$_2$SO$_4$), filtered and concentrated. The crude product was purified by reverse phase C18 chromatography, using acidic eluent, to afford the title compound as an orange solid (150 mg, 33%).

Example 157

3-cyclopentyl-N-[9-iodo-10-methoxy-4-oxo-3-(trifluoromethyl)-2,5,7-triazatricyclo[6.4.0.0$^{2,6}$]dodeca-1(12),6,8,10-tetraen-3-yl]propanamide (ABR 240067)

A sealed tube was charged with N-[9-bromo-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (405 mg, 0.83 mmol), potassium iodide (412 mg, 2.48 mmol), copper(I) iodide (63 mg, 0.33 mmol), N,N'-dimethylethane-1,2-diamine (71 μl, 0.66 mmol) and anhydrous dioxane (4 mL). The tube was flushed with nitrogen, sealed and stirred at 120° C. for 16 h and then 100° C. for 4 h. The reaction mixture was then concentrated. The resulting residue was diluted with EtOAc (20 mL) and saturated citric acid$_{(aq)}$ (20 mL). The aqueous phase was extracted with EtOAc (15 mL). The combined organic extracts were washed with water (2×15 mL), dried (MgSO$_4$), filtered and concentrated to afford the title compound as a green solid (350 mg, 51%).

Example 158

3-cyclopentyl-N-[9-(hydroxymethyl)-4-oxo-3-(trifluoromethyl)-2,5,7-triazatricyclo[6.4.0.0$^{2,6}$]dodeca-1(12),6,8,10-tetraen-3-yl]propanamide (ABR 239922)

To a stirred solution of methyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (480 mg, 1.09 mmol) in anhydrous THF (5 mL), at 0° C. under nitrogen, was added 1M lithium tetrahydridoaluminate in THF (4.38 mL, 4.38 mmol). The reaction was allowed to warm up to room temperature over 2 h. The reaction mixture was then diluted with diethyl ether (20 mL). Water was added slowly at 0° C. followed by 15% NaOH$_{(aq)}$. The reaction mixture was stirred for 1 hr. The precipitate was collected by filtration and then dissolved in EtOAc (30 mL) and acidified to pH2 using 2M HCl$_{(aq)}$. The organic phase was washed with brine (10 mL), dried (MgSO$_4$), filtered and concentrated. The crude product was purified by trituration in DCM to give the title compound as a yellow solid (180 mg, 40%).

Example 159

N-[9-butyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239938)

To a solution of N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (300 mg, 0.65 mmol), 2-methylprop-1-en-1-yl acetate (149 mg, 1.31 mmol) and tributyl(methoxy)stannane (375 μL, 1.31 mmol) in de-gassed DMSO (1 mL) in a sealed tube was added dichlorobis(tri-o-tolylphosphine)palladium(II) (16 mg, 33 μmop. The tube was flushed with nitrogen and sealed. The reaction mixture was stirred at 100° C. for 16 h. The reaction mixture was diluted with EtOAc (5 mL) and 4M KF$_{(aq)}$ (1 mL) was added. After stirring for 1 h the reaction mixture was filtered through Celite™ and rinsed with EtOAc. The organic phase was washed with water (2×5 mL) and brine (5 mL) and then dried (Na$_2$SO$_4$), filtered and concentrated. The crude product was purified by automated reverse phase HPLC (low pH Method A) to afford the title compound as a white solid (30 mg, 11%).

Example 160

3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid (ABR 239943)

To a stirred solution of methyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (500 mg, 1.14 mmol) in MeOH/H$_2$O (1:1, 12 mL) was added LiOH.H$_2$O (144 mg, 3.42 mmol). The reaction mixture was stirred at 60° C. for 16 h and then concentrated. The residue was dissolved in water and acidified with 1M HCl$_{(aq)}$ to pH 1. The resulting precipitate was collected by filtration, washed with water and hexane to afford the title compound as a brown solid (422 mg, 87%).

Example 161

3-cyclopentyl-N-{9-[1-(methoxyimino)ethyl]-4-oxo-3-(trifluoromethyl)-2,5,7-triazatricyclo[6.4.0.0$^{2,6}$]dodeca-1(12),6,8,10-tetraen-3-yl}propanamide (ABR 239950)

To a stirred solution of N-[9-acetyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (70%, 175 mg, 0.29 mmol) and pyridine (82 μL, 1.0 mmol) in EtOH (2 mL) was added O-methylhydroxylamine hydrochloride (92 mg, 1.1 mmol). The reaction was heated at 80° C. for 1 h and then concentrated. The residue was dissolved in EtOAc (15 mL) and washed with water (15 mL). The aqueous layer was extracted with EtOAc (2×10 mL). The combined organic extracts were washed with brine (20 mL), dried (Na$_2$SO$_4$), filtered and concentrated. The crude product was purified by automated reverse phase HPLC (low pH Method A) to afford the title compound as a white solid (61 mg, 47%).

Example 162

3-(3-cyclopentylpropanamido)-N-methyl-4-oxo-3-(trifluoromethyl)-2,5,7-triazatricyclo[6.4.0.0$^{2,6}$]dodeca-1(12),6,8,10-tetraene-9-carboxamide (ABR 239951)

A sealed tube was charged with a 50% solution of propylphosphonic anhydride in EtOAc (90 mg, 0.14 mmol), MeCN (1.2 mL), triethylamine (66 µL, 0.47 mmol) and 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid (50 mg, 0.12 mmol). The reaction was stirred at room temperature for 30 min and then methylamine hydrochloride (8 mg, 0.1 mmol) was added. The reaction mixture was stirred for a further 60 h. The reaction mixture was diluted with EtOAc. The organic phase was washed with 1M HCl$_{(aq)}$ and brine and then dried (MgSO$_4$), filtered and concentrated. The crude product was purified by automated reverse phase HPLC (low pH Method A) with subsequent purification by silica chromatography, using 0-10% MeOH in DCM as eluent, to afford the title compound as a brown solid (15 mg, 28%).

Example 163

3-cyclopentyl-N-[9-ethynyl-4-oxo-3-(trifluoromethyl)-2,5,7-triazatricyclo[6.4.0.0$^{2,6}$]dodeca-1(12),6,8,10-tetraen-3-yl]propanamide (ABR 239986)

To a stirred solution of 3-cyclopentyl-N-[4-oxo-3-(trifluoromethyl)-9-{2-[tris(propan-2-yl)silyl]ethynyl}-2,5,7-triazatricyclo[6.4.0.0$^{2,6}$]dodeca-1(12),6,8,10-tetraen-3-yl]propanamide (100 mg, 0.18 mmol) in THF (1 mL), at 0° C. under nitrogen, was added 1M TBAF in THF (232 µL, 0.23 mmol). The reaction was stirred at room temperature for 10 min. The reaction was cooled to 0° C. and re-treated with 1M TBAF in THF (232 µL, 0.23 mmol). The reaction was stirred at room temperature for 1 h and then concentrated. The residue was dissolved in DCM (10 mL), washed with water (5 mL) and brine (5 mL) and then dried (Na$_2$SO$_4$), filtered and concentrated. The crude product was purified by silica chromatography, using 0-2% MeOH in DCM as eluent, with subsequent purification by automated reverse phase HPLC (low pH Method A) to afford the title compound as a brown solid (22 mg, 31%).

Example 164

3-cyclopentyl-N-[4-oxo-9-(trifluoromethoxy)-3-(trifluoromethyl)-2,5,7-triazatricyclo[6.4.0.0$^{2,6}$]dodeca-1(12),6,8,10-tetraen-3-yl]propanamide (ABR 239991)

To a stirred solution of 3-cyclopentylpropanamide (98 mg, 0.69 mmol) in anhydrous DCM (10 mL) was added methyl 3,3,3-trifluoro-2-oxopropanoate (141 µL, 1.38 mmol) followed by pyridine (56 µL, 0.69 mmol) at room temperature under nitrogen. The reaction mixture was stirred at room temperature for 2 h. Thionyl chloride (50 µL, 0.69 mmol) was added at 0° C. and the reaction mixture was then stirred at 0° C. for 1 h. The reaction mixture was concentrated and the residue filtered through a short pad of silica, eluting with DCM, under nitrogen. The filtrate was concentrated and the acyl intermediate that remained was dissolved in DMF (5 mL) under nitrogen. The solution of acyl intermediate was added to a solution of 4-(trifluoromethoxy)-1H-1,3-benzodiazol-2-amine (125 mg, 0.58 mmol) in DMF (10 mL) followed by triethylamine (230 µL, 1.73 mmol). The reaction mixture was stirred at room temperature for 18 h and was then concentrated. The residue was diluted with EtOAc (50 mL) and washed with saturated citric acid$_{(aq)}$ (30 mL). The aqueous phase was extracted with EtOAc (50 mL). The combined organic extracts were washed with brine (2×15 mL), dried (MgSO$_4$), filtered, and concentrated. The crude product was triturated in DCM. A portion of this material underwent subsequent purification by automated reverse phase HPLC (low pH Method A) to afford the title compound as a white solid (50 mg).

Example 165

3-cyclopentyl-N-[9-cyclopropanesulfonamido-4-oxo-3-(trifluoromethyl)-2,5,7-triazatricyclo[6.4.0.0$^{2,6}$]dodeca-1(12),6,8,10-tetraen-3-yl]propanamide (ABR 239995)

To a solution of 3-cyclopentyl-N-[9-iodo-4-oxo-3-(trifluoromethyl)-2,5,7-triazatricyclo[6.4.0.0$^{2,6}$]dodeca-1(12),6,8,10-tetraen-3-yl]propanamide (150 mg, 0.30 mmol) in 2-methyltetrahydrofuran (3 mL), in a sealed tube, was added cyclopropylsulfonamide (43 mg, 0.36 mmol) followed by K$_2$CO$_3$ (82 mg, 0.59 mmol). The resulting suspension was de-gassed with nitrogen and then di-tert-butyl[2',4',6'-tri(propan-2-yl)biphenyl-2-yl]phosphane (3 mg, 0.01 mmol) was added followed by bis(chloro(prop-2-en-1-yl)palladium) (7 mg, 0.02 mmol). The reaction was de-gassed with nitrogen, sealed and stirred at 80° C. for 3 h. Additional di-tert-butyl[2',4',6'-tri(propan-2-yl)biphenyl-2-yl]phosphane (3 mg, 0.01 mmol) and bis(chloro(prop-2-en-1-yl) palladium) (7 mg, 0.02 mmol) were added. The reaction mixture was de-gassed and stirred for a further 16 h at 80° C. The reaction was then concentrated. The residue was dissolved in EtOAc (30 mL) and washed with 1M HCl$_{(aq)}$ (30 mL), water (2×30 mL) and brine (2×30 mL). The combined aqueous washings were extracted with EtOAc (30 mL). The combined organic extracts were washed with brine (30 mL), dried (MgSO$_4$), filtered and concentrated. The crude product was purified by automated reverse phase HPLC (low pH Method A) to afford the title compound as a white solid (24 mg, 16%).

Example 166

3-(3-cyclopentylpropanamido)-N-methanesulfonyl-4-oxo-3-(trifluoromethyl)-2,5,7-triazatricyclo[6.4.0.0$^{2,6}$]dodeca-1(12),6,8,10-tetraene-9-carboxamide (ABR 239996)

To a stirred solution of methanesulfonamide (114 mg, 1.2 mmol) in DMF (10 mL), at 0° C. under nitrogen, was added sodium hydride (60%, 48 mg, 1.2 mmol). After stiffing at 0° C. for 15 min a solution of phenyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (150 mg, 0.3 mmol) in DMF (2 mL) was added. The reaction mixture was allowed to warm to room temperature and was then heated at 50° C. After 1 h the reaction mixture was cooled to 0° C. and quenched with saturated NH$_4$Cl$_{(aq)}$. The reaction mixture was concentrated. The residue was dissolved in EtOAc (50 mL), washed with water (3×25 mL) and brine (2×25 mL), dried (MgSO$_4$), filtered and concentrated. The crude product was purified by automated reverse phase HPLC (low pH Method A) to afford the title compound as a white solid (19 mg, 13%)

Example 167

3-cyclopentyl-N-[9-methanesulfonamido-4-oxo-3-(trifluoromethyl)-2,5,7-triazatricyclo[6.4.0.0$^{2,6}$]dodeca-1(12),6,8,10-tetraen-3-yl]propanamide (ABR 239999)

A stirred suspension of N-[9-bromo-4-oxo-3-(trifluoromethyl)-2,5,7-triazatricyclo[6.4.0.0$^{2,6}$]dodeca-1(12),6,8,10- tetraen-3-yl]-3-cyclopentylpropanamide (200 mg, 0.44 mmol), methanesulfonamide (50 mg, 0.52 mmol), di-tert-butyl[2',4',6'-tri(propan-2-yl)biphenyl-2-yl]phosphane (2 mg, 4 ☐mol), bis(chloro(prop-2-en-1-yl)palladium) (5 mg, 13 ☐mol) and $K_2CO_3$ (120 mg, 0.87 mmol) in de-gassed 2-methyltetrahydrofuran (3 mL) was heated at 80° C. for 5 h. The reaction was re-treated with methanesulfonamide (50 mg, 0.52 mmol), di-tert-butyl[2',4',6'-tri(propan-2-yl)biphenyl-2-yl]phosphane (2 mg, 4 ☐mol) and bis(chloro(prop-2-en-1-yl)palladium) (5 mg, 13 ☐mol), de-gassed and heated at 80° C. for 18 h. The reaction was diluted with EtOAc (15 mL) and washed with 1M $HCl_{(aq)}$ (15 mL). The aqueous phase was extracted with EtOAc (2×15 mL). The combined organic extracts were washed with brine (30 mL), dried ($Na_2SO_4$), filtered and concentrated. The crude product was purified by automated reverse phase HPLC (low pH Method A) to afford the title compound as a white solid (22 mg, 11%).

Example 168

N-[9-bromo-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]-1,3-thiazole-4-carboxamide (ABR 240004)

To a stirred solution of 2-bromo-1,3-thiazole-4-carboxamide (2.93 g, 14.2 mmol) in DMF (80 mL) was added methyl 3,3,3-trifluoro-2-oxopropanoate (4.42 g, 28.3 mmol) followed by pyridine (1.14 mL, 14.2 mmol) under nitrogen. The reaction was stirred at room temperature for 16 h. Additional methyl 3,3,3-trifluoro-2-oxopropanoate (4.42 g, 28.3 mmol) was added and the reaction was stirred at a further 4 h. Thionyl chloride (1.03 mL, 14.2 mmol) was added at 0° C. The reaction was stirred for 2 h at 0° C. and then concentrated. The residue was filtered through a short pad of silica, eluting with DCM, under nitrogen. The filtrate was concentrated, and the acyl intermediate that remained was dissolved in DMF (10 mL) under nitrogen. The solution of acyl intermediate was added to a solution of 4-bromo-1H-1,3-benzodiazol-2-amine (2.50 g, 11.8 mmol) in DMF (40 mL) followed by triethylamine (1.88 mL, 14.2 mmol). The reaction mixture was stirred for a further 2 h and then concentrated. The residue was dissolved in EtOAc (200 mL), washed with 10% citric acid$_{(aq)}$ (2×100 mL), water (2×100 mL) and brine (2×100 mL) and then dried ($MgSO_4$), filtered and concentrated. The crude product was purified by trituration in DCM to afford a mixture of 2-bromo-N-[9-bromo-4-oxo-3-(trifluoromethyl)-2,5,7-triazatricyclo [6.4.0.0$^{2,6}$]dodeca-1(12),6,8,10-tetraen-3-yl]-1,3-thiazole-4-carboxamide and N-[9-bromo-4-oxo-3-(trifluoromethyl)-2,5,7-triazatricyclo[6.4.0.0$^{2,6}$]dodeca-1(12),6,8,10-tetraen-3-yl]-2-chloro-1,3-thiazole-4-carboxamide (3.70 g).

A sealed tube was charged with a portion of the mixture of 2-bromo-N-[9-bromo-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide and N-[9-bromo-4-oxo-3-(trifluoromethyl)-2,5,7-triazatricyclo[6.4.0.0$^{2,6}$]dodeca-1(12),6,8,10-tetraen-3-yl]-2-chloro-1,3-thiazole-4-carboxamide (0.40 g), $K_2CO_3$ (0.53 g, 3.8 mmol), 2-methoxyethan-1-amine (327 µL, 3.81 mmol) and dioxane (5 mL). Initially, the reaction was heated at 130° C. for 3 h. The reaction was then heated at 130° C. for a further 9 h. During this period, additional 2-methoxyethan-1-amine (982 µL, 11.4 mmol) and $K_2CO_3$ (1.58 g, 11.4 mmol) were added portionwise with the reaction at room temperature during retreatment. The reaction mixture was then heated at 130° C. for 16 h, without further re-treatment, and then concentrated. The residue was dissolved in EtOAc (50 mL) and washed with saturated $NH_4Cl_{(aq)}$ (50 mL), water (50 mL) and brine (50 mL). The combined aqueous washings were extracted with EtOAc (25 mL) and these organic extracts washed with brine (50 mL). The combined organic extracts were dried ($MgSO_4$), filtered and concentrated. The crude product was purified by automated reverse phase HPLC (low pH Method A) to afford the title compound as a yellow solid (130 mg).

Example 169

N-[9-acetyl-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]-1,3-thiazole-4-carboxamide (ABR 240005)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]-1,3-thiazole-4-carboxamide (110 mg, 0.21 mmol), palladium(II) acetate (2.4 mg, 0.01 mmol), propane-1,3-diylbis(diphenylphosphane) (8.7 mg, 0.02 mmol), $K_2CO_3$ (41 mg, 0.30 mmol), 1-(ethenyloxy)butane (138 µL, 1.06 mmol) and de-gassed DMF/water (4:1, 1.3 mL), under nitrogen. The reaction was stirred at 100° C. for 3 h and then concentrated. The residue was dissolved in THF (20 mL) and 1M $HCl_{(aq)}$ (5 mL) was added. The reaction was stirred at room temperature for 1 h and then diluted with EtOAc (25 mL) and washed with water (25 mL). The organic phase was washed with 1M $HCl_{(aq)}$ (25 mL), water (25 mL) and brine (25 mL) and then dried ($MgSO_4$), filtered and concentrated. The crude product was purified by automated reverse phase HPLC (low pH Method A) to afford the title compound as a white solid (47 mg, 46%).

Example 170

3-(3,3-difluoropyrrolidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239907)

To a solution of N-[10,11-dimethyl-4-oxo-3-(trifluoromethyl)-2,5,7-triazatricyclo[6.4.0.0$^{2,6}$]dodeca-1(12),6,8,10-tetraen-3-yl]prop-2-enamide (125 mg, 0.37 mmol) in MeCN (10 mL), in a sealed tube, was added 3,3-difluoropyrrolidine hydrochloride (69 mg, 0.48 mmol), silica (18 mg) and triethylamine (98 µL, 0.74 mmol). The reaction was heated at 80° C. for 3 h. The silica was removed by filtration and the filtrate was concentrated. The crude product was purified by automated reverse phase HPLC (low pH Method A) to afford the title compound as a white solid (42 mg, 26%).

Example 171

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(3-fluoroazetidin-1-yl)propanamide (ABR 239909)

The procedure for the preparation of 3-(3,3-difluoropyrrolidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide was used, except that 3-fluoroazetidine hydrochloride was used instead of 3,3-difluoropyrrolidine hydrochloride (61%).

Example 172

3-(3,3-difluoropiperidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239911)

The procedure for the preparation of 3-(3,3-difluoropyrrolidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide was used, except that 3,3-difluoropiperidine hydrochloride was used instead of 3,3-difluoropyrrolidine hydrochloride (13%).

Example 173

N-[9-acetyl-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239928)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (500 mg, 1.03 mmol), palladium(II) acetate (7 mg, 0.03 mmol), propane-1,3-diylbis(diphenylphosphane) (27 mg, 0.06 mmol), K$_2$CO$_3$ (184 mg, 1.33 mmol), 1-(ethenyloxy)butane (667 µL, 5.13 mmol) and de-gassed DMF/water (4:1, 4 mL), under nitrogen. The reaction was stirred at 100° C. for 3 h. Additional palladium(II) acetate (7 mg, 0.03 mmol), propane-1,3-diylbis(diphenylphosphane) (27 mg, 0.06 mmol) and 1-(ethenyloxy)butane (667 µL, 5.13 mmol) were added. The reaction was heated at 100° C. for a further 13 h and then concentrated. The residue was dissolved in THF (25 mL) and 1M HCl$_{(aq)}$ (10 mL) was added. The reaction was stirred at room temperature for 3 h and then diluted with EtOAc (100 mL). The aqueous phase was extracted with EtOAc (2×50 mL). The combined organic extracts were washed with brine (50 mL), dried (MgSO$_4$), filtered and concentrated. The crude product was purified by silica chromatography, using 0-5% MeOH in DCM as eluent, and subsequent trituration in DCM to afford the title compound as a brown solid (160 mg, 35%).

Example 174

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide (ABR 239987)

To a stirred solution of 2-methoxypyridine-3-carboxamide, available via a literature method: PCT Int. Appl., 2010101949; (300 mg, 1.97 mmol) in DMF (5 mL) was added methyl 3,3,3-trifluoro-2-oxopropanoate (0.24 mL, 2.4 mmol) followed by pyridine (0.16 mL, 2.0 mmol) under nitrogen. The reaction was stirred at room temperature for 16 h. Thionyl chloride (0.14 mL, 2.0 mmol) was added at 0° C. The reaction was stirred for 1 h at 0° C. and then concentrated. The residue was filtered through a short pad of silica, eluting with DCM, under nitrogen. The filtrate was concentrated and the acyl intermediate that remained was dissolved in DMF (5 mL) under nitrogen. The solution of acyl intermediate was added to a solution of 5,6-dimethyl-1H-benzimidazol-2-amine (254 mg, 1.58 mmol) in DMF (5 mL), followed by triethylamine (0.26 mL, 2.0 mmol). The reaction mixture was stirred for a further 4 h and then concentrated. The residue was dissolved in EtOAc (30 mL), washed with saturated citric acid$_{(aq)}$ (30 mL). The aqueous phase was extracted with EtOAc (2×20 mL). The combined organic extracts were washed with water (2×20 mL) and brine (2×20 mL), and then dried (MgSO$_4$), filtered and concentrated. The crude product was purified by trituration in diethyl ether to afford the title compound as a pink solid (215 mg, 30%).

Example 175

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide (ABR 239989)

To a stirred solution of N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide (235 mg, 0.52 mmol) in DCM (5 mL), at 0° C. under nitrogen, was added 1M tribromoborane in DCM (1.54 mL, 1.54 mmol). The reaction mixture was allowed to warm to room temperature and stirred for 18 h. The reaction was then stirred at room temperature for a further 8 h. During this period, 1M tribromoborane in DCM (3.08 mL, 3.08 mmol) was added portionwise with the reaction at 0° C. during retreatment. The reaction mixture then was cooled to 0° C. and water (10 mL) and 2M HCl$_{(aq)}$ (10 mL) was added. The resulting suspension was stirred at room temperature for 16 h. The precipitate was collected by filtration and washed with DCM (10 mL) and water (10 mL). The crude product was purified by automated reverse phase HPLC (low pH Method A) to afford the title compound as a white solid (80 mg, 42%).

Example 176

N-[11-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239914)

To a solution of 3-cyclopentyl-N-[4-oxo-3-(trifluoromethyl)-2,5,7-triazatricyclo[6.4.0.0$^{2,6}$]dodeca-1(12),6,8,10-tetraen-3-yl]propanamide (2.5 g, 6.6 mmol) in DCM (250 mL) was added NBS (1.4 g, 7.9 mmol). The reaction mixture was stirred at room temperature for 5 h and then concentrated. The residue was dissolved in EtOAc (250 mL), washed with water (2×250 mL) and brine (2×150 mL), dried (MgSO$_4$), filtered and concentrated. The crude product was purified by silica chromatography, using 0-10% MeOH in DCM as eluent, and subsequent automated reverse phase HPLC (low pH Method A) to afford the title compound as a yellow solid (1.2 g, 40%).

Example 177

N-[10-bromo-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239927)

To a stirred solution of 3-cyclopentylpropanamide (368 mg, 2.61 mmol) in DMF (10 mL) was added methyl 3,3,3-trifluoro-2-oxopropanoate (0.40 mL, 3.9 mmol) followed by pyridine (0.21 mL, 2.6 mmol), under nitrogen. The reaction was stirred at room temperature for 1.5 h. Thionyl chloride (0.19 mL, 2.6 mmol) was added at 0° C. and the reaction mixture was then stirred for 1.5 h at 0° C. The reaction mixture was concentrated and filtered through a short pad of silica, eluting with DCM, under nitrogen. The filtrate was concentrated, and the acyl intermediate that remained was dissolved in DMF (5 mL) under nitrogen. The solution of acyl intermediate was added to a solution of 5-bromo-4-fluoro-1H-1,3-benzodiazol-2-amine (500 mg, 2.17 mmol) in DMF (10 mL) followed by triethylamine (0.35 mL, 2.6 mmol). The reaction mixture was stirred for 2 h and then concentrated. The residue was dissolved in EtOAc (20 mL) washed with 10% citric acid$_{(aq)}$ (20 mL). The aqueous layer was extracted with EtOAc (2×20 mL). The combined organic extracts were washed with 10% citric acid$_{(aq)}$ (2×20 mL) and brine (2×20 mL) and then dried (MgSO$_4$), filtered and concentrated. The crude product was triturated in DCM to give the title compound as a brown solid (401 mg, 39%).

Example 178

N-[9-bromo-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239933)

To a solution of 3-cyclopentylpropanamide (0.44 g, 3.1 mmol) in anhydrous DCM (17 mL) was added pyridine (250 µL, 3.10 mmol) followed by methyl 3,3,3-trifluoro-2-oxopropanoate (967 mg, 6.20 mmol) under nitrogen. The reaction was stirred at room temperature for 2 h. Thionyl chloride (245 µL, 3.10 mmol) was added at 0° C. The reaction mixture was stirred at 0° C. for 1 h and then filtered through a short pad of silica, eluting with DCM, under nitrogen. The filtrate was concentrated, and the acyl intermediate that remained was dissolved in DMF (14 mL) under nitrogen. A solution of 4-bromo-5-methoxy-1H-1,3-benzodiazol-2-amine (625 mg, 2.6 mmol) in DMF (3 mL) was added followed by triethylamine (432 µL, 3.1 mmol). The reaction was stirred for 16 h before being concentrated. The residue was dissolved in EtOAc and washed with brine (4×), dried (MgSO$_4$), filtered and concentrated. The crude product was purified by trituration in DCM to afford the title compound as a yellow solid (0.76 g, 60%).

Example 179

3-cyclopentyl-N-[9-fluoro-10-(1-hydroxyethyl)-4-oxo-3-(trifluoromethyl)-2,5,7-triazatricyclo[6.4.0.0$^{2,6}$]dodeca-1(12),6,8,10-tetraen-3-yl]propanamide (ABR 239937)

A sealed tube was charged with N-[10-bromo-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (156 mg, 0.30 mmol), palladium(II) acetate (2 mg, 0.01 mmol), propane-1,3-diylbis(diphenylphosphane) (8 mg, 0.02 mmol), K$_2$CO$_3$ (54 mg, 0.39 mmol), 1-(ethenyloxy)butane (196 µl, 1.51 mmol) and de-gassed DMF/water (3:1, 4 mL), under nitrogen. The reaction was stirred at 100° C. for 3 h. Additional palladium(II) acetate (2 mg, 0.01 mmol), propane-1,3-diylbis(diphenylphosphane) (8 mg, 0.02 mmol), K$_2$CO$_3$ (27 mg, 0.2 mmol) and 1-(ethenyloxy)butane (78 µl, 0.6 mmol) were added. The reaction was de-gassed and stirred at 100° C. for a further 16 h. The reaction was concentrated. The resulting residue was dissolved in EtOAc (10 mL) and washed with brine (10 mL). The aqueous phase was extracted with EtOAc (2×15 mL). The combined organic extracts were washed with brine (2×15 mL), dried (MgSO$_4$), filtered and concentrated to afford N-[10-acetyl-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide as a brown solid (152 mg).

To a stirred solution of N-[10-acetyl-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (25%, 152 mg, 0.09 mmol) in anhydrous MeOH (3 mL), at 0° C. under nitrogen, was added sodium tetrahydroborate (33 mg, 0.86 mmol). The resulting solution was allowed to warm to room temperature over 16 h. Additional sodium tetrahydroborate (49 mg, 1.3 mmol) was added at 0° C. The reaction was allowed to warm to room temperature over 4 h and was then concentrated. The residue was dissolved in EtOAc (10 mL) and washed with brine (10 mL). The aqueous phase was extracted with EtOAc (2×10 mL). The combined organic extracts were washed with brine (2×10 mL), dried (MgSO$_4$), filtered and concentrated. The crude product was purified by silica chromatography, using 0-50% MeOH in DCM as eluent, with subsequent purification by automated reverse phase HPLC (high pH) to afford the title compound as a white solid (8 mg, 19%).

Example 180

N-[9-acetyl-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239946)

A sealed tube was charged with N-[9-bromo-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (2.00 g, 0.40 mmol), Pd(PPh$_3$)$_2$Cl$_2$ (29 mg, 0.04 mmol), tributyl(1-ethoxyethenyl)stannane (275 µL, 0.80 mmol) and toluene (2 mL) under nitrogen. Initially, the reaction was stirred at 110° C. for 16 h. The reaction was then heated for a further 30 h. During this period, additional Pd(PPh$_3$)$_2$Cl$_2$ (44 mg, 0.06 mmol) was added portionwise with the reaction at room temperature during retreatment. The reaction mixture was diluted with 2M HCl$_{(aq)}$ (2 mL) and was stirred at room temperature for 1 h. EtOAc was added and the resulting suspension was filtered through Celite™. The organic phase of the filtrate was washed with brine, dried (MgSO$_4$), filtered and concentrated. The crude product was purified initially by automated reverse phase HPLC (low pH Method A). Subsequent purification by silica chromatography, using 0-50% DCM/MeOH/AcOH/H$_2$O (90:18:3:2) in DCM as eluent, and then trituration in cold DCM afforded the title compound as a white solid (33 mg, 18%).

Example 181

N-[9-bromo-11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239916)

To a stirred solution of 3-cyclopentylpropanamide (0.61 g, 4.29 mmol) in anhydrous DCM (24 mL) was added pyridine (346 µL, 4.29 mmol) followed by methyl 3,3,3-trifluoro-2-oxopropanoate (1.34 g, 8.58 mmol), under nitrogen. The reaction mixture was stirred for 2 h. Thionyl chloride (311 µL, 4.29 mmol) was added at 0° C. and the reaction mixture was then stirred for 1 h at 0° C. The reaction mixture was filtered through a short pad of silica, eluting with DCM, under nitrogen. The filtrate was concentrated, and the acyl intermediate that remained was dissolved in DMF (20 mL) under nitrogen. A solution of 4-bromo-6-chloro-1H-1,3-benzodiazol-2-amine (881 mg, 3.57 mmol) in DMF (4 mL) was added followed by triethylamine (343 µL, 2.46 mmol). The reaction mixture was stirred at room temperature for 16 h and then concentrated. The residue was diluted with EtOAc and washed with brine (4×). The organic phase was dried (MgSO$_4$), filtered and concentrated. The crude product was triturated with DCM to afford the title compound as a yellow solid (884 mg, 50%).

Example 182

N-[9-acetyl-11-chloro-4-oxo-3-(trifluoromethyl)-2,5, 7-triazatricyclo[6.4.0.0$^{2,6}$]dodeca-1(12),6,8,10-tetraen-3-yl]-3-cyclopentylpropanamide (ABR 239936)

The procedure for the preparation of N-[9-acetyl-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide was used, except that N-[9-bromo-11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide was used instead of N-[9-bromo-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide. No re-treatment was necessary. The crude product was purified by automated reverse phase HPLC (low pH Method A) (23%).

Example 183

N-[11-bromo-9-fluoro-4-oxo-3-(trifluoromethyl)-2, 5,7-triazatricyclo[6.4.0.0$^{2,6}$]dodeca-1(12),6,8,10-tetraen-3-yl]-3-cyclopentylpropanamide (ABR 239926)

To a stirred solution of 3-cyclopentylpropanamide (1.01 g, 7.17 mmol) in DMF (20 mL) was added methyl 3,3,3-trifluoro-2-oxopropanoate (878 µL, 8.61 mmol) followed by pyridine (578 µL, 7.17 mmol), under nitrogen. The reaction was stirred at room temperature for 16 h. Thionyl chloride (521 µL, 7.17 mmol) was added at 0° C. and the reaction mixture was then stirred for 1 h at 0° C. The reaction mixture was concentrated and filtered through a short pad of silica, eluting with DCM, under nitrogen. The filtrate was concentrated, and the acyl intermediate that remained was dissolved in DMF (20 mL) under nitrogen. A solution of 6-bromo-4-fluoro-1H-1,3-benzodiazol-2-amine (1.32 g, 5.74 mmol) in DMF (20 mL) was added followed by triethylamine (1.15 mL, 8.61 mmol). The reaction mixture was stirred at room temperature for 2 h and then concentrated. The residue was dissolved in EtOAc (200 mL), washed with water (3×100 mL) and brine (100 mL) and then dried (Na$_2$SO$_4$), filtered and concentrated. The crude product was triturated in DCM to give the title compound as a white solid (1.20 g, 44%).

Example 184

N-[11-acetyl-4-oxo-3,9-bis(trifluoromethyl)-2,5,7-triazatricyclo[6.4.0.0$^{2,6}$]dodeca-1(12),6,8,10-tetraen-3-yl]-3-cyclopentylpropanamide (ABR 239942)

A sealed tube was charged with N-[11-bromo-4-oxo-3,9-bis(trifluoromethyl)-2,5,7-triazatricyclo[6.4.0.0$^{2,6}$]dodeca-1(12),6,8,10-tetraen-3-yl]-3-cyclopentylpropanamide (150 mg, 0.28 mmol), palladium(II) acetate (2 mg, 8.5 µmop, propane-1,3-diylbis(diphenylphosphane) (8 mg, 0.02 mmol), K$_2$CO$_3$ (51 mg, 0.37 mmol), 1-(ethenyloxy)butane (185 µL, 1.42 mmol) and de-gassed DMF/water (3:1, 4 mL), under nitrogen. Initially, the reaction was stirred at 100° C. for 4 h. The reaction was then heated for a further 4 h. During this period, additional palladium(II) acetate (2 mg, 8.5 µmop, propane-1,3-diylbis(diphenylphosphane) (8 mg, 0.02 mmol) and 1-(ethenyloxy)butane (185 µL, 1.42 mmol) were added portionwise with the reaction at room temperature during retreatment. The reaction was allowed to cool to room temperature and was then concentrated. The residue was dissolved in THF (15 mL) and 1M HCl$_{(aq)}$ (4 mL) was added. The reaction was stirred at room temperature for 20 min and was then concentrated. The residue was dissolved in EtOAc (10 mL) and washed with brine (10 mL). The aqueous phase was extracted with EtOAc (15 mL). The combined organic extracts were washed with brine (15 mL), dried (MgSO$_4$), filtered and concentrated. The crude product was purified by reverse phase C18 chromatography, using acidic eluent. Further purification by trituration in DCM and subsequent automated reverse phase HPLC (high pH) afforded the title compound as a white solid (29 mg, 21%).

Example 185

N-[11-chloro-10-methoxy-4-oxo-3-(trifluoromethyl)-2,5,7-triazatricyclo[6.4.0.0$^{2,6}$]dodeca-1(12),6, 8,10-tetraen-3-yl]-3-cyclopentylpropanamide and N-[10-chloro-11-methoxy-4-oxo-3-(trifluoromethyl)-2,5,7-triazatricyclo[6.4.0.0$^{2,6}$]dodeca-1(12),6, 8,10-tetraen-3-yl]-3-cyclopentylpropanamide (ABR 239941)

To a stirred solution of 3-cyclopentylpropanamide (128 mg, 0.90 mmol) in DCM (1.5 mL) was added methyl 3,3,3-trifluoro-2-oxopropanoate (138 µL, 1.35 mmol) followed by pyridine (73 µL, 0.9 mmol) under nitrogen. The reaction was stirred for 1 h at room temperature. Thionyl chloride (66 µL, 0.90 mmol) was added at 0° C. The reaction was stirred for 1 h at 0° C. and then filtered through a short pad of silica, eluting with DCM, under nitrogen. The filtrate was concentrated, and the acyl intermediate that remained was dissolved in DMF (2 mL) under nitrogen. The solution of acyl intermediate was added to a solution of 6-chloro-5-methoxy-1H-1,3-benzodiazol-2-amine (150 mg, 0.75 mmol) in DMF (2 mL) followed by triethylamine (120 µL, 0.90 mmol). The reaction mixture was stirred for a further 4 h and then concentrated. The residue was dissolved in EtOAc (15 mL) and washed with saturated citric acid$_{(aq)}$ (15 mL). The aqueous phase was extracted with EtOAc (15 mL). The combined organic extracts were washed with brine (2×15 mL) and then dried (MgSO$_4$), filtered and concentrated to afford the title compound as a 1:1 mixture of regioisomers as a brown solid (52 mg, 15%).

Example 186

3-cyclopentyl-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239731)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (50 mg, 0.11 mmol), (4-methoxyphenyl)boronic acid (21 mg, 0.14 mmol), Na$_2$CO$_3$ (21 mg, 0.2 mmol), water (0.4 mL), DME (1.4 mL), and EtOH (0.6 mL). The solution was de-gassed with nitrogen. Pd(PPh$_3$)$_4$ (7 mg, 0.01 mmol) was added, the solution was de-gassed with nitrogen and the tube was sealed. The reaction was stirred at 100° C. for 6 h. The reaction mixture was diluted with EtOAc (10 mL) and washed with water (5 mL). The aqueous phase was extracted with EtOAc (3×5 mL). The combined organic extracts were washed with brine (2×15 mL), dried (MgSO$_4$), filtered and concentrated. The crude product was purified by automated reverse phase HPLC (low pH Method A) to afford the title compound as a white solid (18 mg, 34%).

Example 187

3-cyclopentyl-N-[9-(1-methyl-1H-pyrazol-4-yl)-4-oxo-3-(trifluoromethyl)-2,5,7-triazatricyclo[6.4.0.0$^{2,6}$]dodeca-1(12),6,8,10-tetraen-3-yl]propanamide (ABR 239732)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (1-methyl-1H-pyrazol-4-yl)boronic acid (39 mg, 0.3 mmol), Na$_2$CO$_3$ (42 mg, 0.39 mmol), water (0.8 mL), DME (2.8 mL), and EtOH (1.2 mL). The solution was de-gassed with nitrogen. Pd(PPh$_3$)$_4$ (25 mg, 0.02 mmol) was added, the solution was de-gassed with nitrogen and the tube was sealed. The reaction was stirred at 100° C. for 2 h. The reaction mixture was diluted with EtOAc (10 mL) and washed with water (10 mL). The aqueous phase was extracted with EtOAc (2×10 mL). The combined organic extracts were washed with brine (2×10 mL), dried (MgSO$_4$), filtered and concentrated. The crude product was purified by automated reverse phase HPLC (low pH Method A) to afford the title compound as a white solid (42 mg, 41%).

Example 188

3-cyclopentyl-N-[9-(6-methoxypyridin-3-yl)-4-oxo-3-(trifluoromethyl)-2,5,7-triazatricyclo[6.4.0.0$^{2,6}$]dodeca-1(12),6,8,10-tetraen-3-yl]propanamide (ABR 239944)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (160 mg, 0.15 mmol), (6-methoxypyridin-3-yl)boronic acid (66 mg, 0.44 mmol), Na$_2$CO$_3$ (66 mg, 0.69 mmol), water (1.8 mL), DME (6.0 mL), and EtOH (2.5 mL). The solution was de-gassed with nitrogen. Pd(PPh$_3$)$_4$ (40 mg, 0.04 mmol) was added, the solution was de-gassed with nitrogen and the tube was sealed. The reaction was stirred at 100° C. for 2 h and then concentrated. The residue was dissolved in EtOAc (100 mL), washed with water (50 mL), saturated citric acid$_{(aq)}$ (50 mL) and brine (2×10 mL). The organic phase was dried (MgSO$_4$), filtered and concentrated. The crude product was purified by trituration in DCM and subsequent purification by automated reverse phase HPLC (low pH Method A) to afford the title compound as a white solid (100 mg, 59%).

Example 189

3-cyclopentyl-N-[9-(3-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239948)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (3-methoxyphenyl)boronic acid (46 mg, 0.3 mmol), Na$_2$CO$_3$ (46 mg, 0.44 mmol), water (0.8 mL), DME (2.8 mL), and EtOH (1.2 mL). The solution was de-gassed with nitrogen. Pd(PPh$_3$)$_4$ (13 mg, 0.01 mmol) was added, the solution was de-gassed with nitrogen and the tube was sealed. The reaction was stirred at 100° C. for 16 h. The reaction mixture was concentrated. The residue was dissolved in EtOAc (50 mL), washed with water (25 mL), 1M HCl$_{(aq)}$ (25 mL) and brine (25 mL). The organic phase was dried (MgSO$_4$), filtered and concentrated. The crude product was purified by automated reverse phase HPLC (low pH Method A) to afford the title compound as a yellow solid (44 mg, 42%).

Example 190

3-cyclopentyl-N-[9-(1,3-oxazol-2-yl)-4-oxo-3-(trifluoromethyl)-2,5,7-triazatricyclo[6.4.0.0$^{2,6}$]dodeca-1(12),6,8,10-tetraen-3-yl]propanamide (ABR 239953)

To a suspension of N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (200 mg, 0.44 mmol), sodium tert-butoxide (84 mg, 0.87 mmol) and Pd(PPh$_3$)$_4$ (25 mg, 0.02 mmol) in de-gassed dioxane (3 mL) was added 1,3-oxazole (43 μL, 0.65 mmol). The reaction was flushed with nitrogen, sealed and heated at 100° C. for 4 h. The reaction was retreated with sodium tert-butoxide (84 mg, 0.87 mmol), Pd(PPh$_3$)$_4$ (25 mg, 0.02 mmol) and 1,3-oxazole (43 μL, 0.65 mmol), de-gassed and heated for a further 3.5 h at 100° C. The reaction was diluted with EtOAc (30 mL) and washed with water (15 mL) and brine (15 mL). The organic phase was dried (Na$_2$SO$_4$), filtered and concentrated. The crude product was purified by automated reverse phase HPLC (low pH Method A) to afford the title compound as a white solid (83 mg, 43%).

Example 191

N-[9-(4-tert-butylphenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239954)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (50 mg, 0.11 mmol), (4-tert-butylphenyl)boronic acid (24 mg, 0.14 mmol), Na$_2$CO$_3$ (21 mg, 0.20 mmol), water (0.90 mL), DME (3.00 mL), and EtOH (1.25 mL). The solution was de-gassed with nitrogen. Pd(PPh$_3$)$_4$ (13 mg, 0.01 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The residue was dissolved in EtOAc (20 mL), washed with water (30 mL), saturated citric acid$_{(aq)}$ (30 mL) and brine (30 mL) and then dried (MgSO$_4$), filtered and concentrated. The crude product was purified by silica chromatography, using 0-100% EtOAc in heptane as eluent, to afford the title compound as a white solid (39 mg, 70%).

Example 192

N-[9-(4-cyanophenyl)-4-oxo-3-(trifluoromethyl)-2,5, 7-triazatricyclo[6.4.0.0$^{2,6}$]dodeca-1(12),6,8,10-tetraen-3-yl]-3-cyclopentylpropanamide (ABR 239956)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (50 mg, 0.11 mmol), (4-cyanophenyl)boronic acid (21 mg, 0.14 mmol), Na$_2$CO$_3$ (21 mg, 0.20 mmol), water (0.90 mL), DME (3.00 mL), and EtOH (1.25 mL). The solution was de-gassed with nitrogen. Pd(PPh$_3$)$_4$ (13 mg, 0.01 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The residue was dissolved in EtOAc (20 mL), washed with water (30 mL), saturated citric acid$_{(aq)}$ (30 mL) and brine (30 mL) and then dried (MgSO$_4$), filtered and concentrated. The crude product was purified by silica chromatography, using 0-100% EtOAc in heptane as eluent, to afford the title compound as a brown solid (21 mg, 40%).

Example 193

3-cyclopentyl-N-[9-(4-nitrophenyl)-4-oxo-3-(trifluoromethyl)-2,5,7-triazatricyclo[6.4.0.0$^{2,6}$]dodeca-1(12),6,8,10-tetraen-3-yl]propanamide (ABR 239957)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (4-nitrophenyl)boronic acid (46 mg, 0.27 mmol), Na$_2$CO$_3$ (42 mg, 0.39 mmol), water (0.90 mL), DME (3.00 mL), and EtOH (1.25 mL). The solution was de-gassed with nitrogen. Pd(PPh$_3$)$_4$ (25 mg, 0.02 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The residue was dissolved in EtOAc (20 mL), washed with water (30 mL), saturated citric acid$_{(aq)}$ (30 mL) and brine (30 mL) and then dried (MgSO$_4$), filtered and concentrated. The crude product was purified by silica chromatography, using 0-100% EtOAc in heptane as eluent, to afford the title compound as an orange solid (70 mg, 64%).

Example 194

N-[9-(4-aminophenyl)-4-oxo-3-(trifluoromethyl)-2, 5,7-triazatricyclo[6.4.0.0$^{2,6}$]dodeca-1(12),6,8,10-tetraen-3-yl]-3-cyclopentylpropanamide (ABR 239965)

To a stirred solution of 3-cyclopentyl-N-[9-(4-nitrophenyl)-4-oxo-3-(trifluoromethyl)-2,5,7-triazatricyclo[6.4.0.0$^{2,6}$]dodeca-1(12),6,8,10-tetraen-3-yl]propanamide (50 mg, 0.10 mmol) in EtOAc (5 mL) was added tin(II) chloride dihydrate (86 mg, 0.38 mmol). The reaction was heated at 70° C. for 18 h. The reaction was allowed to cool to room temperature, diluted with EtOAc (10 mL) and filtered through Celite™, rinsing with EtOAc (30 mL). The filtrate was concentrated. The crude product was loaded onto an acidic SCX-2 column, washed with 50% MeOH in DCM and then eluted with 3.5M ammonia in MeOH. Subsequent purification by automated reverse phase HPLC (low pH Method A) afforded the title compound as a brown solid (8 mg, 17%).

Example 195

3-cyclopentyl-N-[4-oxo-9-phenyl-3-(trifluoromethyl)-2,5,7-triazatricyclo[6.4.0.0$^{2,6}$]dodeca-1(12),6,8,10-tetraen-3-yl]propanamide (ABR 239967)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (150 mg, 0.32 mmol), phenylboronic acid (55 mg, 0.45 mmol), Na$_2$CO$_3$ (68 mg, 0.64 mmol), water (0.7 mL), DME (1.4 mL), and EtOH (0.6 mL). The solution was de-gassed with nitrogen. Pd(PPh$_3$)$_4$ (37 mg, 0.03 mmol) was added, the solution was de-gassed with nitrogen and the tube was sealed. The reaction was stirred at 100° C. for 3 h. Additional phenylboronic acid (27 mg, 0.22 mmol), Na$_2$CO$_3$ (34 mg, 0.32 mmol) and Pd(PPh$_3$)$_4$ (18 mg, 0.02 mmol) were added and the reaction was stirred at 100° C. for a further 16 h. The reaction mixture was concentrated. The residue was dissolved in EtOAc (25 mL) and washed with brine (25 mL). The aqueous layer was extracted with EtOAc (25 mL). The combined organic extracts were washed with brine (2×50 mL). The organic phase was dried (MgSO$_4$), filtered and concentrated. The crude product was purified by automated reverse phase HPLC (low pH Method A) to afford the title compound as an orange solid (47 mg, 32%).

Example 196

3-cyclopentyl-N-[9-(2-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239970)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (2-methoxyphenyl)boronic acid (46 mg, 0.3 mmol), Na$_2$CO$_3$ (46 mg, 0.44 mmol), water (0.8 mL), DME (2.8 mL), and EtOH (1.2 mL). The solution was de-gassed with nitrogen. Pd(PPh$_3$)$_4$ (13 mg, 0.01 mmol) was added, the solution was de-gassed with nitrogen and the tube was sealed. The reaction was stirred at 100° C. for 16 h. The reaction mixture was concentrated. The residue was dissolved in EtOAc (50 mL), washed with water (25 mL), 1M HCl$_{(aq)}$ (25 mL) and brine (25 mL). The organic phase was dried (MgSO$_4$), filtered and concentrated. The crude product was purified by automated reverse phase HPLC (low pH Method A) to afford the title compound as a white solid (80 mg, 75%).

Example 197

2-hydroxy-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]pyridine-3-carboxamide (ABR 239988)

A sealed tube was charged with N-[9-(4-bromophenyl)-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide (100 mg, 0.22 mmol), (4-methoxyphenyl)boronic acid (47 mg, 0.31 mmol), Na$_2$CO$_3$ (46 mg, 0.44 mmol), water (0.2 mL), DME (2.8 mL), and EtOH (1.2 mL). The solution was de-gassed with nitrogen. Pd(PPh$_3$)$_4$ (13 mg, 0.01 mmol) was added, the solution was de-gassed with nitrogen and the tube was sealed. The reaction was stirred at 100° C. for 4 h. Additional (4-methoxyphenyl)boronic acid (23 mg, 0.15 mmol), Na$_2$CO$_3$ (46 mg, 0.44 mmol) and Pd(PPh$_3$)$_4$ (13 mg, 0.01 mmol) were added and the reaction was stirred at 100° C. for a further 16 h. The reaction mixture was concentrated. The residue was dissolved in EtOAc (25 mL) and washed with water (25 mL). The aqueous phase was extracted with EtOAc (2×20 mL) and IPA/CHCl$_3$ (1:1, 5×20 mL). The combined organic extracts were dried (MgSO$_4$), filtered and concentrated. The crude product was purified by automated reverse phase HPLC (high pH) to afford the title compound as a white solid (24 mg, 22%).

Example 198

3-cyclopentyl-N-[9-(2-hydroxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239978)

To a stirred solution of 3-cyclopentyl-N-[9-(2-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (55 mg, 0.11 mmol) in DCM (10 mL) was added 1M boron tribromide in DCM (0.34 mL, 0.34 mmol) under nitrogen. Initially, the reaction was stirred at room temperature for 1 h. Then the reaction was stirred for a further 4 h. During this period, additional 1M boron tribromide in DCM (1.02 mL, 1.02 mmol) was added portionwise. The reaction was then quenched with water at 0° C. The organic phase was washed with 1M HCl$_{(aq)}$ (25 mL) and water (25 mL), dried (MgSO$_4$), filtered and concentrated. The crude product was purified by automated reverse phase HPLC (low pH Method A) to afford the title compound as a white solid (29 mg, 54%).

Example 199

3-cyclopentyl-N-[4-oxo-9-(1H-1,2,3,4-tetrazol-5-yl)-3-(trifluoromethyl)-2,5,7-triazatricyclo[6.4.0.0$^{2,6}$]dodeca-1(12),6,8,10-tetraen-3-yl]propanamide (ABR 239990)

To a stirred suspension of N-[9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (500 mg, 1.23 mmol) and dibutyl(oxo)stannane (353 µL, 1.23 mmol) in xylene (10 mL), in a sealed tube under nitrogen, was added azido(trimethyl)silane (490 µL, 3.70 mmol). The reaction was heated at 130° C. for 1.5 h. The reaction was diluted with MeOH (10 mL) at room temperature. The reaction was stirred for 2 h and then concentrated. The crude product was purified by silica chromatography, using 0-20% MeOH in DCM as eluent, to afford the title compound as a beige solid (142 mg, 25%).

Example 200

3-[3-(3-cyclopentylpropanamido)-4-oxo-3-(trifluoromethyl)-2,5,7-triazatricyclo[6.4.0.0$^{2,6}$]dodeca-1(12),6,8,10-tetraen-9-yl]benzoic acid (ABR 239992)

To a stirred solution of methyl 3-[3-(3-cyclopentylpropanamido)-4-oxo-3-(trifluoromethyl)-2,5,7-triazatricyclo[6.4.0.0$^{2,6}$]dodeca-1(12),6,8,10-tetraen-9-yl]benzoate (48 mg, 0.09 mmol) in MeOH (3 mL) was added 2M NaOH$_{(aq)}$ (0.28 mL, 0.56 mmol). The reaction mixture was stirred at 50° C. for 4 h and then concentrated. The residue was dissolved in water and acidified using 1M HCl$_{(aq)}$ to pH2. The resulting precipitate was collected by filtration. The crude product was purified by automated reverse phase HPLC (low pH Method A) to afford the title compound as a yellow solid (14 mg, 30%).

Example 201

N-[9-(4-chlorophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 240000)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (4-chlorophenyl)boronic acid (43 mg, 0.27 mmol), Na$_2$CO$_3$ (42 mg, 0.39 mmol), water (0.20 mL), DME (1.00 mL), and EtOH (0.35 mL) and the solution was de-gassed with nitrogen. Pd(PPh$_3$)$_4$ (25 mg, 0.02 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The crude product was purified by automated reverse phase HPLC (low pH Method A) to afford the title compound as a yellow solid (60 mg, 56%).

Example 202

3-cyclopentyl-N-[9-(4-methylphenyl)-4-oxo-3-(trifluoromethyl)-2,5,7-triazatricyclo[6.4.0.0$^{2,6}$]dodeca-1(12),6,8,10-tetraen-3-yl]propanamide (ABR 240001)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (4-methylphenyl)boronic acid (37 mg, 0.27 mmol) Na$_2$CO$_3$ (42 mg, 0.39 mmol), water (0.20 mL), DME (1.00 mL), and EtOH (0.35 mL). The solution was de-gassed with nitrogen. Pd(PPh$_3$)$_4$ (25 mg, 0.02 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The crude product was purified by automated reverse phase HPLC (low pH Method A) to afford the title compound as a yellow solid (50 mg, 49%).

Example 203

3-cyclopentyl-N-[9-(3,4-dichlorophenyl)-4-oxo-3-(trifluoromethyl)-2,5,7-triazatricyclo[6.4.0.0$^{2,6}$]dodeca-1(12),6,8,10-tetraen-3-yl]propanamide (ABR 240002)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), (3,4-dichlorophenyl)boronic acid (52 mg, 0.27 mmol) Na$_2$CO$_3$ (42 mg, 0.39 mmol), water (0.20 mL), DME (1.00 mL), and EtOH (0.35 mL) and the solution was de-gassed with nitrogen. Pd(PPh$_3$)$_4$ (25 mg, 0.02 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The crude product was purified by automated reverse phase HPLC (low pH Method A) to afford the title compound as a white solid (56 mg, 49%).

Example 204

3-cyclopentyl-N-[9-(3,4-dihydro-2H-pyran-5-yl)-4-oxo-3-(trifluoromethyl)-2,5,7-triazatricyclo[6.4.0. 0$^{2,6}$]dodeca-1(12),6,8,10-tetraen-3-yl]propanamide (ABR 239733)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (50 mg, 0.11 mmol), 4-(4,4,5,5-tetramethyl-1,3,2-dioxaborolan-2-yl)-3,6-dihydro-2H-pyran (30 mg, 0.14 mmol), Na$_2$CO$_3$ (21 mg, 0.20 mmol), water (0.4 mL), DME (1.4 mL), and EtOH (0.6 mL). The solution was de-gassed with nitrogen. Pd(PPh$_3$)$_4$ (13 mg, 0.01 mmol) was added, the solution was de-gassed with nitrogen and the tube was sealed. The reaction was stirred at 100° C. for 18 h. The reaction mixture was diluted with EtOAc (10 mL) and washed with water (10 mL). The aqueous phase was extracted with EtOAc (2×10 mL). The combined organic extracts were washed with brine (2×10 mL), dried (MgSO$_4$), filtered and concentrated. The crude product was purified by automated reverse phase HPLC (low pH Method A) to afford the title compound as a brown solid (10 mg, 20%).

Example 205

3-cyclopentyl-N-[10,11-dimethyl-9-(1-methyl-1H-pyrazol-4-yl)-4-oxo-3-(trifluoromethyl)-2,5,7-triazatricyclo[6.4.0.0$^{2,6}$]dodeca-1(12),6,8,10-tetraen-3-yl]propanamide (ABR 239729)

A sealed tube was charged with N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (75 mg, 0.15 mmol), (1-methyl-1H-pyrazol-4-yl)boronic acid (24 mg, 0.19 mmol), Na$_2$CO$_3$ (29 mg, 0.28 mmol), water (0.8 mL), DME (2.8 mL), and EtOH (1.2 mL). The solution was de-gassed with nitrogen. Pd(PPh$_3$)$_4$ (18 mg, 0.02 mmol) was added, the solution was de-gassed with nitrogen and the tube was sealed. The reaction was stirred at 100° C. for 2 h. The reaction mixture was concentrated. The residue was dissolved in EtOAc (100 mL), washed with water (50 mL), saturated citric acid$_{(aq)}$ (50 mL) and brine (50 mL) and then dried (MgSO$_4$), filtered and concentrated. The crude product was purified by automated reverse phase HPLC (low pH Method A) to afford the title compound as a white solid (35 mg, 47%).

Example 206

3-cyclopentyl-N-[10,11-dimethyl-4-oxo-9-(1,2-thiazol-4-yl)-3-(trifluoromethyl)-2,5,7-triazatricyclo[6.4.0.0$^{2,6}$]dodeca-1(12),6,8,10-tetraen-3-yl]propanamide (ABR 239738)

A sealed tube was charged with N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (75 mg, 0.15 mmol), 4-(tetramethyl-1,3,2-dioxaborolan-2-yl)-1,2-thiazole (42 mg, 0.20 mmol), Na$_2$CO$_3$ (29 mg, 0.28 mmol), water (0.8 mL), DME (2.8 mL), and EtOH (1.2 mL). The solution was de-gassed with nitrogen. Pd(PPh$_3$)$_4$ (18 mg, 0.02 mmol) was added, the solution was de-gassed with nitrogen and the tube was sealed. The reaction was stirred at 100° C. for 2 h. The reaction mixture was concentrated. The residue was dissolved in EtOAc (100 mL), washed with water (50 mL), saturated citric acid$_{(aq)}$ (50 mL) and brine (50 mL) and then dried (MgSO$_4$), filtered and concentrated. The crude product was purified by automated reverse phase HPLC (low pH Method A) to afford the title compound as a white solid (29 mg, 38%).

Example 207

3-cyclopentyl-N-[9-(furan-3-yl)-10,11-dimethyl-4-oxo-3-(trifluoromethyl)-2,5,7-triazatricyclo[6.4.0. 0$^{2,6}$]dodeca-1(12),6,8,10-tetraen-3-yl]propanamide (ABR 239739)

A sealed tube was charged with N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (75 mg, 0.15 mmol), (furan-3-yl)boronic acid (22 mg, 0.2 mmol), Na$_2$CO$_3$ (29 mg, 0.28 mmol), water (0.8 mL), DME (2.8 mL), and EtOH (1.2 mL). The solution was de-gassed with nitrogen. Pd(PPh$_3$)$_4$ (18 mg, 0.02 mmol) was added, the solution was de-gassed with nitrogen and the tube was sealed. The reaction was stirred at 100° C. for 2 h. The reaction mixture was concentrated. The residue was dissolved in EtOAc (100 mL), washed with water (50 mL), saturated citric acid$_{(aq)}$ (50 mL) and brine (50 mL) and then dried (MgSO$_4$), filtered and concentrated. The crude product was purified by automated reverse phase HPLC (low pH Method A) to afford the title compound as a white solid (18 mg, 25%).

Example 208

N-[9-(4-methoxyphenyl)-10,11-dimethyl-4-oxo-3-(trifluoromethyl)-2,5,7-triazatricyclo[6.4.0.0$^{2,6}$]dodeca-1(12),6,8,10-tetraen-3-yl]acetamide (ABR 239929)

A sealed tube was charged with N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]acetamide (100 mg, 0.25 mmol), (4-methoxyphenyl)boronic acid (47 mg, 0.31 mmol), Na$_2$CO$_3$ (47 mg, 0.44 mmol), water (0.9 mL), DME (3.0 mL), and EtOH (1.3 mL). The solution was de-gassed with nitrogen. Pd(PPh$_3$)$_4$ (29 mg, 0.03 mmol) was added, the solution was de-gassed with nitrogen and the tube was sealed. The reaction was stirred at 100° C. for 2 h. The reaction mixture was concentrated. The residue was dissolved in EtOAc (100 mL), washed with water (50 mL), saturated citric acid$_{(aq)}$ (50 mL) and brine (50 mL) and then dried (MgSO$_4$), filtered and concentrated. The crude product was purified by automated reverse phase HPLC (low pH Method A) to afford the title compound as a white solid (28 mg, 26%).

Example 209

3-cyclopentyl-N-[9-fluoro-10-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239924)

A sealed tube was charged with N-[10-bromo-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (194 mg, 0.39 mmol), (4-methoxyphenyl)boronic acid (90 mg, 0.59 mmol), Na$_2$CO$_3$ (84 mg, 0.79 mmol), water (0.40 mL), DME (1.50 mL), and EtOH (0.50 mL). The solution was de-gassed with nitrogen. Pd(PPh$_3$)$_4$ (46 mg, 0.04 mmol) was added, the solution was de-gassed with nitrogen and the tube was sealed. The reaction was stirred at 100° C. for 16 h. Additional (4-methoxyphenyl)boronic acid (45 mg, 0.30 mmol), Na$_2$CO$_3$ (42 mg, 0.38 mmol) and Pd(PPh$_3$)$_4$ (23 mg, 0.02 mmol) were added. The solution was de-gassed with nitrogen and the tube was sealed. The reaction was stirred at 100° C. for 3 h. The reaction mixture was concentrated. The residue was dissolved in EtOAc (10 mL) and washed with water (10 mL). The aqueous phase was extracted with EtOAc (2×10 mL). The combined organic extracts were washed with water (15 mL) and brine (2×15 mL) and then dried (MgSO$_4$), filtered and concentrated. The crude product was purified by silica chromatography, using 0-5% MeOH in DCM as eluent, and subsequent trituration in MeOH to afford the title compound as a cream solid (11 mg, 5%).

Example 210

3-cyclopentyl-N-[11-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239923)

A sealed tube was charged with N-[11-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (200 mg, 0.44 mmol), (4-methoxyphenyl)boronic acid (83 mg, 0.54 mmol), Na$_2$CO$_3$ (83 mg, 0.78 mmol), water (1.80 mL), DME (6.0 mL), and EtOH (1.50 mL). The solution was de-gassed with nitrogen. Pd(PPh$_3$)$_4$ (50 mg, 0.04 mmol) was added, the solution was de-gassed with nitrogen and the tube was sealed. The reaction was stirred at 100° C. for 3 h. The reaction mixture was concentrated. The residue was dissolved in EtOAc (100 mL), washed with water (50 mL), saturated citric acid$_{(aq)}$(50 mL), water (50 mL) and brine (50 mL) and then dried (MgSO$_4$), filtered and concentrated. The crude product was purified by automated reverse phase HPLC (low pH Method A) to afford the title compound as a beige solid (74 mg, 35%).

Example 211

(a) Diastereomer 1: (2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methyl-butoxy)propanamide (ABR 239949)

(b) Diastereomer 2: (2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methyl-butoxy)propanamide (ABR 239952)

A flask charged with a solution of (2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(3-methylbut-2-en-1-yl)oxy]propanamide (250 mg, 0.589 mmol) in ethanol (10 mL) was evacuated and flushed with nitrogen (×3). 10% Pd/C (35 mg, 0.33 mmol) was added to the stirred solution. The flask was evacuated and flushed with nitrogen (×3) and then evacuated and flushed with hydrogen (×3). After stirring for 20 h the reaction was re-treated with 10% Pd/C (10 mg, 0.09 mmol) and stirred under an atmosphere of hydrogen for a further 2 h. The reaction was then filtered through Celite™, rinsed with EtOH and concentrated. The crude product was purified by silica chromatography, using 0-5% MeOH in DCM as eluent, with subsequent purification by automated reverse phase HPLC (low pH Method A) to afford Diastereomer 1 as a single diastereomer of undefined stereochemistry at the quaternary centre as a white solid (34 mg, 14%) and Diastereomer 2 as a single diastereomer of undefined stereochemistry at the quaternary centre as a white solid (29 mg, 11%).

(c) Diastereomer 3: (2R)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methyl-butoxy)propanamide (ABR 239958)

(d) Diastereomer 4: (2R)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methyl-butoxy)propanamide (ABR 239959)

The procedure for the preparation of (2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methyl-butoxy)propanamide was used, except that (2R)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(3-methylbut-2-en-1-yl)oxy]propanamide was used instead of (2S)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(3-methylbut-2-en-1-yl)oxy]propanamide. Purification afforded Diastereomer 3 as a single diastereomer of undefined stereochemistry at the quaternary centre as a white solid (8%) and Diastereomer 4 as a single diastereomer of undefined stereochemistry at the quaternary centre as a white solid (6%).

Example 212

(a) Diastereomer 1: (2R)-2-(3-chlorophenoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239968)

(b) Diastereomer 2: (2R)-2-(3-chlorophenoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239969)

To a stirred solution of (2R)-2-(3-chlorophenoxy)propanamide (0.22 g, 1.1 mmol) in DMF (5 mL) was added methyl 3,3,3-trifluoro-2-oxopropanoate (0.16 mL, 1.6 mmol) followed by pyridine (0.09 mL, 1.1 mmol) under nitrogen. The reaction was stirred at room temperature for 2 h. Thionyl chloride (0.08 mL, 1.1 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (5 mL) under nitrogen. The solution of acyl intermediate was added to a solution of 5,6-dimethyl-1H-1,3-benzodiazol-2-amine (0.14 g, 0.87 mmol) in DMF (5 mL) followed by triethylamine (0.17 mL, 1.3 mmol). The reaction mixture was stirred for a further 3 h and then concentrated. The residue was dissolved in EtOAc (50 mL), washed with 10% citric acid$_{(aq)}$ (2×25 mL), water (3×25 mL) and brine (3×25 mL) and then dried (MgSO$_4$), filtered and concentrated. The crude product was purified by silica chromatography, using 1-3% MeOH in DCM as eluent, with subsequent purification by automated reverse phase HPLC (low pH Method A) to afford Diastereomer 1 as a single diastereomer of undefined stereochemistry at the quaternary centre as a white solid (33 mg, 8%) and Diastereomer 2 as a single diastereomer of undefined stereochemistry at the quaternary centre as a white solid (32 mg, 6%).

Example 213

(2S)—N-[9-acetyl-4-oxo-3-(trifluoromethyl)-2,5,7-triazatricyclo[6.4.0.0$^{2,6}$]dodeca-1(12),6,8,10-tetraen-3-yl]-2-cyclohexylpropanamide (ABR 239985)

A sealed tube was charged with (2 S)—N-[9-bromo-4-oxo-3-(trifluoromethyl)-2,5,7-triazatricyclo[6.4.0.0$^{2,6}$]dodeca-1(12),6,8,10-tetraen-3-yl]-2-cyclohexylpropanamide (230 mg, 0.47 mmol), palladium(II) acetate (11 mg, 47 µmol), propane-1,3-diylbis(diphenylphosphane) (39 mg, 0.09 mmol), K$_2$CO$_3$ (85 mg, 0.61 mmol), 1-(ethenyloxy)butane (307 µL, 2.36 mmol) and de-gassed DMF/water (3:1, 4 mL), under nitrogen. The reaction was stirred at 100° C. for 16 h and then concentrated. The residue was dissolved in EtOAc (10 mL) and washed with brine (10 mL). The aqueous phase was extracted with EtOAc (15 mL). The combined organic extracts were washed with brine (2×15 mL), dried (MgSO$_4$), filtered and concentrated. The crude product was purified by automated reverse phase HPLC (low pH Method A) to afford the title compound as a single diastereomer of undefined stereochemistry at the quaternary centre as a white solid (34 mg, 16%).

Example 214

(2S)-3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-hydroxypropanamide (ABR 239994)

To a stirred solution of (2S)-2-(acetyloxy)-3-cyclopentylpropanoic acid available via a literature method: PCT Int. Appl., 2000059502; (1.00 g, 5.40 mmol) in DCM (15 mL) was added oxalyl chloride (732 mg, 5.77 mmol) followed by DMF (2 drops). The reaction was stirred for 30 min and then concentrated. The resulting residue was dissolved in DCM (3 mL) and aqueous ammonia (0.5 mL) was added. The reaction was concentrated and the residue was stirred in DCM (10 mL) and filtered. The filtrate was concentrated to afford (1S)-1-carbamoyl-2-cyclopentylethyl acetate (838 mg).

To a stirred solution of (1S)-1-carbamoyl-2-cyclopentylethyl acetate (408 mg, 2.05 mmol) in DMF (4 mL) was added methyl 3,3,3-trifluoro-2-oxopropanoate (0.34 mL, 3.4 mmol) followed by pyridine (0.18 mL, 2.2 mmol) under nitrogen. The reaction was stirred at room temperature for 1 h. Thionyl chloride (0.16 mL, 2.2 mmol) was added at 0° C. The reaction was stirred for 1 h at 0° C. and then filtered through a short pad of silica, eluting with DCM, under nitrogen. The filtrate was concentrated, and the acyl intermediate that remained was dissolved in DMF (3 mL) under nitrogen. The solution of acyl intermediate was added to a solution of 5,6-dimethyl-1H-1,3-benzodiazol-2-amine (300 mg, 1.86 mmol) in DMF (5 mL) followed by triethylamine (0.30 mL, 2.2 mmol). The reaction mixture was stirred for a further 1 h and then concentrated. The residue was dissolved in MeOH (10 mL) and water (5 mL). 2M NaOH$_{(aq)}$ (5 mL) was added and the resulting solution was stirred at room temperature for 1 h. The reaction was concentrated and the residue dissolved in EtOAc (60 mL). The organic phase was washed with water (3×20 mL) and brine (2×20 mL) and then dried (Na$_2$SO$_4$), filtered and concentrated. The crude product was purified by silica chromatography, using 0-10% MeOH in DCM as eluent, with subsequent purification by automated reverse phase HPLC (high pH) to afford the title compound as a single diastereomer of undefined stereochemistry at the quaternary centre as a white solid (28 mg, 4%).

Example 215

(a) Diastereomer 1: (2S)-2-(cyclopentylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239997)

(b) Diastereomer 2: (2S)-2-(cyclopentylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239998)

A flask charged with a solution of (2S)-2-(cyclopent-1-en-1-ylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (750 mg, 1.72 mmol) and EtOH (10 mL), evacuated and flushed with nitrogen (×3). Dioxoplatinum (39 mg, 0.17 mmol) was then added to the stirred solution. The flask was evacuated and flushed with nitrogen (×3) and then evacuated and flushed with hydrogen (×3). After stirring for 18 h the reaction was filtered through Celite™, rinsed with EtOH and concentrated. The crude product was purified by automated reverse phase HPLC (low pH Method A) to afford Diastereomer 1 as a single diastereomer of undefined stereochemistry at the quaternary centre as a white solid (260 mg, 35%) and Diastereomer 2 as a single diastereomer of undefined stereochemistry at the quaternary centre as a white solid (197 mg, 26%).

Example 216

(a) Enantiomer 1: 3-cyclopentyl-N-[4-oxo-3-(trifluoromethyl)-2,5,7-triazatricyclo[6.4.0.0$^{2,6}$]dodeca-1(12),6,8,10-tetraen-3-yl]propanamide (ABR 238851)

(b) Enantiomer 2: 3-cyclopentyl-N-[4-oxo-3-(trifluoromethyl)-2,5,7-triazatricyclo[6.4.0.0$^{2,6}$]dodeca-1(12),6,8,10-tetraen-3-yl]propanamide (ABR 238856)

3-Cyclopentyl-N-[4-oxo-3-(trifluoromethyl)-2,5,7-triazatricyclo[6.4.0.0$^{2,6}$]dodeca-1(12),6,8,10-tetraen-3-yl]propanamide (40 mg, 0.11 mmol) was resolved by SFC using a Chiralpak AD-H column with 23% Ethanol/77% CO$_2$ as

Example 217

(a) Enantiomer 1: 3-cyclohexyl-N-[4-oxo-3-(trifluoromethyl)-2,5,7-triazatricyclo[6.4.0.0$^{2,6}$]dodeca-1(12),6,8,10-tetraen-3-yl]propanamide (ABR 238924)

(b) Enantiomer 2: 3-cyclohexyl-N-[4-oxo-3-(trifluoromethyl)-2,5,7-triazatricyclo[6.4.0.0$^{2,6}$]dodeca-1(12),6,8,10-tetraen-3-yl]propanamide (ABR 238941)

3-Cyclohexyl-N-[4-oxo-3-(trifluoromethyl)-2,5,7-triazatricyclo[6.4.0.0$^{2,6}$]dodeca-1(12),6,8,10-tetraen-3-yl]propanamide (20 mg, 0.05 mmol) was resolved by SFC using a Chiralpak AD-H column with 23% EtOH/77% $CO_2$ as the mobile phase. Enantiomer 1 was isolated as a brown solid (4 mg, 21%). Enantiomer 2 was isolated as a white solid (5 mg, 24%).

Example 218

(a) Enantiomer 1: 3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239071)

(b) Enantiomer 2: 3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239105)

3-Cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (200 mg, 0.49 mmol) was resolved by SFC using a Chiralpak AD-H column with 15% EtOH/85% $CO_2$ as the mobile phase. Enantiomer 1 was isolated as a white solid (77 mg, 39%). Enantiomer 2 underwent further purification by automated reverse phase HPLC (low pH Method A) to give the title compound as a white solid (67 mg, 34%).

Example 219

(a) Enantiomer 1: 3-cyclopentyl-N-[10,11-dichloro-4-oxo-3-(trifluoromethyl)-2,5,7-triazatricyclo[6.4.0.0$^{2,6}$]dodeca-1(12),6,8,10-tetraen-3-yl]propanamide (ABR 239396)

(b) Enantiomer 2: 3-cyclopentyl-N-[10,11-dichloro-4-oxo-3-(trifluoromethyl)-2,5,7-triazatricyclo[6.4.0.0$^{2,6}$]dodeca-1(12),6,8,10-tetraen-3-yl]propanamide (ABR 239397)

3-Cyclopentyl-N-[10,11-dichloro-4-oxo-3-(trifluoromethyl)-2,5,7-triazatricyclo[6.4.0.0$^{2,6}$]dodeca-1(12),6,8,10-tetraen-3-yl]propanamide (120 mg, 0.27 mmol) was resolved by SFC using a Chiralpak AD-H column with 7% MeOH/93% $CO_2$ as the mobile phase. Enantiomer 1 was isolated as a white solid (46 mg, 38%). Enantiomer 2 was isolated as a white solid (46 mg, 38%).

eluent. Enantiomer 1 was isolated as a white solid (15 mg, 38%). Enantiomer 2 was isolated as a white solid (13 mg, 33%).

Example 220

(a) Enantiomer 1: N-[10,11-dimethyl-4-oxo-3-(trifluoromethyl)-2,5,7-triazatricyclo[6.4.0.0$^{2,6}$]dodeca-1(12),6,8,10-tetraen-3-yl]-6-[(2-methoxyethyl)amino]pyridine-2-carboxamide (ABR 239662)

(b) Enantiomer 2: N-[10,11-dimethyl-4-oxo-3-(trifluoromethyl)-2,5,7-triazatricyclo[6.4.0.0$^{2,6}$]dodeca-1(12),6,8,10-tetraen-3-yl]-6-[(2-methoxyethyl)amino]pyridine-2-carboxamide (ABR 239663)

N-[10,11-Dimethyl-4-oxo-3-(trifluoromethyl)-2,5,7-triazatricyclo[6.4.0.0$^{2,6}$]dodeca-1(12),6,8,10-tetraen-3-yl]-6-[(2-methoxyethyl)amino]pyridine-2-carboxamide (100 mg, 0.22 mmol) was resolved by SFC using a Chiralpak IC column with 12% MeOH/88% $CO_2$ as the mobile phase. Enantiomer 1 was isolated as a white solid (40 mg, 40%). Enantiomer 2 was isolated as a white solid (46 mg, 40%).

Example 221

(a) Enantiomer 1: N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(1-hydroxycyclopentyl)propanamide (ABR 239707)

(b) Enantiomer 2: N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(1-hydroxycyclopentyl)propanamide (ABR 239714)

N-[10,11-Dimethyl-4-oxo-3-(trifluoromethyl)-2,5,7-triazatricyclo[6.4.0.0$^{2,6}$]dodeca-1(12),6,8,10-tetraen-3-yl]-3-(1-hydroxycyclopentyl)propanamide (125 mg, 0.29 mmol) was resolved by SFC using a ChiralPak AS column with 80% MeOH/20% $CO_2$ as the mobile phase. Enantiomer 1 was isolated as a white solid (44 mg, 35%). Enantiomer 2 underwent further purification by automated reverse phase HPLC (low pH Method A) to give the title compound as a white solid (6 mg, 4%).

Example 222

(a) Enantiomer 1: 3-cyclopentyl-N-[9-methanesulfonyl-4-oxo-3-(trifluoromethyl)-2,5,7-triazatricyclo[6.4.0.0$^{2,6}$]dodeca-1(12),6,8,10-tetraen-3-yl]propanamide (ABR 239709)

(b) Enantiomer 2: 3-cyclopentyl-N-[9-methanesulfonyl-4-oxo-3-(trifluoromethyl)-2,5,7-triazatricyclo[6.4.0.0$^{2,6}$]dodeca-1(12),6,8,10-tetraen-3-yl]propanamide (ABR 239710)

3-Cyclopentyl-N-[9-methanesulfonyl-4-oxo-3-(trifluoromethyl)-2,5,7-triazatricyclo[6.4.0.0$^{2,6}$]dodeca-1(12),6,8,10-tetraen-3-yl]propanamide (110 mg, 0.23 mmol) was resolved by SFC using a ChiralPak AS column with 80% MeOH/20% $CO_2$ as the mobile phase. Enantiomer 1 was isolated as a beige solid (26 mg, 24%). Enantiomer 2 was isolated as a beige solid (34 mg, 32%).

Example 223

(a) Enantiomer 1: 3-cyclopentyl-N-[9,10-difluoro-4-oxo-3-(trifluoromethyl)-2,5,7-triazatricyclo[6.4.0.0$^{2,6}$]dodeca-1(12),6,8,10-tetraen-3-yl]propanamide (ABR 239712)

(b) Enantiomer 2: 3-cyclopentyl-N-[9,10-difluoro-4-oxo-3-(trifluoromethyl)-2,5,7-triazatricyclo[6.4.0.0$^{2,6}$]dodeca-1(12),6,8,10-tetraen-3-yl]propanamide (ABR 239713)

3-Cyclopentyl-N-[9,10-difluoro-4-oxo-3-(trifluoromethyl)-2,5,7-triazatricyclo[6.4.0.0$^{2,6}$]dodeca-1(12),6,8,10-tetraen-3-yl]propanamide (110 mg, 0.26 mmol) was resolved by SFC using ChiralPak AD column with 70% MeOH/30% CO$_2$ as the mobile phase. Enantiomer 1 was isolated as a white solid (53 mg, 48%). Enantiomer 2 was isolated as a white solid (53 mg, 48%).

Example 224a (a) Enantiomer 1: N-[9-acetyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239727)

(b) Enantiomer 2: N-[9-acetyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239728)

N-[9-Acetyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (110 mg, 0.26 mmol) was resolved by SFC using a ChiralPak IC column with 30% IPA/70% CO$_2$ as the mobile phase. Enantiomer 1 was isolated as a white solid (40 mg, 36%). Enantiomer 2 was isolated as a white solid (41 mg, 37%).

Example 225a (a) Enantiomer 1: 3-(3,3-difluoroazetidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239825)

(b) Enantiomer 2: 3-(3,3-difluoroazetidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (ABR 239824)

3-(3,3-Difluoroazetidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide (116 mg, 0.27 mmol) was resolved by SFC using a ChiralPak IC column with 20% IPA/80% CO$_2$ as the mobile phase. Enantiomer 1 was isolated as a white solid (35 mg, 30%). Enantiomer 2 was isolated as a white solid (37 mg, 32%).

Example 226

(a) Enantiomer 1: N-[9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239962)

(b) Enantiomer 2: N-[9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 239961)

N-[9-Cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.25 mmol) was resolved by SFC using an Amy-C column with 70% IPA/30% CO$_2$ as the mobile phase. Enantiomer 1 was isolated as a white solid (32 mg, 32%). Enantiomer 2 was dissolved in EtOAc (2 mL) and washed with 0.5M HCl$_{(aq)}$ (1 mL), water (1 mL) and brine (1 mL). The organic phase was concentrated to give the title product as a white solid (19 mg, 19%).

Example 227

(a) Enantiomer 1: 3-cyclopentyl-N-[9-(2-methylpropanoyl)-4-oxo-3-(trifluoromethyl)-2,5,7-triazatricyclo[6.4.0.0$^{2,6}$]dodeca-1(12),6,8,10-tetraen-3-yl]propanamide (ABR 239975)

(b) Enantiomer 2: 3-cyclopentyl-N-[9-(2-methylpropanoyl)-4-oxo-3-(trifluoromethyl)-2,5,7-triazatricyclo[6.4.0.0$^{2,6}$]dodeca-1(12),6,8,10-tetraen-3-yl]propanamide (ABR 239972)

To a stirred solution of N-[9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (177 mg, 0.44 mmol) in THF (5 mL), at 0° C. under nitrogen, was added 2M chloro(propan-2-yl)magnesium in THF (655 µL, 1.31 mmol) dropwise. Copper(I) bromide (0.6 mg, 4 µmol) was added and the reaction was heated at 80° C. for 15 min. The reaction was cooled to 0° C. and quenched by the addition of water (3 mL). 1M HCl$_{(aq)}$ (3 mL) was added and the reaction was heated at 100° C. for 1 h. The reaction was basified with saturated NaHCO$_{3(aq)}$ and extracted with EtOAc (3×15 mL). The combined organic extracts were washed with brine (20 mL), dried (Na$_2$SO$_4$), filtered and concentrated. The crude product was purified by automated reverse phase HPLC (low pH Method A) to afford 3-cyclopentyl-N-[9-(2-methylpropanoyl)-4-oxo-3-(trifluoromethyl)-2,5,7-triazatricyclo[6.4.0.0$^{2,6}$]dodeca-1(12),6,8,10-tetraen-3-yl]propanamide as a racemic mixture a yellow solid (70 mg, 36%).

3-Cyclopentyl-N-[9-(2-methylpropanoyl)-4-oxo-3-(trifluoromethyl)-2,5,7-triazatricyclo[6.4.0.0$^{2,6}$]dodeca-1(12),6,8,10-tetraen-3-yl]propanamide (60 mg, 0.13 mmol) was resolved by SFC using a Chiralpak AD-H column with 30% MeOH/70% CO$_2$ as the mobile phase. Enantiomer 1 was isolated as a white solid (24 mg, 40%). Enantiomer 2 was isolated as a white solid (26 mg, 43%).

Example 228

(a) Enantiomer 1: N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-phenylpropanamide (ABR 239976)

(b) Enantiomer 2: N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-phenylpropanamide (ABR 239974)

N-[10,11-Dimethyl-4-oxo-3-(trifluoromethyl)-2,5,7-triazatricyclo[6.4.0.0$^{2,6}$]dodeca-1(12),6,8,10-tetraen-3-yl]-3-phenylpropanamide (206 mg, 0.50 mmol) was resolved by SFC using an Amy-C column with 75% MeOH/25% $CO_2$ as the mobiled phase and diethylamine as modifier. Enantiomer 1 was dissolved in EtOAc and washed with 1M $HCl_{(aq)}$ (2×) and brine. The organic phase was dried ($MgSO_4$) and concentrated to give the title product as a brown solid (75 mg, 36%). Enantiomer 2 was dissolved in EtOAc and washed with 1M $HCl_{(aq)}$ (2×) and brine. The organic phase was dried ($MgSO_4$) and concentrated to give the title product as a brown solid (88 mg, 43%).

Example 229

(a) Enantiomer 1: 3,5-dichloro-N-[10,11-dichloro-4-oxo-3-(trifluoromethyl)-2,5,7-triazatricyclo[6.4.0.0$^{2,6}$]dodeca-1(12),6,8,10-tetraen-3-yl]benzamide (ABR 239981)

(b) Enantiomer 2: 3,5-dichloro-N-[10,11-dichloro-4-oxo-3-(trifluoromethyl)-2,5,7-triazatricyclo[6.4.0.0$^{2,6}$]dodeca-1(12),6,8,10-tetraen-3-yl]benzamide (ABR 239980)

3,5-Dichloro-N-[10,11-dichloro-4-oxo-3-(trifluoromethyl)-2,5,7-triazatricyclo[6.4.0.0$^{2,6}$]dodeca-1(12),6,8,10-tetraen-3-yl]benzamide (62 mg, 0.13 mmol) was resolved by SFC using an Amy-C column with 85% MeOH/15% $CO_2$ as the mobile phase. Enantiomer 1 was isolated as a white solid (20 mg, 32%). Enantiomer 2 was isolated as a white solid (22 mg, 35%).

Example 230

(a) Enantiomer 1: 3-cyclopentyl-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239984)

(b) Enantiomer 2: 3-cyclopentyl-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (ABR 239979)

3-Cyclopentyl-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide (96 mg, 0.20 mmol) was resolved by SFC using a Chiralcel OJ-H column with 15% MeOH/85% $CO_2$ as the mobile phase. Enantiomer 1 was isolated as a white solid (38 mg, 40%). Enantiomer 2 was isolated as a white solid (42 mg, 44%).

Example 231

(a) Enantiomer 1: 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid (ABR 240007)

(b) Enantiomer 2: 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid (ABR 240006)

3-(3-Cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid (180 mg, 0.42 mmol) was resolved by SFC using a Chiralpak AD-H column with 15% MeOH/85% $CO_2$ as the mobile phase and diethylamine as modifier. Enantiomer 1 was isolated as a white solid (70 mg, 37%). Enantiomer 2 was isolated as a white solid (60 mg, 32%).

Example 232

3-cyclopentyl-N-{9-[4-(methylsulfanyl)phenyl]-4-oxo-3-(trifluoromethyl)-2,5,7-triazatricyclo[6.4.0.0$^{2,6}$]dodeca-1(12),6,8,10-tetraen-3-yl}propanamide (ABR 240016)

A sealed tube was charged with N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]acetamide (100 mg, 0.25 mmol), [4-(methylsulfanyl)phenyl]boronic acid (32 mg, 0.20 mmol), 2M $Na_2CO_{3(aq)}$ (326 µL, 0.65 mmol) and anhydrous dioxane (0.82 mL). The solution was de-gassed with nitrogen. $Pd(PPh_3)_4$ (19 mg, 0.02 mmol) was added, the solution was de-gassed with nitrogen and the tube was sealed. The reaction was stirred at 110° C. for 16 h. The reaction was allowed to cool to room temperature. 2M $HCl_{(aq)}$ (2 mL) was added and resulting mixture was stirred for 1 h. The reaction diluted with EtOAc. The organic phase was washed with brine, dried ($MgSO_4$), filtered and concentrated. The crude product was purified by silica chromatography, using 0-5% MeOH in DCM as eluent, with subsequent purification by automated reverse phase HPLC (low pH Method A) to afford the title compound as a brown solid (50 mg, 60%).

Example 233

11-chloro-3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid (ABR 240015)

To a stirred solution of phenyl 11-chloro-3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate (74 mg, 0.14 mmol) in THF (5 mL), under nitrogen, was added 2M $NaOH_{(aq)}$ (343 µL, 0.69 mmol). The reaction was stirred at room temperature for 1 h and then concentrated. The residue was diluted with 2M $HCl_{(aq)}$ (2 mL) and extracted with EtOAc (2×5 mL). The combined organic extracts were washed with water (5 mL), dried ($MgSO_4$), filtered and concentrated. The crude product was purified by automated reverse phase HPLC (low pH Method A) to afford the title compound as a white solid (3 mg, 5%).

Example 234

N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]butanamide (ABR 240014)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]butanamide (650 mg, 1.60 mmol), (4-methoxyphenyl)boronic acid (341 mg, 2.25 mmol), Na$_2$CO$_3$ (680 mg, 6.42 mmol), water (2.0 mL), DME (7.0 mL), and EtOH (3.5 mL). The solution was de-gassed with nitrogen. Pd(PPh$_3$)$_4$ (93 mg, 80 µmol) was added, the solution de-gassed with nitrogen and the tube was sealed. The reaction was stirred at 100° C. for 4 h. The reaction mixture was concentrated. The residue was dissolved in EtOAc (25 mL) and washed with water (25 mL). The aqueous layer was extracted with EtOAc (2×20 mL). The combined organic extracts were washed with brine (30 mL) and then dried (Na$_2$SO$_4$), filtered and concentrated. The crude product was purified by silica chromatography with subsequent purification by automated reverse phase HPLC (low pH Method A) to afford the title compound as a white solid (35 mg, 5%).

Example 235

2-[(2-methoxyethyl)amino]-N-[9-(4-methoxyphenyl)-4-oxo-3-(trifluoromethyl)-2,5,7-triazatricyclo [6.4.0.0$^{2,6}$]dodeca-1(12),6,8,10-tetraen-3-yl]-1,3-thiazole-4-carboxamide (ABR 240013)

A sealed tube was charged N-[9-bromo-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]-1,3-thiazole-4-carboxamide (150 mg, 0.29 mmol) (4-methoxyphenyl) boronic acid (66 mg, 0.43 mmol), Na$_2$CO$_3$ (61 mg, 0.58 mmol), water (1 mL), DME (3 mL), and EtOH (2 mL). The solution was de-gassed with nitrogen. Pd(PPh$_3$)$_4$ (17 mg, 0.01 mmol) was added, the solution was de-gassed with nitrogen and the tube was sealed. The reaction was stirred at 100° C. for 16 h. Additional (4-methoxyphenyl)boronic acid (66 mg, 0.43 mmol), Na$_2$CO$_3$ (61 mg, 0.58 mmol) and Pd(PPh$_3$)$_4$ (17 mg, 0.01 mmol) were added. The solution was de-gassed with nitrogen and the tube was sealed. The reaction was stirred at 100° C. for 5 h. The reaction mixture was concentrated. The residue was dissolved in EtOAc (50 mL), washed with 1M HCl$_{(aq)}$ (50 mL), water (50 mL) and brine (50 mL) and then dried (MgSO$_4$), filtered and concentrated. The crude product was purified by automated reverse phase HPLC (low pH Method A) to afford the title compound as a yellow solid (39 mg, 25%).

Example 236

N-[9-bromo-4-oxo-3-(trifluoromethyl)-2,5,7-triazatricyclo[6.4.0.0$^{2,6}$]dodeca-1(12),6,8,10-tetraen-3-yl]-2-hydroxy-1,3-thiazole-4-carboxamide (ABR 240018)

To a stirred solution of 2-bromo-1,3-thiazole-4-carboxamide (2.93 g, 14.2 mmol) in DMF (80 mL) was added methyl 3,3,3-trifluoro-2-oxopropanoate (4.42 g, 28.3 mmol) followed by pyridine (1.14 mL, 14.2 mmol) under nitrogen.

The reaction was stirred at room temperature for 16 h. Additional methyl 3,3,3-trifluoro-2-oxopropanoate (4.42 g, 28.3 mmol) was added and the reaction was stirred at a further 4 h. Thionyl chloride (1.03 mL, 14.2 mmol) was added at 0° C. The reaction was stirred for 2 h at 0° C. and then concentrated. The residue was filtered through a short pad of silica, eluting with DCM, under nitrogen. The filtrate was concentrated, and the acyl intermediate that remained was dissolved in DMF (10 mL) under nitrogen. The solution of acyl intermediate was added to a solution of 4-bromo-1H-1,3-benzodiazol-2-amine (2.50 g, 11.8 mmol) in DMF (40 mL) followed by triethylamine (1.88 mL, 14.2 mmol). The reaction mixture was stirred for a further 2 h and then concentrated. The residue was dissolved in EtOAc (200 mL), washed with 10% citric acid$_{(aq)}$ (2×100 mL), water (2×100 mL) and brine (2×100 mL) and then dried (MgSO$_4$), filtered and concentrated. The crude product was purified by trituration in DCM to afford a mixture of 2-bromo-N-[9-bromo-4-oxo-3-(trifluoromethyl)-2,5,7-triazatricyclo [6.4.0.0$^{2,6}$]dodeca-1(12),6,8,10-tetraen-3-yl]-1,3-thiazole-4-carboxamide and N-[9-bromo-4-oxo-3-(trifluoromethyl)-2,5,7-triazatricyclo[6.4.0.0$^{2,6}$]dodeca-1(12),6,8,10-tetraen-3-yl]-2-chloro-1,3-thiazole-4-carboxamide (3.70 g).

To a suspension of NaH (60%, 11 mg, 0.27 mmol) in DMF (2 mL), at 0° C. under nitrogen, was added methanesulfonamide (24 mg, 0.25 mmol). After stiffing at 0° C. for 10 min, a portion of the mixture of 2-bromo-N-[9-bromo-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide and N-[9-bromo-4-oxo-3-(trifluoromethyl)-2,5,7-triazatricyclo[6.4.0.0$^{2,6}$]dodeca-1(12),6,8,10-tetraen-3-yl]-2-chloro-1,3-thiazole-4-carboxamide (100 mg) was added. The reaction was allowed to warm to room temperature and stirred 2 h. Then the temperature was increased to 80° C. for 4 h. The reaction was quenched with saturated NH$_4$Cl$_{(aq)}$ at 0° C. and diluted with EtOAc (50 mL). The organic phase was washed with water (2×25 mL), dried (MgSO$_4$), filtered and concentrated. The crude product was purified by automated reverse phase HPLC (low pH Method A) to afford the title compound as a white solid (11 mg, 11%).

Example 237

N-[10,11-dichloro-4-oxo-3-(trifluoromethyl)-2,5,7-triazatricyclo[6.4.0.0$^{2,6}$]dodeca-1(12),6,8,10-tetraen-3-yl]-2-[(2-methylpropyl)amino]-1,3-thiazole-4-carboxamide (ABR 240019)

To a stirred solution of 2-bromo-1,3-thiazole-4-carboxamide (360 mg, 1.74 mmol) in DMF (15 mL) was added methyl 3,3,3-trifluoro-2-oxopropanoate (543 mg, 3.48 mmol) followed by pyridine (140 µL, 1.74 mmol) at room temperature under nitrogen. The reaction mixture was stirred at room temperature for 16 h. Thionyl chloride (126 µL, 1.74 mmol) was added at 0° C. and the reaction mixture was then stirred for 1 h. The reaction mixture was concentrated and the residue was filtered through a short pad of silica, eluting with DCM, under nitrogen. The filtrate was concentrated, and the acyl intermediate that remained was dissolved in DMF (10 mL) under nitrogen. A solution of 5,6-dichloro-1H-1,3-benzodiazol-2-amine (293 mg, 1.45 mmol) in DMF (10 mL) and triethylamine (231 µL, 1.74 mmol) were added and the reaction mixture was stirred at room temperature for 2 h. The reaction mixture was concentrated. The residue was diluted with EtOAc (50 mL), washed with washed with 10% citric acid$_{(aq)}$ (2×25 mL), water (2×25 mL) and brine (2×25 mL). The organic phase was dried (MgSO$_4$), filtered and concentrated. The crude product was triturated in DCM to afford a mixture of 2-bromo-N-[10,11-dichloro-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide and 2-chloro-N-[10,11-dichloro-4-oxo-3-(trifluoromethyl)-2,5,7-triazatricyclo [6.4.0.0$^{2,6}$]dodeca-1(12),6,8,10-tetraen-3-yl]-1,3-thiazole-4-carboxamide (746 mg).

A sealed tube was charged with a portion of the mixture of 2-bromo-N-[10,11-dichloro-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide and 2-chloro-N-[10,11-dichloro-4-oxo-3-(trifluoromethyl)-2,5,7-triazatricyclo [6.4.0.0$^{2,6}$]dodeca-1(12),6,8,10-tetraen-3-yl]-1,3-thiazole-4-carboxamide (190 mg), K$_2$CO$_3$ (255 mg, 1.84 mmol), anhydrous dioxane (3 mL) and 2-methylpropan-1-amine (184 µL, 1.84 mmol). The tube was sealed and stirred at 130° C. for 1 h. Additional K$_2$CO$_3$ (255 mg, 1.84 mmol) and 2-methylpropan-1-amine (184 µL, 1.84 mmol) were added. The reaction was stirred at 130° C. for a further 18 h and was then concentrated. The residue was diluted with EtOAc (30 mL) and brine (30 mL). The aqueous layer was extracted with EtOAc (3×30 mL). The combined organic extracts were washed with brine, dried (MgSO$_4$), filtered and concentrated. The crude product was purified by automated reverse phase HPLC (low pH Method A) to afford the title compound as a brown solid (40 mg, 21%).

Example 238

3-cyclopentyl-N-{9-[4-(dimethylamino)phenyl]-4-oxo-3-(trifluoromethyl)-2,5,7-triazatricyclo[6.4.0. 0$^{2,6}$]dodeca-1(12),6,8,10-tetraen-3-yl}propanamide (ABR 240028)

A sealed tube was charged with N-[9-bromo-10,11-dimethyl-4-oxo-3-(trifluoromethyl)-2,5,7-triazatricyclo [6.4.0.0$^{2,6}$]dodeca-1(12),6,8,10-tetraen-3-yl]acetamide (75 mg, 0.16 mmol), [4-(dimethylamino)phenyl]boronic acid (38 mg, 0.23 mmol), 2M Na$_2$CO$_3$ (326 µL, 0.65 mmol) 1,4-dioxane (0.82 mL). The solution was de-gassed with nitrogen. Pd(PPh$_3$)$_4$ (38 mg, 0.04 mmol) was added, the solution was de-gassed with nitrogen and the tube was sealed. The reaction was stirred at 110° C. for 16 h. This reaction was allowed to cool to room temperature and was diluted with EtOAc and 2M NaHCO$_{3(aq)}$. The organic phase was washed with brine, dried (MgSO$_4$), filtered and concentrated. The crude product was purified firstly by silica chromatography, using 0-5% MeOH in DCM as eluent. Subsequent purification by automated reverse phase HPLC (low pH Method A) and then by silica chromatography, using 0-20% MeOH in DCM as eluent, afforded the title compound as a white solid (20 mg, 25%).

Example 239

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2,2,2-trifluoroacetamide (ABR 240031)

To a stirred solution of trifluoroacetamide (210 mg, 1.86 mmol) in anhydrous DCM (8.3 mL) was added pyridine (120 µL, 1.48 mmol) followed by methyl 3,3,3-trifluoro-2-oxopropanoate (380 µL, 3.72 mmol) under nitrogen. The reaction was stirred at room temperature for 2 h. Thionyl chloride (107 µL, 1.48 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (6 mL) under nitrogen. A solution of 5,6-dimethyl-1H-1,3-benzodiazol-2-amine (250 mg, 1.24 mmol) in DMF (2.3 mL) and triethylamine (207 µL, 1.48 mmol) were added. The reaction was stirred for 60 h before being concentrated. The residue was dissolved in EtOAc and washed with brine (4×). The organic phase was dried (MgSO$_4$), filtered and concentrated. The crude product was purified by silica chromatography, using 0-10% MeOH in DCM as eluent, to afford the title compound as a white solid (155 mg, 26%).

Example 240

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(2-methoxyethoxy)pyridine-4-carboxamide (ABR 240032)

To a stirred solution of 2-(2-methoxyethoxy)pyridine-4-carboxamide (190 mg, 0.97 mmol) in anhydrous DCM (5 mL) was added pyridine (79 µL, 0.97 mmol) followed by methyl 3,3,3-trifluoro-2-oxopropanoate (303 mg, 1.94 mmol) under nitrogen. The reaction was stirred at room temperature for 2 h. Thionyl chloride (70 µL, 0.97 mmol) was added at 0° C. The reaction was stirred for 1 h at 0° C. and then filtered through a short pad of silica, eluting with DCM, under nitrogen. The filtrate was concentrated, and the acyl intermediate that remained was dissolved in DMF (3 mL) under nitrogen. A solution of 5,6-dimethyl-1H-1,3-benzodiazol-2-amine (130 mg, 0.81 mmol) in DMF (2 mL) and triethylamine (136 µL, 0.97 mmol) were added. The reaction was stirred for 18 h before being concentrated. The residue was diluted with EtOAc and brine. The organic phase was dried (MgSO$_4$), filtered and concentrated. The crude product was triturated in MeCN with subsequent purification by automated reverse phase HPLC (low pH Method A) affording the title compound as a white solid (10 mg, 3%).

Example 241

3-cyclopentyl-N-[9-(4-methanesulfonylphenyl)-4-oxo-3-(trifluoromethyl)-2,5,7-triazatricyclo[6.4.0. 0$^{2,6}$]dodeca-1(12),6,8,10-tetraen-3-yl]propanamide (ABR 240029)

To a stirred solution of 3-cyclopentyl-N-{9-[4-(methylsulfanyl)phenyl]-4-oxo-3-(trifluoromethyl)-2,5,7-triazatricyclo[6.4.0.0$^{2,6}$]dodeca-1(12),6,8,10-tetraen-3-yl}propanamide (40 mg, 80 µmol) in MeOH (5 mL) at 0° C. was added a solution of oxone (122 mg, 0.2 mmol) in water (1 mL). The reaction was stirred at room temperature for 2 h, quenched with saturated Na$_2$S$_2$O$_{3(aq)}$ and then concentrated. The resulting residue was diluted with EtOAc (15 mL) and water (10 mL). The aqueous phase was extracted with EtOAc (2×15 mL). The combined organic extracts were washed with water (20 mL), brine (40 mL) and water (2×10 mL). The organic phase was then dried (Na$_2$SO$_4$), filtered and concentrated to afford the title compound as a white solid (4 mg, 11%).

Example 242

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2,2-dimethylpropanamide (ABR 240030)

To a stirred solution of 2,2-dimethylpropanamide (392 mg, 3.88 mmol) in anhydrous DCM (5 mL) under nitrogen was added methyl 3,3,3-trifluoro-2-oxopropanoate (475 μL, 4.65 mmol) followed by pyridine (313 μL, 3.88 mmol). The reaction was stirred at room temperature 16 h. Thionyl chloride (281 μL, 3.88 mmol) added at 0° C. The reaction was stirred for 1.5 h at 0° C. and then filtered through a short pad of silica, eluting with DCM, under nitrogen. The filtrate was concentrated, and the acyl intermediate that remained was dissolved in DMF (5 mL) under nitrogen. The solution of acyl intermediate was added to a solution of 5,6-dimethyl-1H-1,3-benzodiazol-2-amine (500 mg, 3.1 mmol) in DMF (5 mL) followed by triethylamine (516 μL, 3.88 mmol). The reaction mixture was stirred for a further 1 h and then concentrated. The residue was dissolved in EtOAc (20 mL) and washed with saturated citric acid$_{(aq)}$ (30 mL). The aqueous layer was extracted with EtOAc (20 mL). The combined organic extracts were washed with water (2×20 mL) and brine (25 mL) and then dried (MgSO$_4$), filtered and concentrated. The crude product was purified by trituration in DCM to afford the title compound as a pink solid (505 mg, 61%).

Example 243

N-[9-acetyl-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide (ABR 240024)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide (150 mg, 0.26 mmol), palladium(II) acetate (6 mg, 26 μmop, propane-1,3-diylbis(diphenylphosphane) (21 mg, 0.05 mmol), K$_2$CO$_3$ (47 mg, 0.34 mmol), 1-(ethenyloxy)butane (170 μL, 1.30 mmol) and de-gassed DMF/water (3:1, 4 mL) under nitrogen. The reaction was stirred at 100° C. for 20 h and then concentrated. The resulting residue was diluted with EtOAc (10 mL) and brine (10 mL). The aqueous phase was washed with EtOAc (15 mL) and the organic washings discarded. The aqueous phase was then extracted with IPA/CHCl$_3$ (2×25 mL). The combined organic extracts were dried (MgSO$_4$), filtered and concentrated. The crude product was purified by automated reverse phase HPLC (low pH Method A) to afford the title compound as a white solid (24 mg, 19%).

Example 244

N-[9-(3-chlorophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (ABR 240025)

A microwave tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (75 mg, 0.16 mmol), (3-chlorophenyl)boronic acid (32 mg, 0.2 mmol), 2M Na$_2$CO$_{3(aq)}$ (0.15 mL), DME (0.80 mL) and EtOH (0.30 mL). The solution was de-gassed with nitrogen. Pd(PPh$_3$)$_4$ (19 mg, 0.02 mmol) was added, the solution was de-gassed with nitrogen and the tube was sealed. The reaction was stirred in the microwave at 120° C. for 1.5 h. The reaction mixture was filtered through Celite™, rinsing with MeOH (30 mL). The filtrate was concentrated. The crude product was purified by automated reverse phase HPLC (low pH Method A) to afford the title compound as a yellow solid (35 mg, 44%).

Example 245

3-cyclopentyl-N-[4-oxo-3-(trifluoromethyl)-9-[4-(trifluoromethyl)phenyl]-2,5,7-triazatricyclo[6.4.0.0$^{2,6}$]dodeca-1(12),6,8,10-tetraen-3-yl]propanamide (ABR 240022)

The procedure for the preparation of N-[9-(3-chlorophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide was used, except that [4-(trifluoromethyl)phenyl]boronic acid was used instead of (3-chlorophenyl)boronic acid (47%).

Example 246

3-cyclopentyl-N-[9-(4-fluorophenyl)-4-oxo-3-(trifluoromethyl)-2,5,7-triazatricyclo[6.4.0.0$^{2,6}$]dodeca-1(12),6,8,10-tetraen-3-yl]propanamide (ABR 240023)

The procedure for the preparation of N-[9-(3-chlorophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide was used, except that (4-fluorophenyl)boronic acid was used instead of (3-chlorophenyl)boronic acid (29%).

Example 247

3-(3-cyclopentylpropanamido)-N-methanesulfonyl-10-methoxy-4-oxo-3-(trifluoromethyl)-2,5,7-triazatricyclo[6.4.0.0$^{2,6}$]dodeca-1(12),6,8,10-tetraene-9-carboxamide (ABR 240026)

To a stirred solution of methanesulfonamide (50 mg, 0.53 mmol) in DMF (3 mL) at 0° C. under nitrogen was added NaH (60%, 21 mg, 0.53 mmol). The reaction was stirred at 0° C. for 30 min and then a solution of phenyl 3-(3-cyclopentylpropanamido)-10-methoxy-4-oxo-3-(trifluoromethyl)-2,5,7-triazatricyclo[6.4.0.0$^{2,6}$]dodeca-1(12),6,8,10-tetraene-9-carboxylate (70 mg, 0.13 mmol) in DMF (2 mL) was added. The reaction was allowed to warm to room temperature and was then heated at 50° C. for 4 h. The reaction was quenched with saturated NH$_4$Cl$_{(aq)}$ at 0° C. and then concentrated. The resulting residue was diluted with EtOAc (50 mL) and water (25 mL). The organic layer was washed with water (2×25 mL), brine (2×25 mL), dried (MgSO$_4$), filtered and concentrated. The crude product was purified by automated reverse phase HPLC (low pH Method A) to afford the title compound as a beige solid (30 mg, 43%).

Example 248

3-cyclopentyl-N-[9-(methoxymethyl)-4-oxo-3-(trifluoromethyl)-2,5,7-triazatricyclo[6.4.0.0$^{2,6}$]dodeca-1(12),6,8,10-tetraen-3-yl]propanamide (ABR 240027)

To a stirred solution of 3-cyclopentyl-N-[9-(hydroxymethyl)-4-oxo-3-(trifluoromethyl)-2,5,7-triazatricyclo[6.4.0.0$^{2,6}$]dodeca-1(12),6,8,10-tetraen-3-yl]propanamide (60 mg, 0.13 mmol) in MeOH (1.0 mL) at 0° C. was added concentrated H$_2$SO$_4$ (0.01 mL, 0.15 mol). The reaction was heated at 50° C. for 24 h. Additional concentrated H₂SO₄ (0.02 mL, 0.30 mol) was added at 0° C. The reaction was heated at 60° C. for 24 h. The reaction was concentrated, the residue was dissolved in EtOAc (5 mL) and washed with saturated NaHCO$_{3(aq)}$ (3 mL), water (3 mL) and brine (3 mL). The organic phase was dried (Na₂SO₄), filtered and concentrated. The crude was purified by automated reverse phase HPLC (low pH Method A) to afford the title compound as a white solid (13 mg, 23%).

Example 249 tert-butyl 3-{[10,11-dimethyl-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate (ABR 240049)

The procedure to prepare tert-butyl 6-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}-2-azaspiro-[3.3]heptane-2-carboxylate was used, except that tert-butyl 3-carbamoylpyrrolidine-1-carboxylate was used instead of tert-butyl 6-carbamoyl-2-azaspiro[3.3]heptane-2-carboxylate and 5,6-dimethyl-1H-1,3-benzodiazol-2-amine used instead of 5,6-dichloro-1H-1,3-benzodiazol-2-amine. An additional 1 equivalent of methyl 3,3,3-trifluoro-2-oxopropanoate was added 2 h after the initial charge. Final purification was carried out using automated reverse phase HPLC (high pH Method A); (20%); m/z=426.1 (MH-tBu)⁺.

Example 250 tert-butyl 4-{[10,11-dimethyl-4-oxo-3-(trifluoromethyl)-2,5,7-triazatricyclo-[6.4.0.0$^{2,6}$]dodeca-1(12),6,8,10-tetraen-3-yl]carbamoyl}piperidine-1-carboxylate (ABR 240050)

The procedure to prepare tert-butyl 6-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}-2-azaspiro[3.3]heptane-2-carboxylate was used, except that tert-butyl 4-carbamoylpiperidine-1-carboxylate was used instead of tert-butyl 6-carbamoyl-2-azaspiro[3.3]heptane-2-carboxylate and 5,6-dimethyl-1H-benzo[d]imidazol-2-amine used instead of 5,6-dichloro-1H-benzo[d]imidazol-2-amine; (40%); m/z=440.1 (MH-$^t$Bu)⁺.

Example 251 tert-butyl (2S)-2-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate (ABR 240051)

The procedure to prepare tert-butyl 6-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}-2-azaspiro[3.3]heptane-2-carboxylate was used, except that tert-butyl (2S)-2-carbamoylpyrrolidine-1-carboxylate was used instead of tert-butyl 6-carbamoyl-2-azaspiro[3.3]heptane-2-carboxylate; (29%); m/z=465.8, 467.8 (MH-$^t$Bu)⁺.

Example 252 tert-butyl 3-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate (ABR 240052)

The procedure to prepare tert-butyl 6-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}-2-azaspiro[3.3]heptane-2-carboxylate was used, except that tert-butyl 3-carbamoylpyrrolidine-1-carboxylate was used instead of tert-butyl 6-carbamoyl-2-azaspiro[3.3]heptane-2-carboxylate. Final purification was carried out using automated reverse phase HPLC (high pH Method A) to afford the title compound as mixture of diastereomers; (32%); m/z=466.1, 468.1 (MH-tBu)⁺.

Example 253 tert-butyl 4-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}piperidine-1-carboxylate (ABR 240053)

The procedure to prepare tert-butyl 6-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}-2-azaspiro[3.3]heptane-2-carboxylate was used, except that tert-butyl 4-carbamoylpiperidine-1-carboxylate was used instead of tert-butyl 6-carbamoyl-2-azaspiro[3.3]heptane-2-carboxylate; (40%); m/z=480.1, 482.1 (MH-tBu)⁺.

Example 254 tert-butyl 3-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}azetidine-1-carboxylate (ABR 240054)

The procedure to prepare tert-butyl 6-{[10,11-dichloro-4-oxo-3-(trifluoromethyl)-2,5,7-triazatricyclo[6.4.0.0$^{2,6}$]dodeca-1(12),6,8,10-tetraen-3-yl]carbamoyl}-2-azaspiro[3.3]heptane-2-carboxylate was used, except that tert-butyl 3-carbamoylazetidine-1-carboxylate was used instead of tert-butyl 6-carbamoyl-2-azaspiro[3.3]heptane-2-carboxylate; (22%); m/z=451.8, 453.8 (MH-tBu)⁺.

Example 255 tert-butyl 4-({[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}methyl)piperidine-1-carboxylate (ABR 240055)

To a stirred solution of tert-butyl 4-(carbamoylmethyl)piperidine-1-carboxylate (1.00 g, 4.00 mmol) in DMF (8 mL) were added pyridine (316 μL, 4.00 mmol) and ethyl 3,3,3-trifluoro-2-oxopropanoate (104 μL, 4.00 mmol) under argon. The reaction mixture was stirred at room temperature for 1 h and then thionyl chloride (300 μL, 4.00 mmol) was added dropwise. The reaction mixture was stirred at room temperature for further 16 h and then concentrated to provide the acyl imine intermediate. The acyl imine intermediate was dissolved in DMF (5 mL) and added to a solution of 5,6-dichloro-1H-1,3-benzodiazol-2-amine (804 mg, 4.00 mmol) in DMF (7 mL), followed by triethylamine (0.56 mL, 4.00 mmol). The reaction mixture was stirred at room temperature for 4 h. The reaction was diluted with brine (25 mL) and extracted with EtOAc (2×50 mL). The combined organic phases were washed with water, dried (Na₂SO₄), filtered and concentrated. The crude product was purified by silica chromatography, using 2% MeOH in DCM as eluent, to afford the title compound as a red solid (65 mg, 6%); m/z=450.4, 452.4 (MH-CO₂tBu)⁺.

Example 256 tert-butyl 2-(2-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}ethyl)piperidine-1-carboxylate (ABR 240056)

The procedure for the preparation of tert-butyl 4-({[10,11-dichloro-4-oxo-3-(trifluoromethyl)-2,5,7-triazatricyclo [6.4.0.0$^{2,6}$]dodeca-1(12),6,8,10-tetraen-3-yl]-carbamoyl}methyl)piperidine-1-carboxylate was used except that tert-butyl 2-(2-carbamoylethyl)piperidine-1-carboxylate was used instead of tert-butyl 4-(carbamoylmethyl)piperidine-1-carboxylate (17%); m/z=463.4, 465.4 (MH-CO$_2$$^t$Bu)$^+$.

Example 257 tert-butyl 3-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}-3-fluoroazetidine-1-carboxylate (ABR 240057)

To a stirred solution of tert-butyl 3-carbamoyl-3-fluoroazetidine-1-carboxylate (285 mg, 1.30 mmol) in DMF (25 mL) were added pyridine (105 □L, 1.30 mmol) followed by methyl 3,3,3-trifluoro-2-oxopropanoate (407 mg, 2.61 mmol) under nitrogen. The reaction was stirred at room temperature for 2 h. Thionyl chloride (95 µl, 1.30 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (10 mL) under nitrogen. A solution of 5,6-dichloro-1H-1,3-benzodiazol-2-amine (220 mg, 1.08 mmol) in DMF (10 mL) and triethylamine (182 µl, 1.30 mmol) were added. The reaction was stirred for 2 h before being concentrated. The residue was dissolved in EtOAc (50 mL) and washed with water (4×50 mL) and brine (3×50 mL). The organic phase was dried (Na$_2$SO$_4$), filtered and concentrated. The crude product was purified using automated reverse phase HPLC (low pH Method A) to afford the title compound as a yellow solid (59 mg, 10%); m/z=469.8, 471.8 (MH-$^t$Bu)$^+$

Example 258 methyl 3-[3-(3-cyclopentylpropanamido)-4-oxo-3-(trifluoromethyl)-2,5,7-triazatricyclo[6.4.0.0$^{2,6}$]dodeca-1(12),6,8,10-tetraen-9-yl]benzoate (ABR 240058)

A sealed tube was charged with N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide (100 mg, 0.22 mmol), [3-(methoxycarbonyl)phenyl]boronic acid (49 mg, 0.27 mmol), Na$_2$CO$_3$ (42 mg, 0.39 mmol), water (0.20 mL), DME (3.00 mL), and EtOH (1.25 mL). The solution was de-gassed with nitrogen. Pd(PPh$_3$)$_4$ (25 mg, 0.02 mmol) was added, the solution was de-gassed with nitrogen and the tube was sealed. The reaction was stirred at 100° C. for 18 h. The reaction mixture was filtered through Celite™, rinsing with MeOH (30 mL) and the filtrate was concentrated. The resulting residue was dissolved in EtOAc (20 mL), washed with water (30 mL), saturated citric acid$_{(aq)}$ (30 mL) and brine (30 mL) and then dried (MgSO$_4$), filtered and concentrated. The crude product was purified by silica chromatography, using 0-100% EtOAc in heptane and then 0-10% MeOH in DCM as eluent, to afford the title compound as a brown solid (50 mg, 30%); m/z=515.3 (MH)$^+$.

Example 259

N-[10,11-dimethyl-4-oxo-3-(trifluoromethyl)-2,5,7-triazatricyclo[6.4.0.0$^{2,6}$]dodeca-1(12),6,8,10-tetraen-3-yl]acetamide (ABR 238786)

To a solution of acetamide (220 mg, 3.72 mmol) in DMF (50 mL) was added methyl 3,3,3-trifluoro-2-oxopropanoate (678 mg, 4.34 mmol) followed by pyridine (300 µL, 3.72 mmol) under nitrogen. The reaction was stirred at room temperature for 2 h. Thionyl chloride (270 µL, 3.72 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (25 mL) under nitrogen. The solution of acyl intermediate was added to a solution of 5,6-dimethyl-1H-1,3-benzodiazol-2-amine (0.50 g, 3.1 mmol) in DMF (25 mL) followed by triethylamine (519 µL, 3.72 mmol). The reaction mixture was stirred for a further 16 h and then concentrated. The residue was dissolved in EtOAc (100 mL), washed with 10% citric acid$_{(aq)}$ (3×50 mL), water (3×50 mL) and brine (3×50 mL) and then dried (MgSO$_4$), filtered and concentrated. The crude product was purified by trituration in DCM to afford the title compound as a white solid (182 mg, 18%); m/z=327.0 (MH)$^+$.

Example 260

N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]acetamide (ABR 240059)

To a stirred solution of N-[10,11-dimethyl-4-oxo-3-(trifluoromethyl)-2,5,7-triazatricyclo[6.4.0.0$^{2,6}$]dodeca-1(12),6,8,10-tetraen-3-yl]acetamide (150 mg, 0.46 mmol) in DCM (25 mL) was added NBS (82 mg, 0.46 mmol). Initially, the reaction was stirred at room temperature for 3 h. The reaction was then stirred for a further 20 h. During this period, additional NBS (164 mg, 0.92 mmol) was added portionwise. The reaction was then concentrated. The residue was dissolved in EtOAc (50 mL) and washed with water (2×50 mL) and brine (50 mL). The organic phase was dried (MgSO$_4$), filtered and concentrated. The crude product was triturated in DCM to afford the title compound as a yellow solid (122 mg, 66%); m/z=404.8, 406.8 (MH)$^+$.

Example 261

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]pyrimidine-4-carboxamide (ABR 239626)

To a stirred solution of 2-chloropyrimidine-4-carboxamide, available via a literature method: PCT Int. Appl., 2001068612 (330 mg, 2.08 mmol) in DMF (6 mL) was added methyl 3,3,3-trifluoro-2-oxopropanoate (355 μL, 3.47 mmol) followed by pyridine (170 μL, 2.08 mmol) under nitrogen. The reaction was stirred at room temperature for 2 h. Thionyl chloride (150 μL, 2.08 mmol) was added at 0° C. The reaction was stirred for 1 h at 0° C. and then concentrated. The residue was filtered through a short pad of silica, eluting with DCM, under nitrogen. The filtrate was concentrated, and the acyl intermediate that remained was dissolved in DMF (5 mL) under nitrogen. The solution of acyl intermediate was added to a solution of 5,6-dimethyl-1H-1, 3-benzodiazol-2-amine (280 mg, 1.74 mmol) in DMF (8 mL) followed by triethylamine (280 μL, 2.08 mmol). The reaction mixture was stirred for a further 16 h and then concentrated. The residue was dissolved in EtOAc (50 mL) and washed with water (3×50 mL) and brine (2×50 mL) and then dried (MgSO$_4$), filtered and concentrated to afford 2-chloro-N-[10,11-dimethyl-4-oxo-3-(trifluoromethyl)-2,5, 7-triazatricyclo[6.4.0.0$^{2,6}$]dodeca-1(12),6,8,10-tetraen-3-yl] pyrimidine-4-carboxamide. (260 mg, 15%). m/z=424.95 (MH)$^+$.

A sealable tube was charged with a portion of 2-chloro-N-[10,11-dimethyl-4-oxo-3-(trifluoromethyl)-2,5,7-triazatricyclo[6.4.0.0$^{2,6}$]dodeca-1(12),6,8,10-tetraen-3-yl]pyrimidine-4-carboxamide (250 mg, 0.35 mmol), 2-methoxyethan-1-amine (92 μL, 1.06 mmol), K2CO3 (150 mg, 1.06 mmol) and DMF (5 mL). The tube was flushed with nitrogen, sealed and stirred at 100° C. for 6 h. Then reaction mixture was concentrated and the resulting residue was diluted with EtOAc (20 mL) and water (20 mL). The aqueous phase was extracted with EtOAc (2×10 mL). The combined organic extracts were washed with 10% citric acid (aq) (2×20 mL) and brine (20 mL) and then dried (MgSO4), filtered and concentrated. The crude product was purified by automated reverse phase HPLC (low pH Method A) to afford the title compound as a white solid (50 mg, 31%).

Structural formulas for the compounds of the above Examples are shown in Table 1.

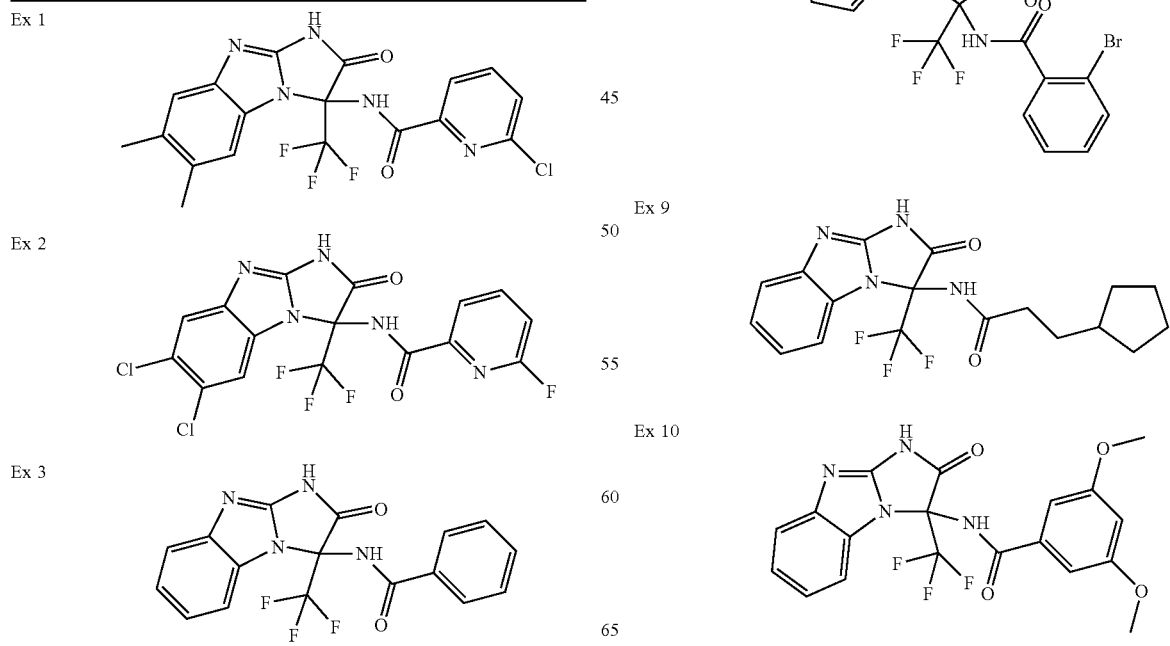

TABLE 1

TABLE 1-continued
Ex 11 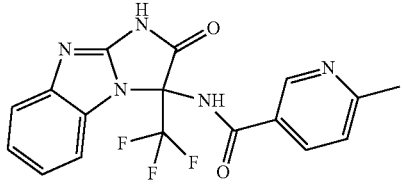 [SMILES: Cc1ccc(C(=O)NC2(C(F)(F)F)C(=O)Nc3nc4ccccc4n32)cn1]
Ex 12 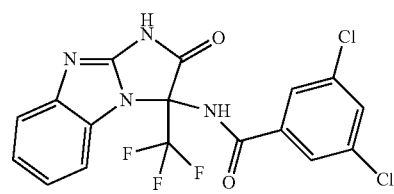 [SMILES: O=C(NC1(C(F)(F)F)C(=O)Nc2nc3ccccc3n21)c1cc(Cl)cc(Cl)c1]
Ex 13 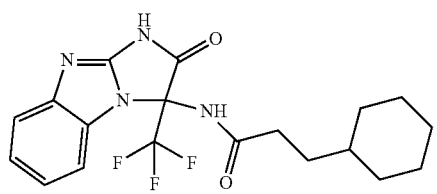 [SMILES: O=C(CCC1CCCCC1)NC1(C(F)(F)F)C(=O)Nc2nc3ccccc3n21]
Ex 14 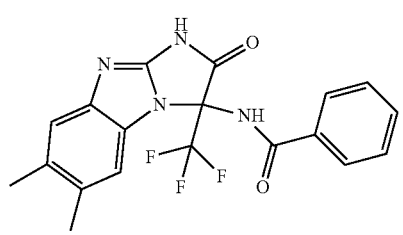 [SMILES: Cc1cc2nc3n(c2cc1C)C(NC(=O)c1ccccc1)(C(F)(F)F)C(=O)N3]
Ex 15 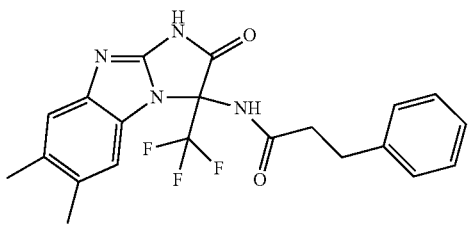 [SMILES: Cc1cc2nc3n(c2cc1C)C(NC(=O)CCc1ccccc1)(C(F)(F)F)C(=O)N3]
Ex 16 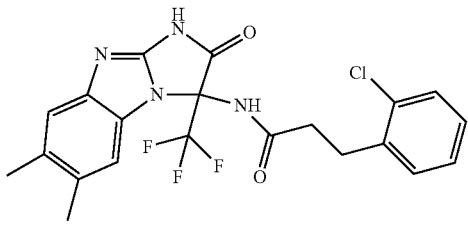 [SMILES: Cc1cc2nc3n(c2cc1C)C(NC(=O)CCc1ccccc1Cl)(C(F)(F)F)C(=O)N3]
Ex 17 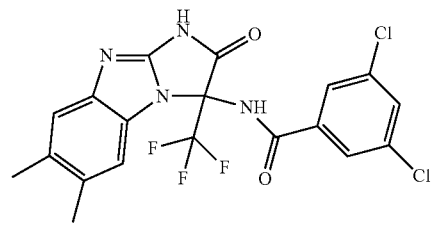 [SMILES: Cc1cc2nc3n(c2cc1C)C(NC(=O)c1cc(Cl)cc(Cl)c1)(C(F)(F)F)C(=O)N3]
TABLE 1-continued
Ex 18 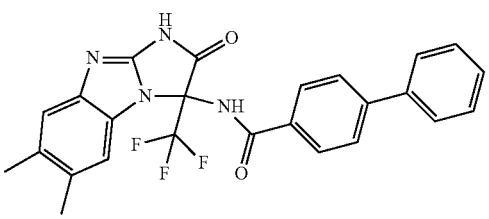 [SMILES: Cc1cc2nc3n(c2cc1C)C(NC(=O)c1ccc(-c2ccccc2)cc1)(C(F)(F)F)C(=O)N3]
Ex 19 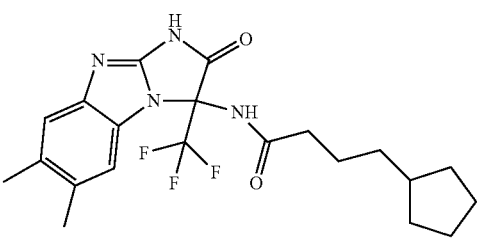 [SMILES: Cc1cc2nc3n(c2cc1C)C(NC(=O)CCCC1CCCC1)(C(F)(F)F)C(=O)N3]
Ex 20 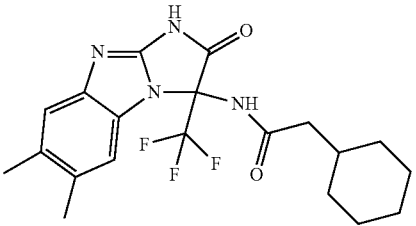 [SMILES: Cc1cc2nc3n(c2cc1C)C(NC(=O)CC1CCCCC1)(C(F)(F)F)C(=O)N3]
Ex 21 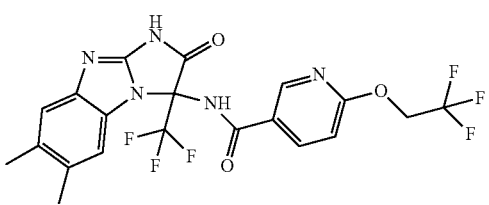 [SMILES: Cc1cc2nc3n(c2cc1C)C(NC(=O)c1ccc(OCC(F)(F)F)nc1)(C(F)(F)F)C(=O)N3]
Ex 22 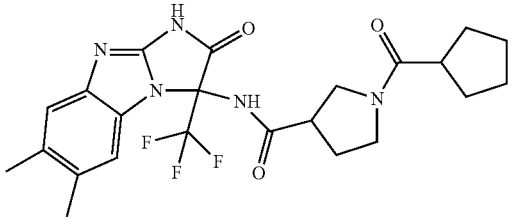 [SMILES: Cc1cc2nc3n(c2cc1C)C(NC(=O)C1CCN(C(=O)C2CCCC2)C1)(C(F)(F)F)C(=O)N3]
Ex 23 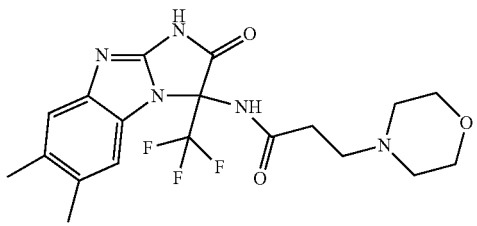 [SMILES: Cc1cc2nc3n(c2cc1C)C(NC(=O)CCN1CCOCC1)(C(F)(F)F)C(=O)N3]
Ex 24 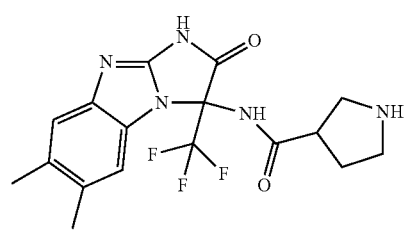 [SMILES: Cc1cc2nc3n(c2cc1C)C(NC(=O)C1CCNC1)(C(F)(F)F)C(=O)N3]

TABLE 1-continued
| Ex 25 | 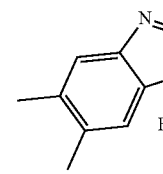 |
| Ex 26 | |
| Ex 27 | |
| Ex 28 | |
| Ex 29 | |
| Ex 30 | |
| Ex 31 | |
| Ex 32 | |
TABLE 1-continued
| Ex 33 | 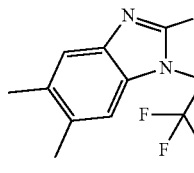 |
| Ex 34 | |
| Ex 35 | |
| Ex 36 | |
| Ex 37 | |
| Ex 38 | |
| Ex 39 | |

TABLE 1-continued
Ex 40 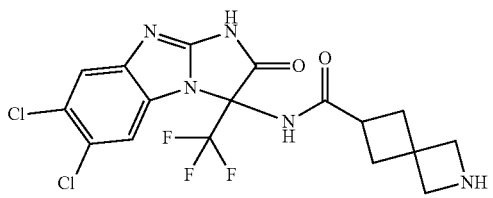 [SMILES: O=C(NC1(C(F)(F)F)C(=O)Nc2nc3cc(Cl)c(Cl)cc3n21)C1CC2(CNC2)C1]
Ex 41 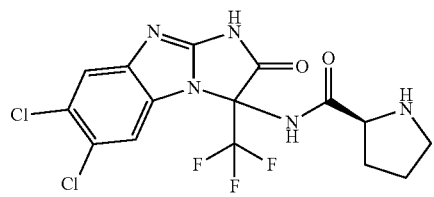 [SMILES: O=C(NC1(C(F)(F)F)C(=O)Nc2nc3cc(Cl)c(Cl)cc3n21)[C@@H]1CCCN1]
Ex 42 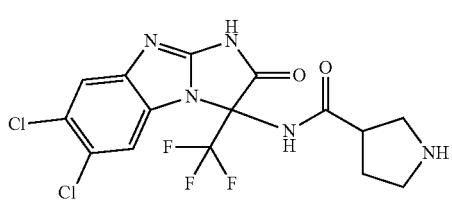 [SMILES: O=C(NC1(C(F)(F)F)C(=O)Nc2nc3cc(Cl)c(Cl)cc3n21)C1CCNC1]
Ex 43 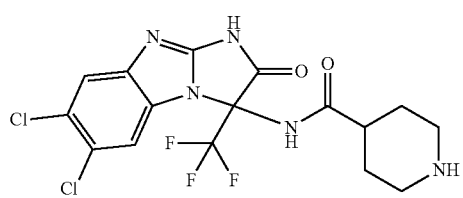 [SMILES: O=C(NC1(C(F)(F)F)C(=O)Nc2nc3cc(Cl)c(Cl)cc3n21)C1CCNCC1]
Ex 44 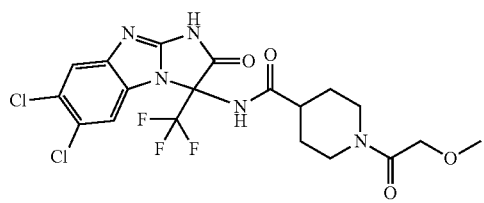 [SMILES: COCC(=O)N1CCC(C(=O)NC2(C(F)(F)F)C(=O)Nc3nc4cc(Cl)c(Cl)cc4n32)CC1]
Ex 45 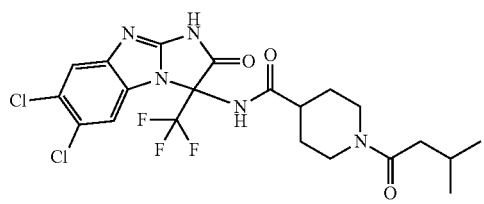 [SMILES: CC(C)CC(=O)N1CCC(C(=O)NC2(C(F)(F)F)C(=O)Nc3nc4cc(Cl)c(Cl)cc4n32)CC1]
Ex 46 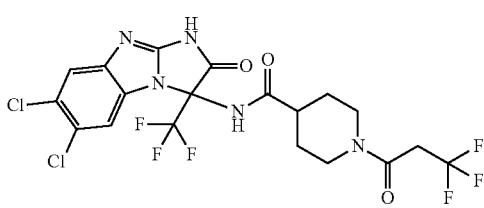 [SMILES: O=C(NC1(C(F)(F)F)C(=O)Nc2nc3cc(Cl)c(Cl)cc3n21)C1CCN(C(=O)CC(F)(F)F)CC1]
Ex 47 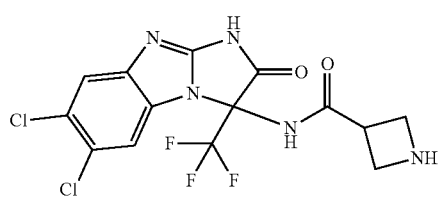 [SMILES: O=C(NC1(C(F)(F)F)C(=O)Nc2nc3cc(Cl)c(Cl)cc3n21)C1CNC1]
TABLE 1-continued
Ex 48 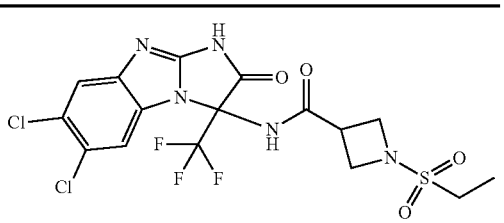
Ex 49 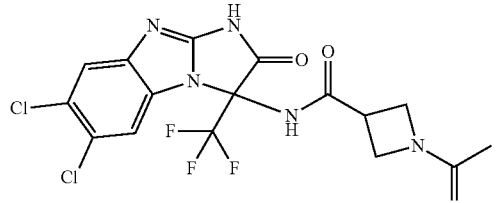
Ex 50 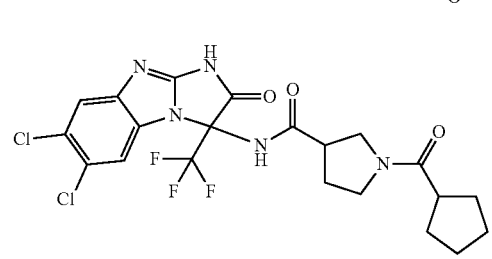
Ex 51 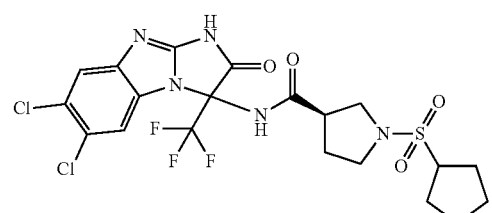
Ex 52 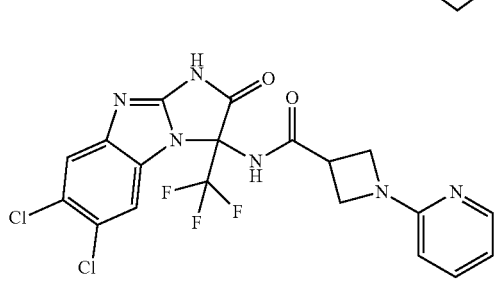
Ex 53 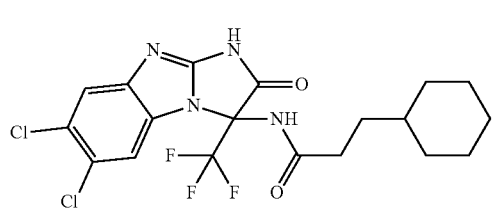 [SMILES: O=C(CCC1CCCCC1)NC1(C(F)(F)F)C(=O)Nc2nc3cc(Cl)c(Cl)cc3n21]
Ex 54 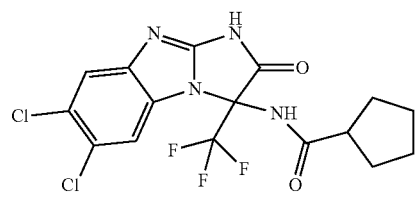 [SMILES: O=C(NC1(C(F)(F)F)C(=O)Nc2nc3cc(Cl)c(Cl)cc3n21)C1CCCC1]

TABLE 1-continued
Ex 55 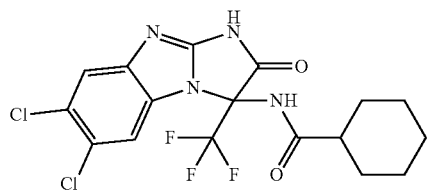 [SMILES: O=C(NC1(C(F)(F)F)C(=O)Nc2nc3cc(Cl)c(Cl)cc3n21)C1CCCCC1]
Ex 56 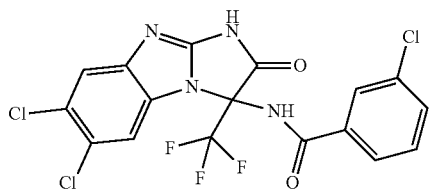 [SMILES: O=C(NC1(C(F)(F)F)C(=O)Nc2nc3cc(Cl)c(Cl)cc3n21)c1cccc(Cl)c1]
Ex 57 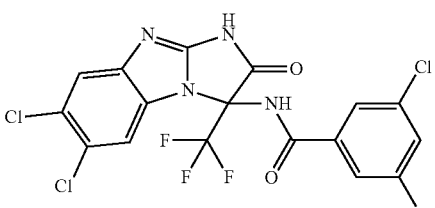
Ex 58 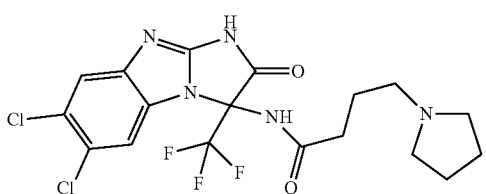 [SMILES: O=C(CCCN1CCCC1)NC1(C(F)(F)F)C(=O)Nc2nc3cc(Cl)c(Cl)cc3n21]
Ex 59 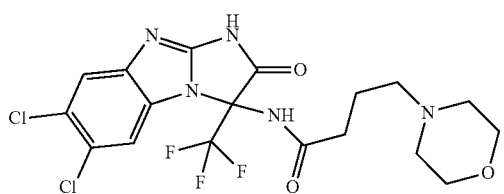 [SMILES: O=C(CCCN1CCOCC1)NC1(C(F)(F)F)C(=O)Nc2nc3cc(Cl)c(Cl)cc3n21]
Ex 60 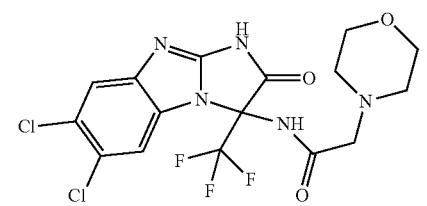 [SMILES: O=C(CN1CCOCC1)NC1(C(F)(F)F)C(=O)Nc2nc3cc(Cl)c(Cl)cc3n21]
Ex 61 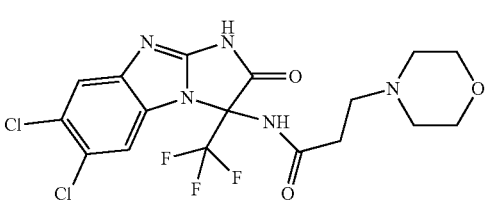 [SMILES: O=C(CCN1CCOCC1)NC1(C(F)(F)F)C(=O)Nc2nc3cc(Cl)c(Cl)cc3n21]
Ex 62 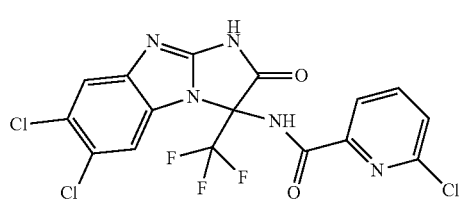 [SMILES: O=C(NC1(C(F)(F)F)C(=O)Nc2nc3cc(Cl)c(Cl)cc3n21)c1cccc(Cl)n1]
TABLE 1-continued
Ex 63 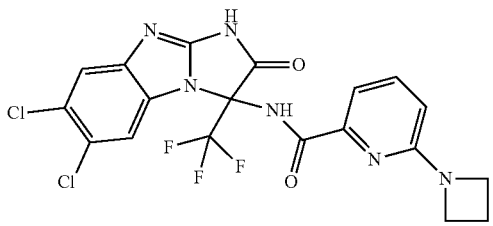 [SMILES: O=C(NC1(C(F)(F)F)C(=O)Nc2nc3cc(Cl)c(Cl)cc3n21)c1cccc(N2CCC2)n1]
Ex 64 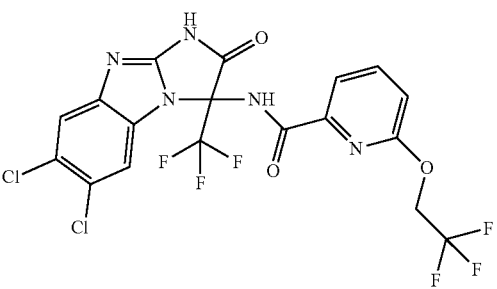 [SMILES: O=C(NC1(C(F)(F)F)C(=O)Nc2nc3cc(Cl)c(Cl)cc3n21)c1cccc(OCC(F)(F)F)n1]
Ex 65 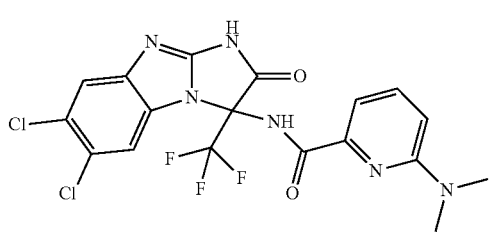 [SMILES: CN(C)c1cccc(C(=O)NC2(C(F)(F)F)C(=O)Nc3nc4cc(Cl)c(Cl)cc4n32)n1]
Ex 66 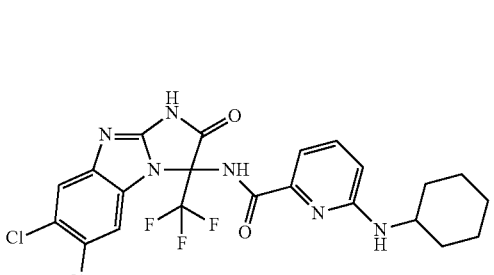
Ex 67 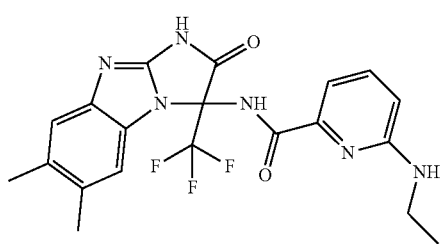 [SMILES: CCNc1cccc(C(=O)NC2(C(F)(F)F)C(=O)Nc3nc4cc(C)c(C)cc4n32)n1]
Ex 68 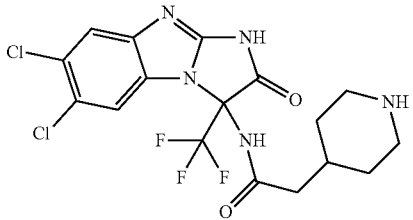 [SMILES: O=C(CC1CCNCC1)NC1(C(F)(F)F)C(=O)Nc2nc3cc(Cl)c(Cl)cc3n21]

TABLE 1-continued
Ex 69 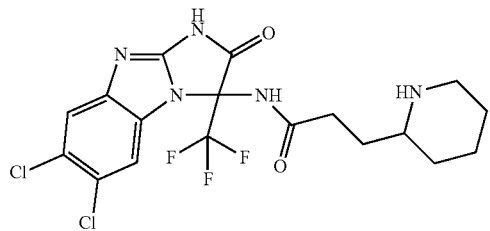 [SMILES: O=C(CCC1CCCCN1)NC1(C(F)(F)F)C(=O)Nc2nc3cc(Cl)c(Cl)cc3n21]
Ex 70 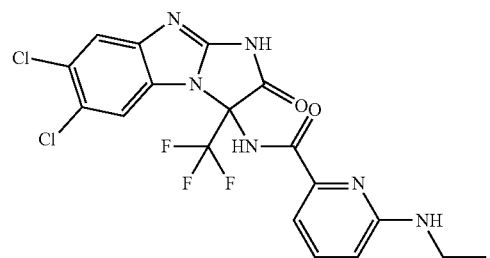 [SMILES: CCNc1cccc(C(=O)NC2(C(F)(F)F)C(=O)Nc3nc4cc(Cl)c(Cl)cc4n32)n1]
Ex 71 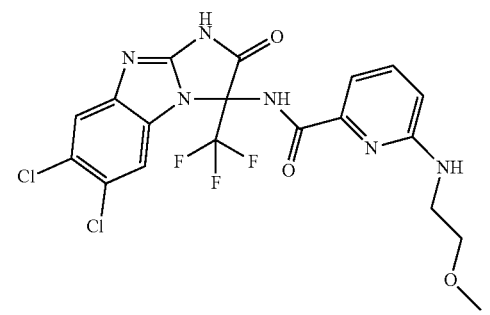 [SMILES: COCCNc1cccc(C(=O)NC2(C(F)(F)F)C(=O)Nc3nc4cc(Cl)c(Cl)cc4n32)n1]
Ex 72 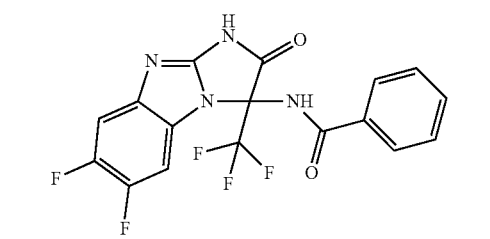 [SMILES: O=C(NC1(C(F)(F)F)C(=O)Nc2nc3cc(F)c(F)cc3n21)c1ccccc1]
Ex 73 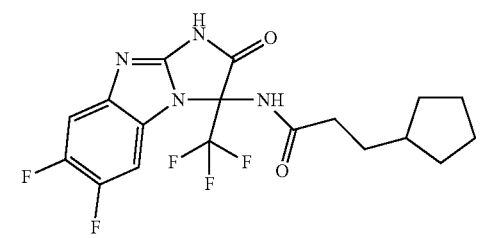 [SMILES: O=C(CCC1CCCC1)NC1(C(F)(F)F)C(=O)Nc2nc3cc(F)c(F)cc3n21]
Ex 74 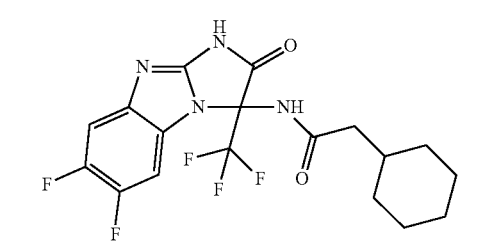 [SMILES: O=C(CC1CCCCC1)NC1(C(F)(F)F)C(=O)Nc2nc3cc(F)c(F)cc3n21]
TABLE 1-continued
Ex 75 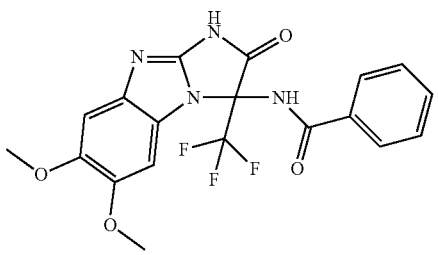 [SMILES: COc1cc2nc3n(c2cc1OC)C(NC(=O)c1ccccc1)(C(F)(F)F)C(=O)N3]
Ex 76 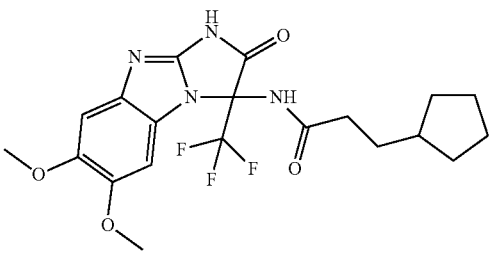 [SMILES: COc1cc2nc3n(c2cc1OC)C(NC(=O)CCC1CCCC1)(C(F)(F)F)C(=O)N3]
Ex 77 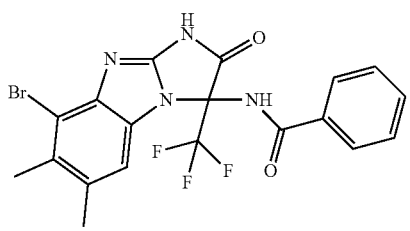 [SMILES: Cc1cc2c(nc3n2C(NC(=O)c2ccccc2)(C(F)(F)F)C(=O)N3)c(Br)c1C]
Ex 78 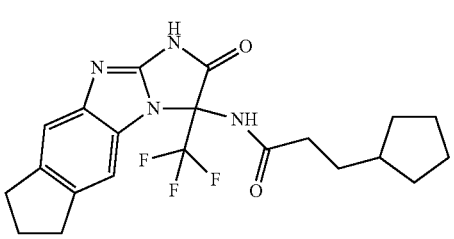 [SMILES: O=C(CCC1CCCC1)NC1(C(F)(F)F)C(=O)Nc2nc3cc4c(cc3n21)CCC4]
Ex 79 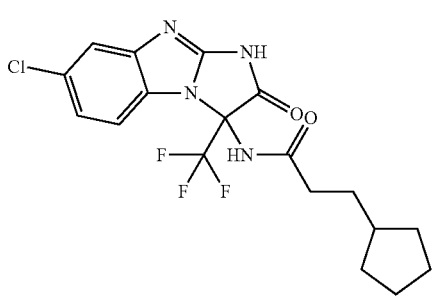 [SMILES: O=C(CCC1CCCC1)NC1(C(F)(F)F)C(=O)Nc2nc3cc(Cl)ccc3n21]
(regioisomer1)
Ex 79 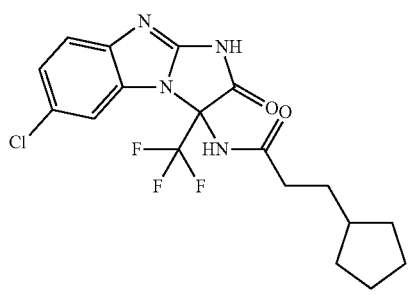 [SMILES: O=C(CCC1CCCC1)NC1(C(F)(F)F)C(=O)Nc2nc3ccc(Cl)cc3n21]
(regioisomer2)

TABLE 1-continued
| | |
|---|---|
| Ex 80 | 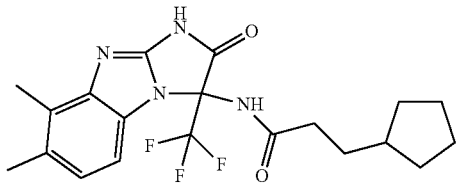 [SMILES: Cc1ccc2c(nc3n2C(NC(=O)CCC2CCCC2)(C(F)(F)F)C(=O)N3)c1C] |
| Ex 81 | 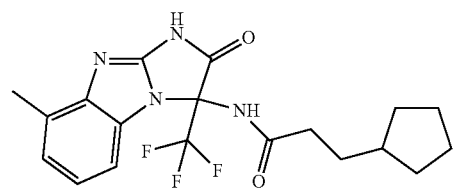 [SMILES: Cc1cccc2c1nc1n2C(NC(=O)CCC2CCCC2)(C(F)(F)F)C(=O)N1] |
| Ex 82 | 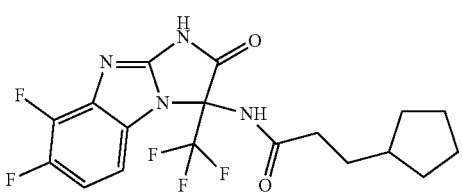 [SMILES: O=C(CCC1CCCC1)NC1(C(F)(F)F)C(=O)Nc2nc3c(F)c(F)ccc3n21] |
| Ex 83 | 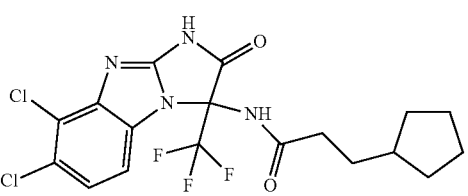 [SMILES: O=C(CCC1CCCC1)NC1(C(F)(F)F)C(=O)Nc2nc3c(Cl)c(Cl)ccc3n21] |
| Ex 84 | 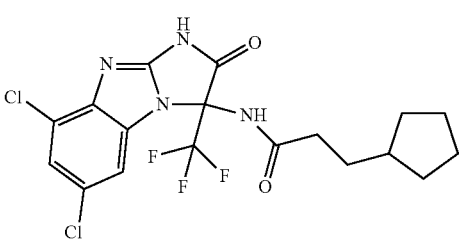 [SMILES: O=C(CCC1CCCC1)NC1(C(F)(F)F)C(=O)Nc2nc3c(Cl)cc(Cl)cc3n21] |
| Ex 85 | 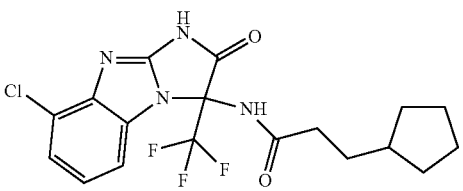 [SMILES: O=C(CCC1CCCC1)NC1(C(F)(F)F)C(=O)Nc2nc3c(Cl)cccc3n21] |
| Ex 86 | 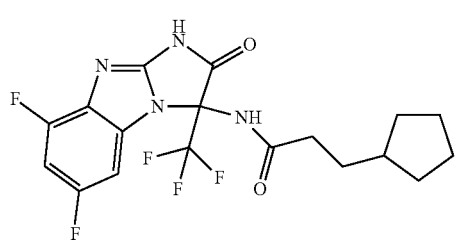 [SMILES: O=C(CCC1CCCC1)NC1(C(F)(F)F)C(=O)Nc2nc3c(F)cc(F)cc3n21] |
| Ex 87 | 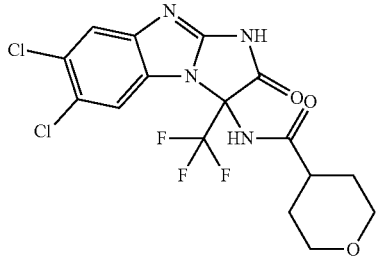 [SMILES: O=C(NC1(C(F)(F)F)C(=O)Nc2nc3cc(Cl)c(Cl)cc3n21)C1CCOCC1] |
| Ex 88 | 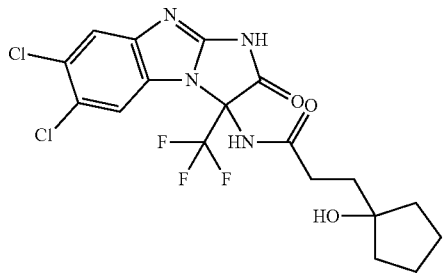 [SMILES: O=C(CCC1(O)CCCC1)NC1(C(F)(F)F)C(=O)Nc2nc3cc(Cl)c(Cl)cc3n21] |
| Ex 89 | 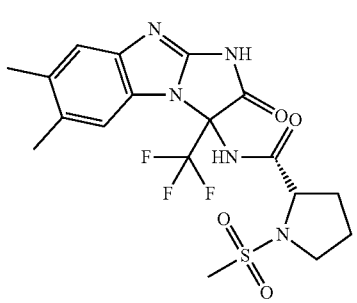 |
| Ex 90 | 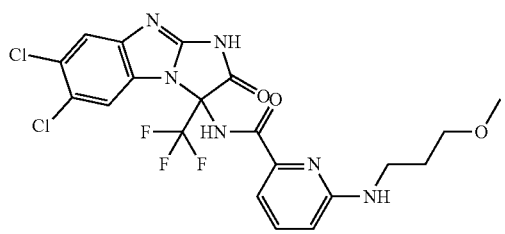 [SMILES: COCCCNc1cccc(C(=O)NC2(C(F)(F)F)C(=O)Nc3nc4cc(Cl)c(Cl)cc4n32)n1] |
| Ex 91 | 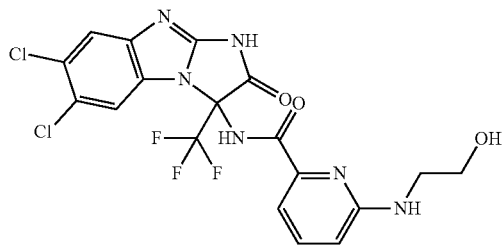 [SMILES: O=C(NC1(C(F)(F)F)C(=O)Nc2nc3cc(Cl)c(Cl)cc3n21)c1cccc(NCCO)n1] |
| Ex 92 | 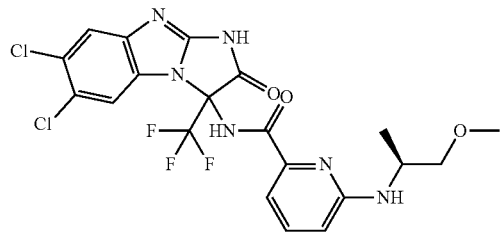 [SMILES: COC[C@H](C)Nc1cccc(C(=O)NC2(C(F)(F)F)C(=O)Nc3nc4cc(Cl)c(Cl)cc4n32)n1] |

TABLE 1-continued
Ex 93 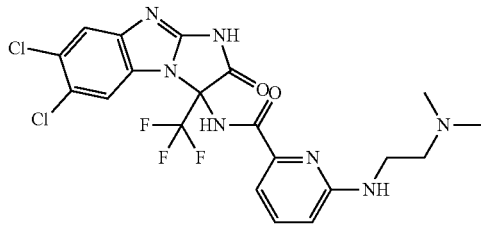 [SMILES: CN(C)CCNc1cccc(C(=O)NC2(C(F)(F)F)C(=O)Nc3nc4cc(Cl)c(Cl)cc4n32)n1]
Ex 94 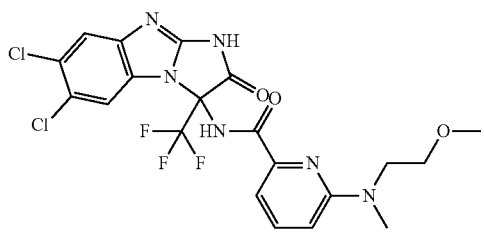 [SMILES: COCCN(C)c1cccc(C(=O)NC2(C(F)(F)F)C(=O)Nc3nc4cc(Cl)c(Cl)cc4n32)n1]
Ex 95 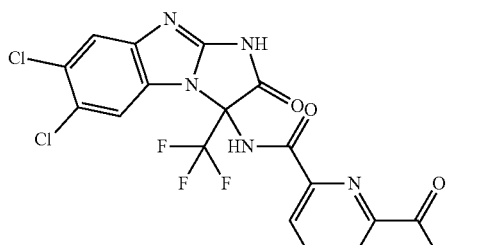
Ex 96 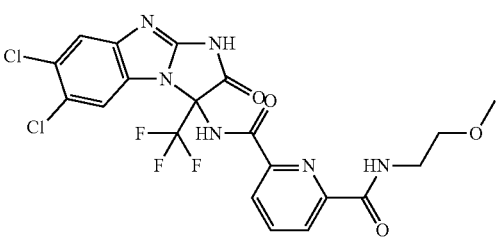 [SMILES: COCCNC(=O)c1cccc(C(=O)NC2(C(F)(F)F)C(=O)Nc3nc4cc(Cl)c(Cl)cc4n32)n1]
Ex 97 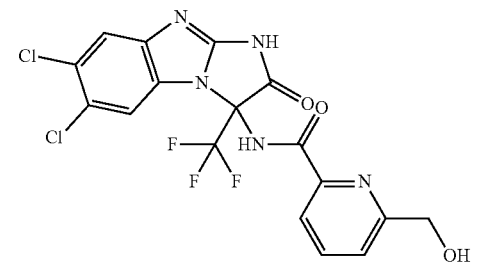 [SMILES: O=C(NC1(C(F)(F)F)C(=O)Nc2nc3cc(Cl)c(Cl)cc3n21)c1cccc(CO)n1]
Ex 98 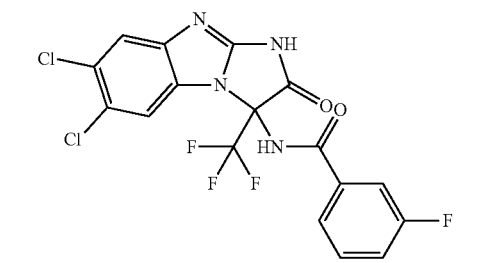 [SMILES: O=C(NC1(C(F)(F)F)C(=O)Nc2nc3cc(Cl)c(Cl)cc3n21)c1cccc(F)c1]
TABLE 1-continued
Ex 99 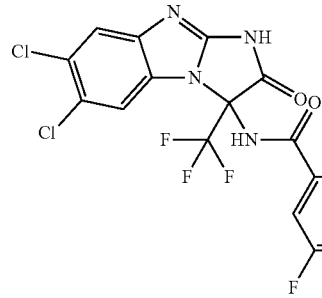
Ex 100 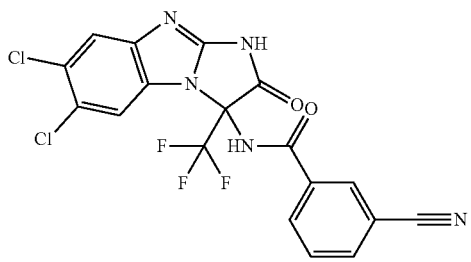 [SMILES: N#Cc1cccc(C(=O)NC2(C(F)(F)F)C(=O)Nc3nc4cc(Cl)c(Cl)cc4n32)c1]
Ex 101 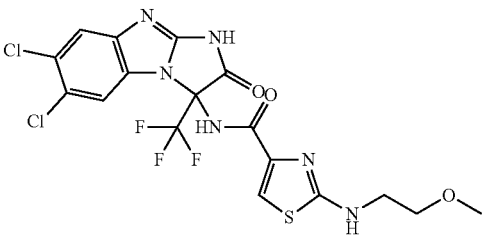 [SMILES: COCCNc1nc(C(=O)NC2(C(F)(F)F)C(=O)Nc3nc4cc(Cl)c(Cl)cc4n32)cs1]
Ex 102 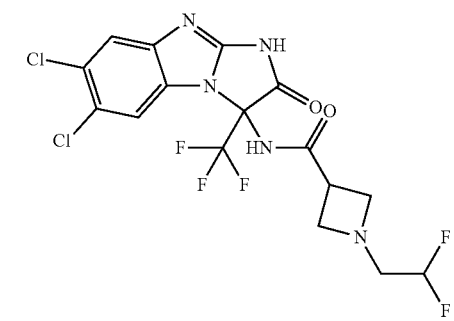 [SMILES: O=C(NC1(C(F)(F)F)C(=O)Nc2nc3cc(Cl)c(Cl)cc3n21)C1CN(CC(F)F)C1]
Ex 103 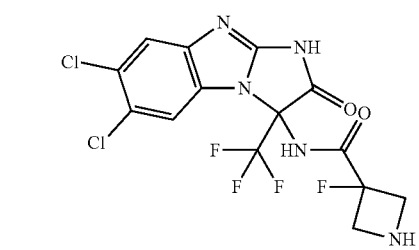 [SMILES: O=C(NC1(C(F)(F)F)C(=O)Nc2nc3cc(Cl)c(Cl)cc3n21)C1(F)CNC1]

TABLE 1-continued
Ex 104
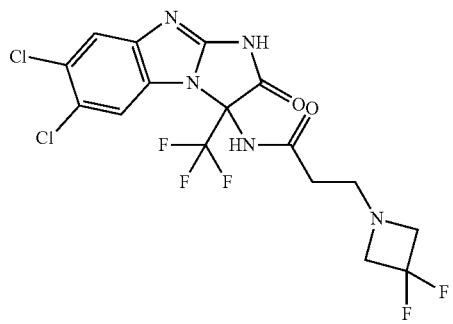 [SMILES: O=C(CCN1CC(F)(F)C1)NC1(C(F)(F)F)C(=O)Nc2nc3cc(Cl)c(Cl)cc3n21]
Ex 109
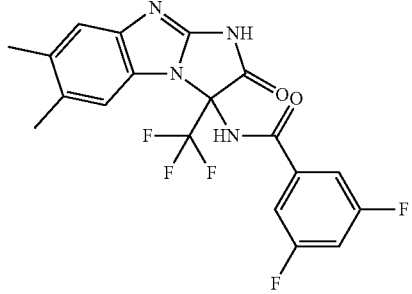
Ex 105
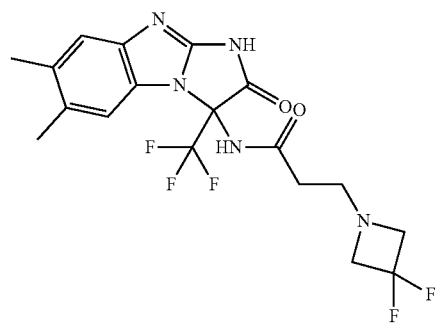 [SMILES: Cc1cc2nc3n(c2cc1C)C(NC(=O)CCN1CC(F)(F)C1)(C(F)(F)F)C(=O)N3]
Ex 110
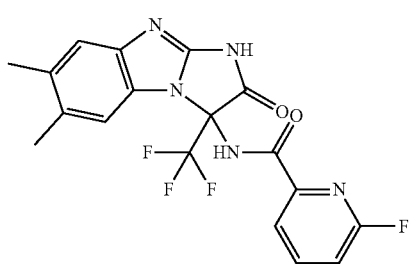
Ex 106
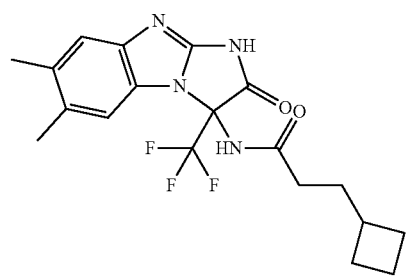 [SMILES: Cc1cc2nc3n(c2cc1C)C(NC(=O)CCC1CCC1)(C(F)(F)F)C(=O)N3]
Ex 111
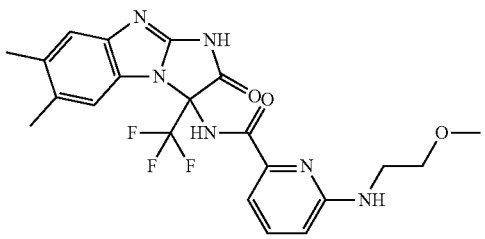
Ex 107
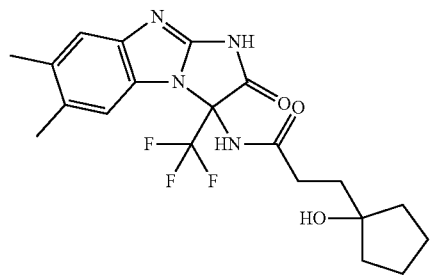 [SMILES: Cc1cc2nc3n(c2cc1C)C(NC(=O)CCC1(O)CCCC1)(C(F)(F)F)C(=O)N3]
Ex 112
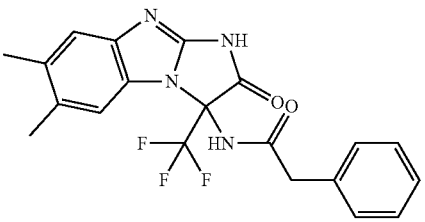
Ex 108
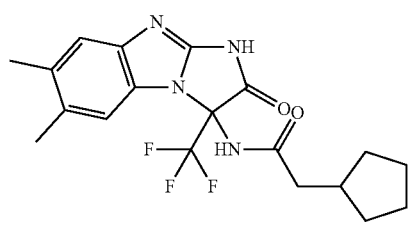 [SMILES: Cc1cc2nc3n(c2cc1C)C(NC(=O)CC1CCCC1)(C(F)(F)F)C(=O)N3]
Ex 113
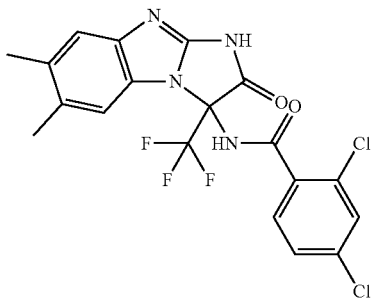 [SMILES: Cc1cc2nc3n(c2cc1C)C(NC(=O)c1ccc(Cl)cc1Cl)(C(F)(F)F)C(=O)N3]

TABLE 1-continued
Ex 114 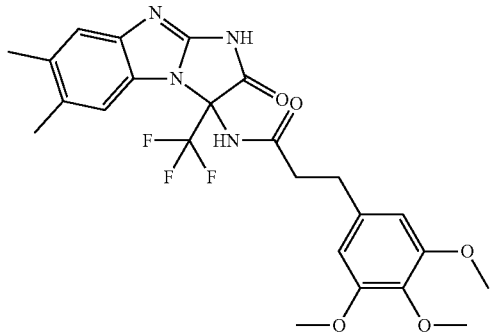
Ex 115 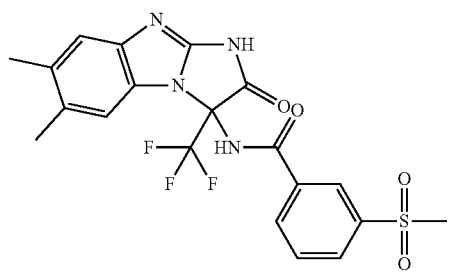
Ex 116 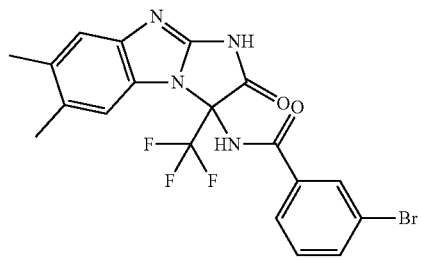 [SMILES: Cc1cc2nc3n(c2cc1C)C(NC(=O)c1cccc(Br)c1)(C(F)(F)F)C(=O)N3]
Ex 117 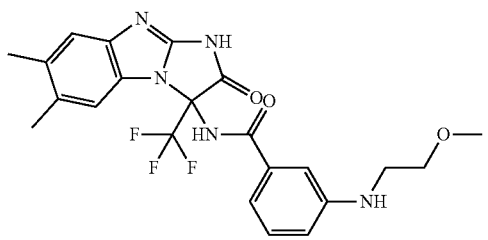
Ex 118 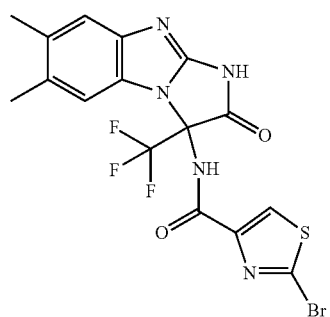 [SMILES: Cc1cc2nc3n(c2cc1C)C(NC(=O)c1csc(Br)n1)(C(F)(F)F)C(=O)N3]
TABLE 1-continued
Ex 119 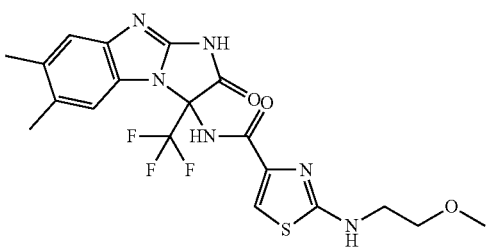
Ex 120 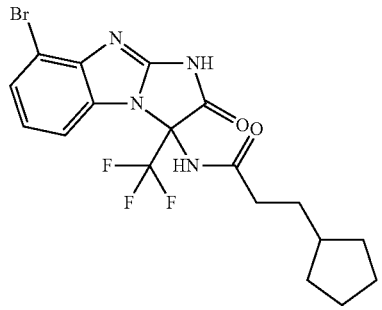 [SMILES: O=C(CCC1CCCC1)NC1(C(F)(F)F)C(=O)Nc2nc3c(Br)cccc3n21]
Ex 121 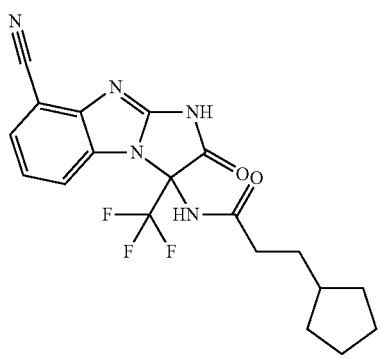 [SMILES: N#Cc1cccc2c1nc1n2C(NC(=O)CCC2CCCC2)(C(F)(F)F)C(=O)N1]
Ex 122 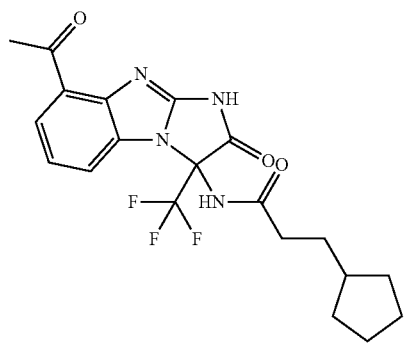 [SMILES: CC(=O)c1cccc2c1nc1n2C(NC(=O)CCC2CCCC2)(C(F)(F)F)C(=O)N1]
Ex 123 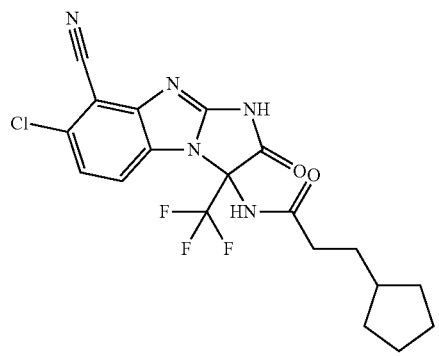 [SMILES: N#Cc1c(Cl)ccc2c1nc1n2C(NC(=O)CCC2CCCC2)(C(F)(F)F)C(=O)N1]

TABLE 1-continued
Ex 124 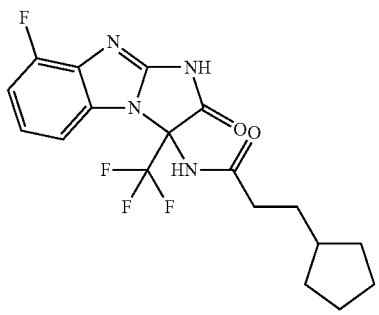
Ex 125 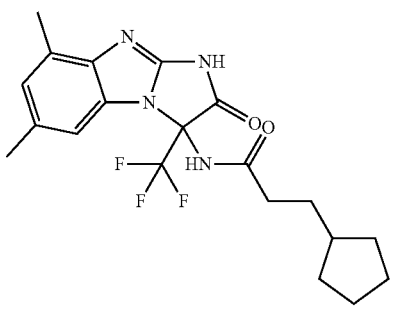 [SMILES: Cc1cc(C)c2nc3n(c2c1)C(NC(=O)CCC1CCCC1)(C(F)(F)F)C(=O)N3]
Ex 126 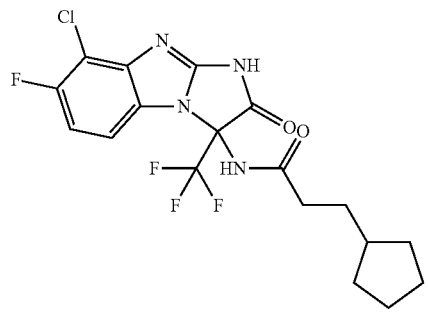 [SMILES: O=C(CCC1CCCC1)NC1(C(F)(F)F)C(=O)Nc2nc3c(Cl)c(F)ccc3n21]
Ex 127 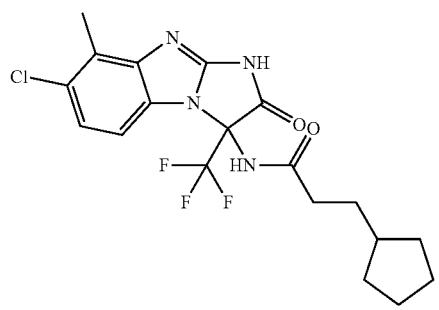 [SMILES: Cc1c(Cl)ccc2c1nc1n2C(NC(=O)CCC2CCCC2)(C(F)(F)F)C(=O)N1]
Ex 128 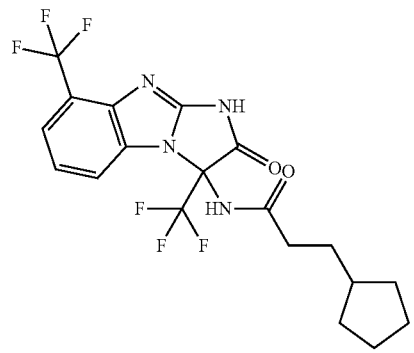 [SMILES: O=C(CCC1CCCC1)NC1(C(F)(F)F)C(=O)Nc2nc3c(C(F)(F)F)cccc3n21]
TABLE 1-continued
Ex 129 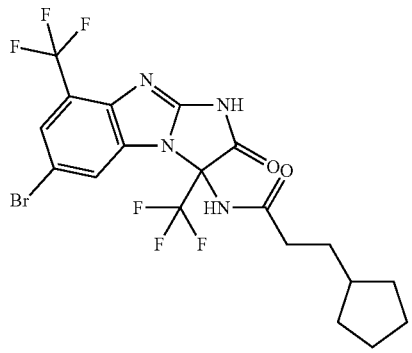 [SMILES: O=C(CCC1CCCC1)NC1(C(F)(F)F)C(=O)Nc2nc3c(C(F)(F)F)cc(Br)cc3n21]
Ex 130 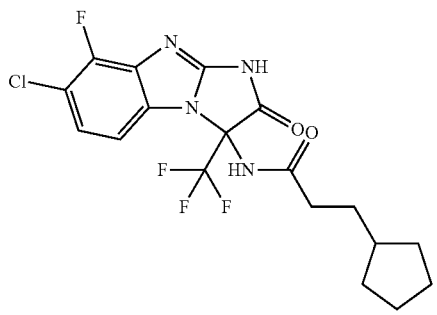 [SMILES: O=C(CCC1CCCC1)NC1(C(F)(F)F)C(=O)Nc2nc3c(F)c(Cl)ccc3n21]
Ex 131 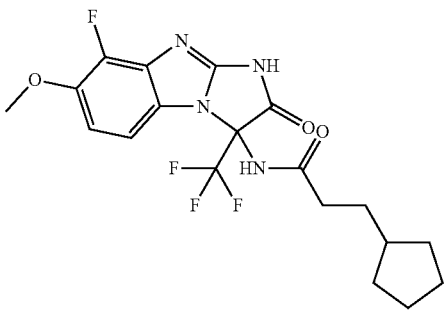 [SMILES: COc1ccc2c(nc3n2C(NC(=O)CCC2CCCC2)(C(F)(F)F)C(=O)N3)c1F]
Ex 132 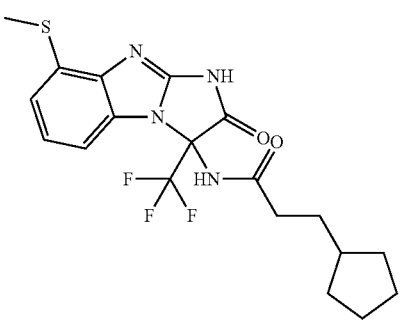 [SMILES: CSc1cccc2c1nc1n2C(NC(=O)CCC2CCCC2)(C(F)(F)F)C(=O)N1]
Ex 133 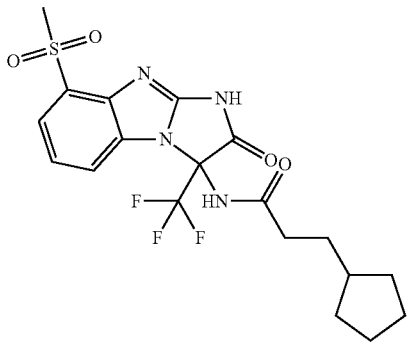 [SMILES: CS(=O)(=O)c1cccc2c1nc1n2C(NC(=O)CCC2CCCC2)(C(F)(F)F)C(=O)N1]

TABLE 1-continued
Ex 134 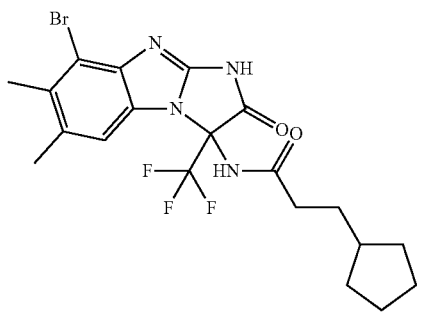 [SMILES: Cc1cc2c(nc3n2C(NC(=O)CCC2CCCC2)(C(F)(F)F)C(=O)N3)c(Br)c1C]
Ex 135 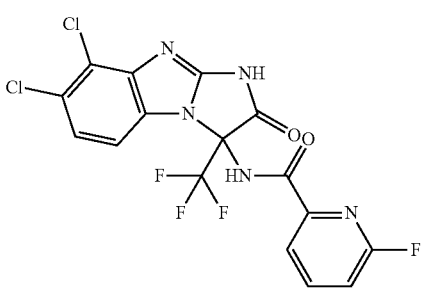 [SMILES: O=C(NC1(C(F)(F)F)C(=O)Nc2nc3c(Cl)c(Cl)ccc3n21)c1cccc(F)n1]
Ex 136 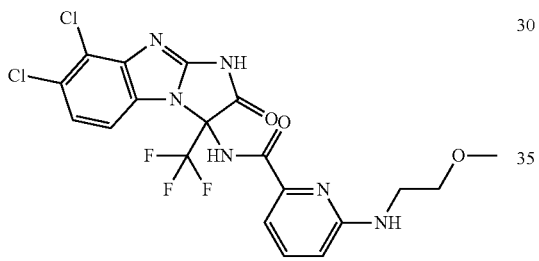
Ex 137 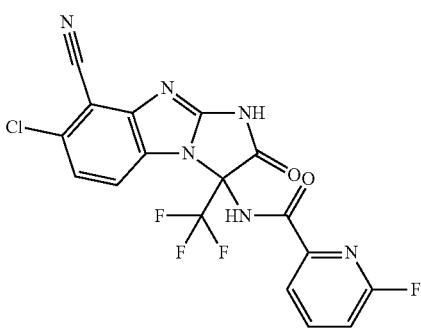 [SMILES: N#Cc1c(Cl)ccc2c1nc1n2C(NC(=O)c2cccc(F)n2)(C(F)(F)F)C(=O)N1]
Ex 138 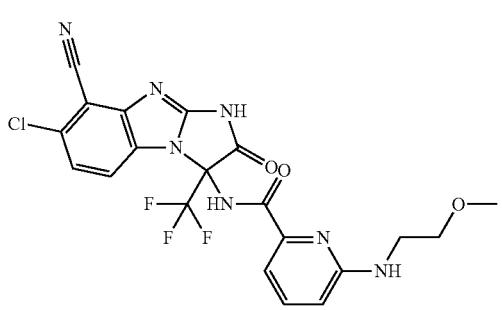 [SMILES: COCCNc1cccc(C(=O)NC2(C(F)(F)F)C(=O)Nc3nc4c(C#N)c(Cl)ccc4n32)n1]
TABLE 1-continued
Ex 139 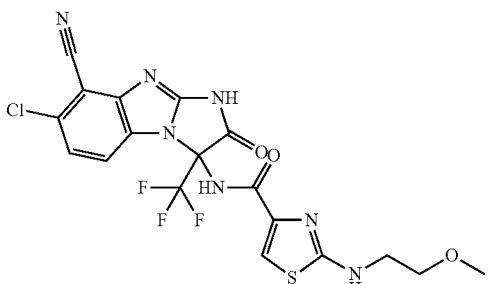
Ex 140 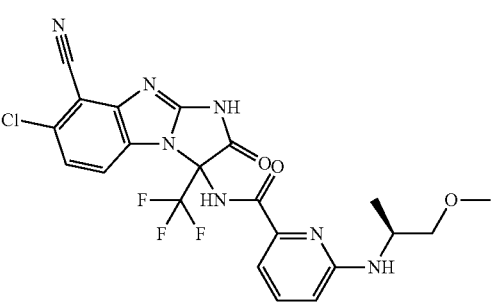 [SMILES: COC[C@H](C)Nc1cccc(C(=O)NC2(C(F)(F)F)C(=O)Nc3nc4c(C#N)c(Cl)ccc4n32)n1]
Ex 141 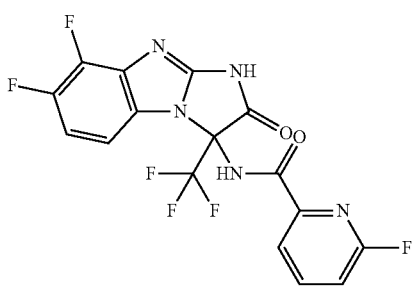 [SMILES: O=C(NC1(C(F)(F)F)C(=O)Nc2nc3c(F)c(F)ccc3n21)c1cccc(F)n1]
Ex 142 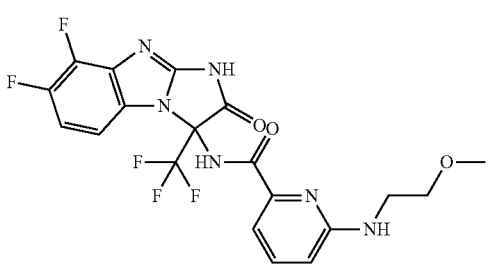 [SMILES: COCCNc1cccc(C(=O)NC2(C(F)(F)F)C(=O)Nc3nc4c(F)c(F)ccc4n32)n1]
Ex 143 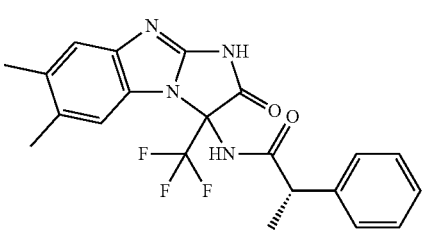 [SMILES: Cc1cc2nc3n(c2cc1C)C(NC(=O)[C@@H](C)c1ccccc1)(C(F)(F)F)C(=O)N3]
Ex 144 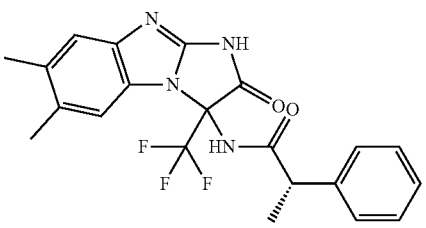 [SMILES: Cc1cc2nc3n(c2cc1C)C(NC(=O)[C@@H](C)c1ccccc1)(C(F)(F)F)C(=O)N3]

TABLE 1-continued
| Ex 145a-c | 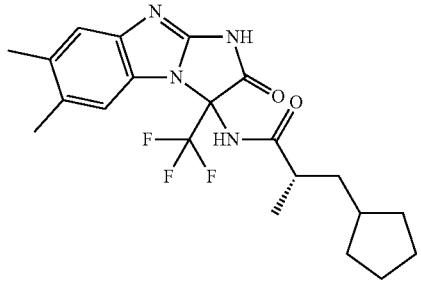 [SMILES: Cc1cc2nc3n(c2cc1C)C(NC(=O)[C@@H](C)CC1CCCC1)(C(F)(F)F)C(=O)N3] |
| Ex 146a-b | 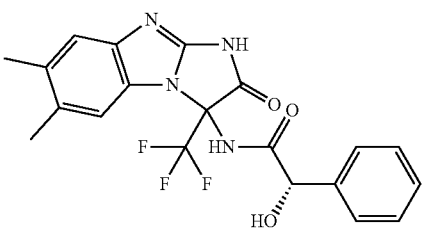 [SMILES: Cc1cc2nc3n(c2cc1C)C(NC(=O)[C@@H](O)c1ccccc1)(C(F)(F)F)C(=O)N3] |
| Ex 147a-b | 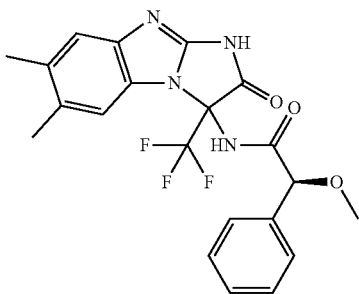 |
| Ex 148 | 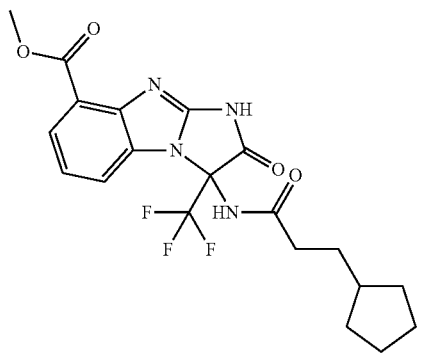 [SMILES: COC(=O)c1cccc2c1nc1n2C(NC(=O)CCC2CCCC2)(C(F)(F)F)C(=O)N1] |
| Ex 149 | 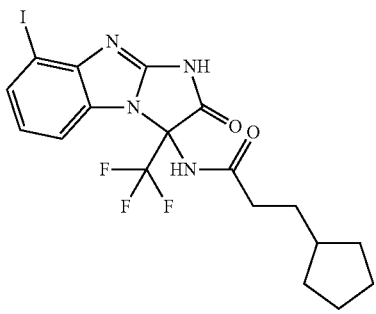 [SMILES: O=C(CCC1CCCC1)NC1(C(F)(F)F)C(=O)Nc2nc3c(I)cccc3n21] |
TABLE 1-continued
| Ex 150 | 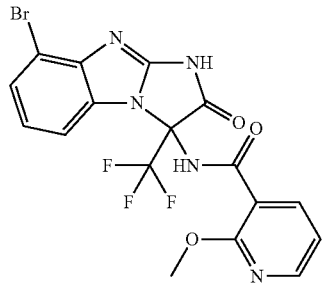 [SMILES: COc1ncccc1C(=O)NC1(C(F)(F)F)C(=O)Nc2nc3c(Br)cccc3n21] |
| Ex 151 | 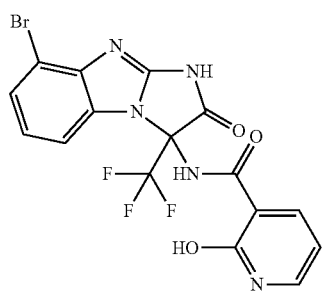 [SMILES: O=C(NC1(C(F)(F)F)C(=O)Nc2nc3c(Br)cccc3n21)c1cccnc1O] |
| Ex 152 | 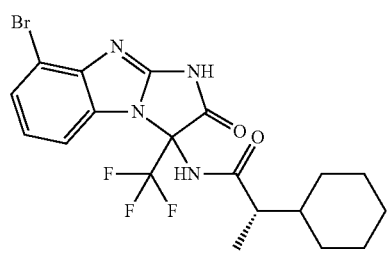 [SMILES: C[C@H](C(=O)NC1(C(F)(F)F)C(=O)Nc2nc3c(Br)cccc3n21)C1CCCCC1] |
| Ex 153 | 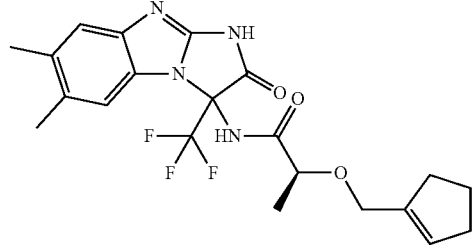 [SMILES: Cc1cc2nc3n(c2cc1C)C(NC(=O)[C@H](C)OCC1=CCCC1)(C(F)(F)F)C(=O)N3] |
| Ex 154 | 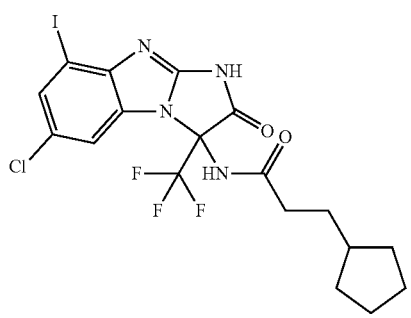 [SMILES: O=C(CCC1CCCC1)NC1(C(F)(F)F)C(=O)Nc2nc3c(I)cc(Cl)cc3n21] |

TABLE 1-continued
Ex 155 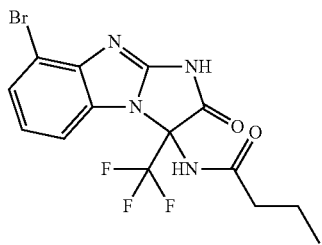 [SMILES: CCCC(=O)NC1(C(F)(F)F)C(=O)Nc2nc3c(Br)cccc3n21]
Ex 156 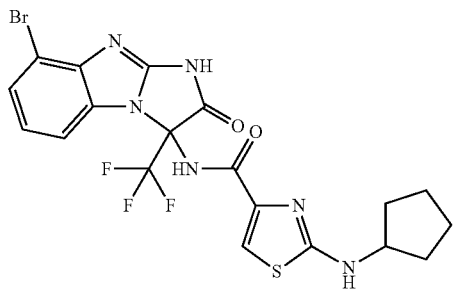 [SMILES: O=C(NC1(C(F)(F)F)C(=O)Nc2nc3c(Br)cccc3n21)c1csc(NC2CCCC2)n1]
Ex 157 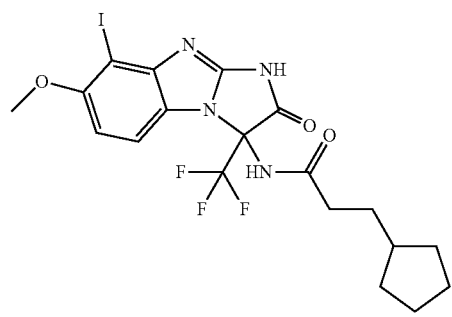 [SMILES: COc1ccc2c(nc3n2C(NC(=O)CCC2CCCC2)(C(F)(F)F)C(=O)N3)c1I]
Ex 158 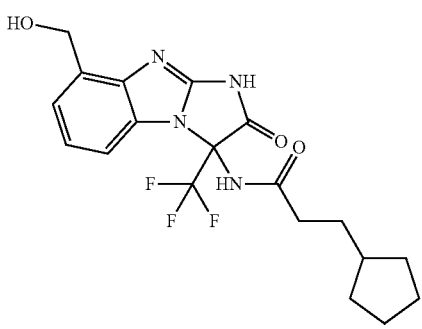 [SMILES: O=C(CCC1CCCC1)NC1(C(F)(F)F)C(=O)Nc2nc3c(CO)cccc3n21]
Ex 159 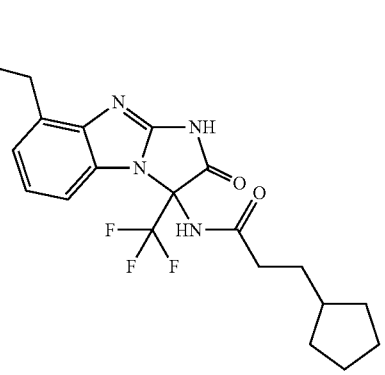
TABLE 1-continued
Ex 160 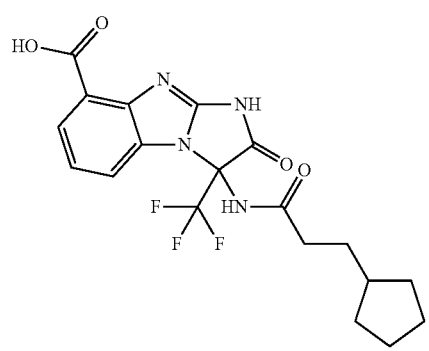 [SMILES: O=C(CCC1CCCC1)NC1(C(F)(F)F)C(=O)Nc2nc3c(C(=O)O)cccc3n21]
Ex 161 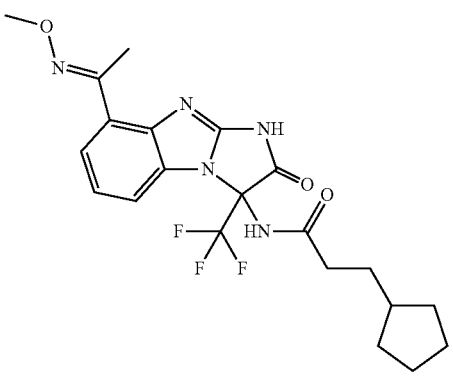 [SMILES: CO/N=C(\C)c1cccc2c1nc1n2C(NC(=O)CCC2CCCC2)(C(F)(F)F)C(=O)N1]
Ex 162 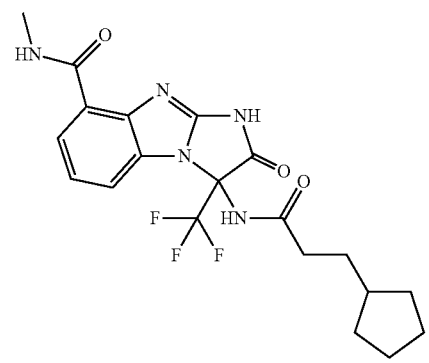 [SMILES: CNC(=O)c1cccc2c1nc1n2C(NC(=O)CCC2CCCC2)(C(F)(F)F)C(=O)N1]
Ex 163 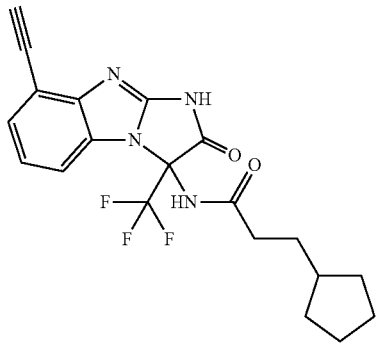 [SMILES: C#Cc1cccc2c1nc1n2C(NC(=O)CCC2CCCC2)(C(F)(F)F)C(=O)N1]

TABLE 1-continued
Ex 164 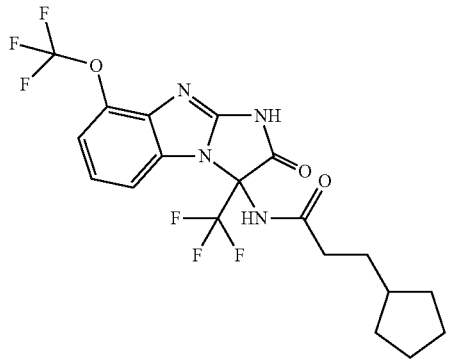 [SMILES: O=C(CCC1CCCC1)NC1(C(F)(F)F)C(=O)Nc2nc3c(OC(F)(F)F)cccc3n21]
Ex 165 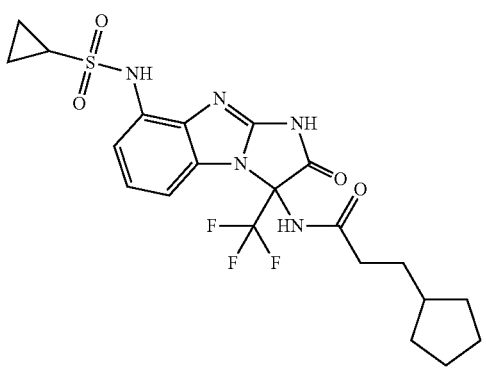 [SMILES: O=C(CCC1CCCC1)NC1(C(F)(F)F)C(=O)Nc2nc3c(NS(=O)(=O)C4CC4)cccc3n21]
Ex 166 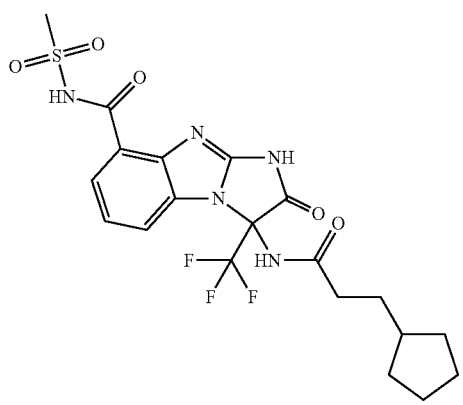 [SMILES: CS(=O)(=O)NC(=O)c1cccc2c1nc1n2C(NC(=O)CCC2CCCC2)(C(F)(F)F)C(=O)N1]
Ex 167 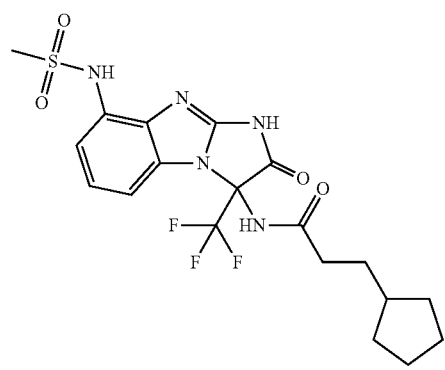 [SMILES: CS(=O)(=O)Nc1cccc2c1nc1n2C(NC(=O)CCC2CCCC2)(C(F)(F)F)C(=O)N1]
TABLE 1-continued
Ex 168 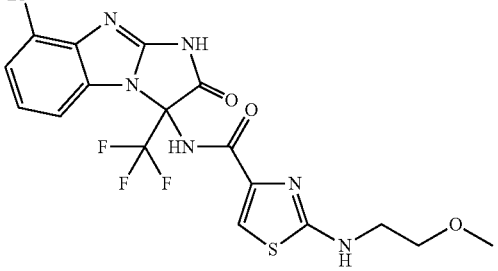
Ex 169 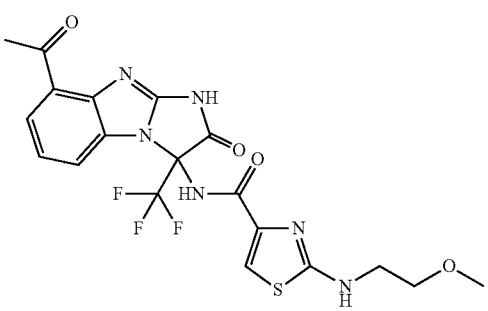 [SMILES: COCCNc1nc(C(=O)NC2(C(F)(F)F)C(=O)Nc3nc4c(C(C)=O)cccc4n32)cs1]
Ex 170 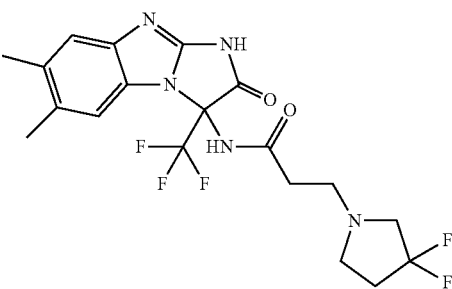 [SMILES: Cc1cc2nc3n(c2cc1C)C(NC(=O)CCN1CCC(F)(F)C1)(C(F)(F)F)C(=O)N3]
Ex 171 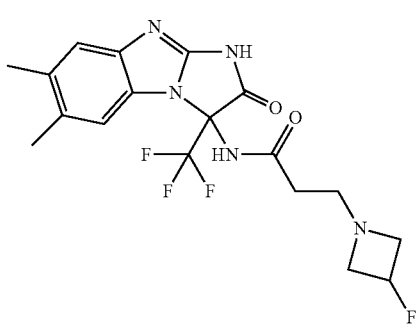 [SMILES: Cc1cc2nc3n(c2cc1C)C(NC(=O)CCN1CC(F)C1)(C(F)(F)F)C(=O)N3]
Ex 172 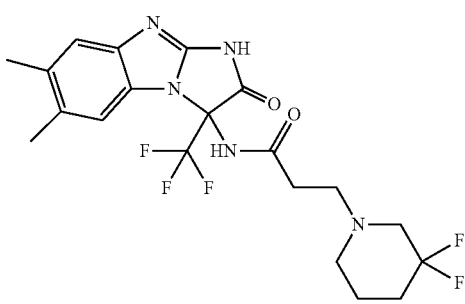 [SMILES: Cc1cc2nc3n(c2cc1C)C(NC(=O)CCN1CCCC(F)(F)C1)(C(F)(F)F)C(=O)N3]

TABLE 1-continued
Ex 173 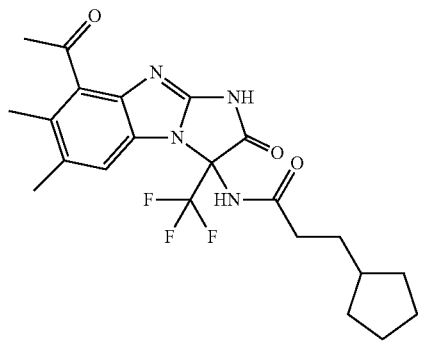 [SMILES: CC(=O)c1c(C)c(C)cc2c1nc1n2C(NC(=O)CCC2CCCC2)(C(F)(F)F)C(=O)N1]
Ex 174 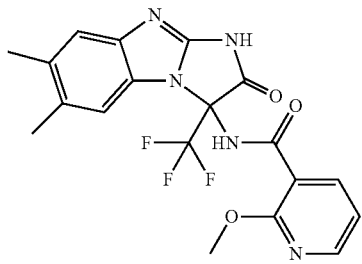 [SMILES: COc1ncccc1C(=O)NC1(C(F)(F)F)C(=O)Nc2nc3cc(C)c(C)cc3n21]
Ex 175 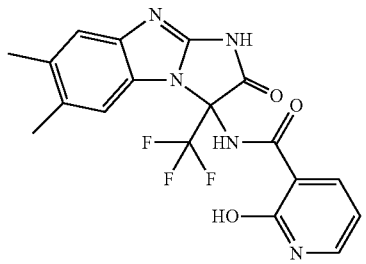
Ex 176 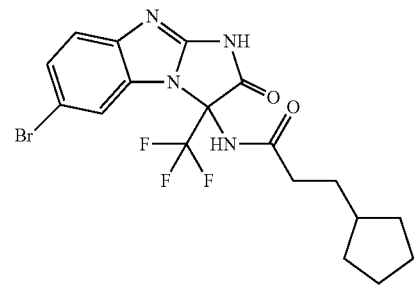 [SMILES: O=C(CCC1CCCC1)NC1(C(F)(F)F)C(=O)Nc2nc3ccc(Br)cc3n21]
Ex 177 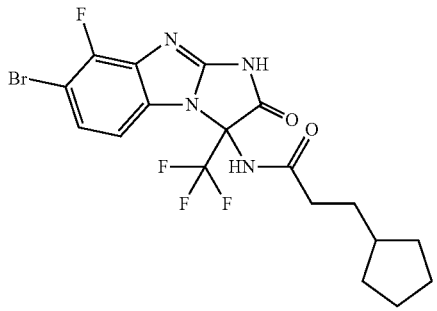 [SMILES: O=C(CCC1CCCC1)NC1(C(F)(F)F)C(=O)Nc2nc3c(F)c(Br)ccc3n21]
TABLE 1-continued
Ex 178 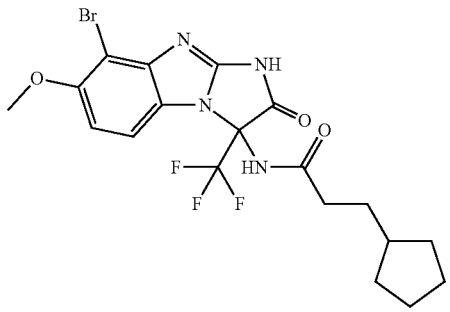 [SMILES: COc1ccc2c(nc3n2C(NC(=O)CCC2CCCC2)(C(F)(F)F)C(=O)N3)c1Br]
Ex 179 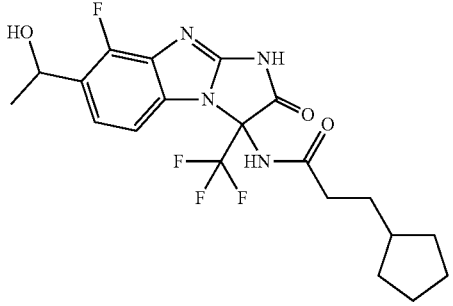
Ex 180 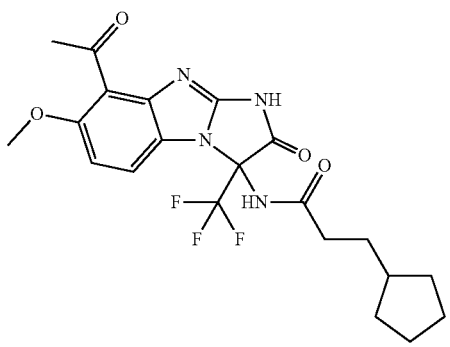 [SMILES: COc1ccc2c(nc3n2C(NC(=O)CCC2CCCC2)(C(F)(F)F)C(=O)N3)c1C(C)=O]
Ex 181 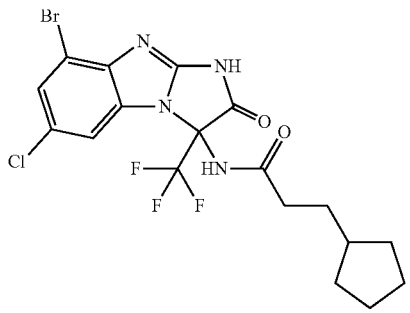 [SMILES: O=C(CCC1CCCC1)NC1(C(F)(F)F)C(=O)Nc2nc3c(Br)cc(Cl)cc3n21]
Ex 182 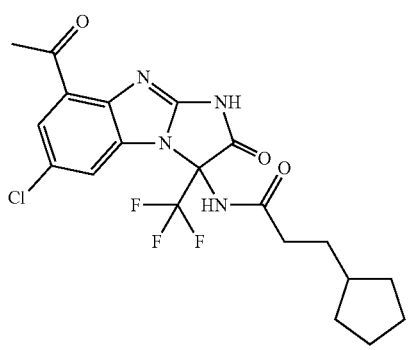 [SMILES: CC(=O)c1cc(Cl)cc2c1nc1n2C(NC(=O)CCC2CCCC2)(C(F)(F)F)C(=O)N1]

TABLE 1-continued
Ex 183 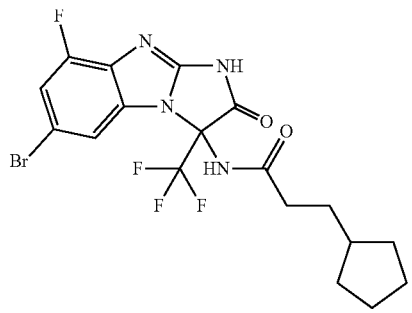 [SMILES: O=C(CCC1CCCC1)NC1(C(F)(F)F)C(=O)Nc2nc3c(F)cc(Br)cc3n21]
Ex 184 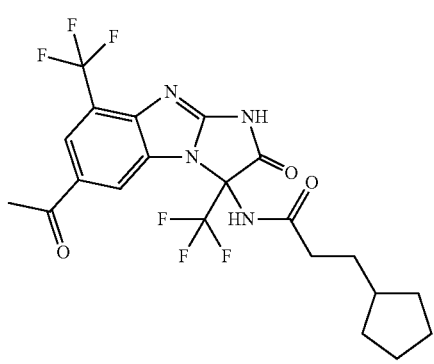 [SMILES: CC(=O)c1cc(C(F)(F)F)c2nc3n(c2c1)C(NC(=O)CCC1CCCC1)(C(F)(F)F)C(=O)N3]
Ex 185a 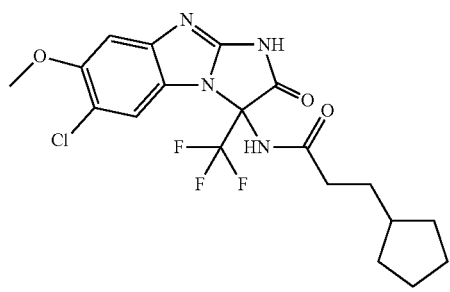 [SMILES: COc1cc2nc3n(c2cc1Cl)C(NC(=O)CCC1CCCC1)(C(F)(F)F)C(=O)N3]
Ex 185b 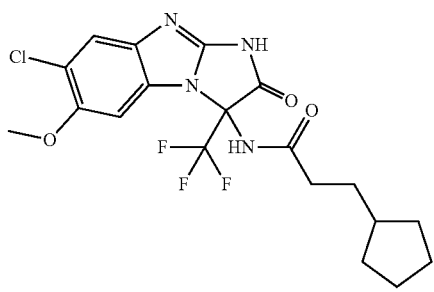 [SMILES: COc1cc2c(cc1Cl)nc1n2C(NC(=O)CCC2CCCC2)(C(F)(F)F)C(=O)N1]
TABLE 1-continued
Ex 186 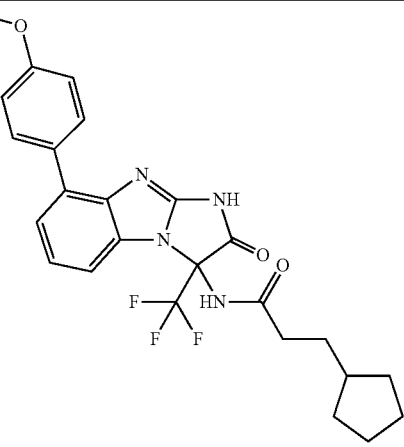
Ex 187 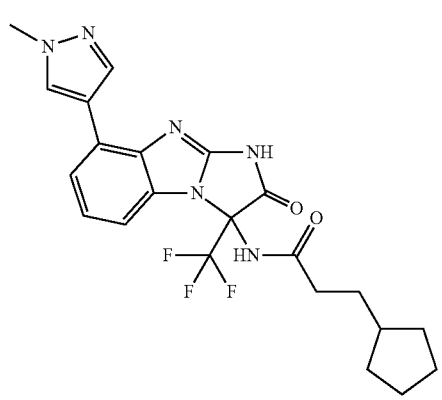 [SMILES: Cn1cc(-c2cccc3c2nc2n3C(NC(=O)CCC3CCCC3)(C(F)(F)F)C(=O)N2)cn1]
Ex 188 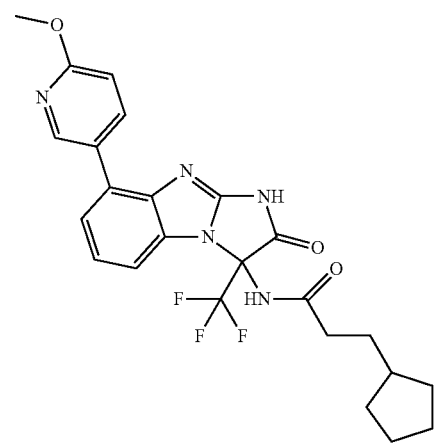 [SMILES: COc1ccc(-c2cccc3c2nc2n3C(NC(=O)CCC3CCCC3)(C(F)(F)F)C(=O)N2)cn1]
Ex 189 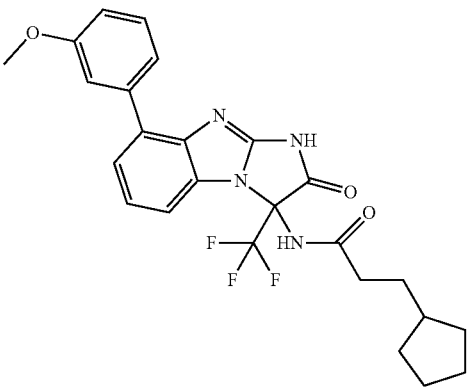 [SMILES: COc1cccc(-c2cccc3c2nc2n3C(NC(=O)CCC3CCCC3)(C(F)(F)F)C(=O)N2)c1]

TABLE 1-continued
Ex 190
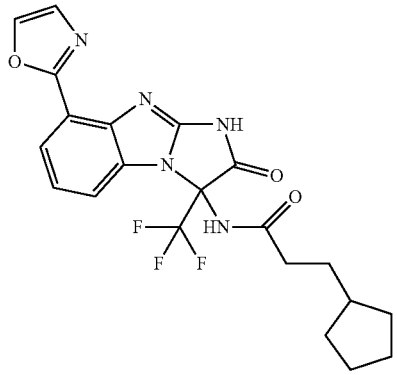 [SMILES: O=C(CCC1CCCC1)NC1(C(F)(F)F)C(=O)Nc2nc3c(-c4ncco4)cccc3n21]
Ex 193
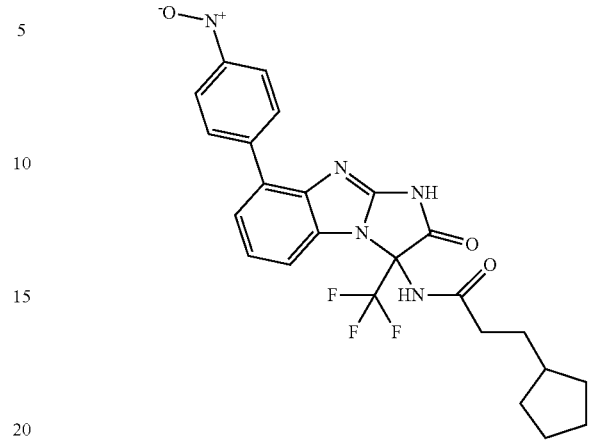
Ex 191
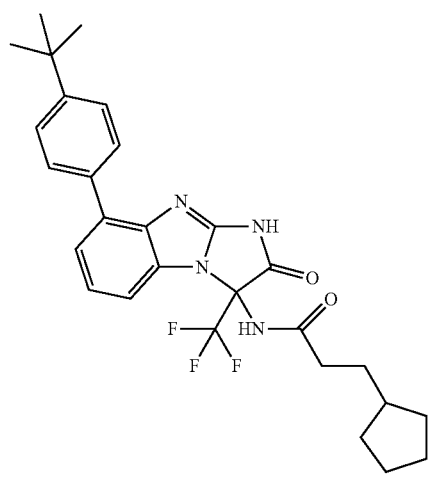 [SMILES: CC(C)(C)c1ccc(-c2cccc3c2nc2n3C(NC(=O)CCC3CCCC3)(C(F)(F)F)C(=O)N2)cc1]
Ex 194
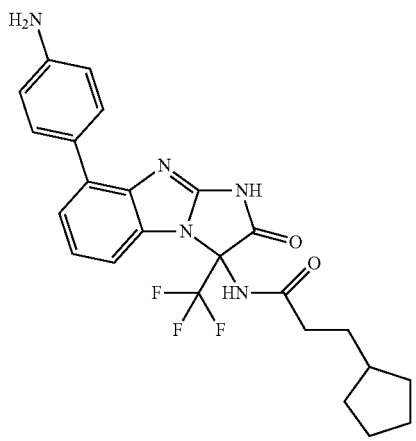
Ex 192
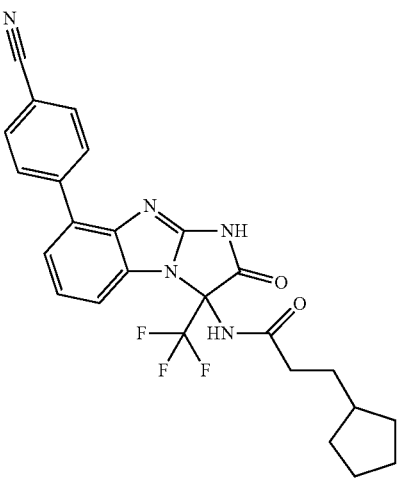 [SMILES: N#Cc1ccc(-c2cccc3c2nc2n3C(NC(=O)CCC3CCCC3)(C(F)(F)F)C(=O)N2)cc1]
Ex 195
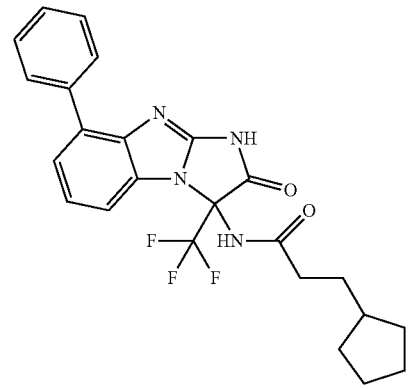 [SMILES: O=C(CCC1CCCC1)NC1(C(F)(F)F)C(=O)Nc2nc3c(-c4ccccc4)cccc3n21]

TABLE 1-continued
Ex 196
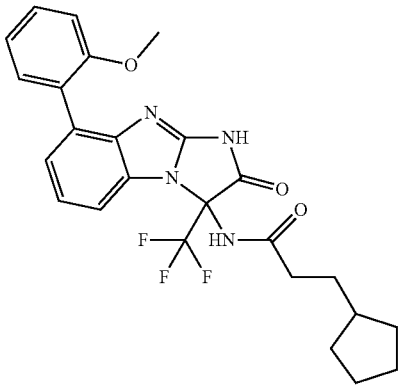 [SMILES: COc1ccccc1-c1cccc2c1nc1n2C(NC(=O)CCC2CCCC2)(C(F)(F)F)C(=O)N1]
Ex 197
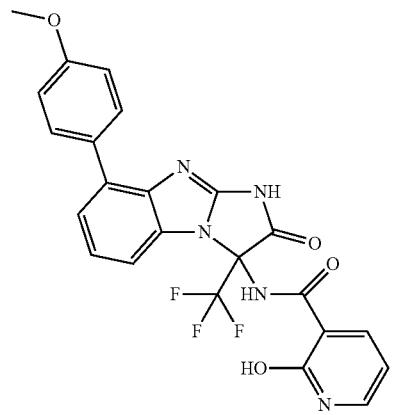 [SMILES: COc1ccc(-c2cccc3c2nc2n3C(NC(=O)c3cccnc3O)(C(F)(F)F)C(=O)N2)cc1]
Ex 198
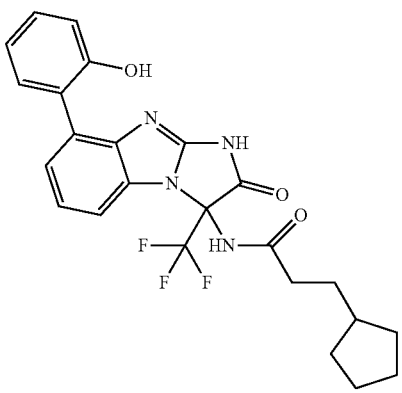 [SMILES: O=C(CCC1CCCC1)NC1(C(F)(F)F)C(=O)Nc2nc3c(-c4ccccc4O)cccc3n21]
Ex 199
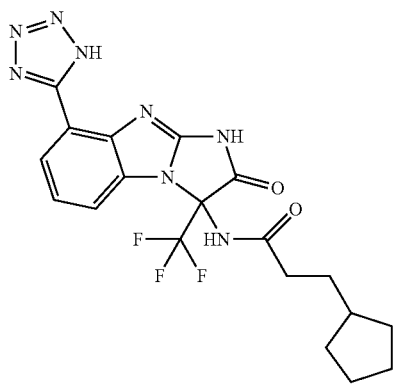 [SMILES: O=C(CCC1CCCC1)NC1(C(F)(F)F)C(=O)Nc2nc3c(-c4nnn[nH]4)cccc3n21]
TABLE 1-continued
Ex 200
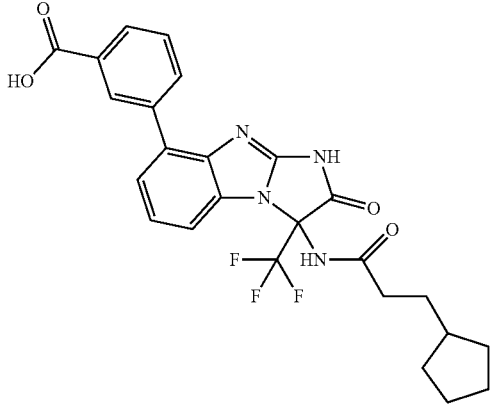 [SMILES: O=C(CCC1CCCC1)NC1(C(F)(F)F)C(=O)Nc2nc3c(-c4cccc(C(=O)O)c4)cccc3n21]
Ex 201
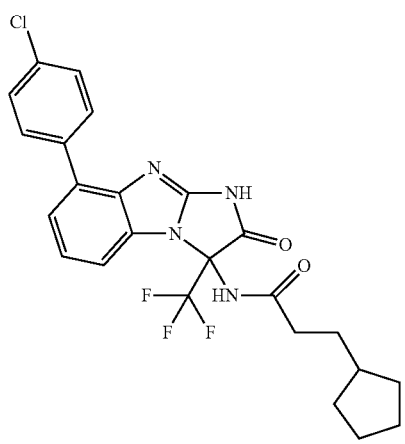 [SMILES: O=C(CCC1CCCC1)NC1(C(F)(F)F)C(=O)Nc2nc3c(-c4ccc(Cl)cc4)cccc3n21]
Ex 202
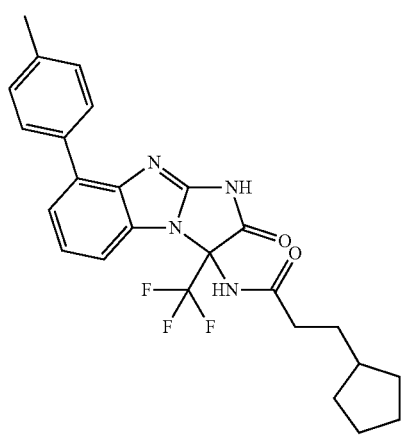 [SMILES: Cc1ccc(-c2cccc3c2nc2n3C(NC(=O)CCC3CCCC3)(C(F)(F)F)C(=O)N2)cc1]

TABLE 1-continued
| Ex 203 | 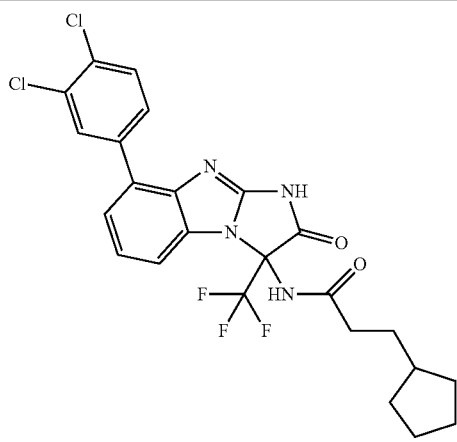 [SMILES: O=C(CCC1CCCC1)NC1(C(F)(F)F)C(=O)Nc2nc3c(-c4ccc(Cl)c(Cl)c4)cccc3n21] |
| --- | --- |
| Ex 204 | 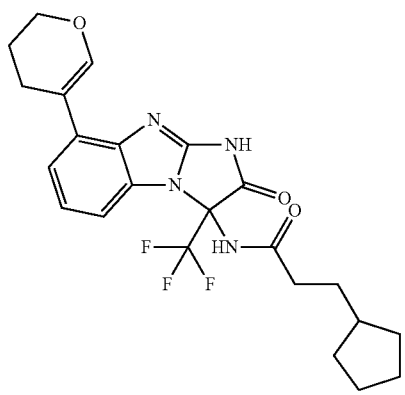 [SMILES: O=C(CCC1CCCC1)NC1(C(F)(F)F)C(=O)Nc2nc3c(C4=COCCC4)cccc3n21] |
| Ex 205 | 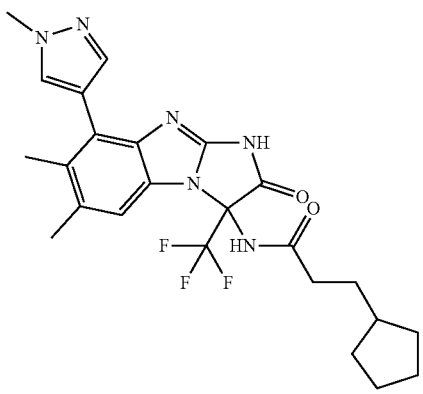 [SMILES: Cc1cc2c(nc3n2C(NC(=O)CCC2CCCC2)(C(F)(F)F)C(=O)N3)c(-c2cnn(C)c2)c1C] |
| Ex 206 | 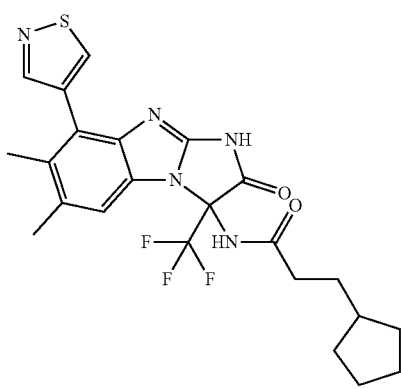 [SMILES: Cc1cc2c(nc3n2C(NC(=O)CCC2CCCC2)(C(F)(F)F)C(=O)N3)c(-c2cnsc2)c1C] |
TABLE 1-continued
| Ex 207 | 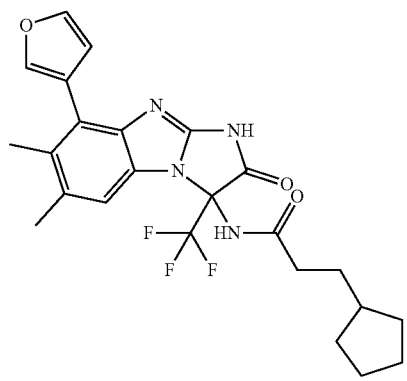 [SMILES: Cc1cc2c(nc3n2C(NC(=O)CCC2CCCC2)(C(F)(F)F)C(=O)N3)c(-c2ccoc2)c1C] |
| --- | --- |
| Ex 208 | 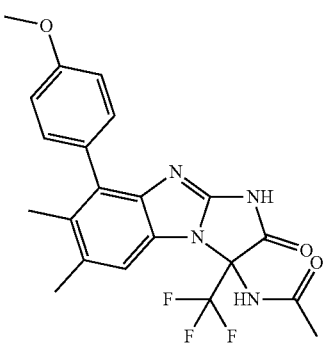 [SMILES: COc1ccc(-c2c(C)c(C)cc3c2nc2n3C(NC(C)=O)(C(F)(F)F)C(=O)N2)cc1] |
| Ex 209 | 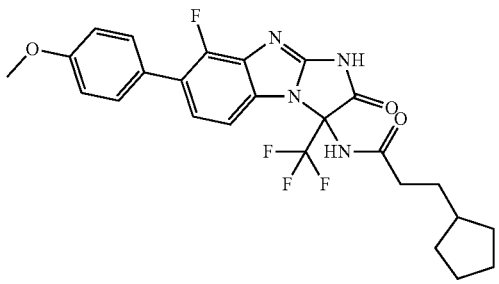 [SMILES: COc1ccc(-c2ccc3c(nc4n3C(NC(=O)CCC3CCCC3)(C(F)(F)F)C(=O)N4)c2F)cc1] |
| Ex 210 | 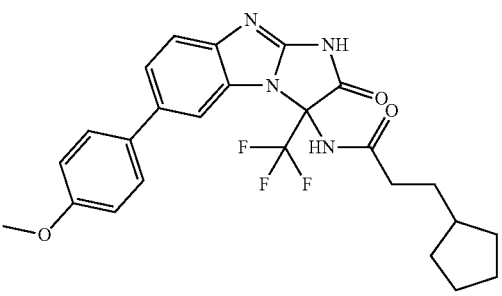 [SMILES: COc1ccc(-c2ccc3nc4n(c3c2)C(NC(=O)CCC2CCCC2)(C(F)(F)F)C(=O)N4)cc1] |
| Ex 211a-b | 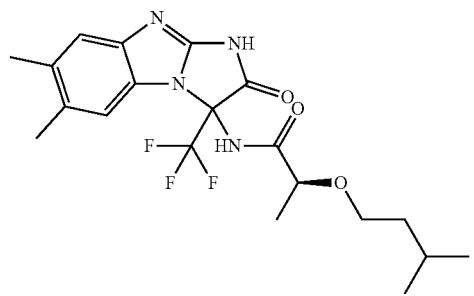 [SMILES: Cc1cc2nc3n(c2cc1C)C(NC(=O)[C@H](C)OCCC(C)C)(C(F)(F)F)C(=O)N3] |

TABLE 1-continued
| Ex 211c-d | 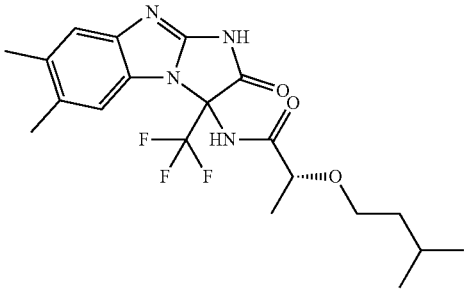 [SMILES: Cc1cc2nc3n(c2cc1C)C(NC(=O)[C@@H](C)OCCC(C)C)(C(F)(F)F)C(=O)N3] |
| Ex 212a-b | 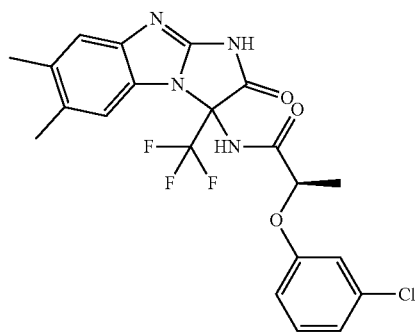 [SMILES: Cc1cc2nc3n(c2cc1C)C(NC(=O)[C@@H](C)Oc1cccc(Cl)c1)(C(F)(F)F)C(=O)N3] |
| Ex 213 | 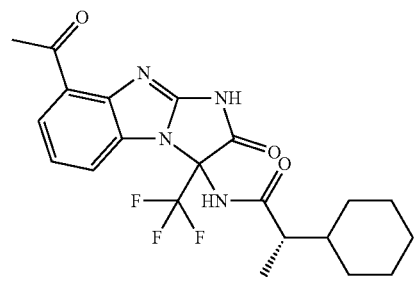 [SMILES: CC(=O)c1cccc2c1nc1n2C(NC(=O)[C@@H](C)C2CCCCC2)(C(F)(F)F)C(=O)N1] |
| Ex 214 | 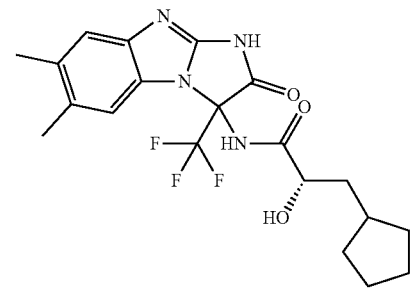 [SMILES: Cc1cc2nc3n(c2cc1C)C(NC(=O)[C@@H](O)CC1CCCC1)(C(F)(F)F)C(=O)N3] |
| Ex 215a-b | 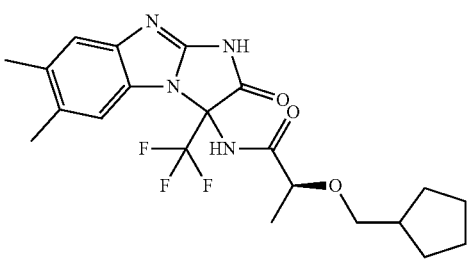 [SMILES: Cc1cc2nc3n(c2cc1C)C(NC(=O)[C@H](C)OCC1CCCC1)(C(F)(F)F)C(=O)N3] |
TABLE 1-continued
| Ex 216a-b | 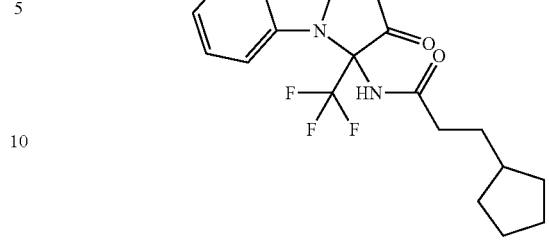 |
| Ex 217a-b | 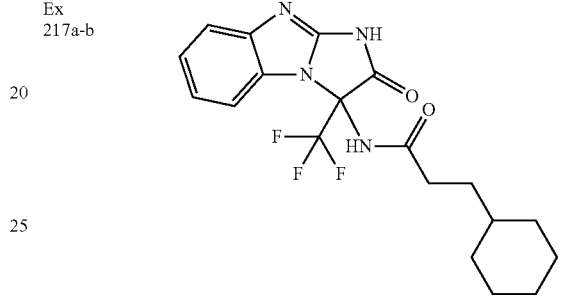 |
| Ex 218a-b | 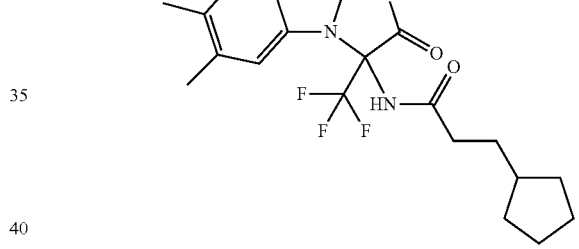 |
| Ex 219a-b | 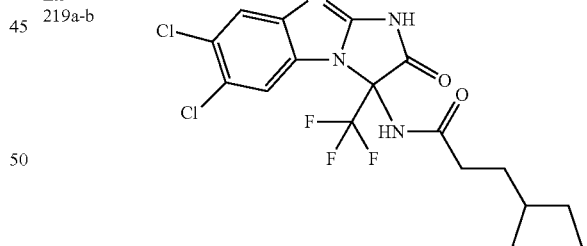 |
| Ex 220a-b | 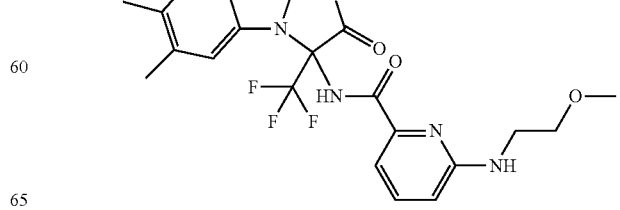 |

TABLE 1-continued
| Ex 221a-b | 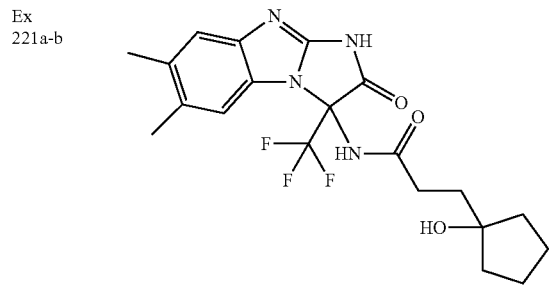 |
| Ex 222a-b | 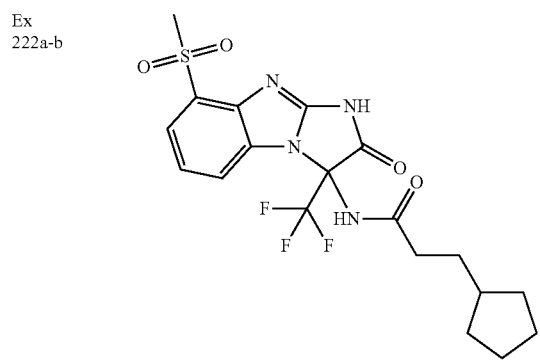 |
| Ex 223a-b | 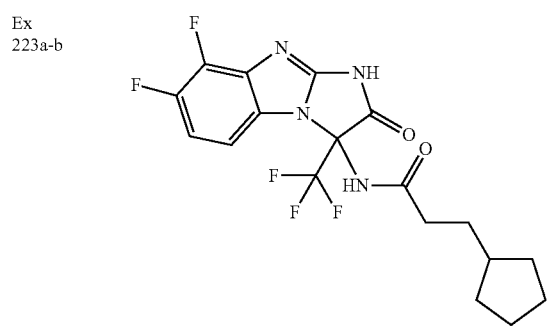 |
| Ex 224a-b | 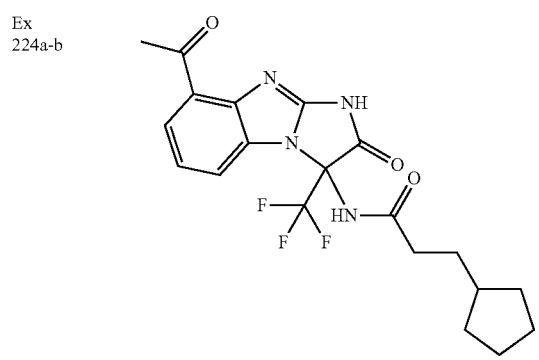 |
| Ex 225a-b | 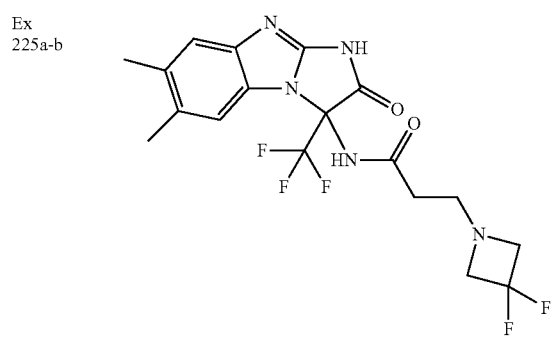 |
TABLE 1-continued
| Ex 226a-b | 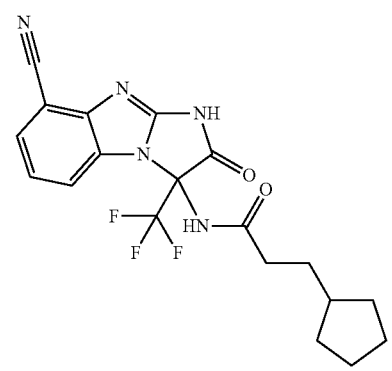 [SMILES: N#Cc1cccc2c1nc1n2C(NC(=O)CCC2CCCC2)(C(F)(F)F)C(=O)N1] |
| Ex 227a-b | 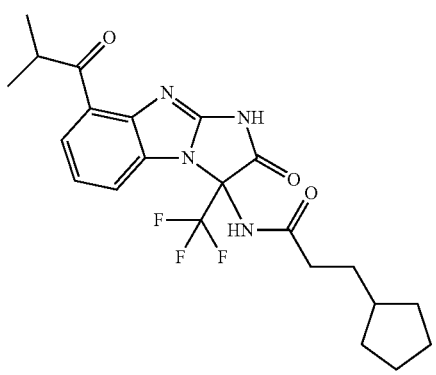 [SMILES: CC(C)C(=O)c1cccc2c1nc1n2C(NC(=O)CCC2CCCC2)(C(F)(F)F)C(=O)N1] |
| Ex 228a-b | 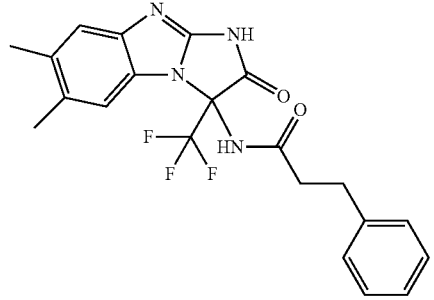 [SMILES: Cc1cc2nc3n(c2cc1C)C(NC(=O)CCc1ccccc1)(C(F)(F)F)C(=O)N3] |
| Ex 229a-b | 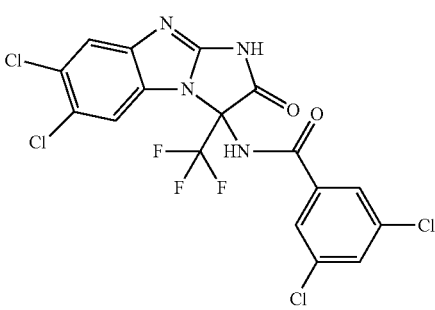 [SMILES: O=C(NC1(C(F)(F)F)C(=O)Nc2nc3cc(Cl)c(Cl)cc3n21)c1cc(Cl)cc(Cl)c1] |

TABLE 1-continued
Ex 230a-b
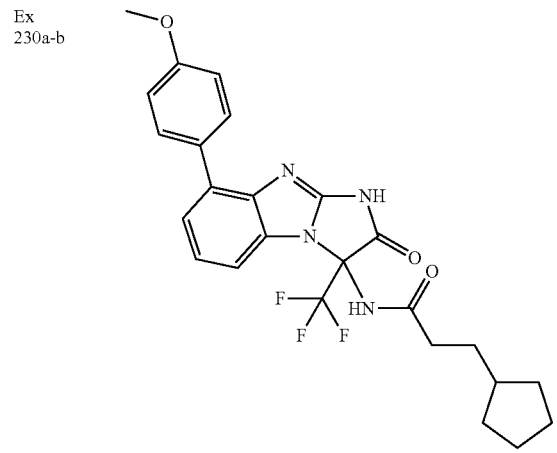
Ex 231a-b
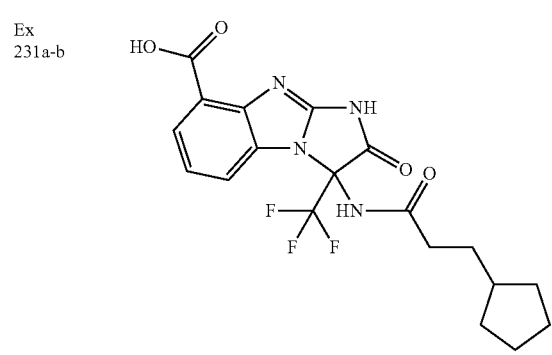
Ex 232
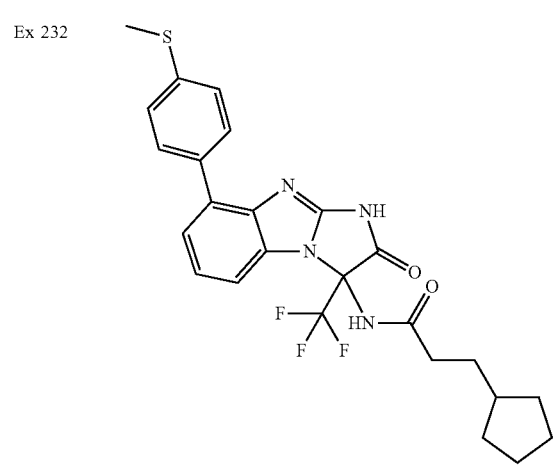
Ex 233
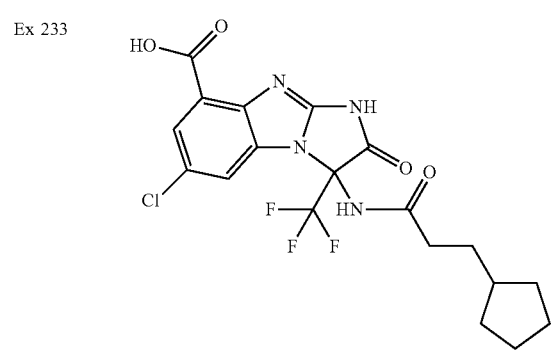
Ex 234
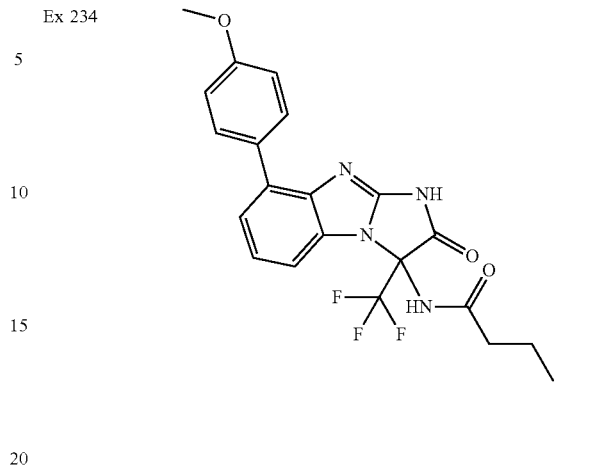
Ex 235
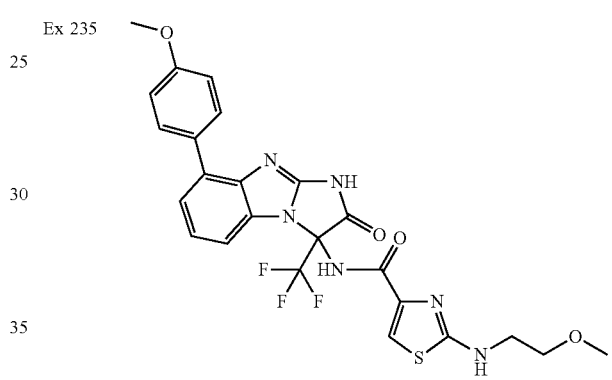
Ex 236
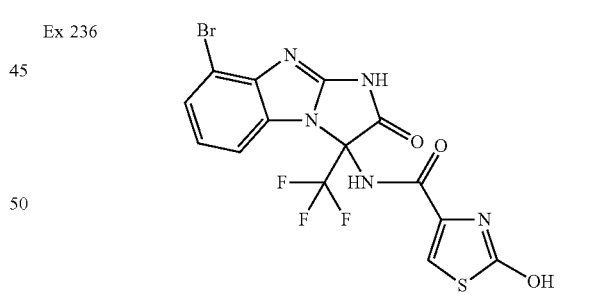
Ex 237
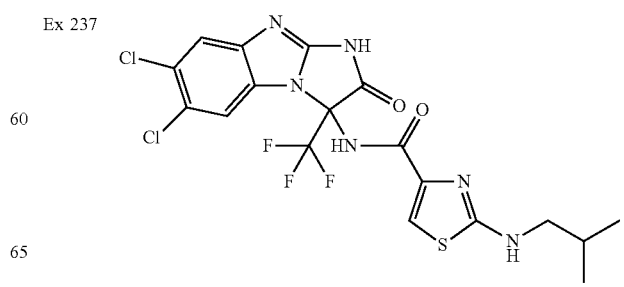

TABLE 1-continued
Ex 238 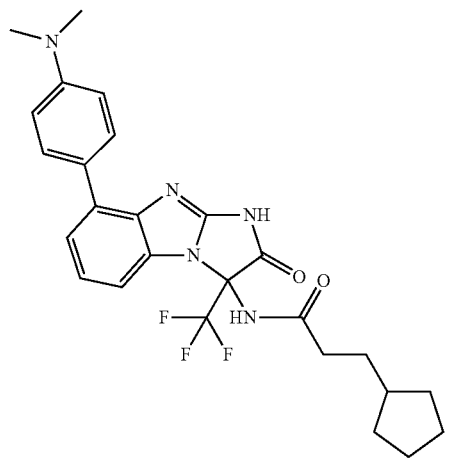 [SMILES: CN(C)c1ccc(-c2cccc3c2nc2n3C(NC(=O)CCC3CCCC3)(C(F)(F)F)C(=O)N2)cc1]
Ex 239 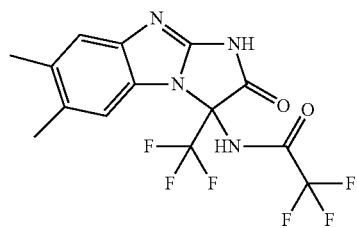 [SMILES: Cc1cc2nc3n(c2cc1C)C(NC(=O)C(F)(F)F)(C(F)(F)F)C(=O)N3]
Ex 240 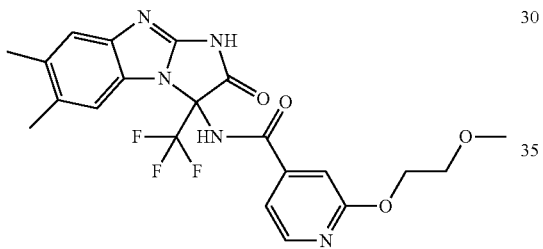
Ex 241 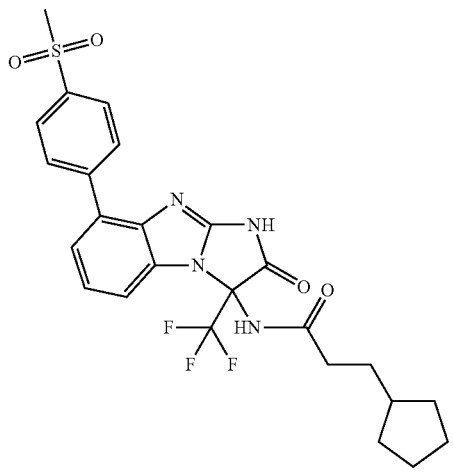 [SMILES: CS(=O)(=O)c1ccc(-c2cccc3c2nc2n3C(NC(=O)CCC3CCCC3)(C(F)(F)F)C(=O)N2)cc1]
Ex 242 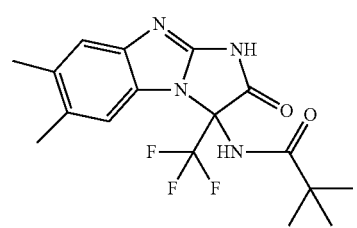 [SMILES: Cc1cc2nc3n(c2cc1C)C(NC(=O)C(C)(C)C)(C(F)(F)F)C(=O)N3]
TABLE 1-continued
Ex 243 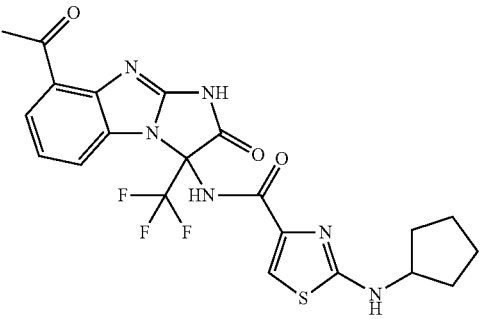 [SMILES: CC(=O)c1cccc2c1nc1n2C(NC(=O)c2csc(NC3CCCC3)n2)(C(F)(F)F)C(=O)N1]
Ex 244 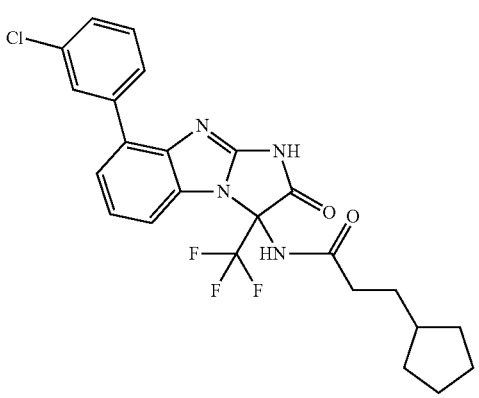 [SMILES: O=C(CCC1CCCC1)NC1(C(F)(F)F)C(=O)Nc2nc3c(-c4cccc(Cl)c4)cccc3n21]
Ex 245 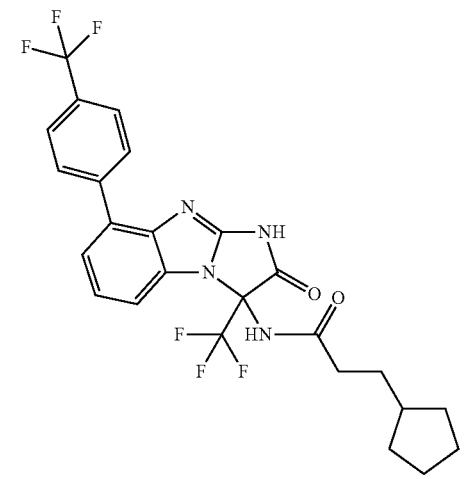 [SMILES: O=C(CCC1CCCC1)NC1(C(F)(F)F)C(=O)Nc2nc3c(-c4ccc(C(F)(F)F)cc4)cccc3n21]
Ex 246 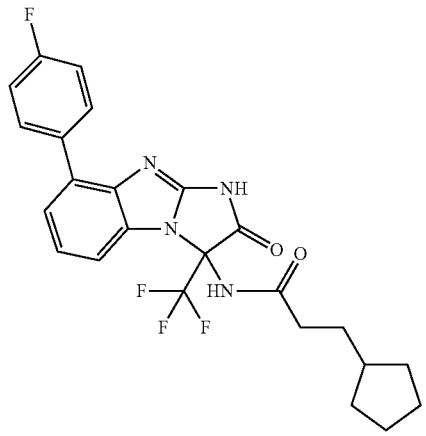 [SMILES: O=C(CCC1CCCC1)NC1(C(F)(F)F)C(=O)Nc2nc3c(-c4ccc(F)cc4)cccc3n21]

TABLE 1-continued
Ex 247
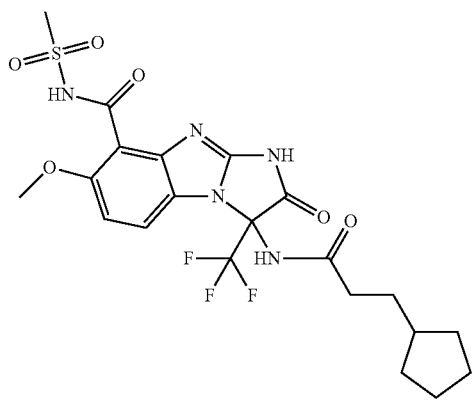 [SMILES: COc1ccc2c(nc3n2C(NC(=O)CCC2CCCC2)(C(F)(F)F)C(=O)N3)c1C(=O)NS(C)(=O)=O]
Ex 248
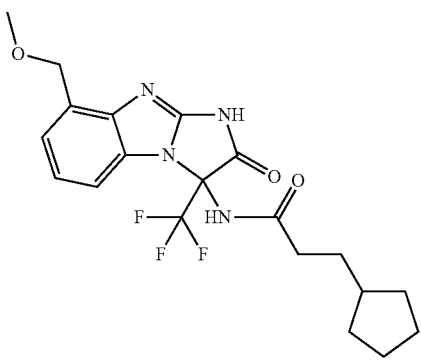 [SMILES: COCc1cccc2c1nc1n2C(NC(=O)CCC2CCCC2)(C(F)(F)F)C(=O)N1]
Ex 249
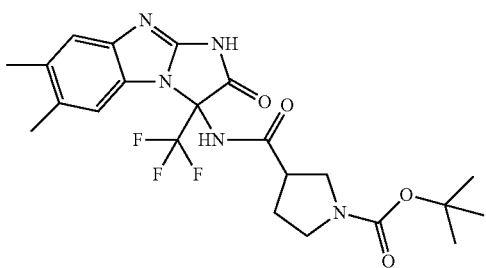 [SMILES: Cc1cc2nc3n(c2cc1C)C(NC(=O)C1CCN(C(=O)OC(C)(C)C)C1)(C(F)(F)F)C(=O)N3]
Ex 250
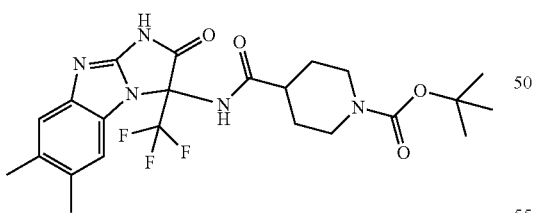
Ex 251
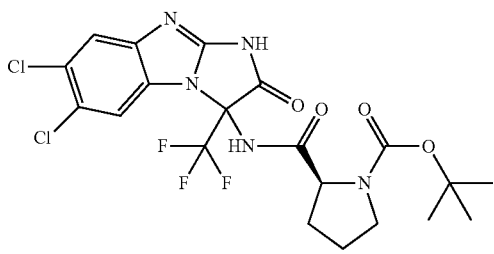 [SMILES: CC(C)(C)OC(=O)N1CCC[C@H]1C(=O)NC1(C(F)(F)F)C(=O)Nc2nc3cc(Cl)c(Cl)cc3n21]
TABLE 1-continued
Ex 252
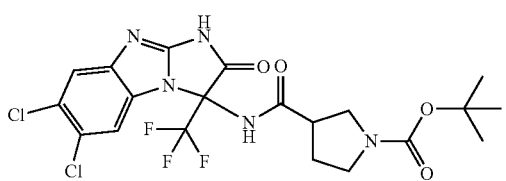 [SMILES: CC(C)(C)OC(=O)N1CCC(C(=O)NC2(C(F)(F)F)C(=O)Nc3nc4cc(Cl)c(Cl)cc4n32)C1]
Ex 253
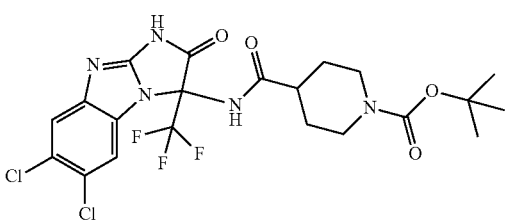 [SMILES: CC(C)(C)OC(=O)N1CCC(C(=O)NC2(C(F)(F)F)C(=O)Nc3nc4cc(Cl)c(Cl)cc4n32)CC1]
Ex 254
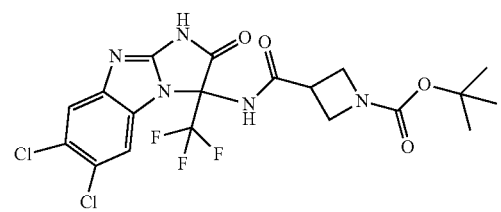 [SMILES: CC(C)(C)OC(=O)N1CC(C(=O)NC2(C(F)(F)F)C(=O)Nc3nc4cc(Cl)c(Cl)cc4n32)C1]
Ex 255
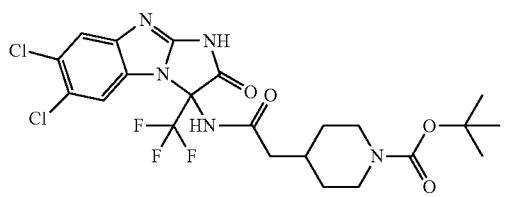 [SMILES: CC(C)(C)OC(=O)N1CCC(CC(=O)NC2(C(F)(F)F)C(=O)Nc3nc4cc(Cl)c(Cl)cc4n32)CC1]
Ex 256
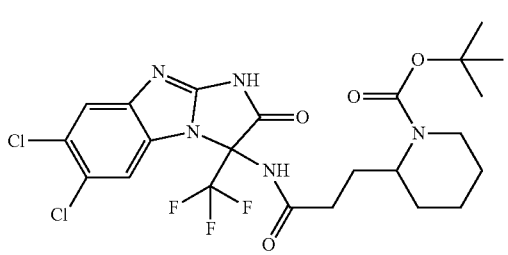 [SMILES: CC(C)(C)OC(=O)N1CCCCC1CCC(=O)NC1(C(F)(F)F)C(=O)Nc2nc3cc(Cl)c(Cl)cc3n21]
Ex 257
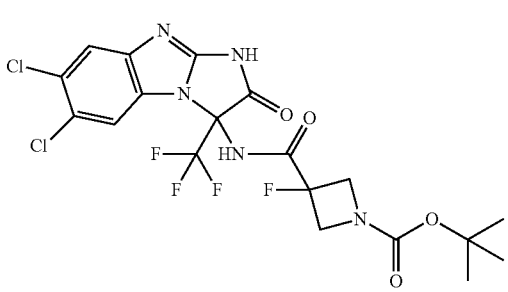 [SMILES: CC(C)(C)OC(=O)N1CC(F)(C(=O)NC2(C(F)(F)F)C(=O)Nc3nc4cc(Cl)c(Cl)cc4n32)C1]

TABLE 1-continued

Ex 258

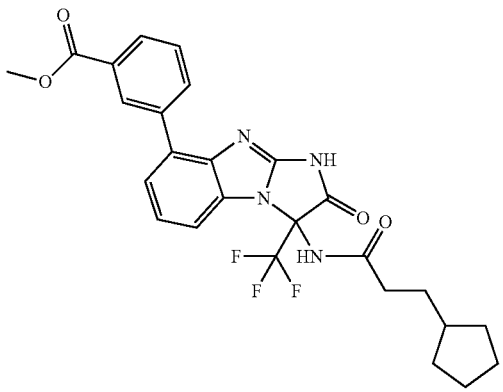 [SMILES: COC(=O)c1cccc(-c2cccc3c2nc2n3C(NC(=O)CCC3CCCC3)(C(F)(F)F)C(=O)N2)c1]

Ex 259

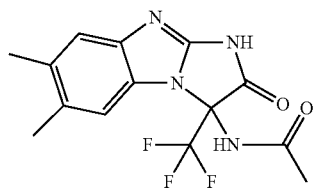 [SMILES: CC(=O)NC1(C(F)(F)F)C(=O)Nc2nc3cc(C)c(C)cc3n21]

Ex 260

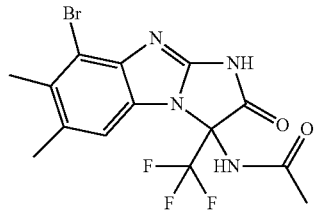 [SMILES: CC(=O)NC1(C(F)(F)F)C(=O)Nc2nc3c(Br)c(C)c(C)cc3n21]

Ex 261

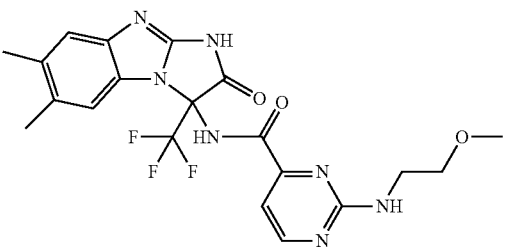

NMR and mass spectral data for Examples of the invention are shown in Table 2.

TABLE 2

| Ex | ABR | Name | M ± H⁺ (m/z) | $^1$H NMR |
|---|---|---|---|---|
| 1 | 239471 | 6-chloro-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-pyridine-2-carboxamide | | 1H NMR (400 MHz, DMSO) δ 2.27 (s, 3H), 2.27 (s, 3H), 7.15 (s, 1H), 7.40 (s, 1H), 7.70 (d, 1H), 8.28 (dd, 1H), 8.84 (d, 1H), 9.73 (s, 1H), 10.58 (s, 1H). |
| 2 | 239472 | N[10,11-dichloro-4-oxo-3-(trifluoromethyl)-2,5,7-triazatricyclo[6.4.0.0$^{2,6}$]dodeca-1(12),6,8,10-tetraen-3-yl]-6-fluoropyridine-2-carboxamide | | 1H NMR (300 MHz, DMSO) δ 7.54 (dd, 1H), 7.91-7.75 (m, 3H), 8.23-8.11 (m, 1H), 10.88 (s, 1H), 13.39 (s, 1H). |
| 3 | 238128 | N-[4-oxo-3-(trifluoromethyl)-2,5,7-triazatricyclo-[6.4.0.0$^{2,6}$]dodeca-1(12),6,8,10-tetraen-3-yl]-benzamide | 361.0 | $^1$H NMR (500 MHz, DMSO-d$_6$) δ 7.13-7.21 (m, 2H), 7.29-7.34 (m, 1H), 7.49 (t, 3H), 7.61 (t, 1H), 7.83 (d, 2H), 10.57 (s, 1H), 13.05 (s, 1H). |
| 4 | 238883 | 2-cyclohexyl-N-[4-oxo-3-(trifluoromethyl)-2,5,7-tri-azatricyclo[6.4.0.0$^{2,6}$]dodeca-1(12),6,8,10-tetraen-3-yl]-acetamide | 381.0 | $^1$H NMR (500 MHz, DMSO-d$_6$) δ 0.73-0.83 (m, 2H), 1.01-1.12 (m, 3H), 1.39 (dd, 2H), 1.48-1.67 (m, 4H), 2.02-2.14 (m, 2H), 7.15-7.23 (m, 3H), 7.48 (d, 1H), 10.19 (s, 1H), 12.92 (s, 1H). |
| 5 | 238798 | 3-(morpholin-4-yl)-N-[4-oxo-3-(trifluoromethyl)-2,5,7-tri-azatricyclo[6.4.0.0$^{2,6}$]dodeca-1(12),6,8,10-tetraen-3-yl]-propanamide | 398.1 | $^1$H NMR (500 MHz, DMSO-d$_6$) δ 2.20-2.33 (m, 4H), 2.35-2.47 (m, 4H), 3.44 (t, 4H), 7.17-7.22 (m, 3H), 7.46-7.49 (m, 1H), 10.45 (s, 1H), 12.88 (s, 1H). |
| 6 | 238799 | N-[4-oxo-3-(trifluoromethyl)-2,5,7-triazatricyclo-[6.4.0.0$^{2,6}$]dodeca-1(12),6,8,10-tetraen-3-yl]-3-(pyrrolidin-1-yl)propanamide | 382.0 | $^1$H NMR (500 MHz, DMSO-d$_6$) δ 1.65-1.72 (m, 4H), 2.34-2.46 (m, 2H), 2.52-2.56 (m, 4H), 2.65 (t, 2H), 6.91-6.99 (m, 2H), 7.05 (d, 1H), 7.25 (d, 1H), 10.18 (s, 1H). |
| 7 | 238816 | 3-(oxan-4-yl)-N-[4-oxo-3-(trifluoromethyl)-2,5,7-triaza-tricyclo[6.4.0.0$^{2,6}$]dodeca-1(12),6,8,10-tetraen-3-yl]-propanamide | 397.0 | $^1$H NMR (500 MHz, DMSO-d$_6$) δ 0.90-1.03 (m, 2H), 1.08-1.17 (m, 1H), 1.22-1.36 (m, 3H), 1.43 (d, 1H), 2.20-2.31 (m, 2H), 2.98-3.10 (m, 2H), 3.70 (ddd, 2H), 7.15-7.23 (m, 3H), 7.48 (d, 1H), 10.23 (s, 1H), 12.94 (s, 1H). |
| 8 | 238803 | 2-bromo-N-[3-oxo-4-(tri-fluoromethyl)-2,5,7-triaza-tricyclo[6.4.0.0$^{2,6}$]dodeca-1(12),6,8,10-tetraen-4-yl]-benzamide | 439.1 | $^1$H NMR (400 MHz, DMSO-d$_6$) δ 7.18-7.26 (m, 2H), 7.30 (dd, 2H), 7.39-7.51 (m, 3H), 7.65 (dd, 1H), 10.99 (s, 1H), 13.07 (s, 1H). |

TABLE 2-continued

| Ex | ABR | Name | M ± H⁺ (m/z) | ¹H NMR |
|---|---|---|---|---|
| 9 | 238789 | 3-cyclopentyl-N-[4-oxo-3-(trifluoromethyl)-2,5,7-triazatricyclo[6.4.0.0$^{2,6}$]dodeca-1(8),6,9,11-tetraen-3-yl]-propanamide | 381.4 | ¹H NMR (400 MHz, DMSO-d$_6$) 0.85-0.99 (m, 2H), 1.27-1.64 (m, 9H), 2.22 (t, 2H), 7.15-7.23 (m, 3H), 7.46 (s, 1H), 10.20 (s, 1H), 12.91 (s, 1H). |
| 10 | 238802 | 3,5-dimethoxy-N-[3-oxo-4-(trifluoromethyl)-2,5,7-triazatricyclo[6.4.0.0$^{2,6}$]dodeca-1(12),6,8,10-tetraen-4-yl]-benzamide | 421.3 | ¹H NMR (400 MHz, Chloroform-d) δ 3.77 (s, 6H), 6.59 (t, 1H), 6.84 (d, 2H), 7.14-7.22 (m, 2H), 7.28-7.31 (m, 1H), 7.68 (d, 1H). |
| 11 | 238843 | 6-methyl-N-[3-oxo-4-(trifluoromethyl)-2,5,7-triazatricyclo[6.4.0.0$^{2,6}$]dodeca-1(12),6,8,10-tetraen-4-yl]-pyridine-3-carboxamide | 376.3 | ¹H NMR (400 MHz, DMSO-d$_6$) δ 2.53 (s, 3H), 7.18 (t, 1H), 7.29 (t, 1H), 7.40 (d, 2H), 7.61 (d, 1H), 8.14 (dd, 1H), 8.89 (d, 1H), 9.89 (s, 1H), 10.49 (s, 1H). |
| 12 | 238895 | 3,5-dichloro-N-[4-oxo-3-(trifluoromethyl)-2,5,7-triazatricyclo[6.4.0.0$^{2,6}$]dodeca-1(12),6,8,10-tetraen-3-yl]-benzamide | 429.2 | ¹H NMR (400 MHz, DMSO-d$_6$) δ 7.15-7.21 (m, 1H), 7.29 (t, 1H), 7.33-7.41 (m, 1H), 7.61 (d, 1H), 7.88-8.03 (m, 3H), 9.91 (s, 1H), 10.57 (s, 1H). |
| 13 | 238219 | 3-cyclohexyl-N-[3-oxo-4-(trifluoromethyl)-2,5,7-triazatricyclo[6.4.0.0$^{2,6}$]dodeca-1(12),6,8,10-tetraen-4-yl]-propanamide | 395.4 | ¹H NMR (400 MHz, DMSO-d$_6$) δ 0.63-0.78 (m, 2H), 0.86-1.04 (m, 4H), 1.19-1.30 (m, 2H), 1.43-1.67 (m, 5H), 2.14-2.34 (m, 2H), 7.10-7.26 (m, 3H), 7.42-7.52 (m, 1H), 10.18 (s, 1H), 12.90 (s, 1H). |
| 14 | 238786 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-benzamide | 389.0 | ¹H NMR (500 MHz, DMSO-d$_6$) δ 2.21 (s, 3H), 2.23 (s, 3H), 7.08 (s, 1H), 7.26 (s, 1H), 7.49 (t, 2H), 7.61 (t, 1H), 7.78-7.86 (m, 2H), 10.44 (s, 1H), 12.91 (s, 1H). |
| 15 | 238787 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-3-phenylpropanamide | 417.2 | ¹H NMR (500 MHz, DMSO-d$_6$) δ 2.25 (s, 3H), 2.27 (s, 3H), 2.53-2.57 (m, 2H), 2.63-2.71 (m, 2H), 6.91 (s, 1H), 7.04 (dd, 2H), 7.10-7.14 (m, 3H), 7.25 (s, 1H), 10.12 (s, 1H), 12.83 (s, 1H). |
| 16 | 238908 | 3-(2-chlorophenyl)-N[10,11-dimethyl-4-oxo-3-(trifluoromethyl)-2,5,7-triazatricyclo-[6.4.0.0$^{2,6}$]dodeca-1(8),6,9,11-tetraen-3-yl]-propanamide | 451.1 | ¹H NMR (500 MHz, Methanol-d$_4$) δ 2.30 (s, 3H), 2.35 (s, 3H), 2.63 (t, 2H), 2.86-2.92 (m, 2H), 6.85-6.89 (m, 2H), 6.98 (d, 1H), 7.05-7.10 (m, 1H), 7.24 (s, 1H), 7.27 (d, 1H). |
| 17 | 239340 | 3,5-dichloro-N-[10,11-dimethyl-4-oxo-3-(trifluoromethyl)-2,5,7-triazatricyclo-[6.4.0.0$^{2,6}$]dodeca-1(8),6,9,11-tetraen-3-yl]benzamide | 456.8, | ¹H NMR (500 MHz, Methanol-d$_4$) δ 2.29 (s, 3H), 2.31 (s, 3H), 7.10 (s, 1H), 7.24 (s, 1H), 7.66 (t, 1H), 7.76 (d, 2H). |
| 18 | 239078 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-4-phenylbenzamide | -463.2 | ¹H NMR (500 MHz, DMSO-d$_6$) δ 2.22 (s, 3H), 2.24 (s, 3H), 7.09 (s, 1H), 7.26 (s, 1H), 7.42 (t, 1H), 7.50 (t, 2H), 7.71-7.74 (m, 2H), 7.80 (d, 2H), 7.94 (d, 2H), 10.44 (s, 1H), 12.87 (s, 1H). |
| 19 | 238854 | 4-cyclopentyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-butanamide | 423.1 | ¹H NMR (500 MHz, Methanol-d$_4$) δ 0.82-0.94 (m, 2H), 0.95-1.06 (m, 1H), 1.09-1.19 (m, 1H), 1.38-1.55 (m, 6H), 1.55-1.68 (m, 3H), 2.21-2.31 (m, 2H), 2.32 (s, 6H), 7.03 (s, 1H), 7.24 (s, 1H). |
| 20 | 238884 | 2-cyclohexyl-N-[10,11-dimethyl-4-oxo-3-(trifluoromethyl)-2,5,7-triazatricyclo[6.4.0.0$^{2,6}$]dodeca-1(8),6,9,11-tetraen-3-yl]-acetamide | 409.1 | ¹H NMR (500 MHz, DMSO-d$_6$) δ 0.69-0.91 (m, 2H), 0.99-1.09 (m, 3H), 1.41 (dd, 2H), 1.47-1.56 (m, 4H), 1.98-2.18 (m, 2H), 2.24 (s, 6H), 6.93 (s, 1H), 7.24 (s, 1H), 10.03 (s, 1H), 12.78 (s, 1H). |
| 21 | 238950 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-6-(2,2,2-trifluoroethoxy)-pyridine-3-carboxamide | 487.9 | ¹H NMR (500 MHz, DMSO-d$_6$) δ 2.21 (s, 3H), 2.23 (s, 3H), 5.07 (q, 2H), 7.07 (s, 1H), 7.09 (d, 1H), 7.25 (s, 1H), 8.21 (dd, 1H), 8.68 (d, 1H), 10.51 (s, 1H), 12.94 (s, 1H). |
| 22 | 239208 | 1-cyclopentanecarbonyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]- | 478.3 | ¹H NMR (500 MHz, Methanol-d$_4$) δ 1.51-1.94 (m, 8H), 2.05-2.18 (m, 1H), 2.29 (s, 3H), 2.30 (s, 3H), 2.74-2.89 (m, 1H), 3.03 (q, 2H), 3.13-3.27 (m, 1H), 3.37-3.62 (m, 2H), |

TABLE 2-continued

| Ex | ABR | Name | M ± H+ (m/z) | 1H NMR |
|----|-----|------|--------------|--------|
|  |  | pyrrolidine-3-carboxamide |  | 3.69 (dd, 1H), 6.95-6.97 (m, 1H), 7.17 (s, 1H). |
| 23 | 238814 | N-[10,11-dimethyl-4-oxo-3-(trifluoromethyl)-2,5,7-triazatricyclo[6.4.0.0^{2,6}]dodeca-1(12),6,8,10-tetraen-3-yl]-3-(morpholin-4-yl)propanamide | 426.1 | 1H NMR (500 MHz, Methanol-$d_4$) δ 2.33 (s, 3H), 2.33 (s, 3H), 2.89-2.98 (m, 2H), 3.06 (s, 4H), 3.22-3.28 (m, 2H), 3.76-3.90 (m, 4H), 7.11 (s, 1H), 7.24 (s, 1H). |
| 24 | 239077 | N-[10,11-dimethyl-4-oxo-3-(trifluoromethyl)-2,5,7-triazatricyclo[6.4.0.0^{2,6}]dodeca-1(12),6,8,10-tetraen-3-yl]-pyrrolidine-3-carboxamide hydrochloride | 382.1 | 1H NMR (500 MHz, Methanol-$d_4$) δ 1.23-1.43 (m, 1H), 1.75-1.85 (m, 0.5H), 2.13-2.25 (m, 0.5H), 2.28-2.34 (m, 0.5H), 2.36 (s, 3H), 2.37 (s, 3H) 2.39-2.46 (m, 0.5H), 2.99-3.07 (m, 1H), 3.17-3.27 (m, 1H), 3.38-3.50 (m, 2H), 7.16 (s, 1H), 7.32 (s, 1H). |
| 25 | 239205 | N-[10,11-dimethyl-4-oxo-3-(trifluoromethyl)-2,5,7-triazatricyclo[6.4.0.0^{2,6}]dodeca-1(12),6,8,10-tetraen-3-yl]-piperidine-4-carboxamide hydrochloride | 396.1 | 1H NMR (500 MHz, DMSO-$d_6$) δ 1.35-1.45 (m, 1H), 1.57-1.89 (m, 3H), 2.25 (s, 6H), 2.67-2.87 (m, 3H), 3.16 (dd, 2H), 6.97 (s, 1H), 7.25 (s, 1H), 8.67 (s, 1H), 9.11 (s, 1H), 10.34 (s, 1H). |
| 26 | 239227 | N-[10,11-dimethyl-4-oxo-3-(trifluoromethyl)-2,5,7-triazatricyclo[6.4.0.0^{2,6}]dodeca-1(12),6,8,10-tetraen-3-yl]-1-(2-methoxyacetyl)-piperidine-4-carboxamide | 468.3 | 1H NMR (500 MHz, Methanol-$d_4$) δ 1.25-1.45 (m, 1H), 1.46-1.73 (m, 2H), 1.80-1.92 (m, 1H), 2.34 (s, 3H), 2.35 (s, 3H), 2.65-2.84 (m, 2H), 3.02-3.17 (m, 1H), 3.35 (s, 1.5H), 3.37 (s, 1.5H), 3.80 (dd, 1H), 4.00-4.17 (m, 2H), 4.33 (dd, 1H), 7.06 (s, 1H), 7.25 (s, 1H). Rotomers present. |
| 27 | 238788 | 3-cyclopentyl-N-[10,11-dimethyl-4-oxo-3-(trifluoromethyl)-2,5,7-triazatricyclo[6.4.0.0^{2,6}]dodeca-1(12),6,8,10-tetraen-3-yl]-propanamide | 409.5 | 1H NMR (400 MHz, DMSO-$d_6$) δ 0.86-1.08 (m, 2H), 1.28-1.66 (m, 9H), 2.15-2.30 (m, 8H), 6.94 (s, 1H), 7.23 (s, 1H), 10.05 (s, 1H), 12.78 (s, 1H) |
| 28 | 238911 | 6-chloro-N-[10,11-dimethyl-4-oxo-3-(trifluoromethyl)-2,5,7-triazatricyclo-[6.4.0.0^{2,6}]dodeca-1(12),6,8,10-tetraen-3-yl]-pyridine-3-carboxamide | 424.1 | 1H NMR (400 MHz, DMSO-$d_6$) δ 2.27 (s, 6H), 7.15 (s, 1H), 7.40 (s, 1H), 7.70 (d, 1H), 8.28 (dd, 1H), 8.84 (d, 1H), 9.73 (s, 1H), 10.58 (s, 1H). |
| 29 | 238998 | 3-(2,6-dichlorophenyl)-N-[10,11-dimethyl-4-oxo-3-(trifluoromethyl)-2,5,7-triazatricyclo[6.4.0.0^{2,6}]dodeca-1(8),6,9,11-tetraen-3-yl]-propanamide | 485.2 | 1H NMR (400 MHz, DMSO-$d_6$) δ 2.25 (s, 3H), 2.27 (s, 3H), 2.47-2.50 (m, 2H), 2.88 (d, 2H), 6.93 (s, 1H), 7.24 (t, 2H), 7.39 (d, 2H), 10.19 (s, 1H), 12.84 (s, 1H). |
| 30 | 239004 | 2-bromo-N-[10,11-dimethyl-4-oxo-3-(trifluoromethyl)-2,5,7-triazatricyclo-[6.4.0.0^{2,6}]dodeca-1(8),6,9,11-tetraen-3-yl]-benzamide | 467.2 | 1H NMR (400 MHz, DMSO-$d_6$) δ 2.26 (s, 6H), 7.15 (s, 1H), 7.56-7.35 (m, 4H), 7.68 (d, 1H), 9.86 (s, 1H), 10.68 (s, 1H). |
| 31 | 239024 | 6-(cyclohexylamino)-N-[10,11-dimethyl-4-oxo-3-(trifluoromethyl)-2,5,7-triazatricyclo[6.4.0.0^{2,6}]dodeca-1(12),6,8,10-tetraen-3-yl]-pyridine-3-carboxamide | 487.6 | 1H NMR (400 MHz, Methanol-$d_4$) δ 1.22-1.41 (m, 5H), 1.66 (d, 1H), 1.77 (d, 2H), 1.97 (d, 2H), 2.25 (s, 3H), 2.27 (s, 3H), 3.67-3.79 (m, 1H), 6.45 (d, 1H), 7.10 (s, 1H), 7.43 (s, 1H), 7.76 (dd, 1H), 8.49 (d, 1H). |
| 32 | 239031 | N-[10,11-dimethyl-4-oxo-3-(trifluoromethyl)-2,5,7-triazatricyclo[6.4.0.0^{2,6}]dodeca-1(12),6,8,10-tetraen-3-yl]-6-methylpyridine-3-carbox-amide | 404.5 | 1H NMR (400 MHz, DMSO-$d_6$) δ 2.27 (s, 6H), 2.53 (s, 3H), 7.15 (s, 1H), 7.39 (d, 2H), 8.13 (dd, 1H), 8.88 (d, 1H), 9.74 (s, 1H), 10.40 (s, 1H). |
| 33 | 238804 | 3-cyclohexyl-N-[10,11-dimethyl-3-oxo-4-(trifluoromethyl)-2,5,7-triazatricyclo-[6.4.0.0^{2,6}]dodeca-1(12),6,8,10-tetraen-4-yl]-propanamide | 423.4 | 1H NMR (400 MHz, DMSO-$d_6$) δ 0.64-0.78 (m, 2H), 0.85-1.07 (m, 4H), 1.19-1.30 (m, 2H), 1.43-1.63 (m, 5H), 2.10-2.33 (m, 8H), 6.92 (s, 1H), 7.21 (s, 1H), 9.93 (s, 1H), 13.12 (s, 1H). |
| 34 | 239084 | N-[10,11-dimethyl-4-oxo-3-(trifluoromethyl)-2,5,7-triazatricyclo[6.4.0.0^{2,6}]dodeca-1(12),6,8,10-tetraen-3-yl]-3-(pyridin-3-yl)propanamide | 417.8 | 1H NMR (400 MHz, DMSO-$d_6$) δ 2.25 (s, 3H), 2.27 (s, 3H), 2.53-2.61 (m, 2H), 2.63-2.71 (m, 2H), 6.86 (s, 1H), 7.05-7.11 (m, 1H), 7.19-7.31 (m, 1H), 7.41 (d, 1H), 8.16-8.42 (m, 2H), 10.05 (s, 1H), 12.82 (s, 1H). |

TABLE 2-continued

| Ex | ABR | Name | M ± H⁺ (m/z) | ¹H NMR |
|---|---|---|---|---|
| 35 | 238974 | 6-(cyclohexylamino)-N-[10,11-dimethyl-4-oxo-3-(trifluoromethyl)-2,5,7-triazatricyclo[6.4.0.0²,⁶]dodeca-1(12),6,8,10-tetraen-3-yl]pyridine-2-carboxamide | 487.5 | ¹H NMR (400 MHz, DMSO-d₆) δ 1.23-1.47 (m, 5H), 1.60-1.70 (m, 1H), 1.71-1.85 (m, 2H), 1.96-2.10 (m, 2H), 2.20 (s, 3H), 2.22 (s, 3H), 3.65-3.77 (m, 1H), 6.73 (d, 1H), 6.96 (d, 1H), 6.99 (d, 1H), 7.04 (s, 1H), 7.21 (s, 1H), 7.49 (dd, 1H), 9.43 (s, 1H), 13.12 (s, 1H). |
| 36 | 239059 | 6-cyclohexyl-N-[10,11-dimethyl-4-oxo-3-(trifluoromethyl)-2,5,7-triazatricyclo-[6.4.0.0²,⁶]dodeca-1(12),6,8,10-tetraen-3-yl]-pyridine-2-carboxamide | 472.6 | ¹H NMR (400 MHz, Methanol-d₄) δ 1.34-1.42 (m, 1H), 1.46-1.67 (m, 4H), 1.81 (d, 1H), 1.92 (d, 2H), 2.02 (d, 2H), 2.25 (s, 3H), 2.27 (s, 3H), 2.82-2.92 (m, 1H), 7.11 (s, 1H), 7.22 (s, 1H), 7.52 (d, 1H), 7.74 (d, 1H), 7.83 (t, 1H). |
| 37 | 239019 | N-[10,11-dichloro-4-oxo-3-(trifluoromethyl)-2,5,7-triazatricyclo[6.4.0.0²,⁶]dodeca-1(8),6,9,11-tetraen-3-yl]-3-phenylpropanamide | 457.0 | ¹H NMR (500 MHz, DMSO-d₆) δ 2.58-2.64 (m, 2H), 2.66-2.73 (m, 2H), 6.98-7.01 (m, 2H), 7.05-7.10 (m, 3H), 7.29 (s, 1H), 7.83 (s, 1H), 10.34 (s, 1H), 13.21 (s, 1H). |
| 38 | 238949 | N-[10,11-dichloro-4-oxo-3-(trifluoromethyl)-2,5,7-triazatricyclo[6.4.0.0²,⁶]dodeca-1(8),6,9,11-tetraen-3-yl]-benzamide | 428.9 | ¹H NMR (500 MHz, Methanol-d₄) δ 7.48 (t, 2H), 7.52 (s, 1H) 7.61 (t, 1H), 7.68 (s, 1H), 7.79-7.85 (m, 2H). |
| 39 | 238926 | 3-cyclopentyl-N-[10,11-dichloro-4-oxo-3-(trifluoromethyl)-2,5,7-triazatricyclo-[6.4.0.0²,⁶]dodeca-1(12),6,8,10-tetraen-3-yl]-propanamide | 448.9 | ¹H NMR (500 MHz, DMSO-d₆) δ 0.84-0.97 (m, 2H), 1.27-1.54 (m, 8H), 1.56-1.64 (m, 1H), 2.21-2.31 (m, 2H), 7.40 (s, 1H), 7.81 (s, 1H), 10.27 (s, 1H), 13.16 (s, 1H). |
| 40 | 239424 | N-[10,11-dichloro-4-oxo-3-(trifluoromethyl)-2,5,7-triazatricyclo[6.4.0.0²,⁶]dodeca-1(12),6,8,10-tetraen-3-yl]-2-azaspiro[3.3]heptane-6-carboxamide TFA salt | 447.8 | ¹H NMR (500 MHz, Methanol-d₄) δ 2.11 (ddd, 1H), 2.38 (ddd, 1H), 2.47 (t, 1H), 2.55 (t, 1H), 3.09-3.17 (m, 1H), 3.83 (d, 1H), 3.93 (d, 1H), 3.97-4.03 (m, 2H), 7.39 (s, 1H), 7.67 (s, 1H). |
| 41 | 239426 | Diastereomeric mixture. (2S)-N[10,11-dichloro-4-oxo-3-(trifluoromethyl)-2,5,7-triazatricyclo-[6.4.0.0²,⁶]dodeca-1(12),6,8,10-tetraen-3-yl]pyrrolidine-2-carboxamide TFA salt | 421.8 | ¹H NMR (500 MHz, Methanol-d₄) δ 1.68-1.01 (m, 1H), 1.96-2.15 (m, 2H), 2.45-2.57 (m, 1H), 3.19-3.30 (m, 2H), 4.45 (ddd, 1H), 7.47 (s, 0.5H), 7.47 (s, 0.5H), 7.68 (s, 0.5H), 7.69 (s, 0.5H). |
| 42 | 239136 | Diastereomeric mixture N[10,11-dichloro-4-oxo-3-(trifluoromethyl)-2,5,7-triazatricyclo[6.4.0.0²,⁶]dodeca-1(12),6,8,10-tetraen-3-yl]-pyrrolidine-3-carboxamide hydrochloride salt | 422.0 | ¹H NMR (500 MHz, DMSO-d₆) δ 1.59-1.67 (m, 0.5H), 1.86-1.94 (m, 0.5H), 2.14-2.25 (m, 1H), 2.95-3.21 (m, 4H), 7.21 (s, 0.5H), 7.22 (s, 0.5H), 7.42-7.44 (m, 1H), 8.79 (s, 2H), 9.80 (s, 1H). |
| 43 | 239206 | N-[10,11-dichloro-4-oxo-3-(trifluoromethyl)-2,5,7-triazatricyclo[6.4.0.0²,⁶]dodeca-1(12),6,8,10-tetraen-3-yl]-piperidine-4-carboxamide | 436.0 | ¹H NMR (500 MHz, DMSO-d₆) δ 1.44-1.54 (m, 1H), 1.57-1.67 (m, 1H), 1.73-1.83 (m, 2H), 2.61-2.68 (m, 1H), 2.77-2.88 (m, 2H), 3.17-3.27 (m, 2H), 7.13 (s, 1H), 7.33 (s, 1H), 8.29 (s, 1H), 9.32 (s, 1H). |
| 44 | 239228 | N-[10,11-dichloro-4-oxo-3-(trifluoromethyl)-2,5,7-triazatricyclo[6.4.0.0²,⁶]dodeca-1(12),6,8,10-tetraen-3-yl]-1-(2-methoxyacetyl)-piperidine-4-carboxamide | 507.9 | ¹H NMR (500 MHz, Methanol-d₄) δ 1.35-1.62 (m, 2H), 1.60-1.69 (m, 1H), 1.81-1.85 (m, 1H), 2.61-2.72 (m, 1H), 2.72-2.82 (m, 1H), 3.01-3.15 (m, 1H), 3.33-3.37 (m, 3H), 3.71-3.86 (m, 1H), 4.02-4.16 (m, 2H), 4.33 (dd, 1H), 7.39 (s, 1H), 7.63 (s, 1H). Approx 75% purity. Aliphatic impurity in NMR. |
| 45 | 239229 | N-[10,11-dichloro-4-oxo-3-(trifluoromethyl)-2,5,7-triazatricyclo[6.4.0.0²,⁶]dodeca-1(12),6,8,10-tetraen-3-yl]-1-(3-methylbutanoyl)-piperidine-4-carboxamide | 519.9 | ¹H NMR (500 MHz, Methanol-d₄) δ 0.94 (t, 6H), 1.29-1.62 (m, 2H), 1.67-1.74 (m, 1H), 1.81-1.90 (m, 1H), 1.97-2.09 (m, 1H), 2.20-2.27 (m, 2H), 2.65-2.78 (m, 2H), 3.09-3.16 (m, 1H), 3.95 (dd, 1H), 4.42 (dd, 1H), 7.26 (s, 1H), 7.47 (s, 1H). Approx 75% purity. Aliphatic impurity in NMR. |

TABLE 2-continued

| Ex | ABR | Name | M ± H+ (m/z) | 1H NMR |
|---|---|---|---|---|
| 46 | 239232 | N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(3,3,3-trifluoropropanoyl)-piperidine-4-carboxamide | 545.9 | 1H NMR (500 MHz, Methanol-d$_4$) δ 1.27-1.64 (m, 2H), 1.67 (d, 1H), 1.82-1.87 (m, 1H), 2.65-2.74 (m, 1H), 2.75-2.84 (m, 1H), 3.10-3.22 (m, 1H), 3.3 7-3.49 (m, 2H), 3.77-3.95 (m, 1H), 4.35 (dd, 1H), 7.40 (s, 1H), 7.65 (s, 1H). |
| 47 | 239257 | N-[10,11-dichloro-4-oxo-3-(trifluoromethyl)-2,5,7-triazatricyclo[6.4.0.0$^{2,6}$]dodeca-1(12),6,8,10-tetraen-3-yl]-azetidine-3-carboxamide | 407.9 | 1H NMR (500 MHz, Methanol-d$_4$) δ 3.72-3.80 (m, 1H), 3.97 (dd, 1H), 4.11-4.24 (m, 3H), 7.19 (s, 1H), 7.43 (s, 1H). |
| 48 | 239402 | N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(ethanesulfonyl)azetidine-3-carboxamide | 499.8 | 1H NMR (500 MHz, Methanol-d$_4$) δ 1.23 (t, 3H), 2.90-3.03 (m, 2H), 3.52-3.58 (m, 1H), 3.81 (dd, 1H), 3.98 (dd, 1H), 4.01 (t, 1H), 4.08 (t, 1H), 7.40 (s, 1H), 7.68 (s, 1H). |
| 49 | 239403 | 1-acetyl-N-[10,11-dichloro-4-oxo-3-(trifluoromethyl)-2,5,7-triazatricyclo-[6.4.0.0$^{2,6}$]dodeca-1(12),6,8,10-tetraen-3-yl]-azetidine-3-carboxamide | 449.8 | 1H NMR (500 MHz, Methanol-d$_4$) δ 1.78 (s, 1.5H), 1.78 (s, 1.5H), 3.53-3.59 (m, 1H), 3.73 (dd, 0.5H), 3.94 (dd, 0.5H), 4.03-4.09 (m, 1H), 4.15 (t, 0.5H), 4.20-4.27 (m, 1H), 4.34 (t, 0.5H), 7.41 (s, 1H), 7.68 (s, 1H). Rotomers present. |
| 50 | 239137 | Diastereomeric mixture 1-cyclopentanecarbonyl-N-[10,11-dichloro-4-oxo-3-(trifluoromethyl)-2,5,7-triazatricyclo[6.4.0.0$^{2,6}$]dodeca-1(12),6,8,10-tetraen-3-yl]-pyrrolidine-3-carboxamide | 518.1 | 1H NMR (250 MHz, Methanol-d$_4$) δ 1.40-1.88 (m, 8H), 2.03-2.36 (m, 2H), 2.68-2.95 (m, 1H), 3.35-3.86 (m, 5H), 7.29-7.35 (m, 1H), 7.51-7.56 (m, 1H). Suspected rotomers present. |
| 51 | 239139 | (3R)-1-(cyclopentane-sulfonyl)-N-[10,11-dichloro-4-oxo-3-(trifluoromethyl)-2,5,7-triazatricyclo-[6.4.0.0$^{2,6}$]dodeca-1(12),6,8,10-tetraen-3-yl]-pyrrolidine-3-carboxamide | 553.8 | 1H NMR (500 MHz, Methanol-d$_4$) δ 1.45-1.83 (m, 7H), 1.83-1.99 (m, 2H), 2.08-2.18 (m, 1H), 3.10-3.28 (m, 2H), 3.33-3.47 (m, 2H), 3.53-3.61 (m, 2H), 7.42 (s, 0.75H), 7.45 (s, 0.25H), 7.67 (s, 1H). |
| 52 | 239404 | N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(pyridin-2-yl)azetidine-3-carboxamide formic acid salt | 484.8 | 1H NMR (500 MHz, Methanol-d$_4$) δ 3.66-3.73 (m, 1H), 3.84 (dd, 1H), 4.05 (dd, 1H), 4.12 (t, 1H), 4.20 (t, 1H), 6.39 (d, 1H), 6.65-6.69 (m, 1H), 7.40 (s, 1H), 7.52-7.57 (m, 1H), 7.63 (s, 1H), 7.95 (dd, 1H), 8.19 (s, 1H). |
| 53 | 239034 | 3-cyclohexyl-N-[10,11-dichloro-4-oxo-3-(trifluoromethyl)-2,5,7-triazatricyclo-[6.4.0.0$^{2,6}$]dodeca-1(12),6,8,10-tetraen-3-yl]-propanamide | 404.5 | 1H NMR (400 MHz, Methanol-d$_4$) δ 0.68-0.84 (m, 2H), 0.87-0.96 (m, 1H), 1.00-1.12 (m, 3H), 1.28-1.42 (m, 2H), 1.50-1.69 (m, 5H), 2.23-2.37 (m, 2H), 7.40 (d, 1H), 7.65 (s, 1H). |
| 54 | 239114 | N-[10,11-dichloro-4-oxo-3-(trifluoromethyl)-2,5,7-triazatricyclo[6.4.0.0$^{2,6}$]dodeca-1(12),6,8,10-tetraen-3-yl]-cyclopentanecarboxamide | 421.2 | 1H NMR (400 MHz, DMSO) δ 1.14-1.30 (m, 1H), 1.36-1.59 (m, 5H), 1.64-1.80 (m, 2H), 2.73-2.85 (m, 1H), 7.41 (s, 1H), 7.82 (s, 1H), 10.25 (s, 1H), 13.16 (s, 1H). |
| 55 | 239115 | N-[10,11-dichloro-4-oxo-3-(trifluoromethyl)-2,5,7-triazatricyclo[6.4.0.0$^{2,6}$]dodeca-1(12),6,8,10-tetraen-3-yl]-cyclohexanecarboxamide | 435.2 | 1H NMR (400 MHz, DMSO-d$_6$) δ 0.95-1.24 (m, 5H), 1.49-1.73 (m, 5H), 2.30-2.41 (m, 1H), 7.41 (s, 1H), 7.83 (s, 1H), 10.23 (s, 1H), 13.15 (s, 1H). |
| 56 | 239414 | 3-chloro-N-[10,11-dichloro-4-oxo-3-(trifluoromethyl)-2,5,7-triazatricyclo-[6.4.0.0$^{2,6}$]dodeca-1(12),6,8,10-tetraen-3-yl]-benzamide | 463.1 | 1H NMR (400 MHz, DMSO-d$_6$) δ 7.56 (t, 1H), 7.63 (s, 1H), 7.70-7.75 (m, 1H), 7.78-7.88 (m, 2H), 7.96 (t, 1H), 10.76 (s, 1H), 13.38 (s, 1H). |
| 57 | 239427 | 3,5-dichloro-N-[10,11-dichloro-4-oxo-3-(trifluoromethyl)-2,5,7-triazatricyclo[6.4.0.0$^{2,6}$]dodeca-1(12),6,8,10-tetraen-3-yl]-benzamide | 497.0 | 1H NMR (400 MHz, DMSO-d$_6$) δ 7.62 (s, 1H), 7.83 (s, 1H), 7.89-8.00 (m, 3H), 10.82 (s, 1H), 13.41 (s, 1H). |
| 58 | 239155 | N-[10,11-dichloro-4-oxo-3-(trifluoromethyl)-2,5,7-triazatricyclo[6.4.0.0$^{2,6}$]dodeca- | 464.5 | 1H NMR (400 MHz, DMSO-d$_6$) δ 1.47-1.55 (m, 2H), 1.55-1.67 (m, 4H), 2.15-2.27 (m, 4H), 2.28- |

TABLE 2-continued

| Ex | ABR | Name | M ± H⁺ (m/z) | ¹H NMR |
|---|---|---|---|---|
| | | 1(12),6,8,10-tetraen-3-yl]-4-(pyrrolidin-1-yl)butanamide | | 2.34 (m, 4H), 7.13 (s, 1H), 7.30 (s, 1H), 8.35 (s, 1H), 9.15 (s, 1H). |
| 59 | 239161 | N-[10,11-dichloro-4-oxo-3-(trifluoromethyl)-2,5,7-triaza-tricyclo[6.4.0.0²,⁶]dodeca-1(12),6,8,10-tetraen-3-yl]-4-(morpholin-4-yl)butanamide | 480.5 | ¹H NMR (400 MHz, DMSO-d₆) δ 1.53-1.63 (m, 2H), 2.26-2.38 (m, 4H), 3.13-3.17 (m, 3H), 3.53-3.61 (m, 4H), 4.10 (s, 1H), 7.37 (s, 1H), 7.70 (s, 1H), 10.12 (s, 1H), 11.89(s, 1H). |
| 60 | 239358 | N-[10,11-dichloro-4-oxo-3-(trifluoromethyl)-2,5,7-triaza-tricyclo[6.4.0.0²,⁶]dodeca-1(12),6,8,10-tetraen-3-yl]-2-(morpholin-4-yl)acetamide | 452.4 | ¹H NMR (400 MHz, DMSO-d₆) δ 2.35-2.44 (m, 4H), 2.96-3.12 (m, 2H), 3.50-3.61 (m, 4H), 7.36 (s, 1H), 7.39 (s, 1H), 8.82 (s, 1H). |
| 61 | 239259 | N-[10,11-dichloro-4-oxo-3-(trifluoromethyl)-2,5,7-triaza-tricyclo[6.4.0.0²,⁶]dodeca-1(12),6,8,10-tetraen-3-yl]-3-(morpholin-4-yl)propanamide | 466.2 | ¹H NMR (400 MHz, DMSO-d₆) δ 2.21-2.37 (m, 4H), 2.39-2.48 (m, 4H), 3.48-3.60 (m, 4H), 7.67 (s, 1H), 7.82 (s, 1H), 10.21 (s, 1H), 10.38 (s, 1H). |
| 62 | 239356 | 6-chloro-N-[10,11-dichloro-4-oxo-3-(trifluoromethyl)-2,5,7-triazatricyclo-[6.4.0.0²,⁶]dodeca-1(12),6,8,10-tetraen-3-yl]-pyridine-2-carboxamide | 464.3 | ¹H NMR (400 MHz, DMSO-d₆) δ 7.77-7.92 (m, 4H), 8.04 (t, 1H), 10.84 (s, 1H), 13.40 (s, 1H). |
| 63 | 239354 | 6-(azetidin-1-yl)-N-[10,11-dichloro-4-oxo-3-(trifluoro-methyl)-2,5,7-triazatricyclo-[6.4.0.0²,⁶]dodeca-1(12),6,8,10-tetraen-3-yl]-pyridine-2-carboxamide | 485.4 | 1H NMR (400 MHz, DMSO-d₆) δ 2.31-2.44 (m, 2H), 3.94-4.17 (m, 4H), 6.63 (d, 1H), 7.10 (d, 1H), 7.64 (dd, 1H), 7.76 (s, 1H), 7.84 (s, 1H), 9.80 (s, 1H), 13.43 (s, 1H) |
| 64 | 239390 | N-[10,11-dichloro-4-oxo-3-(trifluoromethyl)-2,5,7-triaza-tricyclo[6.4.0.0²,⁶]dodeca-1(12),6,8,10-tetraen-3-yl]-6-(2,2,2-trifluoroethoxy)-pyridine-2-carboxamide | 528.1 | ¹H NMR (400 MHz, DMSO-d₆) δ 5.16-5.38 (m, 2H), 7.29 (dd, 1H), 7.59-7.66 (m, 2H), 7.72 (s, 1H), 7.98 (dd, 1H), 9.90 (s, 1H), 13.45 (s, 1H). |
| 65 | 239391 | N-[10,11-dichloro-4-oxo-3-(trifluoromethyl)-2,5,7-triaza-tricyclo[6.4.0.0²,⁶]dodeca-1(12),6,8,10-tetraen-3-yl]-6-(dimethylamino)pyridine-2-carboxamide | 473.1 | ¹H NMR (400 MHz, DMSO-d₆) δ 3.14 (s, 3H), 3.16 (s, 3H), 6.94 (d, 1H), 7.00-7.07 (m, 1H), 7.63 (dd, 1H), 7.81 (s, 1H), 7.87 (s, 1H), 9.88 (s, 1H), 13.41 (s, 1H). |
| 66 | 239409 | 6-(cyclohexylamino)-N-[10,11-dichloro-4-oxo-3-(tri-fluoromethyl)-2,5,7-triaza-tricyclo[6.4.0.0²,⁶]dodeca-1(12),6,8,10-tetraen-3-yl]-pyridine-2-carboxamide | 527.5 | ¹H NMR (400 MHz, DMSO-d₆) δ 1.13-1.47 (m, 5H), 1.60-1.70 (m, 1H), 1.72-1.78 (m, 2H), 1.99-2.09 (m, 2H), 3.74-3.86 (m, 1H), 6.73 (d, 1H), 6.83-7.00 (m, 2H), 7.43-7.53 (m, 1H), 7.78 (s, 1H), 7.83 (s, 1H), 9.77 (s, 1H), 13.48 (s, 1H). |
| 67 | 239101 | N-[10,11-dimethyl-4-oxo-3-(trifluoromethyl)-2,5,7-triaza-tricyclo[6.4.0.0²,⁶]dodeca-1(12),6,8,10-tetraen-3-yl]-6-(ethylamino)pyridine-2-carboxamide | 433.3 | ¹H NMR (300 MHz, DMSO-d₆) δ 1.22 (t, 3H), 2.21 (s, 3H), 2.23 (s, 3H), 3.25-3.45 (m, 2H), 6.71 (d, 1H), 6.97 (d, 1H), 7.05 (t, 1H), 7.12 (s, 1H), 7.23 (s, 1H), 7.44-7.59 (m, 1H), 9.50 (s, 1H), 13.08 (s, 1H). |
| 68 | 239386 | N-[10,11-dichloro-4-oxo-3-(trifluoromethyl)-2,5,7-triaza-tricyclo[6.4.0.0²,⁶]dodeca-1(12),6,8,10-tetraen-3-yl]-2-(piperidin-4-yl)acetamide hydrochloride salt | 450.2 | 1H NMR (400 MHz, DMSO-d₆) δ 1.18-1.34 (m, 2H), 1.40-1.50 (m, 1H), 1.54-1.63 (m, 1H), 1.70-1.86 (m, 1H), 2.17-2.33 (m, 2H), 2.60-2.80 (m, 2H), 3.06-3.20 (m, 2H), 7.44 (s, 1H), 7.84 (s, 1H), 8.37-8.63 (m, 2H), 10.51 (s, 1H), 13.22 (s, 1H). |
| 69 | 239393 | Diastereomeric mixture N-[10,11-dichloro-4-oxo-3-(trifluoromethyl)-2,5,7-triaza-tricyclo[6.4.0.0²,⁶]dodeca-1(12),6,8,10-tetraen-3-yl]-3-(piperidin-2-yl)propanamide hydrochloride salt | 464.2 | 1H NMR (400 MHz, DMSO-d₆) δ 1.05-1.28 (m, 3H), 1.45-1.79 (m, 7H), 2.58-2.84 (m, 2H), 3.10-3.20 (m, 1H), 7.48 (s, 0.5H), 7.50 (s, 0.5H), 7.81 (s, 1H), 8.41-8.87 (m, 2H), 10.45-10.65 (m, 1H), 13.25 (s, 1H). |
| 70 | 239355 | N-[10,11-dichloro-4-oxo-3-(trifluoromethyl)-2,5,7-triaza-tricyclo[6.4.0.0²,⁶]dodeca-1(12),6,8,10-tetraen-3-yl]-6-(ethylamino)pyridine-2-carboxamide | 474.1 | ¹H NMR (400 MHz, DMSO-d₆) δ 1.39 (t, 3H), 4.40-4.58 (m, 2H), 7.10 (dd, 1H), 7.45 (d, 1H), 7.77-7.92 (m, 3H), 10.04 (s, 1H), 13.43 (s, 1H). |

TABLE 2-continued

| Ex | ABR | Name | M ± H+ (m/z) | $^1$H NMR |
|---|---|---|---|---|
| 71 | 239432 | N-[10,11-dichloro-4-oxo-3-(trifluoromethyl)-2,5,7-triazatricyclo[6.4.0.0$^{2,6}$]dodeca-1(12),6,8,10-tetraen-3-yl]-6-[(2-methoxyethyl)amino]-pyridine-2-carboxamide | 503.2 | $^1$H NMR (400 MHz, DMSO-d$_6$) δ 3.31 (s, 3H), 3.47-3.66 (m, 4H), 6.78 (dd, 1H), 7.00 (d, 1H), 7.04-7.13 (m, 1H), 7.50 (dd, 1H), 7.75 (s, 1H), 7.80 (s, 1H), 9.73 (s, 1H). |
| 72 | 238928 | N-[10,11-difluoro-4-oxo-3-(trifluoromethyl)-2,5,7-triazatricyclo[6.4.0.0$^{2,6}$]dodeca-1(12),6,8,10-tetraen-3-yl]-benzamide | 397.0 | $^1$H NMR (500 MHz, DMSO-d$_6$) δ 7.44 (dd, 1H), 7.52 (t, 2H), 7.64 (t, 1H), 7.69 (dd, 1H), 7.83-7.88 (m, 2H), 10.62 (s, 1H), 13.20 (s, 1H). |
| 73 | 238925 | 3-cyclopentyl-N-[10,11-difluoro-4-oxo-3-(trifluoromethyl)-2,5,7-triazatricyclo-[6.4.0.0$^{2,6}$]dodeca-1(12),6,8,10-tetraen-3-yl]-propanamide | 417.1 | $^1$H NMR (500 MHz, Methanol-d$_4$) δ 0.91-1.06 (m, 2H), 1.36-1.74 (m, 9H), 2.32 (t, 2H), 7.19 (dd, 1H), 7.44 (dd, 1H). |
| 74 | 238929 | 2-cyclohexyl-N-[10,11-difluoro-4-oxo-3-(trifluoromethyl)-2,5,7-triazatricyclo-[6.4.0.0$^{2,6}$]dodeca-1(8),6,9,11-tetraen-3-yl]-acetamide | 417.0 | $^1$H NMR (500 MHz, DMSO-d$_6$) δ 0.70-0.85 (m, 2H), 1.05-1.10 (m, 3H), 1.30-1.40 (m, 2H), 1.48-1.55 (m, 4H), 2.07 (dd, 1H), 2.15 (dd, 1H), 7.20 (dd, 1H), 7.68 (dd, 1H), 10.29 (s, 1H), 13.05 (s, 1H). |
| 75 | 238995 | N-[10,11-dimethoxy-4-oxo-3-(trifluoromethyl)-2,5,7-triazatricyclo[6.4.0.0$^{2,6}$]dodeca-1(12),6,8,10-tetraen-3-yl]-benzamide | 421.0 | $^1$H NMR (500 MHz, DMSO-d$_6$) δ 3.72 (s, 3H), 3.77 (s, 3H), 7.00 (s, 1H), 7.14 (s, 1H), 7.51 (t, 2H), 7.62 (t, 1H), 7.83-7.86 (m, 2H), 10.49 (s, 1H), 12.86 (s, 1H). |
| 76 | 238927 | 3-cyclopentyl-N-[10,11-dimethoxy-4-oxo-3-(trifluoromethyl)-2,5,7-triazatricyclo[6.4.0.0$^{2,6}$]dodeca-1(12),6,8,10-tetraen-3-yl]-propanamide | 441.0 | $^1$H NMR (500 MHz, Methanol-d$_4$) δ 0.94-1.06 (m, 2H), 1.37-1.60 (m, 7H), 1.60-1.73 (m, 2H), 2.27-2.36 (m, 2H), 3.86 (s, 3H), 3.87 (s, 3H), 6.87 (s, 1H), 7.13 (s, 1H). |
| 77 | 239170 | N-[9-bromo-10,11-dimethyl-4-oxo-3-(trifluoromethyl)-2,5,7-triazatricyclo-[6.4.0.0$^{2,6}$]dodeca-1(8),6,9,11-tetraen-3-yl]-benzamide | 467.0 | $^1$H NMR (500 MHz, DMSO-d$_6$) δ 2.32 (s, 3H), 2.35 (s, 3H), 7.14 (s, 1H), 7.51 (t, 2H), 7.63 (t, 1H), 7.80-7.88 (m, 2H), 10.67 (s, 1H), 13.03 (s, 1H). |
| 78 | 239320 | 3-cyclopentyl-N-[12-oxo-11-(trifluoromethyl)-10,13,15-triazatetracyclo-[7.6.0.0$^{3,7}$.0$^{10,14}$]pentadeca-1(9),2,7,14-tetraen-11-yl]-propanamide | 421.0 | $^1$H NMR (500 MHz, DMSO-d$_6$) δ 0.84-1.04 (m, 2H), 1.27-1.41 (m, 4H), 1.41-1.58 (m, 4H), 1.58-1.67 (m, 1H), 1.95-2.10 (m, 2H), 2.16-2.29 (m, 2H), 2.80-2.96 (m, 4H), 7.00 (s, 1H), 7.27 (s, 1H), 10.02 (s, 1H), 12.73 (s, 1H). |
| 79 | 239329 | N-[10-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide and N-[11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 415.1 | $^1$H NMR (500 MHz, DMSO-d$_6$) δ 0.86-0.99 (m, 2H), 1.22-1.43 (m, 5H), 1.44-1.56 (m, 3H), 1.57-1.67 (m, 1H), 2.19-2.32 (m, 2H), 7.16-7.29 (m, 2H), 7.52 (d, 0.5H), 7.59 (s, 0.5H), 10.26 (s, 0.5H), 10.33 (s, 0.5H), 12.99 (s, 1H). |
| 80 | 239330 | 3-cyclopentyl-N-[9,10-dimethyl-4-oxo-3-(trifluoromethyl)-2,5,7-triazatricyclo-[6.4.0.0$^{2,6}$]dodeca-1(12),6,8,10-tetraen-3-yl]-propanamide | 409.0 | $^1$H NMR (500 MHz, DMSO-d$_6$) δ 0.86-1.05 (m, 2H), 1.28-1.44 (m, 4H), 1.44-1.60 (m, 4H), 1.60-1.69 (m, 1H), 2.22 (t, 2H), 2.27 (s, 3H), 2.35 (s, 3H), 6.89 (d, 1H), 7.00 (d, 1H), 10.05 (s, 1H), 12.84 (s, 1H). |
| 81 | 239343 | 3-cyclopentyl-N[9-methyl-4-oxo-3-(trifluoromethyl)-2,5,7-triazatricyclo-[6.4.0.0$^{2,6}$]dodeca-1(12),6,8,10-tetraen-3-yl]-propanamide | 395.2 | $^1$H NMR (500 MHz, DMSO-d$_6$) δ 0.86-1.01 (m, 2H), 1.26-1.42 (m, 4H), 1.42-1.59 (m, 4H), 1.59-1.68 (m, 1H), 2.23 (t, 2H), 2.43 (s, 3H), 7.01 (t, 2H), 7.10 (t, 1H), 10.13 (s, 1H), 12.91 (s, 1H). |
| 82 | 239371 | 3-cyclopentyl-N-[9,10-difluoro-4-oxo-3-(trifluoromethyl)-2,5,7-triazatricyclo-[6.4.0.0$^{2,6}$]dodeca-1(12),6,8,10-tetraen-3-yl]-propanamide | 417.0 | $^1$H NMR (500 MHz, DMSO-d$_6$) δ 0.85-1.00 (m, 2H), 1.28-1.56 (m, 8H), 1.57-1.66 (m, 1H), 2.25 (t, 2H), 7.00 (dd, 1H), 7.28 (dt, 1H), 10.41 (s, 1H), 13.15 (s, 1H). |
| 83 | 239375 | 3-cyclopentyl-N-[9,10-dichloro-4-oxo-3-(trifluoromethyl)-2,5,7-triazatricyclo- | 448.9 | $^1$H NMR (250 MHz, DMSO-d$_6$) δ 0.79-1.03 (m, 2H), 1.26-1.67 (m, 9H), 2.25 (t, 2H), 7.18 (d, 1H), 7.45 |

TABLE 2-continued

| Ex | ABR | Name | M ± H+ (m/z) | 1H NMR |
|---|---|---|---|---|
| | | [6.4.0.0$^{2,6}$]dodeca-1(12),6,8,10-tetraen-3-yl]-propanamide | | (s, 1H), 10.46 (s, 1H), 13.25 (s, 1H). |
| 84 | 239394 | 3-cyclopentyl-N-[9,11-dichloro-4-oxo-3-(trifluoromethyl)-2,5,7-triazatricyclo-[6.4.0.0$^{2,6}$]dodeca-1(12),6,8,10-tetraen-3-yl]-propanamide | 449.0 | $^1$H NMR (250 MHz, DMSO-d$_6$) δ 0.77-1.06 (m, 2H), 1.16-1.75 (m, 9H), 2.16-2.37 (m, 2H), 7.22 (s, 1H), 7.46 (d, 1H), 10.39 (s, 1H), 13.26 (s, 1H). |
| 85 | 239399 | N-[9-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 415.0 | $^1$H NMR (500 MHz, DMSO-d$_6$) δ 0.85-0.99 (m, 2H), 1.28-1.56 (m, 8H), 1.57-1.66 (m, 1H), 2.25 (t, 2H), 7.15-7.24 (m, 2H), 7.29 (dd, 1H), 10.41 (s, 1H), 13.06 (s, 1H). |
| 86 | 239422 | 3-cyclopentyl-N-[9,11-difluoro-4-oxo-3-(trifluoromethyl)-2,5,7-triazatricyclo-[6.4.0.0$^{2,6}$]dodeca-1(12),6,8,10-tetraen-3-yl]-propanamide | 416.9 | $^1$H NMR (500 MHz, DMSO-d$_6$) δ 0.85-1.00 (m, 2H), 1.27-1.57 (m, 8H), 1.57-1.67 (m, 1H), 2.19-2.34 (m, 2H), 6.87-6.96 (m, 1H), 7.16 (td, 1H), 10.38 (s, 1H), 13.10 (s, 1H). |
| 87 | 239441 | N-[10,11-dichloro-4-oxo-3-(trifluoromethyl)-2,5,7-triazatricyclo[6.4.0.0$^{2,6}$]dodeca-1(12),6,8,10-tetraen-3-yl]oxane-4-carboxamide | 437.2 | $^1$H NMR (400 MHz, DMSO-d$_6$) δ 1.15-1.27 (m, 1H), 1.35-1.47 (m, 2H), 1.59 (d, 1H), 2.62-2.67 (m, 1H), 3.18-3.28 (m, 2H), 3.75 (dd, 2H), 7.41 (s, 1H), 7.83 (s, 1H), 10.31 (s, 1H), 13.16 (s, 1H). |
| 88 | 239702 | N-[10,11-dichloro-4-oxo-3-(trifluoromethyl)-2,5,7-triazatricyclo[6.4.0.0$^{2,6}$]dodeca-1(8),6,9,11-tetraen-3-yl]-3-(1-hydroxycyclopentyl)propanamide | 464.0 | $^1$H NMR (500 MHz, DMSO-d$_6$) δ 1.20-1.33 (m, 2H), 1.34-1.46 (m, 4H), 1.49-1.67 (m, 4H), 2.36 (t, 2H), 4.04 (s, 1H), 7.40 (s, 1H), 7.76 (s, 1H), 10.16 (s, 1H), 13.15 (s, 1H). |
| 89 | 239679 | Diastereomer 1: (2S)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-1-methanesulfonylpyrrolidine-2-carboxamide | 460.1 | $^1$H NMR (500 MHz, DMSO-d$_6$) δ 1.68-1.93 (m, 3H), 2.08-2.23 (m, 1H), 2.24 (s, 3H), 2.26 (s, 3H), 2.59 (s, 3H), 3.21-3.26 (m, 2H), 4.40 (dd, 1H), 6.99 (s, 1H), 7.21 (s, 1H), 10.14 (s, 1H), 12.78 (s,1H). |
| 90 | 239523 | N[10,11-dichloro-4-oxo-3-(trifluoromethyl)-2,5,7-triazatricyclo[6.4.0.0$^{2,6}$]dodeca-1(8),6,9,11-tetraen-3-yl]-6-[(3-methoxypropyl)-amino]-pyridine-2-carboxamide | 517.1 | $^1$H NMR (500 MHz, Methanol-d$_4$) δ 1.93 (p, 2H), 3.38 (s, 3H), 3.45-3.61 (m, 4H), 6.70 (d, 1H), 7.09 (d, 1H), 7.47 (dd, 1H), 7.59 (s, 1H), 7.65 (s, 1H). No exchangeable protons observed. |
| 91 | 239539 | N-[10,11-dichloro-4-oxo-3-(trifluoromethyl)-2,5,7-triazatricyclo[6.4.0.0$^{2,6}$]dodeca-1(8),6,9,11-tetraen-3-yl]-6-[(2-hydroxyethyl)amino]pyridine-2-carboxamide | 488.9 | $^1$H NMR (500 MHz, DMSO-d$_6$) δ 3.40-3.52(m, 2H), 3.63 (t, 2H), 4.80 (s, 1H), 6.80 (d, 1H), 6.96-6.99 (m, 2H), 7.51 (dd, 1H), 7.84(s, 2H), 9.93 (s, 1H), 13.44 (s, 1H). |
| 92 | 239540 | N-[10,11-dichloro-4-oxo-3-(trifluoromethyl)-2,5,7-triazatricyclo[6.4.0.0$^{2,6}$]dodeca-1(8),6,9,11-tetraen-3-yl]-6-{[(2S)-1-methoxypropan-2-yl]amino}pyridine-2-carboxamide | 516.9 | $^1$H NMR (500 MHz, Methanol-d$_4$) δ 1.30(dd, 3H), 3.38-3.49 (m, 4H), 3.53-3.57 (m, 1H), 4.29 (dq, 1H), 6.74 (dd, 1H), 7.10 (dd, 1H), 7.44-7.53 (m, 1H), 7.54 (s, 0.5H), 7.58 (s, 0.5H), 7.66 (2s, 0.5H x 2). No exchangeable protons observed. Mixture of diastereomers present. |
| 93 | 239587 | N-[10,11-dichloro-4-oxo-3-(trifluoromethyl)-2,5,7-triazatricyclo[6.4.0.0$^{2,6}$]dodeca-1(8),6,9,11-tetraen-3-yl]-6-{[2-(dimethylamino)-ethyl]amino-pyridine-2-carboxamide | 516.1 | $^1$H NMR (500 MHz, DMSO-d$_6$) δ 2.81 (s, 6H), 3.19-3.24 (m, 2H), 3.57-3.67 (m, 2H), 6.80 (d, 1H), 7.21 (t, 1H), 7.28 (d, 1H), 7.43 (s, 1H), 7.62 (t, 1H), 7.77 (s, 1H), 8.13 (s, 1H), 9.14 (s, 1H), 11.0 (br.s, 1H). Formic acid salt. |
| 94 | 239537 | N[10,11-dichloro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)(methyl)amino]-pyridine-2-carboxamide | 517.0 | $^1$H NMR (500 MHz, Methanol-d$_4$) δ 3.19 (s, 3H), 3.41 (s, 3H), 3.70 (t, 2H), 3.79-3.86 (m, 1H), 3.92-3.98 (m, 1H), 6.92 (d, 1H), 7.16 (d, 1H), 7.58 (s, 1H), 7.62 (dd, 1H), 7.64 (s, 1H). No exchangeable protons observed. |
| 95 | 239572 | methyl 6-{[10,11-dichloro-4-oxo-3-(trifluoromethyl)-2,5,7-triazatricyclo[6.4.0.0$^{2,6}$]-dodeca-1(8),6,9,11-tetraen-3-yl]carbamoyl}pyridine-2-carboxylate | 487.8 | $^1$H NMR (500 MHz, DMSO-d$_6$) δ 3.97 (s, 3H), 7.81 (s, 1H), 7.86 (s, 1H), 8.08 (d, 1H), 8.18 (t, 1H), 8.29 (d, 1H), 10.79 (s, 1H), 13.38 (s, 1H). |

TABLE 2-continued

| Ex | ABR | Name | M ± H+ (m/z) | 1H NMR |
|---|---|---|---|---|
| 96 | 239588 | 2-N-[10,11-dichloro-4-oxo-3-(trifluoromethyl)-2,5,7-triazatricyclo[6.4.0.0²,⁶]dodeca-1(8),6,9,11-tetraen-3-yl]-6-N-(2-methoxyethyl)pyridine-2,6-dicarboxamide | 531.0 | 1H NMR (500 MHz, Methanol-d₄) δ 3.44 (s, 3H), 3.64-3.74 (m, 4H), 7.50 (s, 1H), 7.60 (s, 1H), 8.09-8.18 (m, 2H), 8.33 (dd, 1H). No exchangeable protons observed. |
| 97 | 239602 | N-[10,11-dichloro-4-oxo-3-(trifluoromethyl)-2,5,7-triaza-tricyclo[6.4.0.0²,⁶]dodeca-1(8),6,9,11-tetraen-3-yl]-6-(hydroxymethyl)pyridine-2-carboxamide | 459.9 | 1H NMR (500 MHz, DMSO-d₆) δ 4.61-4.92 (m, 2H), 5.63 (s, 1H), 7.75 (t, 2H), 7.80 (s, 1H), 7.83 (s, 1H), 7.99 (t, 1H), 10.49 (s, 1H), 13.39 (s, 1H). |
| 98 | 239440 | N-[10,11-dichloro-4-oxo-3-(trifluoromethyl)-2,5,7-triaza-tricyclo[6.4.0.0²,⁶]dodeca-1(12),6,8,10-tetraen-3-yl]-3-fluorobenzamide | 447.4 | 1H NMR (400 MHz, DMSO-d₆) δ 7.47-7.58 (m, 2H), 7.60 (d, 1H), 7.67-7.72 (m, 2H), 7.81 (s, 1H), 10.66 (s, 1H), 13.36 (s, 1H). |
| 99 | 239446 | N-[10,11-dichloro-4-oxo-3-(trifluoromethyl)-2,5,7-triaza-tricyclo[6.4.0.0²,⁶]dodeca-1(12),6,8,10-tetraen-3-yl]-3,5-difluorobenzamide | 465.4 | 1H NMR (400 MHz, DMSO-d₆) δ 7.62-7.70 (m, 4H), 7.83 (s, 1H), 10.76 (s, 1H), 13.46 (br. s, 1H). |
| 100 | 239453 | 3-cyano-N-[10,11-dichloro-4-oxo-3-(trifluoromethyl)-2,5,7-triazatricyclo[6.4.0.0²,⁶]-dodeca-1(8),6,9,11-tetraen-3-yl]benzamide | 454.1 | 1H NMR (400 MHz, DMSO-d₆) δ 7.61 (s, 1H), 7.71 (t, 1H), 7.79 (s, 1H), 8.05-8.16 (m, 2H), 8.40 (s, 1H), 10.73 (s, 1H), 13.46 (s, 1H). |
| 101 | 239601 | N-[10,11-dichloro-4-oxo-3-(trifluoromethyl)-2,5,7-triazatricyclo[6.4.0.0²,⁶]dodeca-1(8),6,9,11-tetraen-3-yl]-2-[(2-methoxyethyl)amino]-1,3-thiazole-4-carboxamide | 508.9 | 1H NMR (500 MHz, Methanol-d₄) δ 3.40 (s, 3H), 3.55-3.59 (m, 2H), 3.60-3.63 (m, 2H), 7.34 (s, 1H), 7.58 (s, 1H), 7.65 (s, 1H). No exchangeable protons observed. |
| 102 | 239437 | N[10,11-dichloro-4-oxo-3-(trifluoromethyl)-triazatricyclo[6.4.0.0²,⁶]dodeca-1(12),6,8,10-tetraen-3-yl]-1-(2,2-difluoroethyl)azetidine-3-carboxamide | 471.8 | 1H NMR (500 MHz, Methanol-d₄) δ 2.82 (td, 2H), 3.25 (t, 1H), 3.47 (dt, 2H), 3.60 (t, 1H), 3.67 (t, 1H), 5.77 (tt, 1H), 7.38 (s, 1H), 7.66 (s, 1H), 8.10 (s, 2H). Formic acid salt. No exchangeable protons observed. |
| 103 | 239689 | N-[10,11-dichloro-4-oxo-3-(trifluoromethyl)-2,5,7-triazatricyclo[6.4.0.0²,⁶]dodeca-1(8),6,9,11-tetraen-3-yl]-3-fluoroazetidine-3-carboxamide | 425.8 | 1H NMR (500 MHz, Methanol-d₄) δ 4.16-4.32 (m, 3H), 4.44 (dd, 1H), 7.31 (s, 1H), 7.45 (s, 1H). No exchangeable protons observed. |
| 104 | 239705 | N[10,11-dichloro-4-oxo-3-(trifluoromethyl)-2,5,7-triazatricyclo[6.4.0.0²,⁶]dodeca-1(8),6,9,11-tetraen-3-yl]-3-(3,3-difluoroazetidin-1-yl)-propanamide | 471.9 | 1H NMR (500 MHz, Methanol-d₄) δ 2.42 (td, 2H), 2.76 (t, 2H), 3.42-3.61 (m, 4H), 7.41 (s, 1H), 7.64 (s, 1H). No exchangeable protons observed. |
| 105 | 239647 | 3-(3,3-difluoroazetidin-1-yl)-N-[10,11-dimethyl-4-oxo-3-(trifluoromethyl)-2,5,7-triazatricyclo[6.4.0.0²,⁶]dodeca-1(8),6,9,11-tetraen-3-yl]-propanamide | 432.4 | 1H NMR (500 MHz, DMSO-d₆) δ 2.25 (s, 6H), 2.31 (t, 2H), 2.59 (t, 2H), 3.38-3.49 (m, 4H), 6.96 (s, 1H), 7.23 (s, 1H), 10.10 (s, 1H), 12.76(s, 1H). |
| 106 | 239536 | 3-cyclobutyl-N-[10,11-dimethyl-4-oxo-3-(trifluoromethyl)-2,5,7-triazatricyclo-[6.4.0.0²,⁶]dodeca-1(8),6,9,11-tetraen-3-yl]propanamide | 395.0 | 1H NMR (500 MHz, DMSO-d₆) δ 1.35-1.53 (m, 4H), 1.64-1.74 (m, 2H), 1.81-1.85 (m, 1H), 1.86-1.93 (m, 1H), 1.97 (dt, 1H), 2.13 (t, 2H), 2.27 (s, 6H), 6.97 (s, 1H), 7.25 (s, 1H), 10.02 (s, 1H), 12.78 (s, 1H). |
| 107 | 239578 | N-[10,11-dimethyl-4-oxo-3-(trifluoromethyl)-2,5,7-triazatricyclo[6.4.0.0²,⁶]dodeca-1(8),6,9,11-tetraen-3-yl]-3-(1-hydroxycyclopentyl)propan-amide | 425.2 | 1H NMR (500 MHz, DMSO-d₆) δ 1.23-1.33 (m, 2H), 1.37-1.47 (m, 4H), 1.53 (t, 2H), 1.57-1.69 (m, 2H), 2.25 (s, 3H), 2.25 (s, 3H), 2.28-2.37 (m, 2H), 4.05 (s, 1H), 6.96 (s, 1H), 7.23 (s, 1H), 10.04 (s, 1H), 12.71 (s, 1H). |
| 108 | 239558 | 2-cyclopentyl-N-[10,11-dimethyl-4-oxo-3-(trifluoro-methyl)-2,5,7-triazatricyclo-[6.4.0.0²,⁶]dodeca-1(8),6,9,11-tetraen-3-yl]acetamide | 395.00 | 1H NMR (500 MHz, DMSO-d₆) δ 0.95-1.05 (m, 2H), 1.36-1.55 (m, 6H), 1.90-1.98 (m, 1H), 2.21 (dd, 2H), 2.26 (s, 6H), 6.96 (s, 1H), 7.24 (s, 1H), 10.02 (s, 1H), 12.77 (s, 1H). |
| 109 | 239456 | N-[10,11-dimethyl-4-oxo-3-(trifluoromethyl)-2,5,7-triazatricyclo[6.4.0.0²,⁶]dodeca- | 425.5 | 1H NMR (400 MHz, DMSO-d₆) δ 2.23 (s, 3H), 2.25 (s, 3H), 7.07 (s, 1H), 7.24 (s, 1H), 7.58 (m, 3H), |

TABLE 2-continued

| Ex | ABR | Name | M ± H+ (m/z) | 1H NMR |
|---|---|---|---|---|
| | | 1(8),6,9,11-tetraen-3-yl]-3,5-difluorobenzamide | | 10.57 (s, 1H), 12.95 (s, 1H). |
| 110 | 239784 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide | 408.1 | 1H NMR (500 MHz, DMSO-d$_6$) δ 2.21 (s, 3H), 2.24 (s, 3H), 7.20 (s, 1H), 7.24 (s, 1H), 7.52 (dd, 1H), 7.81(dd, 1H), 8.15-8.19 (m, 1H), 10.47 (s, 1H), 13.00 (s, 1H). |
| 111 | 239496 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]pyridine-2-carboxamide | 463.6 | 1H NMR (400 MHz, DMSO-d$_6$) δ 2.21 (s, 3H), 2.23 (s, 3H), 3.32 (s, 3H), 3.62-3.46 (m, 4H), 6.78 (dd, 1H), 6.98 (d, 1H), 7.12 (s, 2H), 7.23 (s, 1H), 7.51 (dd, 1H), 9.48 (s, 1H), 13.13-12.85 (m, 1H). |
| 112 | 239500 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-phenylacetamide | 403.4 | 1H NMR (400 MHz, DMSO-d$_6$) δ 2.24 (s, 6H), 3.57 (dd, 2H), 6.90 (s, 1H), 7.07-7.13 (m, 2H), 7.14-7.25 (m, 4H), 10.36 (s, 1H), 12.82 (s, 1H). |
| 113 | 239503 | 2-(3,5-dichlorophenyl)-N-[10,11-dimethyl-4-oxo-3-(trifluoromethyl)-2,5,7-triazatricyclo[6.4.0.0$^{2,6}$]dodeca-1(8),6,9,11-tetraen-3-yl]acetamide | 471.5 | 1H NMR (400 MHz, DMSO-d$_6$) δ 2.22 (s, 3H), 2.23 (s, 3H), 3.63 (dd, 2H), 6.85 (s, 1H), 7.13 (d, 2H), 7.21 (s, 1H), 7.43 (t, 1H), 10.41 (s, 1H), 12.87 (s, 1H). |
| 114 | 239529 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(3,4,5-trimethoxyphenyl)-propanamide | 507.5 | 1H NMR (400 MHz, DMSO-d$_6$) δ 2.23 (s, 3H), 2.25 (s, 3H), 2.50-2.57 (m, 2H), 2.59-2.66 (m, 2H), 3.57 (s, 3H), 3.65 (s, 6H), 6.40 (s, 2H), 6.92 (s, 1H), 7.24 (s, 1H), 10.09 (s, 1H), 12.81 (s, 1H). |
| 115 | 239489 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-3-methanesulfonylbenzamide | 466.9 | 1H NMR (400 MHz, DMSO-d$_6$) δ 2.27 (s, 6H), 3.27 (s, 3H), 7.18 (s, 1H), 7.41 (s, 1H), 7.79 (t, 1H), 8.20-8.14 (m, 2H), 8.43 (s, 1H), 9.72 (s, 1H), 10.65 (s, 1H). |
| 116 | 239785 | 3-bromo-N-[10,11-dimethyl-4-oxo-3-(trifluoromethyl)-2,5,7-triazatricyclo[6.4.0.0$^{2,6}$]dodeca-1(8),6,9,11-tetraen-3-yl]benzamide | 466.9 | 1H NMR (500 MHz, DMSO-d6) δ 2.22 (s, 3H), 2.24 (s, 3H), 7.05 (s, 1H), 7.24 (s, 1H), 7.46 (t, 1H), 7.74-7.86 (m, 2H), 8.06 (t, 1H), 10.49 (s, 1H), 12.88 (s, 1H). |
| 117 | 239638 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-3-[(2-methoxyethyl)amino]benzamide | 462.2 | 1H NMR (500 MHz, DMSO-d$_6$) δ 2.21 (s, 3H), 2.23 (s, 3H), 3.17-3.22 (m, 2H), 3.26 (s, 3H), 3.44-3.50 (m, 2H), 5.90 (t, 1H), 6.80 (dd, 1H), 6.92 (s, 1H), 6.97 (d, 1H), 7.06 (s, 1H), 7.16 (t, 1H), 7.22 (s, 1H), 10.10 (s, 1H), 12.84 (s, 1H). |
| 118 | 239786 | 2-bromo-N-[10,11-dimethyl-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide | 473.8 | 1H NMR (500 MHz, DMSO-d6) δ 2.23 (s, 3H), 2.25 (s, 3H), 7.19 (s, 1H), 7.25 (s, 1H), 8.41 (s, 1H), 10.49 (s, 1H), 12.97 (s, 1H). |
| 119 | 239655 | N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-[(2-methoxyethyl)amino]-1,3-thiazole-4-carboxamide | 469.1 | 1H NMR (500 MHz, DMSO-d$_6$) δ 2.24 (s, 3H), 2.25 (s, 3H), 3.29 (s, 3H), 3.45-3.55 (m, 4H), 7.17 (s, 1H), 7.24 (s, 1H), 7.37 (s, 1H), 7.88-8.01 (m, 1H), 9.29 (s, 1H), 12.90 (s, 1H). |
| 120 | 239508 | N-[9-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 458.9 | 1H NMR (500 MHz, DMSO-d$_6$) δ 0.86-1.01 (m, 2H), 1.28-1.42 (m, 4H), 1.42-1.58 m, 4H), 1.58-1.68 (m, 1H), 2.24 (t, 2H), 7.11 (t, 1H), 7.19 (d, 1H), 7.39 (d, 1H), 10.32 (s, 1H), 12.98 (s, 1H). |
| 121 | 239436 | N-[9-cyano-4-oxo-3-(trifluoromethyl)-2,5,7-triazatricyclo[6.4.0.0$^{2,6}$]-dodeca-1(12),6,8,10-tetraen-3-yl]-3-cyclopentylpropanamide | 406.0 | 1H NMR (500 MHz, Methanol-d$_4$) δ 0.92-1.07 (m, 2H), 1.36-1.74 (m, 9H), 2.28-2.34 (m, 2H), 7.32 (t, 1H), 7.54 (d, 1H), 7.57 (d, 1H). No exchangeable protons observed. |
| 122 | 239448 | N[9-acetyl-4-oxo-3-(trifluoromethyl)-2,5,7-triazatricyclo-[6.4.0.0$^{2,6}$]dodeca-1(12),6,8,10-tetraen-3-yl]-3-cyclopentylpropanamide | 423.1 | 1H NMR (500 MHz, DMSO-d$_6$) δ 0.87-1.02 (m, 2H), 1.29-1.42 (m, 4H), 1.42-1.58 (m, 4H), 1.58-1.68 (m, 1H), 2.24 (t, 2H), 2.82 (s, 3H), 7.29 (s, 1H), 7.40 (d, 1H), 7.67 (s, 1H), 10.33 (s, 1H), 13.13 (s, 1H). |
| 123 | 239521 | N-[10-chloro-9-cyano-4-oxo-3-(trifluoromethyl)-2,5,7-triaza- | 439.9 | 1H NMR (500 MHz, DMSO-d$_6$) δ 0.87-1.04 (m, 2H), 1.27-1.44 (m, |

TABLE 2-continued

| Ex | ABR | Name | M ± H+ (m/z) | 1H NMR |
|---|---|---|---|---|
| | | tricyclo[6.4.0.0²,⁶]dodeca-1(12),6,8,10-tetraen-3-yl]-3-cyclopentylpropanamide | | 4H), 1.44-1.71 (m, 5H), 2.10-2.24 (m, 2H), 7.04 (d, 1H), 7.10 (d, 1H), 9.31 (s, 1H). |
| 124 | 239535 | 3-cyclopentyl-N-[9-fluoro-4-oxo-3-(trifluoromethyl)-2,5,7-triazatricyclo[6.4.0.0²,⁶]-dodeca-1(12),6,8,10-tetraen-3-yl]propanamide | 399.0 | 1H NMR (500 MHz, DMSO-d₆) δ 0.85-1.00 (m, 2H), 1.24-1.57 (m, 8H), 1.57-1.66 (m, 1H), 2.25 (t, 2H), 7.06 (t, 2H), 7.13-7.24 (m, 1H), 10.38 (s, 1H), 13.01 (s, 1H). |
| 125 | 239545 | 3-cyclopentyl-N-[9,11-dimethyl-4-oxo-3-(trifluoromethyl)-2,5,7-triazatricyclo-[6.4.0.0²,⁶]dodeca-1(12),6,8,10-tetraen-3-yl]propanamide | 409.2 | 1H NMR (500 MHz, DMSO-d₆) δ 0.88-1.02 (m, 2H), 1.28-1.43 (m, 4H), 1.43-1.60 (m, 4H), 1.60-1.68 (m, 1H), 2.17-2.29 (m, 2H), 2.32 (s, 3H), 2.38 (s, 3H), 6.80 (s, 1H), 6.84 (s, 1H), 10.04 (s, 1H), 12.83 (s, 1H). |
| 126 | 239559 | N-[9-chloro-10-fluoro-4-oxo-3-(trifluoromethyl)-2,5,7-triaza-tricyclo[6.4.0.0²,⁶]dodeca-1(12),6,8,10-tetraen-3-yl]-3-cyclopentylpropanamide | 433.1 | 1H NMR (500 MHz, DMSO-d₆) δ 0.89-1.04 (m, 2H), 1.28-1.45 (m, 4H), 1.44-1.61 (m, 4H), 1.61-1.70 (m, 1H), 2.10-2.27 (m, 2H), 6.68-7.02 (m, 2H), 9.26 (s, 1H). |
| 127 | 239569 | N-[10-chloro-9-methyl-4-oxo-3-(trifluoromethyl)-2,5,7-triazatricyclo[6.4.0.0²,⁶]-dodeca-1(12),6,8,10-tetraen-3-yl]-3-cyclopentylpropanamide | 429.2 | 1H NMR (500 MHz, DMSO-d₆) δ 0.82-1.03 (m, 2H), 1.27-1.42 (m, 4H), 1.42-1.58 (m, 4H), 1.58-1.70 (m, 1H), 2.23 (t, 2H), 2.47 (s, 3H), 7.03 (d, 1H), 7.26 (d, 1H), 10.29 (s, 1H), 12.94 (s, 1H). |
| 128 | 239544 | 3-cyclopentyl-N-[4-oxo-3,9-bis(trifluoromethyl)-2,5,7-triazatricyclo[6.4.0.0²,⁶]-dodeca-1(8),6,9,11-tetraen-3-yl]propanamide | 448.9 | 1H NMR (500 MHz, DMSO-d₆) δ 0.85-0.97 (m, 2H), 1.26-1.56 (m, 8H), 1.56-1.66 (m, 1H), 2.26(t, 2H), 7.37 (t, 1H), 7.49 (d, 1H), 7.53 (d, 1H),10.48 (s, 1H), 13.16 (s, 1H). |
| 129 | 239577 | N-[11-bromo-4-oxo-3,9-bis-(trifluoromethyl)-2,5,7-triazatricyclo[6.4.0.0²,⁶]dodeca-1(8),6,9,11-tetraen-3-yl]-3-cyclopentylpropanamide | 526.9 | 1H NMR (500 MHz, Methanol-d₄) δ 0.88-1.10 (m, 2H), 1.32-1.79 (m, 9H), 2.28-2.38 (m, 2H), 7.63 (s, 2H). No other exchangeable protons observed. |
| 130 | 239603 | N-[10-chloro-9-fluoro-4-oxo-3-(trifluoromethyl)-2,5,7-triazatricyclo[6.4.0.0²,⁶]dodeca-1(12),6,8,10-tetraen-3-yl]-3-cyclopentylpropanamide | 433.0 | 1H NMR (500 MHz, DMSO-d₆) δ 0.84-1.01 (m, 2H), 1.28-1.57 (m, 8H), 1.57-1.65 (m, 1H), 2.25 (t, 2H), 7.04 (d, 1H), 7.36 (s, 1H), 10.37 (s, 1H), 13.18 (s, 1H). |
| 131 | 239551 | 3-cyclopentyl-N-[9-fluoro-10-methoxy-4-oxo-3-(trifluoro-methyl)-2,5,7-triazatricyclo-[6.4.0.0²,⁶]dodeca-1(12),6,8,10-tetraen-3-yl]propanamide | 429.1 | 1H NMR (500 MHz, DMSO-d₆) δ 0.86-1.00 (m, 2H), 1.28-1.58 (m, 8H), 1.58-1.67 (m, 1H), 2.24 (t, 2H), 3.83 (s, 3H), 6.93 (d, 1H), 7.03 (t, 1H), 10.28 (s, 1H), 12.96 (s, 1H). |
| 132 | 239636 | 3-cyclopentyl-N-[9-(methyl-sulfanyl)-4-oxo-3-(trifluoro-methyl)-2,5,7-triazatricyclo-[6.4.0.0²,⁶]dodeca-1(12),6,8,10-tetraen-3-yl]propanamide | 427.0 | 1H NMR (500 MHz, DMSO-d₆) δ 0.84-1.01 (m, 2H), 1.28-1.42 (m, 4H), 1.43-1.58 (m, 4H), 1.63 (ddt, 1H), 2.24 (t, 2H), 2.53 (s, 3H), 7.01 (d, 1H), 7.05 (d, 1H), 7.17 (t, 1H), 10.37 (s, 1H), 12.87 (s, 1H). |
| 133 | 239639 | 3-cyclopentyl-N-[9-methane-sulfonyl-4-oxo-3-(trifluoro-methyl)-2,5,7-triazatricyclo-[6.4.0.0²,⁶]dodeca-1(12),6,8,10-tetraen-3-yl]propanamide | 459.0 | 1H NMR (500 MHz, DMSO-d₆) δ 0.86-1.00 (m, 2H), 1.30-1.41 (m, 4H), 1.41-1.57 (m, 4H), 1.57-1.66 (m, 1H), 2.23-2.31 (m, 2H), 3.44 (s, 3H), 7.42 (t, 1H), 7.54 (d, 1H), 7.68 (d, 1H), 10.53 (s, 1H), 13.35 (s, 1H). |
| 134 | 239730 | N-[9-bromo-10,11-dimethyl-4-oxo-3-(trifluoromethyl)-2,5,7-triazatricyclo[6.4.0.0²,⁶]dodeca-1(12),6,8,10-tetraen-3-yl]-3-cyclopentylpropanamide | 487.0 | 1H NMR (500 MHz, DMSO-d₆) δ 0.87-0.99 (m, 2H), 1.30-1.40 (m, 4H), 1.40-1.57 (m, 4H), 1.61 (dd, 1H), 2.25 (t, 2H), 2.36 (s, 3H), 2.37 (s, 3H), 7.01 (s, 1H), 10.29 (s, 1H), 12.87 (s, 1H). |
| 135 | 239538 | N-[9,10-dichloro-4-oxo-3-(trifluoromethyl)-2,5,7-triaza-tricyclo[6.4.0.0²,⁶]dodeca-1(8),6,9,11-tetraen-3-yl]-6-fluoropyridine-2-carboxamide | 447.8 | 1H NMR (500 MHz, DMSO-d₆) δ 7.43 (s, 2H), 7.54 (dd, 1H), 7.84 (dd, 1H), 8.15-8.21 (m, 1H), 11.12 (s, 1H), 13.45 (s, 1H). |
| 136 | 239542 | N-[9,10-dichloro-4-oxo-3-(trifluoromethyl)-2,5,7-triazatricyclo[6.4.0.0²,⁶]dodeca- | 503.1 | 1H NMR (500 MHz, DMSO-d₆) δ 3.47-3.62 (m, 4H), 6.78 (d, 1H), 6.99 (d, 1H), 7.06 (s, 1H), 7.31-7.37 |

TABLE 2-continued

| Ex | ABR | Name | M ± H+ (m/z) | 1H NMR |
|---|---|---|---|---|
| | | 1(8),6,9,11-tetraen-3-yl]-6-[(2-methoxyethyl)amino]-pyridine-2-carboxamide | | (m, 1H), 7.41 (d, 1H), 7.51 (dd, 1H), 9.74 (s, 1H), 13.50 (s, 1H). Suspected hidden OMe group under water peak [3.30 (s, 3H)]. |
| 137 | 239579 | N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide | 439.0 | $^1$H NMR (500 MHz, DMSO-d$_6$) δ 7.49 (d, 1H), 7.54 (dd, 1H), 7.73 (d, 1H), 7.84 (dd, 1H), 8.18 (app. q, 1H), 11.13 (s,1H), 13.78 (s, 1H). |
| 138 | 239585 | N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]-pyridine-2-carboxamide | 494.1 | $^1$H NMR (500 MHz, Methanol-d$_4$) δ 3.42 (s, 3H), 3.55-3.67 (m, 4H), 6.74 (d, 1H), 7.10 (d, 1H), 7.32 (d, 1H), 7.43 (t, 1H), 7.60 (d,1H). No other exchangeable protons observed. |
| 139 | 239624 | N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-2-[(2-methoxyethyl)amino]-1,3-thiazole-4-carboxamide | 500.0 | $^1$H NMR (500 MHz, Methanol-d$_4$) δ 3.40 (s, 3H), 3.53-3.57 (m, 2H), 3.59-3.62 (m, 2H), 7.26 (d, 1H), 7.31 (s, 1H), 7.54 (d, 1H). No other exchangeable protons observed. |
| 140 | 239586 | N-[10-chloro-9-cyano-4-oxo-3-(trifluoromethyl)-2,5,7-triazatricyclo[6.4.0.0$^{2,6}$]dodeca-1(8),6,9,11-tetraen-3-yl]-6-{[(2S)-1-methoxypropan-2-yl]amino}pyridine-2-carboxamide | 508.1 | $^1$H NMR (500 MHz, Methanol-d$_4$) δ 1.29 (dd, 3H), 3.41 (s, 1.5H), 3.43 (s, 1.5H), 3.37-3.27 (m, 1H), 3.50-3.61 (m, 1H), 4.18-4.33 (m, 1H), 6.73 (dd, 1H), 7.09 (d, 1H), 7.35 (d, 1H), 7.47 (t, 1H), 7.59 (t, 1H). Mixture of diastereomers present. No other exchangeable protons observed. |
| 141 | 239787 | N-[9,10-difluoro-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide | 415.9 | $^1$H NMR (500 MHz, DMSO-d$_6$) δ 7.23 (d, 2H), 7.53 (dd, 1H), 7.83 (d, 1H), 8.16-8.20 (m, 1H), 11.08 (s, 1H), 13.38 (s, 1H). |
| 142 | 239632 | N-[9,10-difluoro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]-pyridine-2-carboxamide | 471.0 | $^1$H NMR (500 MHz, DMSO-d$_6$) δ 3.32 (s, 3H), 3.47-3.65 (m, 4H), 6.79 (d, 1H), 6.98 (d, 1H), 7.06 (s, 1H), 7.25 (d, 2H), 7.42-7.60 (m, 1H), 9.87 (s, 1H), 13.44 (s, 1H). |
| 143 | 239609 | Diastereomer 1: (2S)-N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-phenylpropanamide | 417.3 | $^1$H NMR (500 MHz, DMSO-d$_6$) δ 1.11 (d, 3H), 2.28 (s, 3H), 2.29 (s, 3H), 3.90 (q, 1H), 7.02 (s, 1H), 7.21-7.26 (m, 4H), 7.28-7.34 (m, 2H), 10.22 (s, 1H), 12.80 (s, 1H). |
| 144 | 239621 | Diastereomer 2: (2S)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-phenyl-propanamide | 417.2 | $^1$H NMR (500 MHz, DMSO-d$_6$) δ 1.22 (d, 3H), 2.09 (s, 3H), 2.22 (s, 3H), 3.91 (q, 1H), 6.46 (s, 1H), 7.02 (d, 2H), 7.09 (t, 2H), 7.13 (d, 1H), 7.16 (s, 1H), 10.19 (s, 1H), 12.80 (s, 1H). |
| 145 | 239666 | (2S)-3-cyclopentyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methyl-propanamide | 423.1 | $^1$H NMR (500 MHz, Methanol-d$_4$) δ 0.78-0.85 (m, 0.5H), 0.90 (d, 1.5H), 0.94-1.03 (m, 0.5H), 1.03-1.12 (m, 2.5H), 1.16-1.26 (m, 1.5 H), 1.31-1.46 (m, 1.5H), 1.46-1.69 (m, 4H), 1.68-1.89 (m, 2H), 2.32 (s, 3H), 2.33 (s, 3H), 2.54-2.65 (m, 1H), 7.02 and 7.06 (s, 1H), 7.24 (s, 1H). No exchangeable protons observed. Mixture of diastereomers present. |
| 145 | 239667 | Diastereomer 1: (2S)-3-cyclopentyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methyl-propanamide | 423.1 | $^1$H NMR (500 MHz, DMSO-d$_6$) δ 0.79 (d, 3H), 0.94-1.08 (m, 2H), 1.09-1.20 (m, 1H), 1.38-1.59 (m, 5H), 1.59-1.69 (m, 2H), 1.69-1.81 (m, 1H), 2.25 (s, 6H), 2.52-2.59 (m, 1H), 6.97 (s, 1H), 7.23 (s, 1H), 9.95 (s, 1H),12.72 (s, 1H). |
| 145 | 239668 | Diastereomer 2: (2S)-3-cyclopentyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methyl-propanamide | 423.2 | $^1$H NMR (500 MHz, DMSO-d$_6$) δ 0.74-0.83 (m, 1H), 0.85-0.92 (m, 1H), 0.94 (d, 3H), 1.00 (ddd, 1H), 1.09-1.22 (m, 2H), 1.24-1.43 (m, 4H), 1.43-1.52 (m, 1H), 1.65-1.72 (m, 1H), 2.23 (s, 3H), 2.25 (s, 3H), 2.55-2.61 (m, 1H), 6.91 (s, 1H), |

TABLE 2-continued

| Ex | ABR | Name | M ± H⁺ (m/z) | ¹H NMR |
|---|---|---|---|---|
| | | | | 7.23 (s, 1H), 10.03 (s, 1H), 12.71 (s, 1H). |
| 146a | 239664 | Diastereomer 1: (2S)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-hydroxy-2-phenylacetamide | 419.0 | ¹H NMR (500 MHz, DMSO-d$_6$) δ 2.15 (s, 3H), 2.21 (s, 3H), 5.16 (d, 1H), 6.10 (d, 1H), 6.67 (s, 1H), 7.13 (s, 1H), 7.21 (dd, 3H), 7.28 (dd, 2H), 9.88 (s, 1H), 12.75 (s, 1H). |
| 146b | 239665 | Diastereomer 2: (2S)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-hydroxy-2-phenylacetamide | 419.0 | ¹H NMR (500 MHz, DMSO-d$_6$) δ 2.24 (s, 3H), 2.26 (s, 3H), 5.07 (d, 1H), 6.26 (d, 1H), 7.04 (s, 1H), 7.19 (s, 1H), 7.22-7.26 (m, 3H), 7.34 (dd, 2H), 9.93 (s, 1H), 12.84 (br. s, 1H). |
| 147a | 239622 | Diastereomer 1: (2S)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methoxy-2-phenylacetamide | 433.2 | ¹H NMR (500 MHz, DMSO-d$_6$) δ 2.13 (s, 3H), 2.21 (s, 3H), 3.25 (s, 3H), 4.93 (s, 1H), 6.57 (s, 1H), 7.15 (s, 1H), 7.19-7.27 (m, 5H), 10.33 (s, 1H), 12.86 (s, 1H). |
| 147b | 239623 | Diastereomer 2: (2S)-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-2-methoxy-2-phenylacetamide | 433.2 | ¹H NMR (500 MHz, DMSO-d$_6$) δ 2.25 (s, 3H), 2.25 (s, 3H), 3.15 (s, 3H), 4.85 (s, 1H), 7.01 (s, 1H), 7.20 (s, 1H), 7.27-7.31 (m, 3H), 7.31-7.36 (m, 2H), 10.28 (s, 1H), 12.86 (s, 1H). |
| 148 | 239934 | methyl3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate | 439.4 | |
| 149 | 240060 | 3-cyclopentyl-N-[9-iodo-4-oxo-3-(trifluoromethyl)-2,5,7-triazatricyclo[6.4.0.0$^{2,6}$]dodeca-1(12),6,8,10-tetraen-3-yl]propanamide | 506.9 | |
| 150 | 240061 | N-[9-bromo-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide | 470.1, 472.1 | |
| 151 | 240062 | N-[9-bromo-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide | 456.0, 458.0 | |
| 152 | 240063 | (2S)-N-[9-bromo-4-oxo-3-(trifluoromethyl)-2,5,7-triazatricyclo[6.4.0.0$^{2,6}$]dodeca-1(12),6,8,10-tetraen-3-yl]-2-cyclohexylpropanamide | 473.0, 474.7 | |
| 153 | 240068 | (2S)-2-(cyclopent-1-en-1-ylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 437.6 | |
| 154 | 240064 | N-[11-chloro-9-iodo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 541.0, 543.0 | |
| 155 | 240065 | N-[9-bromo-4-oxo-3-(trifluoromethyl)-2,5,7-triazatricyclo[6.4.0.0$^{2,6}$]dodeca-1(12),6,8,10-tetraen-3-yl]butanamide | 405.0, 407.0 | |
| 156 | 240066 | N-[9-bromo-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide | 529.0, 531.0 | |

TABLE 2-continued

| Ex | ABR | Name | M ± H+ (m/z) | 1H NMR |
|---|---|---|---|---|
| 157 | 240067 | 3-cyclopentyl-N-[9-iodo-10-methoxy-4-oxo-3-(trifluoromethyl)-2,5,7-triazatricyclo[6.4.0.0²,⁶]dodeca-1(12),6,8,10-tetraen-3-yl]propanamide | 537.1 | |
| 158 | 239922 | 3-cyclopentyl-N-[9-(hydroxymethyl)-4-oxo-3-(trifluoromethyl)-2,5,7-triazatricyclo[6.4.0.0²,⁶]dodeca-1(12),6,8,10-tetraen-3-yl]propanamide | 411.6 | |
| 159 | 239938 | N-[9-butyl-4-oxo-3-(trifluoromethyl)-2,5,7-triazatricyclo[6.4.0.0²,⁶]dodeca-1(12),6,8,10-tetraen-3-yl]-3-cyclopentylpropanamide | 437.2 | $^1$H NMR (500 MHz, DMSO-$d_6$) δ 0.83-1.01 (m, 5H), 1.28-1.41 (m, 6H), 1.41-1.56 (m, 4H), 1.56-1.67 (m, 3H), 2.23 (t, 2H), 2.73-2.86 (m, 2H), 7.01 (d, 2H), 7.10 (t, 1H), 10.10 (s, 1H), 12.86 (s, 1H). |
| 160 | 239943 | 3-(3-cyclopentylpropanamido)-4-oxo-3-(trifluoromethyl)-2,5,7-triazatricyclo[6.4.0.0²,⁶]dodeca-1(12),6,8,10-tetraene-9-carboxylic acid | 425.0 | $^1$H NMR (500 MHz, DMSO-$d_6$) δ 0.86-1.02 (m, 2H), 1.26-1.70 (m, 9H), 2.19-2.28 (m, 2H), 7.24-7.43 (m, 2H), 7.70 (d, 1H), 10.07 (s, 1H), 13.05 (s, 1H). 1 Exchangeable not observed. |
| 161 | 239950 | 3-cyclopentyl-N-{9-[1-(methoxyimino)ethyl]-4-oxo-3-(trifluoromethyl)-2,5,7-triazatricyclo[6.4.0.0²,⁶]dodeca-1(12),6,8,10-tetraen-3-yl}propanamide | 452.2 | $^1$H NMR (500 MHz, DMSO-$d_6$) δ 0.86-1.04 (m, 2H), 1.28-1.42 (m, 4H), 1.42-1.59 (m, 4H), 1.59-1.69 (m, 1H), 2.23 (t, 2H), 2.28-2.42 (m, 3H), 3.96 (s, 3H), 7.20 (s, 2H), 7.33 (s, 1H), 10.15 (s, 1H), 12.84 (s, 1H). |
| 162 | 239951 | 3-(3-cyclopentylpropanamido)-N-methyl-4-oxo-3-(trifluoromethyl)-2,5,7-triazatricyclo[6.4.0.0²,⁶]dodeca-1(12),6,8,10-tetraene-9-carboxamide | 438.5 | $^1$H NMR (500 MHz, Methanol-$d_4$) δ 0.87-1.18 (m, 2H), 1.35-1.85 (m, 9H), 2.33 (t, 2H), 3.06 (s, 3H), 7.20-7.36 (m, 1H), 7.45 (d, 1H), 7.92 (d, 1H). 3 Exchangeables not observed. |
| 163 | 239986 | 3-cyclopentyl-N-[9-ethynyl-4-oxo-3-(trifluoromethyl)-2,5,7-triazatricyclo[6.4.0.0²,⁶]dodeca-1(12),6,8,10-tetraen-3-yl]propanamide | 405.2 | $^1$H NMR (500 MHz, Methanol-$d_4$) δ 0.91-1.08 (m, 2H), 1.37-1.60 (m, 7H), 1.60-1.75 (m, 2H), 2.31 (t, 2H), 3.84 (s, 1H), 7.20 (t, 1H), 7.28 (d, 1H), 7.34 (dd, 1H). 2 Exchangeables not observed. |
| 164 | 239991 | 3-cyclopentyl-N-[4-oxo-9-(trifluoromethoxy)-3-(trifluoromethyl)-2,5,7-triazatricyclo[6.4.0.0²,⁶]dodeca-1(12),6,8,10-tetraen-3-yl]propanamide | 465.2 | $^1$H NMR (500 MHz, Methanol-$d_4$) δ 0.96-1.09 (m, 2H), 1.41-1.60 (m, 7H), 1.62-1.75 (m, 2H), 2.34 (t, 2H), 7.18-7.24 (m, 1H), 7.26-7.32 (m, 2H). 2 Exchangeables not observed. |
| 165 | 239995 | 3-cyclopentyl-N-[9-cyclopropanesulfonamido-4-oxo-3-(trifluoromethyl)-2,5,7-triazatricyclo[6.4.0.0²,⁶]dodeca-1(12),6,8,10-tetraen-3-yl]propanamide | 500.0 | $^1$H NMR (500 MHz, Methanol-$d_4$) δ 0.83-1.05 (m, 6H), 1.38-1.72 (m, 9H), 2.31 (t, 2H), 2.61-2.67 (m, 1H), 7.11 (d, 1H), 7.18 (t, 1H), 7.33 (dd, 1H). 3 Exchangeables not observed. |
| 166 | 239996 | 3-(3-cyclopentylpropanamido)-N-methanesulfonyl-4-oxo-3-(trifluoromethyl)-2,5,7-triazatricyclo[6.4.0.0²,⁶]dodeca-1(12),6,8,10-tetraene-9-carboxamide | 502.2 | $^1$H NMR (500 MHz, Methanol-$d_4$) δ 0.90-1.09 (m, 2H), 1.35-1.74 (m, 9H), 2.31 (t, 2H), 3.38 (s, 3H), 7.35 (t, 1H), 7.51 (d, 1H), 7.96 (dd, 1H). 3 Exchangeables not observed. |
| 167 | 239999 | 3-cyclopentyl-N-[9-methanesulfonamido-4-oxo-3-(trifluoromethyl)-2,5,7-triazatricyclo[6.4.0.0²,⁶]dodeca-1(12),6,8,10-tetraen-3-yl]propanamide | 474.2 | $^1$H NMR (500 MHz, Methanol-$d_4$) δ 0.89-1.08 (m, 2H), 1.38-1.59 (m, 7H), 1.59-1.66 (m, 1H), 1.66-1.75 (m, 1H), 2.30 (t, 2H), 3.03 (s, 3H), 7.10 (d, 1H), 7.19 (t, 1H), 7.29 (d, 1H). 3 Exchangeables not observed. |
| 168 | 240004 | N-[9-bromo-4-oxo-3-(trifluoromethyl)-2,5,7-triazatricyclo[6.4.0.0²,⁶]dodeca-1(12),6,8,10-tetraen-3-yl]-2-[(2-methoxyethyl)amino]-1,3-thiazole-4-carboxamide | 519.05, 521.00 | $^1$H NMR (500 MHz, Methanol-$d_4$) δ 3.40 (s, 3H), 3.53-3.58 (m, 2H), 3.59-3.63 (m, 2H), 7.10 (t, 1H), 7.33 (s, 1H), 7.34 (d, 1H), 7.40 (dd, 1H). 3 Exchangeables not observed. |
| 169 | 240005 | N-[9-acetyl-4-oxo-3-(trifluoromethyl)-2,5,7-triazatricyclo[6.4.0.0²,⁶]dodeca- | 483.2 | $^1$H NMR (500 MHz, Methanol-$d_4$) δ 2.73 (s, 3H), 3.39 (s, 3H), 3.51-3.57 (m, 2H), 3.60 (t, 2H), 7.29 (s, |

TABLE 2-continued

| Ex | ABR | Name | M ± H+ (m/z) | 1H NMR |
|---|---|---|---|---|
| | | 1(12),6,8,10-tetraen-3-yl]-2-[(2-methoxyethyl)amino]-1,3-thiazole-4-carboxamide | | 1H), 7.35 (t, 1H), 7.59 (d, 1H), 7.80-7.89 (m, 1H). 3 Exchangeables not observed. |
| 170 | 239907 | 3-(3,3-difluoropyrrolidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 446.4 | $^1$H NMR (500 MHz, DMSO-d$_6$) δ 2.09 (tt, 2H), 2.26 (s, 6H), 2.35-2.45 (m, 2H), 2.52-2.62 (m, 4H), 2.68-2.85 (m, 2H), 6.97 (s, 1H), 7.24 (s, 1H), 8.14 (s, 1H), 10.19 (s, 1H), 12.79 (s, 1H). Formic acid salt |
| 171 | 239909 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(3-fluoroazetidin-1-yl)propanamide | 414.1 | $^1$H NMR (500 MHz, DMSO-d$_6$) δ 2.19-2.31 (m, 8H), 2.49-2.52 (m, 2H), 2.98 (dtd, 2H), 3.43 (ddt, 2H), 4.94-5.10 (m, 1H), 6.94 (s, 1H), 7.17 (s, 1H), 8.23 (s, 1H), 9.98 (s, 1H). Formic acid salt. |
| 172 | 239911 | 3-(3,3-difluoropiperidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 460.1 | $^1$H NMR (500 MHz, DMSO-d$_6$) δ 1.51-1.57 (m, 2H), 1.81 (dq, 2H), 2.25 (s, 6H), 2.25-2.29 (m, 1H), 2.30-2.45 (m, 3H), 2.51-2.55 (m, 2H), 2.59 (dd, 2H), 6.97 (s, 1H), 7.23 (s, 1H), 10.21 (s, 1H), 12.78 (s, 1H). |
| 173 | 239928 | N-[9-acetyl-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 451.1 | $^1$H NMR (500 MHz, DMSO-d$_6$) δ 0.88-0.98 (m, 2H), 1.30-1.41 (m, 4H), 1.45-1.55 (m, 4H), 1.57-1.63 (m, 1H), 2.15 (s, 3H), 2.25 (t, 2H), 2.30 (s, 3H), 2.65 (s, 3H), 7.09 (s, 1H), 10.29 (s, 1H), 12.85 (s, 1H). |
| 174 | 239987 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide | 420.1 | $^1$H NMR (500 MHz, DMSO-d$_6$) δ 2.26 (s, 3H), 2.28 (s, 3H), 3.96 (s, 3H), 7.09 (m, 2H), 7.26 (s, 1H), 7.82 (dd, 1H), 8.33 (dd, 1H), 10.16 (s, 1H), 12.95 (s, 1H). |
| 175 | 239989 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide | 406.0 | $^1$H NMR (500 MHz, DMSO-d$_6$) δ 2.22 (s, 3H), 2.24 (s, 3H), 6.53 (dd, 1H), 6.96 (s, 1H), 7.25 (s, 1H), 7.87 (d, 1H), 8.18 (dd, 1H), 11.98 (s, 1H), 12.93 (s, 2H). |
| 176 | 239914 | N-[11-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 459.4, 461.0 | $^1$H NMR (500 MHz, DMSO-d$_6$) δ 0.86-0.99 (m, 2H), 1.27-1.43 (m, 5H), 1.44-1.54 (m, 3H), 1.59-1.66 (m, 1H), 2.20-2.33 (m, 2H), 7.34-7.37 (m, 2H), 7.46 (d, 1H), 10.21 (s, 1H), 12.98 (s, 1H). Single regioisomer. |
| 177 | 239927 | N-[10-bromo-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 477.0, 479.0 | $^1$H NMR (500 MHz, DMSO-d$_6$) δ 0.85-0.98 (m, 2H), 1.28-1.65 (m, 9H), 2.25 (t, 2H), 7.02 (d, 1H), 7.44-7.54 (m, 1H), 10.42 (s, 1H), 13.16 (s, 1H). |
| 178 | 239933 | N-[9-bromo-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 489.0, 491.0 | $^1$H NMR (500 MHz, DMSO-d$_6$) d 0.92-0.96 (m, 2H) 1.23-1.38 (m, 3H), 1.45-1.58 (m, 4H), 1.58-1.72 (m, 2H), 2.25 (t, 2H), 3.85 (s, 3H), 7.01 (d, 1H), 7.14 (d, 1H), 10.33 (s, 1H), 12.96 (s, 1H) |
| 179 | 239937 | 3-cyclopentyl-N-[9-fluoro-10-(1-hydroxyethyl)-4-oxo-3-(trifluoromethyl)-2,5,7-triazatricyclo[6.4.0.0$^{2,6}$]dodeca-1(12),6,8,10-tetraen-3-yl]propanamide | 443.1 | $^1$H NMR (500 MHz, Methanol-d$_4$) δ 0.95-1.10 (m, 2H), 1.39-1.80 (m, 12H), 2.24-2.39 (m, 2H), 5.20-5.29 (m, 1H), 7.02 (d, 1H), 7.22-7.30 (m, 1H). Mixture of diastereomers present. 3 Exchangeable not observed. |
| 180 | 239946 | N-[9-acetyl-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 453.1 | $^1$H NMR (500 MHz, Methanol-d$_4$) δ 0.97-1.10 (m, 2H), 1.40-1.79 (m, 9H), 2.32 (t, 2H), 2.69 (s, 3H), 3.99 (s, 3H), 7.08 (d, 1H), 7.37 (d, 1H). 2 Exchangeables not observed. |
| 181 | 239916 | N-[9-bromo-11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide | 493.0, 494.8 | $^1$H NMR (500 MHz, DMSO-d$_6$) δ 0.86-0.99 (m, 2H), 1.19-1.73 (m, 9H), 2.22-2.33 (m, 2H), 7.27 (s, 1H), 7.57 (d, 1H), 10.38 (s, 1H), 13.25 (s, 1H). |
| 182 | 239936 | N-[9-acetyl-11-chloro-4-oxo-3-(trifluoromethyl)-2,5,7- | 457.0, 459.0 | $^1$H NMR (500 MHz, Methanol-d$_4$) δ 0.89-1.12(m, 2H), 1.39-1.79 (m, |

TABLE 2-continued

| Ex | ABR | Name | M ± H⁺ (m/z) | ¹H NMR |
|---|---|---|---|---|
| | | triazatricyclo[6.4.0.0²,⁶]dodeca-1(12),6,8,10-tetraen-3-yl]-3-cyclopentylpropanamide | | 9H), 2.31-2.38 (m, 2H), 2.84 (s, 3H), 7.46 (s, 1H), 7.79 (s, 1H). 2 Exchangeable not observed. |
| 183 | 239926 | N-[11-bromo-9-fluoro-4-oxo-3-(trifluoromethyl)-2,5,7-triazatricyclo[6.4.0.0²,⁶]dodeca-1(12),6,8,10-tetraen-3-yl]-3-cyclopentylpropanamide | 477.1, 478.9 | ¹H NMR (500 MHz, DMSO-d₆) δ 0.84-1.01 (m, 2H), 1.29-1.43 (m, 5H), 1.43-1.57 (m, 3H), 1.57-1.67 (m, 1H), 2.20-2.35 (m, 2H), 7.24 (s, 1H), 7.39 (d, 1H), 10.32 (s, 1H), 13.18 (s, 1H). |
| 184 | 239942 | N-[11-acetyl-4-oxo-3,9-bis(trifluoromethyl)-2,5,7-triazatricyclo[6.4.0.0²,⁶]dodeca-1(12),6,8,10-tetraen-3-yl]-3-cyclopentylpropanamide | 491.0 | ¹H NMR (500 MHz, DMSO-d₆) δ 0.83-0.98 (m, 2H), 1.23-1.61 (m, 9H), 2.22-2.30 (m, 2H), 2.64 (s, 3H), 7.94-8.16 (m, 2H), 10.36 (s, 1H). 1 Exchangeable not observed. |
| 185 | 239941 | N-[11-chloro-10-methoxy-4-oxo-3-(trifluoromethyl)-2,5,7-triazatricyclo[6.4.0.0²,⁶]dodeca-1(12),6,8,10-tetraen-3-yl]-3-cyclopentylpropanamide | 445.0, 447.0 | ¹H NMR (500 MHz, DMSO-d₆) δ 0.85-0.99 (m, 2H), 1.26-1.66 (m, 9H), 2.18-2.33 (m, 2H), 3.82-3.90 (m, 3H), 6.98 (s, 0.5H), 7.22 (s, 0.5H), 7.32 (s, 0.5H), 7.58 (s, 0.5H), 10.08-10.33 (m, 1H), 12.85 (s, 1H). Mixture of regioisomers present. |
| 186 | 239731 | 3-cyclopentyl-N-[9-(4-methoxyphenyl)-4-oxo-3-(trifluoromethyl)-2,5,7-triazatricyclo[6.4.0.0²,⁶]dodeca-1(12),6,8,10-tetraen-3-yl]propanamide | 487.1 | ¹H NMR (500 MHz, Methanol-d₄) δ 0.94-1.08 (m, 2H), 1.41-1.52 (m, 4H), 1.52-1.61 (m, 3H), 1.61-1.78 (m, 2H), 2.32 (t, 2H), 3.86 (s, 3H), 7.02-7.08 (m, 2H), 7.18-7.23 (m, 1H), 7.26-7.30 (m, 2H), 7.65 (d, 2H). 2 Exchangeables not observed. |
| 187 | 239732 | 3-cyclopentyl-N-[9-(1-methyl-1H-pyrazol-4-yl)-4-oxo-3-(trifluoromethyl)-2,5,7-triazatricyclo[6.4.0.0²,⁶]dodeca-1(12),6,8,10-tetraen-3-yl]propanamide | 461.1 | ¹H NMR (500 MHz, DMSO-d₆) δ 0.86-1.01 (m, 2H), 1.29-1.55 (m, 8H), 1.58-1.68 (m, 1H), 2.25 (t, 2H), 3.91 (s, 3H), 7.04 (d, 1H), 7.16 (t, 1H), 7.44 (d, 1H), 8.14 (s, 1H), 8.39 (s, 1H), 10.30 (s, 1H), 12.86 (s, 1H). |
| 188 | 239944 | 3-cyclopentyl-N-[9-(6-methoxypyridin-3-yl)-4-oxo-3-(trifluoromethyl)-2,5,7-triazatricyclo[6.4.0.0²,⁶]dodeca-1(12),6,8,10-tetraen-3-yl]propanamide | 488.1 | ¹H NMR (500 MHz, DMSO-d₆) δ 0.88-0.98 (m, 2H), 1.31-1.41 (m, 4H), 1.43-1.57 (m, 4H), 1.60-1.66 (m, 1H), 2.25 (t, 2H), 3.91 (s, 3H), 6.93 (d, 1H), 7.19 (d, 1H), 7.25 (d, 1H), 7.39 (s, 1H), 8.28 (s, 1H), 8.70 (s, 1H), 10.30 (s, 1H), 12.88 (s, 1H). |
| 189 | 239948 | 3-cyclopentyl-N-[9-(3-methoxyphenyl)-4-oxo-3-(trifluoromethyl)-2,5,7-triazatricyclo[6.4.0.0²,⁶]dodeca-1(12),6,8,10-tetraen-3-yl]propanamide | 487.5 | ¹H NMR (500 MHz, DMSO-d₆) δ 0.90-1.02 (m, 2H), 1.34-1.42 (m, 4H), 1.44-1.60 (m, 4H), 1.60-1.64 (m, 1H), 2.27 (t, 2H), 3.83 (s, 3H), 6.97 (d, 1H), 7.22 (d, 1H), 7.28 (t, 1H), 7.36-7.45 (m, 2H), 7.47-7.55 (m, 2H), 10.38 (s, 1H), 12.86 (s, 1H). |
| 190 | 239953 | 3-cyclopentyl-N-[9-(1,3-oxazol-2-yl)-4-oxo-3-(trifluoromethyl)-2,5,7-triazatricyclo[6.4.0.0²,⁶]dodeca-1(12),6,8,10-tetraen-3-yl]propanamide | 448.4 | ¹H NMR (500 MHz, DMSO-d₆) δ 0.85-1.02 (m, 2H), 1.28-1.42 (m, 4H), 1.42-1.58 (m, 4H), 1.58-1.69 (m, 1H), 2.19-2.32 (m, 2H), 7.29-7.39 (m, 2H), 7.46 (s, 1H), 7.82 (d, 1H), 8.28-8.32 (m, 1H), 10.32 (s, 1H), 13.04 (s, 1H). |
| 191 | 239954 | N-[9-(4-tert-butylphenyl)-4-oxo-3-(trifluoromethyl)-2,5,7-triazatricyclo[6.4.0.0²,⁶]dodeca-1(12),6,8,10-tetraen-3-yl]-3-cyclopentylpropanamide | 513.2 | ¹H NMR (500 MHz, Chloroform-d) δ 0.96-1.05 (m, 2H), 1.36 (s, 9H), 1.40-1.49 (m, 2H), 1.50-1.72 (m, 7H), 2.25-2.37 (m, 2H), 6.77 (s, 1H), 7.21 (d, 1H), 7.28 (d, 1H), 7.33 (dd, 1H), 7.52 (d, 2H), 7.66 (d, 2H). 1 exchangeable not observed. |
| 192 | 239956 | N-[9-(4-cyanophenyl)-4-oxo-3-(trifluoromethyl)-2,5,7-triazatricyclo[6.4.0.0²,⁶]dodeca-1(12),6,8,10-tetraen-3-yl]-3-cyclopentylpropanamide | 482.0 | ¹H NMR (500 MHz, Chloroform-d) δ 1.01-1.10 (m, 2H), 1.43-1.76 (m, 9H), 2.33 (dt, 1H), 2.41 (dt, 1H), 6.74 (s, 1H), 7.28 (d, 1H), 7.34 (t, 1H), 7.38-7.41 (m, 1H), 7.79 (d, 2H), 7.97 (d, 2H). 1 exchangeable not observed. |
| 193 | 239957 | 3-cyclopentyl-N-[9-(4-nitrophenyl)-4-oxo-3-(trifluoromethyl)-2,5,7-triazatricyclo[6.4.0.0²,⁶]dodeca- | 502.1 | ¹H NMR (500 MHz, Chloroform-d) δ 1.00-1.10 (m, 2H), 1.43-1.74 (m, 9H), 2.32 (dt, 1H), 2.41 (dt, 1H), 6.66 (s, 1H), 7.28 (d, 1H), 7.33 |

TABLE 2-continued

| Ex | ABR | Name | M ± H+ (m/z) | 1H NMR |
|---|---|---|---|---|
| | | 1(12),6,8,10-tetraen-3-yl]propanamide | | (t, 1H), 7.41 (d, 1H), 8.01 (d, 2H), 8.33 (d, 2H). 1 exchangeable not observed. |
| 194 | 239965 | N-[9-(4-aminophenyl)-4-oxo-3-(trifluoromethyl)-2,5,7-triazatricyclo[6.4.0.0²,⁶]dodeca-1(12),6,8,10-tetraen-3-yl]-3-cyclopentylpropanamide | 472.0 | 1H NMR (500 MHz, Methanol-d₄) δ 0.98-1.08 (m, 2H), 1.45-1.56 (m, 4H), 1.56-1.65 (m, 3H), 1.65-1.70 (m, 1H), 1.71-1.77 (m, 1H), 2.35 (t, 2H), 6.85-6.89 (m, 2H), 7.19 (d, 1H), 7.26-7.31 (m, 2H), 7.48 (d, 2H). 4 Exchangeables not observed. |
| 195 | 239967 | 3-cyclopentyl-N-[4-oxo-9-phenyl-3-(trifluoromethyl)-2,5,7-triazatricyclo[6.4.0.0²,⁶]dodeca-1(12),6,8,10-tetraen-3-yl]propanamide | 457.0 | 1H NMR (500 MHz, DMSO-d₆) δ 0.89-1.01 (m, 2H), 1.31-1.42 (m, 4H), 1.42-1.59 (m, 4H), 1.59-1.67 (m, 1H), 2.26 (t, 2H), 7.21 (d, 1H), 7.28 (t, 1H), 7.38 (t, 2H), 7.48 (t, 2H), 7.92 (s, 2H), 10.34 (s, 1H), 12.84 (s, 1H). |
| 196 | 239970 | 3-cyclopentyl-N-[9-(2-methoxyphenyl)-4-oxo-3-(trifluoromethyl)-2,5,7-triazatricyclo[6.4.0.0²,⁶]dodeca-1(12),6,8,10-tetraen-3-yl]propanamide | 487.1 | 1H NMR (500 MHz, DMSO-d₆) δ 0.93-0.95 (m, 2H), 1.32-1.42 (m, 4H), 1.42-1.67 (m, 5H), 2.24 (t, 2H), 3.72 (br. s, 3H), 7.01 (s, 1H), 7.10-7.22 (s, 4H), 7.25-7.48 (s, 2H), 9.92 (s, 1H), 12.66 (s, 1H). |
| 197 | 239988 | 2-hydroxy-N-[9-(4-methoxyphenyl)-4-oxo-3-(trifluoromethyl)-2,5,7-triazatricyclo[6.4.0.0²,⁶]dodeca-1(12),6,8,10-tetraen-3-yl]pyridine-3-carboxamide | 484.0 | 1H NMR (500 MHz, DMSO-d₆) δ 3.82 (s, 3H), 6.54 (t, 1H), 7.05 (d, 2H), 7.10-7.15 (m, 1H), 7.17-7.23 (m, 1H), 7.30-7.35 (m, 1H), 7.85-7.95 (m, 3H), 8.20 (dd, 1H), 12.22 (s, 1H), 12.99 (s, 1H), 13.09 (s, 1H). |
| 198 | 239978 | 3-cyclopentyl-N-[9-(2-hydroxyphenyl)-4-oxo-3-(trifluoromethyl)-2,5,7-triazatricyclo[6.4.0.0²,⁶]dodeca-1(12),6,8,10-tetraen-3-yl]propanamide | 473.4 | 1H NMR (500 MHz, DMSO-d₆) δ 0.97 (m, 2H), 1.32-1.44 (m, 4H), 1.44-1.69 (m, 5H), 2.26 (t, 2H), 6.90 (t, 1H), 6.97 (d, 1H), 7.16 (s, 1H), 7.18-7.28 (m, 3H), 7.35 (s, 1H), 9.5 (s, 1H), 10.2 (s, 1H), 12.71 (s, 1H). |
| 199 | 239990 | 3-cyclopentyl-N-[4-oxo-9-(1H-1,2,3,4-tetrazol-5-yl)-3-(trifluoromethyl)-2,5,7-triazatricyclo[6.4.0.0²,⁶]dodeca-1(12),6,8,10-tetraen-3-yl]propanamide | 449.1 | 1H NMR (500 MHz, DMSO-d₆) δ 0.88-1.02 (m, 2H), 1.28-1.44 (m, 4H), 1.44-1.60 (m, 4H), 1.62-1.72 (m, 1H), 2.12-2.33 (m, 2H), 6.98-7.12 (m, 2H), 7.68-7.99 (m, 1H), 9.43 (s, 1H). 2 Exchangeables not observed. |
| 200 | 239992 | 3-[3-(3-cyclopentylpropanamido)-4-oxo-3-(trifluoromethyl)-2,5,7-triazatricyclo[6.4.0.0²,⁶]dodeca-1(12),6,8,10-tetraen-9-yl]benzoic acid | 501.2 | 1H NMR (500 MHz, Methanol-d₄) δ 0.99-1.11 (m, 2H), 1.43-1.65 (m, 7H), 1.64-1.78 (m, 2H), 2.36 (t, 2H), 7.32 (d, 1H), 7.37 (t, 1H), 7.41 (dd, 1H), 7.62 (t, 1H), 8.02 (d, 1H), 8.07-8.10 (m, 1H), 8.43 (s, 1H). 3 Exchangeables not observed. |
| 201 | 240000 | N-[9-(4-chlorophenyl)-4-oxo-3-(trifluoromethyl)-2,5,7-triazatricyclo[6.4.0.0²,⁶]dodeca-1(12),6,8,10-tetraen-3-yl]-3-cyclopentylpropanamide | 491.2, 493.2 | 1H NMR (250 MHz, Methanol-d₄) δ 0.90-1.05 (m, 2H), 1.37-1.84 (m, 9H), 2.35 (t, 2H), 7.26-7.40 (m, 3H), 7.51 (d, 2H), 7.80 (d, 2H). 2 Exchangeables not observed. |
| 202 | 240001 | 3-cyclopentyl-N-[9-(4-methylphenyl)-4-oxo-3-(trifluoromethyl)-2,5,7-triazatricyclo[6.4.0.0²,⁶]dodeca-1(12),6,8,10-tetraen-3-yl]propanamide | 471.1 | 1H NMR (250 MHz, Methanol-d₄) δ 0.95-1.13 (m, 2H), 1.39-1.86 (m, 9H), 2.36 (t, 2H), 2.44 (s, 3H), 7.22-7.29 (m, 1H), 7.29-7.34 (m, 3H), 7.36 (s, 1H), 7.63 (d, 2H). 2 Exchangeables not observed. |
| 203 | 240002 | 3-cyclopentyl-N-[9-(3,4-dichlorophenyl)-4-oxo-3-(trifluoromethyl)-2,5,7-triazatricyclo[6.4.0.0²,⁶]dodeca-1(12),6,8,10-tetraen-3-yl]propanamide | 525.0, 527.0 | 1H NMR (250 MHz, Methanol-d₄) δ 1.04 (s, 2H), 1.36-1.81 (m, 9H), 2.35 (t, 2H), 7.33 (d, 2H), 7.36-7.43 (m, 1H), 7.65 (d, 1H), 7.78 (dd, 1H), 8.09 (d, 1H). 2 Exchangeables not observed. |
| 204 | 239733 | 3-cyclopentyl-N-[9-(3,4-dihydro-2H-pyran-5-yl)-4-oxo-3-(trifluoromethyl)-2,5,7-triazatricyclo[6.4.0.0²,⁶]dodeca-1(12),6,8,10-tetraen-3-yl]propanamide | 463.0 | 1H NMR (500 MHz, Methanol-d₄) δ 0.92-1.08 (m, 2H), 1.39-1.58 (m, 7H), 1.60-1.66 (m, 1H), 1.67-1.74 (m, 1H), 2.30 (t, 2H), 2.53-2.71 (m, 2H), 3.97 (t, 2H), 4.35 (q, 2H), 6.34 (s, 1H), 7.11-7.25 (m, 3H). 2 Exchangeables not observed. |
| 205 | 239729 | 3-cyclopentyl-N-[10,11-dimethyl-9-(1-methyl-1H-pyrazol-4-yl)-4-oxo-3- | 489.5 | 1H NMR (500 MHz, Methanol-d₄) δ 0.95-1.07 (m, 2H), 1.39-1.61 (m, 7H), 1.61-1.77 (m, 2H), 2.22 (s, |

TABLE 2-continued

| Ex | ABR | Name | M ± H+ (m/z) | 1H NMR |
|---|---|---|---|---|
| | | (trifluoromethyl)-2,5,7-triazatricyclo[6.4.0.0²,⁶]dodeca-1(12),6,8,10-tetraen-3-yl]propanamide | | 3H), 2.32 (td, 2H), 2.38 (s, 3H), 4.00 (s, 3H), 7.03 (s, 1H), 7.58 (s, 1H), 7.76 (s, 1H). 2 Exchangeables not observed. |
| 206 | 239738 | 3-cyclopentyl-N-[10,11-dimethyl-4-oxo-9-(1,2-thiazol-4-yl)-3-(trifluoromethyl)-2,5,7-triazatricyclo[6.4.0.0²,⁶]dodeca-1(12),6,8,10-tetraen-3-yl]propanamide | 492.1 | 1H NMR (500 MHz, DMSO-d₆) δ 0.89-1.05 (m, 2H), 1.31-1.41 (m, 4H), 1.45-1.68 (m, 5H), 2.15 (s, 3H), 2.25 (t, 2H), 2.34 (s, 3H), 7.05 (s, 1H), 8.67 (s, 1H), 9.09 (s, 1H), 10.24 (s, 1H), 12.66 (s, 1H). |
| 207 | 239739 | 3-cyclopentyl-N-[9-(furan-3-yl)-10,11-dimethyl-4-oxo-3-(trifluoromethyl)-2,5,7-triazatricyclo[6.4.0.0²,⁶]dodeca-1(12),6,8,10-tetraen-3-yl]propanamide | 475.1 | 1H NMR (500 MHz, DMSO-d₆) δ 0.89-1.03 (m, 2H), 1.30-1.45 (m, 4H), 1.44-1.69 (m, 5H), 2.20 (s, 3H), 2.24 (t, 2H), 2.32 (s, 3H), 6.69 (s, 1H), 6.97 (s, 1H), 7.79 (s, 1H), 7.84 (s, 1H), 10.12 (s, 1H), 12.61 (s, 1H). |
| 208 | 239929 | N-[9-(4-methoxyphenyl)-10,11-dimethyl-4-oxo-3-(trifluoromethyl)-2,5,7-triazatricyclo[6.4.0.0²,⁶]dodeca-1(12),6,8,10-tetraen-3-yl]acetamide | 433.5 | 1H NMR (500 MHz, DMSO-d₆) δ 1.94 (s, 3H), 2.06 (s, 3H), 2.33 (s, 3H), 3.81 (s, 3H), 6.91-7.13 (m, 3H), 7.23 (d, 2H), 10.23 (s, 1H), 12.50 (s, 1H). |
| 209 | 239924 | 3-cyclopentyl-N-[9-fluoro-10-(4-methoxyphenyl)-4-oxo-3-(trifluoromethyl)-2,5,7-triazatricyclo[6.4.0.0²,⁶]dodeca-1(12),6,8,10-tetraen-3-yl]propanamide | 505.1 | 1H NMR (500 MHz, DMSO-d₆) δ 0.93 (m, 2H), 1.44 (m, 9H), 2.27 (t, 2H), 3.80 (s, 3H), 7.05 (d, 2H), 7.10 (d, 1H), 7.27 (s, 1H), 7.46 (d, 2H), 10.39 (s, 1H), 13.03 (s, 1H). |
| 210 | 239923 | 3-cyclopentyl-N-[11-(4-methoxyphenyl)-4-oxo-3-(trifluoromethyl)-2,5,7-triazatricyclo[6.4.0.0²,⁶]dodeca-1(12),6,8,10-tetraen-3-yl]propanamide | 487.1 | 1H NMR (500 MHz, DMSO-d₆) δ 0.82-0.98 (m, 2H), 1.21-1.59 (m, 9H), 2.18-2.31 (m, 2H), 3.80 (s, 3H), 7.01-7.05 (m, 2H), 7.38-7.47 (m, 2H), 7.47-7.61 (m, 3H), 10.15 (s, 1H), 12.88 (s, 1H). |
| 211a | 239949 | (2S)-N-[10,11-dimethyl-4-oxo-3-(trifluoromethyl)-2,5,7-triazatricyclo[6.4.0.0²,⁶]dodeca-1(12),6,8,10-tetraen-3-yl]-2-(3-methylbutoxy)propanamide | 427.1 | 1H NMR (500 MHz, Chloroform-d) δ 1.00 (d, 6H), 1.38 (d, 3H), 1.55-1.60 (m, 2H), 1.77 (dt, 1H), 2.31 (s, 6H), 3.45-3.50 (m, 1H), 3.59-3.65 (m, 1H), 3.79-3.84 (m, 1H), 6.99 (s, 1H), 7.36 (s, 1H), 7.82 (s, 1H). 1 Exchangeable not observed |
| 211b | 239952 | (2S)-N-[10,11-dimethyl-4-oxo-3-(trifluoromethyl)-2,5,7-triazatricyclo[6.4.0.0²,⁶]dodeca-1(12),6,8,10-tetraen-3-yl]-2-(3-methylbutoxy)propanamide | 427.1 | 1H NMR (500 MHz, Chloroform-d) δ 0.98 (dd, 6H), 1.23-1.25 (m, 3H), 1.55-1.61 (m, 2H), 1.72-1.81 (m, 1H), 2.31 (s, 3H), 2.32 (s, 3H), 3.57-3.66 (m, 2H), 3.84-3.89 (m, 1H), 7.02 (s, 1H), 7.35 (s, 1H), 7.83 (s, 1H). 1 Exchangeable not observed. |
| 211c | 239958 | (2R)-N-[10,11-dimethyl-4-oxo-3-(trifluoromethyl)-2,5,7-triazatricyclo[6.4.0.0²,⁶]dodeca-1(12),6,8,10-tetraen-3-yl]-2-(3-methylbutoxy)propanamide | 427.1 | 1H NMR (500 MHz, Chloroform-d) δ 0.98 (dd, 6H), 1.23 (d, 3H), 1.58 (q, 2H), 1.70-1.80 (m, 1H), 2.31 (s, 3H), 2.32 (s, 3H), 3.57-3.65 (m, 2H), 3.86 (q, 1H), 7.01 (s, 1H), 7.34 (s, 1H), 7.83 (s, 1H). 1 exchangeable not observed. |
| 211d | 239959 | (2R)-N-[10,11-dimethyl-4-oxo-3-(trifluoromethyl)-2,5,7-triazatricyclo[6.4.0.0²,⁶]dodeca-1(12),6,8,10-tetraen-3-yl]-2-(3-methylbutoxy)propanamide | 427.1 | 1H NMR (500 MHz, Chloroform-d) δ 1.00 (d, 6H), 1.38 (d, 3H), 1.58 (qd, 2H), 1.73-1.81 (m, 1H), 2.32 (s, 6H), 3.47 (dt, 1H), 3.62 (dt, 1H), 3.81 (q, 1H), 6.99 (s, 1H), 7.35 (s, 1H), 7.82 (s, 1H). 1 exchangeable not observed. |
| 212a | 239968 | (2R)-2-(3-chlorophenoxy)-N-[10,11-dimethyl-4-oxo-3-(trifluoromethyl)-2,5,7-triazatricyclo[6.4.0.0²,⁶]dodeca-1(12),6,8,10-tetraen-3-yl]propanamide | 467.0, 469.0 | 1H NMR (500 MHz, DMSO-d₆) δ 1.33 (d, 3H), 2.20 (s, 3H), 2.25 (s, 3H), 4.89 (q, 1H), 6.74-6.79 (m, 1H), 6.80 (s, 1H), 6.84 (t, 1H), 6.99 (ddd, 1H), 7.21 (s, 1H), 7.25 (t, 1H), 10.39 (s, 1H), 12.86 (s, 1H). |
| 212b | 239969 | (2R)-2-(3-chlorophenoxy)-N-[10,11-dimethyl-4-oxo-3-(trifluoromethyl)-2,5,7-triazatricyclo[6.4.0.0²,⁶]dodeca-1(12),6,8,10-tetraen-3-yl]propanamide | 467.0, 469.0 | 1H NMR (500 MHz, DMSO-d₆) δ 1.42 (d, 3H), 2.25 (s, 3H), 2.28 (s, 3H), 4.94 (q, 1H), 6.61 (d, 1H), 6.77 (t, 1H), 6.89 (dd, 1H), 7.01 (dd, 2H), 7.18 (s, 1H), 10.46 (s, 1H), 12.89 (s, 1H). |

TABLE 2-continued

| Ex | ABR | Name | M ± H+ (m/z) | 1H NMR |
|---|---|---|---|---|
| 213 | 239985 | (2S)-N-[9-acetyl-4-oxo-3-(trifluoromethyl)-2,5,7-triazatricyclo[6.4.0.0$^{2,6}$]dodeca-1(12),6,8,10-tetraen-3-yl]-2-cyclohexylpropanamide | 437.3 | 1H NMR (500 MHz, DMSO-d$_6$) δ 0.73 (d, 3H), 0.79-0.98 (m, 2H), 1.05-1.39 (m, 4H), 1.50-1.71 (m, 5H), 2.26-2.34 (m, 1H), 2.83 (s, 3H), 7.30 (s, 1H), 7.42 (d, 1H), 7.69 (s, 1H), 10.25 (s, 1H), 13.11 (s, 1H). |
| 214 | 239994 | (2S)-3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-hydroxypropanamide | 425.1 | 1H NMR (500 MHz, DMSO-d$_6$) δ 0.85-1.08 (m, 2H), 1.31-1.56 (m, 6H), 1.64 (dd, 2H), 1.74 (dd, 1H), 2.24 (s, 6H), 3.89-3.99 (m, 1H), 4.14 (s, 1H), 5.55 (d, 1H), 7.08 (s, 1H), 7.17 (s, 1H). 1 exchangeable not observed. |
| 215a | 239997 | (2S)-2-(cyclopentylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 439.1 | 1H NMR (500 MHz, DMSO-d$_6$) δ 0.87-1.01 (m, 2H), 1.07-1.16 (d, 3H), 1.21-1.30 (m, 1H), 1.30-1.38 (m, 3H), 1.39-1.46 (m, 1H), 1.46-1.55 (m, 1H), 1.83-1.95 (hept, 1H), 2.22-2.24 (s, 3H), 2.24-2.26 (s, 3H), 2.71-2.83 (t, 1H), 2.95-3.09 (dd, 1H), 3.87-4.06 (q, 1H), 7.02 (s, 1H), 7.23 (s, 1H), 10.03 (s, 1H), 12.85 (s, 1H). |
| 215b | 239998 | (2S)-2-(cyclopentylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 439.1 | 1H NMR (500 MHz, DMSO-d$_6$) δ 1.09 (d, 3H), 1.12-1.23 (m, 2H), 1.38-1.57 (m, 4H), 1.57-1.70 (m, 2H), 1.98-2.11 (m, 1H), 2.24 (s, 3H), 2.25 (s, 3H), 3.08-3.21 (m, 2H), 3.95 (q, 1H), 6.96 (s, 1H), 7.21 (s, 1H), 9.83 (s, 1H), 12.87 (s, 1H). |
| 216a | 238851 | 3-cyclopentyl-N-[4-oxo-3-(trifluoromethyl)-2,5,7-triazatricyclo[6.4.0.0$^{2,6}$]dodeca-1(12),6,8,10-tetraen-3-yl]propanamide | 381.1 | 1H NMR (500 MHz, Methanol-d$_4$) δ 0.95-1.05 (m, 2H), 1.37-1.60 (m, 7H), 1.62-1.67 (m, 1H), 1.67-1.75 (m, 1H), 2.31 (t, 2H), 7.23-7.29 (m, 3H), 7.47-7.51 (m, 1H). 2 Exchangeables not observed. |
| 216b | 238856 | 3-cyclopentyl-N-[4-oxo-3-(trifluoromethyl)-2,5,7-triazatricyclo[6.4.0.0$^{2,6}$]dodeca-1(12),6,8,10-tetraen-3-yl]propanamide | 381.1 | 1H NMR (500 MHz, Methanol-d$_4$) δ 0.93-1.05 (m, 2H), 1.36-1.59 (m, 7H), 1.60-1.66 (m, 1H), 1.68-1.73 (m, 1H), 2.31 (t, 2H), 7.22-7.27 (m, 3H), 7.46-7.49 (m, 1H). 2 Exchangeables not observed. |
| 217a | 238924 | 3-cyclohexyl-N-[4-oxo-3-(trifluoromethyl)-2,5,7-triazatricyclo[6.4.0.0$^{2,6}$]dodeca-1(12),6,8,10-tetraen-3-yl]propanamide | 395.0 | 1H NMR (500 MHz, Methanol-d$_4$) δ 0.70-0.87 (m, 2H), 0.97-1.20 (m, 4H), 1.23-1.42 (m, 4H), 1.54-1.69 (m, 5H), 2.25-2.38 (t, 2H), 7.21-7.31 (m, 3H), 7.44-7.51 (m, 1H). 2 Exchangeables not observed. |
| 217b | 238941 | 3-cyclohexyl-N-[4-oxo-3-(trifluoromethyl)-2,5,7-triazatricyclo[6.4.0.0$^{2,6}$]dodeca-1(12),6,8,10-tetraen-3-yl]propanamide | 395.0 | 1H NMR (500 MHz, Methanol-d$_4$) δ 0.71-0.87 (m, 2H), 0.97-1.21 (m, 4H), 1.27-1.43 (m, 3H), 1.53-1.70 (m, 5H), 2.21-2.38 (m, 2H), 7.14-7.26 (m, 3H), 7.44 (d, 1H). 2 Exchangeables not observed. |
| 218a | 239071 | 3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 409.2 | 1H NMR (500 MHz, Methanol-d$_4$) δ 0.91-1.05 (m, 2H), 1.36-1.59 (m, 7H), 1.59-1.74 (m, 2H), 2.27-2.32 (m, 2H), 2.30 (s, 3H), 2.31 (s, 3H), 7.03 (s, 1H), 7.23 (s, 1H). 2 Exchangeables not observed. |
| 218b | 239105 | 3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide | 409.2 | 1H NMR (500 MHz, Methanol-d$_4$) δ 0.93-1.05 (m, 2H), 1.35-1.59 (m, 7H), 1.58-1.75 (m, 2H), 2.28-2.32 (m, 2H), 2.32 (s, 3H), 2.33 (s, 3H), 7.03 (s, 1H), 7.23 (s, 1H). 2 Exchangeables not observed. |
| 219a | 239396 | 3-cyclopentyl-N-[10,11-dichloro-4-oxo-3-(trifluoromethyl)-2,5,7-triazatricyclo[6.4.0.0$^{2,6}$]dodeca-1(12),6,8,10-tetraen-3-yl]propanamide | 449.0, 451.0 | 1H NMR (500 MHz, DMSO-d$_6$) δ 0.84-1.00 (m, 2H), 1.30-1.42 (m, 5H), 1.44-1.54 (m, 3H), 1.56-1.65 (m, 1H), 2.21-2.33 (m, 2H), 7.39 (s, 1H), 7.79 (s, 1H), 10.22 (s, 1H), 13.14 (s, 1H). |
| 219b | 239397 | 3-cyclopentyl-N-[10,11-dichloro-4-oxo-3-(trifluoromethyl)-2,5,7- | 449.0, 451.0 | 1H NMR (500 MHz, DMSO-d$_6$) δ 0.91 (ddt, 2H), 1.30-1.42 (m, 5H), 1.43-1.55 (m, 3H), 1.57-1.65 (m, |

TABLE 2-continued

| Ex | ABR | Name | M ± H+ (m/z) | 1H NMR |
|---|---|---|---|---|
| | | triazatricyclo[6.4.0.0²,⁶]dodeca-1(12),6,8,10-tetraen-3-yl]propanamide | | 1H), 2.19-2.33 (m, 2H), 7.39 (s, 1H), 7.81 (s, 1H), 10.25 (s, 1H), 13.16 (br s, 1H). |
| 220a | 239662 | N-[10,11-dimethyl-4-oxo-3-(trifluoromethyl)-2,5,7-triazatricyclo[6.4.0.0²,⁶]dodeca-1(12),6,8,10-tetraen-3-yl]-6-[(2-methoxyethyl)amino]pyridine-2-carboxamide | 463.1 | ¹H NMR (500 MHz, Methanol-d₄) δ 2.29 (s, 3H), 2.31 (s, 3H), 3.44 (s, 3H), 3.55-3.74 (m, 4H), 6.75 (d, 1H), 7.05-7.18 (m, 2H), 7.24 (s, 1H), 7.49 (dd, 1H). 3 Exchangeables not observed. |
| 220b | 239663 | N-[10,11-dimethyl-4-oxo-3-(trifluoromethyl)-2,5,7-triazatricyclo[6.4.0.0²,⁶]dodeca-1(12),6,8,10-tetraen-3-yl]-6-[(2-methoxyethyl)amino]pyridine-2-carboxamide | 463.2 | ¹H NMR (500 MHz, Methanol-d₄) δ 2.29 (s, 3H), 2.31 (s, 3H), 3.44 (s, 3H), 3.55-3.73 (m, 4H), 6.75 (d, 1H), 7.07-7.15 (m, 2H), 7.24 (s, 1H), 7.49 (dd, 1H). 3 Exchangeables not observed. |
| 221a | 239707 | N-[10,11-dimethyl-4-oxo-3-(trifluoromethyl)-2,5,7-triazatricyclo[6.4.0.0²,⁶]dodeca-1(12),6,8,10-tetraen-3-yl]-3-(1-hydroxycyclopentyl)propanamide | 425.5 | ¹H NMR (500 MHz, DMSO-d₆) δ 1.24-1.34 (m, 2H), 1.37-1.47 (m, 4H), 1.53 (t, 2H), 1.57-1.69 (m, 2H), 2.25 (s, 6H), 2.29-2.38 (m, 2H), 4.05 (s, 1H), 6.97 (s, 1H), 7.23 (s, 1H), 10.04 (s, 1H), 12.73 (s, 1H). |
| 221b | 239714 | N-[10,11-dimethyl-4-oxo-3-(trifluoromethyl)-2,5,7-triazatricyclo[6.4.0.0²,⁶]dodeca-1(12),6,8,10-tetraen-3-yl]-3-(1-hydroxycyclopentyl)propanamide | 425.2 | ¹H NMR (500 MHz, Methanol-d₄) δ 1.36-1.51 (m, 2H), 1.51-1.63 (m, 4H), 1.66-1.80 (m, 4H), 2.31 (s, 3H), 2.32 (s, 3H), 2.38-2.49 (m, 2H), 7.03 (s, 1H), 7.21 (s, 1H). 3 Exchangeables not observed. |
| 222a | 239709 | 3-cyclopentyl-N-[9-methanesulfonyl-4-oxo-3-(trifluoromethyl)-2,5,7-triazatricyclo[6.4.0.0²,⁶]dodeca-1(12),6,8,10-tetraen-3-yl]propanamide | 459.1 | ¹H NMR (500 MHz, DMSO-d₆) δ 0.87-1.00 (m, 2H), 1.30-1.41 (m, 4H), 1.41-1.58 (m, 4H), 1.58-1.66 (m, 1H), 2.20-2.33 (m, 2H), 3.43 (s, 3H), 7.41 (t, 1H), 7.53 (d, 1H), 7.67 (d, 1H), 10.45 (s, 1H), 13.31 (s, 1H). |
| 222b | 239710 | 3-cyclopentyl-N-[9-methanesulfonyl-4-oxo-3-(trifluoromethyl)-2,5,7-triazatricyclo[6.4.0.0²,⁶]dodeca-1(12),6,8,10-tetraen-3-yl]propanamide | 459.1 | ¹H NMR (500 MHz, DMSO-d₆) δ 0.88-1.00 (m, 2H), 1.31-1.41 (m, 4H), 1.41-1.58 (m, 4H), 1.58-1.66 (m, 1H), 2.20-2.32 (m, 2H), 3.43 (s, 3H), 7.40 (t, 1H), 7.52 (d, 1H), 7.66 (d, 1H), 10.42 (s, 1H), 13.30 (s, 1H). |
| 223a | 239712 | 3-cyclopentyl-N-[9,10-difluoro-4-oxo-3-(trifluoromethyl)-2,5,7-triazatricyclo[6.4.0.0²,⁶]dodeca-1(12),6,8,10-tetraen-3-yl]propanamide | 417.0 | ¹H NMR (500 MHz, DMSO-d₆) δ 0.86-1.00 (m, 2H), 1.29-1.40 (m, 4H), 1.40-1.57 (m, 4H), 1.57-1.65 (m, 1H), 2.25 (t, 2H), 7.00 (dd, 1H), 7.28 (dt, 1H), 10.40 (s, 1H), 13.14 (s, 1H). |
| 223b | 239713 | 3-cyclopentyl-N-[9,10-difluoro-4-oxo-3-(trifluoromethyl)-2,5,7-triazatricyclo[6.4.0.0²,⁶]dodeca-1(12),6,8,10-tetraen-3-yl]propanamide | 417.0 | ¹H NMR (500 MHz, DMSO-d₆) δ 0.86-1.00 (m, 2H), 1.28-1.40 (m, 4H), 1.40-1.57 m, 4H), 1.57-1.65 (m, 1H), 2.25 (t, 2H), 7.00 (dd, 1H), 7.28 (dt, 1H), 10.41 (s, 1H), 13.14 (s, 1H). |
| 224a | 239727 | N-[9-acetyl-4-oxo-3-(trifluoromethyl)-2,5,7-triazatricyclo[6.4.0.0²,⁶⁶]dodeca-1(12),6,8,10-tetraen-3-yl]-3-cyclopentylpropanamide | 423.1 | ¹H NMR (500 MHz, DMSO-d₆) δ 0.86-1.00 (m, 2H), 1.28-1.41 (m, 4H), 1.41-1.58 (m, 4H), 1.58-1.69 (m, 1H), 2.25 (t, 2H), 2.84 (s, 3H), 7.31 (s, 1H), 7.42 (d, 1H), 7.67 (s, 1H), 10.41 (s, 1H), 13.14 (s, 1H). |
| 224b | 239728 | N-[9-acetyl-4-oxo-3-(trifluoromethyl)-2,5,7-triazatricyclo[6.4.0.0²,⁶]dodeca-1(12),6,8,10-tetraen-3-yl]-3-cyclopentylpropanamide | 423.1 | ¹H NMR (500 MHz, DMSO-d₆) δ 0.87-1.00 (m, 2H), 1.29-1.41 (m, 4H), 1.41-1.58 (m, 4H), 1.58-1.67 (m, 1H), 2.25 (t, 2H), 2.85 (s, 3H), 7.30 (s, 1H), 7.41 (s, 1H), 7.65 (s, 1H), 10.44 (s, 1H), 13.14 (s, 1H). |
| 225a | 239825 | 3-(3,3-difluoroazetidin-1-yl)-N-[10,11-dimethyl-4-oxo-3-(trifluoromethyl)-2,5,7-triazatricyclo[6.4.0.0²,⁶]dodeca-1(12),6,8,10-tetraen-3-yl]propanamide | 432.0 | ¹H NMR (500 MHz, DMSO-d₆) δ 2.26 (s, 6H), 2.32 (t, 2H), 2.60 (t, 2H), 3.42-3.48 (m, 4H), 6.97 (s, 1H), 7.24 (s, 1H), 10.10 (s, 1H), 12.79 (s, 1H). |
| 225b | 239824 | 3-(3,3-difluoroazetidin-1-yl)-N-[10,11-dimethyl-4-oxo-3-(trifluoromethyl)-2,5,7- | 432.0 | ¹H NMR (500 MHz, DMSO-d₆) δ 2.26 (s, 6H), 2.32 (t, 2H), 2.60 (t, 2H), 3.36-3.50 (m, 4H), 6.97 (s, |

TABLE 2-continued

| Ex | ABR | Name | M ± H⁺ (m/z) | ¹H NMR |
|---|---|---|---|---|
| | | triazatricyclo[6.4.0.0²,⁶]dodeca-1(12),6,8,10-tetraen-3-yl]propanamide | | 1H), 7.23 (s, 1H), 10.11 (s, 1H), 12.79 (s, 1H). |
| 226a | 239962 | N-[9-cyano-4-oxo-3-(trifluoromethyl)-2,5,7-triazatricyclo[6.4.0.0²,⁶]dodeca-1(12),6,8,10-tetraen-3-yl]-3-cyclopentylpropanamide | 406.0 | ¹H NMR (500 MHz, DMSO-d₆) δ 0.83-1.00 (m, 2H), 1.27-1.40 (m, 4H), 1.40-1.56 (m, 4H), 1.56-1.65 (m, 1H), 2.25 (t, 2H), 7.34 (s, 1H), 7.50 (d, 1H), 7.64 (d, 1H), 10.44 (s, 1H), 13.30 (s, 1H). |
| 226b | 239961 | N-[9-cyano-4-oxo-3-(trifluoromethyl)-2,5,7-triazatricyclo[6.4.0.0²,⁶]dodeca-1(12),6,8,10-tetraen-3-yl]-3-cyclopentylpropanamide | 406.0 | ¹H NMR (500 MHz, Methanol-d₄) δ 0.92-1.07 (m, 2H), 1.37-1.59 (m, 7H), 1.59-1.74 (m, 2H), 2.25-2.37 (m, 2H), 7.33 (t, 1H), 7.56 (dd, 2H). 2 Exchangeables not observed. |
| 227a | 239975 | 3-cyclopentyl-N-[9-(2-methylpropanoyl)-4-oxo-3-(trifluoromethyl)-2,5,7-triazatricyclo[6.4.0.0²,⁶]dodeca-1(12),6,8,10-tetraen-3-yl]propanamide | 451.1 | ¹H NMR (500 MHz, Methanol-d₄) δ0.92-1.08 (m, 2H), 1.22 (d, 6H), 1.37-1.51 (m, 4H),1.51-1.60 (m, 3H), 1.60-1.75 (m, 2H), 2.31 (t, 2H), 3.95 (s, 1H), 7.36 (t, 1H), 7.46 (d, 1H), 7.83 (d, 1H). 2 Exchangeables not observed. |
| 227b | 239972 | 3-cyclopentyl-N-[9-(2-methylpropanoyl)-4-oxo-3-(trifluoromethyl)-2,5,7-triazatricyclo[6.4.0.0²,⁶]dodeca-1(12),6,8,10-tetraen-3-yl]propanamide | 451.1 | ¹H NMR (500 MHz, Methanol-d₄) δ 0.90-1.10 (m, 2H), 1.21 (d, 6H), 1.37-1.60 (m, 7H), 1.60-1.75 (m, 2H), 2.31 (t, 2H), 3.99 (s, 1H), 7.32 (t, 1H), 7.44 (d, 1H), 7.79 (d, 1H). 2 Exchangeables not observed. |
| 228a | 239976 | N-[10,11-dimethyl-4-oxo-3-(trifluoromethyl)-2,5,7-triazatricyclo[6.4.0.0²,⁶]dodeca-1(12),6,8,10-tetraen-3-yl]-3-phenylpropanamide | 417.0 | ¹H NMR (500 MHz, Methanol-d₄) δ 2.33 (s, 3H), 2.37 (s, 3H), 2.69-2.50 (m, 2H), 2.93-2.71 (m, 2H),6.91 (s, 1H), 7.07-7.00 (m, 2H), 7.06-7.09 (m, 3H), 7.26 (s, 1H). 2 Exchangeables not observed. |
| 228b | 239974 | N-[10,11-dimethyl-4-oxo-3-(trifluoromethyl)-2,5,7-triazatricyclo[6.4.0.0²,⁶]dodeca-1(12),6,8,10-tetraen-3-yl]-3-phenylpropanamide | 417.1 | ¹H NMR (500 MHz, Methanol-d₄) δ 2.33 (s, 3H), 2.37 (s, 3H), 2.51-2.67 (m, 2H), 2.67-2.93 (m, 2H), 6.92 (s, 1H), 7.02 (dd, 2H), 7.06-7.09 (m, 3H), 7.27 (s, 1H). 2 Exchangeables not observed. |
| 229a | 239981 | 3,5-dichloro-N-[10,11-dichloro-4-oxo-3-(trifluoromethyl)-2,5,7-triazatricyclo[6.4.0.0²,⁶]dodeca-1(12),6,8,10-tetraen-3-yl]benzamide | 496.6, 498.8 | ¹H NMR (500 MHz, Methanol-d₄) δ 7.52 (s, 1H), 7.69 (s, 1H), 7.74 (s, 1H), 7.83 (d, 2H). 2 Exchangeables not observed. |
| 229b | 239980 | 3,5-dichloro-N-[10,11-dichloro-4-oxo-3-(trifluoromethyl)-2,5,7-triazatricyclo[6.4.0.0²,⁶]dodeca-1(12),6,8,10-tetraen-3-yl]benzamide | 496.5, 498.8 | ¹H NMR (500 MHz, Methanol-d₄) δ 7.50 (s, 1H), 7.67 (s, 1H), 7.73 (s, 1H), 7.82 (s, 2H). 2 Exchangeables not observed. |
| 230a | 239984 | 3-cyclopentyl-N-[9-(4-methoxyphenyl)-4-oxo-3-(trifluoromethyl)-2,5,7-triazatricyclo[6.4.0.0²,⁶]dodeca-1(12),6,8,10-tetraen-3-yl]propanamide | 487.1 | ¹H NMR (500 MHz, DMSO-d₆) δ 0.89-1.00 (m, 2H), 1.31-1.42 (m, 4H), 1.42-1.68 (m, 5H), 2.26 (t, 2H), 3.81 (s, 3H), 7.04 (d, 2H), 7.12-7.17 (m, 1H), 7.21-7.27 (m, 1H), 7.32-7.38 (m, 1H), 7.91 (s, 2H), 10.34 (s, 1H), 12.83 (s, 1H). |
| 230b | 239979 | 3-cyclopentyl-N-[9-(4-methoxyphenyl)-4-oxo-3-(trifluoromethyl)-2,5,7-triazatricyclo[6.4.0.0²,⁶]dodeca-1(12),6,8,10-tetraen-3-yl]propanamide | 487.1 | ¹H NMR (500 MHz, DMSO-d₆) δ 0.89-1.00 (m, 2H), 1.31-1.42 (m, 4H), 1.42-1.68 (m, 5H), 2.26 (t, 2H), 3.81 (s, 3H), 7.04 (d, 2H), 7.12-7.17 (m, 1H), 7.21-7.27 (m, 1H), 7.32-7.38 (m, 1H), 7.90 (s, 2H), 10.33 (s, 1H), 12.83 (s, 1H). |
| 231a | 240007 | 3-(3-cyclopentylpropanamido)-4-oxo-3-(trifluoromethyl)-2,5,7-triazatricyclo[6.4.0.0²,⁶]dodeca-1(12),6,8,10-tetraene-9-carboxylic acid | 425.2 | ¹H NMR (500 MHz, Methanol-d₄) δ 0.97-1.10 (m, 2H), 1.44-1.70 (m, 9H), 2.35 (t, 2H), 7.39 (t, 1H), 7.47 (d, 1H), 7.90 (d, 1H). 3 Exchangeables not observed. |
| 231b | 240006 | 3-(3-cyclopentylpropanamido)-4-oxo-3-(trifluoromethyl)-2,5,7-triazatricyclo[6.4.0.0²,⁶]dodeca-1(12),6,8,10-tetraene-9-carboxylic acid | 425.1 | ¹H NMR (500 MHz, Methanol-d₄) δ 0.94-1.09 (m, 2H), 1.40-1.73 (m, 9H), 2.33 (t, 2H), 7.37 (t, 1H), 7.46 (d, 1H), 7.88 (dd, 1H). 3 Exchangeables not observed. |

TABLE 2-continued

| Ex | ABR | Name | M ± H⁺ (m/z) | ¹H NMR |
|---|---|---|---|---|
| 232 | 240016 | 3-cyclopentyl-N-{9-[4-(methylsulfanyl)phenyl]-4-oxo-3-(trifluoromethyl)-2,5,7-triazatricyclo[6.4.0.0$^{2,6}$]dodeca-1(12),6,8,10-tetraen-3-yl}propanamide | 503.3 | ¹H NMR (500 MHz, Methanol-d$_4$) δ 0.94-1.12 (m, 2H), 1.41-1.79 (m, 9H), 2.34 (t, 2H), 2.55 (s, 3H), 7.25 (d, 1H), 7.29-7.36 (m, 2H), 7.38-7.43 (m, 2H), 7.71 (d, 2H). 2 Exchangeables not observed. |
| 233 | 240015 | 11-chloro-3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid | 459.0, 461.0 | ¹H NMR (500 MHz, Methanol-d$_4$) δ 0.91-1.10 (m, 2H), 1.37-1.79 (m, 9H), 2.25-2.41 (m, 2H), 7.40-7.44 (m, 1H), 7.82 (d, 1H). 3 Exchangeables not observed. |
| 234 | 240014 | N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]butanamide | 433.1 | ¹H NMR (500 MHz, DMSO-d$_6$) δ 0.73 (t, 3H), 1.39 (m, 2H), 2.21 (m, 2H), 3.82 (s, 3H), 7.04 (d, 2H), 7.12 (d, 1H), 7.18 (s, 1H), 7.29 (d, 1H), 7.91 (d, 2H). 2 Exchangeables not observed. |
| 235 | 240013 | 2-[(2-methoxyethyl)amino]-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide | 547.0 | ¹H NMR (500 MHz, DMSO-d$_6$) δ 3.29 (s, 3H), 3.46-3.54 (m, 4H), 3.82 (s, 3H), 7.06 (d, 2H), 7.24 (t, 1H), 7.31-7.39 (m, 2H), 7.43 (s, 1H), 7.86-7.96 (m, 3H), 9.84 (s, 1H), 12.98 (s, 1H). |
| 236 | 240018 | N-[9-bromo-4-oxo-3-(trifluoromethyl)-2,5,7-triazatricyclo[6.4.0.0$^{2,6}$]dodeca-1(12),6,8,10-tetraen-3-yl]-2-hydroxy-1,3-thiazole-4-carboxamide | 461.9, 463.9 | ¹H NMR (500 MHz, Methanol-d$_4$) δ 7.13 (t, 1H), 7.31 (d, 1H), 7.42 (d, 1H), 7.51 (s, 1H). 3 Exchangeables not observed. |
| 237 | 240019 | N[10,11-dichloro-4-oxo-3-(trifluoromethyl)-2,5,7-triazatricyclo[6.4.0.0$^{2,6}$]dodeca-1(12),6,8,10-tetraen-3-yl]-2-[(2-methylpropyl)amino]-1,3-thiazole-4-carboxamide | 507.1, 509.1 | ¹H NMR (500 MHz, Chloroform-d) δ 1.04 (d, 6H), 1.94-2.02 (m, 1H), 3.12 (t, 2H), 5.28 (t, 1H), 7.28 (s, 1H), 7.37 (s, 1H), 7.75 (s, 1H), 8.33 (s, 1H). 1 Exchangeables not observed. |
| 238 | 240028 | 3-cyclopentyl-N-{9-[4-(dimethylamino)phenyl]-4-oxo-3-(trifluoromethyl)-2,5,7-triazatricyclo[6.4.0.0$^{2,6}$]dodeca-1(12),6,8,10-tetraen-3-yl}propanamide | 500.7 | ¹H NMR (500 MHz, Methanol-d$_4$) δ 1.03 (dtd, 2H), 1.38-1.80 (m, 9H), 2.34 (t, 2H), 3.02 (s, 6H), 6.91 (d, 2H), 7.14-7.21 (m, 1H), 7.24-7.31 (m, 2H), 7.58 (d,2H). 2 Exchangeables not observed. |
| 239 | 240031 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-2,2,2-trifluoroacetamide | 381.0 | ¹H NMR (500 MHz, DMSO-d$_6$) δ 2.28 (s, 6H), 6.99 (s, 1H), 7.28 (s, 1H), 12.05 (s, 1H). 1 Exchangeables not observed. |
| 240 | 240032 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(2-methoxyethoxy)pyridine-4-carboxamide | 464.1 | ¹H NMR (500 MHz, Methanol-d$_4$) δ 2.34 (s, 3H), 2.35 (s, 3H), 3.43 (s, 3H), 3.74-3.79 (m, 2H), 4.46-4.50 (m, 2H), 7.13 (s, 1H), 7.16 (s, 1H), 7.24 (dd, 1H), 7.28 (s, 1H), 8.26 (d, 1H). 2 Exchangeables not observed. |
| 241 | 240029 | 3-cyclopentyl-N-[9-(4-methanesulfonylphenyl)-4-oxo-3-(trifluoromethyl)-2,5,7-triazatricyclo[6.4.0.0$^{2,6}$]dodeca-1(12),6,8,10-tetraen-3-yl]propanamide | 535.0 | ¹H NMR (500 MHz, DMSO-d$_6$) δ 0.87-1.02 (m, 2H), 1.29-1.69 (m, 9H), 2.27 (t, 2H), 3.27 (s, 3H), 7.24-7.43 (m, 2H), 7.50 (d, 1H), 8.03 (d, 2H), 8.20 (s, 2H), 10.41 (s, 1H), 12.96 (s, 1H). |
| 242 | 240030 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-2,2-dimethylpropanamide | 369.1 | ¹H NMR (500 MHz, DMSO-d$_6$) δ 1.08 (s, 9H), 2.26 (s, 3H), 2.26 (s, 3H), 7.00 (s, 1H), 7.25 (s, 1H), 9.40 (s, 1H), 12.69 (s, 1H). |
| 243 | 240024 | N-[9-acetyl-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide | 493.0 | ¹H NMR (500 MHz, DMSO-d$_6$) δ 1.43-1.75 (m, 7H), 1.86-2.00 (m, 2H), 2.82 (s, 3H), 3.88-3.98 (m, 1H), 7.26 (s, 1H), 7.40 (s, 1H), 7.66 (d, 2H), 7.94 (d, 1H), 13.26 (s, 1H). |
| 244 | 240025 | N-[9-(3-chlorophenyl)-4-oxo-3-(trifluoromethyl)-2,5,7-triazatricyclo[6.4.0.0$^{2,6}$]dodeca- | 491.2, 493.2 | ¹H NMR (250 MHz, Methanol-d$_4$) δ 0.95-1.13 (m, 2H), 1.40-1.78 (m, 9H), 2.35 (t, 2H), 7.31 (d, 1H), 7.34 |

TABLE 2-continued

| Ex | ABR | Name | M ± H+ (m/z) | ¹H NMR |
|---|---|---|---|---|
| | | 1(12),6,8,10-tetraen-3-yl]-3-cyclopentylpropanamide | | (d, 1H), 7.35-7.41 (m, 1H), 7.42-7.44 (m, 1H), 7.48 (t, 1H), 7.72 (dt, 1H), 7.85 (t, 1H). 2 Exchangeables not observed. |
| 245 | 240022 | 3-cyclopentyl-N-[4-oxo-3-(trifluoromethyl)-9-[4-(trifluoromethyl)phenyl]-2,5,7-triazatricyclo[6.4.0.0²,⁶]dodeca-1(12),6,8,10-tetraen-3-yl]propanamide | 525.2 | ¹H NMR (250 MHz, Methanol-$d_4$) δ 1.03 (d, 2H), 1.32-1.93 (m, 9H), 2.35 (t, 2H), 7.32-7.37 (m, 2H), 7.38-7.45 (m, 1H), 7.80 (d, 2H), 8.02 (d, 2H). 2 Exchangeables not observed. |
| 246 | 240023 | 3-cyclopentyl-N-[9-(4-fluorophenyl)-4-oxo-3-(trifluoromethyl)-2,5,7-triazatricyclo[6.4.0.0²,⁶]dodeca-1(12),6,8,10-tetraen-3-yl]propanamide | 475.1 | ¹H NMR (250 MHz, Methanol-$d_4$) δ 1.05 (s, 2H), 1.41-1.77 (m, 9H), 2.35 (t, 2H), 7.19-7.29 (m, 3H), 7.31-7.34 (m, 2H), 7.76-7.84 (m, 2H). 2 Exchangeables not observed. |
| 247 | 240026 | 3-(3-cyclopentylpropanamido)-N-methanesulfonyl-10-methoxy-4-oxo-3-(trifluoromethyl)-2,5,7-triazatricyclo[6.4.0.0²,⁶]dodeca-1(12),6,8,10-tetraene-9-carboxamide | 532.1 | ¹H NMR (250 MHz, Methanol-$d_4$) δ 0.95-1.12 (m, 2H), 1.44-1.73 (m, 9H), 2.33 (t, 2H), 3.43 (s, 3H), 3.99 (s, 3H), 7.09 (d, 1H), 7.41 (d, 1H). 3 Exchangeables not observed. |
| 248 | 240027 | 3-cyclopentyl-N-[9-(methoxymethyl)-4-oxo-3-(trifluoromethyl)-2,5,7-triazatricyclo[6.4.0.0²,⁶]dodeca-1(12),6,8,10-tetraen-3-yl]propanamide | 425.3 | ¹H NMR (500 MHz, Methanol-$d_4$) δ 0.81-0.93 (m, 2H), 1.24-1.66 (m, 9H), 2.20 (t, 2H), 3.32 (s, 3H), 4.59-4.68 (m, 2H), 7.05-7.17 (m, 3H). 2 Exchangeables not observed. |
| 249 | 240049 | tert-butyl 3-{[10,11-dimethyl-4-oxo-3-(trifluoromethyl)-2,5,7-triazatricyclo-[6.4.0.0²,⁶]dodeca-1(12),6,8,10-tetraen-3-yl]carbamoyl}pyrrolidine-1-carboxylate | 426.1⁽¹⁾ | |
| 250 | 240050 | tert-butyl 4-{[10,11-dimethyl-4-oxo-3-(trifluoromethyl)-2,5,7-triazatricyclo-[6.4.0.0²,⁶]dodeca-1(12),6,8,10-tetraen-3-yl]carbamoyl}piperidine-1-carboxylate | 440.1⁽¹⁾ | |
| 251 | 240051 | tert-butyl (2S)-2-{[10,11-dichloro-4-oxo-3-(trifluoromethyl)-2,5,7-triazatricyclo-[6.4.0.0²,⁶]dodeca-1(12),6,8,10-tetraen-3-yl]carbamoyl}pyrrolidine-1-carboxylate | 465.8, 467.8⁽¹⁾ | |
| 252 | 240052 | tert-butyl 3-{[10,11-dichloro-4-oxo-3-(trifluoromethyl)-2,5,7-triazatricyclo-[6.4.0.0²,⁶]dodeca-1(12),6,8,10-tetraen-3-yl]carbamoyl}pyrrolidine-1-carboxylate | 466.1, 468.1⁽¹⁾ | |
| 253 | 240053 | tert-butyl 4-{[10,11-dichloro-4-oxo-3-(trifluoromethyl)-2,5,7-triazatricyclo-[6.4.0.0²,⁶]dodeca-1(12),6,8,10-tetraen-3-yl]carbamoyl}piperidine-1-carboxylate | 480.1, 482.1⁽¹⁾ | |
| 254 | 240054 | tert-butyl 3-{[10,11-dichloro-4-oxo-3-(trifluoromethyl)-2,5,7-triazatricyclo-[6.4.0.0²,⁶]dodeca-1(12),6,8,10-tetraen-3-yl]carbamoyl}azetidine-1-carboxylate | 451.8, 453.8⁽¹⁾ | |
| 255 | 240055 | tert-butyl 4-({[10,11-dichloro-4-oxo-3-(trifluoromethyl)-2,5,7-triazatricyclo-[6.4.0.0²,⁶]dodeca-1(12),6,8,10-tetraen-3- | 450.4, 452.4⁽²⁾ | |

TABLE 2-continued

| Ex | ABR | Name | M ± H+ (m/z) | $^1$H NMR |
|---|---|---|---|---|
| 256 | 240056 | tert-butyl 2-(2-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}methyl)piperidine-1-carboxylate yl]carbamoyl}ethyl)piperidine-1-carboxylate | 463.4, 465.4$^{(2)}$ | |
| 257 | 240057 | tert-butyl 3-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}-3-fluoroazetidine-1-carboxylate | 469.8, 471.8$^{(1)}$ | |
| 258 | 240058 | methyl 3-[3-(3-cyclopentylpropanamido)-4-oxo-3-(trifluoromethyl)-2,5,7-triazatricyclo[6.4.0.0$^{2,6}$]dodeca-1(12),6,8,10-tetraen-9-yl]benzoate | 515.3 | |
| 259 | 238786 | N-[10,11-dimethyl-4-oxo-3-(trifluoromethyl)-2,5,7-triazatricyclo[6.4.0.0$^{2,6}$]dodeca-1(12),6,8,10-tetraen-3-yl]acetamide | 327.0 | |
| 260 | 240059 | N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]acetamide | 404.8, 406.8 | |
| 261 | 239626 | N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]pyrimidine-4-carboxamide | 464.10 | 1H NMR (500 MHz, Methanol-d$_4$) δ 2.29 (s, 3H), 2.31 (s, 3H), 3.41 (s, 3H), 3.56-3.72 (m, 4H), 6.99 (d, 1H), 7.14 (s, 1H), 7.24 (s, 1H), 8.45 (d, 1H) |

$^{(1)}$—$^t$Bu
$^{(2)}$—CO$_2$$^t$Bu

Biological Assays
Biological Reagents Prepared and Purified for S100A9 Related Assays
Recombinant Human S100A9 Wild Type
Cultivation:

Expression of rhS100A9 wt was performed by shake flask cultivations of the working cell bank BL21(DE3)/pET1120 (pLR757) with 0.25 mM IPTG induction. Cell pellets were frozen.

Purification of Inclusion Bodies:

The *E. coli* pellets were thawed at RT with 150 mL Lysis buffer (50 mM Tris/HCl, 1 mM EDTA, 25% Saccarose, pH 8.0) and sonicated 3×15 s under ice in a beaker. Thereafter 10 μL of 1 M MgCl$_2$ (10 mM end conc.)/mL pellet solution, 1 μL 1 M MnCl$_2$ (1 mM end conc.)/mL pellet solution and 1 μL 10 mg/mL DNase I (10 μg/mL end conc.)/mL pellet solution were added. After 30 min of incubation in RT a detergent buffer (20 mM Tris/HCl, pH 7.5, 2 mM EDTA, 1% Nonidet P-40) with protease inhibitor (Complete Mini Protease Inhibitors, Roche), 1-2 tablets/25 mL was added in a 1:1 volume ratio. The solution was centrifuged at 14,000×g, 5° C., for 20 min. The pellet was resuspended with 90 mL 0.5% Triton X-100, 1 mM EDTA for sonication 3×15 s and was spinned down again. This wash and sonication procedure was repeated for additionally 5 times.

Resuspension and Folding:

Milli-Q water was used in all solutions and dialysis steps. The final pellet was resuspended in 100 mL of 8 M urea, 40 mM DTT in 500 mM NaH$_2$PO$_4$ buffer, pH 1.8. When the solution was clear it was centrifuged at 20,000×g, 5° C. for 25 min. The supernatant containing the resuspended inclusion bodies was set to pH 2 with the 500 mM phosphate buffer, pH 1.8.

First dialysis of the supernatant was against 5 L 50 mM NaH$_2$PO$_4$ buffer, 1.5 mM DTT, pH 2 for 6 h. Second dialysis against 5 L 10 mM Na-acetate buffer, 150 mM NaCl, 1.5 mM DTT, pH 4 for 15 h. Third dialysis against 5 L 10 mM Na-acetate buffer, 150 mM NaCl, 1.5 mM DTT, pH 4 for 8 h. Fourth dialysis against 5 L 20 mM Tris/HCl, 150 mM NaCl, 1.5 mM DTT, pH 7.2 for 16 h. Fifth dialysis against 5 L 20 mM Tris/HCl, 1 mM EDTA, 1 mM EGTA, 1.5 mM DTT, pH 8.5 for 6 h. Centrifugation was done at 22,000×g, 5° C. for 30 min.

Purification by Chromatography:

All chromatography columns and resins were purchased from GE HealthCare, Sweden. DTT was added to a final concentration of 1.5 mM. An anion-exchange chromatography on a HiPrep Q FF 16/10 column was run at a flow-rate of 1.5 mL/min using a 0-1 M NaCl gradient in 20 mM Tris, 1 mM EDTA, 1 mM EGTA, 1.5 mM DTT, pH 8.5 for elution of proteins. The same buffer, without NaCl, was used for equilibration and washing before elution. The pooled fractions containing rhS100A9 wt were concentrated to 1.5 mL using Centriprep YM-3 (Amicon, USA).

The size-exclusion chromatography on a Superdex 75 16/790 column was run at a flow-rate of 0.5 mL/min using a HBS-N buffer (10 mM Hepes, 150 mM NaCl, pH 7.4) supplemented with 10 mM DTT. A PD-10 was run for buffer exchange to 10 mM Hepes, 150 mM NaCl, pH 7.5.

Biacore Binding Assays

The $Ca^{2+}$ and $Zn^{2+}$ dependent interaction of S100A9 with its putative target receptors—e.g. RAGE and TLR4—was studied using the surface plasmon resonance (SPR) technology (Björk et al. 2009). Briefly, S100A9 was injected over RAGE and TLR4, immobilized via primary amines on a Biacore sensor chip, in the presence of physiological concentrations of $Ca^{2+}$ and $Zn^{2+}$ allowing label-free and real-time analysis of these interactions. Obviously, the assay can be reversed in the way that S100A9 is immobilized and RAGE and TLR4 is injected. In FIG. 1, the assay for inhibitory effect on interaction between S100A9 and RAGE is illustrated—this assay is described in detail herein below. The person of ordinary skill in the art will be able to perform essentially the same assay directed to the interaction of S100A9 and TLR4.

Figure 2:
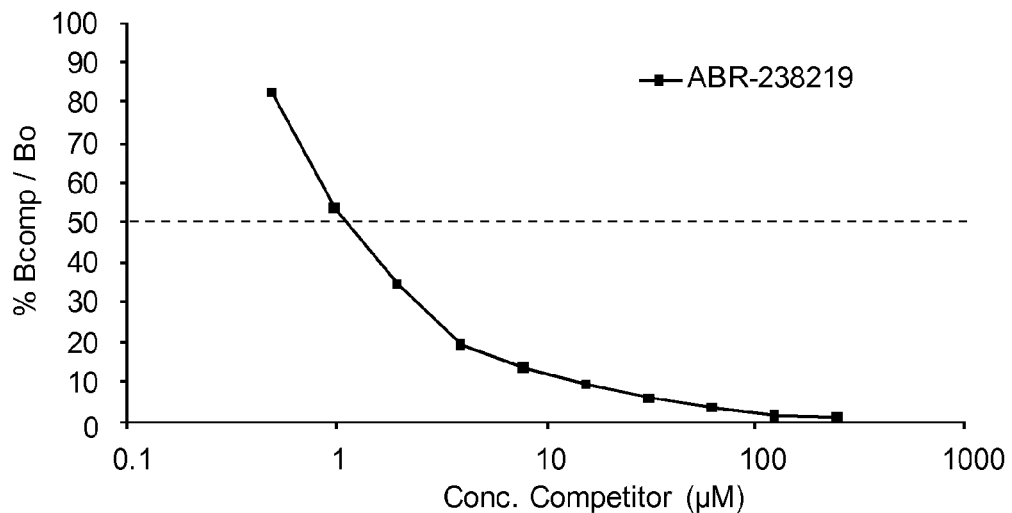
FIG. 2 is a graph showing the competitive binding of the compound of Example 13 (ABR 238219) to S100A9 in the presence of (A) RAGE and (B) TLR4. In the assay, S100A9 was injected (2 min; 30 μL/min) at ~1.3 μg/mL over amine coupled human RAGE/Fc (density ~4.2 kRU)) or TLR4 (density ~2900 Resonance units)±0.391-200 μM ABR-238219. The response (Y-axis), expressed as % S100A9 bound to (A) RAGE or (B) TLR4, was plotted versus competitor concentration and fit to a sigmoidal dose-response model. Assay buffer –10 mM HEPES, 0.15 M NaCl, pH 7.4 (HBS buffer), containing 0.005% v/v Surfactant P20, 1 mM $Ca^{2+}$ and 20 μM $Zn^{2+}$. After each cycle, regeneration was made by a 30 μL pulse of 3 mM EDTA in HBS buffer.
Figure 2:
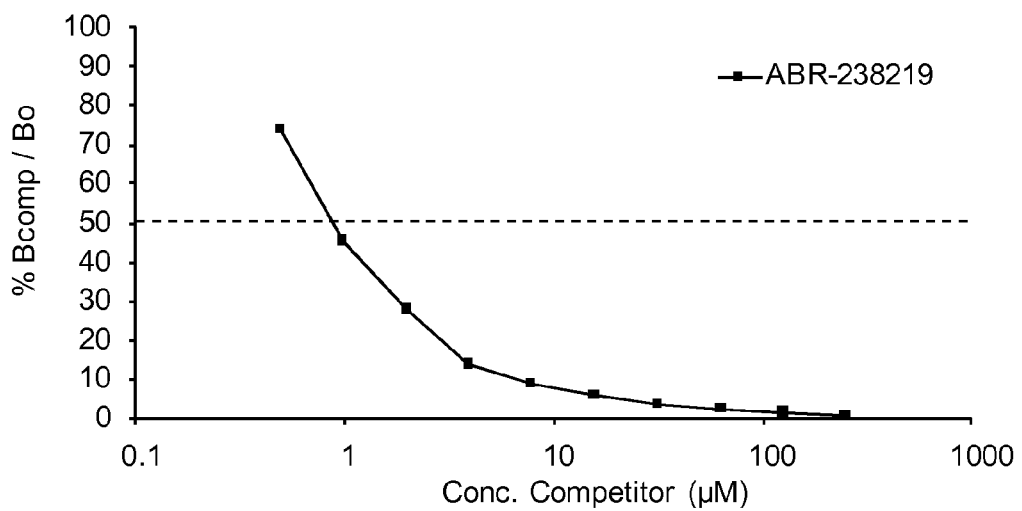

The assay showed the inhibitory effect of studied inventive compounds on protein-protein interactions between S100A9 and RAGE or TLR4, respectively, cf. FIG. 2.

Inhibition Assay, Biot-hS100A9:hRAGE-Fc

Principle.

The AlphaScreen (Amplified Luminescent Proximity Homogeneous Assay) contains two types of beads, Alpha Donor beads and Acceptor beads (PerkinElmer). Upon laser excitation at 680 nm a photosensitizer in the Donor bead converts ambient oxygen to a more excited singlet state. The singlet oxygen molecule diffuses (maximum 200 nm) to react with a thioxene derivative in the Acceptor bead and generates a chemiluminescence reaction. Fluorophores in the Acceptor bead subsequently emit light at 520-620 nm which can be detected in the EnVision® Multilabel plate Reader (PerkinElmer). The beads are light sensitive and all work with the beads is performed under subdued light conditions or using green filters on light sources (Roscolux Chroma Green #389, Rosco).

In the AlphaScreen Inhibition Assay described here, protein A (*Staphylococcus aureus*) conjugated Acceptor beads are used together with streptavidin coated Donor beads (Perkin Elmer 6760617M). The Acceptor beads are pre-incubated with Fc-tagged recombinant human RAGE (rhRAGE-Fc) allowing binding of the rhRAGE-Fc to protein A on the beads. Biotinylated human S100A9 (biot-hS100A9) is pre-incubated with the low molecular test compounds. The pre-mixes are then added to the wells of a micro-plate and incubated allowing interaction between biot-hS100A9 and rhRAGE-Fc. Subsequent addition of streptavidin coated Donor beads causes binding of the streptavidin to the biotinylated hS100A9. After an additional incubation the signal is measured.

Without inhibitory compounds, the interaction of biot-hS100A9 to rhRAGE-Fc will bring the Acceptor and Donor beads in close proximity thus generating a high signal. With an inhibitor present the complex will not form resulting in a decreased signal.

Chemicals and Reagents.

AlphaScreen® General IgG (Protein A) Detection Kit, (PerkinElmer 6760617M)
HBS-P buffer (GE Healthcare, BR-1003-68)
HBS-N buffer (GE Healthcare, BR-1003-69)
$CaCl_2$ in HBS-P
$ZnCl_2$ in Milli-Q water
DMSO
Biotinylated hS100A9, (biotinylated via cystein by EZ-link IA-$PEO_2$-Biotin reagent, Pierce Biotechnology), in HBS-N
rhRAGE-Fc (R&D Systems, 1145-RG-50), in HBS-P Procedure.

The AlphaScreen assay method is used for screening of the inhibitory effect of different compound samples at fixed concentrations or for IC50 determination by varying the compound concentrations. Samples of test compounds and references are prepared from solutions in DMSO. Relevant reference inhibitors and DMSO are used as controls for defined inhibition and non-inhibition, respectively in the assay. The percent inhibition in assay for test compounds and references are calculated by comparing their obtained assay signals with the signal values for the control with only DMSO (no compound).

Assay concentration of biotinylated hS100A9 and rhRAGE-Fc are batch dependent, and are determined and defined by separate cross-titration experiments using this AlphaScreen inhibition method to verify the optimal setup regarding signal strength and achievement of a defined inhibition with relevant reference compounds. The Final assay concentrations of Acceptor and Donor beads are 20 µg/mL.

Experimental Set Up for Screening, Preparation of Solutions and Beads.

Assay buffer is prepared by adding $CaCl_2$ and $ZnCl_2$ to HBS-P and is used freshly prepared in the experiment.

Biotin-hS100A9 solution for the experiment is prepared by dilution of appropriate amount of stock solution biot-hS100A9 in assay buffer (with $CaCl_2$ and $ZnCl_2$) and incubation in room temperature for 30 minutes.

rhRAGE-Fc solution for the experiment is prepared by dilution appropriate amount of rhRAGE-Fc stock in assay buffer.

Protein A Acceptor beads are diluted in assay buffer and are added to an equal volume of the prepared diluted rhRAGE-Fc solution. The beads are light sensitive. The vial is covered with aluminum foil and incubated at room temperature in the dark until biot-hS100A9+compound incubation is finished (see below).

Streptavidin-coated Donor beads are diluted in assay buffer. The beads are very light sensitive. The vial is covered with aluminum foil and incubated at room temperature in the dark until use (see below).

Dilution of Samples and Incubation with Biot-hS100A9

Samples of test compounds, appropriate references and DMSO control are diluted in assay buffer.

The diluted test compounds, references and DMSO control are added to wells on a Greiner micro titer 96 well plate (PP, u-bottom (no. 650201)) and appropriate amount of diluted biot-hS100A9 solution are added to each well with samples (final DMSO conc.≤1.25% (v/v)). The plate is covered with a plate seal and is incubated in the dark on an orbital plate shaker for 1 h at room temperature.

Incubation of Biot-hS100A9+Compound Samples and rhRAGE-Fc-Acceptor Beads in Optiplate When the biot-hS100A9+compound incubation is finished the solutions are transferred to Optiplate (Optiplate 384 white, Perkin Elmer no. 6007299) and rhRAGE-Fc-Acceptor bead solution is added to each well (use green filtered light). The plate is covered with a plate seal and incubated in the dark in a plate incubator at 25° C. nominally for 40 minutes.

Incubation of Biot-hS100A9+Compound Samples and rhRAGE-Fc-Acceptor and Donor Beads in Optiplate After incubation Donor bead solution is added to each well (use green filtered light). The plate is covered with a plate seal and incubated in the dark in a plate incubator at 25° C. nominally. After 50 minutes, the plate is incubated (in the dark) on the bench next to the EnVision® instrument for 10 minutes, for temperature equilibrium.

Reading of Optiplate in EnVision® Multilabel Plate Reader

The plate seal is removed and the plate is placed in the EnVision® for 5 minutes before reading.

Calculations.

Percent (%) inhibition for each sample (test compound or reference) is calculated using the formula: 1-(Signal sample/Signal DMSO)×100%.

The IC50 values for a number of compounds of the invention in the S100A9-RAGE inhibition assay are listed in Table 3

| Example | ABR | IC50 μM |
|---|---|---|
| 9 | 238789 | 10.2 |
| 10 | 238802 | 5.9 |
| 12 | 238895 | 3.0 |
| 13 | 238219 | 5.1 |
| 14 | 238786 | 3.5 |
| 15 | 238787 | 1.4 |
| 16 | 238908 | 1.3 |
| 18 | 239078 | 2.0 |
| 19 | 238854 | 0.4 |
| 20 | 238884 | 1.7 |
| 21 | 238950 | 4.0 |
| 27 | 238788 | 0.4 |
| 28 | 238911 | 3.7 |
| 29 | 238998 | 5.4 |
| 33 | 238804 | 3.0 |
| 35 | 238974 | 2.7 |
| 36 | 239059 | 3.7 |
| 37 | 239019 | 0.8 |
| 38 | 238949 | 1.0 |
| 39 | 238926 | 0.5 |
| 40 | 239424 | 3.3 |
| 41 | 239426 | 2.0 |
| 42 | 239136 | 2.0 |
| 44 | 239228 | 4.7 |
| 45 | 239229 | 3.0 |
| 46 | 239232 | 3.8 |
| 47 | 239257 | 3.9 |
| 49 | 239403 | 3.9 |
| 50 | 239137 | 2.3 |
| 51 | 239139 | 1.2 |
| 52 | 239404 | 0.7 |
| 53 | 239034 | 0.7 |
| 54 | 239114 | 1.6 |
| 55 | 239115 | 1.7 |
| 56 | 239414 | 1.4 |
| 57 | 239427 | 2.8 |
| 60 | 239358 | 4.0 |
| 61 | 239259 | 2.9 |
| 62 | 239356 | 1.1 |
| 64 | 239390 | 1.3 |
| 65 | 239391 | 2.2 |
| 66 | 239409 | 0.4 |
| 67 | 239101 | 2.0 |
| 69 | 239393 | 4.9 |
| 70 | 239355 | 1.3 |
| 71 | 239432 | 0.2 |
| 73 | 238925 | 2.8 |
| 74 | 238929 | 3.6 |
| 76 | 238927 | 11.4 |
| 77 | 239170 | 4.3 |
| 78 | 239320 | 1.2 |
| 79 | 239329 | 2.8 |
| 80 | 239330 | 7.4 |
| 81 | 239343 | 5.6 |
| 82 | 239371 | 1.4 |
| 83 | 239375 | 0.6 |
| 84 | 239394 | 1.4 |
| 85 | 239399 | 2.6 |
| 86 | 239422 | 6.4 |
| 88 | 239702 | 1.61 |
| 89 | 239679 | 5.90 |
| 91 | 239539 | 0.26 |
| 93 | 239587 | 0.60 |
| 94 | 239537 | 1.59 |
| 95 | 239572 | 1.08 |
| 97 | 239602 | 0.19 |
| 100 | 239453 | 2.02 |
| 103 | 239689 | 3.97 |
| 104 | 239705 | 4.02 |
| 111 | 239496 | 1.62 |
| 119 | 239655 | 1.82 |
| 122 | 239448 | 1.50 |
| 129 | 239577 | 2.26 |
| 139 | 239624 | 1.27 |
| 140 | 239586 | 1.45 |
| 144 | 239621 | 6.41 |
| 145 | 239666 | 3.12 |
| 146a | 239664 | 5.39 |
| 147b | 239623 | 3.44 |
| 160 | 239943 | 0.74 |
| 164 | 239991 | 1.47 |
| 165 | 239995 | 1.43 |
| 166 | 239996 | 0.40 |
| 177 | 239927 | 1.63 |
| 181 | 239916 | 1.45 |
| 182 | 239936 | 1.12 |
| 185 | 239941 | 0.84 |
| 186 | 239731 | 0.58 |
| 188 | 239944 | 0.94 |
| 189 | 239948 | 0.95 |
| 191 | 239954 | 1.49 |
| 193 | 239957 | 1.56 |
| 195 | 239967 | 1.27 |
| 198 | 239978 | 1.97 |
| 199 | 239990 | 0.92 |
| 201 | 240000 | 0.85 |
| 202 | 240001 | 0.70 |
| 203 | 240002 | 1.34 |
| 212a | 239968 | 0.61 |
| 212b | 239969 | 4.58 |
| 215a | 239997 | 1.44 |
| 215b | 239998 | 2.66 |
| 218a | 239071 | 3.13 |
| 218b | 239105 | 0.73 |
| 219a | 239396 | 0.94 |
| 219b | 239397 | 0.23 |
| 220a | 239662 | 1.93 |
| 220b | 239663 | 4.00 |
| 224a | 239727 | 0.88 |
| 224b | 239728 | 10.1 |
| 230a | 239984 | 0.26 |
| 230b | 239979 | 2.88 |
| 231a | 240007 | 0.66 |
| 231b | 240006 | 0.84 |
| 232 | 240016 | 0.54 |
| 233 | 240015 | 0.49 |
| 234 | 240013 | 0.92 |
| 237 | 240019 | 1.81 |

Assay for Cell Toxicity

Principle.

By the assay described in this method, both direct toxicity (24 h incubation) and anti-proliferative effect (72 hours incubation) are studied. After incubation of cells with different concentrations of test compounds, cell proliferation reagent is added. Then the formation of the formazan, produced by metabolically active cells, is measured by spectrophotometer.

Chemicals and Reagents.

Jurkat cells, DMSO, Cell Proliferation reagent (Roche Ref no. 11644807001).

Solutions.

R10 media=RPMI 1640 media supplemented with 10% Fetal calf serum, 5% Na-Pyruvate, Lonza, Belgium. Trypan blue solution 0.4%, Sigma. DMSO stock solutions of test compounds. DMSO stock solution of positive co for anti-proliferation. DMSO stock solution of negative control.

Procedure.

Jurkat cells are transferred to a 50 mL test tube. A small volume is diluted in trypan blue solution and the cells are counted. The cell concentration is adjusted to the final concentration of $0.2 \times 10^6$ cells/mL. The cells are seeded in 96-well flat bottomed sterile plates (10.000 cells/well) by adding the cell suspension to all wells except for a couple of wells where just R10 is added and no cells (blank).

The stock solutions are serial diluted in 96 well plates to concentrations within the interval 0.070-25 mM. The solutions in the DMSO dilution plates are then further diluted in R10 medium to get concentrations within the interval 0.28-200 µM The solution from the R10 dilution plates is added to the wells of the cell seeded plates, except to wells containing only R10. Final concentrations of the compounds are 0.14-10004 and final concentration of DMSO in the culture plates will be 0.2%, which is considered not to significantly affect the cell proliferation. Two identical plates will be prepared, one for 24 h incubation and one for 72 h incubation. The plates are incubated at 37° C., 5% CO2 and 90% Rh.

Measurements.

After 24 h incubation, 10 µL Cell proliferation Reagent/well is added to one of the two identical plates and the plates are then incubated (37° C., 5% CO2 and 90% Rh). After 2 h incubation the absorbance is measured at 450 nm in spectrophotometer. This procedure is repeated for the other plate after 72 h incubation.

Calculations.

The value of background is calculated. The absorbance measured for each concentration, including the control (wells with cells and no compound), are corrected for the background. For each concentration the corrected absorbance value is divided by the corrected absorbance value for the control and the values of "% of control" are plotted versus concentration. The IC50 value is then calculated.

In Vivo Model MC38/Mouse.

Figure 3:
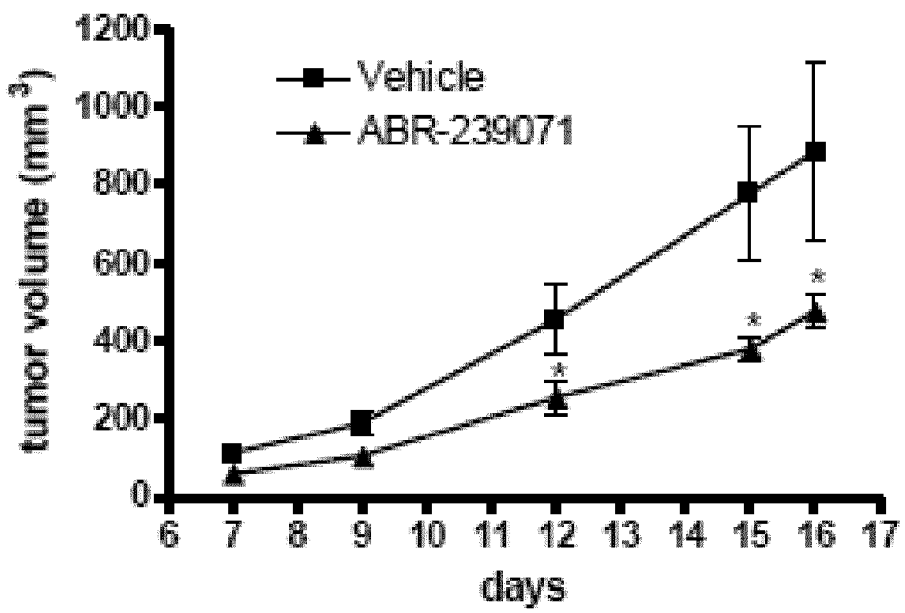
FIG. 3 is (A) a graph showing tumor growth followed by serial caliper measurements. Mice were inoculated with tumor cells s.c. and treatment with the compound of Example 118(a) (ABR 239071) was started the following day. Treatment (30 mg/kg) was given daily per orally. (A) Tumor growth was measured by serial caliper measurements; and (B) a bar chart showing tumor weight at endpoint (day 16). The differences in tumor growth and weight between treatment groups were statistically evaluated by non-parametric Mann-Whitney U test, *$p<0.05$. Error bars indicate SEM.
Figure 3:
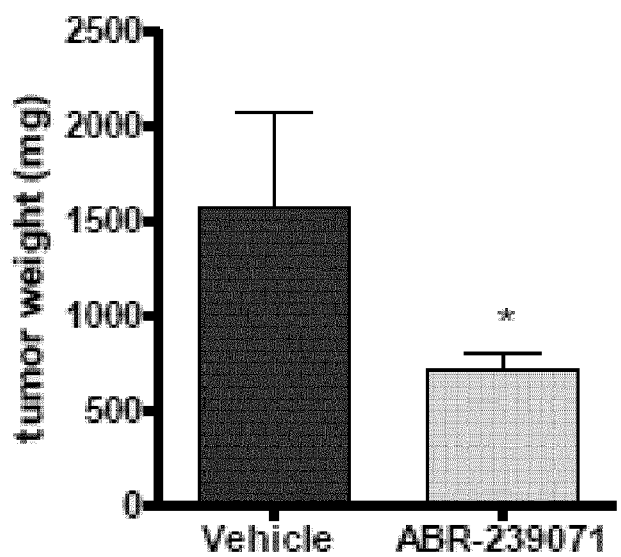

Female C57Bl/6 mice about seven weeks old were purchased. Before the onset of the studies the mice were acclimatized at the laboratory for at least one week. The mice were routinely used at the aged of 8 to 12 weeks. In all experiments a control group of mice was randomly selected. The control group was handled exactly as the treated group but not administrated with any drug compound. Provoking the tumor disease was made by subcutaneous injections with about 500 000 MC38-C215 cells in 100 µl matrigel (day 0). This cell line was C215-transfected murine MC38 colon adenocarcinoma cells which were cultured in R10 medium (RPMI-1640 with Ultraglutamine supplemented with 10% fetal bovine serum, 50 µM β-mercaptoethanol and 0.5 mg/ml G418 Sulfate). From day 7 the tumor growth was measured three times a week with a caliper and tumor volume was calculated. The tumor volume was calculated as $V = L \times W^2 \times 0.4$, where V is the volume (mm$^3$), L is the length (mm) and W is the width (mm) and L>or =W (Attia 1966). When tumors in the control group had reached a suitable size the experiment was completed and all the mice were sacrificed (usually on day 12-16) and the tumors were dissected out and the tumor mass was determined. In FIG. 3, the results obtained using the compound of Example 218a are shown.

Abbreviations Used aq aqueous
CHRM cryopreserved hepatocyte recovery medium
DCE 1,2-dichloroethane
DCM dichloromethane
DME dimethoxyethane
DMF N,N-dimethyl formamide
DMSO dimethyl sulfoxide
DMPU 1,3-dimethyltetrahydropyrimidin-2(1H)-one
dppf 1,1'-bis(diphenylphosphanyl) ferrocene
DTT dithiothreitol
EDC.HCl N-[3-(dimethylamino)propyl]-N'-ethylcarbodiimide hydrochloride (1:1)
EDTA ethylenediaminetetraacetic acid
EGTA ethylene glycol tetraacetic acid
EtOAc ethyl acetate
EtOH ethanol
FACS fluorescence-activated cell sorting
h hour(s)
HPLC high performance liquid chromatography
IPA propan-2-ol
IPTG isopropyl β-D-1-thiogalactopyranoside
KHB Krebs-Henseleit bicarbonate buffer
MeCN acetonitrile
MeOH methanol
min minute(s)
NaHMDS sodium bis(trimethylsilyl)amide
NBS 1-bromo-2,5-pyrrolidinedione
NMP 1-methylpyrrolidin-2-one
Ph phenyl
NMR nuclear magnetic resonance
PBS phosphate buffered saline
PBST phosphate buffered saline Tween-20
RT room temperature
SCX strong cation exchange
SFC supercritical fluid chromatography
SPhos dicyclohexyl(2',6'-dimethoxybiphenyl-2-yl)phosphane
tBu tert-butyl
TFA trifluoroacetic acid
THF tetrahydrofuran
TLC thin layer chromatography
wt weight

REFERENCES

Acharyya S et al., A CXCL1 paracrine network links cancer chemoresistance and metastasis. Cell 2012, 150(1), 165-7

Arai K et al., S100A8 and S100A9 overexpression is associated with poor pathological parameters in invasive ductal carcinoma of the breast. Curr Cancer Drug Targets 2008, 8(4): 243-52

Attia M, et al. (1966). Cancer Res., 26: 1787-1800

Bhardwaj R S et al., The calcium-binding proteins MRP8 and MRP14 form a membrane-associated heterodimer in a subset of monocytes/macrophages present in acute but absent in chronic inflammatory lesions. Eur J Immunol 1992, 22:1891-97

Björk P et al., Identification of human S100A9 as a novel target for treatment of autoimmune disease via binding to quinoline-3-carboxamides. PLoS Biol. 2009, 7(4):e97

Carta A et al., Design, synthesis, and preliminary in vitro and in silico antiviral activity of [4,7]phenantrolines and 1-oxo-1,4-dihydro-[4,7]phenantrolines against single-stranded positive-sense RNA genome viruses Bioorg. Med. Chem. (2007) 15:1914-1927

Chang K A et al., The role of S100a9 in the pathogenesis in Alzheimer's disease: the therapeutic effects of S100a9 knockdown or knockout. Neurodegener Dis 2012, 10(1-4):27-9

Chaudhari K et al., Novel and Facile Transformation of N,N-Disubstituted Glycylamides into Corresponding Cyanamides by Using Pentavalent Iodine Reagents in Combination with Tetraethylammonium Bromide. Synlett 2007, 18, 2815-2818

Cheng P et al., Inhibition of dendritic cell differentiation and accumulation of myeloid-derived suppressor cells in cancer is regulated by S100A9 protein. J Exp Med 2008, 205(10), 2235-49

Deane R et al., A multimodal RAGE-specific inhibitor reduces amyloid b-mediated brain disorder in a mouse model of Alzheimer disease. J Clin Invest 2013. 122(4): 1377-92

Foell D et al., S100 proteins in phagocytes: a novel group of damage-associated molecular pattern molecules. J Leukoc Biol 2007, 81:28-37

Foell D et al., Proinflammatory S100 proteins in arthritis and autoimmune disease. Arthritis Rheum 2004, 50, 3762-3771

Ghavami S et al., S100A8/S100A9 at low concentration promotes tumor cell growth via RAGE ligation and MAP kinase-dependent pathway. J Leukoc Biol 2008, 83(6), 1484-92

Ha T et al., S100a9 knockdown decreases the memory impairment and the neuropathology in Tg2576 mice, AD animal model. PLoS one 2010, 5(1):e8840

Hibino T et al., S100A9 is a novel ligand of EMMPRIN that promotes melanoma metastasis. Cancer Res 2012 November 7 Epub ahead of print Hiratsuka S et al., Tumour-mediated upregulation of chemoattractants and recruitment of myeloid cells predetermines lung metastasis. Nat Cell Biol. 8(12), 1369-75 (2006)

Int. Appl. No. PCT/US2007/020982 (Publ. No. WO2008042282)

Int. Appl. No. PCT/US2009/050797 (Publ. No. WO2010009290)

Int. Appl. No. PCT/US2008/003935 (Pub. No. WO2008118454)

Marenholz I et al., S100 proteins in mouse and man: from evolution to function and pathology (including an update of the nomenclature). BBRC 2004, 322:1111-22

Ryckman C et al., Proinflammatory activities of S100: proteins S100A8, S100A9, and S100A8/A9 induce neutrophil chemotaxis and adhesion J. Immunol. 170, 3233-42 (2003)

Shepherd C E et al., inflammatory S100A9 and S100A12 proteins in Alzheimers disease. Neurobiol Aging 2006, 27:1554-1563

Sinha P et al., Proinflammatory S100 proteins regulate the accumulation of myeloid-derived suppressor cells. J Immunol 2008, 181:4666-4675

Srikrishna G et al., S100A8 and S100A9: New insights into their roles in malignancy. J Innate Immun 2012, 4:31-40

Vogl T et al., Mrp8 and Mrp14 are endogenous activators of Toll-like receptor 4, promoting lethal, endotoxin-induced shock. Nat Med 2007, 13(9):1042-9

Wang L et al., Increased myeloid-derived suppressor cells in gastric cancer correlate with cancer stage and plasma S100A8/A9 proinflammatory proteins. J Immunol 2013, 190:794-804

You L et al., Silica gel accelerated aza-Michael addition of amines to α,β-unsaturated amides. Tetrahedron Lett. 2008, 49, 5147-5149

The invention claimed is:
1. A compound of formula (I)

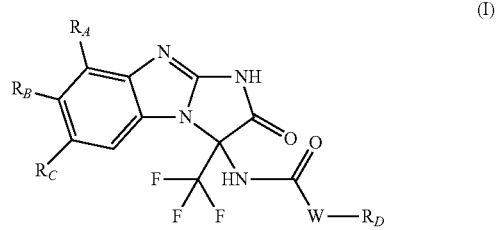

or a pharmaceutically acceptable salt thereof,
wherein $R_A$, $R_B$ and $R_C$ are independently selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$, or one of $R_A$ and $R_C$ together with $R_B$ forms a biradical —$(CH_2)_m$— wherein m is an integer of from 3 to 5, and the other one of $R_A$ and $R_C$ is selected from H, halogen, cyano, $R_1O$, C1-C6 alkyl optionally substituted by $R_1O$, C3-C6 cycloalkyl optionally substituted by $R_1O$, $R_2C(O)$, $R_3S$, $R_4S(O)_2$, $R_5OC(O)$, $(R_6ON)C(R_7)$, $R_8R_9NC(O)$, $R_{10}R_{11}N$, $R_{12}S(O)_2NR_{13}$, $R_{14}S(O)_2NR_{15}C(O)$, phenyl optionally substituted by one or more moieties $R_{16}$, and 5- or 6-membered heterocyclyl optionally substituted by one or more moieties $R_{16}$;

each $R_{16}$ is independently selected from halogen, cyano, nitro, $R_{17}O$, C1-C6 alkyl optionally substituted by $R_{17}O$, C3-C6 cycloalkyl optionally substituted by $R_{17}O$, $R_{18}C(O)$, $R_{19}S$, $R_{20}S(O)_2$, $R_{21}OC(O)$, $(R_{22}ON)C(R_{23})$, $R_{24}R_{25}NC(O)$, $R_{26}R_{27}N$, $R_{28}S(O)_2NR_{29}$, and $R_{30}S(O)_2NR_{31}C(O)$;

each one of $R_1$-$R_{31}$ is independently selected from H, C1-C6 alkyl, and C3-C6 cycloalkyl;

W is a direct bond or $X_1$—$X_2$—$X_3$;

$X_1$ is C1-C2 alkylene, optionally substituted by C1-C4 alkyl or $R_{32}O$;

$X_2$ is O or is absent;

$X_3$ is a direct bond or C1-C2 alkylene, optionally substituted by C1-C4 alkyl or $R_{32}O$;

$R_{32}$ is selected from H and C1-C4 alkyl;

$R_D$ is C1-C6 alkyl, or a cyclic moiety selected from phenyl, 4- to 6-membered heterocyclyl, and C4-C6 cycloalkyl, wherein said cyclic moiety is optionally substituted by one or more $R_{33}$;

each $R_{33}$ is independently selected from halogen, cyano, C1-C6 alkyl optionally substituted by $R_{34}O$, C3-C6 cycloalkyl, phenyl, 5- or 6-membered heterocyclyl, $R_{34}O$, $R_{35}OC(O)$, $R_{36}S(O)_2$, $R_{37}C(O)$, $R_{38}R_{39}N$, $R_{40}R_{41}N(CO)$, or two $R_{33}$, attached to one and the same carbon atom may form, together with the carbon atom to which they are both attached, a 4- to 6-membered ring optionally containing one more heteroatoms in the ring;

$R_{34}$ is independently selected from H, C1-C6 alkyl, and C3-C6 cycloalkyl; wherein said alkyl or cycloalkyl is optionally substituted by $R_{42}O$;

each one of $R_{35}$-$R_{36}$ is independently selected from H, C1-C6 alkyl, and C3-C6 cycloalkyl;

$R_{37}$ is independently selected from C1-C6 alkyl, and C3-C6 cycloalkyl, wherein said alkyl or cycloalkyl is optionally substituted by $R_{43}O$;

$R_{38}$ and $R_{39}$ are independently selected from H, C1-C6 alkyl, and C3-C6 cycloalkyl, wherein said alkyl or cycloalkyl is optionally substituted by $R_{44}R_{45}N$ or $R_{46}O$, or $R_{38}$ and $R_{39}$ together with the nitrogen atom to which they are both attached, form a 4- to 6-membered heterocyclic ring optionally containing one or more further heteroatoms and optionally substituted by C1-C6 alkyl;

$R_{40}$ and $R_{41}$ are independently selected from H, C1-C6 alkyl, and C3-C6 cycloalkyl, wherein said alkyl or cycloalkyl is optionally substituted by $R_{47}R_{48}N$ or $R_{49}O$, or $R_{40}$ and $R_{41}$ together with the nitrogen atom to which they are both attached, form a 4- to 6-membered heterocyclic ring optionally containing one or more further heteroatoms and optionally substituted by C1-C6 alkyl;

$R_{44}$ and $R_{45}$ are independently selected from H, C1-C6 alkyl, and C3-C6 cycloalkyl, or $R_{44}$ and $R_{45}$ together with the nitrogen atom to which they are both attached, form a 4- to 6-membered saturated heterocyclic ring optionally containing one or more further heteroatoms and optionally substituted by C1-C6 alkyl;

$R_{47}$ and $R_{48}$ are independently selected from H, C1-C6 alkyl, and C3-C6 cycloalkyl, or $R_{47}$ and $R_{48}$ together with the nitrogen atom to which they are both attached, form a 4- to 6-membered saturated heterocyclic ring optionally containing one or more further heteroatoms and optionally substituted by C1-C6 alkyl;

$R_{42}$, $R_{43}$, $R_{46}$ and $R_{49}$ are independently selected from H, C1-C6 alkyl, and C3-C6 cycloalkyl; and any alkyl is optionally substituted by one or more F.

2. The compound of claim 1, or a pharmaceutically acceptable salt thereof, wherein $R_D$ is a cyclic moiety selected from phenyl, 4- to 6-membered heterocyclyl, and C4-C6 cycloalkyl, wherein said cyclic moiety is optionally substituted by one or more $R_{33}$.

3. The compound of claim 1, or a pharmaceutically acceptable salt thereof, wherein $R_D$ is a cyclic moiety selected from 4- to 6-membered heterocyclyl, wherein said cyclic moiety is optionally substituted by one or more $R_{33}$.

4. The compound of claim 1, or a pharmaceutically acceptable salt thereof, wherein $R_D$ is a cyclic moiety selected from 5- or 6-membered heteroaryl, wherein said cyclic moiety is optionally substituted by one or more $R_{33}$.

5. The compound of claim 1, or a pharmaceutically acceptable salt thereof, wherein $R_D$ is a cyclic moiety selected from C4-C6 cycloalkyl, wherein said cyclic moiety is optionally substituted by one or more $R_{33}$.

6. The compound of claim 1, or a pharmaceutically acceptable salt thereof, wherein $R_D$ is phenyl optionally substituted by one or more $R_{33}$.

7. The compound of claim 1, or a pharmaceutically acceptable salt thereof, wherein $R_A$, $R_B$ and $R_C$ are independently selected from H, halogen, C1-C4 alkyl and $R_2C(O)$.

8. The compound of claim 1, or a pharmaceutically acceptable salt thereof, wherein one of $R_A$, $R_B$ and $R_C$ is phenyl optionally substituted by one or more moieties $R_{16}$, or 5- or 6-membered heterocyclyl optionally substituted by one or more moieties $R_{16}$, and the two others of $R_A$, $R_B$ and $R_C$ are independently selected from H, halogen, and C1-C4 alkyl.

9. The compound of claim 1, or a pharmaceutically acceptable salt thereof, wherein W is a direct bond.

10. The compound of claim 1, or a pharmaceutically acceptable salt thereof, wherein W is X1-X2-X3.

11. A compound according to claim 1, selected from 6-chloro-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-pyridine-2-carboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-6-fluoropyridine-2-carboxamide;

N-[4-oxo-3-(trifluoromethyl)-2,5,7-triazatricyclo-[6.4.0.0$^{2,6}$]dodeca-1(12),6,8,10-tetraen-3-yl]-benzamide;

2-cyclohexyl-N-[4-oxo-3-(trifluoromethyl)-2,5,7-triazatricyclo[6.4.0.0$^{2,6}$]dodeca-1(12),6,8,10-tetraen-3-yl]-acetamide;

3-(morpholin-4-yl)-N-[4-oxo-3-(trifluoromethyl)-2,5,7-tri-azatricyclo[6.4.0.0$^{2,6}$]dodeca-1(12),6,8,10-tetraen-3-yl]-propanamide;

N-[4-oxo-3-(trifluoromethyl)-2,5,7-triazatricyclo-[6.4.0.0$^{2,6}$]dodeca-1(12),6,8,10-tetraen-3-yl]-3-(pyrrolidin-1-yl)propanamide;

3-(oxan-4-yl)-N-[4-oxo-3-(trifluoromethyl)-2,5,7-triazatricyclo[6.4.0.0$^{2,6}$]dodeca-1(12),6,8,10-tetraen-3-yl]-propanamide;

2-bromo-N-[3-oxo-4-(tri-fluoromethyl)-2,5,7-triaza-tricyclo[6.4.0.0$^{2,6}$]dodeca-1(12),6,8,10-tetraen-4-yl]-benzamide;

3-cyclopentyl-N-[4-oxo-3-(trifluoromethyl)-2,5,7-triaza-tricyclo[6.4.0.0$^{2,6}$]dodeca-1(8),6,9,11-tetraen-3-yl]-propanamide;

3,5-dimethoxy-N-[3-oxo-4-(trifluoromethyl)-2,5,7-tri-azatricyclo[6.4.0.0$^{2,6}$]dodeca-1(12),6,8,10-tetraen-4-yl]-benzamide;

6-methyl-N-[3-oxo-4-(tri-fluoromethyl)-2,5,7-triaza-tricyclo[6.4.0.0$^{2,6}$]dodeca-1(12),6,8,10-tetraen-4-yl]-pyridine-3-carboxamide;

3,5-dichloro-N-[4-oxo-3-(tri-fluoromethyl)-2,5,7-triaza-tricyclo[6.4.0.0$^{2,6}$]dodeca-1(12),6,8,10-tetraen-3-yl]-benzamide;

3-cyclohexyl-N-[3-oxo-4-(trifluoromethyl)-2,5,7-tri-aza-tricyclo[6.4.0.0$^{2,6}$]dodeca-1(12),6,8,10-tetraen-4-yl]-propanamide;

N-[10,11-dimethyl-4-oxo-3-(trifluoromethyl)-2,5,7-tri-azatricyclo[6.4.0.0$^{2,6}$]dodeca-1(8),6,9,11-tetraen-3-yl]-benzamide;

N-[10,11-dimethyl-4-oxo-3-(trifluoromethyl)-2,5,7-tri-azatricyclo[6.4.0.0$^{2,6}$]dodeca-1(8),6,9,11-tetraen-3-yl]-3-phenylpropanamide;

3-(2-chlorophenyl)-N-[10,11-dimethyl-4-oxo-3-(trif-luoro-methyl)-2,5,7-triazatricyclo-[6.4.0.0$^{2,6}$]dodeca-1(8),6,9,11-tetraen-3-yl]-propanamide;

3,5-dichloro-N-[10,11-dimethyl-4-oxo-3-(trifluoro-methyl)-2,5,7-triazatricyclo-[6.4.0.0$^{2,6}$]dodeca-1(8),6,9,11-tetraen-3-yl]benzamide;

N-[10,11-dimethyl-4-oxo-3-(trifluoromethyl)-2,5,7-tri-azatricyclo[6.4.0.0$^{2,6}$]dodeca-1(8),6,9,11-tetraen-3-yl]-4-phenylbenzamide;

4-cyclopentyl-N-[10,11-dimethyl-4-oxo-3-(trifluoro-methyl)-2,5,7-triazatricyclo-[6.4.0.0$^{2,6}$]dodeca-1(8),6,9,11-tetraen-3-yl]-butanamide;

2-cyclohexyl-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-acetamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-6-(2,2,2-trifluoroethoxy)-pyridine-3-carboxamide;

1-cyclopentanecarbonyl-N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-pyrrolidine-3-carboxamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-3-(morpholin-4-yl)propanamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-pyrrolidine-3-carboxamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-piperidine-4-carboxamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-1-(2-methoxyacetyl)-piperidine-4-carboxamide;

3-cyclopentyl-N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-propanamide;

6-chloro-N-[10,11-dimethyl-4-oxo-3-(trifluoromethyl)-2,5,7-triazatricyclo-[6.4.0.0$^{2,6}$]dodeca-1(12),6,8,10-tetraen-3-yl]-pyridine-3-carboxamide;

3-(2,6-dichlorophenyl)-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-propanamide;

2-bromo-N-[10,11-dimethyl-4-oxo-3-(trifluoromethyl)-2,5,7-triazatricyclo-[6.4.0.0$^{2,6}$]dodeca-1(8),6,9,11-tetraen-3-yl]-benzamide;

6-(cyclohexylamino)-N-[10,11-dimethyl-4-oxo-3-(trifluoromethyl)-2,5,7-tri-azatricyclo[6.4.0.0$^{2,6}$]dodeca-1(12),6,8,10-tetraen-3-yl]-pyridine-3-carboxamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-6-methylpyridine-3-carboxamide;

3-cyclohexyl-N-[10,11-dimethyl-3-oxo-4-(trifluoromethyl)-2,5,7-triazatricyclo-[6.4.0.0$^{2,6}$]dodeca-1(12),6,8,10-tetraen-4-yl]-propanamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(pyridin-3-yl)propanamide;

6-(cyclohexylamino)-N-[10,11-dimethyl-4-oxo-3-(trifluoromethyl)-2,5,7-tri-azatricyclo[6.4.0.0$^{2,6}$]dodeca-1(12),6,8,10-tetraen-3-yl]pyridine-2-carboxamide;

6-cyclohexyl-N-[10,11-dimethyl-4-oxo-3-(trifluoromethyl)-2,5,7-triazatricyclo-[6.4.0.0$^{2,6}$]dodeca-1(12),6,8,10-tetraen-3-yl]-pyridine-2-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-3-phenylpropanamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-benzamide;

3-cyclopentyl-N-[10,11-di-chloro-4-oxo-3-(trifluoromethyl)-2,5,7-triazatricyclo-[6.4.0.0$^{2,6}$]dodeca-1(12),6,8,10-tetraen-3-yl]-propanamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-2-azaspiro[3.3]heptane-6-carboxamide;

(2S)—N-[10,11-dichloro-4-oxo-3-(trifluoromethyl)-2,5,7-triazatricyclo-[6.4.0.0$^{2,6}$]dodeca-1(12),6,8,10-tetraen-3-yl]pyrrolidine-2-carboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-pyrrolidine-3-carboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-piperidine-4-carboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(2-methoxyacetyl)-piperidine-4-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-1-(3-methylbutanoyl)-piperidine-4-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-1-(3,3,3-trifluoropropanoyl)-piperidine-4-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-azetidine-3-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-1-(ethanesulfonyl)azetidine-3-carboxamide;

1-acetyl-N-[10,11-dichloro-4-oxo-3-(trifluoromethyl)-2,5,7-triazatricyclo-[6.4.0.0$^{2,6}$]dodeca-1(12),6,8,10-tetraen-3-yl]-azetidine-3-carboxamide;

1-cyclopentanecarbonyl-N-[10,11-dichloro-4-oxo-3-(trifluoromethyl)-2,5,7-triaza-tricyclo[6.4.0.0$^{2,6}$]dodeca-1(12),6,8,10-tetraen-3-yl]-pyrrolidine-3-carboxamide;

(3R)-1-(cyclopentane-sulfonyl)-N-[10,11-dichloro-4-oxo-3-(trifluoromethyl)-2,5,7-triazatricyclo-[6.4.0.0$^{2,6}$]dodeca-1(12),6,8,10-tetraen-3-yl]-pyrrolidine-3-carboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(pyridin-2-yl)azetidine-3-carboxamide;

3-cyclohexyl-N-[10,11-dichloro-4-oxo-3-(trifluoromethyl)-2,5,7-triazatricyclo-[6.4.0.0$^{2,6}$]dodeca-1(12),6,8,10-tetraen-3-yl]-propanamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-cyclopentanecarboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-cyclohexanecarboxamide;

3-chloro-N-[10,11-dichloro-4-oxo-3-(trifluoromethyl)-2,5,7-triazatricyclo-[6.4.0.0$^{2,6}$]dodeca-1(12),6,8,10-tetraen-3-yl]-benzamide;

3,5-dichloro-N-[10,11-di-chloro-4-oxo-3-(trifluoromethyl)-2,5,7-triaza-tricyclo[6.4.0.0$^{2,6}$]dodeca-1(12),6,8,10-tetraen-3-yl]-benzamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-4-(pyrrolidin-1-yl)butanamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-4-(morpholin-4-yl)butanamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-2-(morpholin-4-yl)acetamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-3-(morpholin-4-yl)propanamide;

6-chloro-N-[10,11-dichloro-4-oxo-3-(trifluoromethyl)-2,5,7-triazatricyclo-[6.4.0.0$^{2,6}$]dodeca-1(12),6,8,10-tetraen-3-yl]-pyridine-2-carboxamide;

6-(azetidin-1-yl)-N-[10,11-dichloro-4-oxo-3-(trifluoromethyl)-2,5,7-triazatricyclo-[6.4.0.0$^{2,6}$]dodeca-1(12),6,8,10-tetraen-3-yl]-pyridine-2-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-6-(2,2,2-trifluoroethoxy)-pyridine-2-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-6-(dimethylamino)pyridine-2-carboxamide;

6-(cyclohexylamino)-N-[10,11-dichloro-4-oxo-3-(trifluoromethyl)-2,5,7-triaza-tricyclo[6.4.0.0$^{2,6}$]dodeca-1(12),6,8,10-tetraen-3-yl]-pyridine-2-carboxamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-6-(ethylamino)pyridine-2-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-2-(piperidin-4-yl)acetamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-3-(piperidin-2-yl)propanamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-6-(ethylamino)pyridine-2-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-6-[(2-methoxyethyl)amino]-pyridine-2-carboxamide;

N-[10,11-difluoro-4-oxo-3-(trifluoromethyl)-2,5,7-triazatricyclo[6.4.0.0$^{2,6}$]dodeca-1(12),6,8,10-tetraen-3-yl]-benzamide;

3-cyclopentyl-N-[10,11-difluoro-4-oxo-3-(trifluoromethyl)-2,5,7-triazatricyclo-[6.4.0.0$^{2,6}$]dodeca-1(12),6,8,10-tetraen-3-yl]-propanamide;

2-cyclohexyl-N-[10,11-difluoro-4-oxo-3-(trifluoromethyl)-2,5,7-triazatricyclo-[6.4.0.0$^{2,6}$]dodeca-1(8),6,9,11-tetraen-3-yl]-acetamide;

N-[10,11-dimethoxy-4-oxo-3-(trifluoromethyl)-2,5,7-triaza-tricyclo[6.4.0.0$^{2,6}$]dodeca-1(12),6,8,10-tetraen-3-yl]-benzamide;

3-cyclopentyl-N-[10,11-dimethoxy-4-oxo-3-(trifluoromethyl)-2,5,7-triaza-tricyclo[6.4.0.0$^{2,6}$]dodeca-1(12),6,8,10-tetraen-3-yl]-propanamide;

N-[9-bromo-10,11-dimethyl-4-oxo-3-(trifluoromethyl)-2,5,7-triazatricyclo-[6.4.0.0$^{2,6}$]dodeca-1(8),6,9,11-tetraen-3-yl]-benzamide;

3-cyclopentyl-N-[12-oxo-11-(trifluoromethyl)-10,13,15-triazatetracyclo-[7.6.0.0$^{3,7}$.0$^{10,14}$]pentadeca-1(9),2,7,14-tetraen-11-yl]-propanamide;

N-[10-chloro-4-oxo-3-(tri-fluoromethyl)-2,5,7-triaza-tricyclo[6.4.0.0$^{2,6}$]dodeca-1(12),6,8,10-tetraen-3-yl]-3-cyclopentylpropanamide;

N-[11-chloro-4-oxo-3-(tri-fluoromethyl)-2,5,7-triaza-tricyclo[6.4.0.0$^{2,6}$]dodeca-1(12),6,8,10-tetraen-3-yl]-3-cyclopentylpropanamide;

3-cyclopentyl-N-[9,10-dimethyl-4-oxo-3-(trifluoromethyl)-2,5,7-triazatricyclo-[6.4.0.0$^{2,6}$]dodeca-1(12),6,8,10-tetraen-3-yl]-propanamide;

3-cyclopentyl-N-[9-methyl-4-oxo-3-(trifluoromethyl)-2,5,7-triazatricyclo-[6.4.0.0$^{2,6}$]dodeca-1(12),6,8,10-tetraen-3-yl]-propanamide;

3-cyclopentyl-N-[9,10-difluoro-4-oxo-3-(trifluoromethyl)-2,5,7-triazatricyclo-[6.4.0.0$^{2,6}$]dodeca-1(12),6,8,10-tetraen-3-yl]-propanamide;

3-cyclopentyl-N-[9,10-di-chloro-4-oxo-3-(trifluoromethyl)-2,5,7-triazatricyclo-[6.4.0.0$^{2,6}$]dodeca-1(12),6,8,10-tetraen-3-yl]-propanamide;

3-cyclopentyl-N-[9,11-di-chloro-4-oxo-3-(trifluoromethyl)-2,5,7-triazatricyclo-[6.4.0.0$^{2,6}$]dodeca-1(12),6,8,10-tetraen-3-yl]-propanamide;

N-[9-chloro-4-oxo-3-(tri-fluoromethyl)-2,5,7-triaza-tricyclo[6.4.0.0$^{2,6}$]dodeca-1(12),6,8,10-tetraen-3-yl]-3-cyclopentylpropanamide;

3-cyclopentyl-N-[9,11-di-fluoro-4-oxo-3-(trifluoromethyl)-2,5,7-triazatricyclo-[6.4.0.0$^{2,6}$]dodeca-1(12),6,8,10-tetraen-3-yl]-propanamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]oxane-4-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-3-(1-hydroxycyclopentyl)propan-amide;

(2S)—N-[10,11-dimethyl-4-oxo-3-(trifluoro-methyl)-2,5,7-triazatricyclo-[6.4.0.0$^{2,6}$]dodeca-1(8),6,9,11-tetraen-3-yl]-1-methane-sulfonylpyrrolidine-2-carboxamide;

N-[10,11-dichloro-4-oxo-3-(trifluoromethyl)-2,5,7-triazatricyclo[6.4.0.0$^{2,6}$]dodeca-1(8),6,9,11-tetraen-3-yl]-6-[(3-methoxypropyl)-amino]-pyridine-2-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-6-[(2-hydroxyethyl)amino]pyridine-2-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-6-{[(2S)-1-methoxypropan-2-yl]amino}pyridine-2-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-6-{[2-(dimethylamino)-ethyl]amino}-pyridine-2-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-6-[(2-methoxyethyl)(methyl)amino]-pyridine-2-carboxamide;

methyl 6-{[10,11-dichloro-4-oxo-3-(trifluoromethyl)-2,5,7-triazatricyclo[6.4.0.0$^{2,6}$]-dodeca-1(8),6,9,11-tetraen-3-yl]carbamoyl}pyridine-2-carboxylate;

2-N-[10,11-dichloro-4-oxo-3-(trifluoromethyl)-2,5,7-triazatricyclo[6.4.0.0$^{2,6}$]dodeca-1(8),6,9,11-tetraen-3-yl]-6-N-(2-methoxyethyl)pyridine-2,6-dicarboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-6-(hydroxymethyl)pyridine-2-carboxamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-3-fluorobenzamide;

N-[10,11-dichloro-4-oxo-3-(trifluoromethyl)-2,5,7-triaza-tricyclo[6.4.0.0$^{2,6}$]dodeca-1(12),6,8,10-tetraen-3-yl]-3,5-difluorobenzamide;

3-cyano-N-[10,11-dichloro-4-oxo-3-(trifluoromethyl)-2,5,7-triazatricyclo[6.4.0.0$^{2,6}$]-dodeca-1(8),6,9,11-tetraen-3-yl]benzamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-2-[(2-methoxyethyl)amino]-1,3-thiazole-4-carboxamide;

N-[10,11-dichloro-4-oxo-3-(trifluoromethyl)-2,5,7-triazatricyclo[6.4.0.0$^{2,6}$]dodeca-1(12),6,8,10-tetraen-3-yl]-1-(2,2-difluoroethyl)azetidine-3-carboxamide;

N-[10,11-dichloro-4-oxo-3-(trifluoromethyl)-2,5,7-triazatricyclo[6.4.0.0$^{2,6}$]dodeca-1(8),6,9,11-tetraen-3-yl]-3-fluoroazetidine-3-carboxamide;

N-[10,11-dichloro-4-oxo-3-(trifluoromethyl)-2,5,7-triaza-tricyclo[6.4.0.0$^{2,6}$]dodeca-1(8),6,9,11-tetraen-3-yl]-3-(3,3-difluoroazetidin-1-yl)-propanamide;

3-(3,3-difluoroazetidin-1-yl)-N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-propanamide;

3-cyclobutyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]propanamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-3-(1-hydroxycyclopentyl)propan-amide;

2-cyclopentyl-N-[10,11-dimethyl-4-oxo-3-(trifluoromethyl)-2,5,7-triazatricyclo-[6.4.0.0$^{2,6}$]dodeca-1(8),6,9,11-tetraen-3-yl]acetamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-3,5-difluorobenzamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-6-fluoropyridine-2-carboxamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-6-[(2-methoxyethyl)amino]pyridine-2-carboxamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-2-phenylacetamide;

2-(3,5-dichlorophenyl)-N-[10,11-dimethyl-4-oxo-3-(trifluoromethyl)-2,5,7-triazatricyclo[6.4.0.0$^{2,6}$]dodeca-1(8),6,9,11-tetraen-3-yl]acetamide;

N-[10,11-dimethyl-4-oxo-3-(trifluoromethyl)-2,5,7-triaza-tricyclo[6.4.0.0$^{2,6}$]dodeca-1(12),6,8,10-tetraen-3-yl]-3-(3,4,5-trimethoxyphenyl)-propanamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-3-methanesulfonylbenzamide;

3-bromo-N-[10,11-dimethyl-4-oxo-3-(trifluoromethyl)-2,5,7-triazatricyclo[6.4.0.0$^{2,6}$]dodeca-1(8),6,9,11-tetraen-3-yl]benzamide;

N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-3-[(2-methoxyethyl)amino]benzamide;

2-bromo-N-[10,11-dimethyl-4-oxo-3-(trifluoromethyl)-2,5,7-triazatricyclo[6.4.0.0$^{2,6}$]dodeca-1(8),6,9,11-tetraen-3-yl]-1,3-thiazole-4-carboxamide;

N-[10,11-dimethyl-4-oxo-3-(trifluoromethyl)-2,5,7-triazatricyclo[6.4.0.0$^{2,6}$]dodeca-1(8),6,9,11-tetraen-3-yl]-2-[(2-methoxyethyl)amino]-1,3-thiazole-4-carboxamide;

N-[9-bromo-4-oxo-3-(trifluoro-methyl)-2,5,7-triazatricyclo-[6.4.0.0$^{2,6}$]dodeca-1(12),6,8,10-tetraen-3-yl]-3-cyclopentyl-propanamide;

N-[9-cyano-4-oxo-3-(trifluoromethyl)-2,5,7-triazatricyclo-[6.4.0.0$^{2,6}$]-dodeca-1(12),6,8,10-tetraen-3-yl]-3-cyclopentylpropanamide;

N-[9-acetyl-4-oxo-3-(trifluoro-methyl)-2,5,7-triazatricyclo-[6.4.0.0$^{2,6}$]dodeca-1(12),6,8,10-tetraen-3-yl]-3-cyclopentyl-propanamide;

N-[10-chloro-9-cyano-4-oxo-3-(trifluoromethyl)-2,5,7-triaza-tricyclo[6.4.0.0$^{2,6}$]dodeca-1(12),6,8,10-tetraen-3-yl]-3-cyclopentylpropanamide;

3-cyclopentyl-N-[9-fluoro-4-oxo-3-(trifluoromethyl)-2,5,7-triazatricyclo[6.4.0.0$^{2,6}$]-dodeca-1(12),6,8,10-tetraen-3-yl]propanamide;

3-cyclopentyl-N-[9,11-dimethyl-4-oxo-3-(trifluoromethyl)-2,5,7-triazatricyclo-[6.4.0.0$^{2,6}$]dodeca-1(12),6,8,10-tetraen-3-yl]propanamide;

N-[9-chloro-10-fluoro-4-oxo-3-(trifluoromethyl)-2,5,7-triaza-tricyclo[6.4.0.0$^{2,6}$]dodeca-1(12),6,8,10-tetraen-3-yl]-3-cyclopentylpropanamide;

N-[10-chloro-9-methyl-4-oxo-3-(trifluoromethyl)-2,5,7-triazatricyclo[6.4.0.0$^{2,6}$]-dodeca-1(12),6,8,10-tetraen-3-yl]-3-cyclopentylpropanamide;

3-cyclopentyl-N-[4-oxo-3,9-bis(trifluoromethyl)-2,5,7-triazatricyclo[6.4.0.0$^{2,6}$]-dodeca-1(8),6,9,11-tetraen-3-yl]propanamide;

N-[11-bromo-4-oxo-3,9-bis(trifluoromethyl)-2,5,7-triaza-tricyclo[6.4.0.0$^{2,6}$]dodeca-1(8),6,9,11-tetraen-3-yl]-3-cyclopentylpropanamide;

N-[10-chloro-9-fluoro-4-oxo-3-(trifluoromethyl)-2,5,7-triaza-tricyclo[6.4.0.0$^{2,6}$]dodeca-1(12),6,8,10-tetraen-3-yl]-3-cyclopentylpropanamide;

3-cyclopentyl-N-[9-fluoro-10-methoxy-4-oxo-3-(trifluoro-methyl)-2,5,7-triazatricyclo-[6.4.0.0$^{2,6}$]dodeca-1(12),6,8,10-tetraen-3-yl]propanamide;

3-cyclopentyl-N-[9-(methyl-sulfanyl)-4-oxo-3-(trifluoromethyl)-2,5,7-triazatricyclo-[6.4.0.0$^{2,6}$]dodeca-1(12),6,8,10-tetraen-3-yl]propanamide;

3-cyclopentyl-N-[9-methane-sulfonyl-4-oxo-3-(trifluoromethyl)-2,5,7-triazatricyclo-[6.4.0.0$^{2,6}$]dodeca-1(12),6,8,10-tetraen-3-yl]propanamide;

N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[9,10-dichloro-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide;

N-[9,10-dichloro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]-pyridine-2-carboxamide;

N-[10-chloro-9-cyano-4-oxo-3-(trifluoromethyl)-2,5,7-triaza-tricyclo[6.4.0.0$^{2,6}$]dodeca-1(8),6,9,11-tetraen-3-yl]-6-fluoropyridine-2-carboxamide;

N-[10-chloro-9-cyano-4-oxo-3-(trifluoromethyl)-2,5,7-triaza-tricyclo[6.4.0.0$^{2,6}$]dodeca-1(8),6,9,11-tetraen-3-yl]-6-[(2-methoxyethyl)amino]-pyridine-2-carboxamide;

N-[10-chloro-9-cyano-4-oxo-3-(trifluoromethyl)-2,5,7-triaza-tricyclo[6.4.0.0$^{2,6}$]dodeca-1(8),6,9,11-tetraen-3-yl]-2-[(2-methoxyethyl)amino]-1,3-thiazole-4-carboxamide;

N-[10-chloro-9-cyano-4-oxo-3-(trifluoromethyl)-2,5,7-triaza-tricyclo[6.4.0.0$^{2,6}$]dodeca-1(8),6,9,11-tetraen-3-yl]-6-{[(2S)-1-methoxypropan-2-yl]amino}pyridine-2-carboxamide;

N-[9,10-difluoro-4-oxo-3-(trifluoromethyl)-2,5,7-triazatricyclo[6.4.0.0$^{2,6}$]dodeca-1(8),6,9,11-tetraen-3-yl]-6-fluoropyridine-2-carboxamide;

N-[9,10-difluoro-4-oxo-3-(trifluoromethyl)-2,5,7-triazatricyclo[6.4.0.0$^{2,6}$]dodeca-1(8),6,9,11-tetraen-3-yl]-6-[(2-methoxyethyl)amino]-pyridine-2-carboxamide;

(2S)—N-[10,11-dimethyl-4-oxo-3-(trifluoromethyl)-2,5,7-triaza-tricyclo[6.4.0.0$^{2,6}$]dodeca-1(8),6,9,11-tetraen-3-yl]-2-phenylpropanamide;

(2S)—N-[10,11-dimethyl-4-oxo-3-(trifluoro-methyl)-2,5,7-triazatricyclo-[6.4.0.0$^{2,6}$]dodeca-1(8),6,9,11-tetraen-3-yl]-2-phenyl-propanamide;

(2S)-3-cyclopentyl-N-[10,11-dimethyl-4-oxo-3-(trifluoro-methyl)-2,5,7-triazatricyclo-[6.4.0.0$^{2,6}$]dodeca-1(8),6,9,11-tetraen-3-yl]-2-methyl-propanamide;

(2S)—N-[10,11-dimethyl-4-oxo-3-(trifluoro-methyl)-2,5,7-triazatricyclo-[6.4.0.0$^{2,6}$]dodeca-1(8),6,9,11-tetraen-3-yl]-2-hydroxy-2-phenylacetamide;

(2S)—N-[10,11-dimethyl-4-oxo-3-(trifluoro-methyl)-2,5,7-triazatricyclo-[6.4.0.0$^{2,6}$]dodeca-1(8),6,9,11-tetraen-3-yl]-2-methoxy-2-phenylacetamide;

methyl 3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylate;

3-cyclopentyl-N-[9-iodo-4-oxo-3-(trifluoromethyl)-2,5,7-triazatricyclo[6.4.0.0$^{2,6}$]dodeca-1(12),6,8,10-tetraen-3-yl]propanamide;

N-[9-bromo-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide;

N-[9-bromo-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide;

(2S)—N-[9-bromo-4-oxo-3-(trifluoromethyl)-2,5,7-triazatricyclo[6.4.0.0$^{2,6}$]dodeca-1(12),6,8,10-tetraen-3-yl]-2-cyclohexylpropanamide;

(2S)-2-(cyclopent-1-en-1-ylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

N-[11-chloro-9-iodo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[9-bromo-4-oxo-3-(trifluoromethyl)-2,5,7-triazatricyclo[6.4.0.0$^{2,6}$]dodeca-1(12),6,8,10-tetraen-3-yl]butanamide;

N-[9-bromo-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide;

3-cyclopentyl-N-[9-iodo-10-methoxy-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(hydroxymethyl)-4-oxo-3-(trifluoromethyl)-2,5,7-triazatricyclo[6.4.0.0$^{2,6}$]dodeca-1(12),6,8,10-tetraen-3-yl]propanamide;

N-[9-butyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid;

3-cyclopentyl-N-{9-[1-(methoxyimino)ethyl]-4-oxo-3-(trifluoromethyl)-2,5,7-triazatricyclo[6.4.0.0$^{2,6}$]dodeca-1(12),6,8,10-tetraen-3-yl}propanamide;

3-(3-cyclopentylpropanamido)-N-methyl-4-oxo-3-(trifluoromethyl)-2,5,7-triazatricyclo[6.4.0.0$^{2,6}$]dodeca-1(12),6,8,10-tetraene-9-carboxamide;

3-cyclopentyl-N-[9-ethynyl-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[4-oxo-9-(trifluoromethoxy)-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-cyclopropanesulfonamido-4-oxo-3-(trifluoromethyl)-2,5,7-triazatricyclo[6.4.0.0$^{2,6}$]dodeca-1(12),6,8,10-tetraen-3-yl]propanamide;

3-(3-cyclopentylpropanamido)-N-methanesulfonyl-4-oxo-3-(trifluoromethyl)-2,5,7-triazatricyclo[6.4.0.0$^{2,6}$]dodeca-1(12),6,8,10-tetraene-9-carboxamide;

3-cyclopentyl-N-[9-methanesulfonamido-4-oxo-3-(trifluoromethyl)-2,5,7-triazatricyclo[6.4.0.0$^{2,6}$]dodeca-1(12),6,8,10-tetraen-3-yl]propanamide;

N-[9-bromo-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]-1,3-thiazole-4-carboxamide;

N-[9-acetyl-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]-1,3-thiazole-4-carboxamide;

3-(3,3-difluoropyrrolidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(3-fluoroazetidin-1-yl)propanamide;

3-(3,3-difluoropiperidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

N-[9-acetyl-10,11-dimethyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-methoxypyridine-3-carboxamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-hydroxypyridine-3-carboxamide;

N-[11-bromo-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[10-bromo-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[9-bromo-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-cyclopentyl-N-[9-fluoro-10-(1-hydroxyethyl)-4-oxo-3-(trifluoromethyl)-2,5,7-triazatricyclo[6.4.0.0$^{2,6}$]dodeca-1(12),6,8,10-tetraen-3-yl]propanamide;

N-[9-acetyl-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[9-bromo-11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[9-acetyl-11-chloro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[11-bromo-9-fluoro-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[11-acetyl-4-oxo-3,9-bis(trifluoromethyl)-2,5,7-triazatricyclo[6.4.0.0$^{2,6}$]dodeca-1(12),6,8,10-tetraen-3-yl]-3-cyclopentylpropanamide;

N-[11-chloro-10-methoxy-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-cyclopentyl-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(1-methyl-1H-pyrazol-4-yl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(6-methoxypyridin-3-yl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(3-methoxyphenyl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(1,3-oxazol-2-yl)-4-oxo-3-(trifluoromethyl)-2,5,7-triazatricyclo[6.4.0.0$^{2,6}$]dodeca-1(12),6,8,10-tetraen-3-yl]propanamide;

N-[9-(4-tert-butylphenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

N-[9-(4-cyanophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-cyclopentyl-N-[9-(4-nitrophenyl)-4-oxo-3-(trifluoromethyl)-2,5,7-triazatricyclo[6.4.0.0$^{2,6}$]dodeca-1(12),6,8,10-tetraen-3-yl]propanamide;

N-[9-(4-aminophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-cyclopentyl-N-[4-oxo-9-phenyl-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(2-methoxyphenyl)-4-oxo-3-(trifluoromethyl)-2,5,7-triazatricyclo[6.4.0.0$^{2,6}$]dodeca-1(12),6,8,10-tetraen-3-yl]propanamide;

2-hydroxy-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]pyridine-3-carboxamide;

3-cyclopentyl-N-[9-(2-hydroxyphenyl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[4-oxo-9-(1H-1,2,3,4-tetrazol-5-yl)-3-(trifluoromethyl)-2,5,7-triazatricyclo[6.4.0.0$^{2,6}$]dodeca-1(12),6,8,10-tetraen-3-yl]propanamide;

3-[3-(3-cyclopentylpropanamido)-4-oxo-3-(trifluoromethyl)-2,5,7-triazatricyclo[6.4.0.0$^{2,6}$]dodeca-1(12),6,8,10-tetraen-9-yl]benzoic acid;

N-[9-(4-chlorophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-cyclopentyl-N-[9-(4-methylphenyl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(3,4-dichlorophenyl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(3,4-dihydro-2H-pyran-5-yl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[10,11-dimethyl-9-(1-methyl-1H-pyrazol-4-yl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[10,11-dimethyl-4-oxo-9-(1,2-thiazol-4-yl)-3-(trifluoromethyl)-2,5,7-triazatricyclo[6.4.0.0$^{2,6}$]dodeca-1(12),6,8,10-tetraen-3-yl]propanamide;

3-cyclopentyl-N-[9-(furan-3-yl)-10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

N-[9-(4-methoxyphenyl)-10,11-dimethyl-4-oxo-3-(trifluoromethyl)-2,5,7-triazatricyclo[6.4.0.0$^{2,6}$]dodeca-1(12),6,8,10-tetraen-3-yl]acetamide;

3-cyclopentyl-N-[9-fluoro-10-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[11-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide;

(2S)—N-{10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methylbutoxy)propanamide;

(2R)—N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(3-methylbutoxy)propanamide;

(2R)-2-(3-chlorophenoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

(2S)—N-[9-acetyl-4-oxo-3-(trifluoromethyl)-2,5,7-triazatricyclo[6.4.0.0$^{2,6}$]dodeca-1(12),6,8,10-tetraen-3-yl]-2-cyclohexylpropanamide;

(2S)-3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-hydroxypropanamide;

(2S)-2-(cyclopentylmethoxy)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[4-oxo-3-(trifluoromethyl)-2,5,7-triazatricyclo[6.4.0.0$^{2,6}$]dodeca-1(12),6,8,10-tetraen-3-yl]propanamide;

3-cyclohexyl-N-[4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[10,11-dichloro-4-oxo-3-(trifluoromethyl)-2,5,7-triazatricyclo[6.4.0.0$^{2,6}$]dodeca-1(12),6,8,10-tetraen-3-yl]propanamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-6-[(2-methoxyethyl)amino]pyridine-2-carboxamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-(1-hydroxycyclopentyl)propanamide;

3-cyclopentyl-N-[9-methanesulfonyl-4-oxo-3-(trifluoromethyl)-2,5,7-triazatricyclo[6.4.0.0$^{2,6}$]dodeca-1(12),6,8,10-tetraen-3-yl]propanamide;

3-cyclopentyl-N-[9,10-difluoro-4-oxo-3-(trifluoromethyl)-2,5,7-triazatricyclo[6.4.0.0$^{2,6}$]dodeca-1(12),6,8,10-tetraen-3-yl]propanamide;

N-[9-acetyl-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-(3,3-difluoroazetidin-1-yl)-N-[10,11-dimethyl-4-oxo-3-(trifluoromethyl)-2,5,7-triazatricyclo[6.4.0.0$^{2,6}$]dodeca-1(12),6,8,10-tetraen-3-yl]propanamide;

N-[9-cyano-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;

3-cyclopentyl-N-[9-(2-methylpropanoyl)-4-oxo-3-(trifluoromethyl)-2,5,7-triazatricyclo[6.4.0.0$^{2,6}$]dodeca-1(12),6,8,10-tetraen-3-yl]propanamide;

N-[10,11-dimethyl-4-oxo-3-(trifluoromethyl)-2,5,7-triazatricyclo[6.4.0.0$^{2,6}$]dodeca-1(12),6,8,10-tetraen-3-yl]-3-phenylpropanamide;

3,5-dichloro-N-[10,11-dichloro-4-oxo-3-(trifluoromethyl)-2,5,7-triazatricyclo[6.4.0.0$^{2,6}$]dodeca-1(12),6,8,10-tetraen-3-yl]benzamide;

3-cyclopentyl-N-[9-(4-methoxyphenyl)-4-oxo-3-(trifluoromethyl)-2,5,7-triazatricyclo[6.4.0.0$^{2,6}$]dodeca-1(12),6,8,10-tetraen-3-yl]propanamide;

3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid;

3-cyclopentyl-N-{9-[4-(methylsulfanyl)phenyl]-4-oxo-3-(trifluoromethyl)-2,5,7-triazatricyclo[6.4.0.0$^{2,6}$]dodeca-1(12),6,8,10-tetraen-3-yl}propanamide;

11-chloro-3-(3-cyclopentylpropanamido)-4-oxo-3-(trifluoromethyl)-2,5,7-triazatricyclo[6.4.0.0$^{2,6}$]dodeca-1(12),6,8,10-tetraene-9-carboxylic acid;
N-[9-(4-m ethoxyphenyl)-4-oxo-3-(trifluoromethyl)-2,5,7-triazatricyclo[6.4.0.0$^{2,6}$]dodeca-1(12),6,8,10-tetraen-3-yl]butanamide;
2-[(2-methoxyethyl)amino]-N-[9-(4-m ethoxyphenyl)-4-oxo-3-(trifluoromethyl)-2,5,7-triazatricyclo[6.4.0.0$^{2,6}$]dodeca-1(12),6,8,10-tetraen-3-yl]-1,3-thiazole-4-carboxamide;
N-[9-bromo-4-oxo-3-(trifluoromethyl)-2,5,7-triazatricyclo[6.4.0.0$^{2,6}$]dodeca-1(12),6,8,10-tetraen-3-yl]-2-hydroxy-1,3-thiazole-4-carboxamide;
N-[10,11-dichloro-4-oxo-3-(trifluoromethyl)-2,5,7-triazatricyclo[6.4.0.0$^{2,6}$]dodeca-1(12),6,8,10-tetraen-3-yl]-2-[(2-methylpropyl)amino]-1,3-thiazole-4-carboxamide;
3-cyclopentyl-N-{9-[4-(dimethylamino)phenyl]-4-oxo-3-(trifluoromethyl)-2,5,7-triazatricyclo[6.4.0.0$^{2,6}$]dodeca-1(12),6,8,10-tetraen-3-yl}propanamide;
N-[10,11-dimethyl-4-oxo-3-(trifluoromethyl)-2,5,7-triazatricyclo[6.4.0.0$^{2,6}$]dodeca-1(12),6,8,10-tetraen-3-yl]-2,2,2-trifluoroacetamide;
N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-(2-methoxyethoxy)pyridine-4-carboxamide;
3-cyclopentyl-N-[9-(4-methanesulfonylphenyl)-4-oxo-3-(trifluoromethyl)-2,5,7-triazatricyclo[6.4.0.0$^{2,6}$]dodeca-1(12),6,8,10-tetraen-3-yl]propanamide;
N-[10,11-dimethyl-4-oxo-3-(trifluoromethyl)-2,5,7-triazatricyclo[6.4.0.0$^{2,6}$]dodeca-1(12),6,8,10-tetraen-3-yl]-2,2-dimethylpropanamide;
N-[9-acetyl-4-oxo-3-(trifluoromethyl)-2,5,7-triazatricyclo[6.4.0.0$^{2,6}$]dodeca-1(12),6,8,10-tetraen-3-yl]-2-(cyclopentylamino)-1,3-thiazole-4-carboxamide;
N-[9-(3-chlorophenyl)-4-oxo-3-(trifluoromethyl)-2,5,7-triazatricyclo[6.4.0.0$^{2,6}$]dodeca-1(12),6,8,10-tetraen-3-yl]-3-cyclopentylpropanamide;
3-cyclopentyl-N-[4-oxo-3-(trifluoromethyl)-9-[4-(trifluoromethyl)phenyl]-2,5,7-triazatricyclo[6.4.0.0$^{2,6}$]dodeca-1(12),6,8,10-tetraen-3-yl]propanamide;
3-cyclopentyl-N-[9-(4-fluorophenyl)-4-oxo-3-(trifluoromethyl)-2,5,7-triazatricyclo[6.4.0.0$^{2,6}$]dodeca-1(12),6,8,10-tetraen-3-yl]propanamide;
3-(3-cyclopentylpropanamido)-N-methanesulfonyl-10-methoxy-4-oxo-3-(trifluoromethyl)-2,5,7-triazatricyclo[6.4.0.0$^{2,6}$]dodeca-1(12),6,8,10-tetraene-9-carboxamide;
3-cyclopentyl-N-[9-(methoxymethyl)-4-oxo-3-(trifluoromethyl)-2,5,7-triazatricyclo[6.4.0.0$^{2,6}$]dodeca-1(12),6,8,10-tetraen-3-yl]propanamide;
tert-butyl 3-{[10,11-dimethyl-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate;
tert-butyl 4-{[10,11-dimethyl-4-oxo-3-(trifluoromethyl)-2,5,7-triazatricyclo-[6.4.0.0$^{2,6}$]dodeca-1(12),6,8,10-tetraen-3-yl]carbamoyl}piperidine-1-carboxylate;
tert-butyl (2S)-2-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate;
tert-butyl 3-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}pyrrolidine-1-carboxylate;
tert-butyl 4-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}piperidine-1-carboxylate;
tert-butyl 3-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}azetidine-1-carboxylate;
tert-butyl 4-({[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}methyl)piperidine-1-carboxylate;
tert-butyl 2-(2-{[10,11-dichloro-4-oxo-3-(trifluoromethyl)-2,5,7-triazatricyclo-[6.4.0.0$^{2,6}$]dodeca-1(12),6,8,10-tetraen-3-yl]carbamoyl}ethyl)piperidine-1-carboxylate;
tert-butyl 3-{[10,11-dichloro-4-oxo-3-(trifluoromethyl)-2,5,7-triazatricyclo[6.4.0.0$^{2,6}$]dodeca-1(8),6,9,11-tetraen-3-yl]carbamoyl}-3-fluoroazetidine-1-carboxylate;
methyl 3-[3-(3-cyclopentylpropanamido)-4-oxo-3-(trifluoromethyl)-2,5,7-triazatricyclo[6.4.0.0$^{2,6}$]dodeca-1(12),6,8,10-tetraen-9-yl]benzoate;
N-[10,11-dimethyl-4-oxo-3-(trifluoromethyl)-2,5,7-triazatricyclo[6.4.0.0$^{2,6}$]dodeca-1(12),6,8,10-tetraen-3-yl]acetamide;
N-[9-bromo-10,11-dimethyl-4-oxo-3-(trifluoromethyl)-2,5,7-triazatricyclo[6.4.0.0$^{2,6}$]dodeca-1(12),6,8,10-tetraen-3-yl]acetamide; and
N-[10,11-dimethyl-4-oxo-3-(trifluoromethyl)-2,5,7-triazatricyclo[6.4.0.0$^{2,6}$]dodeca-1(12),6,8,10-tetraen-3-yl]-2-[(2-methoxyethyl)amino]pyrimidine-4-carboxamide;
or a pharmaceutically acceptable salt thereof.

12. A pharmaceutical composition comprising a compound according to claim 1 or a pharmaceutically acceptable salt thereof, and at least one pharmaceutically acceptable excipient.

13. A method of treatment of colon cancer, by administering a compound according to claim 1 to a mammal in need of such treatment.

14. The compound of claim 2, or a pharmaceutically acceptable salt thereof, wherein $R_A$, $R_B$ and $R_C$ are independently selected from H, halogen, C1-C4 alkyl and $R_2C(O)$.

15. The compound of claim 2, or a pharmaceutically acceptable salt thereof, wherein one of $R_A$, $R_B$ and $R_C$ is phenyl optionally substituted by one or more moieties $R_{16}$, or 5- or 6-membered heterocyclyl optionally substituted by one or more moieties $R_{16}$, and the two others of $R_A$, $R_B$ and $R_C$ are independently selected from H, halogen, and C1-C4 alkyl.

16. The compound of claim 2, or a pharmaceutically acceptable salt thereof, wherein W is a direct bond.

17. The compound of claim 2, or a pharmaceutically acceptable salt thereof, wherein W is X1-X2-X3.

18. The compound of claim 3, or a pharmaceutically acceptable salt thereof, wherein $R_A$, $R_B$ and $R_C$ are independently selected from H, halogen, C1-C4 alkyl and $R_2C(O)$.

19. The compound of claim 3, or a pharmaceutically acceptable salt thereof, wherein one of $R_A$, $R_B$ and $R_C$ is phenyl optionally substituted by one or more moieties $R_{16}$, or 5- or 6-membered heterocyclyl optionally substituted by one or more moieties $R_{16}$, and the two others of $R_A$, $R_B$ and $R_C$ are independently selected from H, halogen, and C1-C4 alkyl.

20. The compound of claim 3, or a pharmaceutically acceptable salt thereof, wherein W is a direct bond.

21. The compound of claim 3, or a pharmaceutically acceptable salt thereof, wherein W is X1-X2-X3.

22. The compound of claim 4, or a pharmaceutically acceptable salt thereof, wherein $R_A$, $R_B$ and $R_C$ are independently selected from H, halogen, C1-C4 alkyl and $R_2C(O)$.

23. The compound of claim 4, or a pharmaceutically acceptable salt thereof, wherein one of $R_A$, $R_B$ and $R_C$ is phenyl optionally substituted by one or more moieties $R_{16}$, or 5- or 6-membered heterocyclyl optionally substituted by one or more moieties $R_{16}$, and the two others of $R_A$, $R_B$ and $R_C$ are independently selected from H, halogen, and C1-C4 alkyl.

24. The compound of claim 4, or a pharmaceutically acceptable salt thereof, wherein W is a direct bond.

25. The compound of claim 4, or a pharmaceutically acceptable salt thereof, wherein W is X1-X2-X3.

26. The compound of claim 5, or a pharmaceutically acceptable salt thereof, wherein $R_A$, $R_B$ and $R_C$ are independently selected from H, halogen, C1-C4 alkyl and $R_2C(O)$.

27. The compound of claim 5, or a pharmaceutically acceptable salt thereof, wherein one of $R_A$, $R_B$ and $R_C$ is phenyl optionally substituted by one or more moieties $R_{16}$, or 5- or 6-membered heterocyclyl optionally substituted by one or more moieties $R_{16}$, and the two others of $R_A$, $R_B$ and $R_C$ are independently selected from H, halogen, and C1-C4 alkyl.

28. The compound of claim 5, or a pharmaceutically acceptable salt thereof, wherein W is a direct bond.

29. The compound of claim 5, or a pharmaceutically acceptable salt thereof, wherein W is X1-X2-X3.

30. The compound of claim 6, or a pharmaceutically acceptable salt thereof, wherein $R_A$, $R_B$ and $R_C$ are independently selected from H, halogen, C1-C4 alkyl and $R_2C(O)$.

31. The compound of claim 6, or a pharmaceutically acceptable salt thereof, wherein one of $R_A$, $R_B$ and $R_C$ is phenyl optionally substituted by one or more moieties $R_{16}$, or 5- or 6-membered heterocyclyl optionally substituted by one or more moieties $R_{16}$, and the two others of $R_A$, $R_B$ and $R_C$ are independently selected from H, halogen, and C1-C4 alkyl.

32. The compound of claim 6, or a pharmaceutically acceptable salt thereof, wherein W is a direct bond.

33. The compound of claim 6, or a pharmaceutically acceptable salt thereof, wherein W is X1-X2-X3.

* * * * *